United States Patent
Zhang et al.

(10) Patent No.: US 11,679,109 B2
(45) Date of Patent: Jun. 20, 2023

(54) SMARCA DEGRADERS AND USES THEREOF

(71) Applicant: Kymera Therapeutics, Inc., Watertown, MA (US)

(72) Inventors: Yi Zhang, Belmont, MA (US); Paul R. Fleming, Lexington, MA (US); Xiao Zhu, Winchester, MA (US)

(73) Assignee: Kymera Therapeutics, Inc., Watertown, MA (US)

( * ) Notice: Subject to any disclaimer, the term of this patent is extended or adjusted under 35 U.S.C. 154(b) by 116 days.

(21) Appl. No.: 17/132,764

(22) Filed: Dec. 23, 2020

(65) Prior Publication Data

US 2022/0331317 A1     Oct. 20, 2022

Related U.S. Application Data

(60) Provisional application No. 63/123,176, filed on Dec. 9, 2020, provisional application No. 62/952,578, filed on Dec. 23, 2019.

(51) Int. Cl.
| | | |
|---|---|---|
| *A61K 31/50* | (2006.01) | |
| *A61K 31/506* | (2006.01) | |
| *A61K 47/54* | (2017.01) | |
| *A61P 35/00* | (2006.01) | |

(52) U.S. Cl.
CPC .......... *A61K 31/506* (2013.01); *A61K 47/545* (2017.08); *A61P 35/00* (2018.01)

(58) Field of Classification Search
CPC .................................................. A61K 31/506
See application file for complete search history.

(56) References Cited

U.S. PATENT DOCUMENTS

| | | |
|---|---|---|
| 4,650,750 A | 3/1987 | Giese |
| 4,709,016 A | 11/1987 | Giese |
| 5,217,866 A | 6/1993 | Summerton et al. |
| 5,360,811 A | 11/1994 | Tegeler et al. |
| 5,360,819 A | 11/1994 | Giese |
| 5,516,931 A | 5/1996 | Giese et al. |
| 5,602,273 A | 2/1997 | Giese et al. |
| 5,604,104 A | 2/1997 | Giese et al. |
| 5,610,020 A | 3/1997 | Giese et al. |
| 5,650,270 A | 7/1997 | Giese et al. |
| 5,721,246 A | 2/1998 | Yoshino et al. |
| 6,306,663 B1 | 10/2001 | Kenten et al. |
| 6,552,065 B2 | 4/2003 | Remiszewski et al. |
| 6,559,280 B2 | 5/2003 | Kenten et al. |
| 6,627,754 B2 | 9/2003 | Blumenkopf et al. |
| 6,949,537 B2 | 9/2005 | Garlich et al. |
| 7,041,298 B2 | 5/2006 | Deshaies et al. |
| 7,071,189 B2 | 7/2006 | Kawashima et al. |
| 7,074,620 B2 | 7/2006 | Kenten et al. |
| 7,173,015 B2 | 2/2007 | Schreiber et al. |
| 7,208,157 B2 | 4/2007 | Dashaies et al. |
| 7,273,920 B2 | 9/2007 | Kenten et al. |
| 7,307,077 B2 | 12/2007 | Kawashima et al. |
| 7,390,799 B2 | 6/2008 | Bruncko et al. |
| 7,402,325 B2 | 7/2008 | Addington |
| 7,449,458 B2 | 11/2008 | Bhamidipati et al. |
| 7,501,496 B1 | 3/2009 | Endl et al. |
| 7,514,444 B2 | 4/2009 | Honigberg et al. |
| 7,528,143 B2 | 5/2009 | Noronha et al. |
| 7,557,210 B2 | 7/2009 | Singh et al. |
| 7,598,257 B2 | 10/2009 | Rodgers et al. |
| 7,622,496 B2 | 11/2009 | Larsen et al. |
| 7,667,039 B2 | 2/2010 | Garcia-Echeverria et al. |
| 7,713,943 B2 | 5/2010 | Klippel-Giese et al. |
| 7,781,433 B2 | 8/2010 | Chuckowree et al. |
| 7,932,260 B2 | 4/2011 | Fowler et al. |
| 7,989,622 B2 | 8/2011 | Bajjalieh et al. |
| 8,138,347 B2 | 3/2012 | Knight et al. |
| 8,217,035 B2 | 7/2012 | Burger et al. |
| 8,338,439 B2 | 12/2012 | Singh et al. |
| 8,486,941 B2 | 7/2013 | Burns et al. |
| 8,906,682 B2 | 12/2014 | June et al. |
| 8,999,975 B2 | 4/2015 | Grundl et al. |
| 9,500,653 B2 | 11/2016 | Crews et al. |
| 9,632,089 B2 | 4/2017 | Crews et al. |
| 9,694,084 B2 | 7/2017 | Bradner et al. |
| 9,750,816 B2 | 9/2017 | Bradner et al. |
| 9,770,512 B2 | 9/2017 | Bradner et al. |
| 9,821,068 B2 | 11/2017 | Bradner et al. |
| 10,125,114 B2 | 11/2018 | Bradner et al. |
| 10,336,744 B2 | 7/2019 | Harling et al. |
| 10,874,743 B2 | 12/2020 | Mainolfi et al. |
| 2001/0053782 A1 | 12/2001 | Blumenkopf et al. |
| 2002/0042427 A1 | 4/2002 | Tang et al. |
| 2002/0068063 A1 | 6/2002 | Deshaies et al. |
| 2002/0183360 A1 | 12/2002 | Muller et al. |
| 2004/0029902 A1 | 2/2004 | Singh et al. |

(Continued)

FOREIGN PATENT DOCUMENTS

| | | |
|---|---|---|
| CN | 105085620 B | 5/2018 |
| WO | WO-1996007655 A1 | 3/1996 |

(Continued)

OTHER PUBLICATIONS

Adams et al., "Big opportunities for small molecules in immuno-oncology," Nat Rev Drug Discov. 2015;14(9):603-22.
Aruri et al., "Metal-free Cross-Dehydrogenative Coupling of HN-azoles with a-C(sp3)-H Amides via C-H Activation and Its Mechanistic and Application Studies," J Org Chem. 2017;82(2):1000-1012.
Bailey et al., "Steric effects on [4+4]-photocycloaddition reactions between complementary anthracene derivatives" Dyes and Pigments. 2011;89(3):313-318.
Berge et al., "Pharmaceutical salts," J Pharm Sci. Jan. 1977;66(1):1-19.
Berndsen et al., "New insights into ubiquitin E3 ligase mechanism," Nat Struct Mol Biol. 2014;21(4):301-7.

(Continued)

*Primary Examiner* — Shawquia Jackson
(74) *Attorney, Agent, or Firm* — Dechert LLP; Andrea L.C. Reid; Todd K. Macklin

(57) ABSTRACT

The present invention provides compounds, compositions thereof, and methods of using the same.

16 Claims, No Drawings

(56) References Cited

U.S. PATENT DOCUMENTS

| | | |
|---|---|---|
| 2004/0048859 A1 | 3/2004 | Germann et al. |
| 2004/0106569 A1 | 6/2004 | Klippel-Giese et al. |
| 2004/0116421 A1 | 6/2004 | Kawashima et al. |
| 2004/0242631 A1 | 12/2004 | Garlich et al. |
| 2005/0014802 A1 | 1/2005 | Attardo et al. |
| 2005/0075306 A1 | 4/2005 | Schreiber et al. |
| 2006/0211657 A1 | 9/2006 | Singh et al. |
| 2007/0098719 A1 | 5/2007 | Smith et al. |
| 2007/0135461 A1 | 6/2007 | Rodgers et al. |
| 2007/0191405 A1 | 8/2007 | Noronha et al. |
| 2008/0076768 A1 | 3/2008 | Chuckowree et al. |
| 2008/0108636 A1 | 5/2008 | Honigberg et al. |
| 2008/0194579 A1 | 8/2008 | Garcia-Echeverria et al. |
| 2008/0275067 A1 | 11/2008 | Fowler et al. |
| 2009/0055944 A1 | 2/2009 | Korman et al. |
| 2009/0136494 A1 | 5/2009 | Ponath et al. |
| 2009/0233903 A1 | 9/2009 | Rodgers et al. |
| 2010/0087440 A1 | 4/2010 | Bajjalieh et al. |
| 2010/0150892 A1 | 6/2010 | Han |
| 2010/0197671 A1 | 8/2010 | Burns et al. |
| 2010/0197686 A1 | 8/2010 | Xing et al. |
| 2010/0203056 A1 | 8/2010 | Irving et al. |
| 2010/0233183 A1 | 9/2010 | Triebel et al. |
| 2010/0247554 A1 | 9/2010 | Lemke et al. |
| 2010/0249092 A1 | 9/2010 | Singh et al. |
| 2010/0249126 A1 | 9/2010 | Burger et al. |
| 2011/0008331 A1 | 1/2011 | Triebel |
| 2011/0053941 A1 | 3/2011 | Mautino et al. |
| 2011/0136796 A1 | 6/2011 | Mautino et al. |
| 2011/0165156 A1 | 7/2011 | Dimoudis et al. |
| 2011/0223611 A1 | 9/2011 | Salamone et al. |
| 2011/0274683 A1 | 11/2011 | Wong et al. |
| 2012/0189639 A1 | 7/2012 | Schebye et al. |
| 2012/0277217 A1 | 11/2012 | Mautino et al. |
| 2012/0329997 A1 | 12/2012 | Fertig et al. |
| 2013/0005949 A1 | 1/2013 | Fertig et al. |
| 2013/0149236 A1 | 6/2013 | Johnson et al. |
| 2013/0190340 A1 | 7/2013 | Hedstrom et al. |
| 2014/0066625 A1 | 3/2014 | Mautino et al. |
| 2014/0079699 A1 | 3/2014 | Wong et al. |
| 2014/0079706 A1 | 3/2014 | Cannarile et al. |
| 2014/0093511 A1 | 4/2014 | Lonberg et al. |
| 2014/0302523 A1 | 10/2014 | Crews et al. |
| 2014/0336363 A1 | 11/2014 | Fertig et al. |
| 2014/0341917 A1 | 11/2014 | Nastri et al. |
| 2014/0356322 A1 | 12/2014 | Crews et al. |
| 2015/0225449 A1 | 8/2015 | Donnell et al. |
| 2015/0274738 A1 | 10/2015 | Gray et al. |
| 2015/0291562 A1 | 10/2015 | Crew et al. |
| 2015/0374678 A1 | 12/2015 | Chamberlain et al. |
| 2016/0022642 A1 | 1/2016 | Crews et al. |
| 2016/0045607 A1 | 2/2016 | Crew et al. |
| 2016/0058872 A1 | 3/2016 | Crew et al. |
| 2016/0176916 A1 | 6/2016 | Bradner et al. |
| 2016/0200705 A1 | 7/2016 | Furet et al. |
| 2016/0214972 A1 | 7/2016 | Jin et al. |
| 2016/0235730 A1 | 8/2016 | Bradner et al. |
| 2016/0235731 A1 | 8/2016 | Bradner et al. |
| 2016/0243247 A1 | 8/2016 | Bradner et al. |
| 2016/0256468 A1 | 9/2016 | Schafer et al. |
| 2016/0272596 A1 | 9/2016 | Chen et al. |
| 2016/0272639 A1 | 9/2016 | Crew et al. |
| 2017/0001990 A1 | 1/2017 | Chen et al. |
| 2017/0008904 A1 | 1/2017 | Crew et al. |
| 2017/0022189 A1 | 1/2017 | Zhang |
| 2017/0037004 A1 | 2/2017 | Crew et al. |
| 2017/0065719 A1 | 3/2017 | Qian et al. |
| 2017/0121321 A1 | 5/2017 | Crews et al. |
| 2017/0250346 A1 | 8/2017 | Seo et al. |
| 2017/0281784 A1 | 10/2017 | Wang et al. |
| 2017/0327469 A1 | 11/2017 | Crew et al. |
| 2018/0009779 A1 | 1/2018 | Bradner et al. |
| 2018/0015087 A1 | 1/2018 | Liu et al. |
| 2018/0085465 A1 | 3/2018 | Bradner et al. |
| 2018/0086720 A1 | 3/2018 | Albrecht et al. |
| 2018/0118733 A1 | 5/2018 | Harling et al. |
| 2018/0134684 A1 | 5/2018 | Bradner et al. |
| 2018/0147202 A1 | 5/2018 | Crew et al. |
| 2018/0194724 A1 | 7/2018 | Kemp et al. |
| 2018/0228907 A1 | 8/2018 | Crew et al. |
| 2019/0071415 A1 | 3/2019 | Bradner et al. |
| 2019/0076539 A1 | 3/2019 | Phillips et al. |
| 2019/0076540 A1 | 3/2019 | Phillips et al. |
| 2019/0076541 A1 | 3/2019 | Phillips et al. |
| 2019/0076542 A1 | 3/2019 | Phillips et al. |
| 2019/0151457 A1 | 5/2019 | Bradner et al. |
| 2019/0192668 A1 | 6/2019 | Mainolfi et al. |
| 2019/0276474 A1 | 9/2019 | Chan et al. |
| 2019/0300521 A1 | 10/2019 | Crew et al. |
| 2020/0010468 A1 | 1/2020 | Ji et al. |
| 2020/0078933 A1 | 1/2020 | Ji et al. |
| 2020/0347045 A1 | 11/2020 | Mainolfi et al. |
| 2020/0377469 A1 | 12/2020 | Mainolfi et al. |
| 2021/0002296 A1 | 1/2021 | Mainolfi et al. |

FOREIGN PATENT DOCUMENTS

| | | |
|---|---|---|
| WO | WO-2001042246 A2 | 6/2001 |
| WO | WO-2002020740 A2 | 3/2002 |
| WO | WO-2002088112 A1 | 11/2002 |
| WO | WO-2003063794 A2 | 8/2003 |
| WO | WO-2004019973 A1 | 3/2004 |
| WO | WO-2004089925 A1 | 10/2004 |
| WO | WO-2004106328 A1 | 12/2004 |
| WO | WO-2005007623 A2 | 1/2005 |
| WO | WO-2005113554 A2 | 12/2005 |
| WO | WO-2006029879 A2 | 3/2006 |
| WO | WO-2006078846 A1 | 7/2006 |
| WO | WO-2006105021 A2 | 10/2006 |
| WO | WO-2006122806 A2 | 11/2006 |
| WO | WO-2007005874 A2 | 1/2007 |
| WO | WO-2007016176 A2 | 2/2007 |
| WO | WO-2007044729 A2 | 4/2007 |
| WO | WO-2007053452 A1 | 5/2007 |
| WO | WO-2007070514 A1 | 6/2007 |
| WO | WO-2007084786 A1 | 7/2007 |
| WO | WO-2007129161 A2 | 11/2007 |
| WO | WO-2008039218 A2 | 4/2008 |
| WO | WO-2008109943 A1 | 9/2008 |
| WO | WO-2008118802 A1 | 10/2008 |
| WO | WO-2008132601 A1 | 11/2008 |
| WO | WO-2009009116 A2 | 1/2009 |
| WO | WO-2009044273 A2 | 4/2009 |
| WO | WO-2009073620 A2 | 6/2009 |
| WO | WO-2009114512 A1 | 9/2009 |
| WO | WO-2009132238 A3 | 10/2009 |
| WO | WO-2010019570 A2 | 2/2010 |
| WO | WO-2010077634 A1 | 7/2010 |
| WO | WO-2011028683 A1 | 3/2011 |
| WO | WO-2011056652 A1 | 5/2011 |
| WO | WO-2011070024 A1 | 6/2011 |
| WO | WO-2011090760 A1 | 7/2011 |
| WO | WO-2011107553 A1 | 9/2011 |
| WO | WO-2011109400 A2 | 9/2011 |
| WO | WO-2011131407 A1 | 10/2011 |
| WO | WO-2011140249 A2 | 11/2011 |
| WO | WO-2012003281 A3 | 1/2012 |
| WO | WO-2012032433 A1 | 3/2012 |
| WO | WO-2012078559 A2 | 6/2012 |
| WO | WO-2012145493 A1 | 10/2012 |
| WO | WO-2014142237 A1 | 10/2012 |
| WO | WO-2013079174 A1 | 6/2013 |
| WO | WO-2013087699 A1 | 6/2013 |
| WO | WO-2013106643 A2 | 7/2013 |
| WO | WO-2013106646 A2 | 7/2013 |
| WO | WO-2013119716 A1 | 8/2013 |
| WO | WO-2013132044 A1 | 9/2013 |
| WO | WO-2013169264 A1 | 11/2013 |
| WO | WO-2014008218 A1 | 1/2014 |
| WO | WO-2014036357 A1 | 3/2014 |
| WO | WO-2014044622 A1 | 3/2014 |
| WO | WO-2014063061 A1 | 4/2014 |
| WO | WO-2014108452 A1 | 7/2014 |
| WO | WO-2015071393 A1 | 5/2015 |

(56) References Cited

FOREIGN PATENT DOCUMENTS

| WO | WO-2015100331 A2 | 7/2015 |
|---|---|---|
| WO | WO-2015160845 A3 | 10/2015 |
| WO | WO-2016105518 A1 | 6/2016 |
| WO | WO-2016118666 A1 | 7/2016 |
| WO | WO-2016138114 A1 | 9/2016 |
| WO | WO-2016149668 A1 | 9/2016 |
| WO | WO-2016169989 A1 | 10/2016 |
| WO | WO-2016197032 A1 | 12/2016 |
| WO | WO-2016197114 A1 | 12/2016 |
| WO | WO-2017007612 A1 | 1/2017 |
| WO | WO-2017011371 A1 | 1/2017 |
| WO | WO-2017011590 A1 | 1/2017 |
| WO | WO-2017024317 A2 | 2/2017 |
| WO | WO-2017030814 A1 | 2/2017 |
| WO | WO-2017059280 A1 | 4/2017 |
| WO | WO-2017079267 A1 | 5/2017 |
| WO | WO-2017117473 A1 | 7/2017 |
| WO | WO-2017117474 A1 | 7/2017 |
| WO | WO-2017161119 A1 | 9/2017 |
| WO | WO-2017176708 A1 | 10/2017 |
| WO | WO-2017176957 A1 | 10/2017 |
| WO | WO-2017176958 A1 | 10/2017 |
| WO | WO-2017197036 A1 | 11/2017 |
| WO | WO-2017197046 A1 | 11/2017 |
| WO | WO-2017197051 A1 | 11/2017 |
| WO | WO-2017197055 A1 | 11/2017 |
| WO | WO-2017197056 A1 | 11/2017 |
| WO | WO-2017201449 A1 | 11/2017 |
| WO | WO-2017211924 A1 | 12/2017 |
| WO | WO-2018089736 A1 | 5/2018 |
| WO | WO-2018098367 A1 | 5/2018 |
| WO | WO-2018144649 A1 | 8/2018 |
| WO | WO-2018237026 A1 | 12/2018 |
| WO | WO-2019043214 A1 | 3/2019 |
| WO | WO-2019060693 A1 | 3/2019 |
| WO | WO-2019060742 A1 | 3/2019 |
| WO | WO-2019084026 A1 | 5/2019 |
| WO | WO-2019084030 A1 | 5/2019 |
| WO | WO-2019099868 A1 | 5/2019 |
| WO | WO-2019099926 A1 | 5/2019 |
| WO | WO-2019133531 A1 | 7/2019 |
| WO | WO-2019140380 A1 | 7/2019 |
| WO | WO-2019140387 A1 | 7/2019 |
| WO | WO-2019152437 A1 | 8/2019 |
| WO | WO-2019165229 A1 | 8/2019 |
| WO | WO-2019195201 A1 | 10/2019 |
| WO | WO-2019213005 A1 | 11/2019 |
| WO | WO-2020010177 A1 | 1/2020 |
| WO | WO-2020010210 A1 | 1/2020 |
| WO | WO-2020010227 A1 | 1/2020 |
| WO | WO-2020038378 A1 | 2/2020 |
| WO | WO-2020078933 A1 | 4/2020 |
| WO | WO-2020160100 A1 | 8/2020 |
| WO | WO-2020251974 A1 | 12/2020 |
| WO | WO-2021011631 A1 | 1/2021 |
| WO | WO-2021067606 A1 | 4/2021 |
| WO | WO-2021083949 A1 | 5/2021 |
| WO | WO-2021086785 A1 | 5/2021 |
| WO | WO-2021142247 A1 | 7/2021 |
| WO | WO-2021207291 A1 | 10/2021 |
| WO | WO-2021252666 A1 | 12/2021 |
| WO | WO-2022029617 A1 | 2/2022 |

OTHER PUBLICATIONS

Bevilacqua et al., "SWI/SNF Chromatin-Remodeling Complexes in Cardiovascular Development and Disease," Cardiovasc Pathol. Mar.-Apr., 2014; 23(2): 85-91.
Boehm et al., "Bromodomain Proteins in HIV Infection," Viruses. 2013;5:1571.
Boichenko et al., "A FRET-Based Assay for the Identification and Characterization of Cereblon Ligands," J Med Chem. 2016;59(2):770-4.
CAS STN Abstract, RN 1787975-60-3 (Pub. Jun. 24, 2015).
CAS STN Abstract, RN 1795294-81-3 (Pub. Jul. 6, 2015).
CAS STN Abstract, RN 1795451-20-5 (Pub. Jul. 6, 2015).
CAS STN Abstract, RN 1795527-49-9 (Pub. Jul. 6, 2015).
CAS STN Abstract, RN 1871221-08-7 (Pub. Feb. 21, 2016).
CAS STN Abstract, RN 1878956-45-6 (Pub. Mar. 3, 2016).
CAS STN Abstract, RN 1878983-55-1 (Pub. Mar. 3, 2016).
CAS STN Abstract, RN 742039-47-0 (Pub. Sep. 10, 2004).
CAS STN Abstract, RN 779303-42-3 (Pub. Nov. 12, 2004).
Chang et al., "What is the functional role of the thalidomide binding protein cereblon?" Int J Biochem Mol Biol. 2011;2(3):287-94.
Charrier et al., "Desulfonylative radical ring closure onto aromatics. A modular route to benzazepin-2-ones and 5-arylpiperidin-2-ones," Org Lett. 2012;14(8):2018-21.
Contino-Pepin et al., "Preliminary biological evaluations of new thalidomide analogues for multiple sclerosis application," Bioorg Med Chem Lett. 2009;19(3):878-81.
Crews, "Targeting the Undruggable Proteome: The Small Molecules of My Dreams," Chem Biol. 2010;17(6):551-5.
Cruickshank et al., "SWI/SNF Subunits SMARCA4, SMARCD2 and DPF2 Collaborate in MLL-Rearranged Leukaemia Maintenance," PLoS One. 2015;10(11): e0142806.
Deshaies and Joazeiro, "RING domain E3 ubiquitin ligases," Annu Rev Biochem. 2009;78:399-434.
Filippakopoulos et al., "Histone recognition and large-scale structural analysis of the human bromodomain family," Cell. 2012;149(1):214-31.
Fischer et al., "Structure of the DDB1-CRBN E3 ubiquitin ligase in complex with thalidomide," Nature. 2014;512(7512):49-53.
Gerstenberger et al., "Identification of a Chemical Probe for Family VIII Bromodomains through Optimization of a Fragment Hit," J Med Chem. 2016;59(10):4800-11.
Hagner et al., "CC-122, a pleiotropic pathway modifier, mimics an interferon response and has antitumor activity in DLBCL," Blood. 2015;126(6):779-89.
Hines et al., "MDM2-Recruiting PROTAC Offers Superior, Synergistic Antiproliferative Activity via Simultaneous Degradation of BRD4 and Stabilization of p53," Cancer Res. 2019;79(1):251-62.
Hoffman et al., "Functional epigenetics approach identifies BRM/SMARCA2 as a critical synthetic lethal target in BRG1-deficient cancers," Proc Natl Acad Sci U S A. 2014;111(8):3128-33.
Hohmann and Vakoc, "A rationale to target the SWI/SNF complex for cancer therapy," Trends Genet. 2014;30(8): 356-363.
Iconomou and Saunders, "Systematic approaches to identify E3 ligase substrates," Biochem J. 2016;473(22):4083-4101.
Ito et al., "Identification of a primary target of thalidomide teratogenicity," Science. 2010;327(5971):1345-50.
Jeanmougin et al., "The bromodomain revisited," Trends Biochem Sci. 1997;22(5):151-3.
Kadoch and Crabtree "Mammalian SWI/SNF chromatin remodeling complexes and cancer: Mechanistic insights gained from human genomics," Sci Adv. 2015;1(5):e1500447.
Kester et al., "Optimization of Benzodiazepinones as Selective Inhibitors of the X-Linked Inhibitor of Apoptosis Protein (XIAP) Second Baculovirus IAP Repeat (BIR2) Domain," J Med Chem. 2013;56(20):7788-803.
Koga et al., "Involvement of SMARCA2/BRM in the SWI/SNF chromatin-remodeling complex in schizophrenia," Hum Mol Genet. 2009;18(13):2483-94.
Kosho et al., "Genotype-phenotype correlation of Coffin-Siris syndrome caused by mutations in SMARCB1, SMARCA4, SMARCE1, and ARID1A," Am. J. Med. Genet. 2014;166(3):262.
Krönke et al., "Lenalidomide causes selective degradation of IKZF1 and IKZF3 in multiple myeloma cells" Science. 2014;343(6168):301-305.
Lebakken et al., "A Fluorescence Lifetime Based Binding Assay to Characterize Kinase Inhibitors," J Biomol Screen. 2007;12(6):828-41.
Li et al., "Genome-wide and functional annotation of human E3 ubiquitin ligases identifies MULAN, a mitochondrial E3 that regulates the organelle's dynamics and signaling," PLoS One. 2008;3(1):e1487.
Lu et al., "Hijacking the E3 Ubiquitin Ligase Cereblon to Efficiently Target BRD4," Chem Biol. 2015;2(6):755-63.

(56) References Cited

OTHER PUBLICATIONS

Lu et al., "Identification of small molecule inhibitors targeting the SMARCA2 bromodomain from a high-throughput screening assay," Acta Pharmacol Sin. 2018;39(9): 1544-1552.

Lu et al., "The myeloma drug lenalidomide promotes the cereblon-dependent destruction of Ikaros proteins," Science. 2014;343(6168):305-309.

Lust et al., "Induction of a Chronic Disease State in patients With Smoldering of Indolent Multiple Myeloma by Targeting Interleukin Iß-Induced Interleukin 6 Production and the Myeloma Proliferative Component," Mayo Clin Proc. 2009;84(2):114-22.

Mao et al., "Bioinformatic Analysis of Coronary Disease Associated SNPs and Genes to Identify Proteins Potentially Involved in the Pathogenesis of Atherosclerosis," J Proteom Genom Res. 2017;(1):1-12.

Matyskiela et al., "A Cereblon Modulator (CC-220) with Improved Degradation of Ikaros and Aiolos," J Med Chem. 2018;61(2):535-542.

Medina et al. "Genetic and epigenetic screening for gene alterations of the chromatin-remodeling factor, SMARCA4/BRG1, in lung tumors," Genes Chromosomes Cancer. 2004;41(2):170-7.

Muller et al., "Amino-Substituted Thalidomide Analogs: Potent Inhibitors of TNF-? Production," Bioorg Med Chem Lett. 1999;9(11):1625-30.

Muller et al., "Bromodomains as therapeutics target," Expert Rev Mol Med. 2011;13:e29.

Ohoka et al., "In Vivo Knockdown of Pathogenic Proteins via Specific and Nongenetic Inhibitor of Apoptosis Protein (IAP)-dependent Protein Erasers (SNIPERs)," J Bio Chem. 2017;292(11):4556-4570.

Oike et al., "A synthetic lethality-based strategy to treat cancers harboring a genetic deficiency in the chromatin remodeling factor BRG1," Cancer Res. 2013;73(17):5508-18.

Okazaki et al., "A rheostat for immune responses: the unique properties of PD-1 and their advantages for clinical application," Nat. Immunol. 2013; 14(12): 1212-1218.

Pandey et al., "SMARCA2 and THAP11: potential candidates for polyglutamine disorders as evidenced from polymorphism and protein-folding simulation studies," J. Hum. Genet. 2004;49:596-602.

PCT International Search Report and Written Opinion from PCT/US2018/052181, dated Feb. 26, 2019.
PCT International Search Report and Written Opinion from PCT/US2018/052242, dated Jan. 30, 2019.
PCT International Search Report and Written Opinion from PCT/US2018/067304, dated Apr. 30, 2019.
PCT International Search Report and Written Opinion from PCT/US2019/013481, dated Mar. 15, 2019.
PCT International Search Report and Written Opinion from PCT/US2019/013491, dated Mar. 18, 2019.
PCT International Search Report and Written Opinion from PCT/US2019/040462, dated Sep. 20, 2019.
PCT International Search Report and Written Opinion from PCT/US2019/040520, dated Nov. 13, 2019.
PCT International Search Report and Written Opinion from PCT/US2019/040545, dated Oct. 21, 2019.
PCT International Search Report and Written Opinion from PCT/US2019/064070, dated Apr. 6, 2020.
PCT International Search Report and Written Opinion from PCT/US2020/036913, dated Oct. 5, 2020.
PCT International Search Report and Written Opinion from PCT/US2020/036916, dated Oct. 6, 2020.
PCT International Search Report and Written Opinion from PCT/US2020/036918, dated Oct. 6, 2020.
PCT International Search Report and Written Opinion from PCT/US2020/036921, dated Oct. 6, 2020.
PCT International Search Report and Written Opinion from PCT/US2020/042105, dated Nov. 20, 2020.
PCT International Search Report and Written Opinion from PCT/US2020/066859, dated Apr. 12, 2021.
PCT International Search Report and Written Opinion from PCT/US2020/066864 dated Apr. 12, 2021.
PCT International Search Report and Written Opinion from PCT/US2021/062656 dated Mar. 22, 2022.
PCT International Search Report and Written Opinion from PCT/US2021/062662 dated Jan. 27, 2022.

Piya et al., "BRD4 Proteolysis Targeting Chimera (PROTAC) Leads to Sustained Degradation of BRD4 with Broad Activity Against Acute Leukemias and Overcomes Stroma Mediated Resistance By Modulating Surface Expression of CXCR4," Blood. 2016;126(23): 675-676.

Priyadarshini et al., "Copper catalyzed oxidative cross-coupling of aromatic amines with 2-pyrrolidinone: a facile synthesis of N-aryl-r-amino-r-lactams," Tetrahedron. 2014;70(36):6068-6074.

Pubmed Compound Summary for CID 101524675, "(2R)-3-Fluoro-2-(2-methylpropyl)-3-phenyl-1,3-azasilinan-6-one," *U.S. National Library of Medicine*, created Dec. 18, 2015, https://pubchem.ncbi.nlm.nih.gov/compound/101524675. Date Accessed: Sep. 5, 2019 (5 pages).

Pubmed Compound Summary for CID 102164987, "3-[(4S)-2,5-Dioxo-4-phenylimidazolidine-1-yl]-2,6-piperidinedione," U.S. National Library of Medicine, created Dec. 24, 2015, https://pubchem.ncbi.nlm.nih.gov/compound/102164987. Date Accessed: Feb. 25, 2020 (7 pages).

Pubmed Compound Summary for CID 110491408, '3-(5-Amino-2-oxo-3H-benzimidazol-1-yl)piperidine-2,6-dione, *U.S. Library of Medicine*, created Jan. 18, 2016, https://pubchem.ncbi.nlm.nih.gov/compound/110491408. Date Accessed: Feb. 25, 2020 (7 pages).

Pubmed Compound Summary for CID 110491555, '3-(6-Amino-2-oxo-3H-benzimidazol-1-yl)piperidine-2,6-dione U.S. Library of Medicine, created Jan. 18, 2016, https://pubchem.ncbi.nlm.nih.gov/compound/110491555. Date Accessed: Feb. 25, 2020 (7 pages).

Pubmed Compound Summary for CID 115370667, "5-(2-Oxoimidazolidin-1-yl)piperidin-2-one." U.S. National Library of Medicine, created Oct. 22, 2012, https://pubchem.ncbi.nlm.nih.gov/compound/115370667. Date Accessed: Feb. 25, 2020 (10 pages).

Pubmed Compound Summary for CID 138728787, "3-(6-Ethylpyrido[2,3-b]indol-9-yl)piperidine-2,6-dione," U.S. National Library of Medicine, created Jul. 20, 2019, https://pubchem.ncbi.nlm.nih.gov/compound/138728787. Date Accessed: Sep. 5, 2019 (6 pages).

Pubmed Compound Summary for CID 17607528, "4-(Carbazol-9-ylmethyl)-1,3-oxazolidin-2-one," U.S. National Library of Medicine, Nov. 13, 2007, https://pubchem.ncbi.nlm.nih.gov/compound/17607528. Date Accessed: Feb. 25, 2020 (6 pages).

Pubmed Compound Summary for CID 63661260,"5-[2-(1-Chloroethyl)benzimidazol-1-yl]piperidin-2-one," U.S. National Library of Medicine, created Oct. 22, 2012, https://pubchem.ncbi.nlm.nih.gov/compound/63661260. Date Accessed: Sep. 4, 2019 (6 pages).

Pubmed Compound Summary for CID 63661460, "6-Oxo-1-(6-oxopiperidin-3-yl)piperidine-3-carboxylic acid," U.S. National Library of Medicine, created Oct. 22, 2012, https://pubchem.ncbi.nlm.nih.gov/compound/63661460. Date Accessed: Feb. 25, 2020 (7 pages).

Pubmed Compound Summary for CID 65967733, "3-(2,5-Dioxo-3-phenylpyrrolidin-1-yl)piperidine-2,6-dione," *U.S. National Library of Medicine*, created Dec. 24, 2015, https://pubchem.ncbi.nlm.nih.gov/compound/65967733. Date Accessed: Feb. 25, 2020 (7 pages).

Pubmed Compound Summary for CID 65968760, "1-(2,6-Dioxopiperidin-3-yl)benzimidazole-5-carboxylic acid," U.S. National Library of Medicine, created Oct. 24, 2012, https://pubchem.ncbi.nlm.nih.gov/compound/65968760. Date Accessed: Sep. 4, 2019 (6 pages).

Pubmed Compound Summary for CID 67258040, "[1-(9H-Fluoren-9-yl)-1-(6-oxopiperidin-3-yl)ethyl] hydrogen carbonate," *U.S. National Library of Medicine*, Nov. 30, 2012, https://pubchem.ncbi.nlm.nih.gov/compound/67258040. Date Accessed: Feb. 25, 2020 (9 pages).

Pubmed Compound Summary for CID 83543479, "5(Aminomethyl)-5-(1H-indol-3-yl)piperidin-2-one," *U.S. National Library of Medicine*, created Oct. 20, 2014, https://pubchem.ncbi.nlm.nih.gov/compound/83543479. Date Accessed: Feb. 25, 2020 (6 pages).

(56) References Cited

OTHER PUBLICATIONS

Pubmed Compound Summary for CID 84036945, '1-Piperidin-3-yl-3H-indol-2-one, *U.S. Library of Medicine*, created Oct. 20, 2014, https://pubchem.ncbi.nlm.nih.gov/compound/84036945. Date Accessed: Feb. 25, 2020 (7 pages).
Pubmed Compound Summary for CID 86793742, '3-[(6-chloro-1H-1,3-benzodiazol-2-yl)sulfanyl]piperidine-2,6-dione, created Feb. 7, 2015, https://pubchem.ncbi.nlm.nih.gov/compound/86793742. Date Accessed: Jan. 10, 2022.
Pubmed Compound Summary for CID 91648396, '3-[(4-Fluorophenyl)sulfanyl]piperidine-2,6-dione, created Mar. 20, 2015, https://pubchem.ncbi.nlm.nih.gov/compound/91648396#section=Structures. Date Accessed: Jan. 10, 2022.
Pubmed Compound Summary for CID 99784232, '(3S)-3-(4-fluorophenyl)sulfanylpiperidine-2,6-dione, created Dec. 11, 2015, https://pubchem.ncbi.nlm.nih.gov/compound/99784232. Date Accessed: Jan. 10, 2022.
Raina et al., "Chemical Inducers of Targeted Protein Degradation," J Biol Chem. 2010;285(15):11057-60.
Ramirez et al., "Defining causative factors contributing in the activation of hedgehog signaling in diffuse large B-cell lymphoma," Leuk. Res. 2012;36(10):1267-73.
Ronnebaum et al., "Synthesis of 1, 2, 3-triazole 'click' analogues of thalidomide," Tetrahedron. 2016;72(40): 6136-6141.
Ross et al., "Bispecific T cell engager (BITE®) antibody constructs can mediate bystander tumor cell killing," PLoS ONE. 2017; 12(8): eQ183390.
Rostovtsev et al., "A Stepwise Huisgen Cycloaddition Process: Copper(I)-Catalyzed Regioselective "Ligation" of Azides and Terminal Alkynes," Angew Chem Int Ed Engl. 2002;41(14):2596-9.
Schiaffino-Ortega et al. "SWI/SNF as targets in cancer therapy," J. Hematol. Oncol. 2014;7:81.
Schnnekloth et al., "Chemical approaches to controlling intracellular protein degradation," Chembiochem. 2005;6(1):40-46.
Seela et al., "Pyrazolo[3,4-d][1,2,3]triazine DNA: Synthesis and Base Pairing of 7-Deaza-2,8-diaza-2'-deoxyadenosine," J. Org. Chem. 2004;69(14) 4695-4700.
Seitz et al., "Sulfenylation and Halogenation of Di-and Trianions Derived from Substituted Glutarimides," Synthetic Communications. 1977;7(6):367-374.
Sen et al., "Transcriptional signaling by double-stranded RNA: role of TLR3," Cytokine Growth Factor Rev. 2005;16(1):1-14.
Shain and Pollack "The Spectrum of SWI/SNF Mutations, Ubiquitous in Human Cancers," PLoS One 2013;8:e55119.
Shanmugasundaram et al., "A modular PROTAC design for target destruction using a degradation signal based on a single amino acid," J Biol Chem. 2019;294(41):15172-15175.
Son and Crabtree "The Role of BAF (mSWI/SNF) Complexes in Mammalian Neural Development," Am. J. Med. Genet., Part C. 2014; 166C(3):333-39.
Spradin et al., "Harnessing the Anti-Cancer Natural Product Nimbolide for Targeted Protein Degradation," bioRxiv.org, https://www.biorxiv.org/content/biorxiv/early/2019/04/09/436998.full.pdf. Date Accessed, Oct. 3, 2019.
Spratt et al., "RBR E3 ubiquitin ligases: new structures, new insights, new question," Biochem J. 2014;458(3);421-37.
Stewart et al., "Efforts toward elucidating Thalidomide's molecular target: an expedient synthesis of the first Thalidomide biotin analogue," Organic & Biomolecular Chemistry. 2010;8(18): 4059-4062.
Struhl, "Histone acetylation and transcriptional regulatory mechanisms," Genes Dev. 1998;12(5):599-606.
Sun et al., "Carbohydrate and protein immobilization onto solid surfaces by sequential Diels-Alder and azide-alkyne cycloadditions," Bioconjug Chem. 2006;17(1):52-7.

Sutherell et al. "Identification and Development of 2,3-Dihydropyrrolo[1,2-a]quinazolin-5(1H)-one Inhibitors Targeting Bromodomains within the Switch/Sucrose Nonfermenting Complex," J. Med. Chem. 2016;59:5095-5101.
Tamkun et al., "brahma: a regulator of *Drosophila* homeotic genes structurally related to the yeast transcriptional activator SNF2/SWI2," Cell. 1992;68(3):561-72.
Tanaka et al. "Design and Characterization of Bivalent BET Inhibitors," Nat. Chem. Biol. 2016;12(12):1089-1096.
Tang et al., "New SMARCA2 mutation in a patient with Nicolaides-Baraitser syndrome and myoclonic astatic epilepsy," Am. J. Med. Genet. 2015;173(1):195-199.
Theodoulou et al. "Clinical progress and pharmacology of small molecule bromodomain inhibitors," Curr. Opin. Chem. Bio. 2016;33:58-66.
Tian, "Detection of differentially expressed genes involved in osteoarthritis pathology," J. Orthop. Surg. Res. 2018;13:49.
Toogood, "Small molecule immuno-oncology therapeutic agents," Bioorg. Med. Chem. Lett. 2018;28(3):319-329.
Toure and Crews, "Small-Molecule PROTACS: New Approaches to Protein Degradation," Angew Chem Int Ed Engl. 2016;55(6):1966-73.
Uehara et al., "Selective degradation of splicing factor CAPERα by anticancer sulfonamides," Nat Chem Biol. 2017;13(6):675-680.
Vangamudi et al., "The SMARCA2/4 ATPase domain surpasses the bromodomain as a drug target in SWI/SNF mutant cancers: Insights from cDNA rescue and PFI-3 inhibitor studies," Cancer Res. 2015;75(18):3865-3878.
Varfolomeev et al., "IAP antagonists induce autoubiquitination of c-IAPs, NF-kappaB activation, and TNFalpha-dependent apoptosis," Cell. 2007;131(4):669-81.
Wang et al., "Palladium-Catalyzed Allenylation/Intramolecular Diels-Alder Reaction of Furans with Propargyl Carboxylates for the Synthesis of Polycyclic Compounds," European Journal of Organic Chemistry. 2014;2014(17):3556-3560.
Wang et al., "Roles of F-box proteins in cancer," Nat Rev Cancer. 2014;14(4):233-47.
Wanior et al., "Pan-SMARCA/PB1 Bromodomain Inhibitors and Their Role in Regulating Adipogenesis," J Med Chem. 2020;63(23):14680-14699.
Ward et al., "Covalent Ligand Screening Uncovers a RNF4 E3 Ligase Recruiter for Targeted Protein Degradation Applications," bioRxiv.org, https://www.biorxiv.org/content/biorxiv/early/2018/11/16/439125.full.pdf. Date Accessed, Oct. 3, 2019 (24 pages).
Weaver, "Epidemiology of gout," Cleve Clin J Med. 2008;75 Suppl 5:S9-12.
Wilson and Roberts, "SWI/SNF Nucleosome Remodellers and Cancer," Nat. Rev. Cancer. 2011;11(7):481-92.
Winter et al., "Selective Target Protein Degradation via Phthalimide Conjugation," Science. 2015;348(6241):1376-1381.
Xia and Chen, "Iron-catalyzed N-alkylation of azoles via cleavage of an sp3 C-H bond adjacent to a nitrogen atom," J Org Chem. 2012;77(20):9366-73.
Yang et al., "Exploiting synthetic lethality for the therapy of ABC diffuse large B cell lymphoma," Cancer Cell. 2012;21(6):723-37.
Zhang et al., "Electrophilic PROTACs that degrade nuclear proteins by engaging DCAF16," bioRxiv.org, https://www.biorxiv.org/content/biorxiv/early/2018/10/15/443804.full.pdf. Date Accessed, Oct. 3, 2019.
Zhou et al., "Targets of curcumin," Curr Drug Targets. 2011;12(3):332-347.
Zinc 170596280, Date Added Aug. 8, 2015, https://zinc.docking.org/substances/ZINC000170596280/. Date Accessed: Jan. 10, 2022.
Zou et al., "PD-L1 (B7-H1) and PD-1 pathway blockade for cancer therapy: Mechanisms, response biomarkers, and combinations," Sci. Transl. Med. 2016;8(328):328rv4.
Papillon et al., "Discovery of Orally Active Inhibitors of Brahma Homolog (BRM/SMARCA2 ATPase Activity for the Treatment of Brahman Related Gene 1 (BRG1/SMARCA4-Mutant Cancers," J. Med. Chem. 2018,61:10155-10172.

SMARCA DEGRADERS AND USES THEREOF

REFERENCE TO RELATED APPLICATIONS

This application claims the benefit of U.S. Provisional Appl. No. 62/952,578, filed Dec. 23, 2019 and U.S. Provisional Appl. No. 63/123,176, filed Dec. 9, 2020, the contents of each of which are herein incorporated by reference.

TECHNICAL FIELD OF THE INVENTION

The present invention relates to compounds and methods useful for the modulation of one or more SWI/SNF-related matrix-associated actin-dependent regulator of chromatin subfamily A ("SMARCA") and/or polybromo-1 ("PB1") protein via ubiquitination and/or degradation by compounds according to the description provided herein. The disclosure also provides pharmaceutically acceptable compositions comprising compounds of the present description and methods of using said compositions in the treatment of various disorders.

BACKGROUND OF THE INVENTION

Ubiquitin-Proteasome Pathway (UPP) is a critical pathway that regulates key regulator proteins and degrades misfolded or abnormal proteins. UPP is central to multiple cellular processes, and if defective or imbalanced, it leads to pathogenesis of a variety of diseases. The covalent attachment of ubiquitin to specific protein substrates is achieved through the action of E3 ubiquitin ligases.

There are over 600 E3 ubiquitin ligases which facilitate the ubiquitination of different proteins in vivo, which can be divided into four families: HECT-domain E3s, U-box E3s, monomeric RING E3s and multi-subunit E3s. See e.g., Li et al. "Genome-wide and functional annotation of human E3 ubiquitin ligases identifies MULAN, a mitochondrial E3 that regulates the organelle's dynamics and signaling." *PLOS One* 2008, (3)1487; Berndsen et al. "New insights into ubiquitin E3 ligase mechanism" *Nat. Struct. Mol. Biol.* 2014, 21:301; Deshaies et al. "RING domain E3 ubiquitin ligases" *Ann. Rev. Biochem.* 2009, 78:399; Spratt et al. "RBR E3 ubiquitin ligases: new structures, new insights, new questions" *Biochem.* 2014, 458:421; and Wang et al. "Roles of F-box proteins in cancer" *Nat. Rev. Cancer.* 2014, 14:233.

UPP plays a key role in the degradation of short-lived and regulatory proteins important in a variety of basic cellular processes, including regulation of the cell cycle, modulation of cell surface receptors and ion channels, and antigen presentation. The pathway has been implicated in several forms of malignancy, in the pathogenesis of several genetic diseases (including cystic fibrosis, Angelman's syndrome, and Liddle syndrome), in immune surveillance/viral pathogenesis, and in the pathology of muscle wasting. Many diseases are associated with an abnormal UPP and negatively affect cell cycle and division, the cellular response to stress and to extracellular modulators, morphogenesis of neuronal networks, modulation of cell surface receptors, ion channels, the secretory pathway, DNA repair and biogenesis of organelles.

Aberrations in the process have recently been implicated in the pathogenesis of several diseases, both inherited and acquired. These diseases fall into two major groups: (a) those that result from loss of function with the resultant stabilization of certain proteins, and (b) those that result from gain of function, i.e. abnormal or accelerated degradation of the protein target.

The UPP is used to induce selective protein degradation, including use of fusion proteins to artificially ubiquitinate target proteins and synthetic small-molecule probes to induce proteasome-dependent degradation. Bifunctional compounds composed of a target protein-binding ligand and an E3 ubiquitin ligase ligand, induced proteasome-mediated degradation of selected proteins via their recruitment to E3 ubiquitin ligase and subsequent ubiquitination. These drug-like molecules offer the possibility of temporal control over protein expression. Such compounds are capable of inducing the inactivation of a protein of interest upon addition to cells or administration to an animal or human, and could be useful as biochemical reagents and lead to a new paradigm for the treatment of diseases by removing pathogenic or oncogenic proteins. See e.g., Crews, *Chem & Biol.* 2010, 17(6):551; Schneekloth and Crews, *ChemBioChem* 2005, 6(1): 40.

An ongoing need exists in the art for effective treatments for disease, especially hyperplasia and cancers. However, non-specific effects, and the inability to target and modulate certain classes of proteins altogether, such as transcription factors, remain as obstacles to the development of effective anti-cancer agents. As such, small molecule therapeutic agents that leverage UPP mediated protein degradation to target cancer-associated proteins such as one or more SWI/SNF-related matrix-associated actin-dependent regulator of chromatin subfamily A ("SMARCA") and/or polybromo-1 ("PB1") protein hold promise as therapeutic agents. Accordingly, there remains a need to find compounds that are SMARCA degraders useful as therapeutic agents.

SUMMARY OF THE INVENTION

The present disclosure relates to novel compounds, which function to recruit one or more SMARCA2, SMARCA4, or PB1 protein to E3 ubiquitin ligases for degradation or directly facilitate ubiquitination for degradation, and methods of preparation and uses thereof. In particular, the present disclosure provides bifunctional compounds, which find utility as modulators of targeted ubiquitination of SMARCA and/or PB1 proteins, which are then degraded and/or otherwise inhibited by the bifunctional compounds as described herein. Also provided are monovalent compounds, which find utility as inducers of targeted ubiquitination of SMARCA and/or PB1 proteins, which are then degraded and/or otherwise inhibited by the monovalent compounds as described herein. An advantage of the compounds provided herein is that a broad range of pharmacological activities is possible, consistent with the degradation/inhibition of SMARCA and/or PB1 proteins. In addition, the description provides methods of using an amount of the compounds as described herein for the treatment or amelioration of a disease condition, such as cancer, e.g., lung cancer.

The present application further relates to targeted degradation of SMARCA and/or PB1 proteins through the use of bifunctional molecules, including bifunctional molecules that link a cereblon-binding moiety to a ligand that binds SMARCA and/or PB1 proteins.

It has now been found that compounds of this disclosure, and pharmaceutically acceptable compositions thereof, are effective as degraders of SMARCA and/or PB1 proteins. Such compounds have the general formula I:

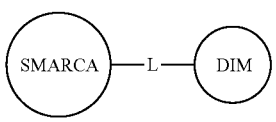

or a pharmaceutically acceptable salt thereof, wherein each variable is as defined and described herein.

Compounds of the present disclosure, and pharmaceutically acceptable compositions thereof, are useful for treating a variety of diseases, disorders or conditions, associated with regulation of signaling pathways implicating SMARCA and/or PB1 proteins. Such diseases, disorders, or conditions include those described herein.

Compounds provided by this disclosure are also useful for the study of SMARCA and/or PB1 proteins in biological and pathological phenomena; the study of intracellular signal transduction pathways occurring in bodily tissues; and the comparative evaluation of new SMARCA and/or PB1 inhibitors or SMARCA and/or PB1 degraders or other regulators of cell cycling, metastasis, angiogenesis, and immune cell evasion, in vitro or in vivo.

DETAILED DESCRIPTION OF CERTAIN EMBODIMENTS

1. General Description of Certain Embodiments of the Invention

Compounds of the present disclosure, and compositions thereof, are useful as degraders and/or inhibitors of SMARCA and/or PB1 proteins. In some embodiments, a provided compound degrades and/or inhibits one or more of SMARCA2, SMARCA4, and PB1 protein.

In certain embodiments, the present invention provides a compound of formula I:

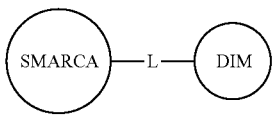

or a pharmaceutically acceptable salt thereof, wherein:
SMARCA is a protein binding moiety capable of binding to one or more of SMARCA2, SMARCA4, and PB1;
L is a bivalent moiety that connects SMARCA to DIM; and
DIM is a degradation inducing moiety selected from an E3 ubiquitin ligase binding moiety (LBM), lysine mimetic, or hydrogen atom.

2. Compounds and Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bridged bicyclics include:

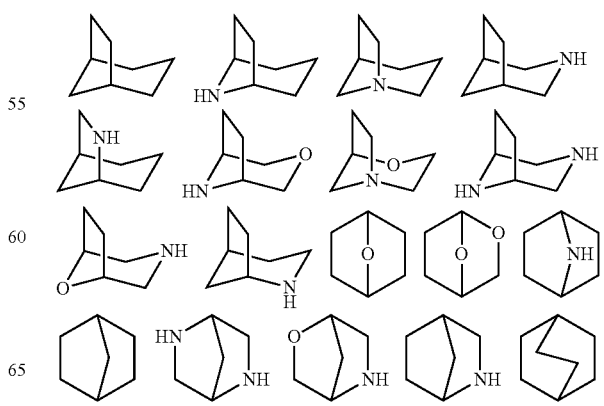

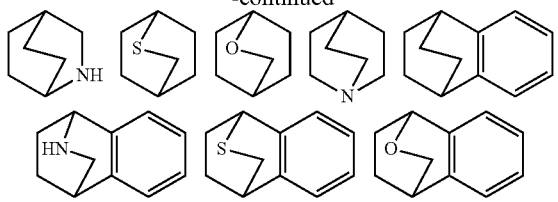

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl). NH (as in pyrrolidinyl) or $NR^+$ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

As used herein, the term "cyclopropylenyl" refers to a bivalent cyclopropyl group of the following structure:

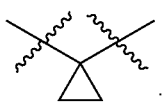 [SMILES: *C1(*)CC1]

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or $14\pi$ electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+NR$ (as in N substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted" means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched alkylene)O—N(R°)$_2$; or —(C$_{1-4}$ straight or branched alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger$$_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger$$_2$, —C(S)NR$^\dagger$$_2$, —C(NH)NR$^\dagger$$_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^{1'}$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S.

M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzene sulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methane sulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention As used herein, the term "provided compound" refers to any genus, subgenus, and/or species set forth herein.

As used herein, the term "and/or" is used in this disclosure to mean either "and" or "or" unless indicated otherwise.

As used herein, the term "inhibitor" is defined as a compound that binds to and/or inhibits a SMARCA and/or PB1 protein with measurable affinity. In certain embodiments, an inhibitor has an $IC_{50}$ and/or binding constant of less than about 50 µM, less than about 1 µM, less than about 500 nM, less than about 100 nM, less than about 10 nM, or less than about 1 nM.

As used herein, the term "degrader" is defined as a monovalent or bifunctional compound that binds to and/or inhibits a SMARCA and/or PB1 protein and optionally an E3 ligase with measurable affinity resulting in the ubiqitination and subsequent degradation of the SMARCA and/or PB1 protein. In certain embodiments, a degrader has an $DC_{50}$ of less than about 50 µM, less than about 1 µM, less than about 500 nM, less than about 100 nM, less than about 10 nM, or less than about 1 nM. As used herein, the term "monovalent" refers to a compound without an appended E3 ligase.

A compound of the present invention may be tethered to a detectable moiety. It will be appreciated that such compounds are useful as imaging agents. One of ordinary skill in the art will recognize that a detectable moiety may be attached to a provided compound via a suitable substituent. As used herein, the term "suitable substituent" refers to a moiety that is capable of covalent attachment to a detectable moiety. Such moieties are well known to one of ordinary skill in the art and include groups containing, e.g., a carboxylate moiety, an amino moiety, a thiol moiety, or a hydroxyl moiety, to name but a few. It will be appreciated that such moieties may be directly attached to a provided compound or via a tethering group, such as a bivalent saturated or unsaturated hydrocarbon chain. In some embodiments, such moieties may be attached via click chemistry. In some embodiments, such moieties may be attached via a 1,3-cycloaddition of an azide with an alkyne, optionally in the presence of a copper catalyst. Methods of using click chemistry are known in the art and include those described by Rostovtsev et al., Angew. Chem. Int. Ed. 2002, 4d, 2596-99 and Sun et al., Bioconjugate Chem., 2006, E7, 52-57.

As used herein, the term "detectable moiety" is used interchangeably with the term "label" and relates to any moiety capable of being detected, e.g., primary labels and secondary labels. Primary labels, such as radioisotopes (e.g., tritium, $^{32}P$, $^{33}P$, $^{35}S$, or $^{14}C$), mass-tags, and fluorescent labels are signal generating reporter groups which can be detected without further modifications. Detectable moieties also include luminescent and phosphorescent groups.

The term "secondary label" as used herein refers to moieties such as biotin and various protein antigens that require the presence of a second intermediate for production of a detectable signal. For biotin, the secondary intermediate may include streptavidin-enzyme conjugates. For antigen labels, secondary intermediates may include antibody-enzyme conjugates. Some fluorescent groups act as secondary labels because they transfer energy to another group in the process of nonradiative fluorescent resonance energy transfer (FRET), and the second group produces the detected signal.

The terms "fluorescent label", "fluorescent dye", and "fluorophore" as used herein refer to moieties that absorb light energy at a defined excitation wavelength and emit light energy at a different wavelength. Examples of fluorescent labels include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethyl-rhodamine (TAMRA), Texas Red, Texas Red-X.

The term "mass-tag" as used herein refers to any moiety that is capable of being uniquely detected by virtue of its mass using mass spectrometry (MS) detection techniques. Examples of mass-tags include electrophore release tags such as N-[3-[4'-[(p-Methoxytetrafluorobenzyl)oxy]phenyl]-3-methylglyceronyl]isonipecotic Acid, 4'-[2,3,5,6-Tetrafluoro-4-(pentafluorophenoxyl)]methyl acetophenone, and their derivatives. The synthesis and utility of these mass-tags is described in U.S. Pat. Nos. 4,650,750, 4,709,016, 5,360, 8191, 5,516,931, 5,602,273, 5,604,104, 5,610,020, and 5,650,270. Other examples of mass-tags include, but are not limited to, nucleotides, dideoxynucleotides, oligonucleotides of varying length and base composition, oligopeptides, oligosaccharides, and other synthetic polymers of varying length and monomer composition. A large variety of organic molecules, both neutral and charged (biomolecules or synthetic compounds) of an appropriate mass range (100-2000 Daltons) may also be used as mass-tags.

The terms "measurable affinity" and "measurably inhibit," as used herein, means a measurable change in a SMARCA and/or PB1 protein activity between a sample comprising a compound of the present invention, or composition thereof, and a SMARCA and/or PB1 protein, and an equivalent sample comprising a SMARCA and/or PB1 protein, in the absence of said compound, or composition thereof.

3. Description of Exemplary Embodiments

As described above, in certain embodiments, the present disclosure provides a compound of formula I:

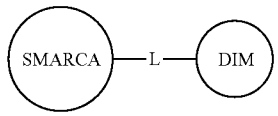

I or a pharmaceutically acceptable salt thereof, wherein:
SMARCA is a protein binding moiety capable of binding to one or more of SMARCA2, SMARCA4, and PB1;
L is a bivalent moiety that connects SMARCA to DIM; and
DIM is a degradation inducing moiety selected from an E3 ubiquitin ligase binding moiety (LBM), lysine mimetic, or hydrogen atom.

SMARCA Binding Moiety (SMARCA)

As defined above and described herein, SMARCA is a SMARCA binding moiety capable of binding to one or more of SMARCA2, SMARCA4, and PB1. In some embodiments, SMARCA is a SMARCA binding moiety capable of degrading one or more of SMARCA2, SMARCA4, and PB1.

In some embodiments SMARCA is a binding moiety capable of selectively binding and degrading SMARCA2 over SMARCA4 and/or PB1. In some embodiments, SMARCA is a binding moiety capable of selectively binding and degrading SMARCA4 over SMARCA2 and/or PB1. In some embodiments, SMARCA is a binding moiety capable of selectively binding and degrading PB1 over SMARCA2 and/or SMARCA4. In some embodiments, SMARCA is a binding moiety capable of selectively binding and degrading SMARCA2 and SMARCA4 over PB1. In some embodiments, SMARCA is a binding moiety capable of selectively binding and degrading SMARCA2 and PB1 over SMARCA4. In some embodiments, SMARCA is a binding moiety capable of selectively binding and degrading SMARCA4 and PB1 over SMARCA2. In some embodiments, SMARCA is a binding moiety capable of binding and degrading SMARCA2, SMARCA4, and PB1.

In certain embodiments, the present invention provides a compound of formula I-a:

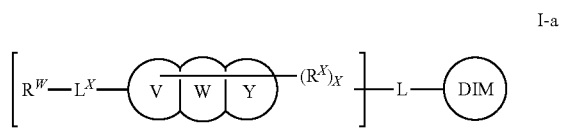

I-a or a pharmaceutically acceptable salt thereof, wherein L and DIM are as defined above and described herein, and wherein:
each of Ring V, Ring W, and Ring Y is independently a fused, spiro-fused, or both fused and spiro-fused ring selected from 6-membered aryl, 5 to 6-membered heteroaryl containing 1-4 heteroatoms independently selected from nitrogen, oxygen, and sulfur, and a 4 to 9-membered saturated or partially unsaturated monocyclic, bicyclic, or bridged bicyclic carbocyclyl or heterocyclyl with 1-4 heteroatoms independently selected from boron, nitrogen, oxygen, silicon, and sulfur, wherein each of Ring V, Ring W, and Ring Y is independently and optionally further substituted with 1-2 oxo groups;
$R^w$ is selected from

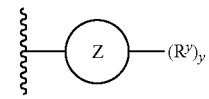

or hydrogen;
Ring Z is phenyl, a 5-7 membered saturated or partially unsaturated carbocyclic or heterocyclic ring having 1-3 heteroatoms independently selected from nitrogen, oxygen, and sulfur, or a 5-6 membered heteroaryl ring having 1-4 heteroatoms independently selected from nitrogen, oxygen, and sulfur, wherein Ring Z is further optionally substituted with 1-2 oxo groups;
each of $R^x$ and $R^y$ is independently hydrogen, deuterium, $R^z$, halogen, —CN, —NO$_2$, —OR, —SR, —NR$_2$, —SiR$_3$, —S(O)$_2$R, —S(O)$_2$NR$_2$, —S(O)R, —CFR$_2$, —CF$_2$R, —CF$_3$, —C(O)R, —C(O)OR, —C(O)NR$_2$, —C(O)N(R) OR, —C(R)$_2$N(R)C(O)R, —C(R)$_2$N(R)C(O)N(R)$_2$, —OC(O)R, —OC(O)N(R)$_2$, —OP(O)R$_2$, —OP(O) (OR)$_2$, —OP(O)(OR)NR$_2$, —OP(O)(NR$_2$)$_2$—, N(R)C(O) OR, —N(R)C(O)R, —N(R)C(O)NR$_2$, —N(R)S(O)$_2$R, —NP(O)R$_2$, —N(R)P(O)(OR)$_2$, —N(R)P(O)(OR)NR$_2$, —N(R)P(O)(NR$_2$)$_2$, or —N(R)S(O)$_2$R; or
two $R^x$ groups or two $R^y$ groups are optionally taken together to form an optionally substituted 5-7 membered partially unsaturated or aryl fused ring having 0-2 heteroatoms independently selected from nitrogen, oxygen, or sulfur;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same atom are taken together with their intervening atoms to form a 4-7 membered saturated, partially unsaturated, or heteroaryl ring having 0-3 heteroatoms, in addition to the atom to which they are attached, independently selected from nitrogen, oxygen, and sulfur;

each $R^z$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

$L^x$ is a covalent bond or a $C_{1-3}$ bivalent straight or branched saturated or unsaturated hydrocarbon chain wherein 1-2 methylene units of the chain are independently and optionally replaced with —O—, —C(O)—, —C(S)—, —C(R)$_2$—, —CF(R)—, —C(F)$_2$—, —N(R)—, —S—, —S(O)$_2$— or —CR=CR—; and x is 0, 1, 2, 3, 4, 5, 6, 7, 8, 9, 10, 11, 12, 13, 14, 15, or 16; and y is 0, 1, 2, 4, or 5.

In certain embodiments, the present invention provides a compound of formula I-b:

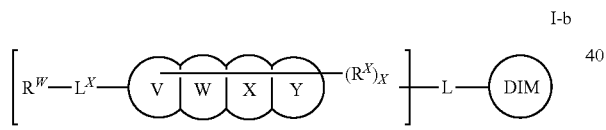

I-b or a pharmaceutically acceptable salt thereof, wherein L and DIM are as defined above and described herein, and wherein:

each of Ring V, Ring W, Ring X, and Ring Y is independently a fused, spiro-fused, or both fused and spiro-fused ring selected from 6-membered aryl, 5 to 6-membered heteroaryl containing 1-4 heteroatoms independently selected from nitrogen, oxygen, and sulfur, and a 4 to 9-membered saturated or partially unsaturated monocyclic, bicyclic, or bridged bicyclic carbocyclyl or heterocyclyl with 1-4 heteroatoms independently selected from boron, nitrogen, oxygen, silicon, and sulfur, wherein each of Ring V, Ring W, Ring X, and Ring Y is independently and optionally further substituted with 1-2 oxo groups;

$R^w$ is selected from

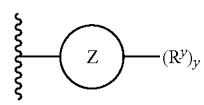

or hydrogen;

Ring Z is phenyl, a 5-7 membered saturated or partially unsaturated carbocyclic or heterocyclic ring having 1-3 heteroatoms independently selected from nitrogen, oxygen, and sulfur, or a 5-6 membered heteroaryl ring having 1-4 heteroatoms independently selected from nitrogen, oxygen, and sulfur, wherein Ring Z is further optionally substituted with 1-2 oxo groups;

each of $R^x$ and $R^y$ is independently hydrogen, deuterium, $R^z$, halogen, —CN, —NO$_2$, —OR, —SR, —NR$_2$, —SiR$_3$, —S(O)$_2$R, —S(O)$_2$NR$_2$, —S(O)R, —CFR$_2$, —CF$_2$R, —CF$_3$, —C(O)R, —C(O)OR, —C(O)NR$_2$, —C(O)N(R)OR, —C(R)$_2$N(R)C(O)R, —C(R)$_2$N(R)C(O)N(R)$_2$, —OC(O)R, —OC(O)N(R)$_2$, —OP(O)R$_2$, —OP(O)(OR)$_2$, —OP(O)(OR)NR$_2$, —OP(O)(NR$_2$)$_2$—, N(R)C(O)OR, —N(R)C(O)R, —N(R)C(O)NR$_2$, —N(R)S(O)$_2$R, —NP(O)R$_2$, —N(R)P(O)(OR)$_2$, —N(R)P(O)(OR)NR$_2$, —N(R)P(O)(NR$_2$)$_2$, or —N(R)S(O)$_2$R; or two $R^x$ groups or two $R^y$ groups are optionally taken together to form an optionally substituted 5-7 membered partially unsaturated or aryl fused ring having 0-2 heteroatoms independently selected from nitrogen, oxygen, or sulfur;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same atom are taken together with their intervening atoms to form a 4-7 membered saturated, partially unsaturated, or heteroaryl ring having 0-3 heteroatoms, in addition to the atom to which they are attached, independently selected from nitrogen, oxygen, and sulfur;

each $R^z$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

$L^x$ is a covalent bond or a $C_{1-3}$ bivalent straight or branched saturated or unsaturated hydrocarbon chain wherein 1-2 methylene units of the chain are independently and optionally replaced with —O—, —C(O)—, —C(S)—, —C(R)$_2$—, —CF(R)—, —C(F)$_2$—, —N(R)—, —S—, —S(O)$_2$— or —CR=CR—; and x is 0, 1, 2, 3, 4, 5, 6, 7, 8, 9, 10, 11, 12, 13, 14, 15, or 16; and y is 0, 1, 2, 4, or 5.

In certain embodiments, the present invention provides a compound of formula I-c or I-d:

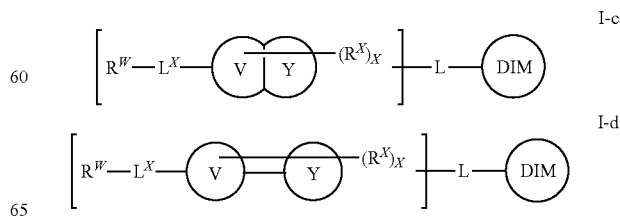

or a pharmaceutically acceptable salt thereof, wherein:
each of Ring V and Ring Y is independently an optionally fused or spiro-fused ring selected from 6-membered aryl, 5 to 6-membered heteroaryl containing 1-4 heteroatoms independently selected from nitrogen, oxygen, and sulfur, and a 4 to 9-membered saturated or partially unsaturated monocyclic, bicyclic, or bridged bicyclic carbocyclyl or heterocyclyl with 1-4 heteroatoms independently selected from boron, nitrogen, oxygen, silicon, and sulfur, wherein each of Ring V and Ring Y is independently and optionally further substituted with 1-2 oxo groups;

$R^w$ is selected from

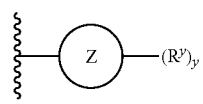

or hydrogen;

Ring Z is phenyl, a 5-7 membered saturated or partially unsaturated carbocyclic or heterocyclic ring having 1-3 heteroatoms independently selected from nitrogen, oxygen, and sulfur, or a 5-6 membered heteroaryl ring having 1-4 heteroatoms independently selected from nitrogen, oxygen, and sulfur, wherein Ring Z is further optionally substituted with 1-2 oxo groups;

each of $R^x$ and $R^y$ is independently hydrogen, deuterium, $R^z$, halogen, —CN, —NO$_2$, —OR, —SR, —NR$_2$, —SiR$_3$, —S(O)$_2$R, —S(O)$_2$NR$_2$, —S(O)R, —CFR$_2$, —CF$_2$R, —CF$_3$, —C(O)R, —C(O)OR, —C(O)NR$_2$, —C(O)N(R)OR, —C(R)$_2$N(R)C(O)R, —C(R)$_2$N(R)C(O)N(R)$_2$, —OC(O)R, —OC(O)N(R)$_2$, —OP(O)R$_2$, —OP(O)(OR)$_2$, —OP(O)(OR)NR$_2$, —OP(O)(NR$_2$)$_2$—, N(R)C(O)OR, —N(R)C(O)R, —N(R)C(O)NR$_2$, —N(R)S(O)$_2$R, —NP(O)R$_2$, —N(R)P(O)(OR)$_2$, —N(R)P(O)(OR)NR$_2$, —N(R)P(O)(NR$_2$)$_2$, or —N(R)S(O)$_2$R; or
two $R^x$ groups or two $R^y$ groups are optionally taken together to form an optionally substituted 5-7 membered partially unsaturated or aryl fused ring having 0-2 heteroatoms independently selected from nitrogen, oxygen, or sulfur;

each R is independently hydrogen, or an optionally substituted group selected from C$_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or: two R groups on the same atom are taken together with their intervening atoms to form a 4-7 membered saturated, partially unsaturated, or heteroaryl ring having 0-3 heteroatoms, in addition to the atom to which they are attached, independently selected from nitrogen, oxygen, and sulfur;

each $R^z$ is independently an optionally substituted group selected from C$_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

$L^x$ is a covalent bond or a C$_{1-3}$ bivalent straight or branched saturated or unsaturated hydrocarbon chain wherein 1-2 methylene units of the chain are independently and optionally replaced with —O—, —C(O)—, —C(S)—, —C(R)$_2$—, —CF(R)—, —C(F)$_2$—, —N(R)—, —S—, —S(O)$_2$— or —CR=CR—; and
n is 0, 1, 2, 3, 4, 5, 6, 7, 8, 9, 10, 11, 12, 13, 14, 15, or 16; and
m is 0, 1, 2, 4, or 5.

As described herein, a core structure depicted as

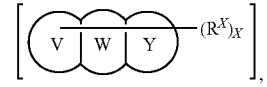

includes for example, structures

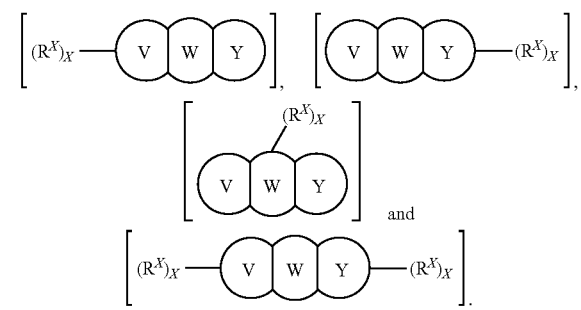

As defined herein and described above, wherein a formula is depicted using square brackets, e.g.,

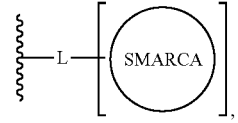

L is attached to a modifiable carbon, oxygen, or nitrogen atom within SMARCA including substitution or replacement of a defined group in SMARCA.

As defined above and described herein, in some embodiments, each of Ring V, Ring W, Ring X, and Ring Y is independently a fused, spiro-fused, or both fused and spiro-fused ring selected from 6-membered aryl, 5 to 6-membered heteroaryl containing 1-4 heteroatoms independently selected from nitrogen, oxygen, and sulfur, and a 4 to 9-membered saturated or partially unsaturated monocyclic, bicyclic, or bridged bicyclic carbocyclyl or heterocyclyl with 1-4 heteroatoms independently selected from boron, nitrogen, oxygen, silicon, and sulfur, wherein each of Ring V, Ring W, Ring X, and Ring Y is independently and optionally further substituted with 1-2 oxo groups.

In some embodiments, one or more of Ring V, Ring W, Ring X, and Ring Y is an optionally fused 6-membered aryl. In some embodiments, one or more of Ring V, Ring W, Ring X, and Ring Y is an optionally fused 6-membered heteroaryl containing 1-4 heteroatoms independently selected from nitrogen, oxygen, and sulfur. In some embodiments, one or more of Ring V, Ring W, Ring X, and Ring Y is an optionally fused and/or spiro-fused 4 to 9-membered saturated or partially unsaturated monocyclic, bicyclic, or bridged bicyclic carbocyclyl. In some embodiments, one or more of Ring V, Ring W, Ring X, and Ring Y is an optionally fused and/or spiro-fused 4 to 9-membered saturated or partially unsaturated monocyclic, bicyclic, or bridged bicyclic heterocyclyl with 1-3 heteroatoms independently selected from boron, nitrogen, oxygen, silicon, and sulfur. In some embodiments, one or more of Ring V, Ring W, Ring X, and Ring Y is an optionally fused 5-membered heteroaryl with 1-3 heteroatoms independently selected from nitrogen, oxygen and sulfur. In some embodiments, one or more of Ring V, Ring W, Ring X, and Ring Y is further substituted with 1-2 oxo groups.

In some embodiments, Ring V is

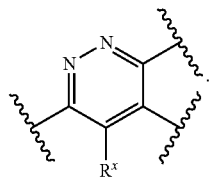

In some embodiments, Ring V is

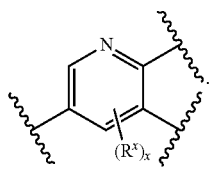

In some embodiments, Ring V is

In some embodiments, Ring V is

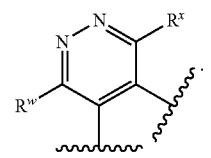

In some embodiments, Ring V is

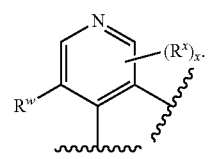

In some embodiments, Ring V is

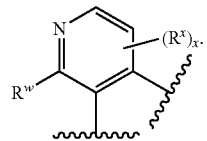

In some embodiments, Ring V is

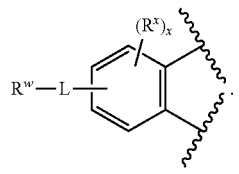

In some embodiments, Ring V is

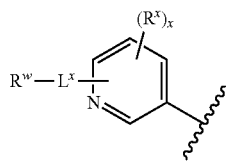

In some embodiments, Ring V is

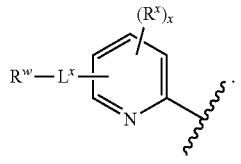

In some embodiments, Ring V is

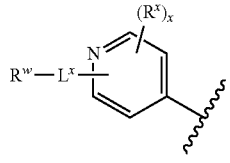

In some embodiments, Ring V is

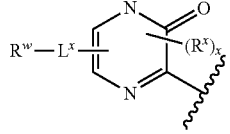

In some embodiments, Ring V is
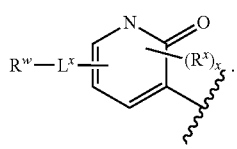
In some embodiments, Ring V is
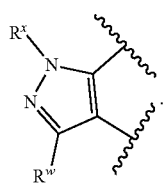
In some embodiments, Ring V is
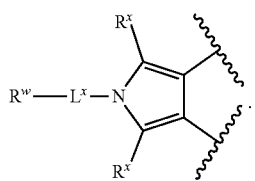
In some embodiments, Ring V is
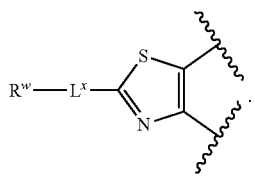
In some embodiments, Ring V is
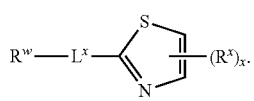
In some embodiments, Ring V is
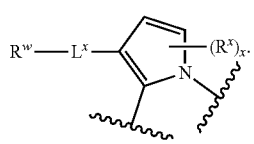
In some embodiments, Ring V is
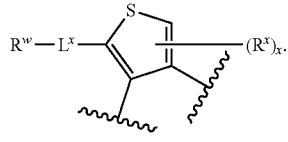
In some embodiments, Ring W is
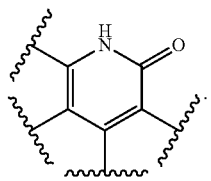 [SMILES: *c1[nH]c(=O)c(*)c(*)c1*]
In some embodiments, Ring W is
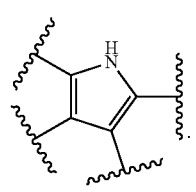 [SMILES: *c1[nH]c(*)c(*)c1*]
In some embodiments, Ring W is
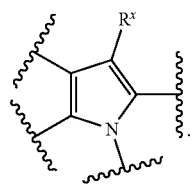
In some embodiments, Ring W is
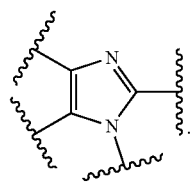 [SMILES: *c1nc(*)n(*)c1*]
In some embodiments, Ring W is
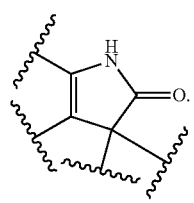 [SMILES: *C1=C(*)C(*)(*)C(=O)N1]

In some embodiments, Ring W is
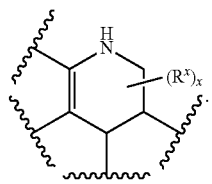
In some embodiments, Ring W is
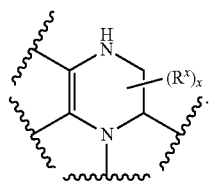
In some embodiments, Ring W is
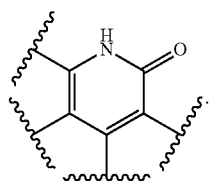 [SMILES: *c1[nH]c(=O)c(*)c(*)c1*]
In some embodiments, Ring W is
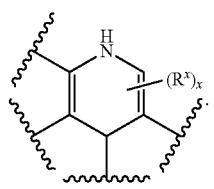
In some embodiments, Ring W is
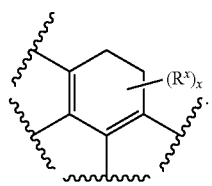
In some embodiments, Ring W is
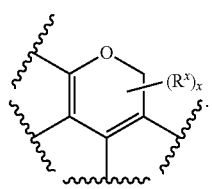
In some embodiments, Ring W is
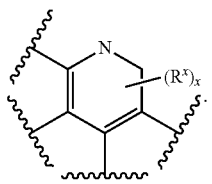
In some embodiments, Ring W is
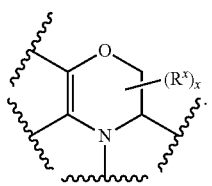
In some embodiments, Ring W is
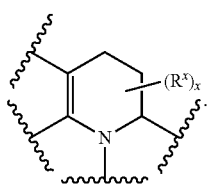
In some embodiments, Ring W is
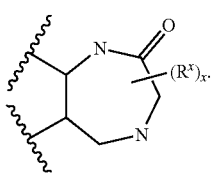
In some embodiments, Ring W is
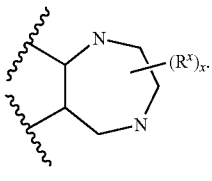
In some embodiments, Ring Y is
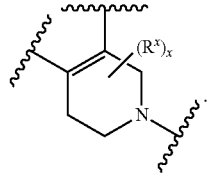

In some embodiments, Ring Y is
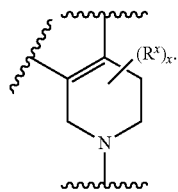
In some embodiments, Ring Y is
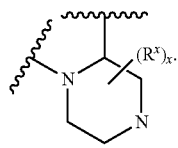
In some embodiments, Ring Y is
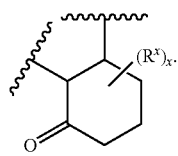
In some embodiments, Ring Y is
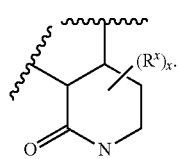
In some embodiments, Ring Y is
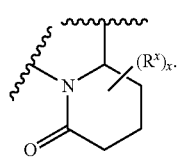
In some embodiments, Ring Y is
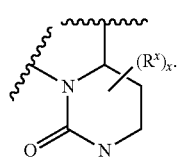
In some embodiments, Ring Y is
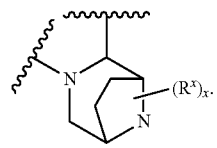
In some embodiments, Ring Y is
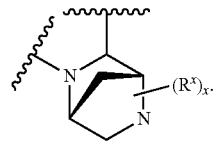
In some embodiments, Ring Y is
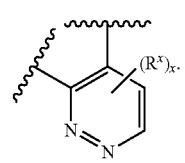
In some embodiments, Ring Y is
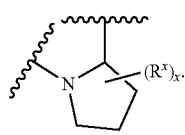
In some embodiments, Ring Y is
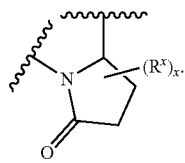
In some embodiments, Ring Y is
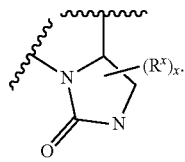

In some embodiments, Ring Y is

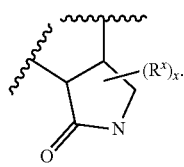

In some embodiments, Ring Y is

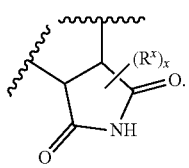

In some embodiments, Ring Y is

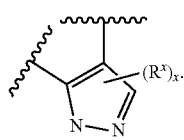

In some embodiments, Ring Y is

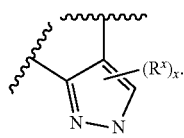

In some embodiments, Ring D is

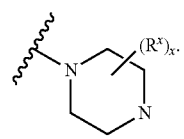

In some embodiments, Ring V, Ring W, Ring X, and Ring Y is independently selected from those depicted in Table 1, below.

As defined above and described herein, in some embodiments, $R^w$ is selected from

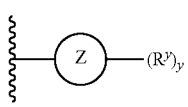

or hydrogen.

In some embodiments, $R^w$ is

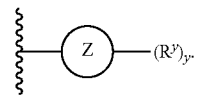

In some embodiments, $R^w$ is hydrogen.

In some embodiments, $R^w$ is selected from those depicted in Table 1, below.

As defined above and described herein, in some embodiments, Ring Z is phenyl, a 5-7 membered saturated or partially unsaturated carbocyclic or heterocyclic ring having 1-3 heteroatoms independently selected from nitrogen, oxygen, and sulfur, and a 5-6 membered heteroaryl ring having 1-4 heteroatoms independently selected from nitrogen, oxygen, and sulfur, wherein Ring Z is further optionally substituted with 1-2 oxo groups.

In some embodiments, Ring Z is phenyl. In some embodiments, Ring Z is a 5-7 membered saturated or partially unsaturated carbocyclic or heterocyclic ring having 1-3 heteroatoms independently selected from nitrogen, oxygen, and sulfur. In some embodiments, Ring Z is a 5-6 membered heteroaryl ring having 1-4 heteroatoms independently selected from nitrogen, oxygen, and sulfur. In some embodiments, Ring Z is further substituted with 1-2 oxo groups.

In some embodiments, Ring Z is

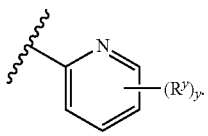

In some embodiments, Ring Z is

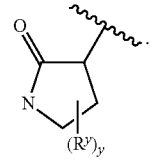

In some embodiments, Ring Z is

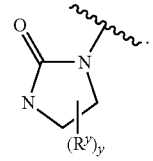

In some embodiments, Ring Z is

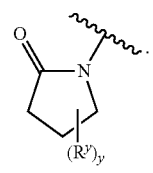

In some embodiments, Ring Z is

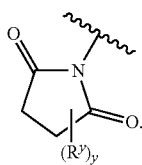

In some embodiments, Ring Z is

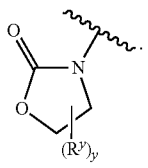

In some embodiments, Ring Z is

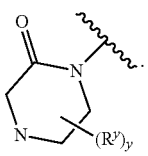

In some embodiments, Ring Z is selected from those depicted in Table 1, below.

As defined above and described herein, in some embodiments, each of $R^x$ and $R^y$ is independently hydrogen, deuterium, $R^z$, halogen, —CN, —NO$_2$, —OR, —SR, —NR$_2$, —SiR$_3$, —S(O)$_2$R, —S(O)$_2$NR$_2$, —S(O)R, —CFR$_2$, —CF$_2$R, —CF$_3$, —C(O)R, —C(O)OR, —C(O)NR$_2$, —C(O)N(R)OR, —C(R)$_2$N(R)C(O)R, —C(R)$_2$N(R)C(O)N(R)$_2$, —OC(O)R, —OC(O)N(R)$_2$, —OP(O)R$_2$, —OP(O)(OR)$_2$, —OP(O)(OR)NR$_2$, —OP(O)(NR$_2$)$_2$—, —N(R)C(O)OR, —N(R)C(O)R, —N(R)C(O)NR$_2$, —N(R)S(O)$_2$R, —NP(O)R$_2$, —N(R)P(O)(OR)$_2$, —N(R)P(O)(OR)NR$_2$, —N(R)P(O)(NR$_2$)$_2$, or —N(R)S(O)$_2$R, or two $R^x$ groups or two $R^v$ groups are optionally taken together to form an optionally substituted 5-7 membered partially unsaturated or aryl fused ring having 0-2 heteroatoms independently selected from nitrogen, oxygen, or sulfur.

In some embodiments, $R^x$ and/or $R^y$ is hydrogen. In some embodiments, $R^x$ and/or $R^y$ is deuterium. In some embodiments, $R^x$ and/or $R^y$ is $R^z$. In some embodiments, $R^x$ and/or $R^y$ is halogen. In some embodiments, $R^x$ and/or $R^y$ is —CN. In some embodiments, $R^x$ and/or $R^y$ is —NO$_2$. In some embodiments, $R^x$ and/or $R^y$ is —OR. In some embodiments, $R^x$ and/or $R^y$ is —SR. In some embodiments, $R^x$ and/or $R^y$ is —NR$_2$. In some embodiments, $R^x$ and/or $R^y$ is —SiR$_3$. In some embodiments, $R^x$ and/or $R^y$ is —S(O)$_2$R. In some embodiments, $R^x$ and/or $R^y$ is —S(O)$_2$NR$_2$. In some embodiments, $R^x$ and/or $R^y$ is —S(O)R. In some embodiments, $R^x$ and/or $R^y$ is —CFR$_2$. In some embodiments, $R^x$ and/or $R^y$ is —CF$_2$R. In some embodiments, $R^x$ and/or $R^y$ is —CF$_3$. In some embodiments, $R^x$ and/or $R^y$ is —C(O)R. In some embodiments, $R^x$ and/or $R^y$ is —C(O)OR. In some embodiments, $R^x$ and/or $R^y$ is —C(O)NR$_2$. In some embodiments, $R^x$ and/or $R^y$ is —C(O)N(R)OR. In some embodiments, $R^x$ and/or $R^y$ is —C(R)$_2$N(R)C(O)R. In some embodiments, $R^x$ and/or $R^y$ is —C(R)$_2$N(R)C(O)N(R)$_2$. In some embodiments, $R^x$ and/or $R^y$ is —OC(O)R. In some embodiments, $R^x$ and/or $R^y$ is —OC(O)N(R)$_2$. In some embodiments, $R^x$ and/or $R^y$ is —OP(O)R$_2$. In some embodiments, $R^x$ and/or $R^y$ is —OP(O)(OR)$_2$. In some embodiments, $R^x$ and/or $R^y$ is —OP(O)(OR)NR$_2$. In some embodiments, $R^x$ and/or $R^y$ is —OP(O)(NR$_2$)$_2$. In some embodiments, $R^x$ and/or $R^y$ is —N(R)C(O)OR. In some embodiments, $R^x$ and/or $R^y$ is —N(R)C(O)R. In some embodiments, $R^x$ and/or $R^y$ is —N(R)C(O)NR$_2$. In some embodiments, $R^x$ and/or $R^y$ is —N(R)S(O)$_2$R. In some embodiments, $R^x$ and/or $R^y$ is —NP(O)R$_2$. In some embodiments, $R^x$ and/or $R^y$ is —N(R)P(O)(OR)$_2$. In some embodiments, $R^x$ and/or $R^y$ is —N(R)P(O)(OR)NR$_2$. In some embodiments, $R^x$ and/or $R^y$ is —N(R)P(O)(NR$_2$)$_2$. In some embodiments, $R^x$ and/or $R^y$ is —N(R)S(O)$_2$R. In some embodiments, two $R^x$ groups or two $Ry^3$ groups are optionally taken together to form an optionally substituted 5-7 membered partially unsaturated or aryl fused ring having 0-2 heteroatoms independently selected from nitrogen, oxygen, or sulfur.

In some embodiments, $R^y$ is —OH.

In some embodiments, $R^x$ is

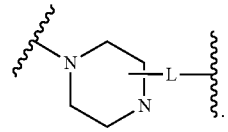

In some embodiments, $R^x$ is

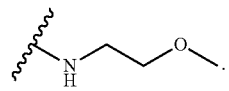

In some embodiments, $R^x$ is

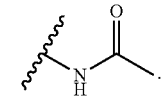

In some embodiments, $R^x$ is methyl.

In some embodiments, $R^x$ and $R^y$ are selected from those depicted in Table 1, below.

As defined above and described herein, in some embodiments, each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or two R groups on the same atom are taken together with their intervening atoms to form a 4-7 membered saturated, partially unsaturated, or heteroaryl ring having 0-3 heteroatoms, in addition to the atom to which they are attached, independently selected from nitrogen, oxygen, and sulfur.

In some embodiments, R is hydrogen. In some embodiments, R is an optionally substituted group selected from $C_{1-6}$ aliphatic. In some embodiments, R is phenyl. In some embodiments, R is a 4-7 membered saturated or partially unsaturated heterocyclic having 1-2 heteroatoms independently selected from nitrogen, oxygen, and sulfur. In some embodiments, R is a 5-6 membered heteroaryl ring having 1-4 heteroatoms independently selected from nitrogen, oxygen, and sulfur. In some embodiments, two R groups on the same atom are taken together with their intervening atoms to form a 4-7 membered saturated, partially unsaturated, or heteroaryl ring having 0-3 heteroatoms, in addition to the atom to which they are attached, independently selected from nitrogen, oxygen, and sulfur.

In some embodiments, R is selected from those depicted in Table 1, below.

As defined above and described herein, in some embodiments, each $R^z$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur.

In some embodiments, $R^z$ is an optionally substituted group selected from $C_{1-6}$ aliphatic. In some embodiments, $R^z$ is phenyl. In some embodiments, $R^z$ is a 4-7 membered saturated or partially unsaturated heterocyclic ring having 1-2 heteroatoms independently selected from nitrogen, oxygen, and sulfur. In some embodiments, $R^z$ is a 5-6 membered heteroaryl ring having 1-4 heteroatoms independently selected from nitrogen, oxygen, and sulfur.

In some embodiments, $R^z$ is selected from those depicted in Table 1, below.

As defined above and described herein, in some embodiments, $L^x$ is a covalent bond or a $C_{1-3}$ bivalent straight or branched saturated or unsaturated hydrocarbon chain wherein 1-2 methylene units of the chain are independently and optionally replaced with —O—, —C(O)—, —C(S)—, —C(R)$_2$—, —CF(R)—, —C(F)$_2$—, —N(R)—, —S—, —S(O)$_2$— or —CR=CR—.

In some embodiments, $L^x$ is a covalent bond. In some embodiments, $L^x$ is a $C_{1-3}$ bivalent straight or branched saturated or unsaturated hydrocarbon chain wherein 1-2 methylene units of the chain are independently and optionally replaced with —O—, —C(O)—, —C(S)—, —C(R)$_2$—, —CF(R)—, —C(F)$_2$—, —N(R)—, —S—, —S(O)$_2$— or —CR=CR—.

In some embodiments, $L^x$ is selected from those depicted in Table 1, below.

As defined above and described herein, in some embodiments, x is 0, 1, 2, 3, 4, 5, 6, 7, 8, 9, 10, 11, 12, 13, 14, 15, or 16.

In some embodiments, x is 0. In some embodiments, x is 1. In some embodiments, x is 2. In some embodiments, x is 3. In some embodiments, x is 4. In some embodiments, x is 5. In some embodiments, x is 6. In some embodiments, x is 7. In some embodiments, x is 8. In some embodiments, x is 9. In some embodiments, x is 10. In some embodiments, x is 11. In some embodiments, x is 12. In some embodiments, x is 13. In some embodiments, x is 14. In some embodiments, x is 15. In some embodiments, x is 16.

In some embodiments, x is selected from those depicted in Table 1, below.

As defined above and described herein, in some embodiments, y is 0, 1, 2, 4, or 5.

In some embodiments, y is 0. In some embodiments, y is 1. In some embodiments, y is 2. In some embodiments, y is 3. In some embodiments, y is 4. In some embodiments, y is 5.

In some embodiments, y is selected from those depicted in Table 1, below.

In certain embodiments, the present invention provides a compound of formula I-a, wherein $R^w$ is

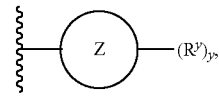

Ring Z is phenyl, one $R^y$ is —OH, and $L^x$ is a covalent bond as shown, to provide a compound of formula I-a-1:

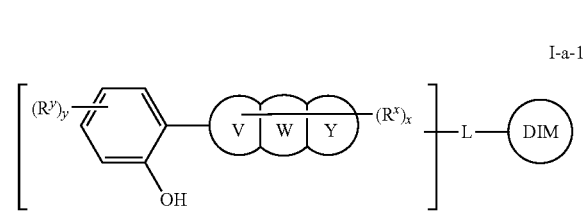

I-a-1 or a pharmaceutically acceptable salt thereof, wherein each of DIM, L, $R^x$, $R^y$, Ring V, Ring W, Ring Y, x, and y is as defined above and described in embodiments herein, both singly and in combination.

In certain embodiments, the present invention provides a compound of formula I-a, wherein $R^w$ is

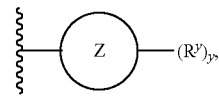

Ring Z is phenyl, one $R^y$ is —OH, $L^x$ is a covalent bond, and Ring B and Ring C are spiro fused as shown, to provide a compound of formula I-a-2:

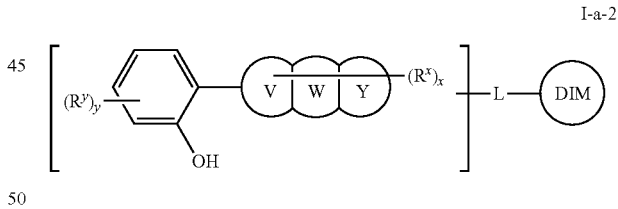

I-a-2 or a pharmaceutically acceptable salt thereof, wherein each of DIM, L, $R^x$, $R^y$, Ring V, Ring W, Ring Y, x, and y is as defined above and described in embodiments herein, both singly and in combination.

In certain embodiments, the present invention provides a compound of formula I-a, wherein $R^w$ is

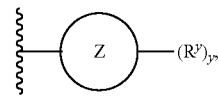

Ring Z is phenyl, one $R^y$ is —OH, $L^x$ is a covalent bond, and Ring V is pyridazinyl as shown, to provide a compound of formula I-a-3:

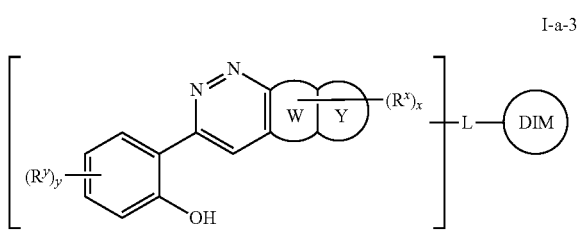
I-a-3

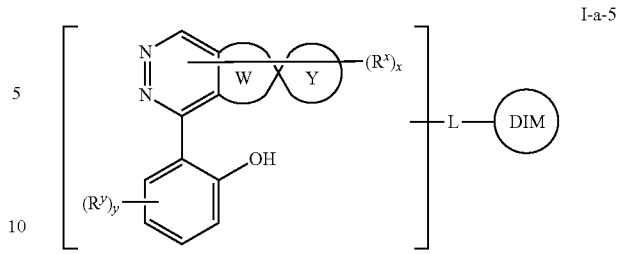
I-a-5 or a pharmaceutically acceptable salt thereof, wherein each of DIM, L, $R^x$, $R^y$, Ring W, Ring Y, x, and y is as defined above and described in embodiments herein, both singly and in combination.

In certain embodiments, the present invention provides a compound of formula I-a, wherein $R^w$ is

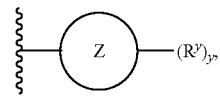

Ring Z is phenyl, one $R^y$ is —OH, $L^x$ is a covalent bond, and Ring V is pyridazinyl as shown, to provide a compound of formula I-a-4:

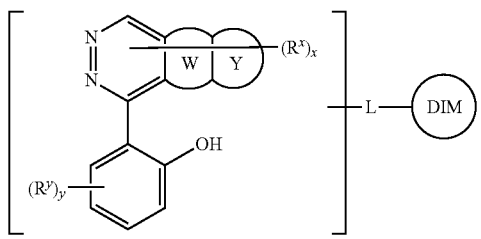
I-a-4 or a pharmaceutically acceptable salt thereof, wherein each of DIM, L, $R^x$, $R^y$, Ring W, Ring Y, x, and y is as defined above and described in embodiments herein, both singly and in combination.

In certain embodiments, the present invention provides a compound of formula I-a, wherein $R^w$ is

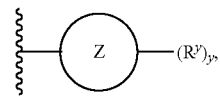

Ring Z is phenyl, one $R^y$ is —OH, $L^x$ is a covalent bond, Ring V is pyridazinyl, and Ring X and Ring Y are spiro fused as shown, to provide a compound of formula I-a-5:

or a pharmaceutically acceptable salt thereof, wherein each of DIM, L, $R^x$, $R^y$, Ring W, Ring Y, x, and y is as defined above and described in embodiments herein, both singly and in combination.

In certain embodiments, the present invention provides a compound of formula I-a, wherein $R^w$ is hydrogen, one $R^x$ is —OH, Ring V is benzo, and $L^x$ is a covalent bond as shown, to provide a compound of formula I-a-6:

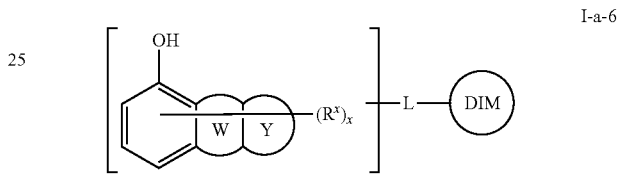
I-a-6 or a pharmaceutically acceptable salt thereof, wherein each of DIM, L, $R^x$, Ring W, Ring Y, and x is as defined above and described in embodiments herein, both singly and in combination.

In certain embodiments, the present invention provides a compound of formula I-a, wherein $R^w$ is hydrogen, one $R^x$ is —OH, Ring V is benzo, Ring Y is pyridazinyl, and $L^x$ is a covalent bond as shown, to provide a compound of formula I-a-7:

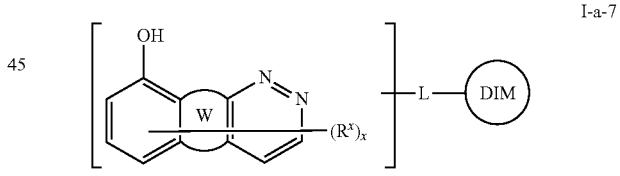
I-a-7 or a pharmaceutically acceptable salt thereof, wherein each of DIM, L, $R^x$, Ring W, and x is as defined above and described in embodiments herein, both singly and in combination.

In certain embodiments, the present invention provides a compound of formula I-a, wherein $R^w$ is

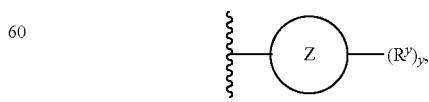

Ring Z is phenyl, one $R^y$ is —OH, $L^x$ is a covalent bond, Ring V is pyridazinyl, and Ring W is pyrrolyl as shown, to provide a compound of formula I-a-8:

I-a-8

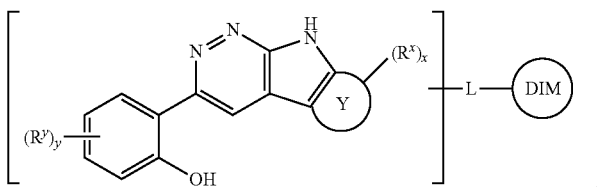

or a pharmaceutically acceptable salt thereof, wherein each of DIM, L, $R^x$, $R^y$, Ring Y, x, and y is as defined above and described in embodiments herein, both singly and in combination.

In certain embodiments, the present invention provides a compound of formula I-a, wherein $R^w$ is

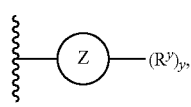

Ring Z is phenyl, one $R^y$ is —OH, $L^x$ is a covalent bond, Ring V is pyridazinyl, and Ring W is piperazinyl as shown, to provide a compound of formula I-a-9:

I-a-9

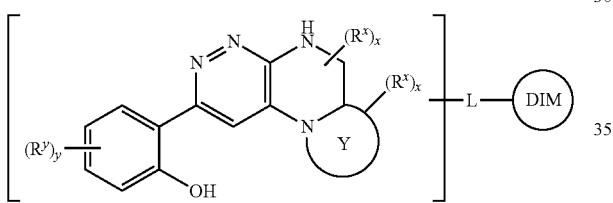

or a pharmaceutically acceptable salt thereof, wherein each of DIM, L, $R^x$, $R^y$, Ring Y, x, and y is as defined above and described in embodiments herein, both singly and in combination.

In certain embodiments, the present invention provides a compound of formula I-b, wherein $R^w$ is

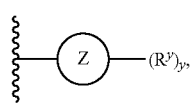

Ring Z is phenyl, one $R^y$ is —OH, and $L^x$ is a covalent bond as shown, to provide a compound of formula I-b-1:

I-b-1

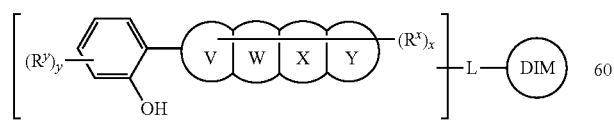

or a pharmaceutically acceptable salt thereof, wherein each of DIM, L, $R^x$, $R^y$, Ring V, Ring W, Ring X, Ring Y, x, and y is as defined above and described in embodiments herein, both singly and in combination.

In certain embodiments, the present invention provides a compound of formula I-b, wherein $R^w$ is

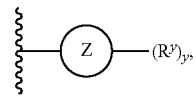

Ring Z is phenyl, one $R^y$ is —OH, $L^x$ is a covalent bond, and Ring X and Ring Y are spiro fused as shown, to provide a compound of formula I-b-2:

I-b-2

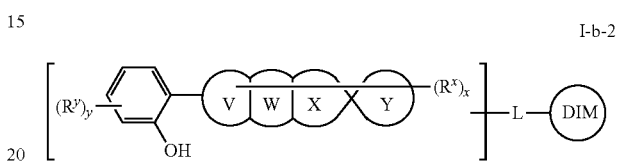

or a pharmaceutically acceptable salt thereof, wherein each of DIM, L, $R^x$, $R^y$, Ring V, Ring W, Ring X, Ring Y, x, and y is as defined above and described in embodiments herein, both singly and in combination.

In certain embodiments, the present invention provides a compound of formula I-b, wherein $R^w$ is

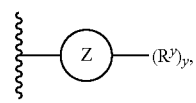

Ring Z is phenyl, one $R^y$ is —OH, and $L^x$ is a covalent bond, and Ring V is pyridazinyl as shown, to provide a compound of formula I-b-3:

I-b-3

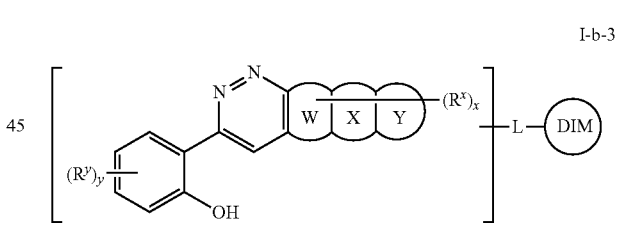

or a pharmaceutically acceptable salt thereof, wherein each of DIM, L, $R^x$, $R^y$, Ring W, Ring X, Ring Y, x, and y is as defined above and described in embodiments herein, both singly and in combination.

In certain embodiments, the present invention provides a compound of formula I-b, wherein $R^w$ is

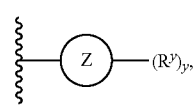

Ring Z is phenyl, one $R^y$ is —OH, and $L^x$ is a covalent bond, and Ring V is pyridazinyl as shown, to provide a compound of formula I-b-4:

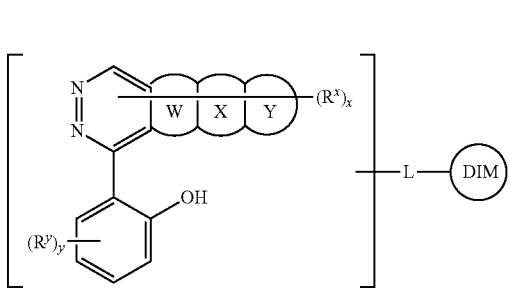

I-b-4 or a pharmaceutically acceptable salt thereof, wherein each of DIM, L, $R^x$, $R^y$, Ring W, Ring X, Ring Y, x, and y is as defined above and described in embodiments herein, both singly and in combination.

In certain embodiments, the present invention provides a compound of formula I-b, wherein $R^w$ is

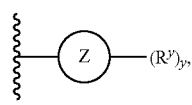

Ring Z is phenyl, one $R^y$ is —OH, $L^x$ is a covalent bond, Ring V is pyridazinyl, and Ring X and Ring Y are spiro fused as shown, to provide a compound of formula I-b-5:

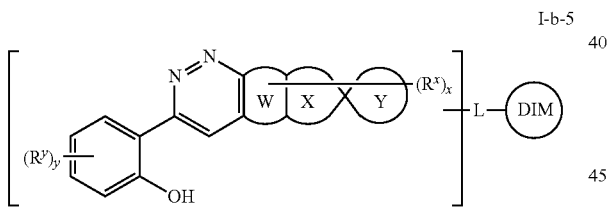

I-b-5 or a pharmaceutically acceptable salt thereof, wherein each of DIM, L, $R^x$, $R^y$, Ring W, Ring X, Ring Y, x, and y is as defined above and described in embodiments herein, both singly and in combination.

In certain embodiments, the present invention provides a compound of formula I-b, wherein $R^w$ is

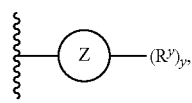

Ring Z is phenyl, one $R^y$ is —OH, $L^x$ is a covalent bond, Ring V is pyridazinyl, and Ring X and Ring Y are spiro fused as shown, to provide a compound of formula I-b-6:

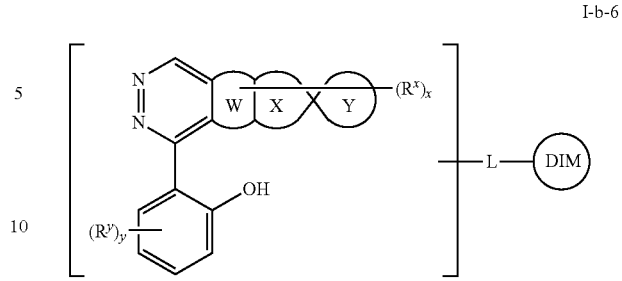

I-b-6 or a pharmaceutically acceptable salt thereof, wherein each of DIM, L, $R^x$, $R^y$, Ring W, Ring X, Ring Y, x, and y is as defined above and described in embodiments herein, both singly and in combination.

In some embodiments, SMARCA is

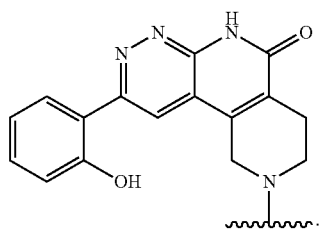 [SMILES: *N1CCc2c(c3cc(-c4ccccc4O)nnc3[nH]c2=O)C1]

In some embodiments, SMARCA is

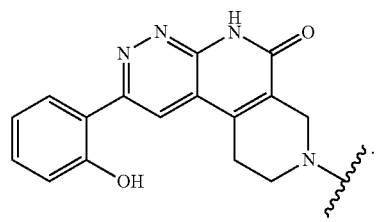 [SMILES: *N1CCc2c(c(=O)[nH]c3nnc(-c4ccccc4O)cc23)C1]

In some embodiments, SMARCA is

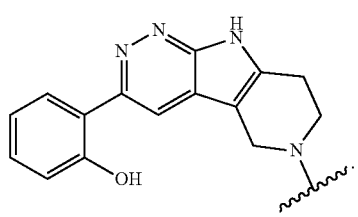 [SMILES: *N1CCc2[nH]c3nnc(-c4ccccc4O)cc3c2C1]

In some embodiments, SMARCA is

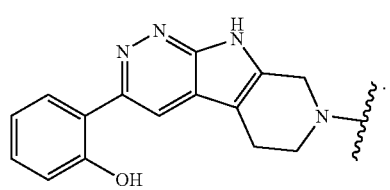 [SMILES: *N1CCc2c([nH]c3nnc(-c4ccccc4O)cc23)C1]

In some embodiments, SMARCA is

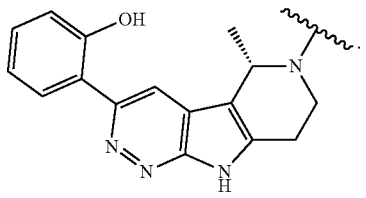 [SMILES: *N1CCc2[nH]c3nnc(-c4ccccc4O)cc3c2[C@@H]1C]

In some embodiments, SMARCA is

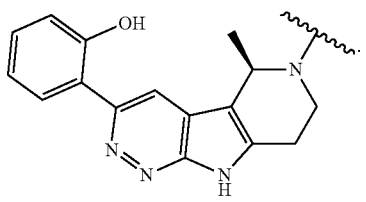 [SMILES: *N1CCc2[nH]c3nnc(-c4ccccc4O)cc3c2[C@H]1C]

In some embodiments, SMARCA is

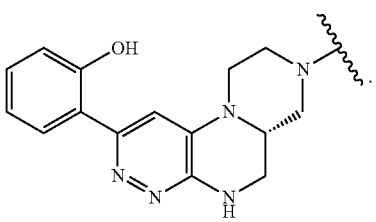 [SMILES: *N1CCN2c3cc(-c4ccccc4O)nnc3NC[C@H]2C1]

In some embodiments, SMARCA is

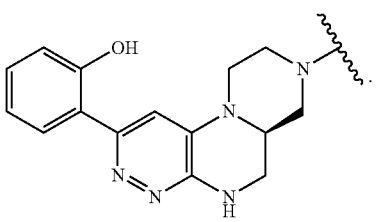 [SMILES: *N1CCN2c3cc(-c4ccccc4O)nnc3NC[C@@H]2C1]

In some embodiments, SMARCA is

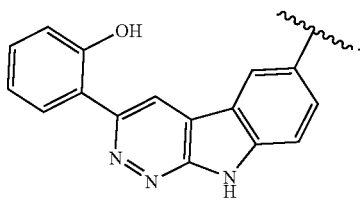 [SMILES: *c1ccc2[nH]c3nnc(-c4ccccc4O)cc3c2c1]

Ligase Binding Moiety (LBM)

As defined herein and described below, wherein a formula is depicted using square brackets, e.g.,

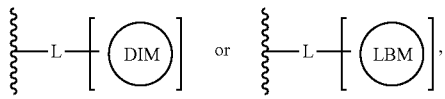

L is attached to a modifiable carbon, oxygen, or nitrogen atom within DIM or LBM including substitution or replacement of a defined group in DIM or LBM.

In some embodiments, DIM is LBM. In certain embodiments, the present invention provides a compound of formula I, wherein LBM is an E3 ubiquitin ligase (cereblon) binding moiety thereby forming a compound of formula I-aa:

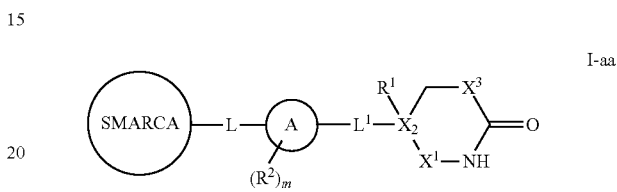

or a pharmaceutically acceptable salt thereof, wherein L and SMARCA are as defined above and described herein, and wherein:

$X^1$ is a bivalent moiety selected from a covalent bond, —$CH_2$—, —$CHCF_3$—, —$SO_2$—, —S(O)—, —P(O)R—, —P(O)OR—, —$P(O)NR_2$—, —C(O)—, —C(S)—, or

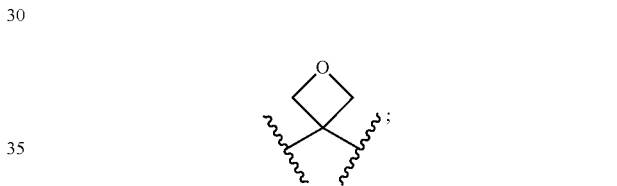

$X^2$ is a carbon atom or silicon atom;
$X^3$ is a bivalent moiety selected from —$CR_2$—, —NR—, —O—, —S—, or —$Si(R_2)$—;
$R^1$ is hydrogen, deuterium, halogen, —CN, —OR, —SR, —S(O)R, —$S(O)_2R$, —$N(R)_2$, —$P(O)(OR)_2$, —P(O)($NR_2$)OR, —$P(O)(NR_2)_2$, —$Si(OH)_2R$, —Si(OH)($R)_2$, —$Si(R)_3$, or an optionally substituted $C_{1-4}$ aliphatic;
each $R^2$ is independently hydrogen, deuterium, —$R^6$, halogen, —CN, —$NO_2$, —OR, —SR, —$N(R)_2$, —$Si(R)_3$, —$S(O)_2R$, —$S(O)_2N(R)_2$, —S(O)R, —C(O)R, —C(O)OR, —C(O)N(R)_2, —C(O)N(R)OR, —C(R)_2N(R)C(O)R, —$C(R)_2N(R)C(O)N(R)_2$, —OC(O)R, —OC(O)N(R)_2, —$OP(O)R_2$, —$OP(O)(OR)_2$, —OP(O)(OR)($NR_2$), —OP(O)($NR_2)_2$—, —N(R)C(O)OR, —N(R)C(O)R, —N(R)C(O)N(R)_2, —$N(R)S(O)_2R$, —$NP(O)R_2$, —N(R)P(O)(OR)_2, —N(R)P(O)(OR)($NR_2$), —N(R)P(O)($NR_2)_2$, or —$N(R)S(O)_2R$;
Ring A is a bi- or tricyclic ring selected from

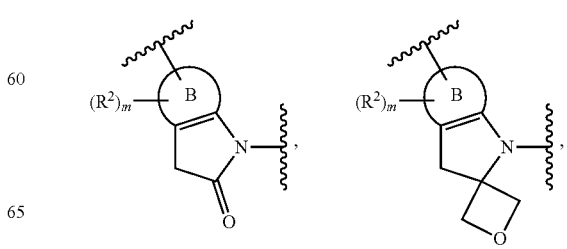

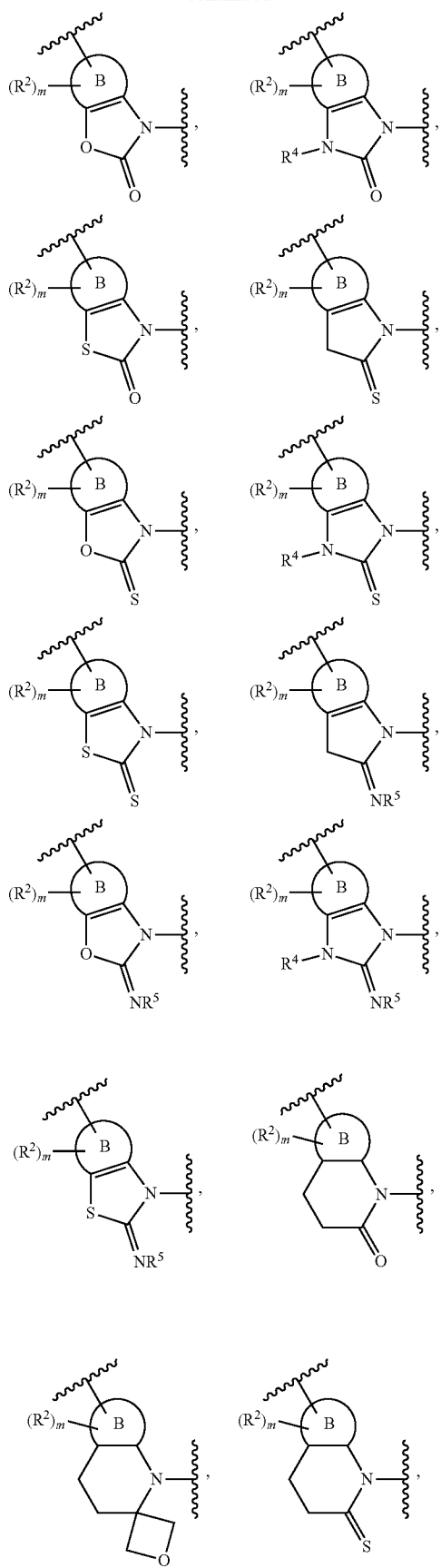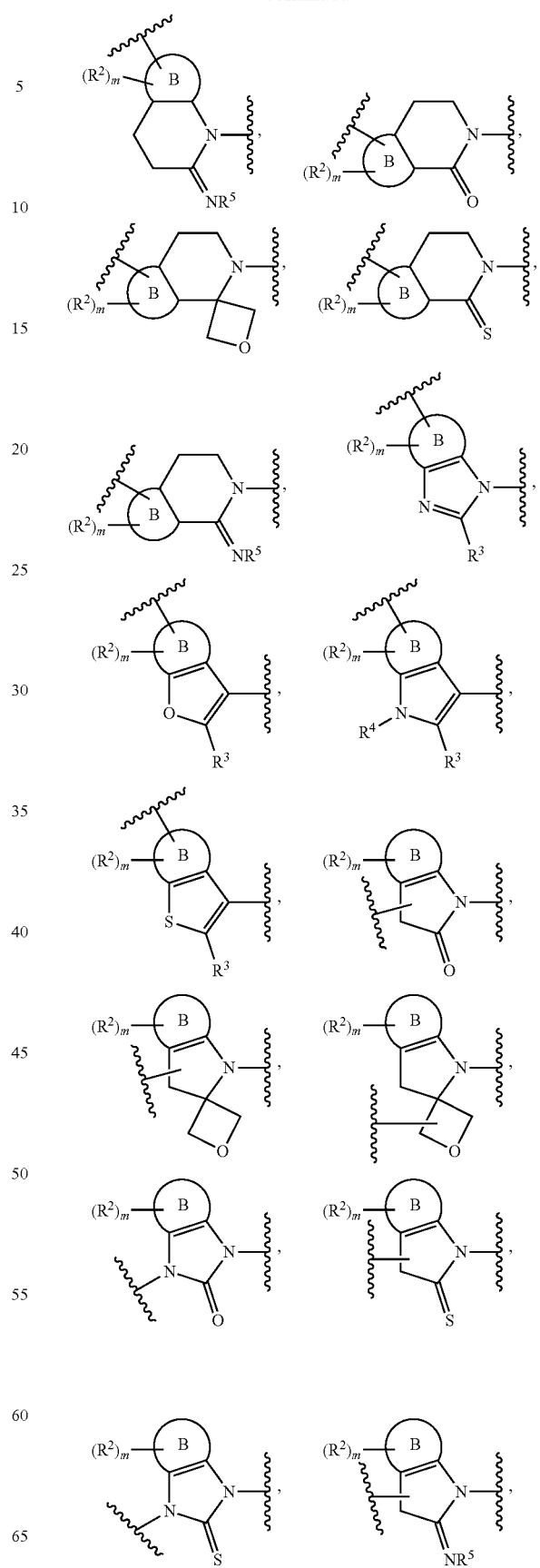

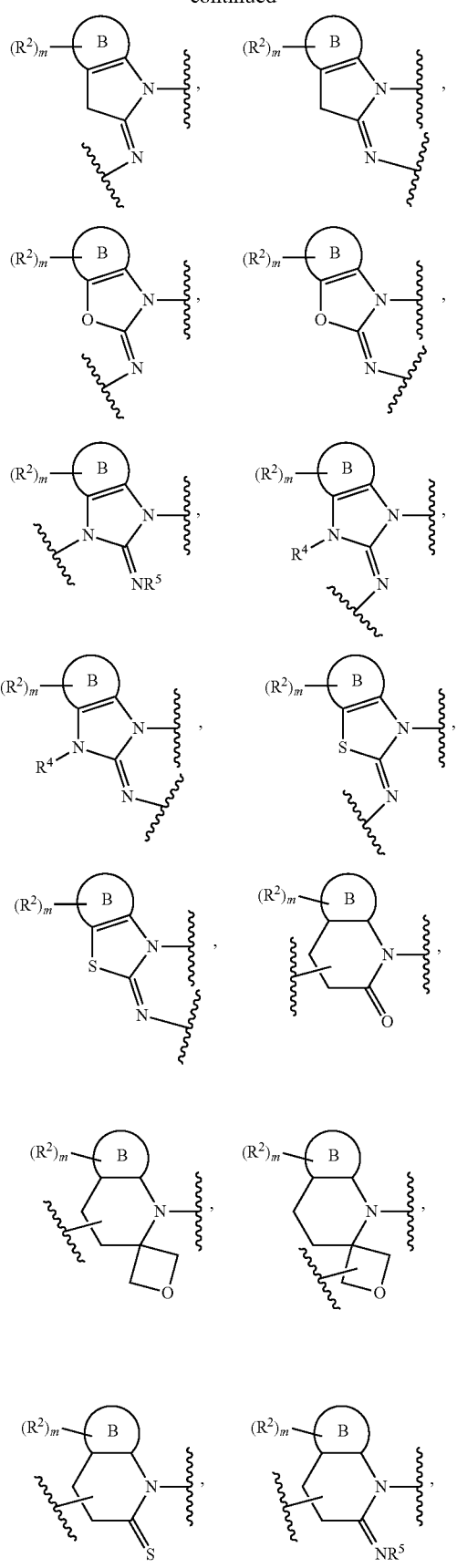
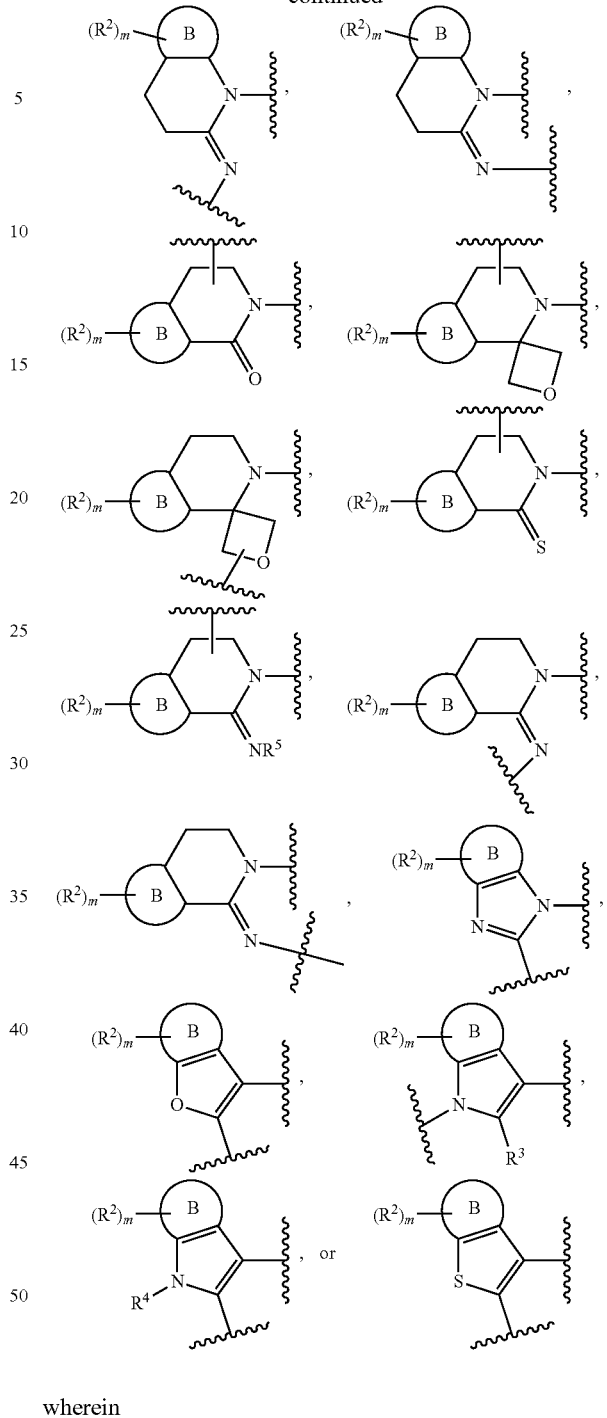

wherein
Ring B is a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur;

$R^3$ is selected from hydrogen, halogen, —OR, —N(R)$_2$, or —SR;

each $R^4$ is independently hydrogen, —$R^6$, halogen, —CN, —NO$_2$, —OR, —SR, —NR$_2$, —S(O)$_2$R, —S(O)$_2$NR$_2$, —S(O)R, —C(O)R, —C(O)OR, C(O)NR$_2$, —C(O)N(R) OR, —OC(O)R, —OC(O)NR$_2$, —N(R)C(O)OR, —N(R) C(O)R, —N(R)C(O)NR$_2$, or —N(R)S(O)$_2$R;

R$^5$ is hydrogen, C$_{1-4}$ aliphatic, or —CN;

each R$^6$ is independently an optionally substituted group selected from C$_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

L$^1$ is a covalent bond or a C$_{1-3}$ bivalent straight or branched saturated or unsaturated hydrocarbon chain wherein 1-2 methylene units of the chain are independently and optionally replaced with —O—, —C(O)—, —C(S)—, —C(R)$_2$—, —CF(R)—, —C(F)$_2$—, —N(R)—, —S—, —S(O)$_2$— or —(C)═CH—;

m is 0, 1, 2, 3 or 4;

each R is independently hydrogen, or an optionally substituted group selected from C$_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

Where a point of attachment of —(R$^2$)$_m$ is depicted on Ring B, it is intended, and one of ordinary skill in the art would appreciate, that the point of attachment of —(R$^2$)$_m$ may be on Ring A and may also be at any available carbon or nitrogen atom on Ring A including the ring to which Ring B is fused. Where —R$^2$ is attached to a nitrogen atom bound to R$^4$ or R$^5$, R$^4$ or R$^5$ is absent and —R$^2$ takes the place of the R$^4$ or R$^5$ group. Where —R$^2$ is attached to a carbon atom bound to R$^3$, R$^3$ is absent and —R$^2$ takes the place of the R$^3$ group.

In some embodiments, a compound of formula I-aa above is provided as a compound of formula I-aa' or formula I-aa":

I-aa'
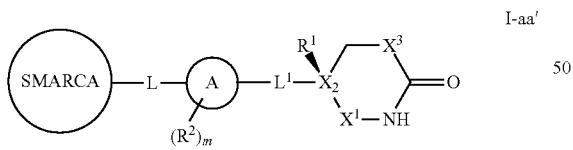

I-aa"
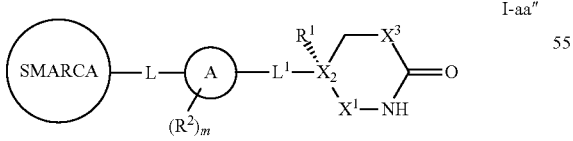

or a pharmaceutically acceptable salt thereof, wherein:
each of SMARCA, Ring A, L, L$^1$, R$^1$, R$^2$, X$^1$, X$^2$, X$^3$, and m is as defined above.

In certain embodiments, the present invention provides a compound of Formula I, wherein LBM is an E3 ubiquitin ligase (cereblon) binding moiety thereby forming a compound of formula I-bb:

I-bb
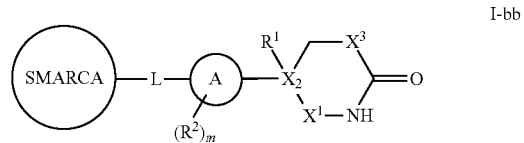

or a pharmaceutically acceptable salt thereof, wherein L and SMARCA are as defined above and described in embodiments herein, and wherein:

X$^1$ is a bivalent moiety selected from a covalent bond, —CH$_2$—, —CHCF$_3$—, —SO$_2$—, —S(O)—, —P(O) R—, —P(O)OR—, —P(O)NR$_2$—, —C(O)—, —C(S)—, or

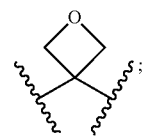 [SMILES: *C1(*)COC1]

X$^2$ is a carbon atom or silicon atom;
X$^3$ is a bivalent moiety selected from —CR$_2$—, —NR—, —O—, —S—, or —Si(R$_2$)—;
R$^1$ is hydrogen, deuterium, halogen, —CN, —OR, —SR, —S(O)R, —S(O)$_2$R, —N(R)$_2$, —P(O)(OR)$_2$, —P(O) (NR$_2$)OR, —P(O)(NR$_2$)$_2$, —Si(OH)$_2$R, —Si(OH)(R)$_2$, —Si(R)$_3$, or an optionally substituted C$_{1-4}$ aliphatic;
each R$^2$ is independently hydrogen, deuterium, —R$^6$, halogen, —CN, —NO$_2$, —OR, —SR, —N(R)$_2$, —Si(R)$_3$, —S(O)$_2$R, —S(O)$_2$N(R)$_2$, —S(O)R, —C(O)R, —C(O) OR, —C(O)N(R)$_2$, —C(O)N(R)OR, —C(R)$_2$N(R)C(O) R, —C(R)$_2$N(R)C(O)N(R)$_2$, —OC(O)R, —OC(O)N(R)$_2$, —OP(O)R$_2$, —OP(O)(OR)$_2$, —OP(O)(OR)(NR$_2$), —OP (O)(NR$_2$)$_2$—, —N(R)C(O)OR, —N(R)C(O)R, —N(R)C (O)N(R)$_2$, —N(R)S(O)$_2$R, —NP(O)R$_2$, —N(R)P(O) (OR)$_2$, —N(R)P(O)(OR)(NR$_2$), —N(R)P(O)(NR$_2$)$_2$, or —N(R)S(O)$_2$R;
Ring A is a bi- or tricyclic ring selected from

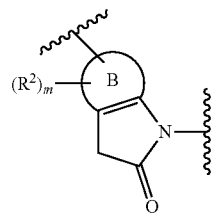

wherein Ring B is other than imidazo or benzo,

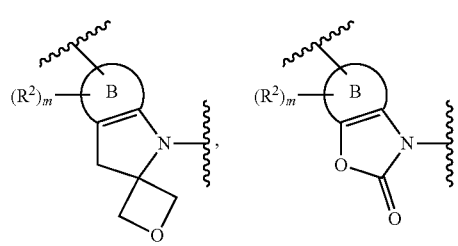

wherein Ring B is other than benzo,
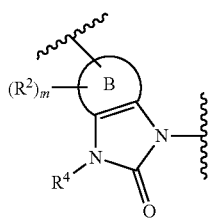
wherein Ring B is other than benzo,
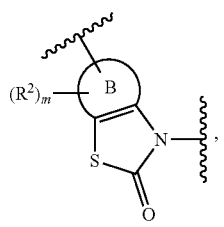 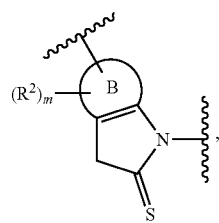
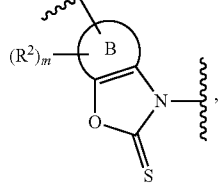 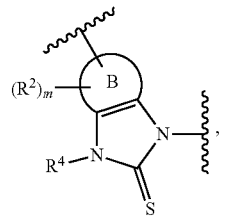
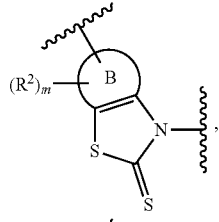 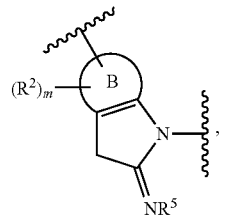
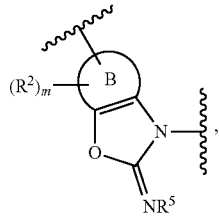 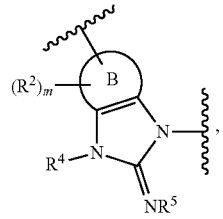
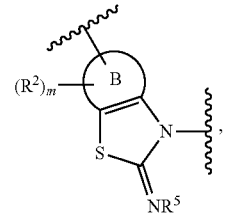 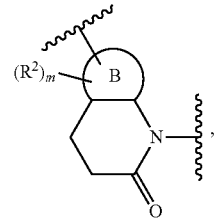
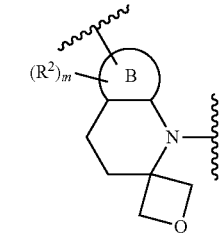 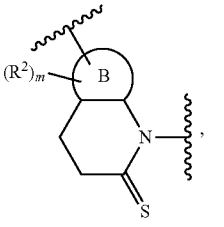
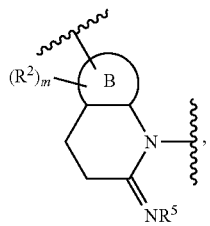 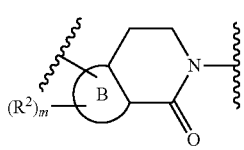
wherein Ring B is other than benzo,
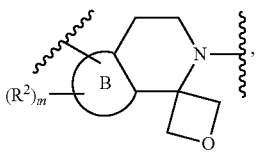 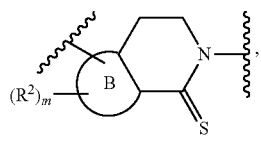
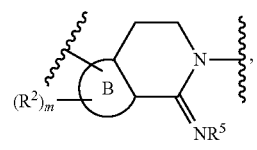 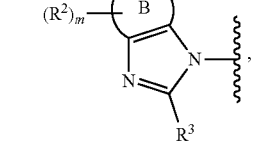
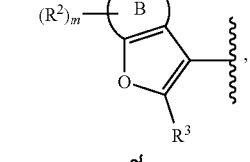 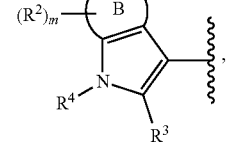
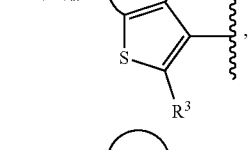 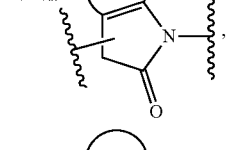
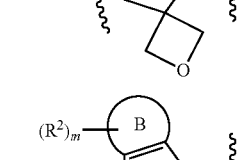 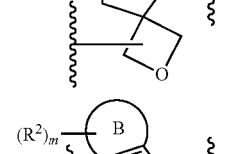
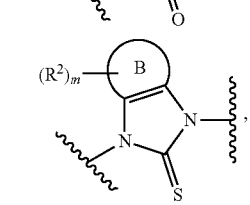 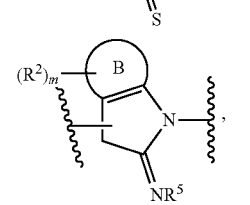

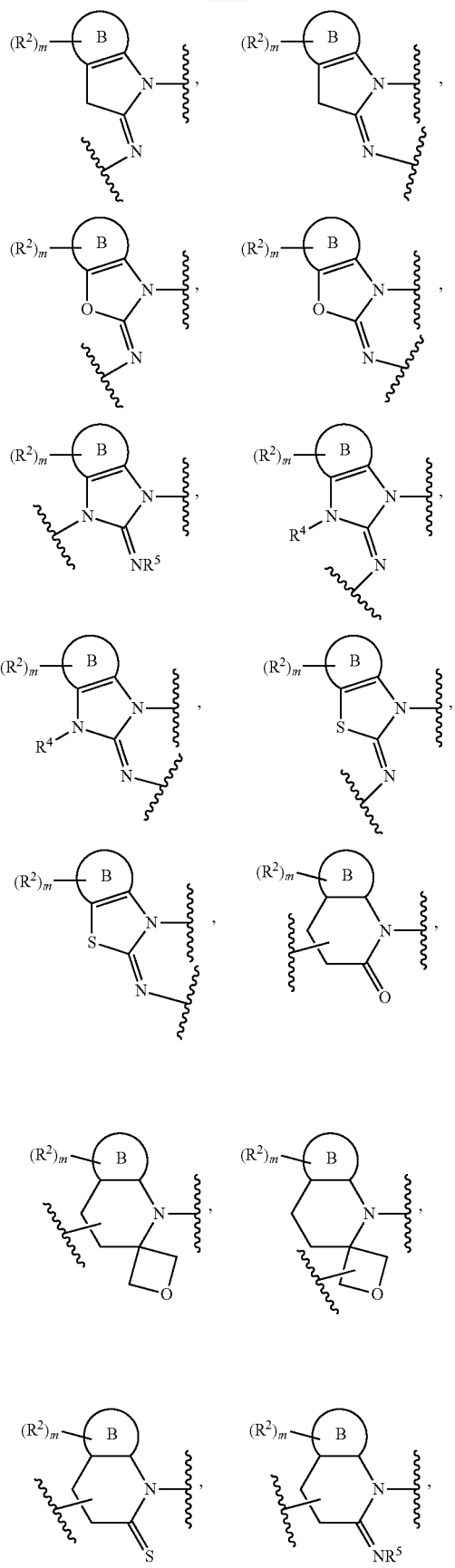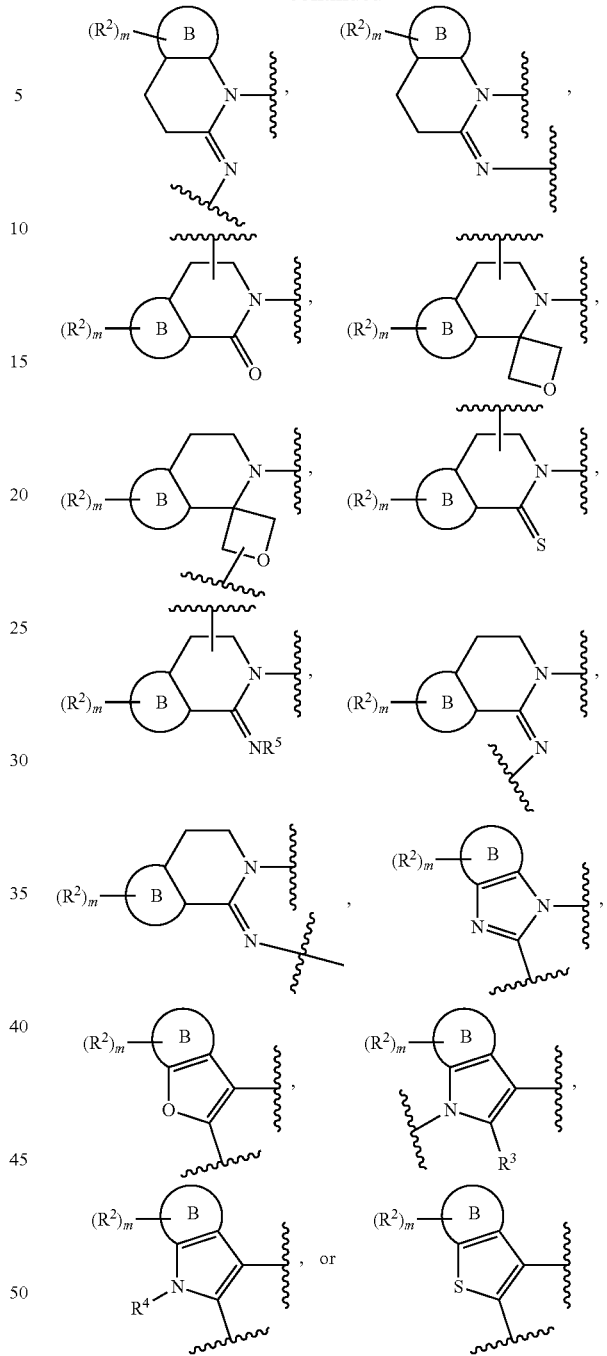

wherein
Ring B is a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur;

$R^3$ is selected from hydrogen, halogen, —OR, —N(R)$_2$, or —SR;

each $R^4$ is independently hydrogen, —R$^6$, halogen, —CN, —NO$_2$, —OR, SR, —NR$_2$, —S(O)$_2$R, —S(O)$_2$NR$_2$, —S(O)R, —C(O)R, —C(O)OR, C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;

R$^5$ is hydrogen, C$_{1-4}$ aliphatic, or —CN;

each R$^6$ is independently an optionally substituted group selected from C$_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

m is 0, 1, 2, 3 or 4; and each R is independently hydrogen, or an optionally substituted group selected from C$_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

Where a point of attachment of —(R$^2$)$_m$ is depicted on Ring B, it is intended, and one of ordinary skill in the art would appreciate, that the point of attachment of —(R$^2$)$_m$ may be on Ring A and may also be at any available carbon or nitrogen atom on Ring A including the ring to which Ring B is fused. Where —R$^2$ is attached to a nitrogen atom bound to R$^4$ or R$^5$, R$^4$ or R$^5$ is absent and —R$^2$ takes the place of the R$^4$ or R$^5$ group. Where —R$^2$ is attached to a carbon atom bound to R$^3$, R$^3$ is absent and —R$^2$ takes the place of the R$^3$ group.

In some embodiments, the compound of formula I-bb above is provided as a compound of formula I-bb' or formula I-bb":

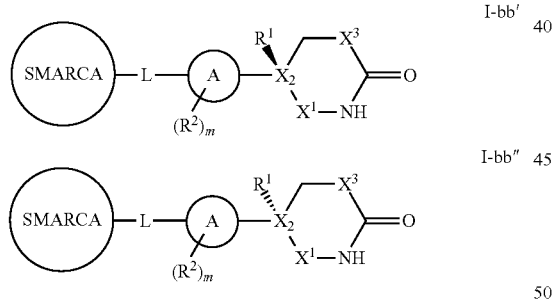

or a pharmaceutically acceptable salt thereof, wherein:
each of SMARCA, Ring A, L, R$^1$, R$^2$, X$^1$, X$^2$, X$^3$, and m is as defined above.

In certain embodiments, the present invention provides a compound of Formula I, wherein LBM is an E3 ubiquitin ligase (cereblon) binding moiety thereby forming a compound of formula I-cc:

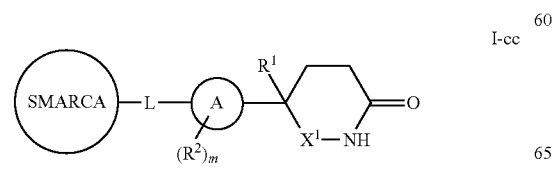

or a pharmaceutically acceptable salt thereof, wherein L and SMARCA are as defined above and described in embodiments herein, and wherein:

X$^1$ is a bivalent moiety selected from a covalent bond, —CH$_2$—, —C(O)—, —C(S)—, or

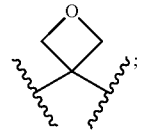 [SMILES: *C1(*)COC1]

R$^1$ is hydrogen, deuterium, halogen, —CN, —OR, —SR, —S(O)R, —S(O)$_2$R, —NR$_2$, or an optionally substituted C$_{1-4}$ aliphatic;

each R$^2$ is independently hydrogen, —R$^6$, halogen, —CN, —NO$_2$, —OR, SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;

Ring A is a bi- or tricyclic ring selected from

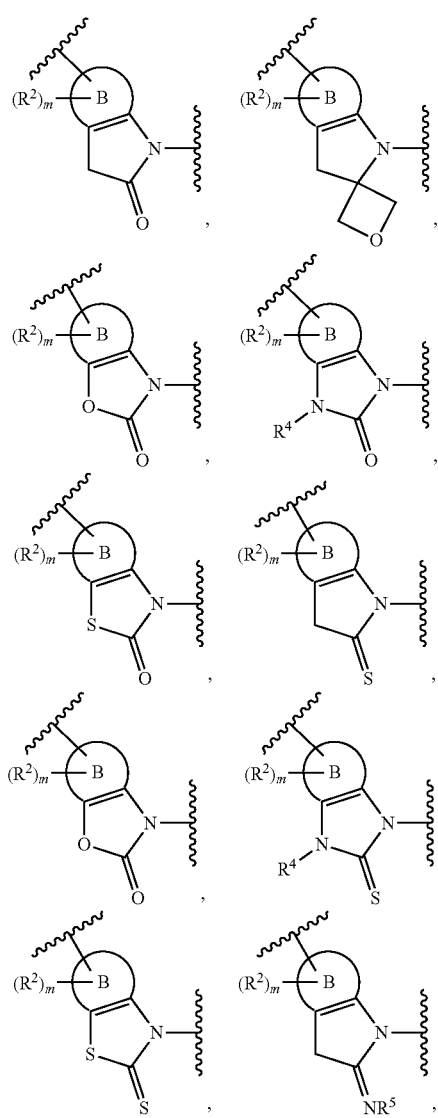

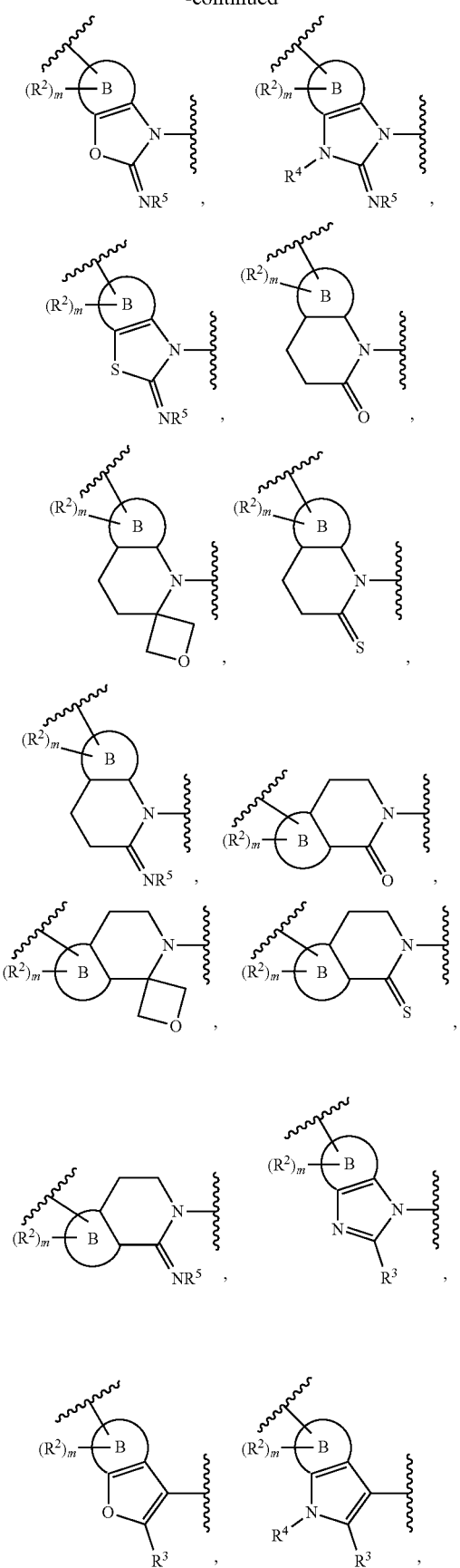
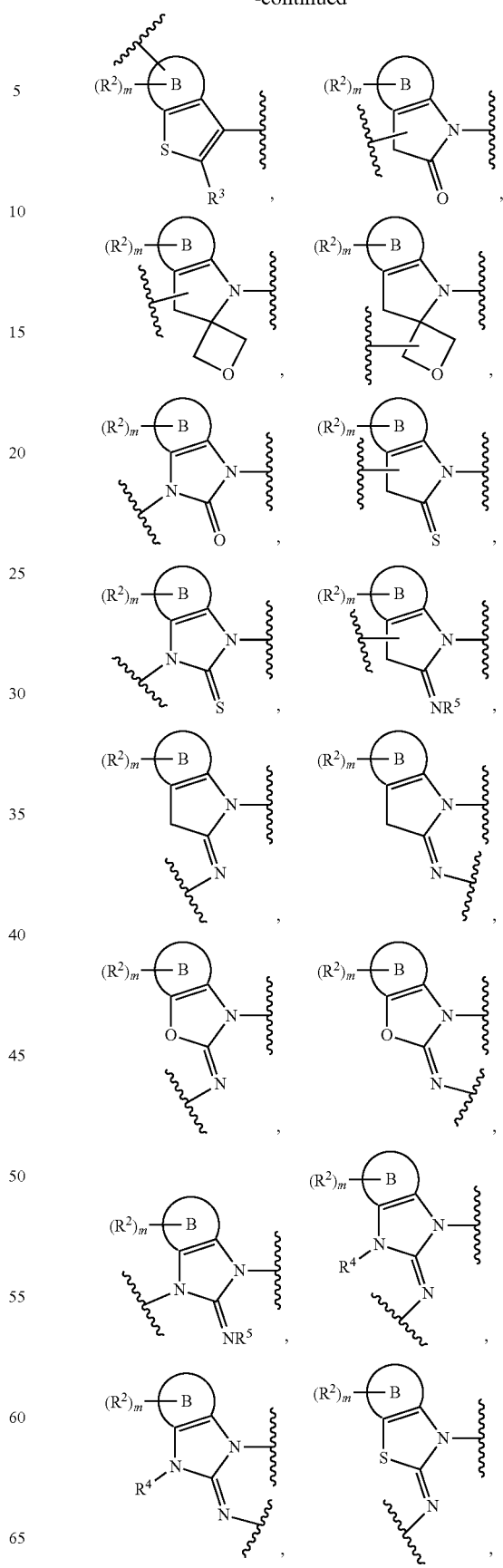

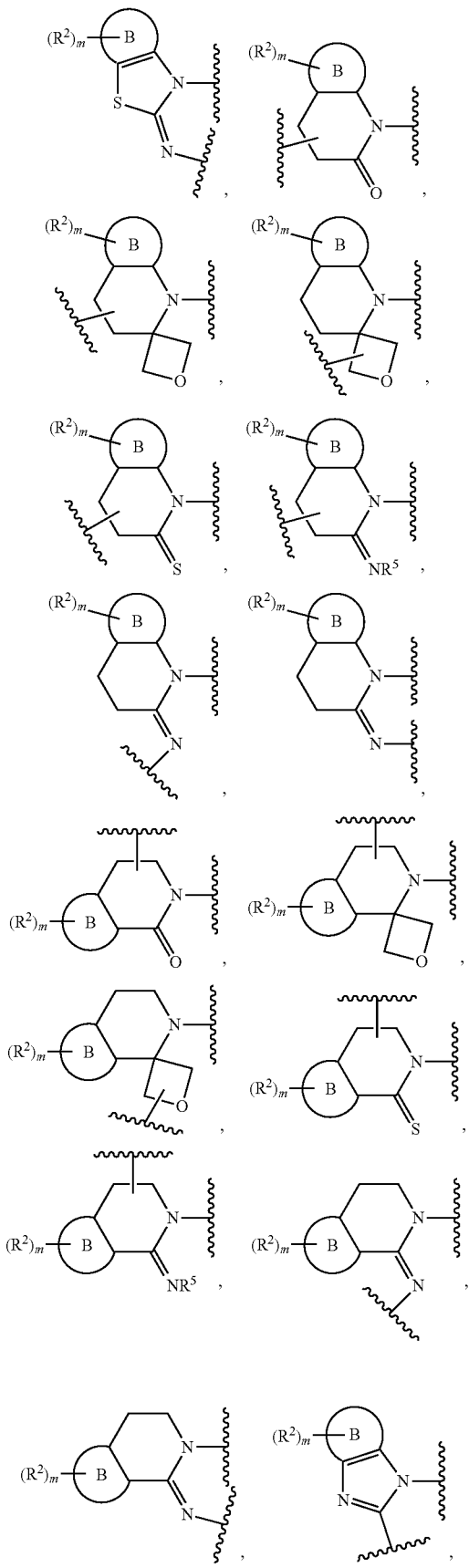

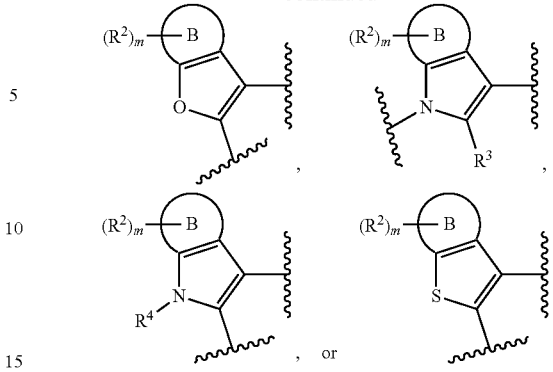

wherein
Ring B is a fused ring selected from 6-membered aryl, 6-membered heteroaryl containing 1-4 heteroatoms independently selected from nitrogen, oxygen, and sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur;

$R^3$ is selected from hydrogen, halogen, —OR, —N(R)$_2$, or —SR;

each $R^4$ is independently hydrogen, —$R^6$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;

$R^5$ is hydrogen, $C_{1-4}$ aliphatic, or —CN;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

m is 0, 1, 2, 3 or 4; and each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:
two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

Where a point of attachment of —(R$^2$)$_m$ is depicted on Ring B, it is intended, and one of ordinary skill in the art would appreciate, that the point of attachment of —(R$^2$)$_m$ may be on Ring A and may also be at any available carbon or nitrogen atom on Ring A including the ring to which Ring B is fused. Where —R$^2$ is attached to a nitrogen atom bound to R$^4$ or R$^5$, R$^4$ or R$^5$ is absent and —R$^2$ takes the place of the R$^4$ or R$^5$ group. Where —R$^2$ is attached to a carbon atom bound to R$^3$, R$^3$ is absent and —R$^2$ takes the place of the R$^3$ group.

In some embodiments, the compound of formula I-cc above is provided as a compound of formula I-cc' or formula I-cc":

I-cc'

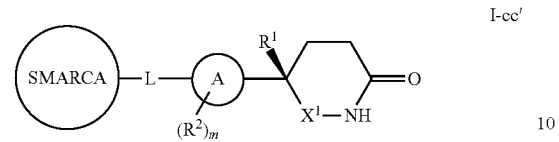

I-cc"

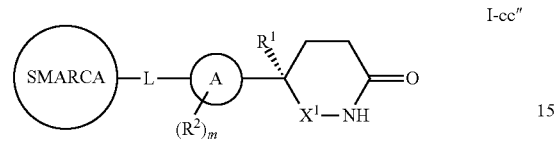

or a pharmaceutically acceptable salt thereof, wherein:
each of SMARCA, Ring A, L, $R^1$, $R^2$, $X^1$, and m is as defined above.

In certain embodiments, the present invention provides a compound of formula I, wherein LBM is an E3 ubiquitin ligase (cereblon) binding moiety thereby forming a compound of formula I-dd:

I-dd

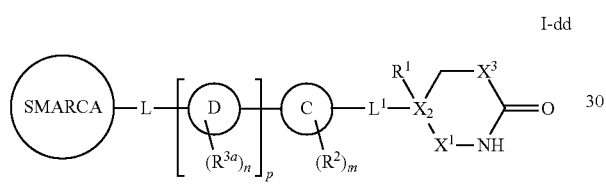

or a pharmaceutically acceptable salt thereof, wherein, L and SMARCA are as defined above and described in embodiments herein, and wherein:

$X^1$ is a bivalent moiety selected from a covalent bond, —CH$_2$—, —CHCF$_3$—, —SO$_2$—, —S(O)—, —P(O)R—, —P(O)OR—, —P(O)NR$_2$—, —C(O)—, —C(S)—, or

$X^2$ is a carbon atom or silicon atom;
$X^3$ is a bivalent moiety selected from —CR$_2$—, —NR—, —O—, —S—, or —Si(R$_2$)—;
$R^1$ is hydrogen, deuterium, halogen, —CN, —OR, —SR, —S(O)R, —S(O)$_2$R, —NR$_2$, —P(O)(OR)$_2$, —P(O)(NR$_2$)OR, —P(O)(NR$_2$)$_2$, —Si(OH)$_2$R, —Si(OH)(R)$_2$, —Si(R)$_3$, or an optionally substituted C$_{1-4}$ aliphatic;
Ring C is a mono- or bicyclic ring selected from

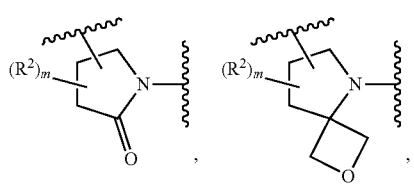

-continued

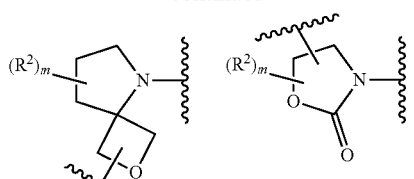

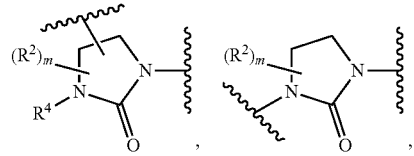

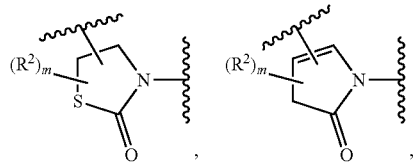

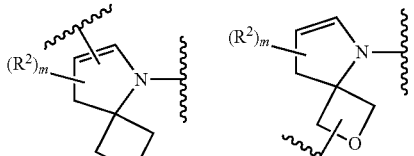

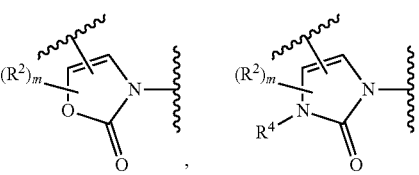

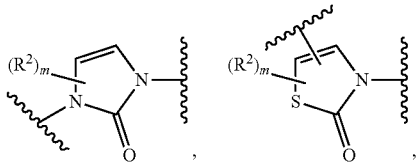

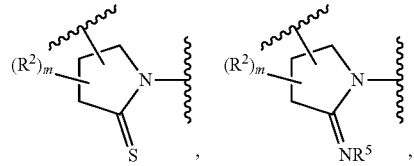

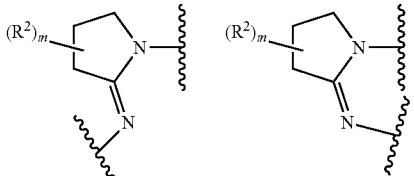

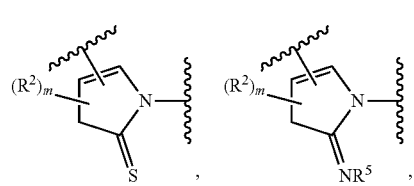

-continued

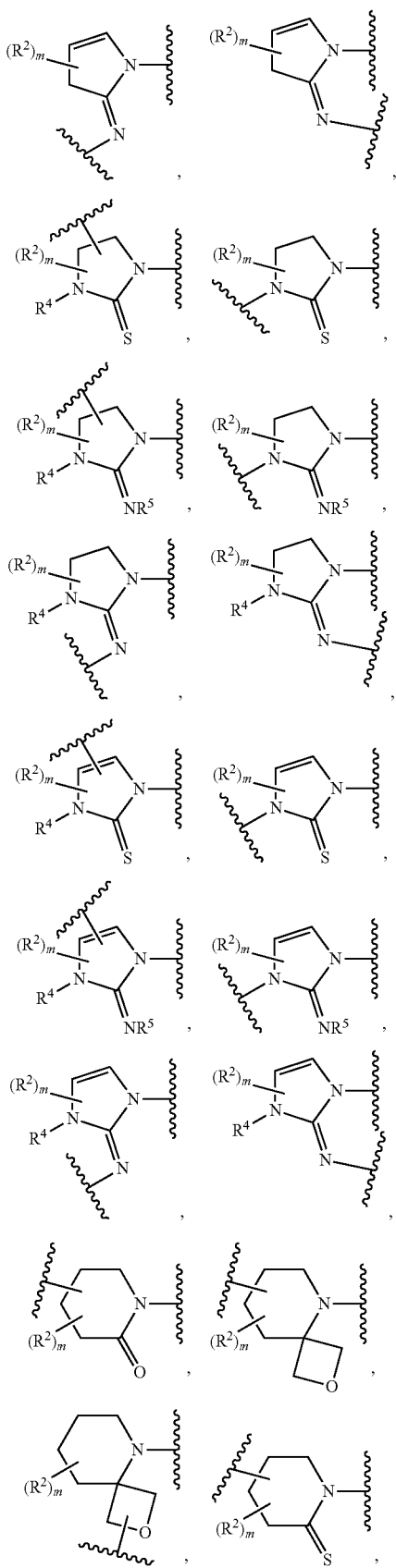

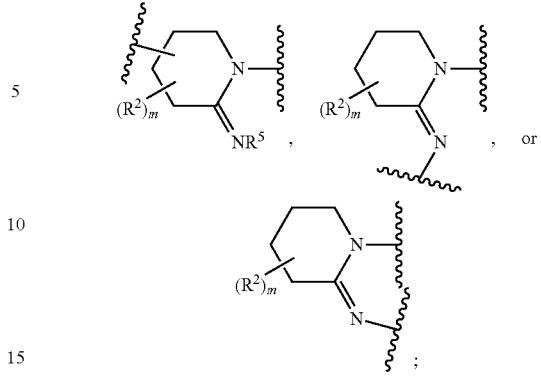

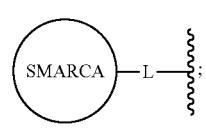

each of $R^2$ and $R^{3a}$ is independently hydrogen, deuterium, —$R^6$, halogen, —CN, —$NO_2$, —OR, —SR, —$N(R)_2$, —$Si(R)_3$, —$S(O)_2R$, —$S(O)_2N(R)_2$, —S(O)R, —C(O)R, —C(O)OR, —C(O)N(R)$_2$, —C(O)N(R)OR, —C(R)$_2$N(R)C(O)R, —C(R)$_2$N(R)C(O)N(R)$_2$, —OC(O)R, —OC(O)N(R)$_2$, —OP(O)R$_2$, —OP(O)(OR)$_2$, —OP(O)(OR)(NR$_2$), —OP(O)(NR$_2$)$_2$—, —N(R)C(O)OR, —N(R)C(O)R, —N(R)C(O)N(R)$_2$, —N(R)S(O)$_2$R, —NP(O)R$_2$, —N(R)P(O)(OR)$_2$, —N(R)P(O)(OR)(NR$_2$), —N(R)P(O)(NR$_2$)$_2$, or —N(R)S(O)$_2$R;

Ring D is selected from a 6-membered aryl, 6-membered heteroaryl containing 1-4 heteroatoms independently selected from nitrogen, oxygen, and sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur;

each $R^4$ is independently hydrogen, —$R^6$, halogen, —CN, —$NO_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;

$R^5$ is hydrogen, $C_{1-4}$ aliphatic, or —CN;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

$L^1$ is a covalent bond or a $C_{1-3}$ bivalent straight or branched saturated or unsaturated hydrocarbon chain wherein 1-2 methylene units of the chain are independently and optionally replaced with —O—, —C(O)—, —C(S)—, —C(R)$_2$—, —CF(R)—, —C(F)$_2$—, —N(R)—, —S—, —S(O)$_2$— or —(C)=CH—;

m is 0, 1, 2, 3 or 4;

n is 0, 1, 2, 3 or 4;

p is 0 or 1, wherein when p is 0, the bond connecting Ring C and Ring D is connected to and each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, a compound of formula I-dd above is provided as a compound of formula I-dd' or formula I-dd":

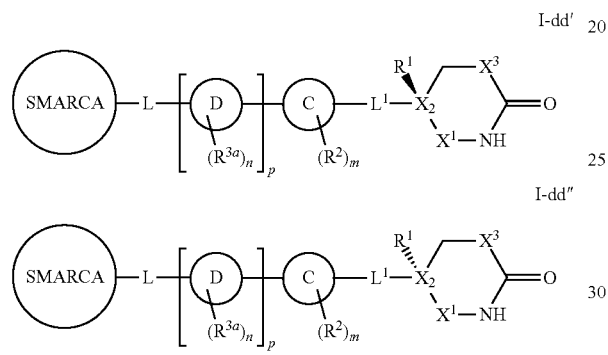

I-dd'

I-dd"

or a pharmaceutically acceptable salt thereof, wherein:
each of SMARCA, Ring C, Ring D, L, $L^1$, $R^1$, $R^2$, $R^{3a}$, $X^1$, $X^2$, $X^3$, n, m, and p is as defined above.

In certain embodiments, the present invention provides a compound of Formula I, wherein LBM is an E3 ubiquitin ligase (cereblon) binding moiety thereby forming a compound of formula I-ee:

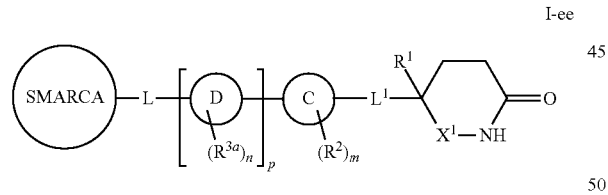

I-ee or a pharmaceutically acceptable salt thereof, wherein L and SMARCA are as defined above and described in embodiments herein, and wherein:

$X^1$ is a bivalent moiety selected from a covalent bond, —$CH_2$—, —C(O)—, —C(S)—, or

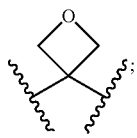 [SMILES: *C1(*)COC1]

$R^1$ is hydrogen, deuterium, halogen, —CN, —OR, —SR, —S(O)R, —S(O)$_2$R, —NR$_2$, or an optionally substituted $C_{1-4}$ aliphatic;

Ring C is a mono- or bicyclic ring selected from

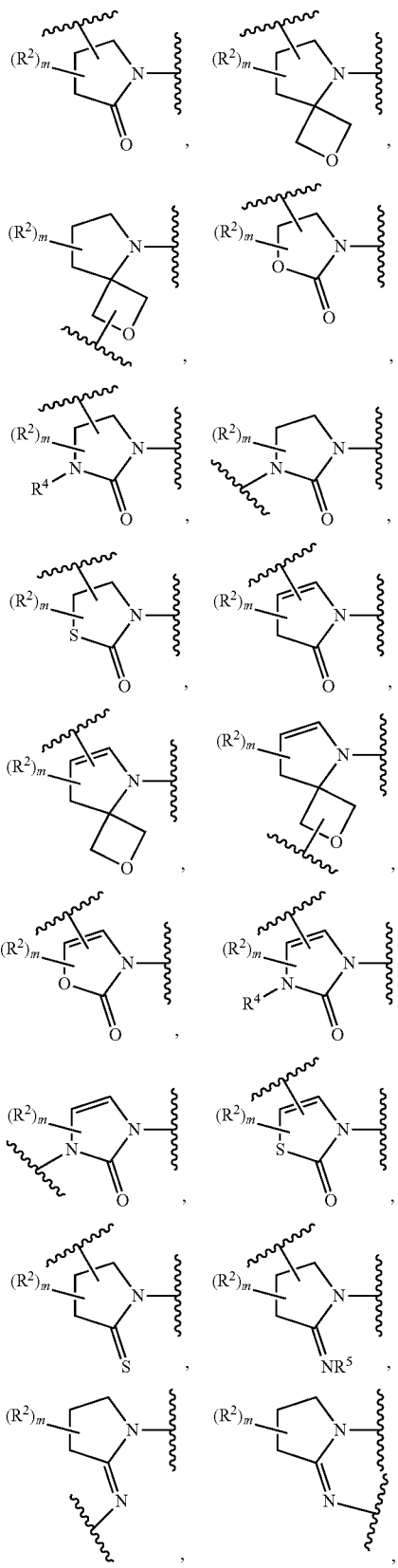

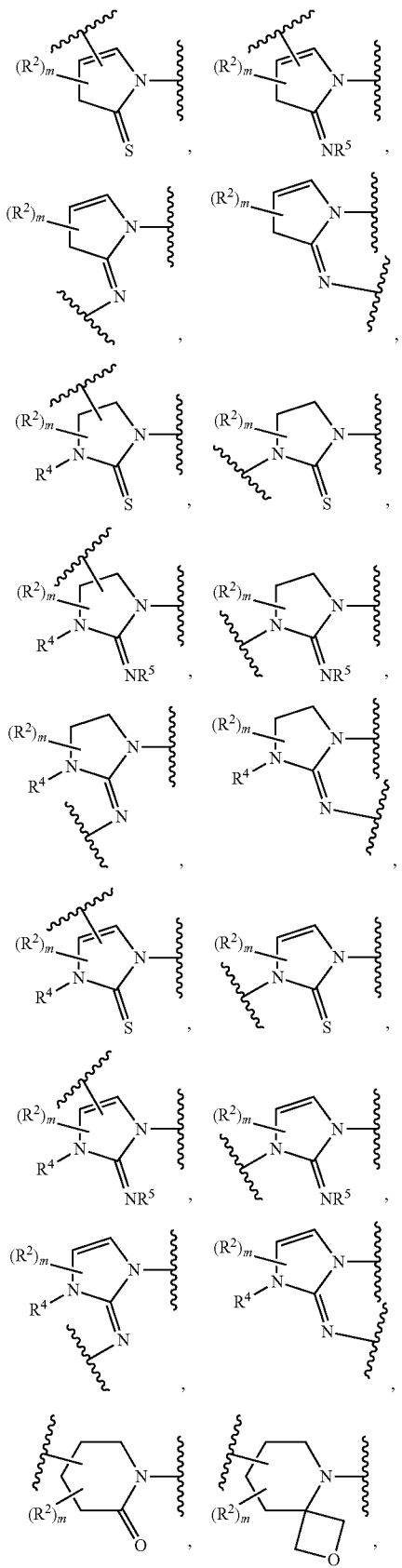

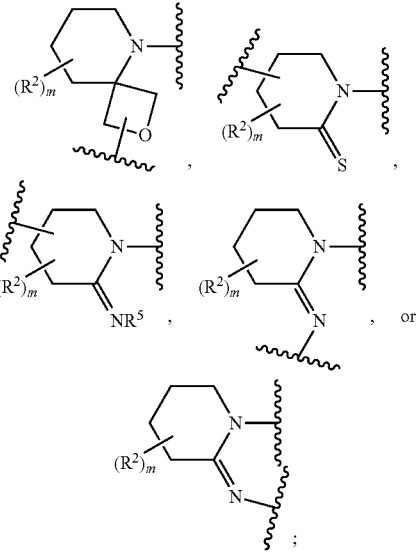

, or

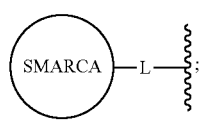

;

each of $R^2$ and $R^{3a}$ is independently hydrogen, —$R^6$, halogen, —CN, —$NO_2$, —OR, —SR, —$NR_2$, —$S(O)_2R$, —$S(O)_2NR_2$, —S(O)R, —C(O)R, —C(O)OR, $C(O)NR_2$, —C(O)N(R)OR, —OC(O)R, —$OC(O)NR_2$, —N(R)C(O)OR, —N(R)C(O)R, —$N(R)C(O)NR_2$, or —$N(R)S(O)_2R$;

Ring D is selected from 6-membered aryl, 6-membered heteroaryl containing 1-4 heteroatoms independently selected from nitrogen, oxygen, and sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur;

each $R^4$ is independently hydrogen, —$R^6$, halogen, —CN, —$NO_2$, —OR, —SR, —$NR_2$, —$S(O)_2R$, —$S(O)_2NR_2$, —S(O)R, —C(O)R, —C(O)OR, $C(O)NR_2$, —C(O)N(R) OR, —OC(O)R, —$OC(O)NR_2$, —N(R)C(O)OR, —N(R) C(O)R, —$N(R)C(O)NR_2$, or —$N(R)S(O)_2R$;

$R^5$ is hydrogen, $C_{1-4}$ aliphatic, or —CN;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

m is 0, 1, or 2;

n is 0, 1, 2, 3 or 4;

p is 0 or 1, wherein when p is 0, the bond connecting Ring C and Ring D is connected to and each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, a compound of formula I-ee above is provided as a compound of formula I-ee' or formula I-ee":

I-ee'

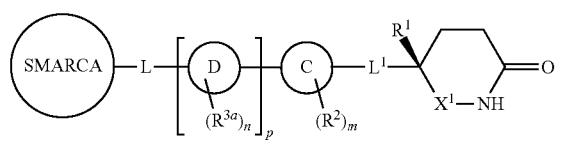

I-ee"

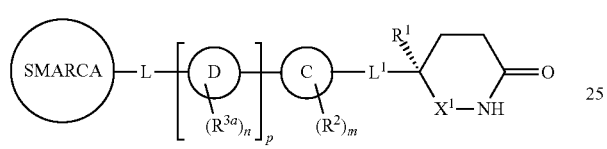

or a pharmaceutically acceptable salt thereof, wherein:
each of SMARCA, Ring C, Ring D, L, $R^1$, $R^2$, $R^{3a}$, $X^1$, n, m, and p is as defined above.

In certain embodiments, the present invention provides a compound of formula I, wherein LBM is an E3 ubiquitin ligase (cereblon) binding moiety thereby forming a compound of formula I-ff:

I-ff

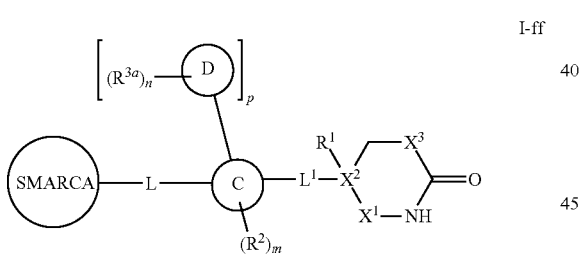

or a pharmaceutically acceptable salt thereof, wherein L and SMARCA are as defined above and described in embodiments herein, and wherein:
$X^1$ is a bivalent moiety selected from a covalent bond, —$CH_2$—, —$CHCF_3$—, —$SO_2$—, —$S(O)$—, —$P(O)R$—, —$P(O)OR$—, —$P(O)NR_2$—, —$C(O)$—, —$C(S)$—, or

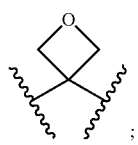
;

$X^2$ is a carbon atom or silicon atom;
$X^3$ is a bivalent moiety selected from —$CR_2$—, —NR—, —O—, —S—, or —$Si(R_2)$—;

$R^1$ is hydrogen, deuterium, halogen, —CN, —OR, —SR, —S(O)R, —$S(O)_2R$, —$NR_2$, —$P(O)(OR)_2$, —$P(O)(NR_2)$OR, —$P(O)(NR_2)_2$, —$Si(OH)_2R$, —$Si(OH)(R)_2$, —$Si(R)_3$, or an optionally substituted $C_{1-4}$ aliphatic;

Ring C is a mono- or bicyclic ring selected from

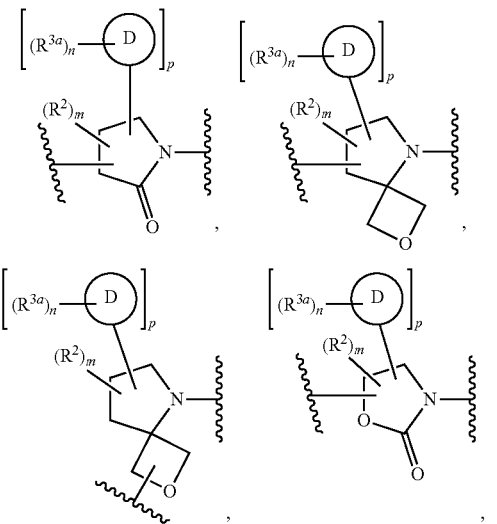

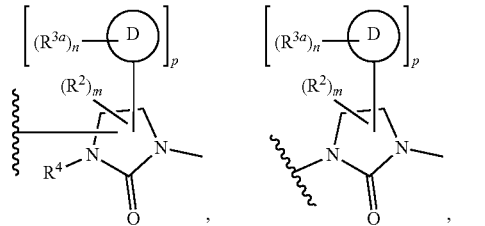

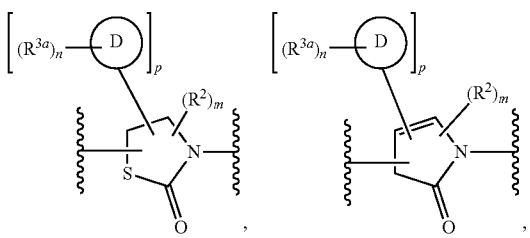

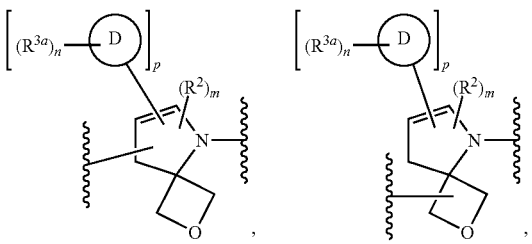

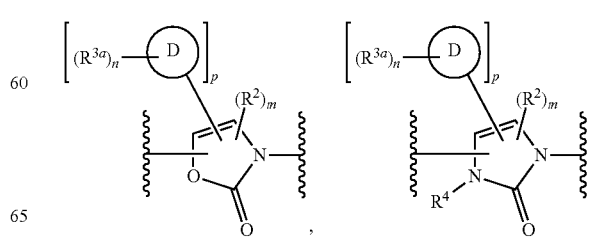

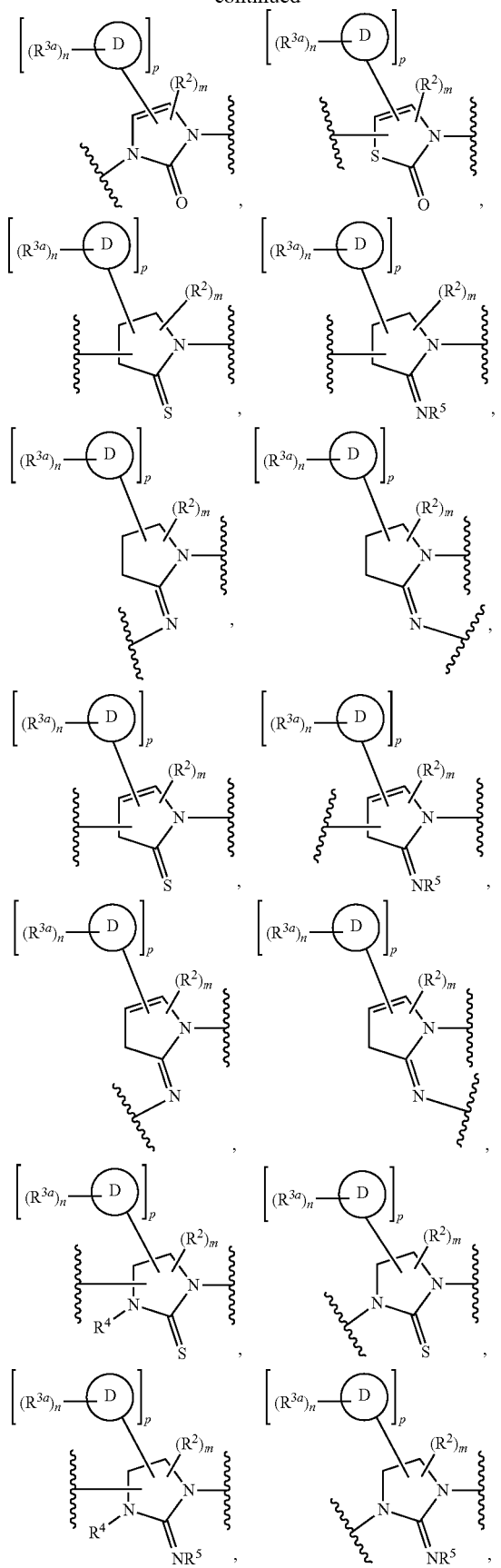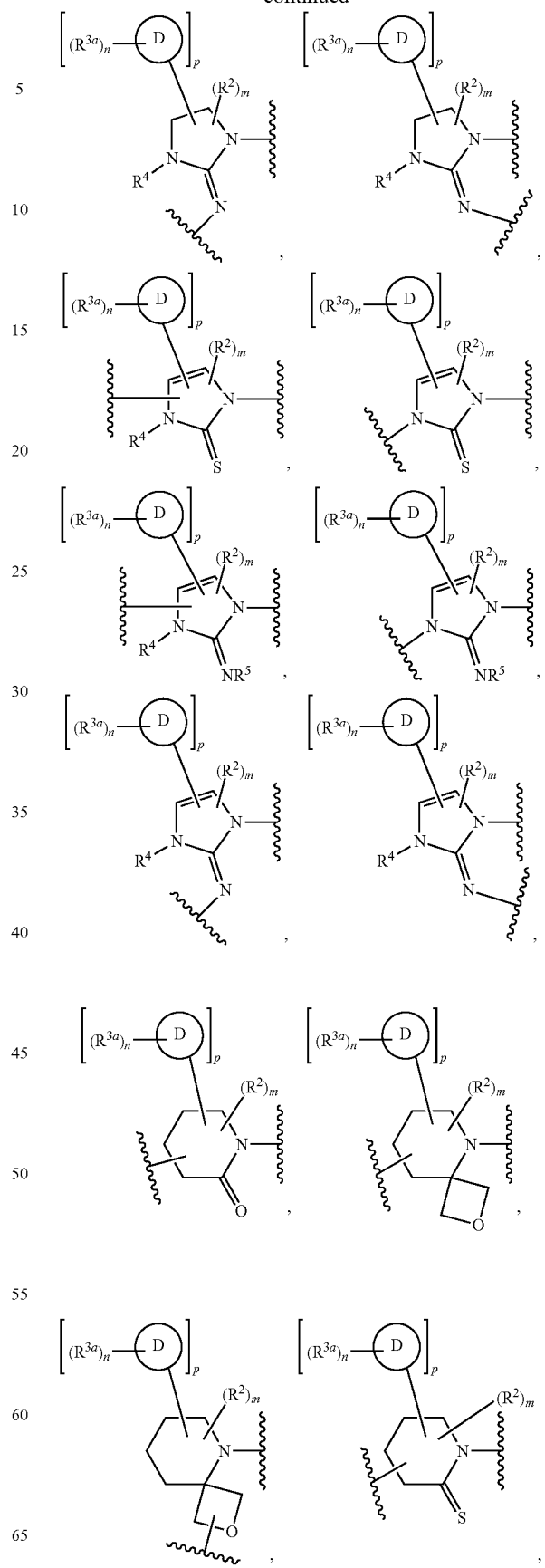

-continued

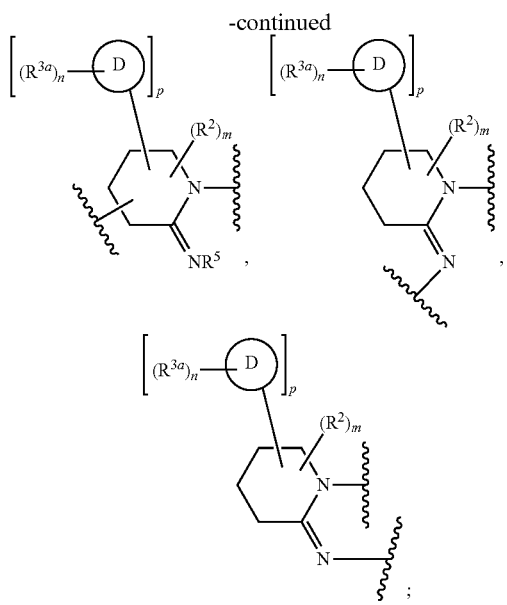

each or R² and R³ᵃ is independently hydrogen, deuterium, —R⁶, halogen, —CN, —NO₂, —OR, —SR, —N(R)₂, —Si(R)₃, —S(O)₂R, —S(O)₂N(R)₂, —S(O)R, —C(O)R, —C(O)OR, —C(O)N(R)₂, —C(O)N(R)OR, —C(R)₂N(R)C(O)R, —C(R)₂N(R)C(O)N(R)₂, —OC(O)R, —OC(O)N(R)₂, —OP(O)R₂, —OP(O)(OR)₂, —OP(O)(OR)(NR₂), —OP(O)(NR₂)₂—, —N(R)C(O)OR, —N(R)C(O)R, —N(R)C(O)N(R)₂, —N(R)S(O)₂R, —NP(O)R₂, —N(R)P(O)(OR)₂, —N(R)P(O)(OR)(NR₂), —N(R)P(O)(NR₂)₂, or —N(R)S(O)₂R;

Ring D is selected from 6-membered aryl, 6-membered heteroaryl containing 1-4 heteroatoms independently selected from nitrogen, oxygen, and sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur;

each R⁴ is independently hydrogen, —R⁶, halogen, —CN, —NO₂, —OR, —SR, —NR₂, —S(O)₂R, —S(O)₂NR₂, —S(O)R, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, or —N(R)S(O)₂R;

R⁵ is hydrogen, C₁₋₄ aliphatic, or —CN;

each R⁶ is independently an optionally substituted group selected from C₁₋₆ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

L¹ is a covalent bond or a C₁₋₃ bivalent straight or branched saturated or unsaturated hydrocarbon chain wherein 1-2 methylene units of the chain are independently and optionally replaced with —O—, —C(O)—, —C(S)—, —C(R)₂—, —CF(R)—, —C(F)₂—, —N(R)—, —S—, —S(O)₂— or —(C)═CH—;

m is 0, 1, 2, 3 or 4;
n is 0, 1, 2, 3 or 4;
p is 0 or 1; and each R is independently hydrogen, or an optionally substituted group selected from C₁₋₆ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, a compound of formula I-ff above is provided as a compound of formula I-ff' or formula I-ff":

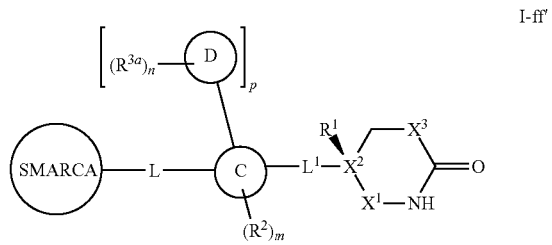

I-ff'

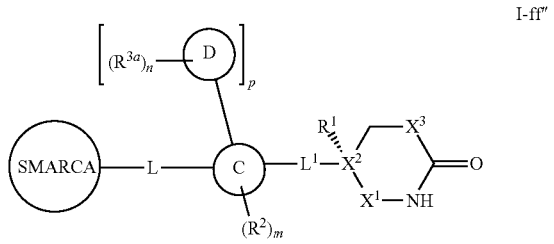

I-ff"

or a pharmaceutically acceptable salt thereof, wherein:
each of SMARCA, Ring C, Ring D, L, L¹, R¹, R², R³ᵃ, X¹, X², X³, m, n, and p is as defined above.

In certain embodiments, the present invention provides a compound of Formula I, wherein LBM is an E3 ubiquitin ligase (cereblon) binding moiety thereby forming a compound of formula I-gg:

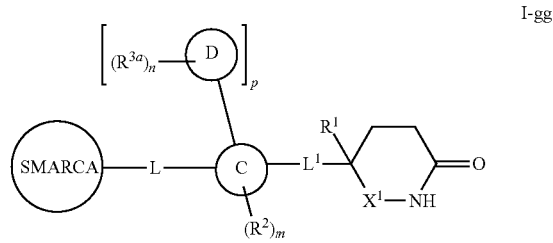

I-gg or a pharmaceutically acceptable salt thereof, wherein L and SMARCA are as defined above and described in embodiments herein, and wherein:

X¹ is a bivalent moiety selected from a covalent bond, —CH₂—, —C(O)—, —C(S)—, or

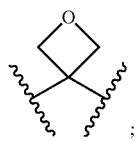
R[1] is hydrogen, deuterium, halogen, —CN, —OR, —SR, —S(O)R, —S(O)$_2$R, —NR$_2$, or an optionally substituted C$_{1-4}$ aliphatic;
Ring C is a mono- or bicyclic ring selected from
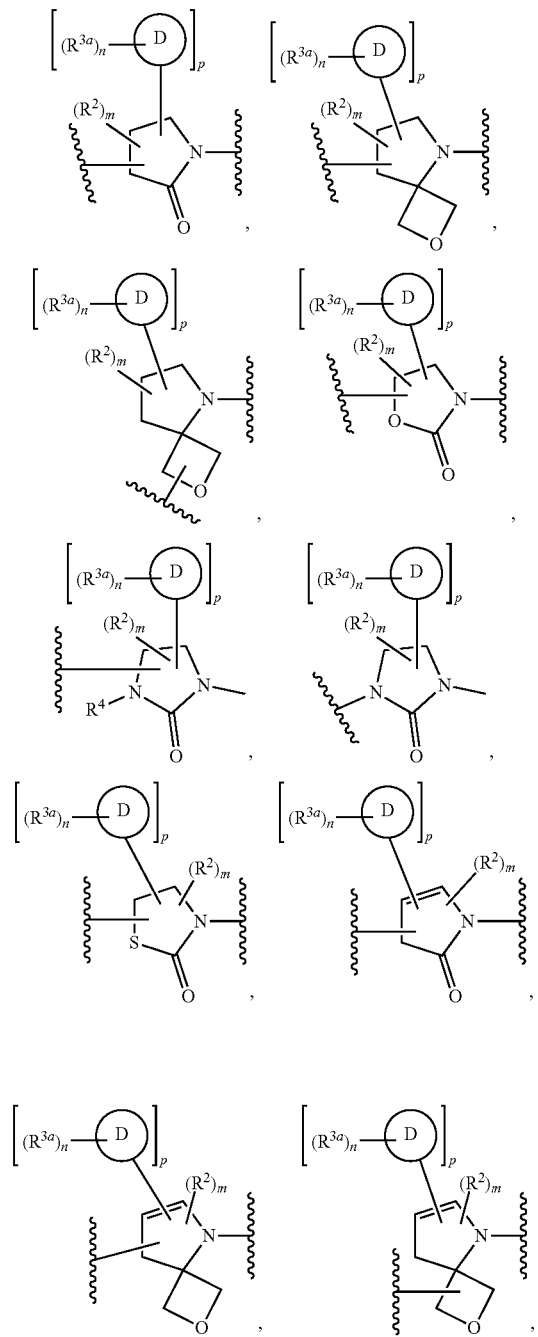
-continued
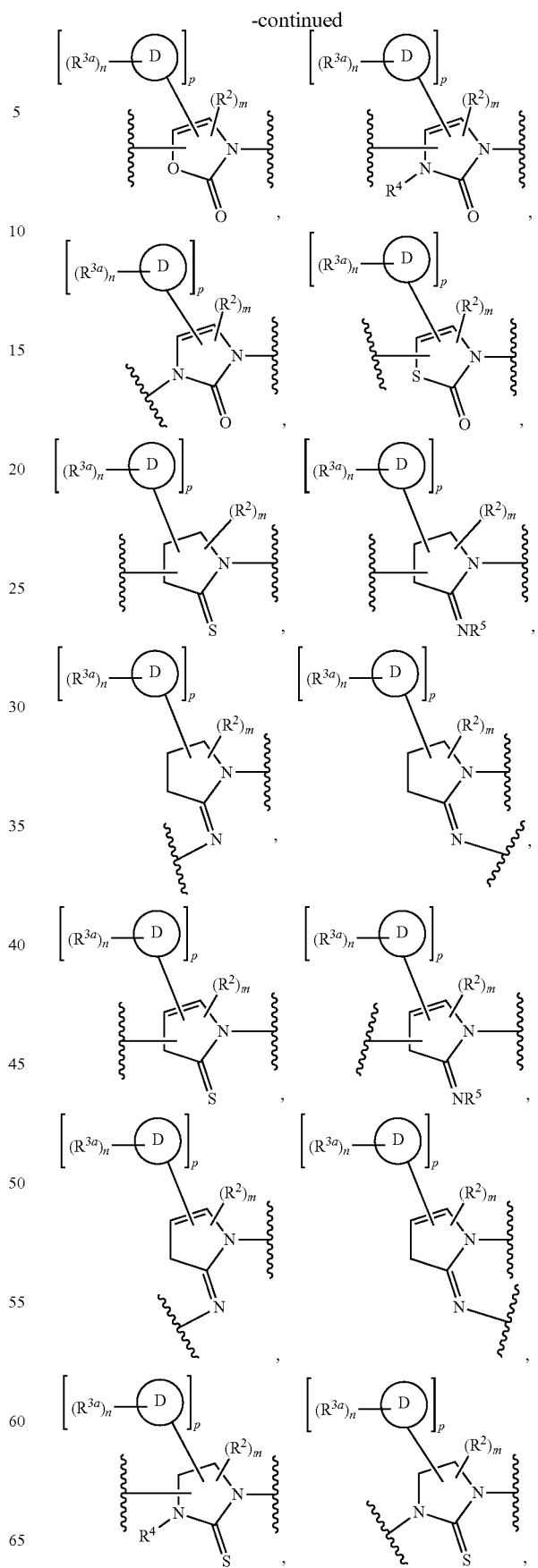

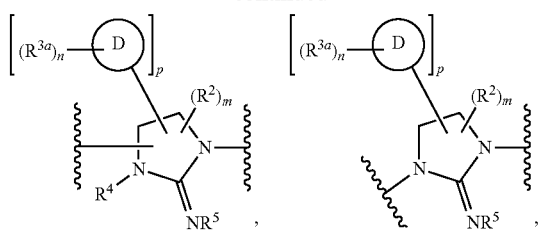

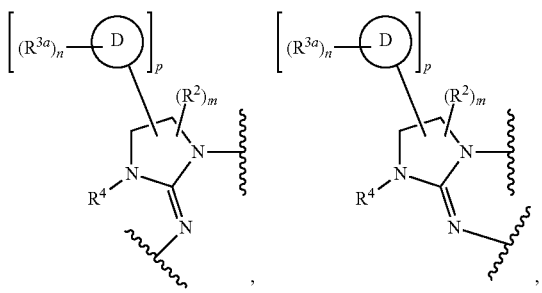

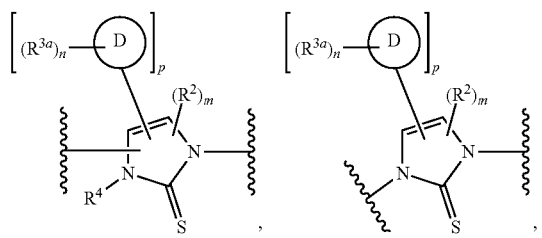

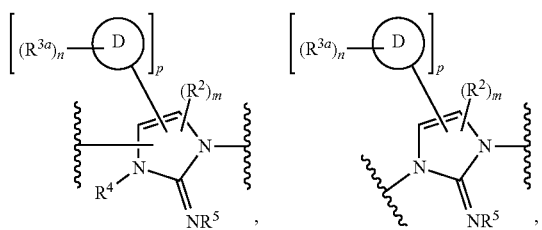

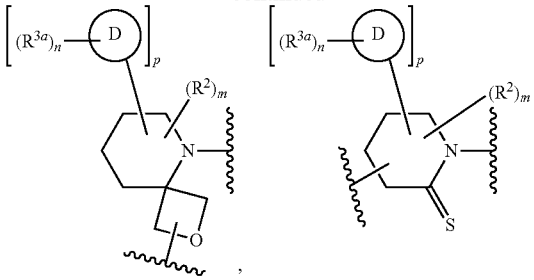

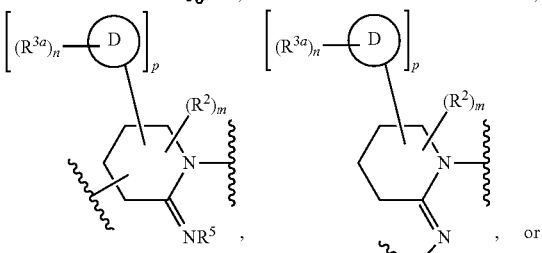

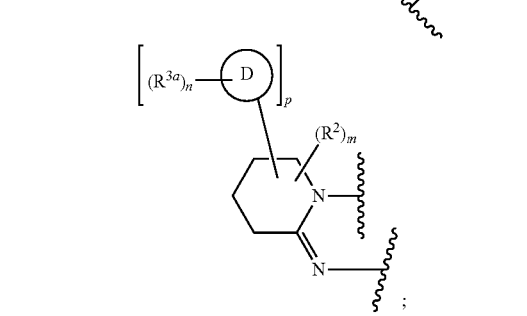

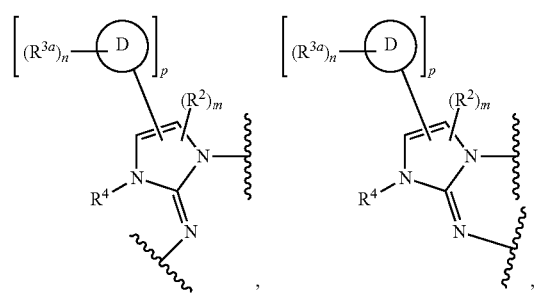

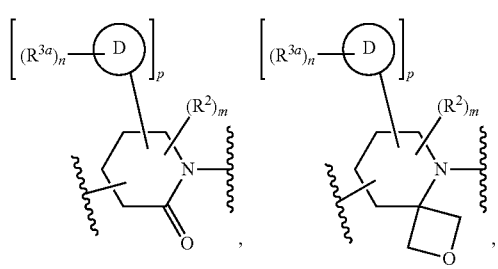

each of $R^2$, $R^{3a}$, and $R^4$ is independently hydrogen, $-R^6$, halogen, $-CN$, $-NO_2$, $-OR$, $-SR$, $-NR_2$, $-S(O)_2R$, $-S(O)_2NR_2$, $-S(O)R$, $-C(O)R$, $-C(O)OR$, $-C(O)NR_2$, $-C(O)N(R)OR$, $-OC(O)R$, $-OC(O)NR_2$, $-N(R)C(O)OR$, $-N(R)C(O)R$, $-N(R)C(O)NR_2$, or $-N(R)S(O)_2R$;

Ring D is selected from 6-membered aryl, 6-membered heteroaryl containing 1-4 heteroatoms independently selected from nitrogen, oxygen, and sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur;

$R^5$ is hydrogen, $C_{1-4}$ aliphatic, or $-CN$;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

m is 0, 1, or 2;

n is 0, 1, 2, 3, or 4;

p is 0 or 1; and each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, a compound of formula I-gg above is provided as a compound of formula I-gg' or formula I-gg":

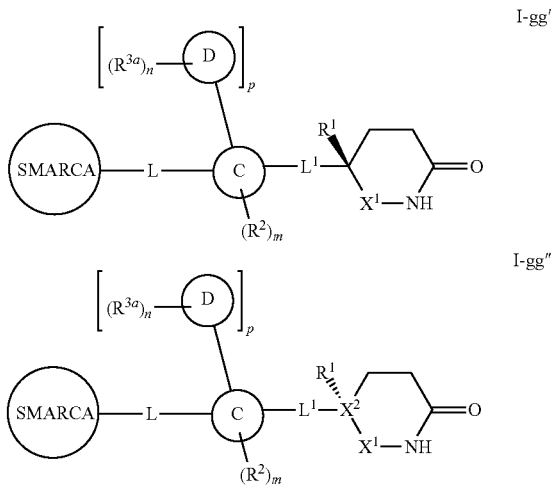

or a pharmaceutically acceptable salt thereof, wherein:
each of SMARCA, Ring C, Ring D, L, $R^1$, $R^2$, $R^{3a}$, $X^1$, m, n, and p is as defined above.

In certain embodiments, the present invention provides a compound of Formula I, wherein LBM is an E3 ubiquitin ligase (cereblon) binding moiety thereby forming a compound of formula I-hh:

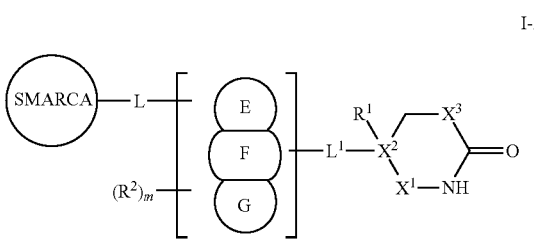

or a pharmaceutically acceptable salt thereof, wherein L and SMARCA are as defined above and described in embodiments herein, and wherein:

$X^1$ is a bivalent moiety selected from a covalent bond, —$CH_2$—, —$CHCF_3$—, —$SO_2$—, —S(O)—, —P(O)R—, —P(O)OR—, —P(O)$NR_2$—, —C(O)—, —C(S)—, or

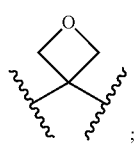
;

$X^2$ is a carbon atom, nitrogen atom, or silicon atom;

$X^3$ is a bivalent moiety selected from a covalent bond, —$CR_2$—, —NR—, —O—, —S—, or —$SiR_2$—;

$R^1$ is absent, hydrogen, deuterium, halogen, —CN, —OR, —SR, —S(O)R, —S(O)$_2$R, —$NR_2$, —P(O)(OR)$_2$, —P(O)($NR_2$)OR, —P(O)($NR_2$)$_2$, —Si(OH)$_2$R, —Si(OH)$R_2$, —$SiR_3$, or an optionally substituted $C_{1-4}$ aliphatic;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently hydrogen, deuterium, —$R^6$, halogen, —CN, —$NO_2$, —OR, —SR, —$NR_2$, —$SiR_3$, —S(O)$_2$R, —S(O)$_2NR_2$, —S(O)R, —C(O)R, —C(O)OR, —C(O)$NR_2$, —C(O)N(R)OR, —C(R)$_2$N(R)C(O)R, —C(R)$_2$N(R)C(O)N(R)$_2$, —OC(O)R, —OC(O)N(R)$_2$, —OP(O)$R_2$, —OP(O)(OR)$_2$, —OP(O)(OR)$NR_2$, —OP(O)($NR_2$)$_2$, —N(R)C(O)OR, —N(R)C(O)R, —N(R)C(O)$NR_2$, —N(R)S(O)$_2$R, —NP(O)$R_2$, —N(R)P(O)(OR)$_2$, —N(R)P(O)(OR)$NR_2$, —N(R)P(O)($NR_2$)$_2$, or —N(R)S(O)$_2$R;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

each of Ring E, Ring F, and Ring G is independently a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur;

$L^1$ is a covalent bond or a $C_{1-3}$ bivalent straight or branched saturated or unsaturated hydrocarbon chain wherein 1-2 methylene units of the chain are independently and optionally replaced with —O—, —C(O)—, —C(S)—, —C(R)$_2$—, —CF(R)—, —C(F)$_2$—, —N(R)—, —S—, —S(O)$_2$— or —(C)=CH—; and m is 0, 1, 2, 3, 4, 5, 6, 7, 8, 9, 10, 11, 12, 13, 14, 15, or 16.

Where a point of attachment of

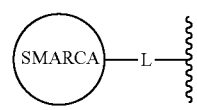

is depicted on Ring E, Ring F, or Ring G, it is intended, and one of ordinary skill in the art would appreciate, that the point of attachment of

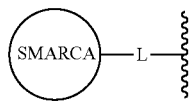

may be on any available carbon or nitrogen atom on Ring E, Ring F, or Ring G, including the ring to which Ring E or Ring G is fused to Ring F.

Where a point of attachment of —(R$^2$)$_m$ is depicted on Ring E, Ring F, or Ring G, it is intended, and one of ordinary skill in the art would appreciate, that the point of attachment of —(R$^2$)$_m$ may be at any available carbon or nitrogen atom on Ring E, Ring F, or Ring G including the carbon atom to which Ring F or Ring H are fused to Ring G.

Where a point of attachment of

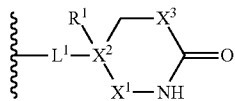

is depicted on Ring E, Ring F, or Ring G, it is intended, and one of ordinary skill in the art would appreciate, that the point of attachment of

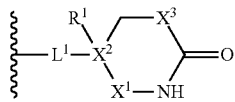

may be on any available carbon or nitrogen atom on Ring E, Ring F, or Ring G, including the carbon atom to which Ring F or Ring H are fused to Ring G.

In some embodiments, a compound of formula I-hh above is provided as a compound of formula I-hh' or formula I-hh":

I-hh'

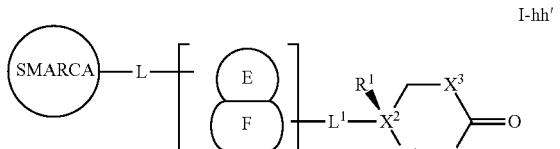

I-hh"

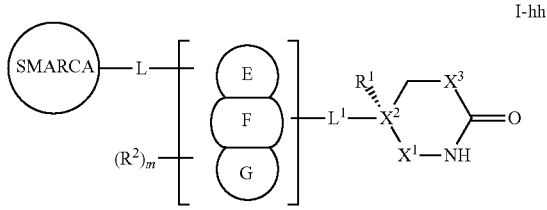

or a pharmaceutically acceptable salt thereof, wherein:
each of SMARCA, Ring E, Ring F, Ring G, L, L$^1$, R$^1$, R$^2$, X$^1$, X$^2$, X$^3$, and m is as defined above.

In certain embodiments, the present invention provides a compound of Formula I, wherein LBM is an E3 ubiquitin ligase (cereblon) binding moiety thereby forming a compound of formula I-hh-1 or I-hh-2:

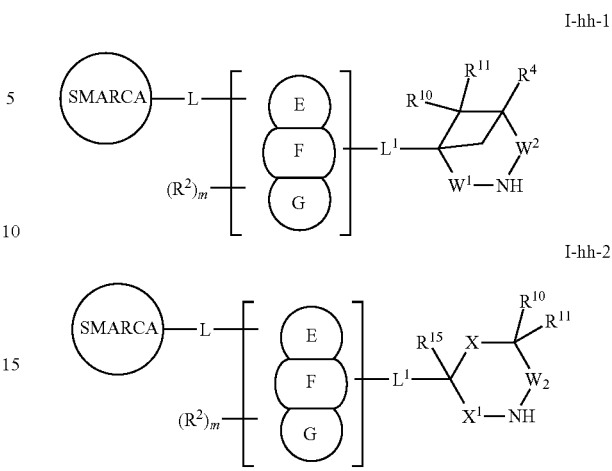

or a pharmaceutically acceptable salt thereof, wherein F and SMARCA are as defined above and described in embodiments herein, and wherein:

each R$^2$ is independently hydrogen, deuterium, —R$^6$, halogen, —CN, —NO$_2$, —OR, —SR, —NR$_2$, —SiR$_3$, —S(O)$_2$R, —S(O)$_2$NR$_2$, —S(O)R, —C(O)R, —C(O)OR, —C(O)NR$_2$, —C(O)N(R)OR, —C(R)$_2$N(R)C(O)R, —C(R)$_2$N(R)C(O)N(R)$_2$, —OC(O)R, —OC(O)N(R)$_2$, —OP(O)R$_2$, —OP(O)(OR)$_2$, —OP(O)(OR)NR$_2$, —OP(O)(NR$_2$)$_2$—, —N(R)C(O)OR, —N(R)C(O)R, —N(R)C(O)NR$_2$, —N(R)S(O)$_2$R, —NP(O)R$_2$, —N(R)P(O)(OR)$_2$, —N(R)P(O)(OR)NR$_2$, —N(R)P(O)(NR$_2$)$_2$, or —N(R)S(O)$_2$R;

each R$^6$ is independently an optionally substituted group selected from C$_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

each of Ring E, Ring F, and Ring G is independently a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur;

each R is independently hydrogen, or an optionally substituted group selected from C$_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

L$^1$ is a covalent bond or a C$_{1-3}$ bivalent straight or branched saturated or unsaturated hydrocarbon chain wherein 1-2 methylene units of the chain are independently and optionally replaced with —O—, —C(O)—, —C(S)—, —C(R)$_2$—, —CF(R)—, —C(F)$_2$—, —N(R)—, —S—, —S(O)$_2$— or —(C)=CH—;

m is 0, 1, 2, 3, 4, 5, 6, 7, 8, 9, 10, 11, 12, 13, 14, 15, or 16; and

R$^4$, R$^{10}$, R$^{11}$, R$^{15}$, W$^1$, W$^2$, and X is as defined in WO 2019/099868, the entirety of each of which is herein incorporated by reference.

Where a point of attachment of

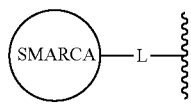

is depicted on Ring E, Ring F, or Ring G, it is intended, and one of ordinary skill in the art would appreciate, that the point of attachment of

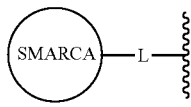

may be on any available carbon or nitrogen atom on Ring E, Ring F, or Ring G, including the ring to which Ring E or Ring G is fused to Ring F.

Where a point of attachment of —(R$^2$)$_m$ is depicted on Ring E, Ring F, or Ring G, it is intended, and one of ordinary skill in the art would appreciate, that the point of attachment of —(R$^2$)$_m$ may be at any available carbon or nitrogen atom on Ring E, Ring F, or Ring G including the carbon atom to which Ring F or Ring H are fused to Ring G.

Where a point of attachment of

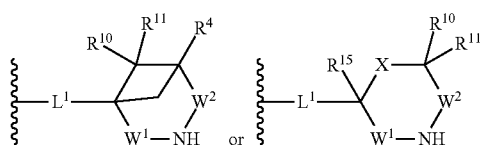

is depicted on Ring E, Ring F, or Ring G, it is intended, and one of ordinary skill in the art would appreciate, that the point of attachment of

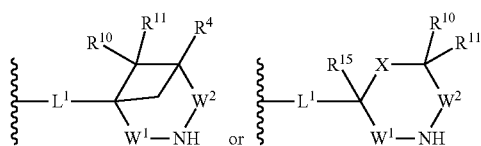

may be on any available carbon or nitrogen atom on Ring E, Ring F, or Ring G, including the carbon atom to which Ring F or Ring H are fused to Ring G.

In certain embodiments, the present invention provides a compound of Formula I, wherein LBM is an E3 ubiquitin ligase (cereblon) binding moiety thereby forming a compound of formula I-ii:

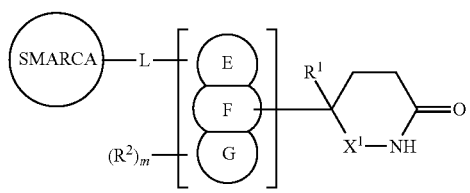

I-ii or a pharmaceutically acceptable salt thereof, wherein F and SMARCA are as defined above and described in embodiments herein, and wherein:

X$^1$ is a bivalent moiety selected from a covalent bond, —CH$_2$—, —C(O)—, —C(S)—, or

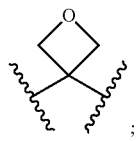 [SMILES: *C1(*)COC1]

;

R$^1$ is hydrogen, deuterium, halogen, —CN, —OR, —SR, —S(O)R, —S(O)$_2$R, —N(R)$_2$, —Si(R)$_3$, or an optionally substituted C$_{1-4}$ aliphatic;

each R is independently hydrogen, or an optionally substituted group selected from C$_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each R$^2$ is independently hydrogen, deuterium, —R$^6$, halogen, —CN, —NO$_2$, —OR, —SR, —N(R)$_2$, —Si(R)$_3$, —S(O)$_2$R, —S(O)$_2$N(R)$_2$, —S(O)R, —C(O)R, —C(O)OR, —C(O)N(R)$_2$, —C(O)N(R)OR, —C(R)$_2$N(R)C(O)R, —C(R)$_2$N(R)C(O)N(R)$_2$, —OC(O)R, —OC(O)N(R)$_2$, N(R)C(O)OR, —N(R)C(O)R, —N(R)C(O)N(R)$_2$, or —N(R)S(O)$_2$R;

each R$^6$ is independently an optionally substituted group selected from C$_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

each of Ring E, Ring F, and Ring G is independently a fused ring selected from 6-membered aryl containing 0-3 nitrogens, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-3 heteroatoms independently selected from nitrogen, oxygen or sulfur; and m is 0, 1, 2, 3, or 4.

Where a point of attachment of

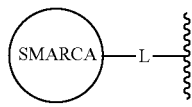

is depicted on Ring E, Ring F, or Ring G, it is intended, and one of ordinary skill in the art would appreciate, that the point of attachment of

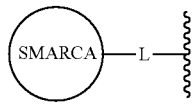

may be on any available carbon or nitrogen atom on Ring E, Ring F, or Ring G, including the ring to which Ring E or Ring G is fused to Ring F.

Where a point of attachment of $-(R^2)_m$ is depicted on Ring E, Ring F, or Ring G, it is intended, and one of ordinary skill in the art would appreciate, that the point of attachment of $-(R^2)_m$ may be at any available carbon or nitrogen atom on Ring E, Ring F, or Ring G including the carbon atom to which Ring F or Ring H are fused to Ring G.

In some embodiments, a compound of formula I-ii above is provided as a compound of formula I-ii' or formula I-ii":

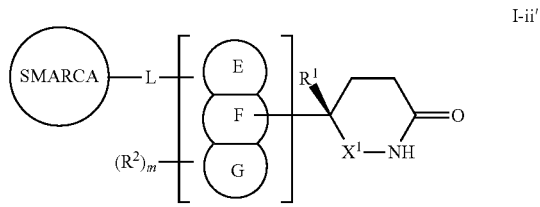

I-ii'

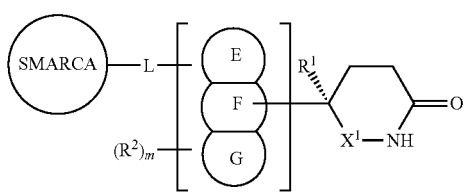

I-ii"

or a pharmaceutically acceptable salt thereof, wherein:
each of SMARCA, L, Ring E, Ring F, Ring G, L, $R^1$, $R^2$, $X^1$, and m is as defined above.

In certain embodiments, the present invention provides a compound of Formula I, wherein LBM is an E3 ubiquitin ligase (cereblon) binding moiety thereby forming a compound of formula I-j j:

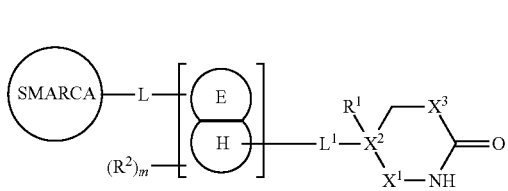

I-jj or a pharmaceutically acceptable salt thereof, wherein F and SMARCA are as defined above and described in embodiments herein, and wherein:

$X^1$ is a bivalent moiety selected from a covalent bond, $-CH_2-$, $-CHCF_3-$, $-SO_2-$, $-S(O)-$, $-P(O)R-$, $-P(O)OR-$, $-P(O)NR_2-$, $-C(O)-$, $-C(S)-$, or

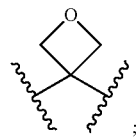 [SMILES: *C1(*)COC1]

$X^2$ is a carbon atom, nitrogen atom, or silicon atom;

$X^3$ is a bivalent moiety selected from a covalent bond, $-CR_2-$, $-NR-$, $-O-$, $-S-$, or $-SiR_2-$;

$R^1$ is absent, hydrogen, deuterium, halogen, $-CN$, $-OR$, $-SR$, $-S(O)R$, $-S(O)_2R$, $-NR_2$, $-P(O)(OR)_2$, $-P(O)(NR_2)OR$, $-P(O)(NR_2)_2$, $-Si(OH)_2R$, $-Si(OH)R_2$, $-SiR_3$, or an optionally substituted $C_{1-4}$ aliphatic;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently hydrogen, deuterium, $-R^6$, halogen, $-CN$, $-NO_2$, $-OR$, $-SR$, $-N(R)_2$, $-Si(R)_3$, $-S(O)_2R$, $-S(O)_2N(R)_2$, $-S(O)R$, $-C(O)R$, $-C(O)OR$, $-C(O)N(R)_2$, $-C(O)N(R)OR$, $-C(R)_2N(R)C(O)R$, $-C(R)_2N(R)C(O)N(R)_2$, $-OC(O)R$, $-OC(O)N(R)_2$, $-OP(O)R_2$, $-OP(O)(OR)_2$, $-OP(O)(OR)(NR_2)$, $-OP(O)(NR_2)_2-$, $-N(R)C(O)OR$, $-N(R)C(O)R$, $-N(R)C(O)N(R)_2$, $-N(R)S(O)_2R$, $-NP(O)R_2$, $-N(R)P(O)(OR)_2$, $-N(R)P(O)(OR)(NR_2)$, $-N(R)P(O)(NR_2)_2$, or $-N(R)S(O)_2R$;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring E is a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur;

Ring H is a fused ring selected from a 7-9 membered saturated or partially unsaturated carbocyclyl or heterocyclyl ring with 1-3 heteroatoms independently selected from boron, nitrogen, oxygen, silicon, or sulfur, wherein Ring E is optionally further substituted with 1-2 oxo groups;

L¹ is a covalent bond or a $C_{1-3}$ bivalent straight or branched saturated or unsaturated hydrocarbon chain wherein 1-2 methylene units of the chain are independently and optionally replaced with —O—, —C(O)—, —C(S)—, —C(R)₂—, —CF(R)—, —C(F)₂—, —N(R)—, —S—, —S(O)₂— or —(C)═CH—;

m is 0, 1, 2, 3, or 4.

Where a point of attachment of

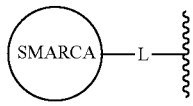

is depicted on Ring E or Ring H, it is intended, and one of ordinary skill in the art would appreciate, that the point of attachment of

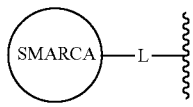

may be on any available carbon or nitrogen atom on Ring E or Ring H including the carbon atom to which Ring E and Ring H are fused.

Where a point of attachment of —(R²)ₘ is depicted on Ring E and Ring H, it is intended, and one of ordinary skill in the art would appreciate, that the point of attachment of —(R²)ₘ may be on any available carbon or nitrogen atom on Ring E or Ring H including the carbon atom to which Ring E and Ring H are fused.

Where a point of attachment of

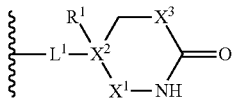

is depicted on Ring E and Ring H, it is intended, and one of ordinary skill in the art would appreciate, that the point of attachment of

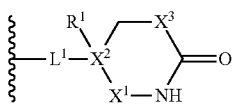

may be on any available carbon or nitrogen atom on Ring E or Ring H including the carbon atom to which Ring E and Ring H are fused.

In some embodiments, a compound of formula I-jj above is provided as a compound of formula I-jj' or formula I-jj":

I-jj'

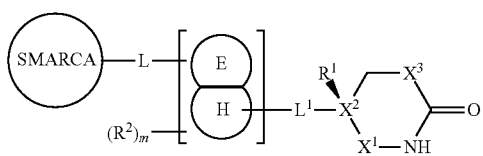

I-jj"

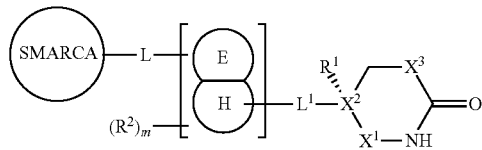

or a pharmaceutically acceptable salt thereof, wherein:
each of SMARCA, Ring E, Ring H, L, L¹, R¹, R², X¹, X², X³, and m is as defined above.

In certain embodiments, the present invention provides a compound of Formula I, wherein LBM is an E3 ubiquitin ligase (cereblon) binding moiety thereby forming a compound of formula I-kk:

I-kk

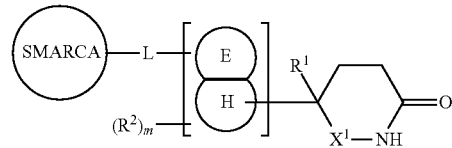

or a pharmaceutically acceptable salt thereof, wherein L and SMARCA are as defined above and described in embodiments herein, and wherein:

X¹ is a bivalent moiety selected from a covalent bond, —CH₂—, —C(O)—, —C(S)—, or

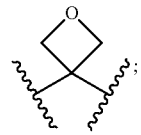 [SMILES: *C1(*)COC1]

R¹ is hydrogen, deuterium, halogen, —CN, —OR, —SR, —S(O)R, —S(O)₂R, —N(R)₂, —Si(R)₃, or an optionally substituted $C_{1-4}$ aliphatic;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:
two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each R² is independently hydrogen, deuterium, —R⁶, halogen, —CN, —NO₂, —OR, —SR, —N(R)₂, —Si(R)₃, —S(O)₂R, —S(O)₂N(R)₂, —S(O)R, —C(O)R, —C(O)OR, —C(O)N(R)₂, —C(O)N(R)OR, —C(R)₂N(R)C(O)R, —C(R)₂N(R)C(O)N(R)₂, —OC(O)R, —OC(O)N(R)₂, N(R)C(O)OR, —N(R)C(O)R, —N(R)C(O)N(R)₂, or —N(R)S(O)₂R;

each R⁶ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring E is a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur;

Ring H is a ring selected from a 7-9 membered saturated or partially unsaturated carbocyclyl or heterocyclyl ring with 1-3 heteroatoms independently selected from boron, nitrogen, oxygen, silicon, or sulfur, wherein Ring E is optionally further substituted with 1-2 oxo groups; and m is 0, 1, 2, 3, or 4.

Where a point of attachment of

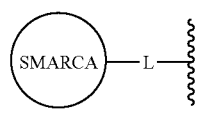

is depicted on Ring E or Ring H, it is intended, and one of ordinary skill in the art would appreciate, that the point of attachment of

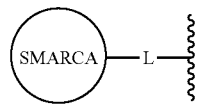

may be on any available carbon or nitrogen atom on Ring E or Ring H including the carbon atom to which Ring E and Ring H are fused.

Where a point of attachment of —(R²)ₘ is depicted on Ring E and Ring H, it is intended, and one of ordinary skill in the art would appreciate, that the point of attachment of —(R²)ₘ may be on any available carbon or nitrogen atom on Ring E or Ring H including the carbon atom to which Ring E and Ring H are fused.

Where a point of attachment of

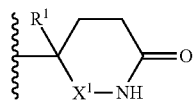

is depicted on Ring E and Ring H, it is intended, and one of ordinary skill in the art would appreciate, that the point of attachment of

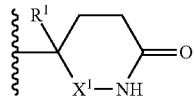

may be on any available carbon or nitrogen atom on Ring E or Ring H including the carbon atom to which Ring E and Ring H are fused.

In some embodiments, a compound of formula I-kk above is provided as a compound of formula I-kk' or formula I-kk":

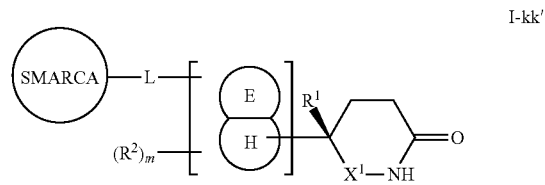

I-kk'

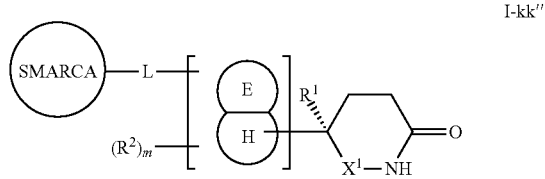

I-kk"

or a pharmaceutically acceptable salt thereof, wherein:

each of SMARCA, Ring E, Ring H, L, $R^1$, $R^2$, $X^1$, and m is as defined above.

In some embodiments, the present invention provides the compound of formula I-kk wherein Ring H is 1,3-dihydro-2H-1,4-diazepin-2-one, thereby forming a compound of formula I-kk-1:

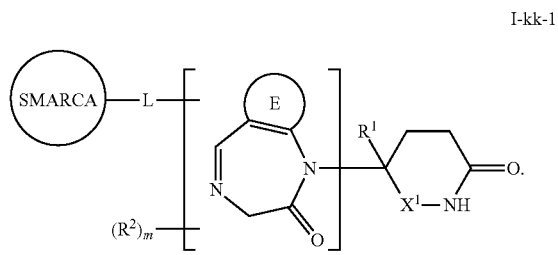

I-kk-1 or a pharmaceutically acceptable salt thereof, wherein:

each of SMARCA, L, Ring E, $X^1$, $R^1$, $R^2$, and m is as defined above.

In certain embodiments, the present invention provides a compound of Formula I, wherein LBM is an E3 ubiquitin ligase (cereblon) binding moiety thereby forming a compound of formula I-ll:

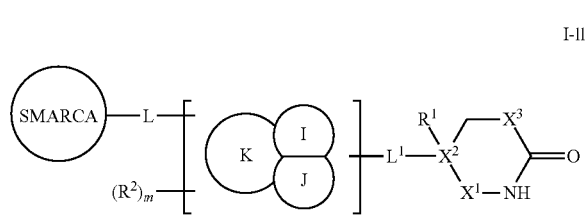

I-ll or a pharmaceutically acceptable salt thereof, wherein L and SMARCA are as defined above and described in embodiments herein, and wherein:

$X^1$ is a bivalent moiety selected from a covalent bond, —$CH_2$—, —$CHCF_3$—, —$SO_2$—, —S(O)—, —P(O)R—, —P(O)OR—, —P(O)$NR_2$—, —C(O)—, —C(S)—, or

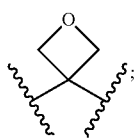

X² is a carbon atom, nitrogen atom, or silicon atom;
X³ is a bivalent moiety selected from a covalent bond, —CR₂—, —NR—, —O—, —S—, or —SiR₂—;
R¹ is absent, hydrogen, deuterium, halogen, —CN, —OR, —SR, —S(O)R, —S(O)₂R, —NR₂, —P(O)(OR)₂, —P(O)(NR₂)OR, —P(O)(NR₂)₂, —Si(OH)₂R, —Si(OH)R₂, —SiR₃, or an optionally substituted C₁₋₄ aliphatic;
each R is independently hydrogen, or an optionally substituted group selected from C₁₋₆ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:
  two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;
each R² is independently hydrogen, deuterium, —R⁶, halogen, —CN, —NO₂, —OR, —SR, —N(R)₂, —Si(R)₃, —S(O)₂R, —S(O)₂N(R)₂, —S(O)R, —C(O)R, —C(O)OR, —C(O)N(R)₂, —C(O)N(R)OR, —C(R)₂N(R)C(O)R, —C(R)₂N(R)C(O)N(R)₂, —OC(O)R, —OC(O)N(R)₂, —OP(O)R₂, —OP(O)(OR)₂, —OP(O)(OR)(NR₂), —OP(O)(NR₂)₂—, —N(R)C(O)OR, —N(R)C(O)R, —N(R)C(O)N(R)₂, —N(R)S(O)₂R, —NP(O)R₂, —N(R)P(O)(OR)₂, —N(R)P(O)(OR)(NR₂), —N(R)P(O)(NR₂)₂, or —N(R)S(O)₂R;
each R⁶ is independently an optionally substituted group selected from C₁₋₆ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;
each of Ring I and J is independently a fused ring selected from 6-membered aryl, 6-membered heteroaryl containing 1-4 heteroatoms independently selected from nitrogen, oxygen, and sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur;
Ring K is a fused ring selected from a 7-12 membered saturated or partially unsaturated carbocyclyl or heterocyclyl ring with 1-3 heteroatoms independently selected from boron, nitrogen, oxygen, silicon, or sulfur, wherein Ring H is optionally further substituted with 1-2 oxo groups;
L¹ is a covalent bond or a C₁₋₃ bivalent straight or branched saturated or unsaturated hydrocarbon chain wherein 1-2 methylene units of the chain are independently and optionally replaced with —O—, —C(O)—, —C(S)—, —C(R)₂—, —CF(R)—, —C(F)₂—, —N(R)—, —S—, —S(O)₂— or —(C)=CH—; and
m is 0, 1, 2, 3, or 4.

Where a point of attachment of

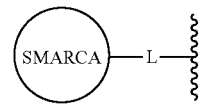

is depicted on Ring I, Ring J, and Ring K, it is intended, and one of ordinary skill in the art would appreciate, that the point of attachment of

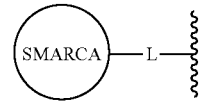

may be on any available carbon or nitrogen atom on Ring I, Ring J, or Ring K, including the carbon atom to which Ring I, Ring J, and Ring K are fused.

Where a point of attachment of —(R²)ₘ is depicted on Ring I, Ring J, and Ring K, it is intended, and one of ordinary skill in the art would appreciate, that the point of attachment of —(R²)ₘ may be on any available carbon or nitrogen atom on Ring I, Ring J, or Ring K, including the carbon atom to which Ring I, Ring J, and Ring K are fused.

Where a point of attachment of

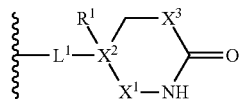

is depicted on Ring I, Ring J, and Ring K, it is intended, and one of ordinary skill in the art would appreciate, that the point of attachment of

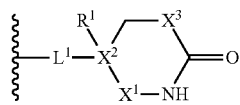

may be on any available carbon or nitrogen atom on Ring I, Ring J, or Ring K, including the carbon atom to which Ring I, Ring J, and Ring K are fused.

In some embodiments, a compound of formula I-ll above is provided as a compound of formula I-ll' or formula I-ll":

I-ll'

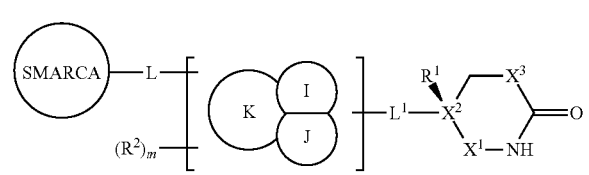

-continued

I-ll''

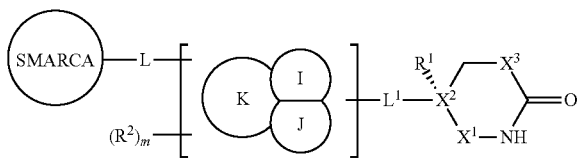

or a pharmaceutically acceptable salt thereof, wherein:
each of SMARCA, Ring I, Ring J, Ring K, L, L$^1$, R$^1$, R$^2$, X$^1$, X$^2$, X$^3$, and m is as defined above.

In certain embodiments, the present invention provides a compound of formula I-mm:

I-mm

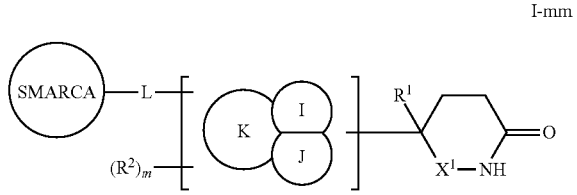

or a pharmaceutically acceptable salt thereof, wherein L and SMARCA are as defined above and described in embodiments herein, and wherein:

X$^1$ is a bivalent moiety selected from a covalent bond, —CH$_2$—, —C(O)—, —C(S)—, or

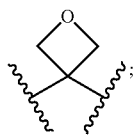 [SMILES: *C1(*)COC1]

R$^1$ is hydrogen, deuterium, halogen, —CN, —OR, —SR, —S(O)R, —S(O)$_2$R, —N(R)$_2$, —Si(R)$_3$, or an optionally substituted C$_{1-4}$ aliphatic;

each R is independently hydrogen, or an optionally substituted group selected from C$_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:
  two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each R$^2$ is independently hydrogen, deuterium, —R$^6$, halogen, —CN, —NO$_2$, —OR, —SR, —N(R)$_2$, —Si(R)$_3$, —S(O)$_2$R, —S(O)$_2$N(R)$_2$, —S(O)R, —C(O)R, —C(O)OR, —C(O)N(R)$_2$, —C(O)N(R)OR, —C(R)$_2$N(R)C(O)R, —C(R)$_2$N(R)C(O)N(R)$_2$, —OC(O)R, —OC(O)N(R)$_2$, N(R)C(O)OR, —N(R)C(O)R, —N(R)C(O)N(R)$_2$, or —N(R)S(O)$_2$R;

each R$^6$ is independently an optionally substituted group selected from C$_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

each of Ring I and J is independently a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur;

Ring K is a fused ring selected from a 7-12 membered saturated or partially unsaturated carbocyclyl or heterocyclyl ring with 1-3 heteroatoms independently selected from boron, nitrogen, oxygen, silicon, or sulfur, wherein Ring H is optionally further substituted with 1-2 oxo groups; and m is 0, 1, 2, 3, or 4.

Where a point of attachment of

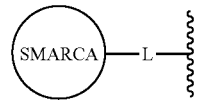

is depicted on Ring I, Ring J, and Ring K, it is intended, and one of ordinary skill in the art would appreciate, that the point of attachment of

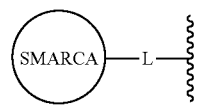

may be on any available carbon or nitrogen atom on Ring I, Ring J, or Ring K, including the carbon atom to which Ring I, Ring J, and Ring K are fused.

Where a point of attachment of —(R$^2$)$_m$ is depicted on Ring I, Ring J, and Ring K, it is intended, and one of ordinary skill in the art would appreciate, that the point of attachment of —(R$^2$)$_m$ may be on any available carbon or nitrogen atom on Ring I, Ring J, or Ring K, including the carbon atom to which Ring I, Ring J, and Ring K are fused.

Where a point of attachment of

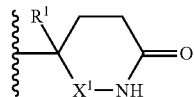

is depicted on Ring I, Ring J, and Ring K, it is intended, and one of ordinary skill in the art would appreciate, that the point of attachment of

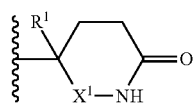

may be on any available carbon or nitrogen atom on Ring I, Ring J, or Ring K, including the carbon atom to which Ring I, Ring J, and Ring K are fused.

In some embodiments, a compound of formula I-mm above is provided as a compound of formula I-mm' or formula I-mm":

I-mm'

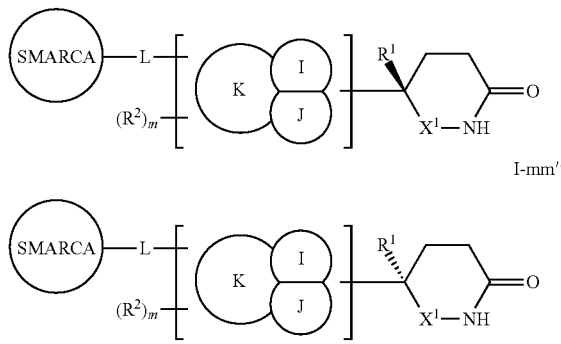

I-mm"

or a pharmaceutically acceptable salt thereof, wherein:
each of SMARCA, Ring I, Ring J, Ring K, L, $R^1$, $R^2$, $X^1$, and m is as defined above.

In some embodiments, the present invention provides the compound of formula I-mm wherein Ring J is pyrrole, thereby forming a compound of formula I-mm-1:

I-mm-1

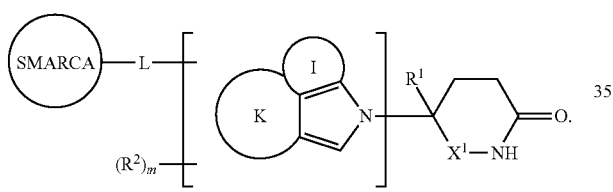

or a pharmaceutically acceptable salt thereof, wherein:
each of SMARCA, L, Ring I, Ring K, $X^1$, $R^1$, $R^2$, and m is as defined above.

As described above, in another aspect, the present invention provides a compound of Formula I-nn:

I-nn

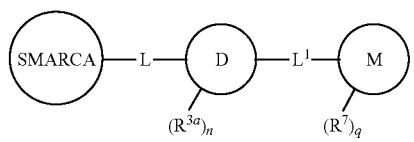

or a pharmaceutically acceptable salt thereof, wherein:
Ring M is selected from

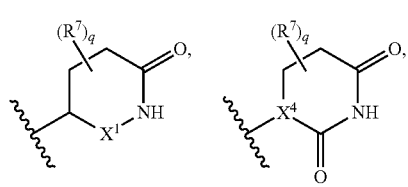

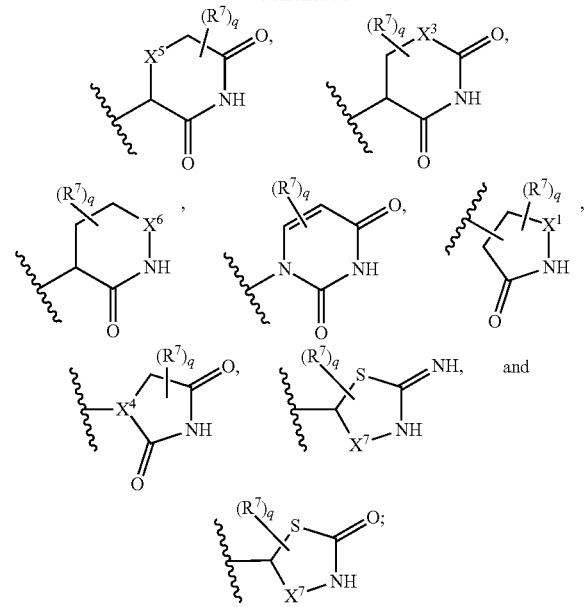

each of $X^1$, $X^6$, and $X^7$ is independently a bivalent moiety selected from a covalent bond, —$CH_2$—, —$CHCF_3$—, —$SO_2$—, —S(O)—, —P(O)R—, —P(O)OR—, —P(O)$NR_2$—, —C(O)—, —C(S)—, and

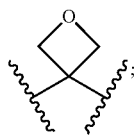 [SMILES: *C1(*)COC1]

each of $X^3$ and $X^5$ is independently a bivalent moiety selected from a covalent bond, —$CR_2$—, —NR—, —O—, —S—, and $SiR_2$—;
$X^4$ is a trivalent moiety selected from

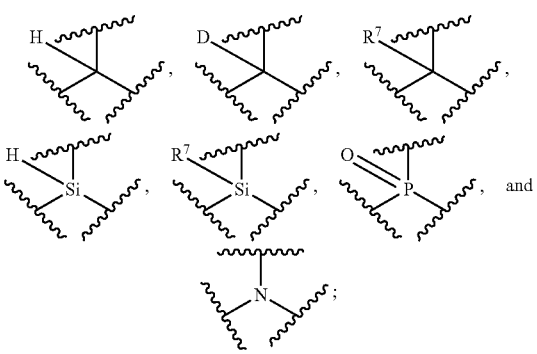

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or: two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^{3a}$ is independently hydrogen, deuterium, —$R^6$, halogen, —CN, —$NO_2$, —OR, —SR, —$NR_2$, —$SiR_3$, —$S(O)_2R$, —$S(O)_2NR_2$, —S(O)R, —C(O)R, —C(O)OR, —$C(O)NR_2$, —C(O)N(R)OR, —$C(R)_2N(R)C(O)R$, —$C(R)_2N(R)C(O)N(R)_2$, —OC(O)R, —$OC(O)N(R)_2$, —$OP(O)R_2$, —$OP(O)(OR)_2$, —$OP(O)(OR)NR_2$, —$OP(O)(NR_2)_2$—, —N(R)C(O)OR, —N(R)C(O)R, —N(R)C(O)$NR_2$, —$N(R)S(O)_2R$, —$NP(O)R_2$, —$N(R)P(O)(OR)_2$, —$N(R)P(O)(OR)NR_2$, —$N(R)P(O)(NR_2)_2$, or —$N(R)S(O)_2R$;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

each $R^7$ is independently hydrogen, deuterium, halogen, —CN, —OR, —SR, —S(O)R, —$S(O)_2R$, —$NR_2$, —$P(O)(OR)_2$, —$P(O)(NR_2)OR$, —$P(O)(NR_2)_2$, —$Si(OH)R_2$, —$Si(OH)_2R$, —$SiR_3$, or an optionally substituted $C_{1-4}$ aliphatic; or $R^7$ and $X^1$ or $X^3$ are taken together with their intervening atoms to form a 5-7 membered saturated, partially unsaturated, carbocyclic ring or heterocyclic ring having 1-3 heteroatoms, independently selected from boron, nitrogen, oxygen, silicon, or sulfur;

two $R^7$ groups on the same carbon are optionally taken together with their intervening atoms to form a 3-6 membered spiro fused ring or a 4-7 membered heterocyclic ring having 1-2 heteroatoms independently selected from boron, nitrogen, oxygen, silicon, or sulfur;

two $R^7$ groups on adjacent carbon atoms are optionally taken together with their intervening atoms to form a 3-7 membered saturated, partially unsaturated, carbocyclic ring or heterocyclic ring having 1-3 heteroatoms independently selected from boron, nitrogen, oxygen, silicon, or sulfur, or a 7-13 membered saturated, partially unsaturated, bridged heterocyclic ring, or a spiro heterocyclic ring having 1-3 heteroatoms, independently selected from boron, nitrogen, oxygen, silicon, or sulfur;

Ring D is selected from 6 to 10-membered aryl or heteroaryl containing 1-4 heteroatoms independently selected from nitrogen, oxygen, and sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur;

$L^1$ is a covalent bond or a $C_{1-3}$ bivalent straight or branched saturated or unsaturated hydrocarbon chain wherein 1-2 methylene units of the chain are independently and optionally replaced with —O—, —C(O)—, —C(S)—, —$C(R)_2$—, —CF(R)—, —$C(F)_2$—, —N(R)—, —S—, —$S(O)_2$— or —(C)=CH—;

n is 0, 1, 2, 3, or 4; and q is 0, 1, 2, 3, or 4.

As defined above and described herein, each of $X^1$, $X^6$, and $X^7$ is independently a bivalent moiety selected from a covalent bond, —$CH_2$—, —$C(R)_2$—, —C(O)—, —C(S)—, —CH(R)—, —$CH(CF_3)$—, —P(O)(OR)—, —P(O)(R)—, —$P(O)(NR_2)$—, —S(O)—, —$S(O)_2$—, of

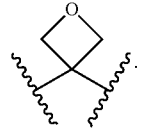 [SMILES: *C1(*)COC1]

In some embodiments, each of $X^1$, $X^6$, and $X^7$ is independently a covalent bond. In some embodiments, each of $X^1$, $X^6$, and $X^7$ is independently —$CH_2$—. In some embodiments, each of $X^1$, $X^6$, and $X^7$ is independently —$CR_2$—. In some embodiments, each of $X^1$, $X^6$, and $X^7$ is independently —C(O)—. In some embodiments, each of $X^1$, $X^6$, and $X^7$ is independently —C(S)—. In some embodiments, each of $X^1$, $X^6$, and $X^7$ is independently —CH(R)—. In some embodiments, each of $X^1$, $X^6$, and $X^7$ is independently —$CH(CF_3)$—. In some embodiments, each of $X^1$, $X^6$, and $X^7$ is independently —P(O)(OR)—. In some embodiments, each of $X^1$, $X^6$, and $X^7$ is independently —P(O)(R)—. In some embodiments, each of $X^1$, $X^6$, and $X^7$ is independently —$P(O)NR_2$— In some embodiments, each of $X^1$, $X^6$, and $X^7$ is independently —S(O)—. In some embodiments, each of $X^1$, $X^6$, and $X^7$ is independently —$S(O)_2$—. In some embodiments, each of $X^1$, $X^6$, and $X^7$ is independently

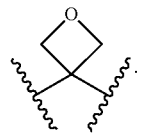 [SMILES: *C1(*)COC1]

In some embodiments, each of $X^1$, $X^6$, and $X^7$ is independently selected from those depicted in Table 1 below.

As defined above and described herein, $X^2$ is a carbon atom, nitrogen atom, or silicon atom.

In some embodiments, $X^2$ is a carbon atom. In some embodiments, $X^2$ is a nitrogen atom. In some embodiments, $X^2$ is a silicon atom.

In some embodiments, $X^2$ is selected from those depicted in Table 1 below.

As defined above and described herein, $X^3$ is a bivalent moiety selected from —$CH_2$—, —$CR_2$—, —NR—, —$CF_2$—, —CHF—, —S—, —CH(R)—, —$SiR_2$—, or —O—.

In some embodiments, each of $X^3$ and $X^5$ is independently —$CH_2$—. In some embodiments, each of $X^3$ and $X^5$ is independently —$CR_2$—. In some embodiments, each of $X^3$ and $X^5$ is independently —NR—.

In some embodiments, each of $X^3$ and $X^5$ is independently —$CF_2$— In some embodiments, each of $X^3$ and $X^5$ is independently —CHF—. In some embodiments, each of $X^3$ and $X^5$ is independently —S—. In some embodiments, each of $X^3$ and $X^5$ is independently —CH(R)—. In some embodiments, each of $X^3$ and $X^5$ is independently —$SiR_2$—. In some embodiments, each of $X^3$ and $X^5$ is independently —O—.

In some embodiments, each of $X^3$ and $X^5$ is independently selected from those depicted in Table 1 below.

As defined above and described herein, $X^4$ is a trivalent moiety selected from

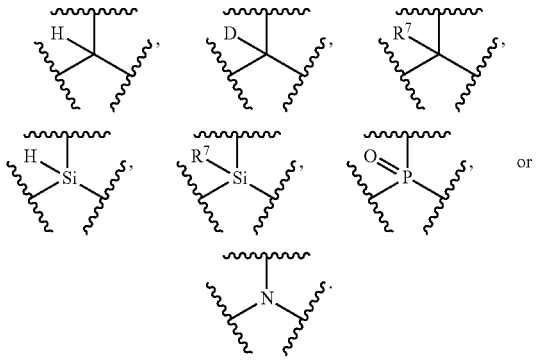

In some embodiments, $X^4$ is

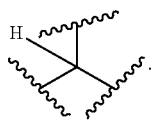

In some embodiments, $X^4$ is

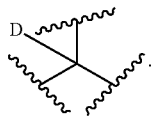 [SMILES: *C(*)(*)[2H]]

In some embodiments, $X^4$ is

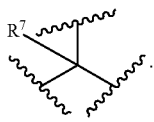

In some embodiments, $X^4$ is

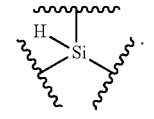

In some embodiments, $X^4$ is

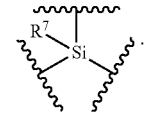

In some embodiments, $X^4$ is

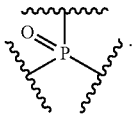

In some embodiments, $X^4$ is

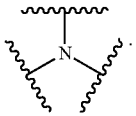 [SMILES: *N(*)*]

In some embodiments, $X^4$ is selected from those depicted in Table 1 below.

As defined above and described herein, $R^1$ is hydrogen, deuterium, halogen, —CN, —OR, —SR, —S(O)R, —S(O)$_2$R, —NR$_2$, —P(O)(OR)$_2$, —P(O)(NR$_2$)OR, —P(O)(NR$_2$)$_2$, —Si(OH)$_2$R, —Si(OH)R$_2$, —SiR$_3$, an optionally substituted C$_{1-4}$ aliphatic, or $R^1$ and $X^1$ or $X^4$ are taken together with their intervening atoms to form a 5-7 membered saturated, partially unsaturated, carbocyclic ring or heterocyclic ring having 1-3 heteroatoms, independently selected from nitrogen, oxygen, or sulfur.

In some embodiments, $R^1$ is hydrogen. In some embodiments, $R^1$ is deuterium. In some embodiments, $R^1$ is halogen. In some embodiments, $R^1$ is —CN. In some embodiments, $R^1$ is —OR. In some embodiments, $R^1$ is —SR. In some embodiments, $R^1$ is —S(O)R. In some embodiments, $R^1$ is —S(O)$_2$R. In some embodiments, $R^1$ is —NR$_2$. In some embodiments, $R^1$ is —P(O)(OR)$_2$. In some embodiments, $R^1$ is —P(O)(NR$_2$)OR. In some embodiments, $R^1$ is —P(O)(NR$_2$)$_2$. In some embodiments, $R^1$ is —Si(OH)$_2$R. In some embodiments, $R^1$ is —Si(OH)R$_2$. In some embodiments, $R^1$ is —SiR$_3$. In some embodiments, $R^1$ is an optionally substituted C$_{1-4}$ aliphatic. In some embodiments, $R^1$ and $X^1$ or $X^4$ are taken together with their intervening atoms to form a 5-7 membered saturated, partially unsaturated, carbocyclic ring or heterocyclic ring having 1-3 heteroatoms, independently selected from nitrogen, oxygen, or sulfur.

In some embodiments, $R^1$ is selected from those depicted in Table 1 below.

As defined above and described herein, each R is independently hydrogen, deuterium, or an optionally substituted group selected from C$_{1-6}$ aliphatic, phenyl, a 4-7 membered saturated or partially unsaturated heterocyclic having 1-3 heteroatoms independently selected from boron, nitrogen, oxygen, silicon, and sulfur, and a 5-6 membered heteroaryl ring having 1-4 heteroatoms independently selected from boron, nitrogen, oxygen, silicon, and sulfur, or two R groups on the same nitrogen are taken together with their intervening atoms to form a 4-7 membered saturated, partially unsaturated, or heteroaryl ring having 0-3 heteroatoms, in addition to the nitrogen, independently selected from boron, nitrogen, oxygen, silicon, and sulfur.

In some embodiments, R is hydrogen. In some embodiments, R is deuterium. In some embodiments, R is optionally substituted C$_{1-6}$ aliphatic. In some embodiments, R is optionally substituted phenyl. In some embodiments, R is optionally substituted 4-7 membered saturated or partially unsaturated heterocyclic having 1-3 heteroatoms independently selected from boron, nitrogen, oxygen, silicon, and sulfur. In some embodiments, R is optionally substituted 5-6 membered heteroaryl ring having 1-4 heteroatoms independently selected from boron, nitrogen, oxygen, silicon, and sulfur. In some embodiments, two R groups on the same nitrogen are taken together with their intervening atoms to form a 4-7 membered saturated, partially unsaturated, or heteroaryl ring having 0-3 heteroatoms, in addition to the nitrogen, independently selected from boron, nitrogen, oxygen, silicon, and sulfur.

In some embodiments, R is selected from those depicted in Table 1 below.

As defined above and described herein, each of $R^2$ and $R^{3a}$ is independently hydrogen, deuterium, —$R^6$, halogen, —CN, —$NO_2$, —OR, —$Si(OH)_2R$, —$Si(OH)R_2$, —SR, —$NR_2$, $SiR_3$, —$S(O)_2R$, —$S(O)_2NR_2$, —S(O)R, —C(O)R, —C(O)OR, —$C(O)NR_2$, —C(O)N(R)OR, —$C(R)_2N(R)C(O)R$, —$C(R)_2N(R)C(O)NR_2$, —OC(O)R, —$OC(O)NR_2$, —$OP(O)R_2$, —$OP(O)(OR)_2$, —$OP(O)(OR)NR_2$, —$OP(O)(NR_2)_2$—, —N(R)C(O)OR, —N(R)C(O)R, —$N(R)C(O)NR_2$, —$N(R)S(O)_2R$, —$NP(O)R_2$, —$N(R)P(O)(OR)_2$, $N(R)P(O)(OR)NR_2$, —$N(R)P(O)(NR_2)_2$, or —$N(R)S(O)_2R$.

In some embodiments, $R^2$ and/or $R^{3a}$ is hydrogen. In some embodiments, $R^2$ and/or $R^{3a}$ is deuterium. In some embodiments, $R^2$ and/or $R^{3a}$ is —$R^6$. In some embodiments, $R^2$ and/or $R^{3a}$ is halogen. In some embodiments, $R^2$ and/or $R^{3a}$ is —CN. In some embodiments, $R^2$ and/or $R^{3a}$ is —$NO_2$. In some embodiments, $R^2$ and/or $R^{3a}$ is —OR. In some embodiments, $R^2$ and/or $R^{3a}$ is —$Si(OH)_2R$. In some embodiments, $R^2$ and/or $R^{3a}$ is —$Si(OH)R_2$. In some embodiments, $R^2$ and/or $R^{3a}$ is —SR. In some embodiments, $R^2$ and/or $R^{3a}$ is —$NR_2$. In some embodiments, $R^2$ and/or $R^{3a}$ is —$SiR_3$. In some embodiments, $R^2$ and/or $R^{3a}$ is —S(O)R. In some embodiments, $R^2$ and/or $R^{3a}$ is —$S(O)_2NR_2$. In some embodiments, $R^2$ and/or $R^{3a}$ is —S(O)R. In some embodiments, $R^2$ and/or $R^{3a}$ is —C(O)R. In some embodiments, $R^2$ and/or $R^{3a}$ is —C(O)OR. In some embodiments, $R^2$ and/or $R^{3a}$ is —$C(O)NR_2$. In some embodiments, $R^2$ and/or $R^{3a}$ is —C(O)N(R)OR. In some embodiments, $R^2$ and/or $R^{3a}$ is —$C(R)_2N(R)C(O)R$. In some embodiments, $R^2$ and/or $R^{3a}$ is —$C(R)_2N(R)C(O)NR_2$. In some embodiments, $R^2$ and/or $R^{3a}$ is —OC(O)R. In some embodiments, $R^2$ and/or $R^{3a}$ is —$OC(O)NR_2$. In some embodiments, $R^2$ and/or $R^{3a}$ is —$OP(O)R_2$. In some embodiments, $R^2$ and/or $R^{3a}$ is —$OP(O)(OR)_2$. In some embodiments, $R^2$ and/or $R^{3a}$ is —$OP(O)(OR)NR_2$. In some embodiments, $R^2$ and/or $R^{3a}$ is —$OP(O)(NR_2)_2$—. In some embodiments, $R^2$ and/or $R^{3a}$ is —N(R)C(O)OR. In some embodiments, $R^2$ and/or $R^{3a}$ is —N(R)C(O)R. In some embodiments, $R^2$ and/or $R^{3a}$ is —$N(R)C(O)NR_2$. In some embodiments, $R^2$ and/or $R^{3a}$ is —$NP(O)R_2$. In some embodiments, $R^2$ and/or $R^{3a}$ is —$N(R)P(O)(OR)_2$. In some embodiments, $R^2$ and/or $R^{3a}$ is —$N(R)P(O)(OR)NR_2$. In some embodiments, $R^2$ and/or $R^{3a}$ is —$N(R)P(O)(NR_2)_2$. In some embodiments, $R^2$ and $R^{3a}$ is independently —$N(R)S(O)_2R$.

In some embodiments, $R^2$ and/or $R^{3a}$ is —OH. In some embodiments, $R^2$ and/or $R^{3a}$ is —$NH_2$. In some embodiments, $R^2$ and/or $R^{3a}$ is —$CH_2NH_2$. In some embodiments, $R^2$ and/or $R^{3a}$ is —$CH_2NHCOMe$. In some embodiments, $R^2$ and/or $R^{3a}$ is —$CH_2NHCONHMe$. In some embodiments, $R^2$ and/or $R^{3a}$ is —NHCOMe. In some embodiments, $R^2$ and/or $R^{3a}$ is —NHCONHEt. In some embodiments, $R^2$ and/or $R^{3a}$ is —$SiMe_3$. In some embodiments, $R^2$ and/or $R^{3a}$ is —$SiMe_2OH$. In some embodiments, $R^2$ and/or $R^{3a}$ is —$SiMe(OH)_2$. In some embodiments $R^2$ and/or $R^{3a}$ is

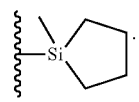

In some embodiments, $R^2$ and/or $R^{3a}$ is Br. In some embodiments, $R^2$ and/or $R^{3a}$ is Cl. In some embodiments, $R^2$ and/or $R^{3a}$ is F. In some embodiments, $R^2$ and/or $R^{3a}$ is Me. In some embodiments, $R^2$ and/or $R^{3a}$ is —NHMe. In some embodiments, $R^2$ and/or $R^{3a}$ is —$NMe_2$. In some embodiments, $R^2$ and/or $R^{3a}$ is —$NHCO_2Et$. In some embodiments, $R^2$ and/or $R^{3a}$ is —CN. In some embodiments, $R^2$ and/or $R^{3a}$ is —$CH_2Ph$. In some embodiments, $R^2$ and/or $R^{3a}$ is —$NHCO_2tBu$. In some embodiments, $R^2$ and/or $R^{3a}$ is —$CO_2tBu$. In some embodiments, $R^2$ and/or $R^{3a}$ is -OMe. In some embodiments, $R^2$ and/or $R^{3a}$ is —$CF_3$.

In some embodiments, $R^2$ and $R^{3a}$ are selected from those depicted in Table 1, below.

As defined above and described herein, $R^3$ is hydrogen, deuterium, halogen, —CN, —$NO_2$, —OR, —$NR_2$, —SR, —$S(O)_2R$, —$S(O)_2NR_2$, —S(O)R, —C(O)R, —C(O)OR, —$C(O)NR_2$, —C(O)NR(OR), —OC(O)R, —$OC(O)NR_2$, —$OP(O)(OR)_2$, —$OP(O)(NR_2)_2$, —$OP(O)(OR)NR_2$, —N(R)C(O)R, N(R)C(O)OR, —$N(R)C(O)NR_2$, —$N(R)S(O)_2R$, —$N(R)S(O)_2NR_2$, —$N(R)P(O)(OR)_2$, —$N(R)P(O)(OR)NR_2$, —$P(O)(OR)_2$, —$P(O)(NR_2)OR$, —$P(O)(NR_2)_2$, —$Si(OH)_2R$, —$Si(OH)(R)_2$, or —$Si(R)_3$.

In some embodiments, $R^3$ is hydrogen. In some embodiments, $R^3$ is deuterium. In some embodiments, $R^3$ is halogen. In some embodiments, $R^3$ is —CN. In some embodiments, $R^3$ is —$NO_2$. In some embodiments, $R^3$ is —OR. In some embodiments, $R^3$ is —$NR_2$. In some embodiments, $R^3$ is —SR. In some embodiments, $R^3$ is —$S(O)_2R$. In some embodiments, $R^3$ is —$S(O)_2NR_2$. In some embodiments, $R^3$ is —S(O)R. In some embodiments, $R^3$ is —C(O)R. In some embodiments, $R^3$ is —C(O)OR. In some embodiments, $R^3$ is —$C(O)NR_2$. In some embodiments, $R^3$ is —C(O)NR(OR). In some embodiments, $R^3$ is —OC(O)R. In some embodiments, $R^3$ is —$OC(O)NR_2$. In some embodiments, $R^3$ is —$OP(O)(OR)_2$. In some embodiments, $R^3$ is —$OP(O)(NR_2)_2$. In some embodiments, $R^3$ is —$OP(O)(OR)NR_2$. In some embodiments, $R^3$ is —N(R)C(O)R. In some embodiments, $R^3$ is —N(R)C(O)OR. In some embodiments, $R^3$ is —$N(R)C(O)NR_2$. In some embodiments, $R^3$ is —$N(R)S(O)_2R$. In some embodiments, $R^3$ is —$N(R)S(O)_2NR_2$. In some embodiments, $R^3$ is —$N(R)P(O)(OR)_2$. In some embodiments, $R^3$ is —$N(R)P(O)(OR)NR_2$. In some embodiments, $R^3$ is —$P(O)(OR)_2$. In some embodiments, $R^3$ is —$P(O)(NR_2)OR$. In some embodiments, $R^3$ is —$P(O)(NR_2)_2$. In some embodiments, $R^3$ is —$Si(OH)_2R$. In some embodiments, $R^3$ is —$Si(OH)(R)_2$. In some embodiments, $R^3$ is —$Si(R)_3$.

In some embodiments, $R^3$ is methyl. In some embodiments, $R^3$ is —$OCH_3$. In some embodiments, $R^3$ is chloro.

In some embodiments, $R^3$ is selected from those depicted in Table 1.

As defined above and described herein, each $R^4$ is independently hydrogen, deuterium, —$R^6$, halogen, —CN, —$NO_2$, —OR, —SR, —$NR_2$, —$S(O)_2R$, —$S(O)_2NR_2$, —S(O)R, —C(O)R, —C(O)OR, —$C(O)NR_2$, —C(O)N(R)OR, —OC(O)R, —$OC(O)NR_2$, —N(R)C(O)OR, —N(R)C(O)R, —$N(R)C(O)NR_2$, —$N(R)S(O)_2R$, —$P(O)(OR)_2$, —$P(O)(NR_2)OR$, or —$P(O)(NR_2)_2$.

In some embodiments, $R^4$ is hydrogen. In some embodiments, $R^4$ is —$R^6$. In some embodiments, $R^4$ is halogen. In some embodiments, $R^4$ is —CN. In some embodiments, $R^4$ is —$NO_2$. In some embodiments, $R^4$ is —OR. In some embodiments, $R^4$ is —SR. In some embodiments, $R^4$ is —$NR_2$. In some embodiments, $R^4$ is —$S(O)_2R$. In some embodiments, $R^4$ is —$S(O)_2NR_2$. In some embodiments, $R^4$ is —S(O)R. In some embodiments, $R^4$ is —C(O)R. In some embodiments, $R^4$ is —C(O)OR. In some embodiments, $R^4$ is —C(O)NR$_2$. In some embodiments, R$^4$ is —C(O)N(R)OR. In some embodiments, R$^4$ is —OC(O)R. In some embodiments, R$^4$ is —OC(O)NR$_2$. In some embodiments, R$^4$ is —N(R)C(O)OR. In some embodiments, R$^4$ is —N(R)C(O)R. In some embodiments, R$^4$ is —N(R)C(O)NR$_2$. In some embodiments, R$^4$ is —N(R)S(O)$_2$R. In some embodiments, R$^4$ is —P(O)(OR)$_2$. In some embodiments, R$^4$ is —P(O)(NR$_2$)OR. In some embodiments, R$^4$ is —P(O)(NR$_2$)$_2$.

In some embodiments, R$^4$ is methyl. In some embodiments, R$^4$ is ethyl. In some embodiments, R$^4$ is cyclopropyl.

In some embodiments, R$^4$ is selected from those depicted in Table 1.

As defined above and described herein, R$^5$ is hydrogen, deuterium, an optionally substitute C$_{1-4}$ aliphatic, or —CN.

In some embodiments, R$^5$ is hydrogen. In some embodiments, R$^5$ is deuterium. In some embodiments, R$^5$ is an optionally substituted C$_{1-4}$ aliphatic. In some embodiments, R$^5$ is —CN.

In some embodiments, R$^5$ is selected from those depicted in Table 1.

As defined above and described herein, each R$^6$ is independently an optionally substituted group selected from C$_{1-6}$ aliphatic, phenyl, a 4-7 membered saturated or partially unsaturated heterocyclic ring having 1-3 heteroatoms independently selected from boron, nitrogen, oxygen, silicon, and sulfur, and a 5-6 membered heteroaryl ring having 1-4 heteroatoms independently selected from boron, nitrogen, oxygen, silicon, and sulfur.

In some embodiments, R$^6$ is an optionally substituted C$_{1-6}$ aliphatic. In some embodiments, R$^6$ is an optionally substituted phenyl. In some embodiments, R$^6$ is an optionally substituted 4-7 membered saturated or partially unsaturated heterocyclic ring having 1-3 heteroatoms independently selected from boron, nitrogen, oxygen, silicon, and sulfur. In some embodiments, R$^6$ is an optionally substituted 5-6 membered heteroaryl ring having 1-4 heteroatoms independently selected from boron, nitrogen, oxygen, silicon, and sulfur.

In some embodiments, R$^6$ is selected from those depicted in Table 1.

As defined generally above, each R$^7$ is independently hydrogen, deuterium, halogen, —CN, —OR, —SR, —S(O)R, —S(O)$_2$R, —N(R)$_2$, —P(O)(R)$_2$, —P(O)(OR)$_2$, —P(O)(NR$_2$)OR, —P(O)(NR$_2$)$_2$, —Si(OH)R$_2$, —Si(OH)$_2$R, —SiR$_3$, or an optionally substituted C$_{1-4}$ aliphatic, or R$^1$ and X$^1$ or X$^3$ are taken together with their intervening atoms to form a 5-7 membered saturated, partially unsaturated, carbocyclic ring or heterocyclic ring having 1-3 heteroatoms, independently selected from boron, nitrogen, oxygen, silicon, or sulfur, or two R$^7$ groups on the same carbon are optionally taken together with their intervening atoms to form a 3-6 membered spiro fused ring or a 4-7 membered heterocyclic ring having 1-2 heteroatoms independently selected from boron, nitrogen, oxygen, silicon, or sulfur, or two R$^7$ groups on adjacent carbon atoms are optionally taken together with their intervening atoms to form a 3-7 membered saturated, partially unsaturated, carbocyclic ring or heterocyclic ring having 1-3 heteroatoms independently selected from boron, nitrogen, oxygen, silicon, or sulfur, or a 7-13 membered saturated, partially unsaturated, bridged heterocyclic ring, or a spiro heterocyclic ring having 1-3 heteroatoms, independently selected from boron, nitrogen, oxygen, silicon, or sulfur.

In some embodiments, R$^7$ is hydrogen. In some embodiments, R$^7$ is deuterium. In some embodiments, R$^7$ is halogen. In some embodiments, R$^7$ is —CN. In some embodiments, R$^7$ is —OR. In some embodiments, R$^7$ is —SR. In some embodiments, R$^7$ is —S(O)R. In some embodiments, R$^7$ is —S(O)$_2$R. In some embodiments, R$^7$ is —NR$_2$. In some embodiments, R$^7$ is —Si(R)$_3$. In some embodiments, R$^7$ is —P(O)(R)$_2$. In some embodiments, R$^7$ is —P(O)(OR)$_2$. In some embodiments, R$^7$ is —P(O)(NR$_2$)OR. In some embodiments, R$^7$ is —P(O)(NR$_2$)$_2$. In some embodiments, R$^7$ is —Si(OH)R$_2$. In some embodiments, R$^7$ is —Si(OH)$_2$R. In some embodiments, R$^7$ is an optionally substituted C$_{1-4}$ aliphatic. In some embodiments, R$^7$ and X$^1$ or X$^3$ are taken together with their intervening atoms to form a 5-7 membered saturated, partially unsaturated, carbocyclic ring or heterocyclic ring having 1-3 heteroatoms, independently selected from boron, nitrogen, oxygen, silicon, or sulfur. In some embodiments, two R$^7$ groups on the same carbon are optionally taken together with their intervening atoms to form a 3-6 membered spiro fused ring or a 4-7 membered heterocyclic ring having 1-2 heteroatoms independently selected from boron, nitrogen, oxygen, silicon, or sulfur. In some embodiments, two R$^7$ groups on adjacent carbon atoms are optionally taken together with their intervening atoms to form a 3-7 membered saturated, partially unsaturated, carbocyclic ring or heterocyclic ring having 1-3 heteroatoms independently selected from boron, nitrogen, oxygen, silicon, or sulfur. In some embodiments, two R$^7$ groups on adjacent carbon atoms are optionally taken together with their intervening atoms to form a 7-13 membered saturated, partially unsaturated, bridged heterocyclic ring, or a spiro heterocyclic ring having 1-3 heteroatoms, independently selected from boron, nitrogen, oxygen, silicon, or sulfur.

In some embodiments, R$^7$ is selected from hydrogen, halogen, —CN, —OR, —NR$_2$, or C$_{1-4}$ alkyl. In some embodiments, R$^7$ is selected from hydrogen, halogen, —CN, or C$_{1-4}$ alkyl. In some embodiments, R$^7$ is fluoro. In some embodiments, two R$^7$ groups on the same carbon are optionally taken together with their intervening atoms to form a 3- or 4-membered spiro fused ring.

In some embodiments, R$^7$ is selected from those depicted in Table 1 below.

As defined above and described herein, Ring A is a bi- or tricyclic ring selected from

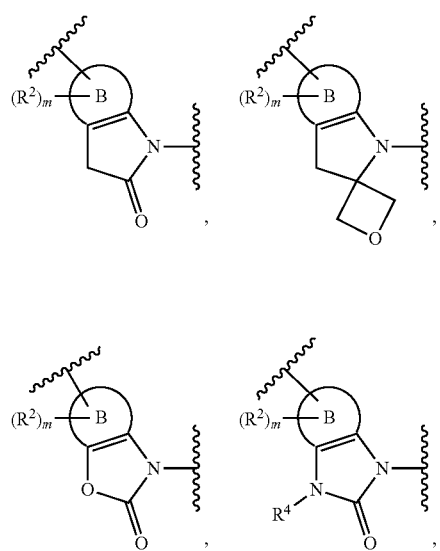

-continued
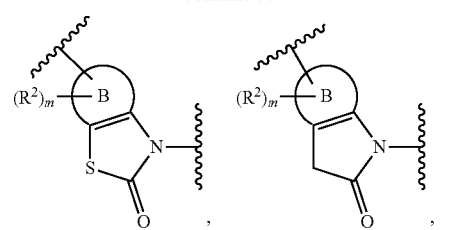
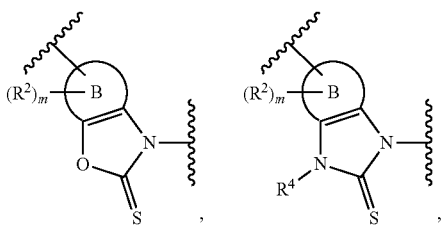
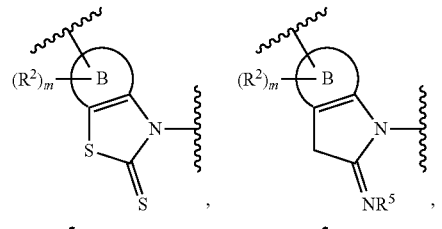
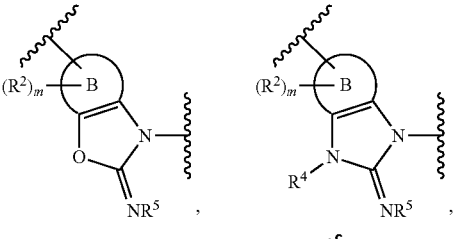
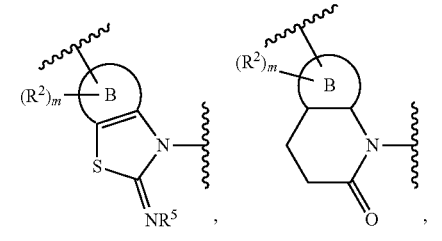
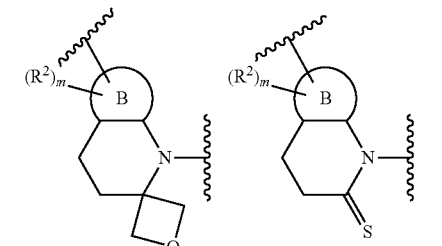
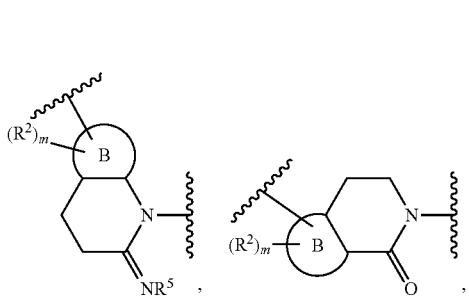
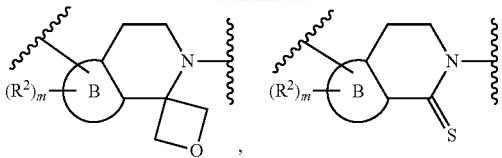
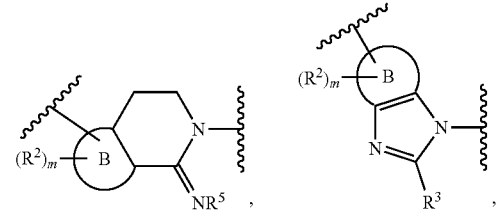
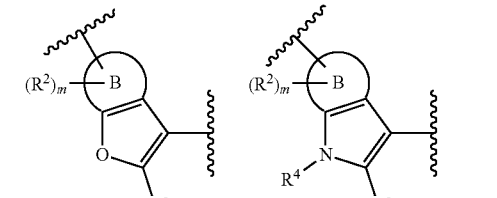
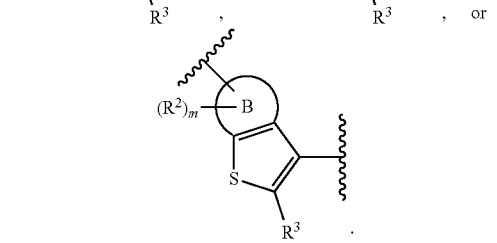
In some embodiments, Ring A is
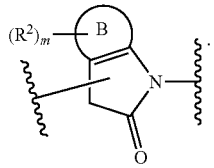
In some embodiments, Ring A is
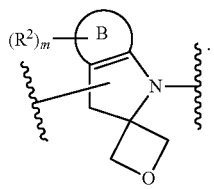
In some embodiments, Ring A is
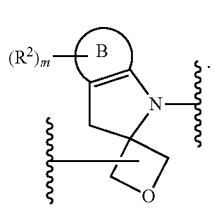

In some embodiments, Ring A is
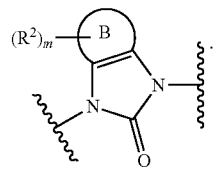
In some embodiments, Ring A is
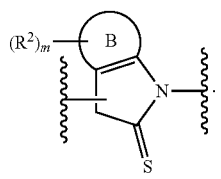
In some embodiments, Ring A is
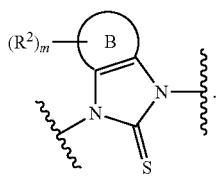
In some embodiments, Ring A is
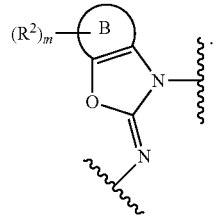
In some embodiments, Ring A is
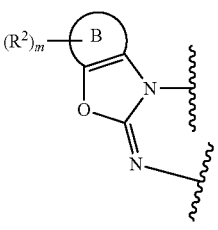
In some embodiments, Ring A is
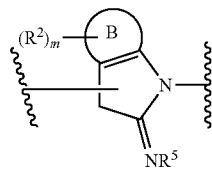
In some embodiments, Ring A is
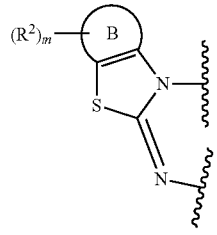
In some embodiments, Ring A is
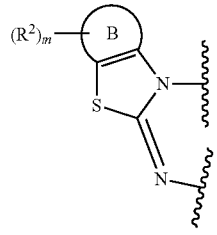
In some embodiments, Ring A is
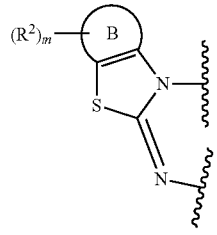
In some embodiments, Ring A is
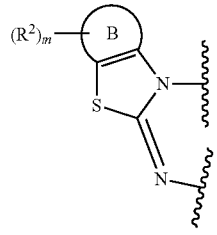

In some embodiments, Ring A is
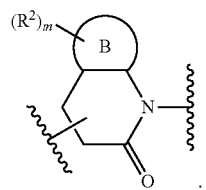
In some embodiments, Ring A is
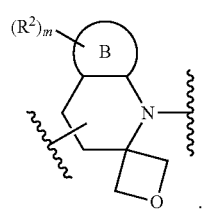
In some embodiments, Ring A is
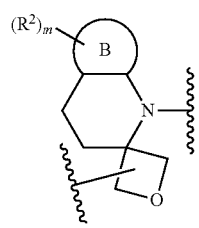
In some embodiments, Ring A is
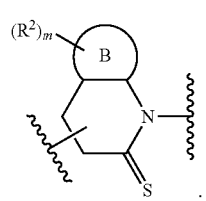
In some embodiments, Ring A is
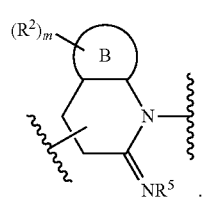
In some embodiments, Ring A is
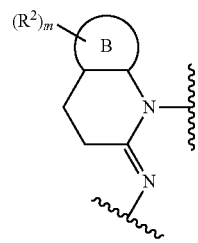
In some embodiments, Ring A is
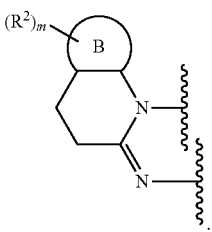
In some embodiments, Ring A is
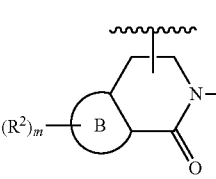
In some embodiments, Ring A is
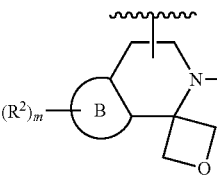
In some embodiments, Ring A is
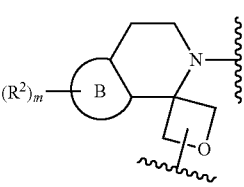

In some embodiments, Ring A is

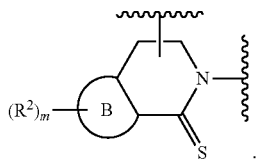

In some embodiments, Ring A is

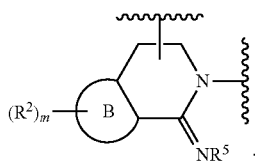

In some embodiments, Ring A is

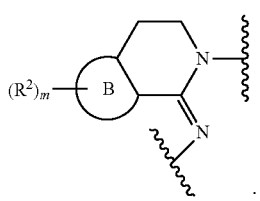

In some embodiments, Ring A is

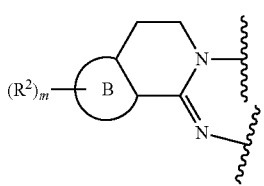

In some embodiments, Ring A is

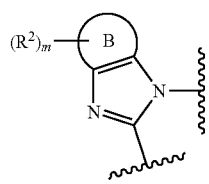

In some embodiments, Ring A is

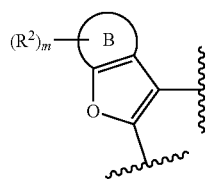

In some embodiments, Ring A is

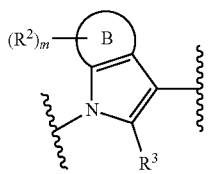

In some embodiments, Ring A is

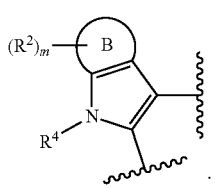

In some embodiments, Ring A is

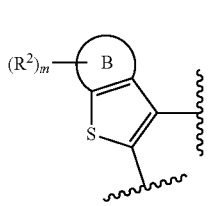

In some embodiments, Ring A is selected from those depicted in Table 1 below.

As defined above and described herein, Ring B is a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur;

In some embodiments, Ring B is a fused 6-membered aryl. In some embodiments, Ring B is a fused 6-membered heteroaryl containing 1-4 heteroatoms independently selected from nitrogen, oxygen, or sulfur. In some embodiments, Ring B is a fused 5 to 7-membered saturated or partially unsaturated carbocyclyl. In some embodiments, Ring B is fused 5 to 7-membered saturated or partially saturated heterocyclyl with 1-3 heteroatoms independently selected from boron, nitrogen, oxygen, silicon, or sulfur. In some embodiments, Ring B is fused 5-membered heteroaryl with 1-4 heteroatoms independently selected from boron, nitrogen, oxygen, silicon, or sulfur.

In some embodiments, Ring B is

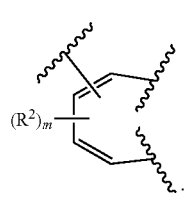

In some embodiments, Ring B is
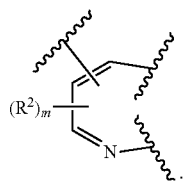
In some embodiments, Ring B is
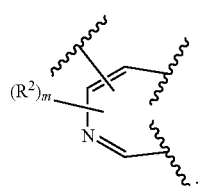
In some embodiments, Ring B is
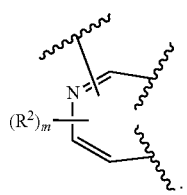
In some embodiments, Ring B is
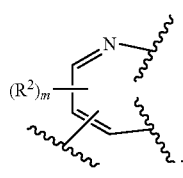
In some embodiments, each Ring B is
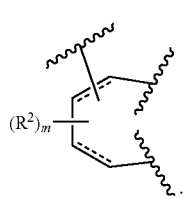
In some embodiments, each Ring B is
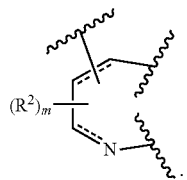
In some embodiments, each Ring B is
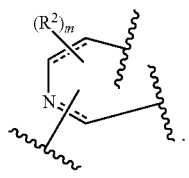
In some embodiments, each Ring B is
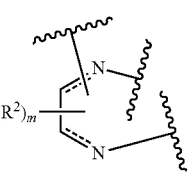
In some embodiments, Ring B is
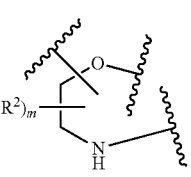
In some embodiments, Ring B is
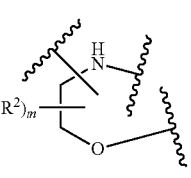
.

In some embodiments, Ring B is
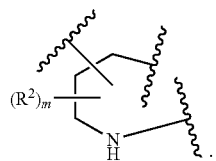
In some embodiments, Ring B is
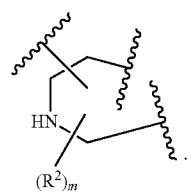
In some embodiments, Ring B is
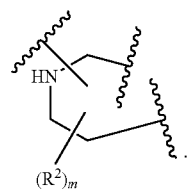
In some embodiments, Ring B is
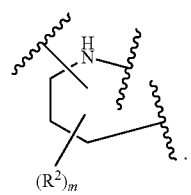
In some embodiments, Ring B is
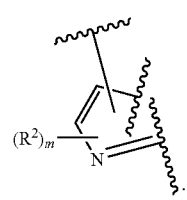
In some embodiments, Ring B is
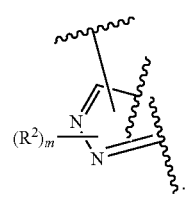
In some embodiments, Ring B is
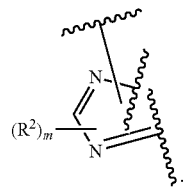
In some embodiments, Ring B is
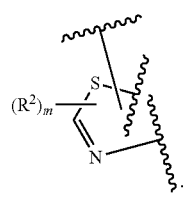
In some embodiments, Ring B is
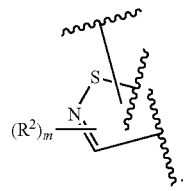
In some embodiments, Ring B is
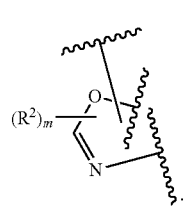
In some embodiments, Ring B is
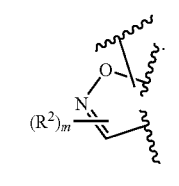
In some embodiments, Ring B is
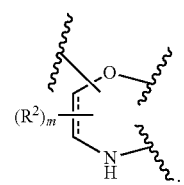

In some embodiments, Ring B is
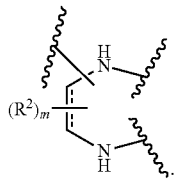
In some embodiments, Ring B is
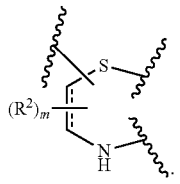
In some embodiments, Ring B is
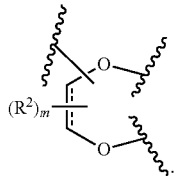
In some embodiments, Ring B is
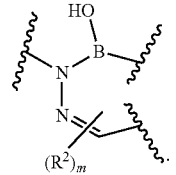
In some embodiments, Ring B is selected from those depicted in Table 1 below.
As defined above and described herein, Ring C is a mono- or bicyclic ring selected from
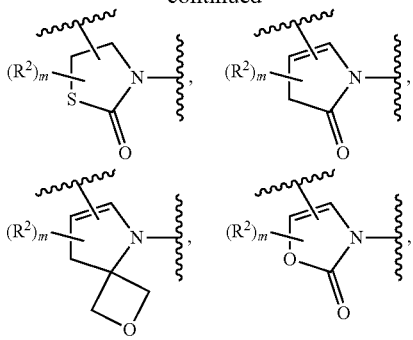
-continued
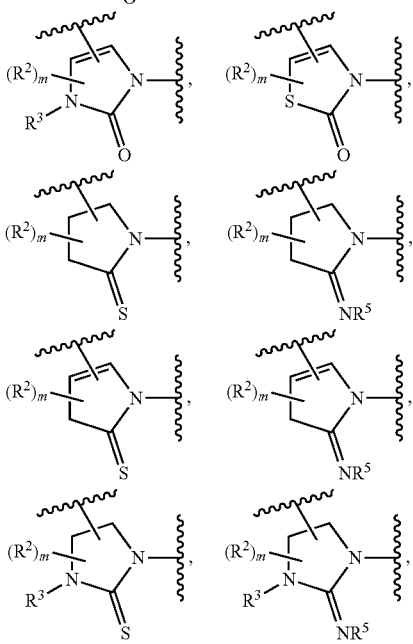
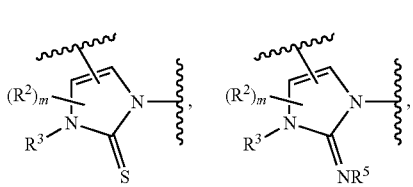
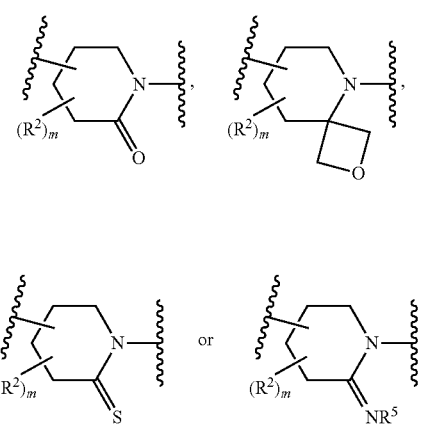

In some embodiments, Ring C is
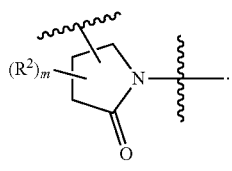
In some embodiments, Ring C is
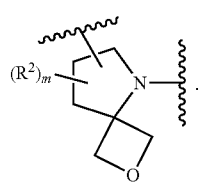
In some embodiments, Ring C is
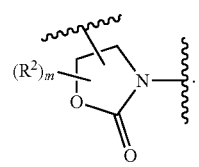
In some embodiments, Ring C is
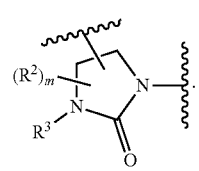
In some embodiments, Ring C is
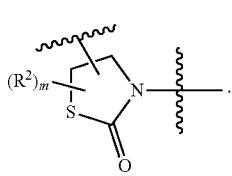
In some embodiments, Ring C is
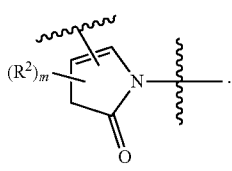
In some embodiments, Ring C is
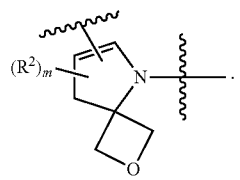
In some embodiments, Ring C is
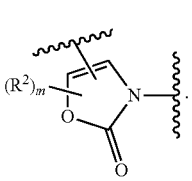
In some embodiments, Ring C is
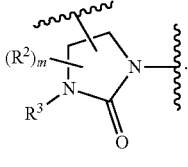
In some embodiments, Ring C is
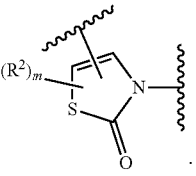
In some embodiments, Ring C is
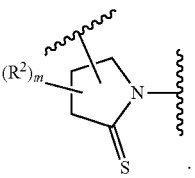
In some embodiments, Ring C is
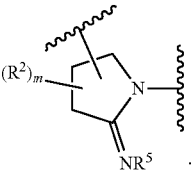

In some embodiments, Ring C is
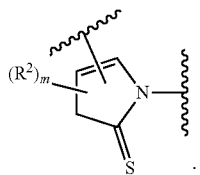
In some embodiments, Ring C is
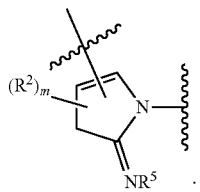
In some embodiments, Ring C is
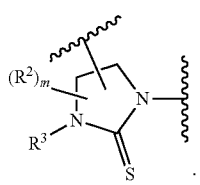
In some embodiments, Ring C is
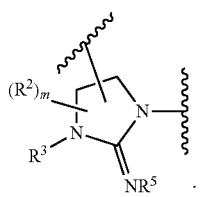
In some embodiments, Ring C is
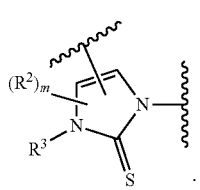
In some embodiments, Ring C is
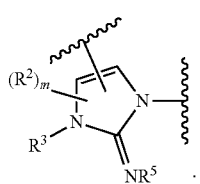
In some embodiments, Ring C is
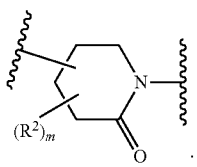
In some embodiments, Ring C is
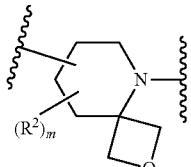
In some embodiments, Ring C is
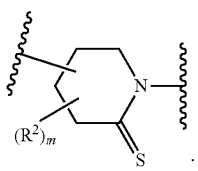
In some embodiments, Ring C is
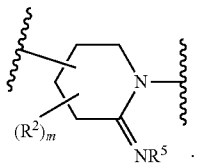
In some embodiments, Ring C is
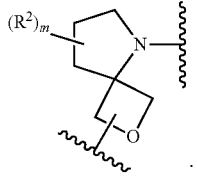
In some embodiments, Ring C is
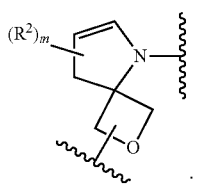

In some embodiments, Ring C is

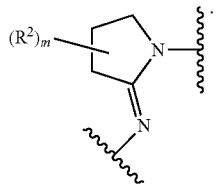

In some embodiments, Ring C is

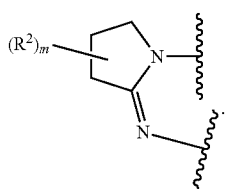

In some embodiments, Ring C is

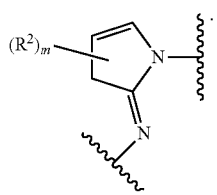

In some embodiments, Ring C is

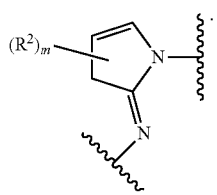

In some embodiments, Ring C is

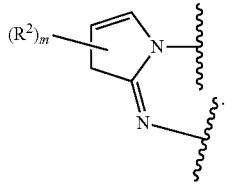

In some embodiments, Ring C is

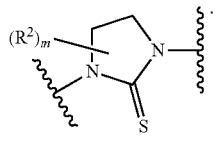

In some embodiments, Ring C is

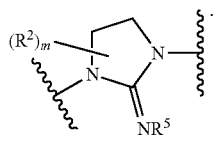

In some embodiments, Ring C is

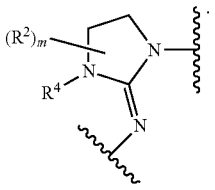

In some embodiments, Ring C is

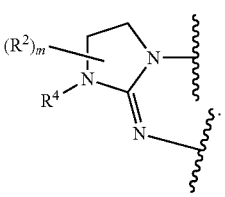

In some embodiments, Ring C is

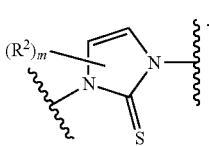

In some embodiments, Ring C is

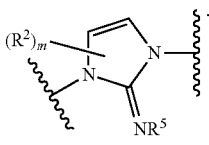

In some embodiments, Ring C is

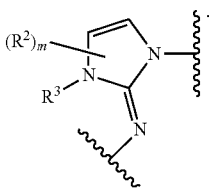

In some embodiments, Ring C is

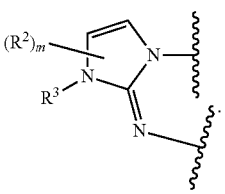

In some embodiments, Ring C is
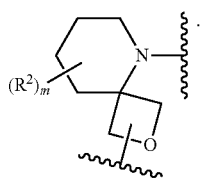
In some embodiments, Ring C is
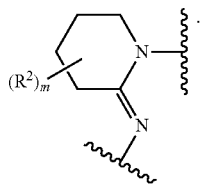
In some embodiments, Ring C is
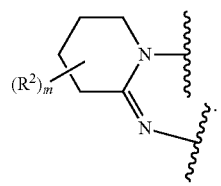
In some embodiments, Ring C is a mono- or bicyclic ring selected from
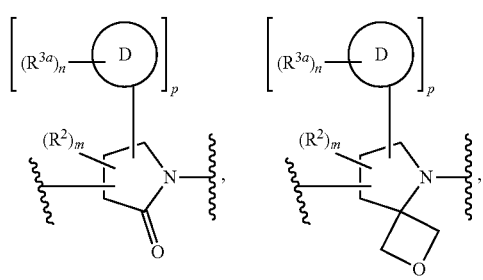
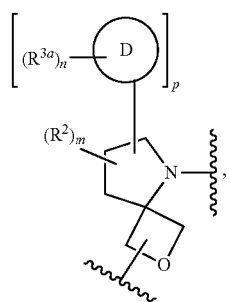
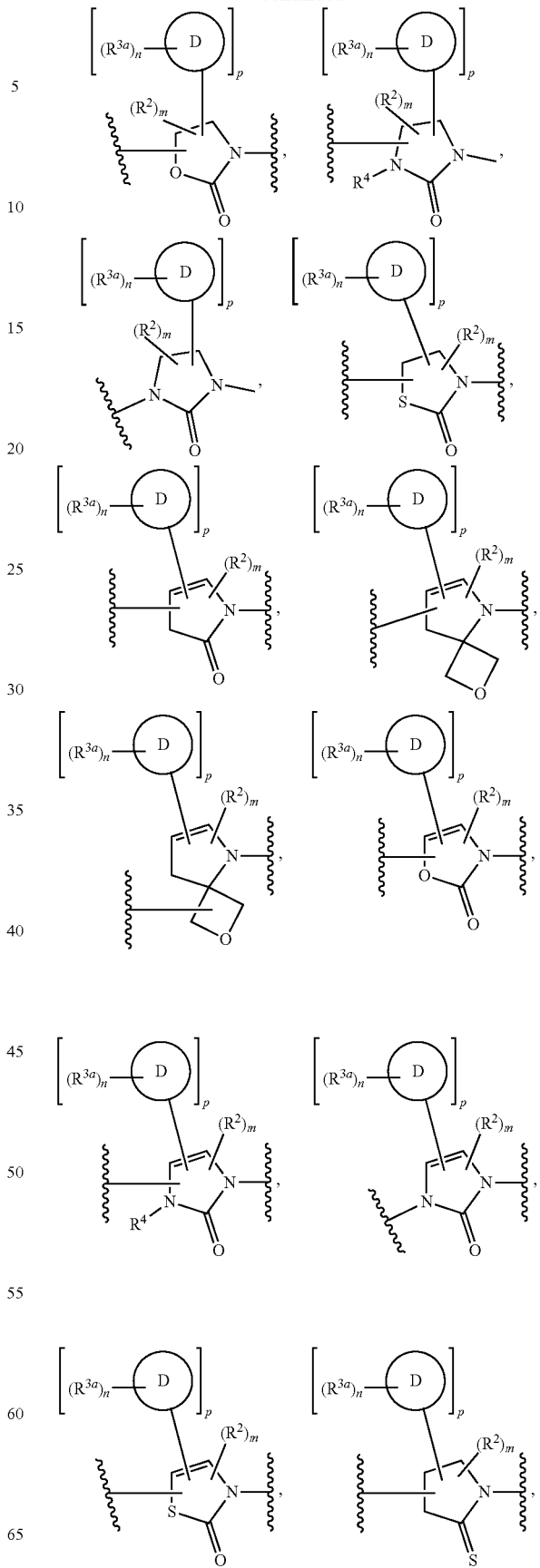

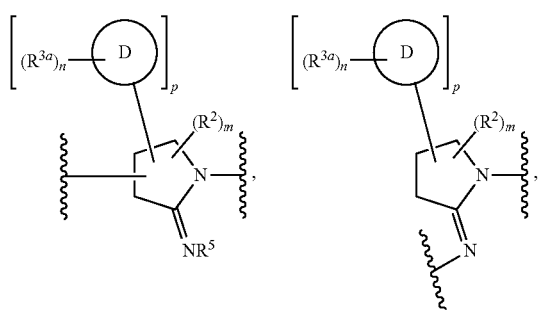
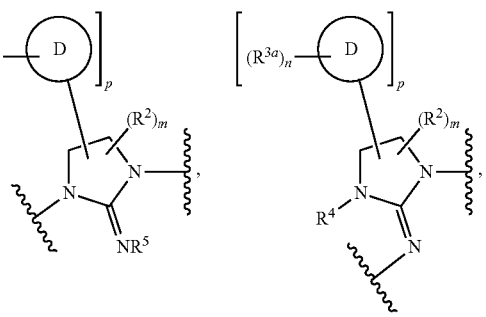
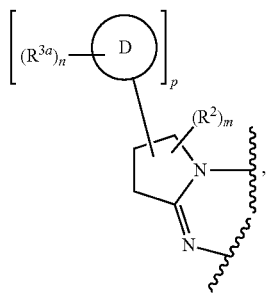
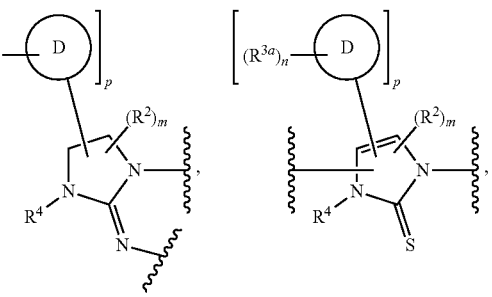
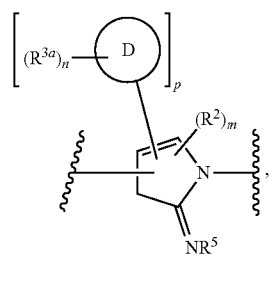
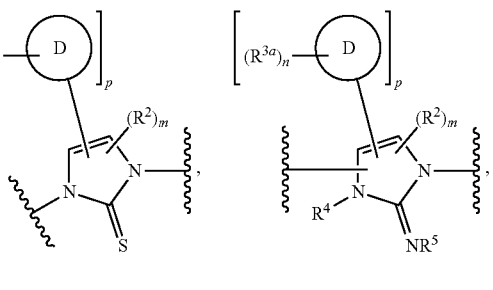
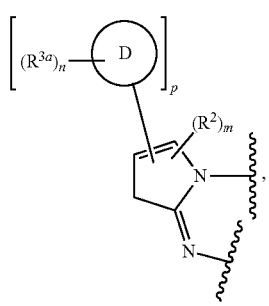
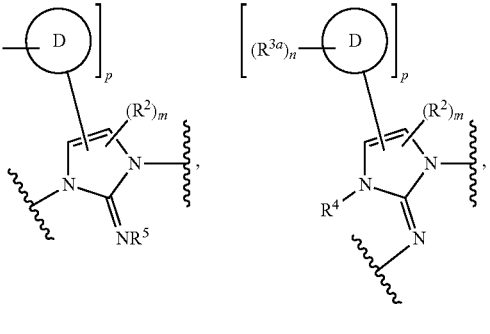
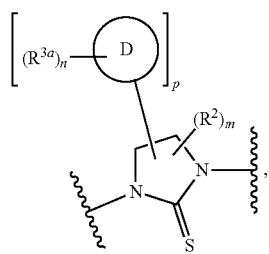
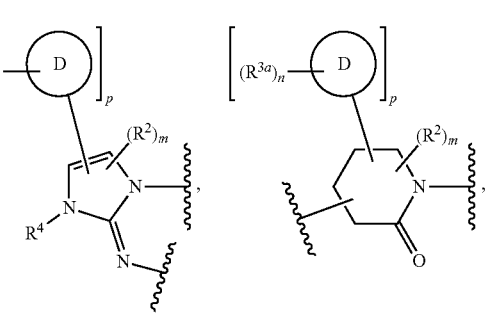

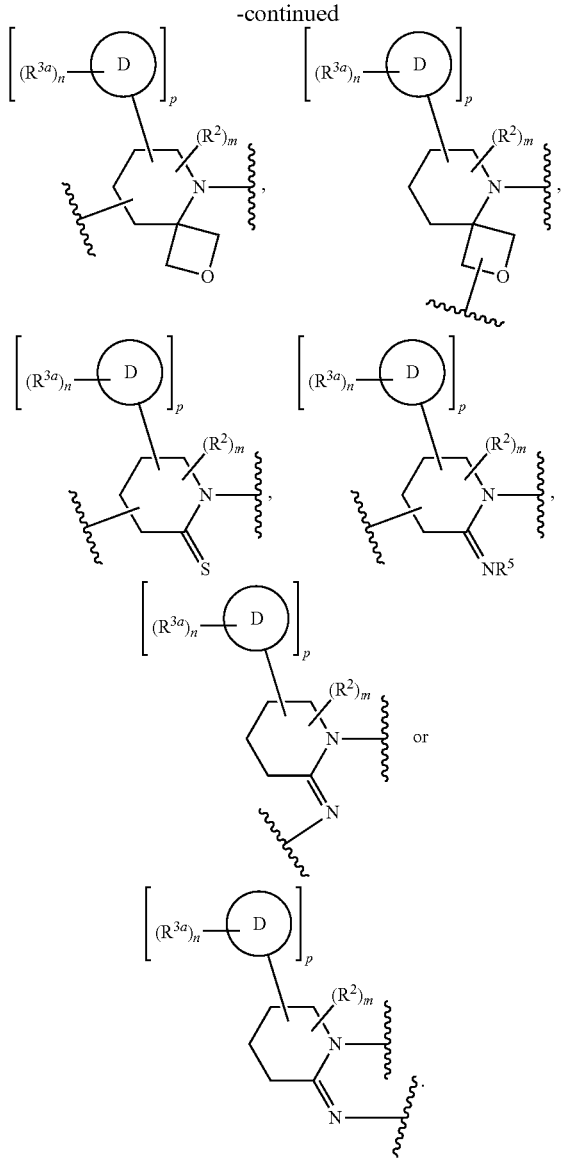

In some embodiments, Ring C is selected from those depicted in Table 1 below.

As defined above and described herein, Ring D is a ring selected from 6 to 10-membered aryl or heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur;

In some embodiments, Ring D is a 6 to 10-membered aryl. In some embodiments, Ring D is a 6 to 10-membered heteroaryl containing 1-4 heteroatoms independently selected from nitrogen, oxygen, or sulfur. In some embodiments, Ring D is a 5 to 7-membered saturated or partially unsaturated carbocyclyl. In some embodiments, Ring D is 5 to 7-membered saturated or partially saturated heterocyclyl with 1-3 heteroatoms independently selected from boron, nitrogen, oxygen, silicon, or sulfur. In some embodiments, Ring D is 5-membered heteroaryl with 1-4 heteroatoms independently selected from boron, nitrogen, oxygen, silicon, or sulfur.

In some embodiments, Ring D is quinoline. In some embodiments, Ring D is isoquinoline. In some embodiments, Ring D is imidazo[1,2-a]pyridine.

In some embodiments, Ring D is selected from those depicted in Table 1 below.

As defined above and described herein, each of Ring E, Ring F, and Ring G is independently a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur.

In some embodiments, each of Ring E, Ring F, and Ring G is independently a fused ring selected from 6-membered aryl. In some embodiments, each of Ring E, Ring F, and Ring G is independently a fused ring selected from 6-membered heteroaryl containing 1-4 heteroatoms independently selected from nitrogen, oxygen, or sulfur. In some embodiments, each of Ring E, Ring F, and Ring G is independently a fused ring selected from a 5 to 7-membered saturated or partially unsaturated carbocyclyl. In some embodiments, each of Ring E, Ring F, and Ring G is independently a fused ring selected from a 5 to 7-membered saturated or partially unsaturated heterocyclyl with 1-3 heteroatoms independently selected from boron, nitrogen, oxygen, silicon, or sulfur. In some embodiments, each of Ring E, Ring F, and Ring G is independently a fused ring selected from a 5-membered heteroaryl with 1-4 heteroatoms independently selected from nitrogen, oxygen or sulfur.

In some embodiments, Ring F is

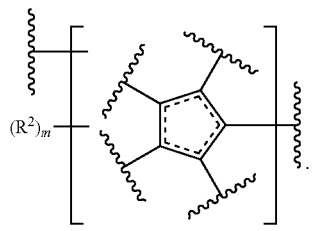

In some embodiments, Ring F is

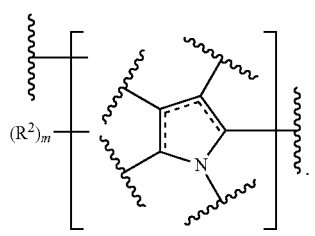

In some embodiments, Ring F is
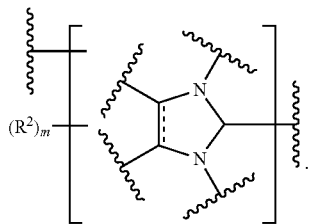
In some embodiments, Ring F is
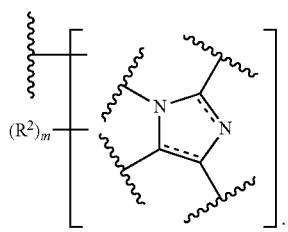
In some embodiments, Ring F is
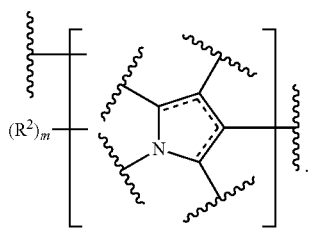
In some embodiments, Ring F is
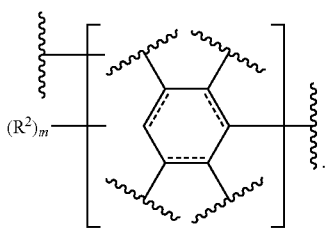
In some embodiments, Ring F is
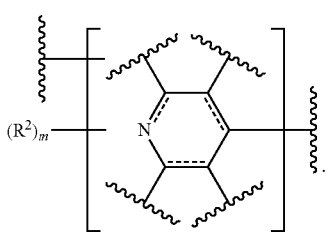
In some embodiments, Ring F is
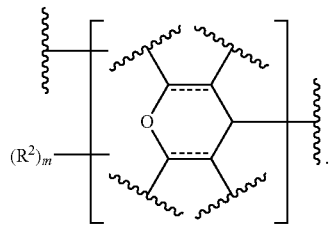
In some embodiments, Ring F is
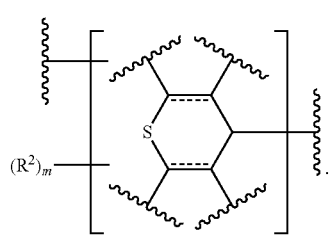
In some embodiments, Ring F is
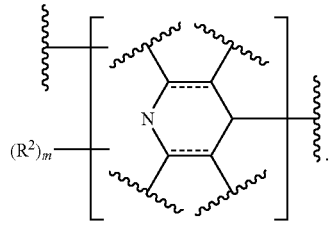
In some embodiments, Ring F is
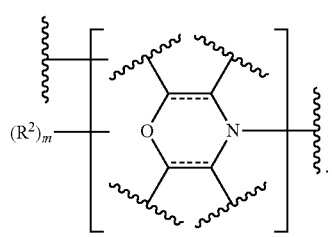
In some embodiments, Ring F is
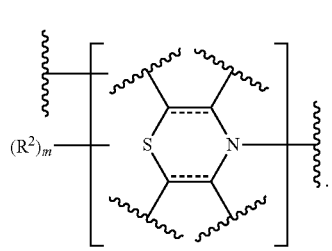

In some embodiments, Ring F is
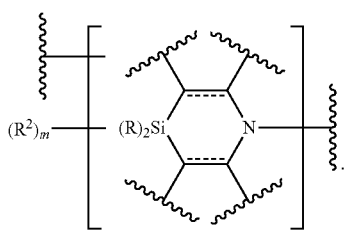
In some embodiments, Ring F is
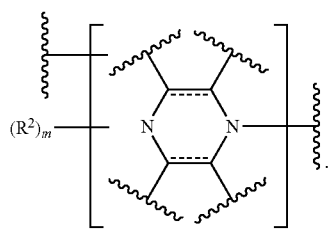
In some embodiments, Ring F is
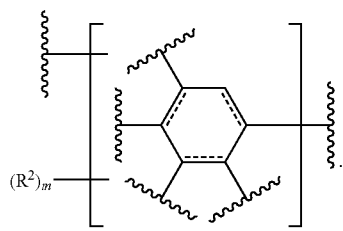
In some embodiments, Ring F is
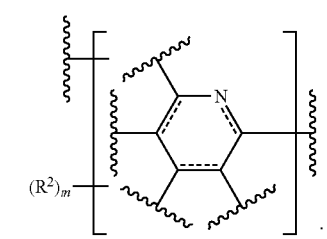
In some embodiments, Ring F is
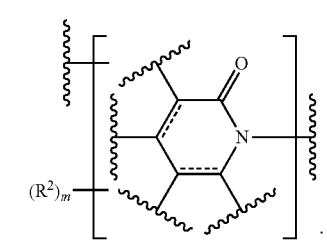
In some embodiments, Ring F is
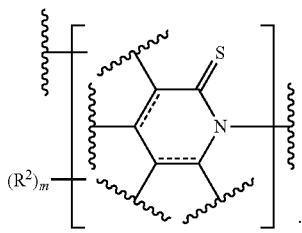
In some embodiments, Ring F is
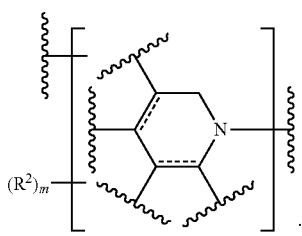
In some embodiments, Ring F is
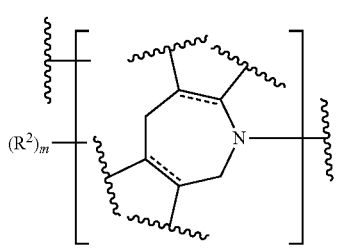
In some embodiments, Ring F is
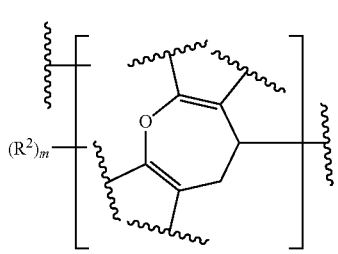

In some embodiments, Ring F is
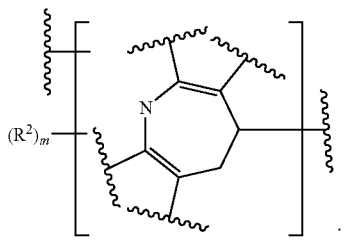
In some embodiments, Ring F is
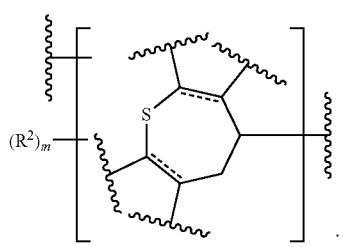
In some embodiments, Ring F is
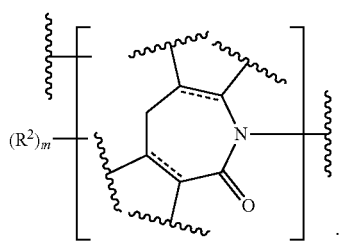
In some embodiments, Ring F is
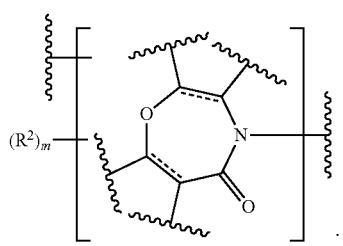
In some embodiments, Ring F is
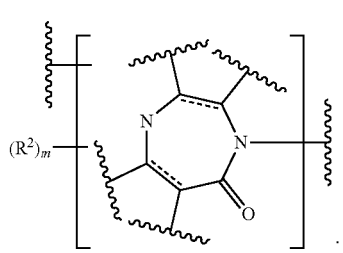
In some embodiments, Ring F is
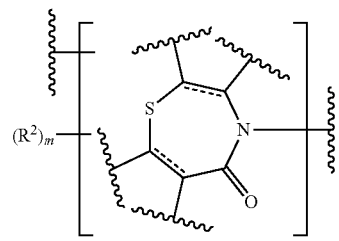
In some embodiments, Ring F is
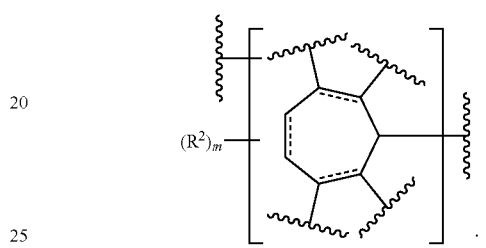
In some embodiments, Ring F is
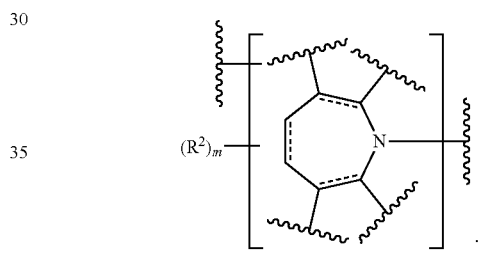
In some embodiments, Ring F is
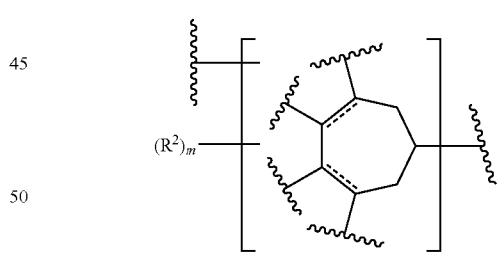
In some embodiments, Ring F is
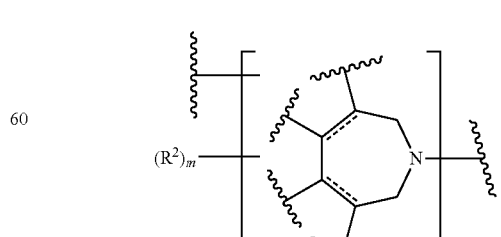

In some embodiments, Ring F is

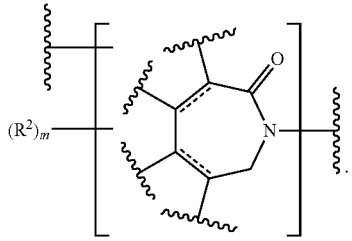

In some embodiments, Ring F is

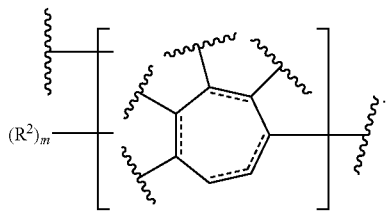

In some embodiments, Ring F is

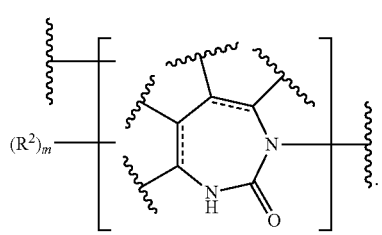

In some embodiments, Ring F is

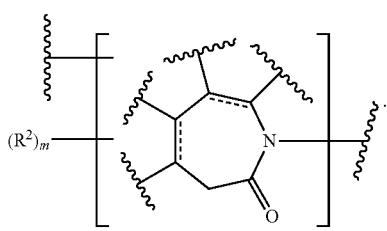

In some embodiments, each of Ring E and Ring G is independently

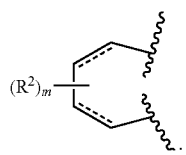

In some embodiments, each of Ring E and Ring G is independently

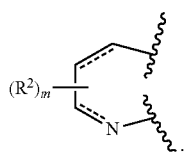

In some embodiments, each of Ring E and Ring G is independently

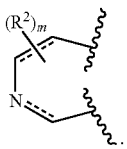

In some embodiments, each of Ring E and Ring G is independently

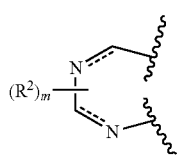

In some embodiments, each of Ring E and Ring G is independently is

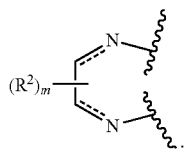

In some embodiments, each of Ring E and Ring G is independently

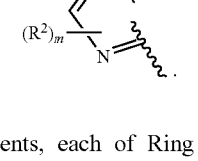

In some embodiments, each of Ring E and Ring G is independently

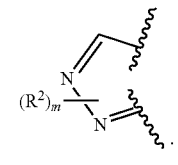

In some embodiments, each of Ring E and Ring G is independently

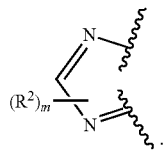

In some embodiments, each of Ring E and Ring G is independently

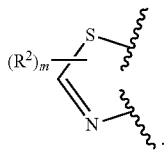

In some embodiments, each of Ring E and Ring G is independently

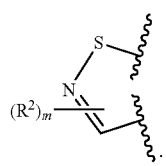

In some embodiments, each of Ring E and Ring G is independently

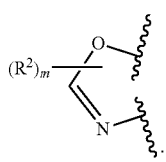

In some embodiments, each of Ring E and Ring G is independently

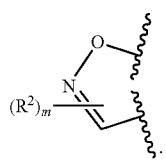

In some embodiments, each of Ring E and Ring G is independently

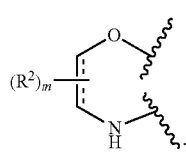

In some embodiments, each of Ring E and Ring G is independently

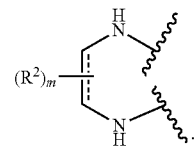

In some embodiments, each of Ring E and Ring G is independently

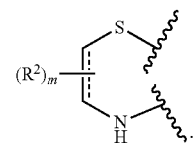

In some embodiments, each of Ring E and Ring G is independently

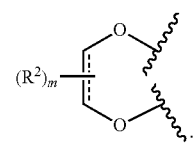

In some embodiments, each of Ring E and Ring G is independently

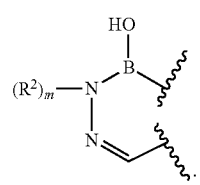

In some embodiments, Ring E, Ring F, and Ring G is

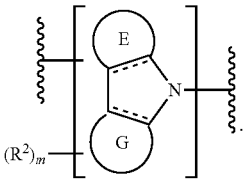

In some embodiments, Ring E, Ring F, and Ring G is

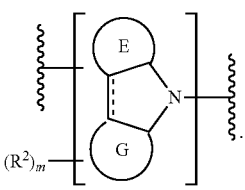

In some embodiment, Ring E, Ring F, and Ring G is

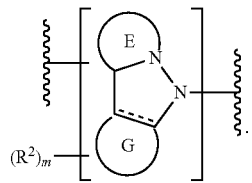

In some embodiments, Ring E, Ring F, and Ring G is

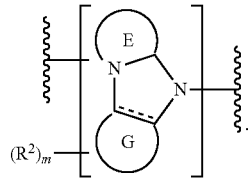

In some embodiments, Ring E, Ring F, and Ring G is

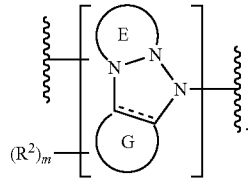

In some embodiments, Ring E, Ring F, and Ring G is

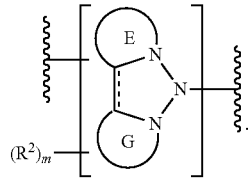

In some embodiments, Ring E, Ring F, and Ring G is

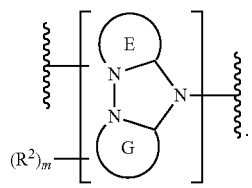

In some embodiments, Ring E, Ring F, and Ring G is

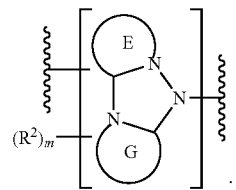

In some embodiments, Ring E, Ring F, and Ring G is

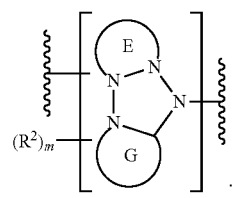

In some embodiments, Ring E, Ring F, and Ring G is

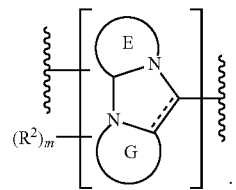

In some embodiments, Ring E, Ring F, and Ring G is

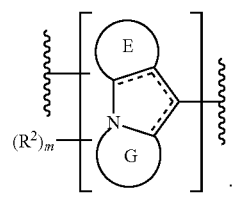

In some embodiments, Ring E, Ring F, and Ring G is

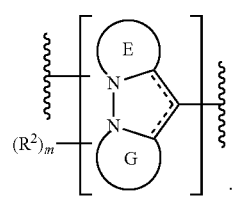

In some embodiments, Ring E, Ring F, and Ring G is

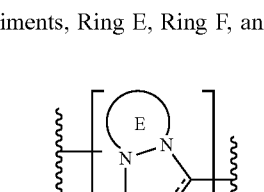

In some embodiments, Ring E, Ring F, and Ring G is

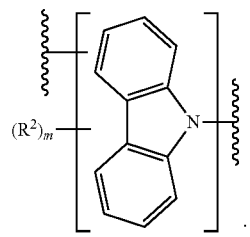

In some embodiments, Ring E, Ring F, and Ring G is

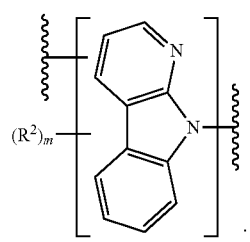

In some embodiments, Ring E, Ring F, and Ring G is

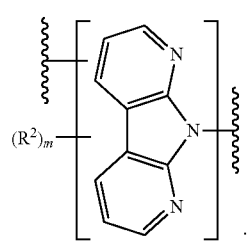

In some embodiments, Ring E, Ring F, and Ring G is

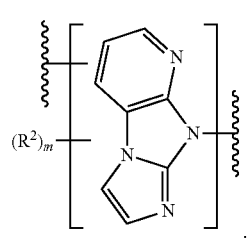

In some embodiments, Ring E, Ring F, and Ring G is

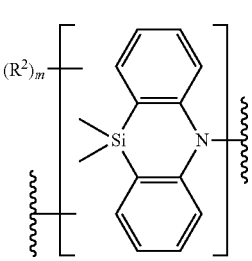

In some embodiments, Ring E, Ring F, and Ring G is

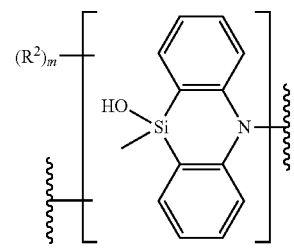

In some embodiments, Ring E, Ring F, and Ring G is

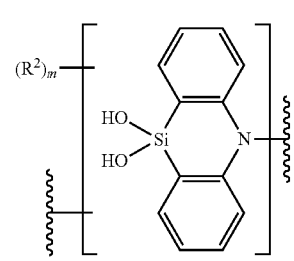

In some embodiments, Ring E, Ring F, and Ring G is

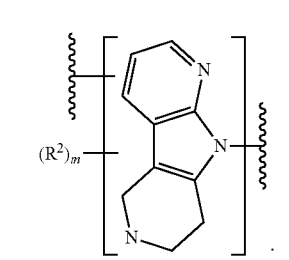

In some embodiments, Ring E, Ring F, and Ring G is

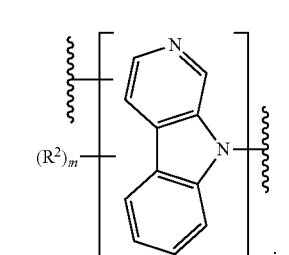

In some embodiments, Ring E, Ring F, and Ring G is

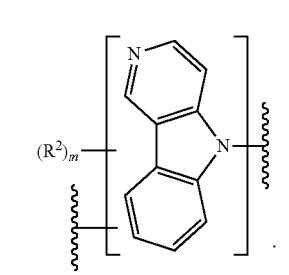

In some embodiments, Ring E, Ring F, and Ring G is

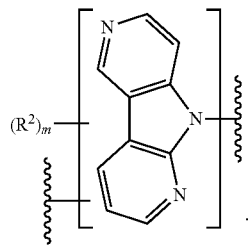

In some embodiments, Ring E, Ring F, and Ring G is

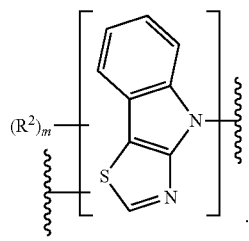

In some embodiments, Ring E, Ring F, and Ring G is

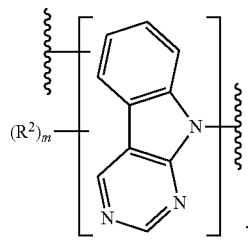

In some embodiments, Ring E, Ring F, and Ring G is

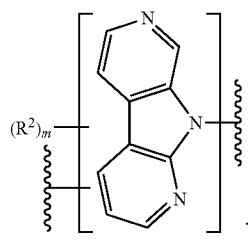

In some embodiments, Ring E, Ring F, and Ring G is

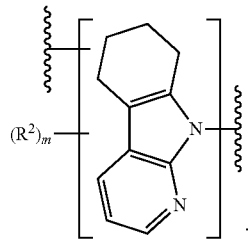

In some embodiments, Ring E, Ring F, and Ring G is

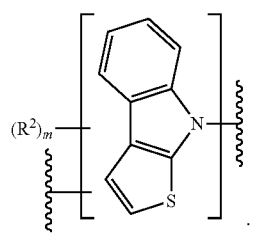

In some embodiments, Ring E, Ring F, and Ring G is

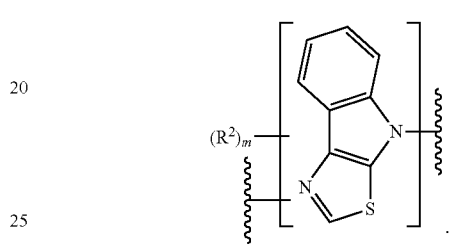

In some embodiments, Ring E, Ring F, and Ring G is

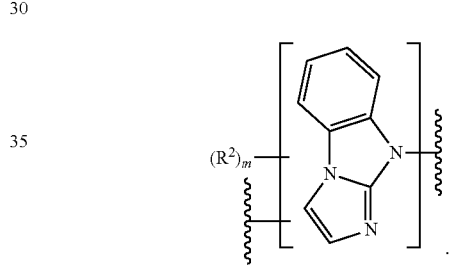

In some embodiments, Ring E, Ring F, and Ring G is

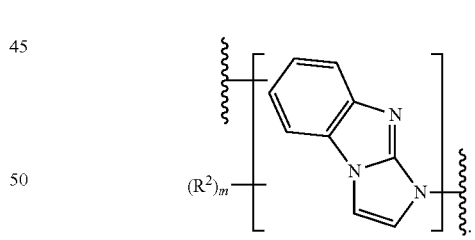

In some embodiments, Ring E, Ring F, and Ring G is

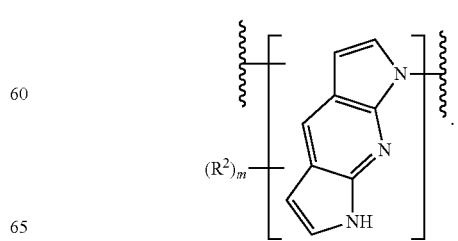

In some embodiments, Ring E, Ring F, and Ring G is

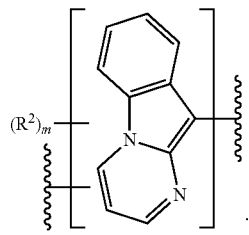

In some embodiments, Ring E, Ring F, and Ring G is

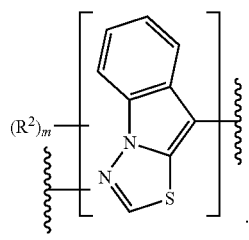

In some embodiments, Ring E, Ring F, and Ring G is selected from those depicted in Table 1, below.

As defined above and described herein, Ring H is a ring selected from a 7-9 membered saturated or partially unsaturated carbocyclyl or heterocyclyl ring with 1-3 heteroatoms independently selected from boron, nitrogen, oxygen, silicon, or sulfur, wherein Ring E is optionally further substituted with 1-2 oxo groups.

In some embodiments, Ring H is a ring selected from a 7-9 membered saturated or partially unsaturated carbocyclyl or heterocyclyl ring with 1-3 heteroatoms independently selected from boron, nitrogen, oxygen, silicon, or sulfur, wherein Ring H is optionally further substituted with 1-2 oxo groups.

In some embodiments, Ring H is

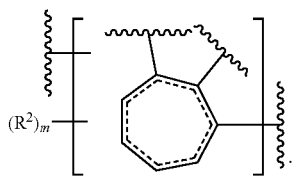

In some embodiments, Ring H is

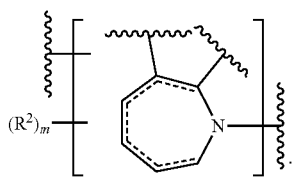

In some embodiments, Ring H is

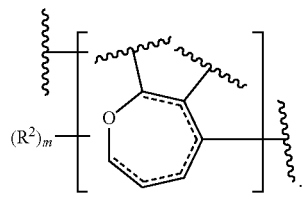

In some embodiments, Ring H is

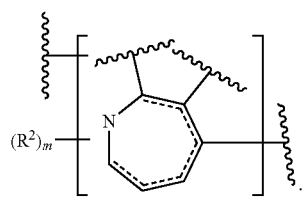

In some embodiments, Ring H is

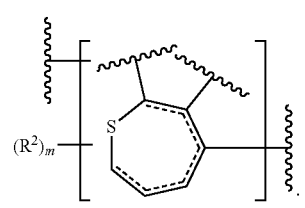

In some embodiments, Ring H is

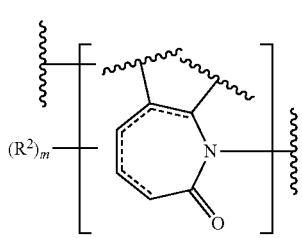

In some embodiments, Ring H is

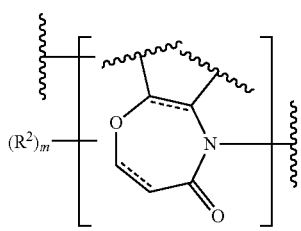

In some embodiments, Ring H is
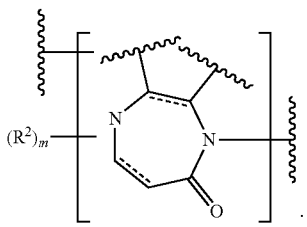
In some embodiments, Ring H is
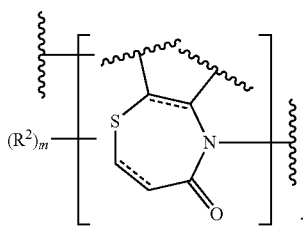
some embodiments, Ring H is
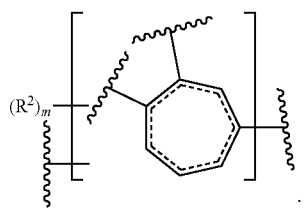
In some embodiments, Ring H is
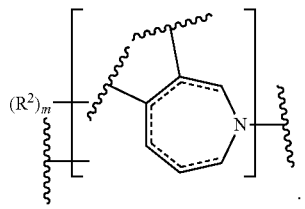
In some embodiments, Ring H is
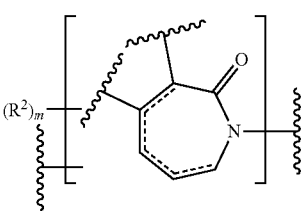
In some embodiments, Ring H is
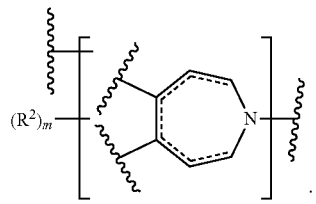
In some embodiments, Ring H is
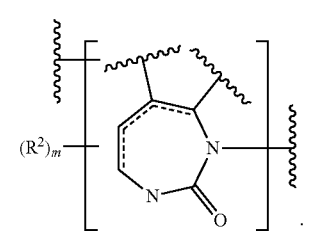
In some embodiments, Ring H is
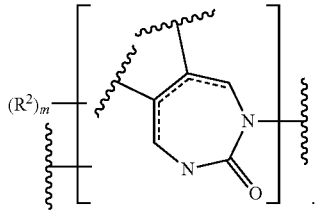
In some embodiments. Ring H is
[image at page position near line 45]
In some embodiments, Ring H is
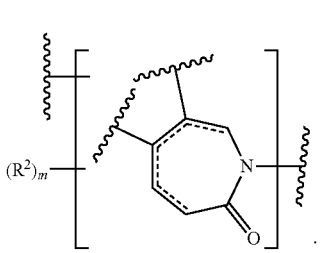

In some embodiments, Ring H is

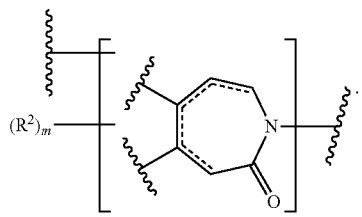

In some embodiments, Ring H is

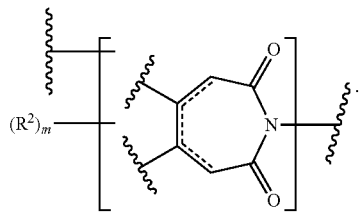

In some embodiments, Ring H is

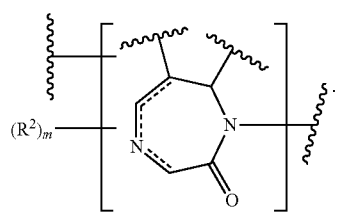

In some embodiments, Ring H is

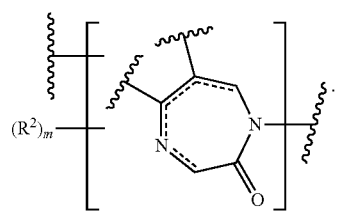

In some embodiments, Ring H is selected from those depicted in Table 1, below.

In some embodiments, Ring E and Ring H is

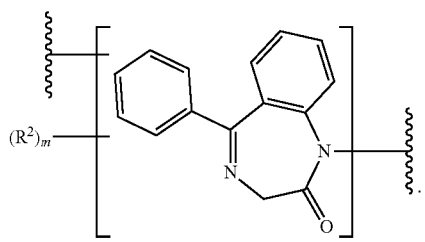

As defined above and described herein, each of Ring I and Ring J is independently a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur In some embodiments, each of Ring I and Ring J is independently a 6-membered aryl. In some embodiments, each of Ring I and Ring J is independently a 6-membered heteroaryl containing 1-4 heteroatoms independently selected from nitrogen, oxygen, or sulfur. In some embodiments, each of Ring I and Ring J is independently a 5 to 7-membered saturated or partially unsaturated carbocyclyl. In some embodiments, each of Ring I and Ring J is independently a 5 to 7-membered saturated or partially unsaturated heterocyclyl with 1-3 heteroatoms independently selected from boron, nitrogen, oxygen, silicon, or sulfur. In some embodiments, each of Ring I and Ring J is independently a 5-membered heteroaryl with 1-3 heteroatoms independently selected from nitrogen, oxygen or sulfur.

In some embodiments, each of Ring I and Ring J is independently


In some embodiments, each of Ring I and Ring J is independently

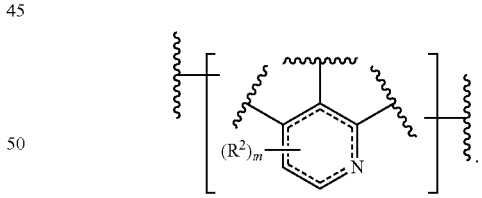

In some embodiments, each of Ring I and Ring J is independently

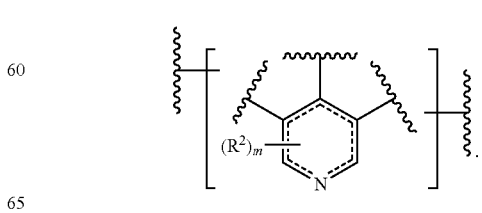

In some embodiments, each of Ring I and Ring J is independently

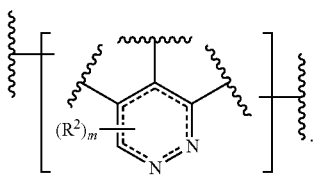

In some embodiments, each of Ring I and Ring J is independently

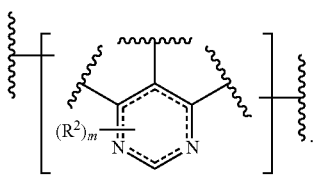

In some embodiments, Ring I and Ring J is independently is

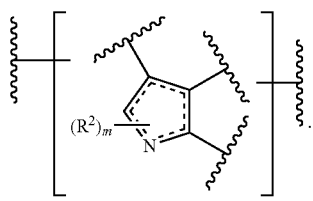

In some embodiments, Ring I and Ring J is independently

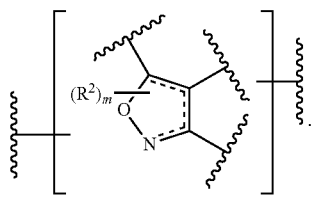

In some embodiments, Ring I and Ring J is independently

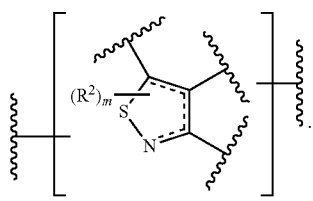

In some embodiments, Ring I and Ring J is selected from those depicted in Table 1, below.

As defined above and described herein, Ring K is a fused ring selected from a 7-12 membered saturated or partially unsaturated carbocyclyl or heterocyclyl with 1-3 heteroatoms independently selected from boron, nitrogen, oxygen, silicon, or sulfur, wherein Ring H is optionally further substituted with 1-2 oxo groups.

In some embodiments, Ring K is a fused ring selected from a 7-12 membered saturated or partially unsaturated carbocyclyl. In some embodiments, Ring K is a 7-12 membered saturated or partially unsaturated heterocyclyl ring with 1-3 heteroatoms independently selected from boron, nitrogen, oxygen, silicon, or sulfur. In some embodiments, Ring K is optionally further substituted with 1-2 oxo groups.

In some embodiments, Ring K is

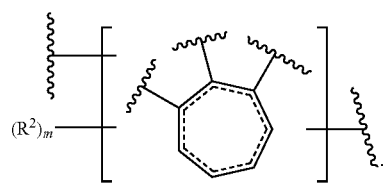

In some embodiments, Ring K is

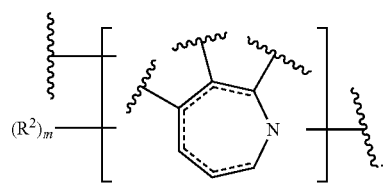

In some embodiments. Ring K is

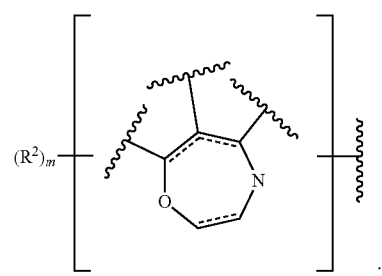

In some embodiments, Ring K is

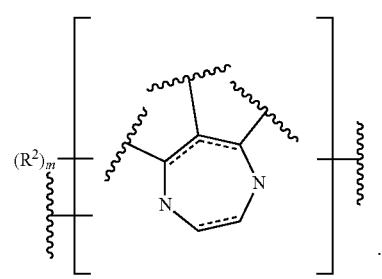

In some embodiments, Ring K is
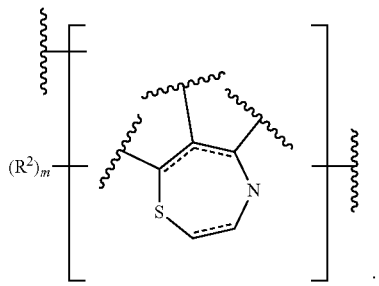
In some embodiments, Ring K is
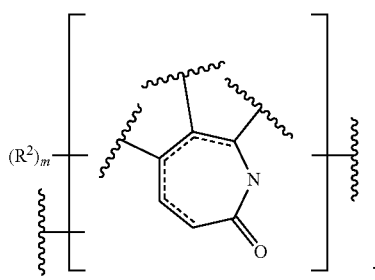
In some embodiments, Ring K is
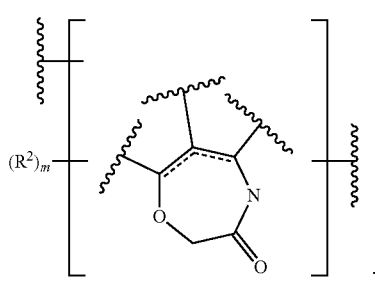
In some embodiments, Ring K is
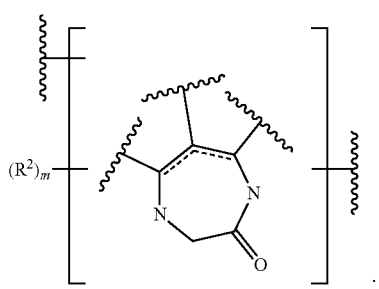
In some embodiments, Ring K is
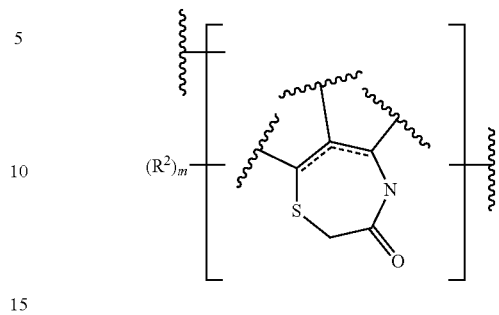
some embodiments, Ring K is
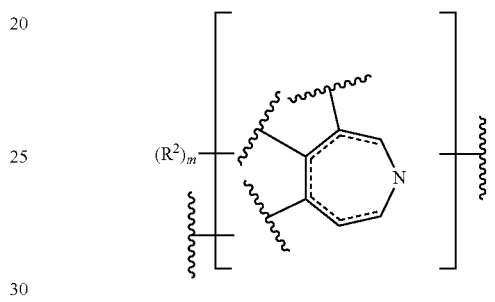
In some embodiments, Ring K is
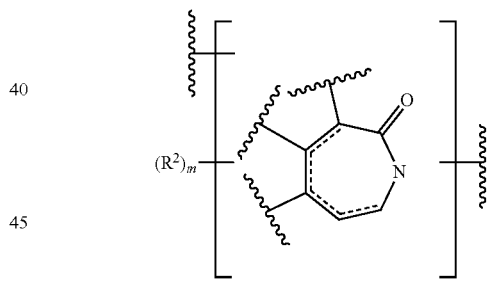
In some embodiments, Ring K is
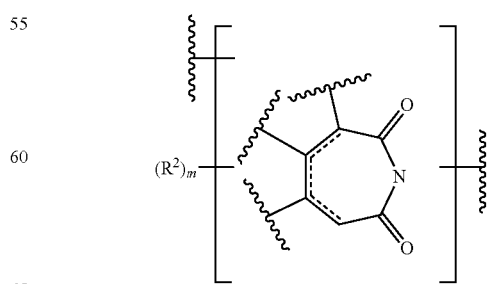

In some embodiments, Ring K is
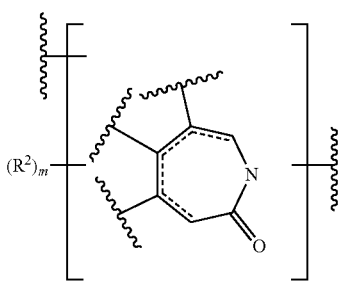
In some embodiments, Ring K is
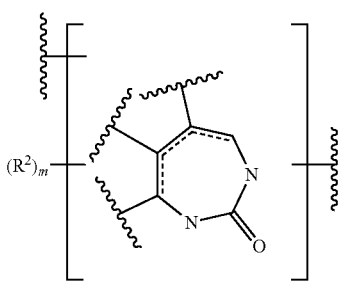
In some embodiments, Ring K is
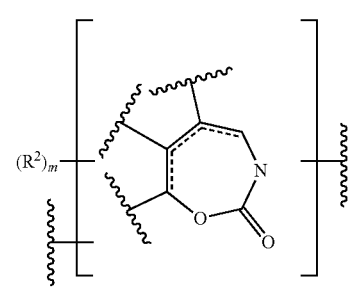
In some embodiments, Ring K is selected from those depicted in Table 1 below.
In some embodiments, Ring I, Ring J, and Ring K is
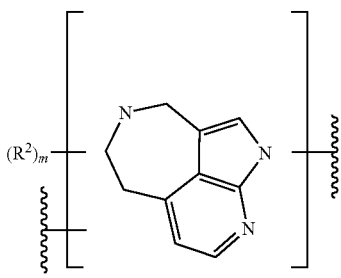
As defined above and described herein, Ring M is selected from
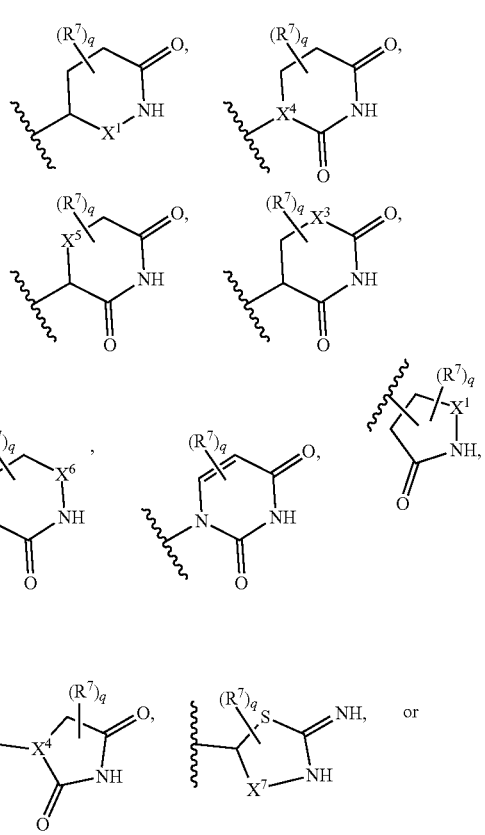
In some embodiments, Ring M is
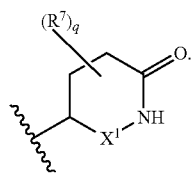
In some embodiments, Ring M is
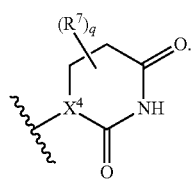

In some embodiments, Ring M is

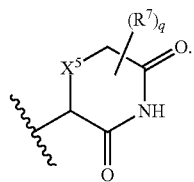

In some embodiments, Ring M is

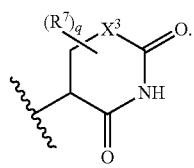

In some embodiments, Ring M is

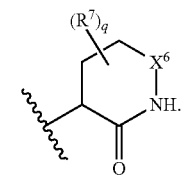

In some embodiments, Ring M is

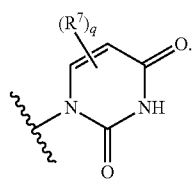

In some embodiments, Ring M is

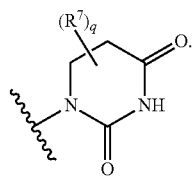

In some embodiments, Ring M is

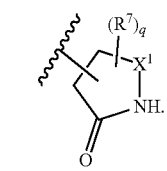

In some embodiments, Ring M is

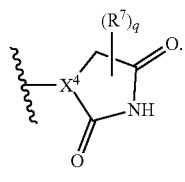

In some embodiments, Ring M is

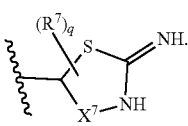

In some embodiments, Ring M is

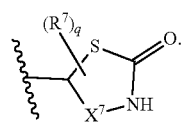

In some embodiments, Ring M is selected from those depicted in Table 1 below.

As defined above and described here, $L^1$ is a covalent bond or a $C_{1-3}$ bivalent straight or branched saturated or unsaturated hydrocarbon chain wherein 1-2 methylene units of the chain are independently and optionally replaced with —O—, —C(O)—, —C(S)—, —C(R)$_2$—, —CF(R)—, —C(F)$_2$—, —N(R)—, —S—, —S(O)$_2$— or —(C)=CH—;

In some embodiments, $L^1$ is a covalent bond. In some embodiments, $L^1$ is a $C_{1-3}$ aliphatic. In some embodiments, $L^1$ is —CH$_2$— In some embodiments, $L^1$ is —C(D)(H)—. In some embodiments, $L^1$ is —C(D)$_2$—. In some embodiments, $L^1$ is —CH$_2$CH$_2$— In some embodiments, $L^1$ is —NR—. In some embodiments, $L^1$ is —CH$_2$NR—. In some embodiments, $L^1$ is or —O—. In some embodiments, $L^1$ is —CH$_2$O—. In some embodiments, $L^1$ is —S—. In some embodiments, $L^1$ is —OC(O)—. In some embodiments, $L^1$ is —C(O)O—. In some embodiments, $L^1$ is —C(O)—. In some embodiments, $L^1$ is —S(O)—. In some embodiments, $L^1$ is —S(O)$_2$—. In some embodiments, $L^1$ is —NRS(O)$_2$—. In some embodiments, $L^1$ is —S(O)$_2$NR—. In some embodiments, $L^1$ is —NRC(O)—. In some embodiments, $L^1$ is —C(O)NR—.

In some embodiments, Ring $L^1$ is selected from those depicted in Table 1 below.

As defined above and described herein, === is a single or double bond.

In some embodiments, === is a single bond. In some embodiments, === is a double bond.

In some embodiments, === is selected from those depicted in Table 1 below.

As defined above and described herein, m is 0, 1, 2, 3, 4, 5, 6, 7, 8, 9, 10, 11, 12, 13, 14, 15, or 16.

In some embodiments, m is 0. In some embodiments, m is 1. In some embodiments, m is 2. In some embodiments, m is 3. In some embodiments, m is 4. In some embodiments, m is 5. In some embodiments, m is 6. In some embodiments, m is 7. In some embodiments, m is 8. In some embodiments, m is 9. In some embodiments, m is 10. In some embodiments, m is 11. In some embodiments, m is 12. In some embodiments, m is 13. In some embodiments, m is 14. In some embodiments, m is 15. In some embodiments, m is 16.

In some embodiments, m is selected from those depicted in Table 1 below.

As defined above and described herein, n is 0, 1, 2, 3 or 4.

In some embodiments, n is 0. In some embodiments, n is 1. In some embodiments, n is 2. In some embodiments, n is 3. In some embodiments, n is 4.

In some embodiments, n is selected from those depicted in Table 1 below.

As defined above and described herein, p is 0 or 1.

In some embodiments, p is 0. In some embodiments, p is 1.

In some embodiments, p is selected from those depicted in Table 1 below.

As defined above and described herein, q is 0, 1, 2, 3 or 4.

In some embodiments, q is 0. In some embodiments, q is 1. In some embodiments, q is 2. In some embodiments, q is 3. In some embodiments, q is 4.

In some embodiments, q is selected from those depicted in Table 1 below.

In some embodiments, LBM is

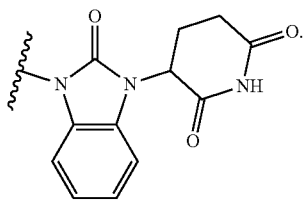 [SMILES: *n1c(=O)n(C2CCC(=O)NC2=O)c2ccccc21]

In some embodiments, LBM is

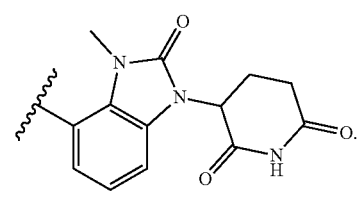 [SMILES: *c1cccc2c1n(C)c(=O)n2C1CCC(=O)NC1=O]

In some embodiments, LBM is

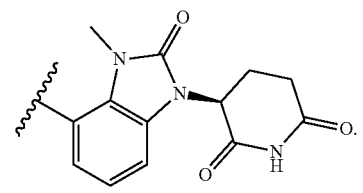 [SMILES: *c1cccc2c1n(C)c(=O)n2[C@H]1CCC(=O)NC1=O]

In some embodiments, LBM is

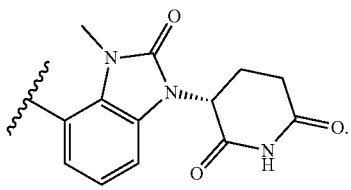 [SMILES: *c1cccc2c1n(C)c(=O)n2[C@@H]1CCC(=O)NC1=O]

In some embodiments, LBM is

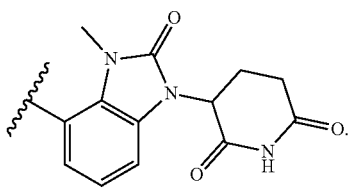 [SMILES: *c1cccc2c1n(C)c(=O)n2C1CCC(=O)NC1=O]

In some embodiments, LBM is

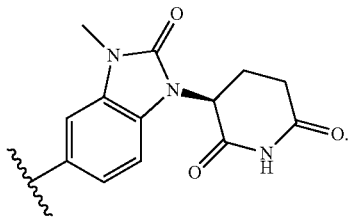 [SMILES: *c1ccc2c(c1)n(C)c(=O)n2[C@H]1CCC(=O)NC1=O]

In some embodiments, LBM is

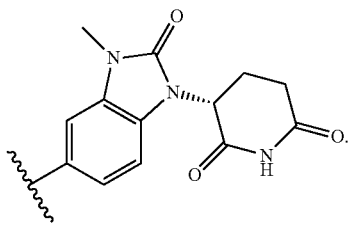 [SMILES: *c1ccc2c(c1)n(C)c(=O)n2[C@@H]1CCC(=O)NC1=O]

In some embodiments, LBM is

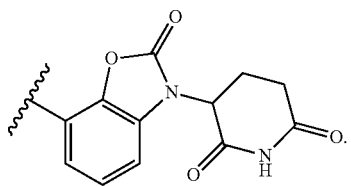 [SMILES: *c1cccc2c1oc(=O)n2C1CCC(=O)NC1=O]

In some embodiments, LBM is
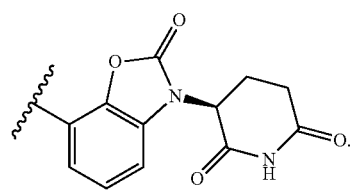 [SMILES: *c1cccc2c1oc(=O)n2[C@H]1CCC(=O)NC1=O]
In some embodiments, LBM is
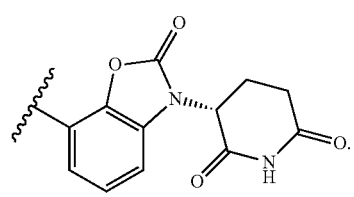 [SMILES: *c1cccc2c1oc(=O)n2[C@@H]1CCC(=O)NC1=O]
In some embodiments, LBM is
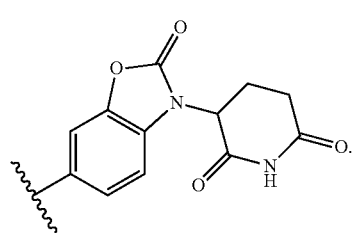 [SMILES: *c1ccc2c(c1)oc(=O)n2C1CCC(=O)NC1=O]
In some embodiments, LBM is
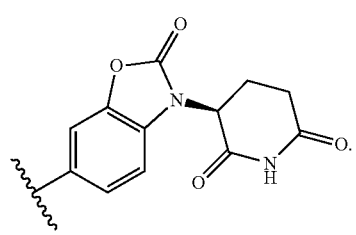 [SMILES: *c1ccc2c(c1)oc(=O)n2[C@H]1CCC(=O)NC1=O]
In some embodiments, LBM is
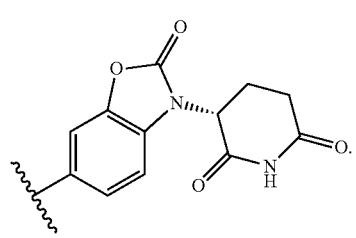 [SMILES: *c1ccc2c(c1)oc(=O)n2[C@@H]1CCC(=O)NC1=O]
In some embodiments, LBM is
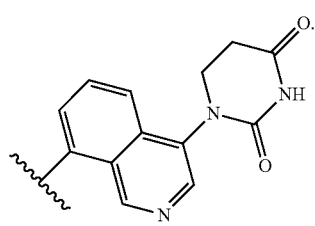 [SMILES: *c1cccc2c(N3CCC(=O)NC3=O)cncc12]
In some embodiments, LBM is
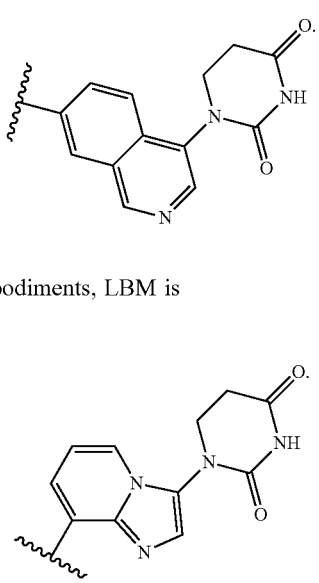
In some embodiments, LBM is
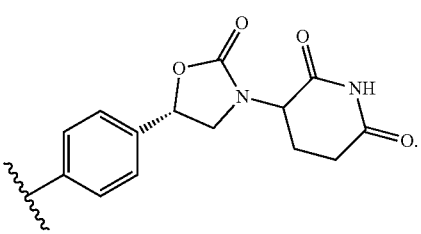 [SMILES: *c1ccc([C@H]2CN(C3CCC(=O)NC3=O)C(=O)O2)cc1]

In some embodiments, LBM is
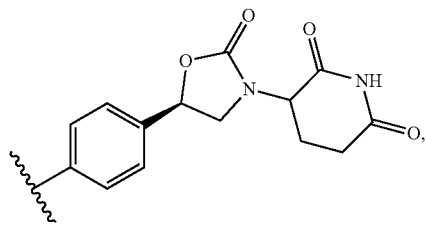
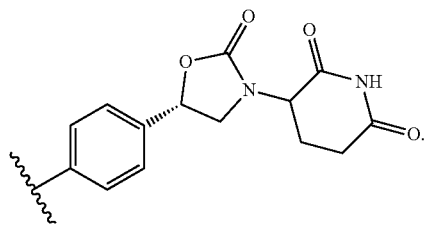
In some embodiments, LBM is
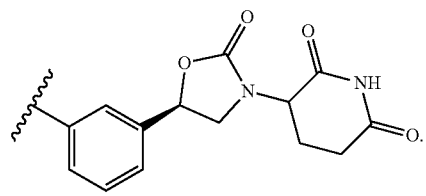 [SMILES: *c1cccc([C@@H]2CN(C3CCC(=O)NC3=O)C(=O)O2)c1]
In some embodiments, LBM is
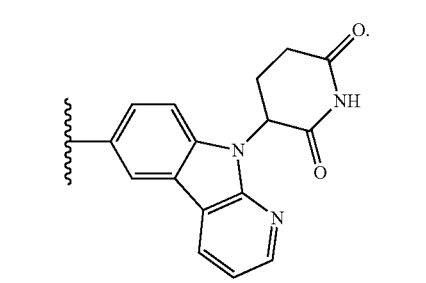 [SMILES: *c1ccc2c(c1)c1cccnc1n2C1CCC(=O)NC1=O]
In some embodiments, LBM is
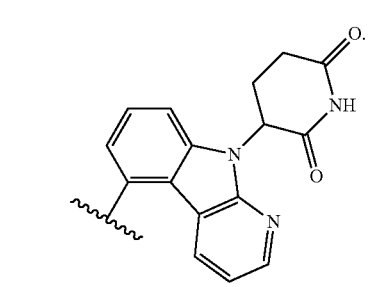 [SMILES: *c1cccc2c1c1cccnc1n2C1CCC(=O)NC1=O]
In some embodiments, LBM is
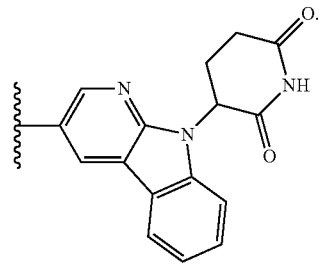 [SMILES: *c1cnc2c(c1)c1ccccc1n2C1CCC(=O)NC1=O]
In some embodiments, LBM is
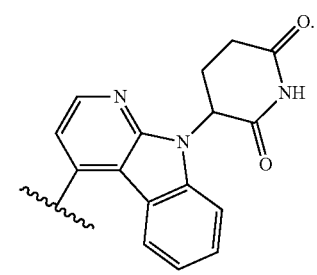 [SMILES: *c1ccnc2c1c1ccccc1n2C1CCC(=O)NC1=O]
In some embodiments, LBM is
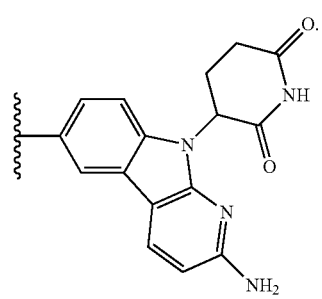 [SMILES: *c1ccc2c(c1)c1ccc(N)nc1n2C1CCC(=O)NC1=O]
In some embodiments, LBM is
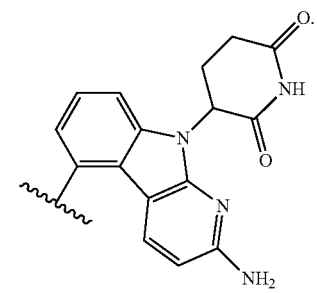 [SMILES: *c1cccc2c1c1ccc(N)nc1n2C1CCC(=O)NC1=O]

In some embodiments, LBM is

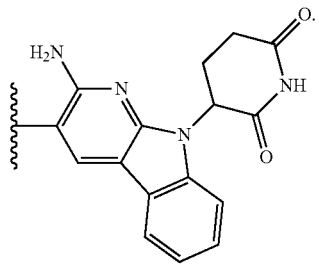 [SMILES: *c1cc2c3ccccc3n(C3CCC(=O)NC3=O)c2nc1N]

In some embodiments, LBM is

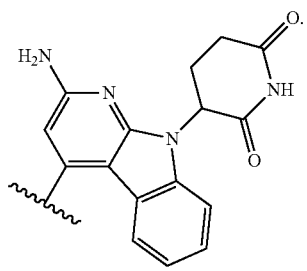 [SMILES: *c1cc(N)nc2c1c1ccccc1n2C1CCC(=O)NC1=O]

In some embodiments, LBM is selected from those in Table 1 below.

In some embodiments, LBM is an E3 ligase ligand well known to one of ordinary skill in the art including those described in M. Toure, C. M. Crews, *Angew. Chem. Int. Ed.* 2016, 55, 1966, T. Uehara et al. *Nature Chemical Biology* 2017, 13, 675, WO 2017/176708, US 2017/0281784, WO 2017/161119, WO 2017/176957, WO 2017/176958, WO 2015/160845, US 2015/0291562, WO 2016/197032, WO 2016/105518, US 2018/0009779, WO 2017/007612, 2018/0134684, WO 2013/106643, US 2014/0356322, WO 2002/020740, US 2002/0068063, WO 2012/078559, US 2014/0302523, WO 2012/003281, US 2013/0190340, US 2016/0022642, WO 2014/063061, US 2015/0274738, WO 2016/118666, US 2016/0214972, WO 2016/149668, US 2016/0272639, WO 2016/169989, US 2018/0118733, WO 2016/197114, US 2018/0147202, WO 2017/011371, US 2017/0008904, WO 2017/011590, US 2017/0037004, WO 2017/079267, US 2017/0121321, WO 2017/117473, WO 2017/117474, WO 2013/106646, WO 2014/108452, WO 2017/197036, US 2019/0076540, WO 2017/197046, US 2019/0076542, WO 2017/197051, US 2019/0076539, WO 2017/197055, US 2019/0076541, and WO 2017/197056, the entirety of each of which is herein incorporated by reference.

In certain embodiments, the present invention provides a compound of Formula I, wherein LBM is an E3 ubiquitin ligase (cereblon) binding moiety thereby forming a compound of formula I-oo-1, I-oo-2, I-oo-3, I-oo-4, I-oo-5, I-oo-6, I-oo-7, I-oo-8, I-oo-9, or I-oo-10 respectively:

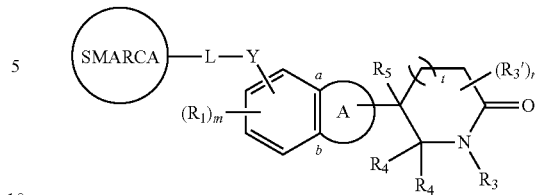

I-oo-1

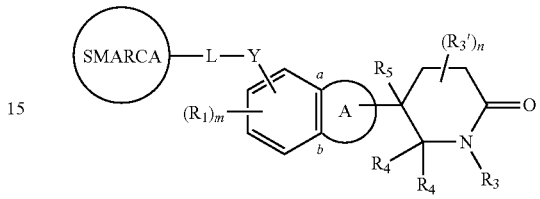

I-oo-2

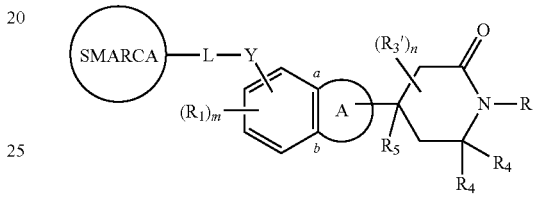

I-oo-3

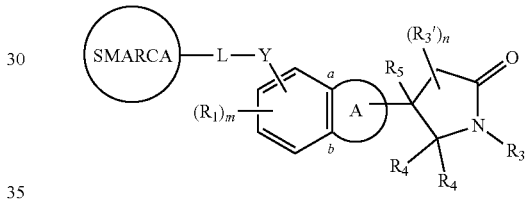

I-oo-4

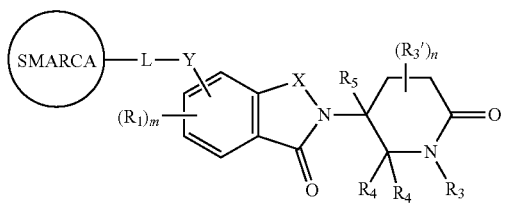

I-oo-5

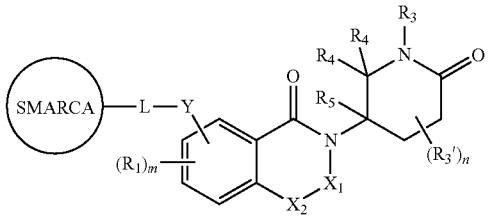

I-oo-6

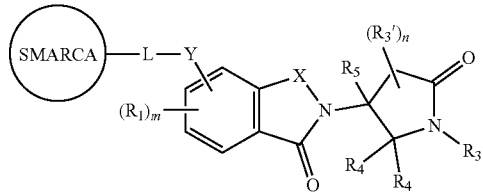

I-oo-7

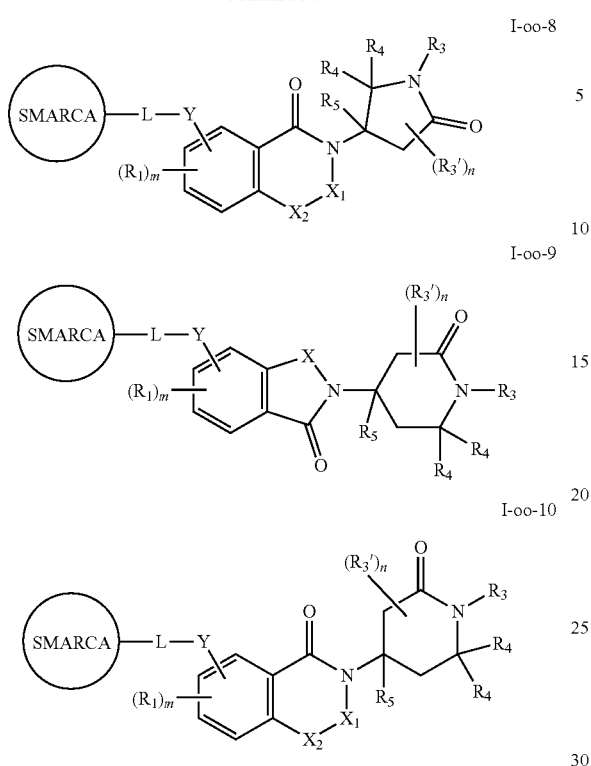
I-oo-8
I-oo-9
I-oo-10
or a compound of formula I-oo'-1, I-oo'-2, I-oo'-3, I-oo'-4, I-oo'-5, I-oo'-6, I-oo'-7, I-oo'-8, I-oo'-9, or I-oo'-10 respectively:
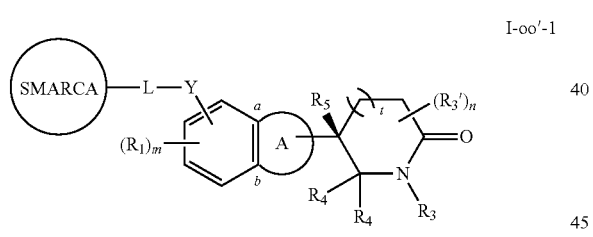
I-oo'-1
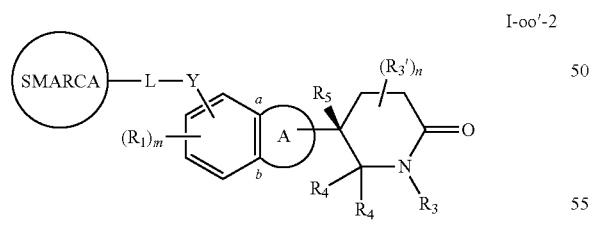
I-oo'-2
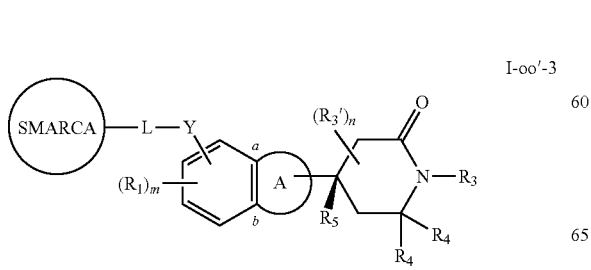
I-oo'-3
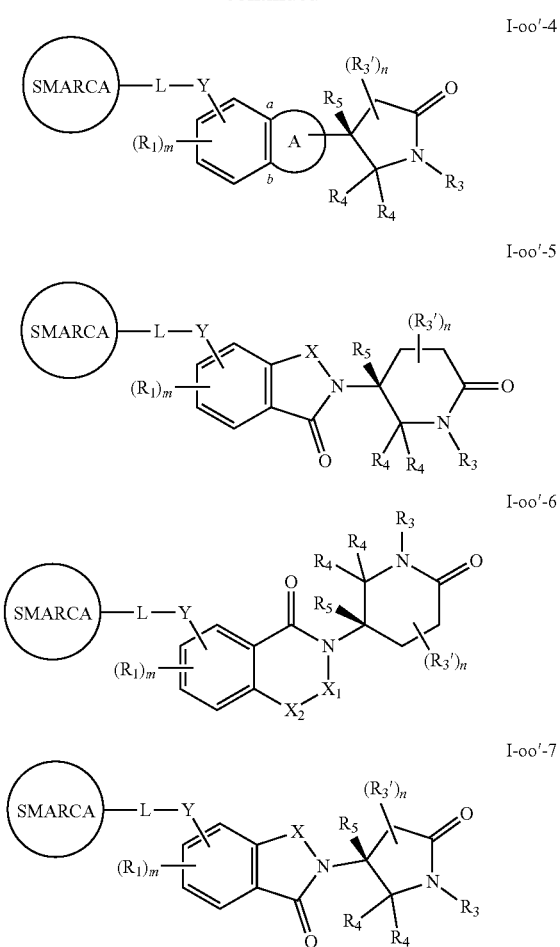
I-oo'-4
I-oo'-5
I-oo'-6
I-oo'-7
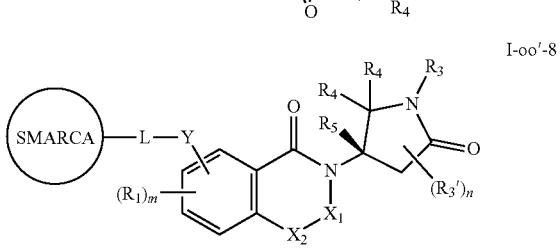
I-oo'-8
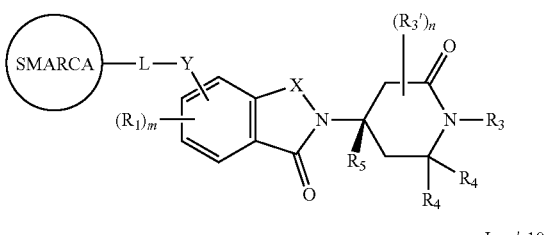
I-oo'-9
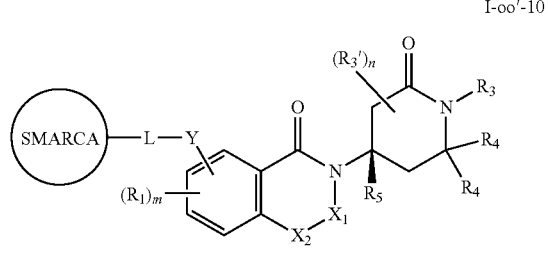
I-oo'-10 or a compound of formula I-oo"-1, I-oo"-2, I-oo"-3, I-oo"-4, I-oo"-5, I-oo"-6, I-oo"-7, I-oo"-8, I-oo"-9, or I-oo'-10 respectively:

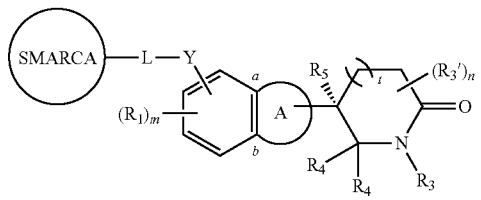

I-oo"-1

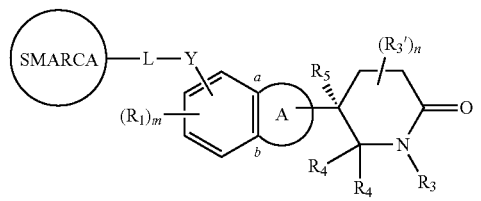

I-oo"-2

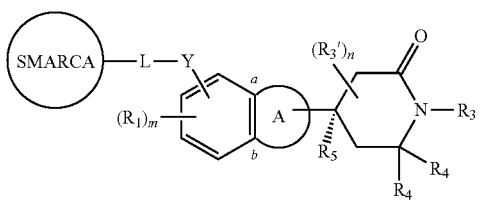

I-oo"-3

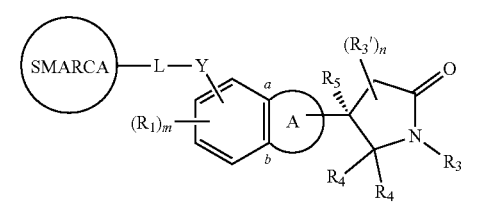

I-oo"-4

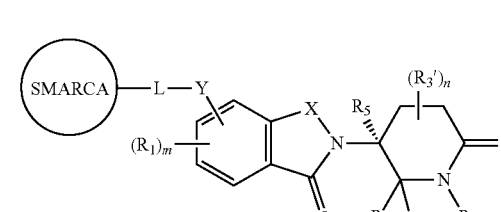

I-oo"-5

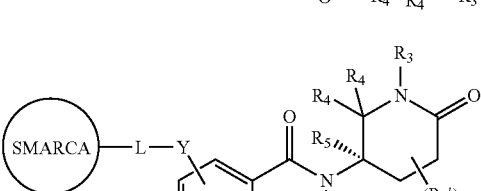

I-oo"-6

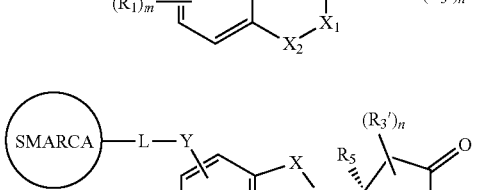

I-oo"-7

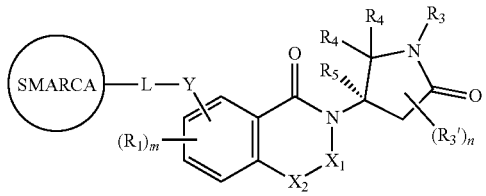

I-oo"-8

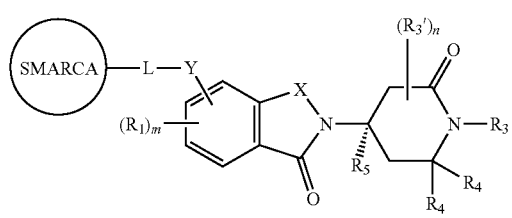

I-oo"-9

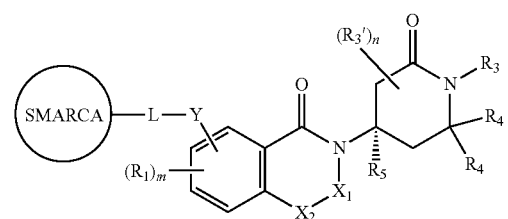

I-oo"-10 or a pharmaceutically acceptable salt thereof, wherein L and SMARCA are as defined above and described in embodiments herein, and wherein each of the variables

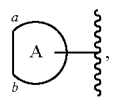

X, $X_1$, $X_2$, Y, $R_1$, $R_3$, $R_3'$, $R_4$, $R_5$, t, m and n is as defined and described in WO 2017/007612 and US 2018/0134684, the entirety of each of which is herein incorporated by reference.

Accordingly in some embodiments, the present invention provides a compound of formula I-oo-1, I-oo-2, I-oo-3, I-oo-4, I-oo-5, I-oo-6, I-oo-7, I-oo-8, I-oo-9, I-oo-10, I-oo'-1, I-oo'-2, I-oo'-3, I-oo'-4, I-oo'-5, I-oo'-6, I-oo'-7, I-oo'-8, I-oo'-9, I-oo'-10, I-oo"-1, I-oo"-2, I-oo"-3, I-oo"-4, I-oo"-5, I-oo"-6, I-oo"-7, I-oo"-8, I-oo"-9, or I-oo"-10, or a pharmaceutically acceptable salt thereof, wherein:

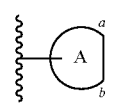

is

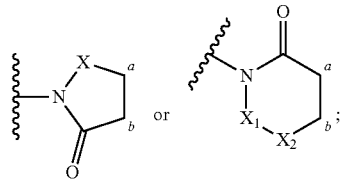

Y is a bond, $Y_1$, O, NH, $NR_2$, C(O)O, OC(O), C(O)$NR_2'$, $NR_2'$C(O), $Y_1$—O, $Y_1$—NH, $Y_1$—$NR_2$, $Y_1$—C(O), $Y_1$—C(O)O, $Y_1$—OC(O), $Y_1$—C(O)$NR_2'$, or $Y_1$—$NR_2'$C(O), wherein $Y_1$ is $C_1$-$C_6$ alkylene, $C_2$-$C_6$ alkenylene, or $C_2$-$C_6$ alkynylene;

X is C(O) or C($R_3$)$_2$;

$X_1$-$X_2$ is C($R_3$)=N or C($R_3$)$_2$—C($R_3$)$_2$;

each $R_1$ is independently halogen, nitro, $NH_2$, OH, C(O)OH, $C_1$-$C_6$ alkyl, or $C_1$-$C_6$ alkoxy;

$R_2$ is $C_1$-$C_6$ alkyl, $C_2$-$C_6$ alkenyl, $C_3$-$C_8$ cycloalkyl, 3- to 8-membered heterocycloalkyl, C(O)—$C_1$-$C_6$ alkyl, C(O)—$C_2$-$C_6$ alkenyl, C(O)—$C_3$-$C_8$ cycloalkyl, or C(O)-3- to 8-membered heterocycloalkyl, and $R_2$ is optionally substituted with one or more of halogen, N($R_a$)$_2$, NHC(O)$R_a$, NHC(O)O$R_a$, O$R_b$, $C_3$-$C_8$ cycloalkyl, 3- to 8-membered heterocycloalkyl, $C_6$-$C_{10}$ aryl, or 5- to 10-membered heteroaryl, wherein each of the $C_3$-$C_8$ cycloalkyl, 3- to 8-membered heterocycloalkyl, $C_6$-$C_{10}$aryl or 5- to 10-membered heteroaryl is optionally further substituted with one or more of halogen, $NH_2$, CN, nitro, OH, C(O)OH, $C_1$-$C_6$ alkyl, $C_1$-$C_6$ haloalkyl, $C_1$-$C_6$ alkoxy, or $C_1$-$C_6$ haloalkoxy;

$R_2'$ is H, $C_1$-$C_6$ alkyl, $C_2$-$C_6$ alkenyl, $C_3$-$C_8$ cycloalkyl, or 3- to 8-membered heterocycloalkyl, and $R_2'$, when not being H, is optionally substituted with one or more of halogen, N($R_a$)$_2$, NHC(O)$R_a$, NHC(O)O$R_a$, O$R_b$, $C_3$-$C_8$ cycloalkyl, 3- to 8-membered heterocycloalkyl, $C_6$-$C_{10}$aryl, or 5- to 10-membered heteroaryl, wherein each of the $C_3$-$C_8$ cycloalkyl, 3- to 8-membered heterocycloalkyl, $C_6$-$C_{10}$aryl or 5- to 10-membered heteroaryl is optionally further substituted with one or more of halogen, $NH_2$, CN, nitro, OH, C(O)OH, $C_1$-$C_6$ alkyl, $C_1$-$C_6$ haloalkyl, $C_1$-$C_6$ alkoxy, or $C_1$-$C_6$ haloalkoxy;

each $R_3$ is independently H or $C_1$-$C_3$ alkyl optionally substituted with $C_6$-$C_{10}$aryl or 5- to 10-membered heteroaryl;

each $R_3'$ is independently $C_1$-$C_3$ alkyl;

each $R_4$ is independently H or $C_1$-$C_3$ alkyl; or two $R_4$, together with the carbon atom to which they are attached, form C(O), a $C_3$-$C_6$ carbocycle, or a 4-, 5-, or 6-membered heterocycle comprising 1 or 2 heteroatoms selected from N and O;

$R_5$ is H, $C_1$-$C_3$ alkyl, F, or Cl;

each $R_a$ independently is H or $C_1$-$C_6$ alkyl;

$R_b$ is H or tosyl;

t is 0 or 1;

m is 0, 1, 2 or 3; and n is 0, 1 or 2.

In certain embodiments, the present invention provides a compound of Formula I, wherein LBM is an E3 ubiquitin ligase (cereblon) binding moiety thereby forming a compound of formula I-pp-1, I-pp-2, I-pp-3, I-pp-4, I-pp-5, or I-pp-6 respectively:

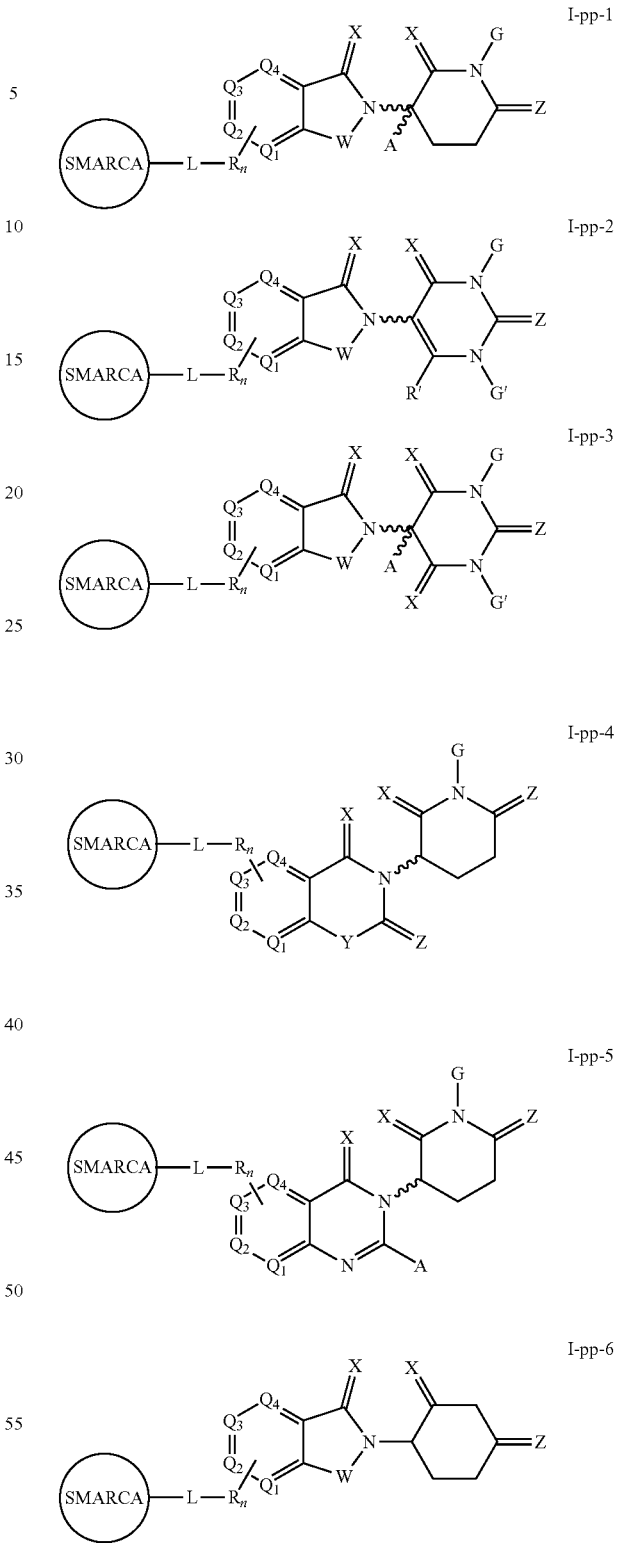

or a pharmaceutically acceptable salt thereof, wherein L and SMARCA are as defined above and described in embodiments herein, and wherein each of the variables A, G, G', $Q_1$, $Q_2$, $Q_3$, $Q_4$, R, R', W, X, Y, Z, ⁓, and n is as defined and described in WO 2016/197114 and US 2018/0147202, the entirety of each of which is herein incorporated by reference.

In some embodiments, LBM is
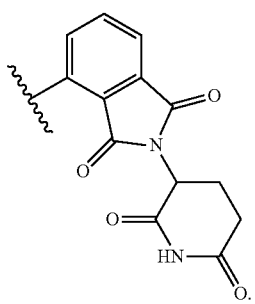 [SMILES: *c1cccc2c1C(=O)N(C1CCC(=O)NC1=O)C2=O]
In some embodiments, LBM is
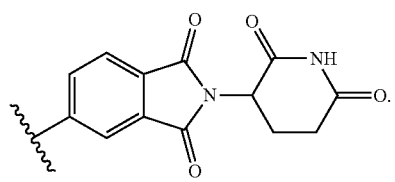 [SMILES: *c1ccc2c(c1)C(=O)N(C1CCC(=O)NC1=O)C2=O]
In some embodiments, LBM is
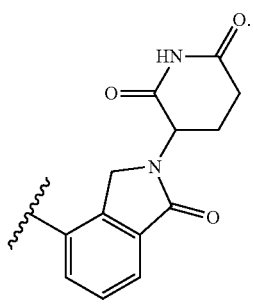 [SMILES: *c1cccc2c1CN(C1CCC(=O)NC1=O)C2=O]
In some embodiments, LBM is
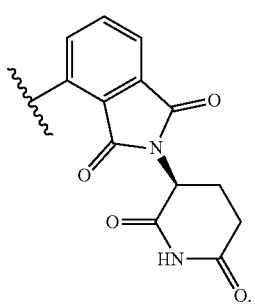 [SMILES: *c1cccc2c1C(=O)N([C@H]1CCC(=O)NC1=O)C2=O]
In some embodiments, LBM is
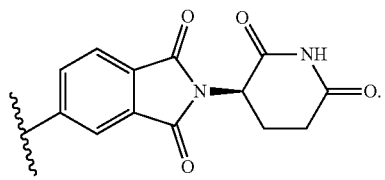 [SMILES: *c1ccc2c(c1)C(=O)N([C@@H]1CCC(=O)NC1=O)C2=O]
In some embodiments, LBM is
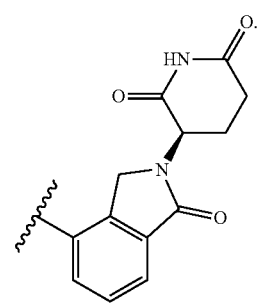 [SMILES: *c1cccc2c1CN([C@@H]1CCC(=O)NC1=O)C2=O]
In some embodiments, LBM is
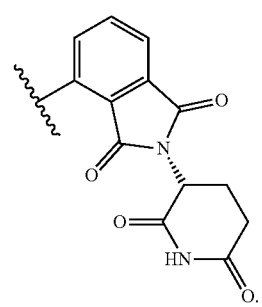
In some embodiments, LBM is
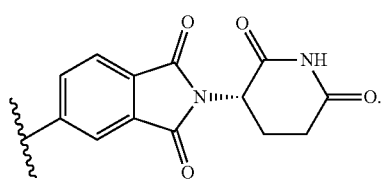 [SMILES: *c1ccc2c(c1)C(=O)N([C@H]1CCC(=O)NC1=O)C2=O]
In some embodiments, LBM is
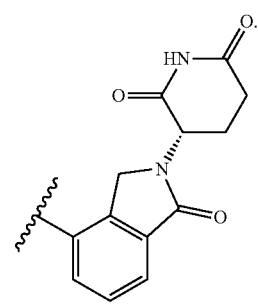

In some embodiments, LBM is selected from those in Table 1 below.

In certain embodiments, the present invention provides a compound of Formula I, wherein LBM is an E3 ubiquitin ligase (cereblon) binding moiety thereby forming a compound of formula I-qq-1, I-qq-2, or I-qq-3 respectively:

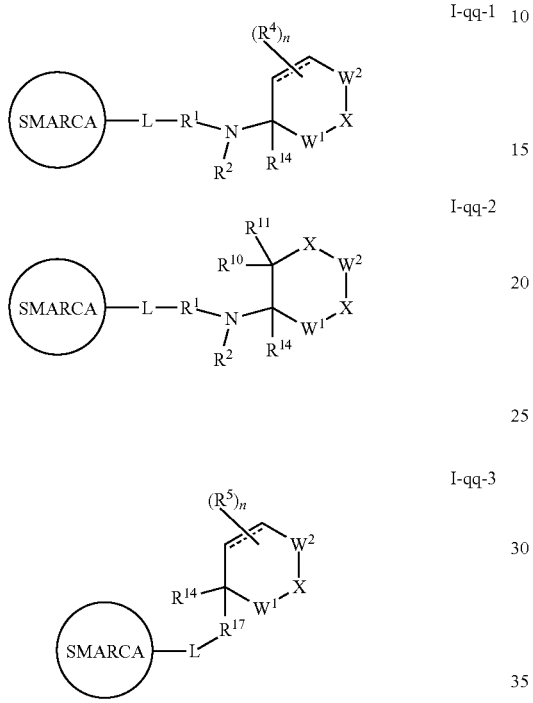

I-qq-1

I-qq-2

I-qq-3 or a pharmaceutically acceptable salt thereof, wherein L and SMARCA are as defined above and described herein, and wherein each of the variables $R^1$, $R^2$, $R^4$, $R^5$, $R^{10}$, $R^{11}$, $R^{14}$, $R^{17}$, $W^1$, $W^2$, X, ===, and n is as defined in WO 2017/197051 which is herein incorporated by reference in its entirety and wherein

is attached to $R^1$, the ring formed by combining $R^1$ and $R^2$, or $R^{17}$ at the site of attachment of $R^{12}$ as defined in WO 2017/197051 such that

takes the place of the $R^{12}$ substituent.

In some embodiments, the present invention provides a compound of formula I, wherein LBM is an E3 ubiquitin ligase (cereblon) binding moiety thereby forming a compound of formula I-rr-1, I-rr-2, I-rr-3, or I-rr-4, respectively:

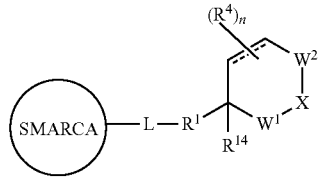

I-rr-1

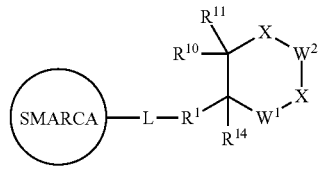

I-rr-2

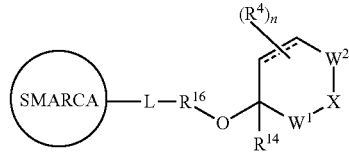

I-rr-3

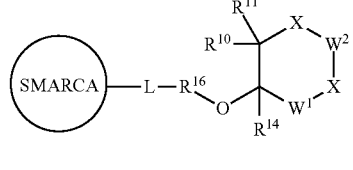

I-rr-4 or a pharmaceutically acceptable salt thereof, wherein L and SMARCA are as defined above and described herein, and wherein each of the variables $R^1$, $R^4$, $R^{10}$, $R^{11}$, $R^{14}$, $R^{16}$, $W^1$, $W^2$, X, === and n is as defined in WO 2018/237026, the entirety of each of which is herein incorporated by reference, and wherein

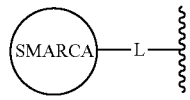

is attached to $R^1$ or $R^{16}$ at the site of attachment of $R^{12}$ as defined in WO 2018/237026, such that

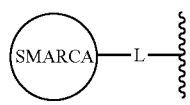

takes the place of the $R^{12}$ substituent.

In some embodiments, the present invention provides a compound of formula I, wherein LBM is an E3 ubiquitin ligase (cereblon) binding moiety thereby forming a compound of formula I-ss-1 or I-ss-3, respectively:

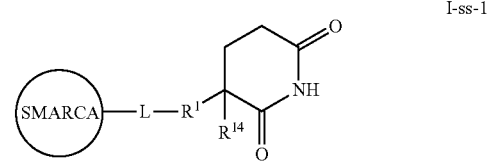

I-ss-1

-continued

I-ss-3

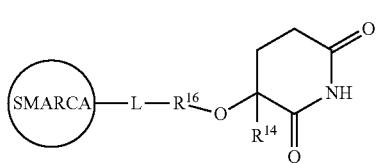

or a pharmaceutically acceptable salt thereof, wherein L and SMARCA are as defined above and described herein, and wherein each of the variables $R^1$, $R^{14}$, and $R^{16}$ is as defined in WO 2018/237026, the entirety of each of which is herein incorporated by reference, and wherein

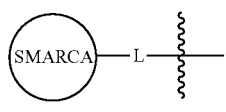

is attached to $R^1$ or $R^{16}$ at the site of attachment of $R^{12}$ as defined in WO 2018/237026, such that

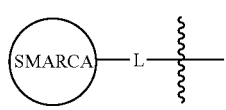

takes the place of the $R^{12}$ substituent.

In certain embodiments, the present invention provides a compound of formula I, wherein LBM is an E3 ubiquitin ligase (cereblon) binding moiety thereby forming a compound of formula I-tt-1, I-tt-2, I-tt-3, I-tt-4, I-tt-5, I-tt-6, I-tt-7, or I-tt-8:

I-tt-1

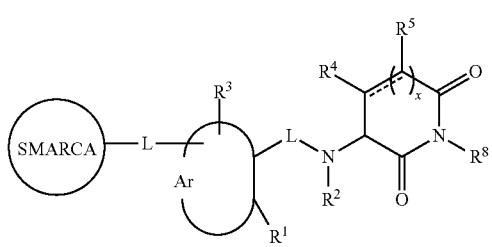

I-tt-2

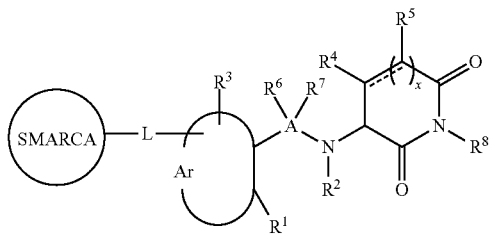

I-tt-3

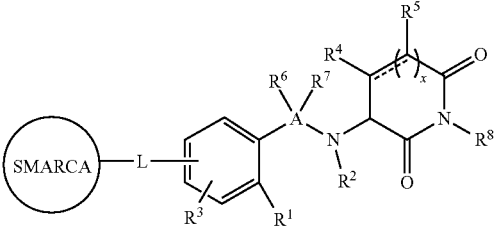

-continued

I-tt-4

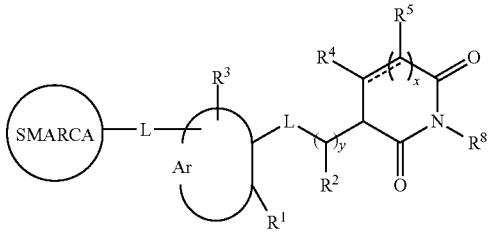

I-tt-5

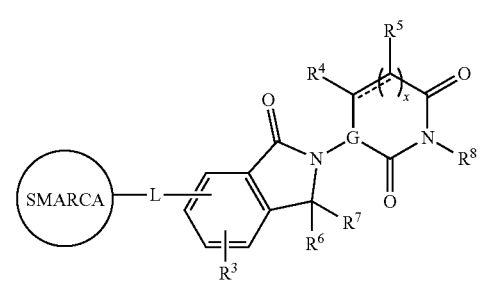

I-tt-6

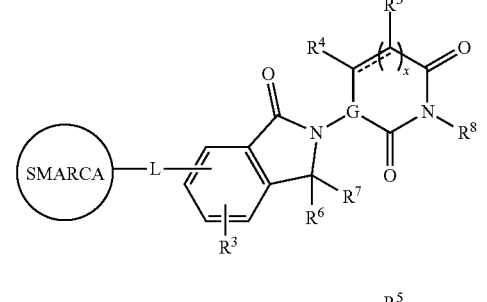

I-tt-7

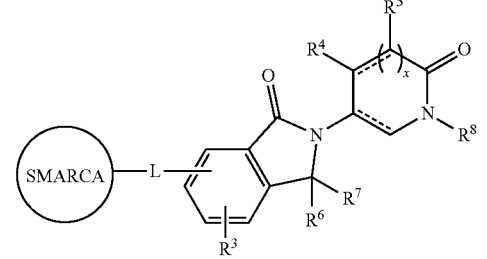

I-tt-8

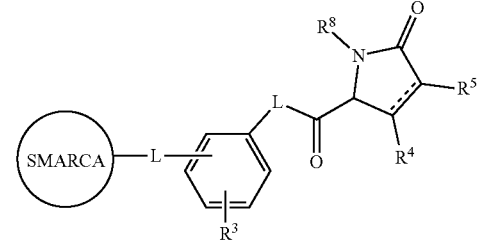

or a pharmaceutically acceptable salt thereof, wherein L and SMARCA are as defined above and described in embodiments herein, and wherein each of the variables Ar, $R^1$, $R^2$, $R^3$, $R^4$, $R^5$, $R^6$, $R^7$, $R^8$, A, L, x, y, and === is as described and defined in WO 2017/161119, the entirety of each of which is herein incorporated by reference.

In certain embodiments, the present invention provides a compound of formula I, wherein LBM is an E3 ubiquitin ligase (cereblon) binding moiety thereby forming a compound of formula I-uu:

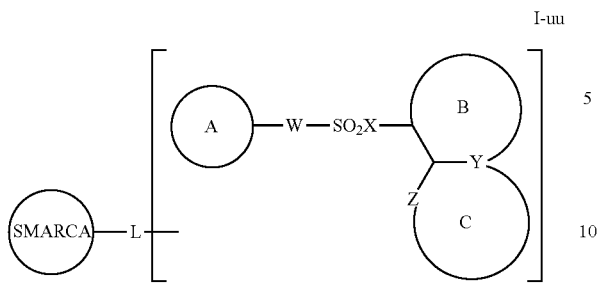

I-uu

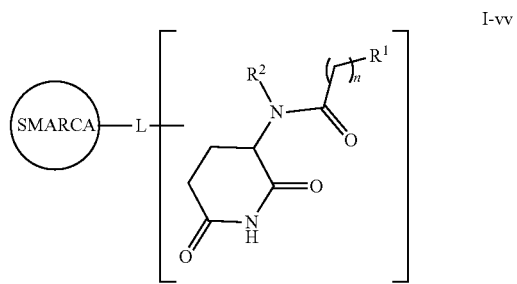

I-vv or a pharmaceutically acceptable salt thereof, wherein L and SMARCA are as defined above and described in embodiments herein, and wherein each of the variables A, B, C, W, X, Y, and Z is as described and defined in U.S. Pat. No. 5,721,246, the entirety of each of which is herein incorporated by reference.

In certain embodiments, the present invention provides a compound of formula I, wherein LBM is an E3 ubiquitin ligase (cereblon) binding moiety thereby forming a compound of formula I-w:

or a pharmaceutically acceptable salt thereof, wherein L and SMARCA are as defined above and described in embodiments herein, and wherein each of the variables $R_1$, $R_2$, and n is as described and defined in WO 2019/043214, the entirety of each of which is herein incorporated by reference.

In some embodiments, LBM is a IAP E3 Ubiquitin ligase binding moiety recited in Varfolomeev, E. et al., *IAP Antagonists Induce Autoubiquitination of c-IAPs, NF-κB activation, and TNFα-Dependent Apoptosis*, Cell, 2007, 131(4): 669-81, such as, for example:

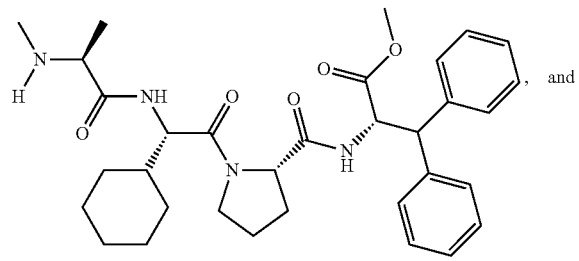

MV1

, and

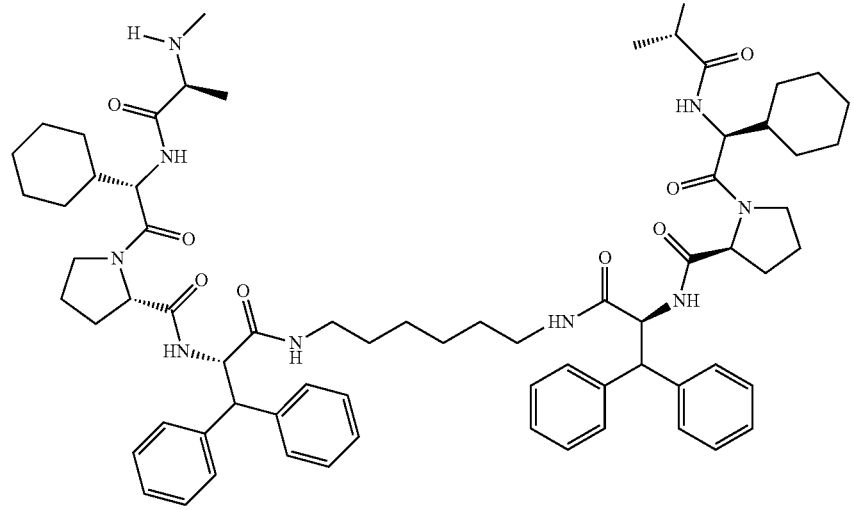

BV6 wherein

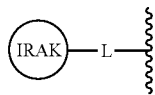

is attached to a modifiable carbon, oxygen, nitrogen or sulfur atom.

In certain embodiments, the present invention provides a compound of Formula I, wherein LBM is a VHL E3 ubiquitin ligase binding moiety thereby forming a compound of formula I-ww-1, I-ww-2, I-ww-3, I-ww-4, or I-ww-5 respectively:

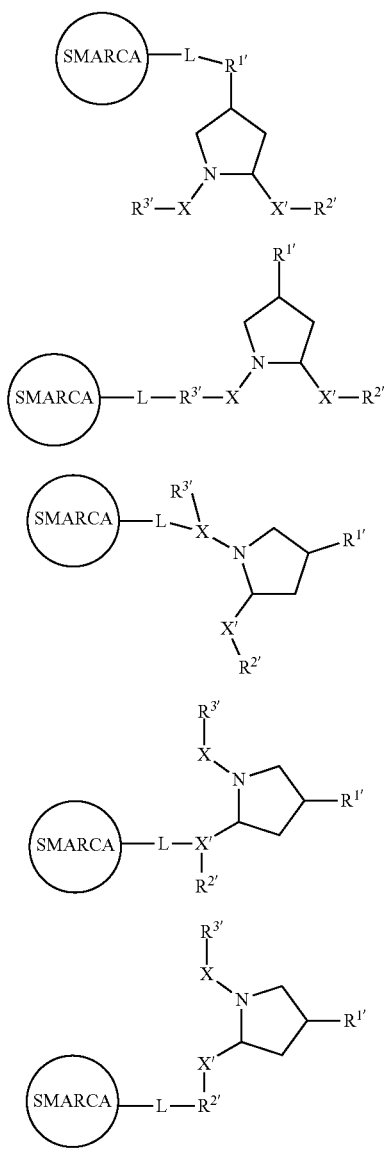

or a pharmaceutically acceptable salt thereof, wherein L and SMARCA are as defined above and described in embodiments herein, and wherein each of the variables $R^{1'}$, $R^{2'}$, $R^{3'}$, X, and X' is as defined and described in WO 2013/106643 and US 2014/0356322, the entirety of each of which is herein incorporated by reference.

In certain embodiments, the present invention provides a compound of Formula I, wherein LBM is a VHL E3 ubiquitin ligase binding moiety thereby forming a compound of formula I-xx-1, I-xx-2, I-xx-3, I-xx-4, T-xx-5 or I-xx-6 respectively:

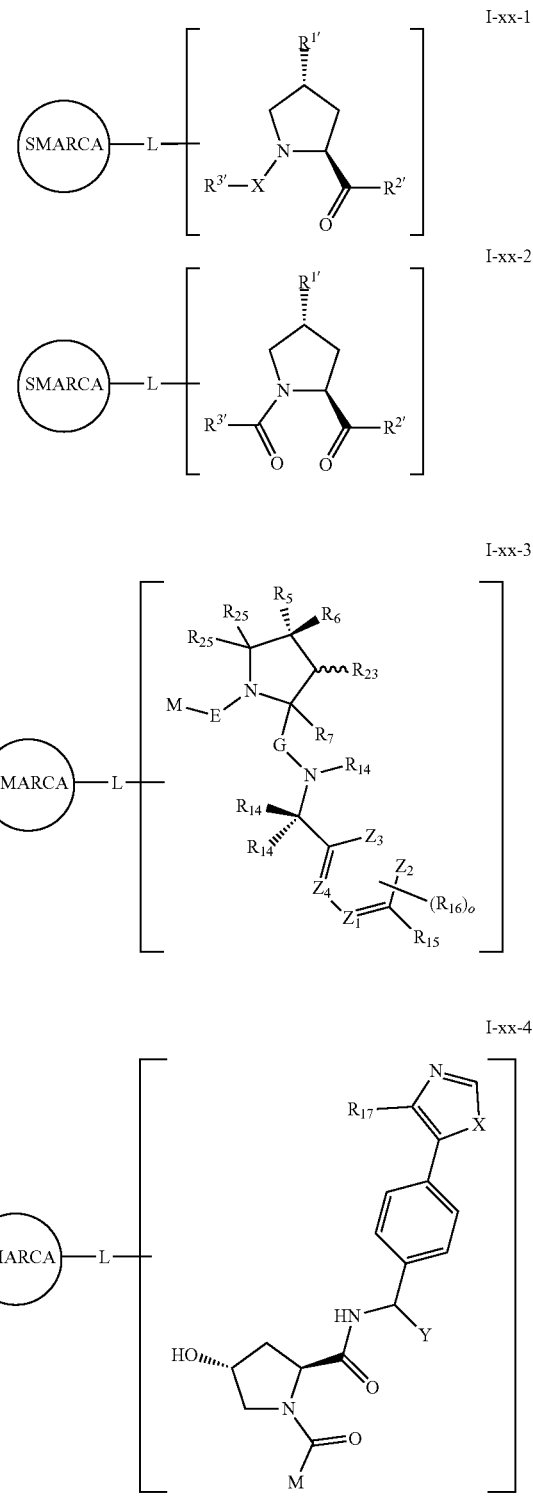

-continued

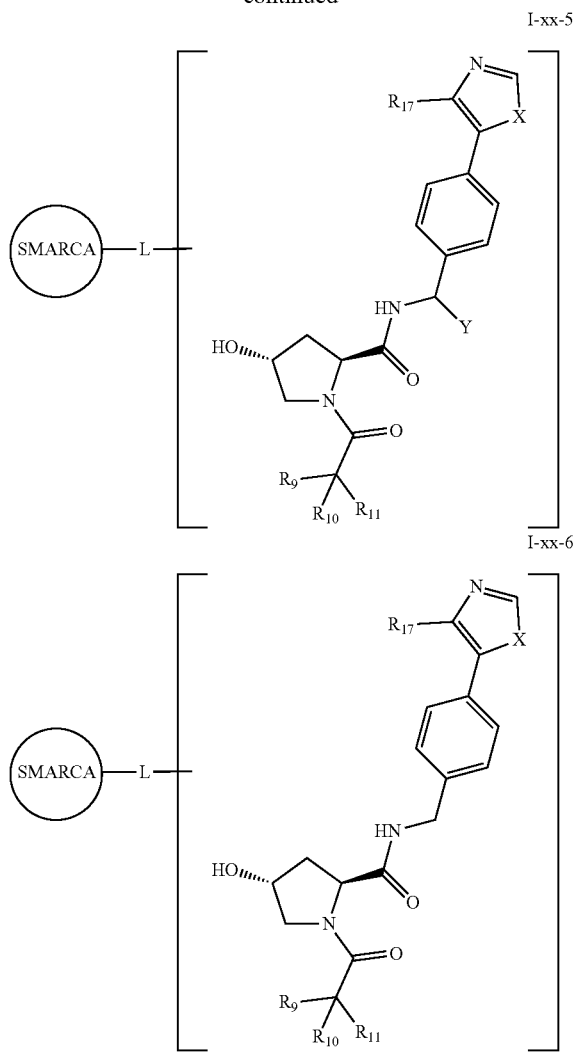

or a pharmaceutically acceptable salt thereof, wherein L and SMARCA are as defined above and described in embodiments herein, and wherein each of the variables $R^{1'}$, $R^{2'}$, $R^{3'}$, $R_5$, $R_6$, $R_7$, $R_9$, $R_{10}$, $R_{11}$, $R_{14}$, $R_{15}$, $R_{16}$, $R_{17}$, $R_{23}$, $R_{25}$, E, G, M, X, X', Y, $Z_1$, $Z_2$, $Z_3$, $Z_4$, and o is as defined and described in WO 2016/149668 and US 2016/0272639, the entirety of each of which is herein incorporated by reference.

As used herein, depiction of brackets around any LBM

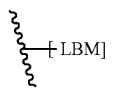

means that the

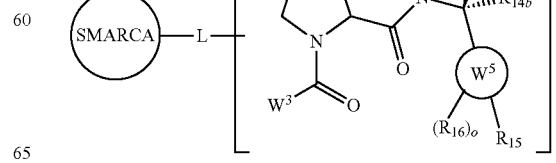

moiety is covalently attached to said LBM at any available modifiable carbon, nitrogen, oxygen, or sulfur atom. For purposes of clarity and by way of example, such available modifiable carbon, nitrogen, oxygen, or sulfur atoms in the following LBM compound structure are depicted below, wherein each wavy bond defines the point of attachment to said

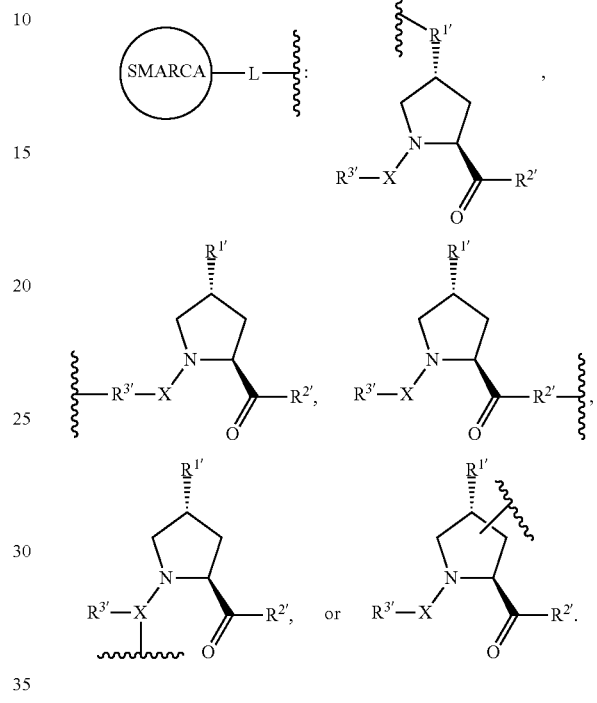

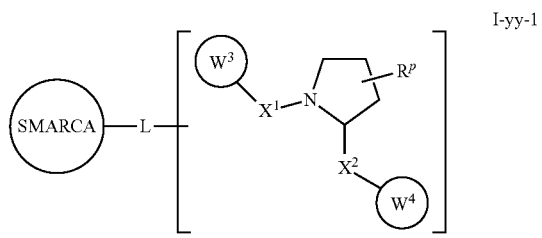

In certain embodiments, the present invention provides a compound of Formula I, wherein LBM is a VHL E3 ubiquitin ligase binding moiety thereby forming a compound of formula I-yy-1, I-yy-2, or I-yy-3 respectively:

I-yy-3

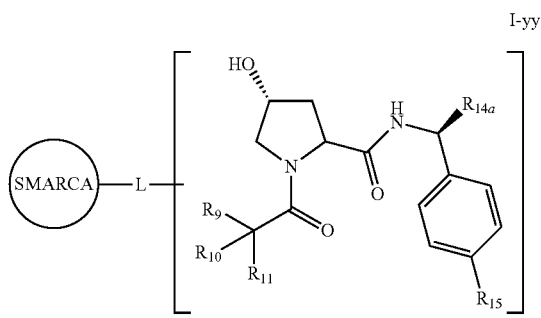

or a pharmaceutically acceptable salt thereof, wherein L and SMARCA are as defined above and described in embodiments herein, and wherein each of the variables $R^p$, $R_9$, $R_{10}$, $R_{11}$, $R_{14a}$, $R_{14b}$, $R_{14b}$, $R_{15}$, $R_{16}$, $W^3$, $W^4$, $W^5$, $X^1$, $X^2$, and o is as defined and described in WO 2016/118666 and US 2016/0214972, the entirety of each of which is herein incorporated by reference.

In certain embodiments, the present invention provides a compound of Formula I, wherein LBM is a CRBN or VHL E3 ubiquitin ligase binding moiety thereby forming a compound of formula I-zz-1, I-zz-2, I-zz-3, I-zz-4, I-zz-5, I-zz-6, or I-zz-7 respectively:

I-zz-1

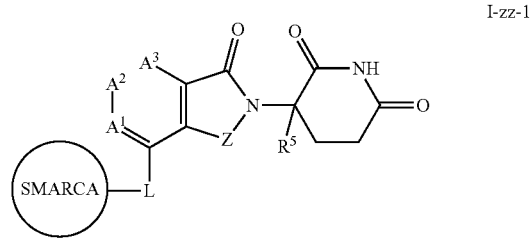

I-zz-2

I-zz-3

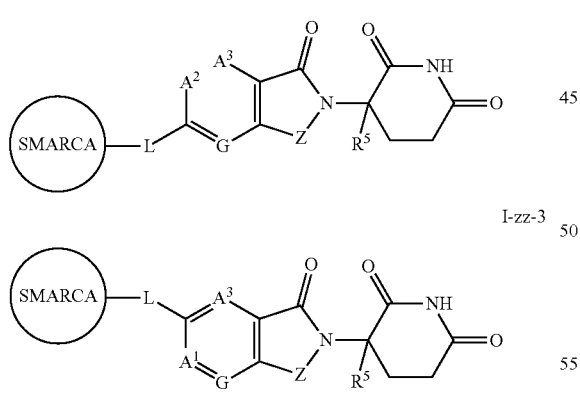

I-zz-4

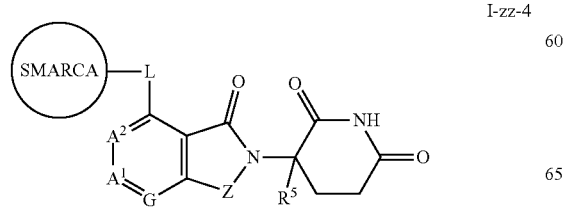

I-zz-5

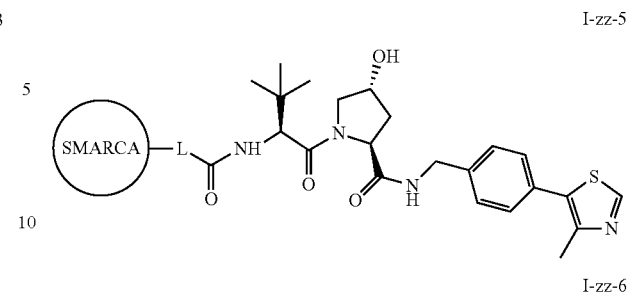

I-zz-6

I-zz-7

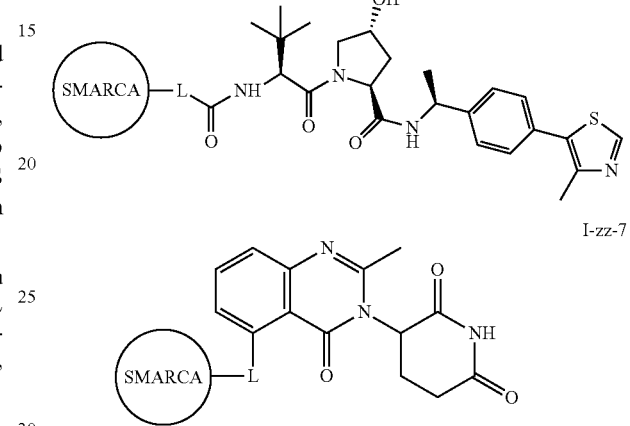

or a pharmaceutically acceptable salt thereof, wherein L and SMARCA are as defined above and described in embodiments herein, and wherein each of the variables $A^1$, $A^2$, $A^3$, $R^5$, G and Z is as defined and described in WO 2017/176958.

In certain embodiments, the present invention provides a compound of Formula I, wherein LBM is a CRBN E3 ubiquitin ligase binding moiety thereby forming a compound of formula I-zz'-1, I-zz''-1, I-zz'-2, I-zz'-2, I-zz'-3, I-zz''-3, I-zz'-4, I-zz''-4, I-zz'-7 or I-zz''-7 respectively:

I-zz'-1

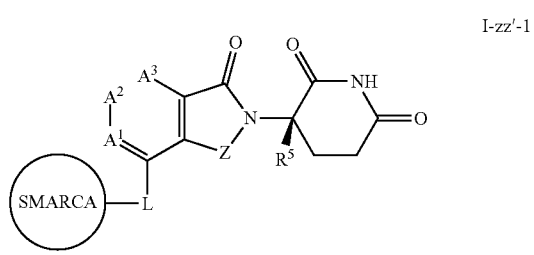

I-zz''-1

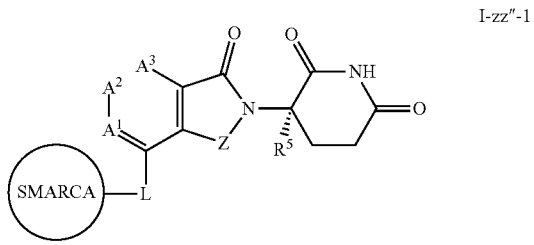

-continued

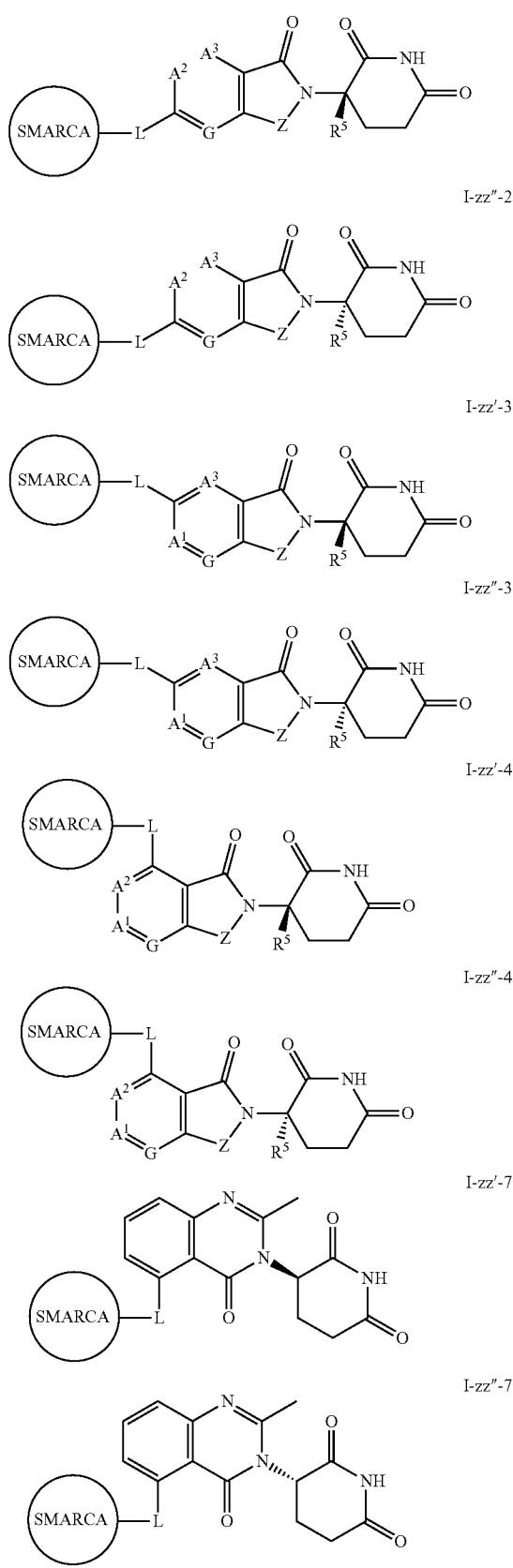

or a pharmaceutically acceptable salt thereof, wherein L and SMARCA are as defined above and described in embodiments herein, and wherein each of the variables $A^1$, $A^2$, $A^3$, $R^5$, G and Z is as defined and described in WO 2017/176958, the entirety of which is herein incorporated by reference.

In certain embodiments, the present invention provides a compound of Formula I, wherein LBM is a MDM2 (i.e. human double minute 2 or HDM2) E3 ligase binding moiety thereby forming a compound of formula I-aaa-1, I-aaa-2, I-aaa-3, I-aaa-4, I-aaa-5, I-aaa-6, I-aaa-7, I-aaa-8, I-aaa-9, I-aaa-10, I-aaa-11, I-aaa-12, I-aaa-13, I-aaa-14, I-aaa-15, I-aaa-16, I-aaa-17, or I-aaa-18 respectively:

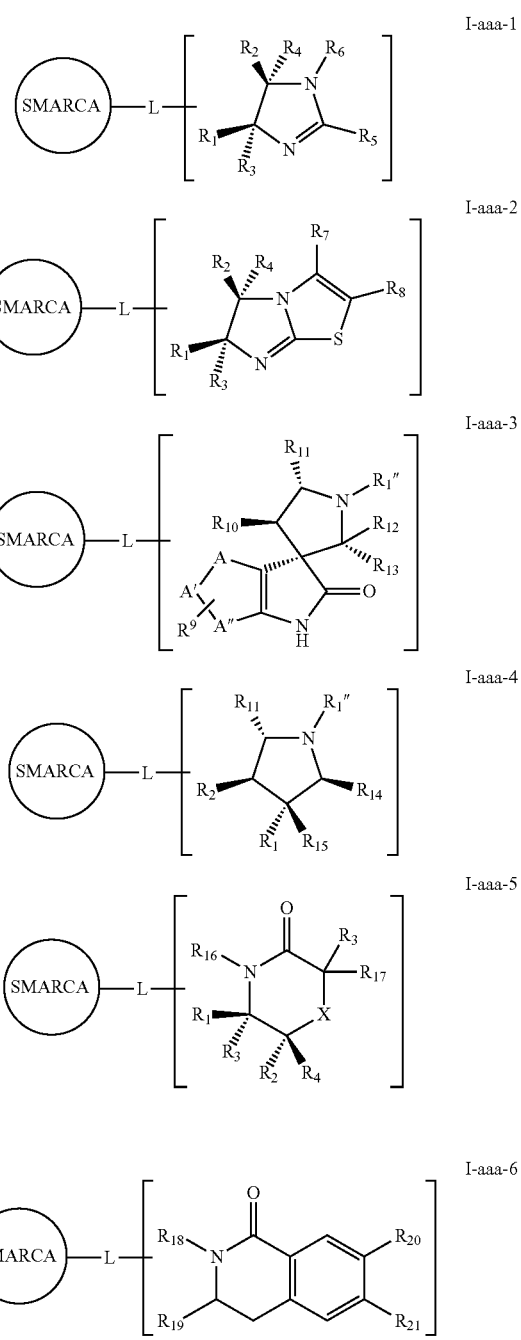

I-aaa-7
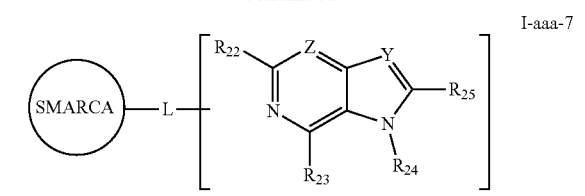
I-aaa-8
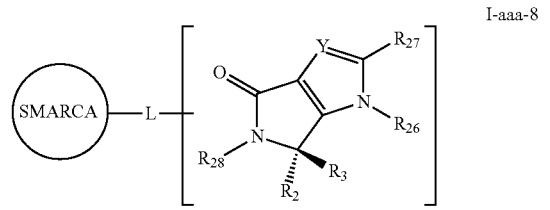
I-aaa-9
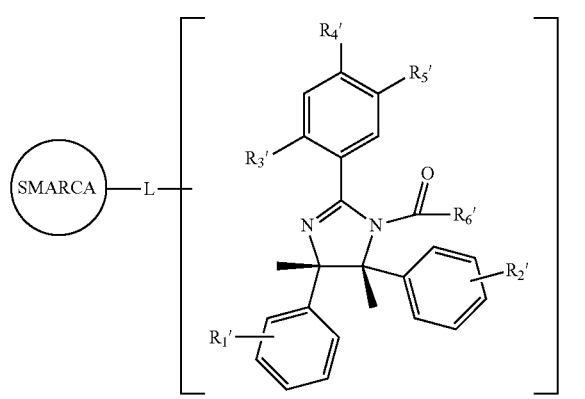
I-aaa-12
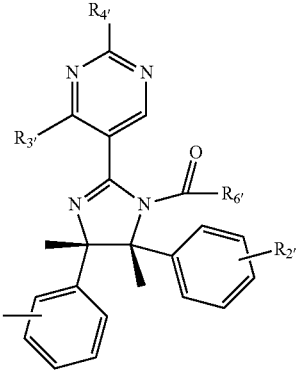
I-aaa-13
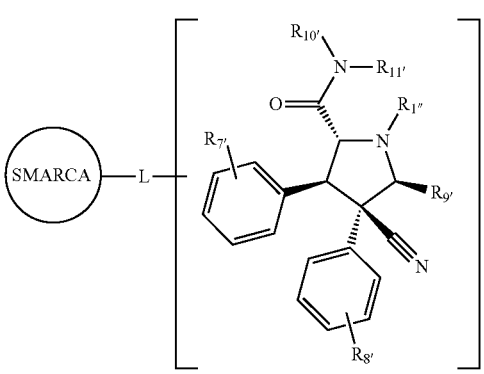
I-aaa-10
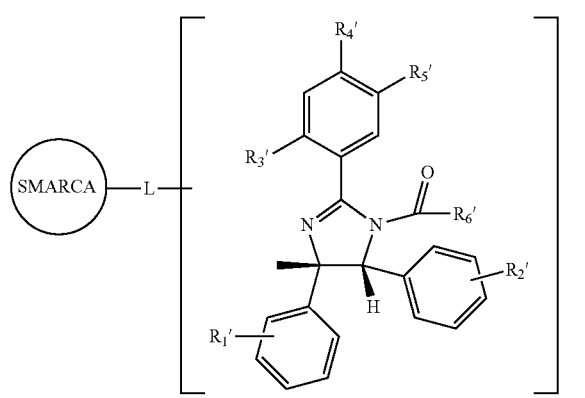
I-aaa-11
I-aaa-14
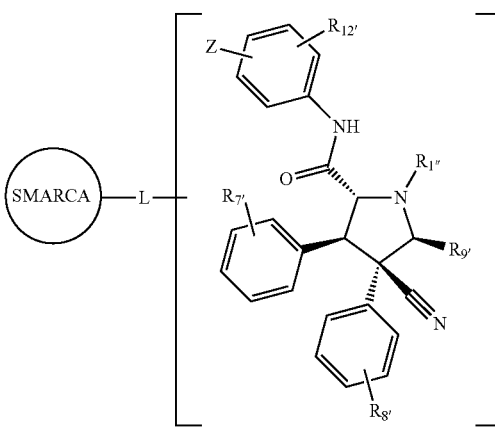

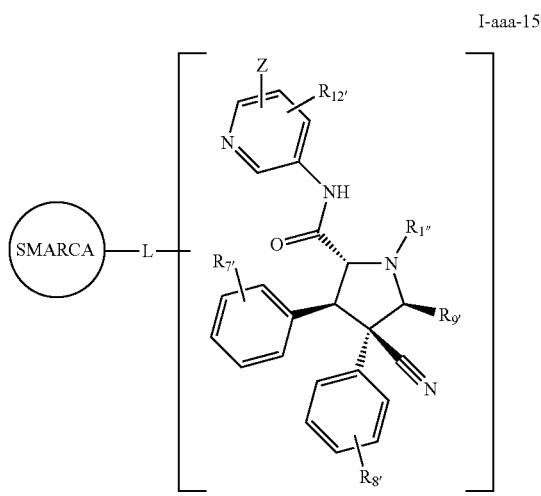

I-aaa-15

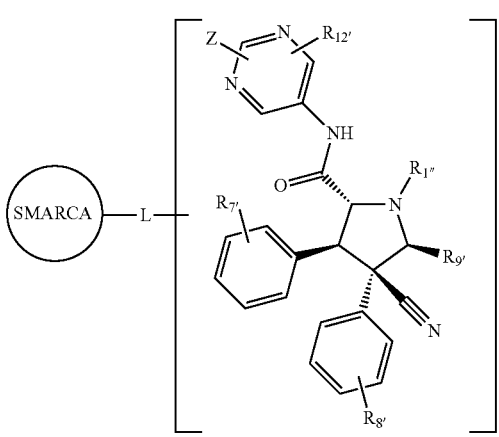

I-aaa-16

I-aaa-17

I-aaa-18 or a pharmaceutically acceptable salt thereof, wherein L and SMARCA are as defined above and described in embodiments herein, and wherein each of the variables $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, $R_{1'}$, $R_{2'}$, $R_{3'}$, $R_{4'}$, $R_{5'}$, $R_{6'}$, $R_{7'}$, $R_{8'}$, $R_{9'}$, $R_{10'}$, $R_{11'}$, $R_{12'}$, $R_{1''}$, A, A', A'', X, Y, and Z is as defined and described in WO 2017/011371 and US 2017/0008904, the entirety of each of which is herein incorporated by reference.

In certain embodiments, the present invention provides a compound of Formula I, wherein LBM is an IAP E3 ubiquitin ligase binding moiety thereby forming a compound of formula I-bbb-1, I-bbb-2, I-bbb-3, or I-bbb-4 respectively:

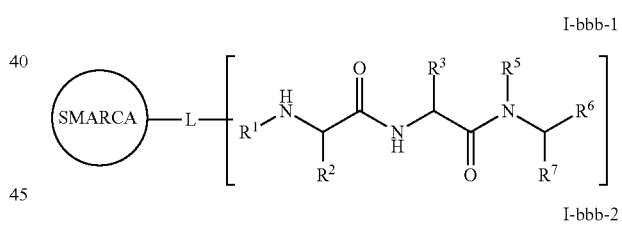

I-bbb-1

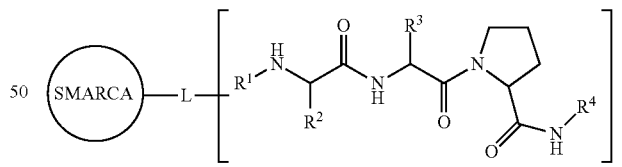

I-bbb-2

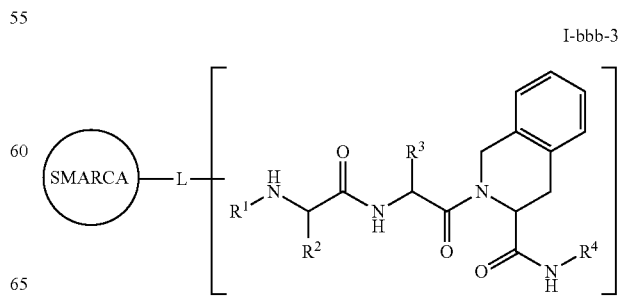

I-bbb-3

-continued

I-bbb-4

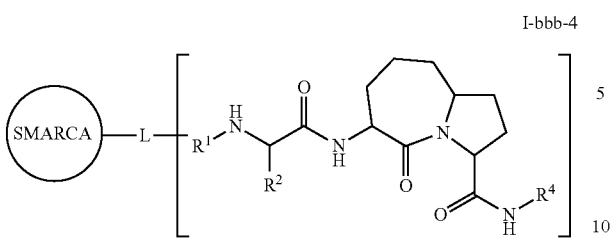

or a pharmaceutically acceptable salt thereof, wherein L and SMARCA are as defined above and described in embodiments herein, and wherein each of the variables $R^1$, $R^2$, $R^3$, $R^4$, $R^5$, $R^6$, and $R^7$, is as defined and described in WO 2017/011590 and US 2017/0037004, the entirety of each of which is herein incorporated by reference.

In certain embodiments, the present invention provides a compound of Formula I, wherein LBM is an E3 ubiquitin ligase (cereblon) binding moiety, a DCAF15 E3 ubiquitin ligase binding moiety, or a VHL E3 ubiquitin ligase binding moiety; thereby forming a compound of formula I-ccc-1, I-ccc-2, or I-ccc-3:

I-ccc-1

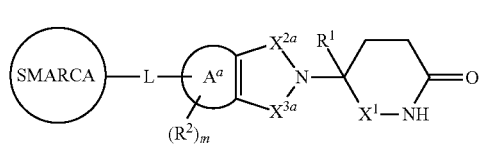

I-ccc-2

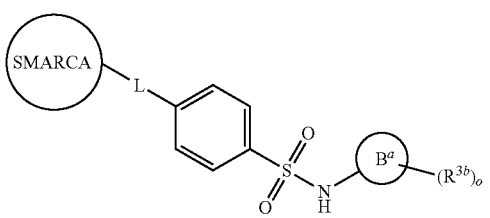

I-ccc-3

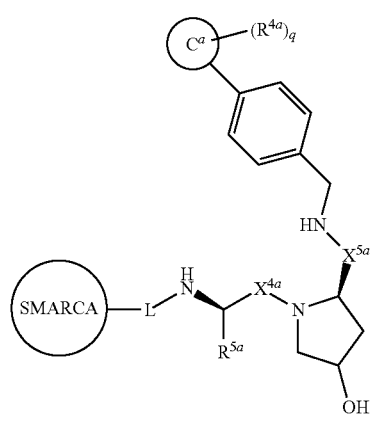

or a pharmaceutically acceptable salt thereof, wherein L and SMARCA is as defined above and described in embodiments herein, and wherein:

each of $X^1$, $X^{2a}$, and $X^{3a}$ is independently a bivalent moiety selected from a covalent bond, —$CH_2$—, —$C(O)$—, —$C(S)$—, or

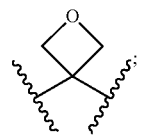 [SMILES: *C1(*)COC1]

each of $X^{4a}$ and $X^{5a}$ is independently a bivalent moiety selected from —$CH_2$—, —$C(O)$—, —$C(S)$—, or

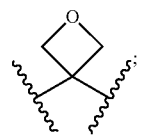 [SMILES: *C1(*)COC1]

$R^1$ is hydrogen, deuterium, halogen, —CN, —OR, —SR, —S(O)R, —S(O)$_2$R, —NR$_2$, or an optionally substituted C$_{1-4}$ aliphatic;

each of $R^2$, $R^{3b}$, and $R^{4a}$ is independently hydrogen, —R$^6$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;

$R^{5a}$ is hydrogen or C$_{1-6}$ aliphatic;

each $R^6$ is independently an optionally substituted group selected from C$_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring $A^a$ is a fused ring selected from 6-membered aryl containing 0-2 nitrogen atoms, 5 to 7-membered partially saturated carbocyclyl, 5 to 7-membered partially saturated heterocyclyl with 1-2 heteroatoms independently selected from nitrogen, oxygen or sulfur, or 5-membered heteroaryl with 1-3 heteroatoms independently selected from nitrogen, oxygen or sulfur;

Ring $B^a$ is selected from 6-membered aryl containing 0-2 nitrogen atoms or a 8-10 membered bicyclic heteroaryl having 1-5 heteroatoms independently selected from nitrogen, oxygen, or sulfur;

Ring $C^a$ is a selected from 6-membered aryl containing 0-2 nitrogen atoms or a 5-membered heteroaryl with 1-3 heteroatoms independently selected from nitrogen, oxygen or sulfur;

m is 0, 1, 2, 3 or 4;
o is 0, 1, 2, 3 or 4;
q is 0, 1, 2, 3 or 4; and
each R is independently hydrogen, or an optionally substituted group selected from C$_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:
two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In certain embodiments, the present invention provides a compound of Formula I-ccc-1, wherein LBM is an E3 ubiquitin ligase (cereblon) binding moiety thereby forming a compound of formula I-ccc'-1 or I-ccc"-1:

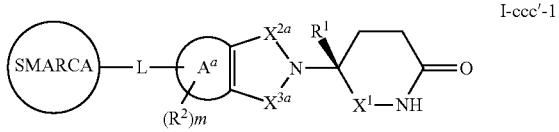
I-ccc'-1

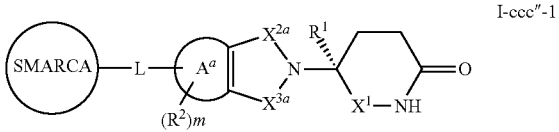
I-ccc"-1 or a pharmaceutically acceptable salt thereof, wherein SMARCA, L, Ring $A^a$, $X^1$, $X^{2a}$, $X^{3a}$, $R^1$, $R^2$ and m are as described above.

As defined above and described herein, each of $X^1$, $X^{2a}$, and $X^{3a}$ is independently a bivalent moiety selected from a covalent bond, —CH$_2$—, —C(O)—, —C(S)—, or

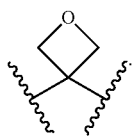 [SMILES: *C1(*)COC1]

In some embodiments, $X^1$ is a covalent bond, —CH$_2$—, —C(O)—, —C(S)—, or

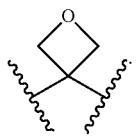 [SMILES: *C1(*)COC1]

In some embodiments, $X^1$ is selected from those depicted in Table 1, below.

In some embodiments, $X^{2a}$ is a covalent bond, —CH$_2$—, —C(O)—, —C(S)—, or

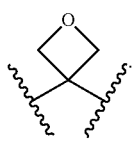 [SMILES: *C1(*)COC1]

In some embodiments, $X^{2a}$ is selected from those depicted in Table 1, below.

In some embodiments, $X^{3a}$ is a covalent bond, —CH$_2$—, —C(O)—, —C(S)—, or

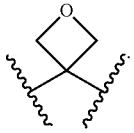 [SMILES: *C1(*)COC1]

In some embodiments, $X^{3a}$ is selected from those depicted in Table 1, below.

As defined above and described herein, each of $X^4$ and $X^5$ is independently a bivalent moiety selected from —CH$_2$—, —C(O)—, —C(S)—, or

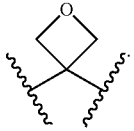

In some embodiments, $X^{4a}$ is —CH$_2$—, —C(O)—, —C(S)—, or

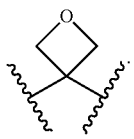 [SMILES: *C1(*)COC1]

In some embodiments, $X^{4a}$ is selected from those depicted in Table 1, below.

In some embodiments, $X^{5a}$ is —CH$_2$—, —C(O)—, —C(S)—, or

,

In some embodiments, $X^{5a}$ is selected from those depicted in Table 1, below.

As defined above and described herein, $R^1$ is hydrogen, deuterium, halogen, —CN, —OR, —SR, —S(O)R, —S(O)$_2$R, —NR$_2$, or an optionally substituted $C_{1-4}$ aliphatic.

In some embodiments, $R^1$ is hydrogen, deuterium, halogen, —CN, —OR, —SR, —S(O)R, —S(O)$_2$R, —NR$_2$, or an optionally substituted $C_{1-4}$ aliphatic.

In some embodiments, $R^1$ is selected from those depicted in Table 1, below.

As defined above and described herein, each of $R^2$, $R^{3b}$, and $R^{4a}$ is independently hydrogen, —$R^6$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R.

In some embodiments, $R^2$ is hydrogen, —$R^6$, halogen, —CN, —NO$_2$, —OR, —SR, —NR$_2$, —S(O)$_2$R, —S(O)$_2$NR$_2$, —S(O)R, —C(O)R, —C(O)OR, C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R.

In some embodiments, $R^2$ is selected from those depicted in Table 1, below.

In some embodiments, R$^{3b}$ is hydrogen, —R$^6$, halogen, —CN, —NO$_2$, —OR, —SR, —NR$_2$, —S(O)$_2$R, —S(O)$_2$NR$_2$, —S(O)R, —C(O)R, —C(O)OR, C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R.

In some embodiments, R$^{3b}$ is methyl.

In some embodiments, R$^{3b}$ is selected from those depicted in Table 1, below.

In some embodiments, R$^{4a}$ is hydrogen, —R$^6$, halogen, —CN, —NO$_2$, —OR, —SR, —NR$_2$, —S(O)$_2$R, —S(O)$_2$NR$_2$, —S(O)R, —C(O)R, —C(O)OR, C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R.

In some embodiments, R$^{4a}$ is methyl.

In some embodiments, R$^{4a}$ is selected from those depicted in Table 1, below.

As defined above and described herein, R$^{5a}$ is hydrogen or C$_{1-6}$ aliphatic.

In some embodiments, R$^{5a}$ is t-butyl.

In some embodiments, R$^{5a}$ is selected from those depicted in Table 1, below.

As defined above and described herein, each R$^6$ is independently an optionally substituted group selected from C$_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur.

In some embodiments, R$^6$ is an optionally substituted C$_{1-6}$ aliphatic group. In some embodiments, R$^6$ is an optionally substituted phenyl. In some embodiments, R$^6$ is an optionally substituted 4-7 membered saturated or partially unsaturated heterocyclic ring having 1-2 heteroatoms independently selected from nitrogen, oxygen, and sulfur. In some embodiments, R$^6$ is an optionally substituted 5-6 membered heteroaryl ring having 1-4 heteroatoms independently selected from nitrogen, oxygen, and sulfur.

In some embodiments, R$^6$ is selected from those depicted in Table 1, below.

As defined above and described herein, Ring A$^a$ is a fused ring selected from 6-membered aryl containing 0-2 nitrogen atoms, 5 to 7-membered partially saturated carbocyclyl, 5 to 7-membered partially saturated heterocyclyl with 1-2 heteroatoms independently selected from nitrogen, oxygen or sulfur, or 5-membered heteroaryl with 1-3 heteroatoms independently selected from nitrogen, oxygen or sulfur.

In some embodiments Ring A$^a$ is a fused 6-membered aryl containing 0-2 nitrogen atoms. In some embodiments Ring A$^a$ is a fused 5 to 7-membered partially saturated carbocyclyl. In some embodiments Ring A$^a$ is a fused 5 to 7-membered partially saturated heterocyclyl with 1-2 heteroatoms independently selected from nitrogen, oxygen or sulfur. In some embodiments Ring A$^a$ is a fused 5-membered heteroaryl with 1-3 heteroatoms independently selected from nitrogen, oxygen or sulfur.

In some embodiments, Ring A$^a$ is a fused phenyl.

In some embodiments, Ring A$^a$ is selected from those depicted in Table 1, below.

As defined above and described herein, Ring B$^a$ is selected from 6-membered aryl containing 0-2 nitrogen atoms or a 8-10 membered bicyclic heteroaryl having 1-5 heteroatoms independently selected from nitrogen, oxygen, or sulfur.

In some embodiments, Ring B$^a$ is a 6-membered aryl containing 0-2 nitrogen atoms. In some embodiments, Ring B$^a$ is a 8-10 membered bicyclic heteroaryl having 1-5 heteroatoms independently selected from nitrogen, oxygen, or sulfur.

In some embodiments, Ring B$^a$ is

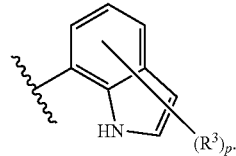

In some embodiments, Ring B$^a$ is selected from those depicted in Table 1, below.

As defined above and described herein, Ring C$^a$ is selected from 6-membered aryl containing 0-2 nitrogen atoms or a 5-membered heteroaryl with 1-3 heteroatoms independently selected from nitrogen, oxygen or sulfur.

In some embodiments, Ring C$^a$ is a 6-membered aryl containing 0-2 nitrogen atoms. In some embodiments, Ring C$^a$ is a 5-membered heteroaryl with 1-3 heteroatoms independently selected from nitrogen, oxygen or sulfur.

In some embodiments, Ring C$^a$ is

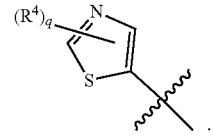

In some embodiments, Ring C$^a$ is selected from those depicted in Table 1, below.

As defined above and described herein, m is 0, 1, 2, 3 or 4.

In some embodiments, m is 0. In some embodiments, m is 1. In some embodiments, m is 2. In some embodiments, m is 3. In some embodiments, m is 4.

In some embodiments, m is selected from those depicted in Table 1, below.

In some embodiments, o is selected from those depicted in Table 1, below.

As defined above and described herein, o is 0, 1, 2, 3 or 4.

In some embodiments, o is 0. In some embodiments, o is 1. In some embodiments, o is 2. In some embodiments, o is 3. In some embodiments, o is 4.

In some embodiments, o is selected from those depicted in Table 1, below.

As defined above and described herein, q is 0, 1, 2, 3 or 4.

In some embodiments, q is 0. In some embodiments, q is 1. In some embodiments, q is 2. In some embodiments, q is 3. In some embodiments, q is 4.

In some embodiments, q is selected from those depicted in Table 1, below.

As defined above and described herein, each R is independently hydrogen, or an optionally substituted group selected from C$_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or: two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, R is hydrogen. In some embodiments, R is phenyl. In some embodiments, R is a 4-7 membered saturated or partially unsaturated heterocyclic having 1-2 heteroatoms independently selected from nitrogen, oxygen, and sulfur. In some embodiments, R is a 5-6 membered heteroaryl ring having 1-4 heteroatoms independently selected from nitrogen, oxygen, and sulfur. In some embodiments, two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, R is selected from those depicted in Table 1, below.

In certain embodiments, the present invention provides a compound of formula I, wherein LBM is a VHL binding moiety thereby forming a compound of formula I-ddd:

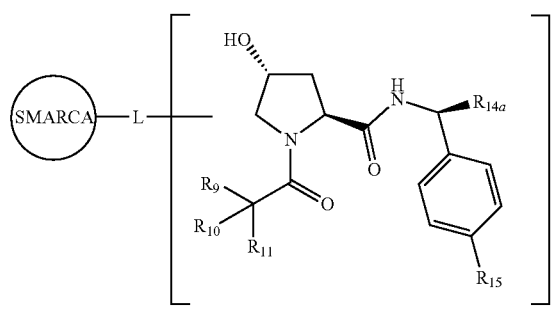

I-ddd or a pharmaceutically acceptable salt thereof, wherein L and SMARCA are as defined above and described in embodiments herein, and wherein each of the variables $R_9$, $R_{10}$, $R_{11}$, $R_{14a}$, and $R_{15}$ is as described and defined in WO 2017/030814, WO 2016/118666, and US 2017/0327469, the entirety of each of which is herein incorporated by reference.

In certain embodiments, the present invention provides a compound of formula I, wherein LBM is a VHL binding moiety thereby forming a compound of formula I-eee-1 or I-eee-2:

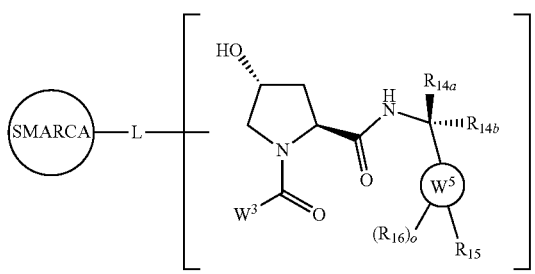

I-eee-1

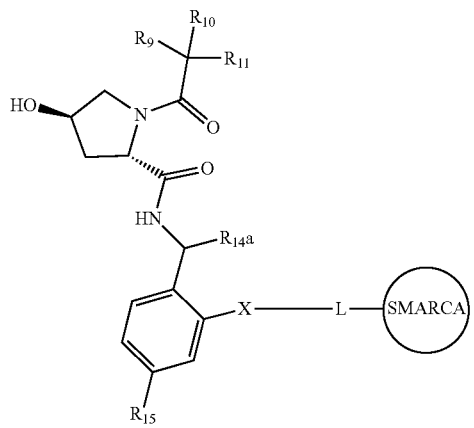

I-eee-2 or a pharmaceutically acceptable salt thereof, wherein L and SMARCA are as defined above and described in embodiments herein, and wherein each of the variables X, W, $R_9$, $R_{10}$, $R_{11}$, $R_{14a}$, and $R_{14b}$, $R_{15}$, $R^{16}$, and o is as described and defined in WO 2017/030814, WO 2016/118666, and US 2017/0327469, the entirety of each of which is herein incorporated by reference.

In certain embodiments, the present invention provides a compound of formula I, wherein LBM is an IAP binding moiety thereby forming a compound of formula I-fff:

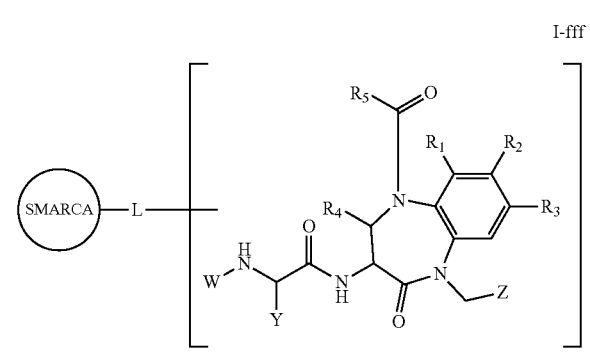

I-fff or a pharmaceutically acceptable salt thereof, wherein L and SMARCA are as defined above and described in embodiments herein, and wherein each of the variables W, Y, Z, $R^1$, $R^2$, $R^3$, $R^4$, and $R^5$ is as described and defined in WO 2014/044622, US 2015/0225449, WO 2015/071393, and US 2016/0272596, the entirety of each of which is herein incorporated by reference.

In certain embodiments, the present invention provides a compound of formula I, wherein LBM is a MDM2 binding moiety thereby forming a compound of formula I-ggg:

I-ggg

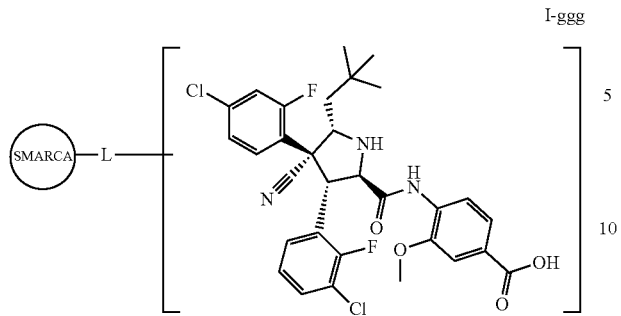

or a pharmaceutically acceptable salt thereof, wherein U and SMARCA are as defined above and described in embodiments herein, as described and defined in Hines, J. et al., Cancer Res. (DOI: 10.1158/0008-5472.CAN-18-2918), the entirety of each of which is herein incorporated by reference.

In certain embodiments, the present invention provides a compound of formula I, wherein LBM is a DCAF16 binding moiety thereby forming a compound of formula I-hhh:

I-hhh

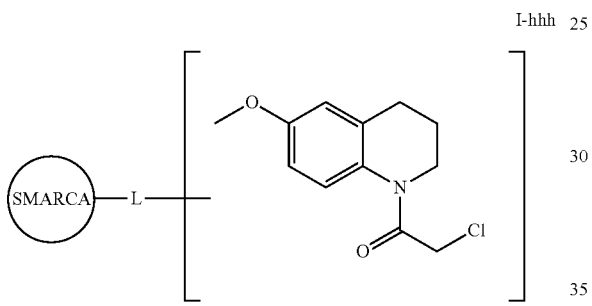

or a pharmaceutically acceptable salt thereof, wherein U and SMARCA are as defined above and described in embodiments herein, as described and defined in Zhang, X. et al., bioRxiv (doi:https://doi.org/10.1101/443804), the entirety of each of which is herein incorporated by reference.

In certain embodiments, the present invention provides a compound of formula I, wherein LBM is a RNF114 binding moiety thereby forming a compound of formula I-iii:

I-iii

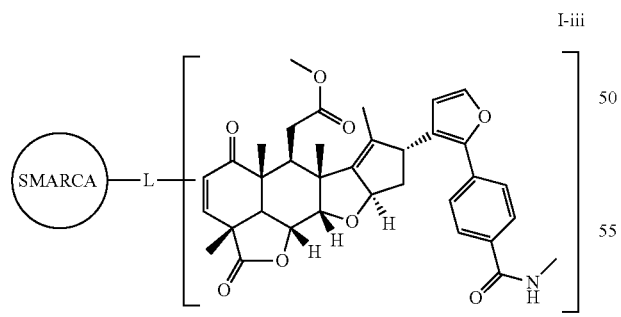

or a pharmaceutically acceptable salt thereof, wherein L and SMARCA are as defined above and described in embodiments herein, as described and defined in Spradin, J. N. et al., bioRxiv (doi:https://doi.org/10.1101/436998), the entirety of each of which is herein incorporated by reference.

In certain embodiments, the present invention provides a compound of formula I, wherein LBM is a RNF4 binding moiety thereby forming a compound of formula I-jjj:

I-jjj

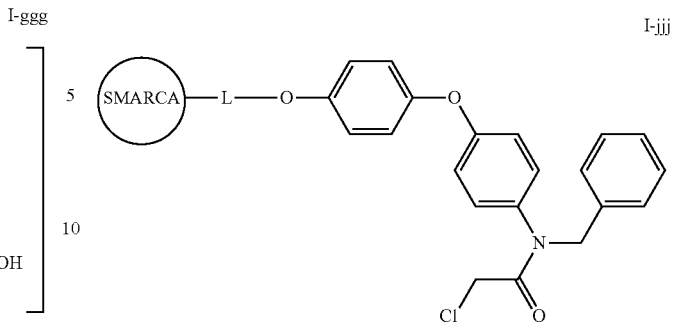

or a pharmaceutically acceptable salt thereof, wherein L and SMARCA are as defined above and described in embodiments herein, as described and defined in Ward, C. C., et al., bioRxiv (doi:https://doi.org/10.1101/439125), the entirety of each of which is herein incorporated by reference.

In certain embodiments, the present invention provides a compound of formula I, wherein LBM is a VHL binding moiety thereby forming a compound of formula I-nnn-1 or I-nnn-2:

I-nnn-1

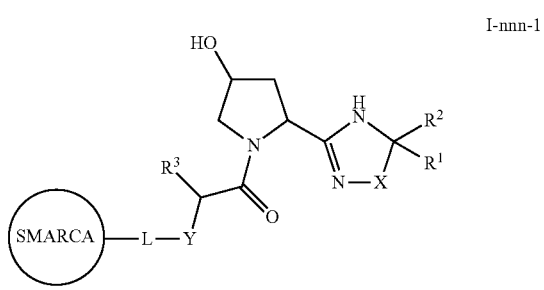

I-nnn-2

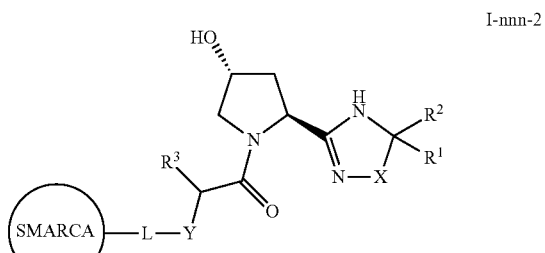

or a pharmaceutically acceptable salt thereof, wherein L and SMARCA are as defined above and described in embodiments herein, and wherein each of the variables $R^1$, $R^2$, $R^3$, X, and Y is as defined and described in WO 2019/084026, the entirety of each of which is herein incorporated by reference.

In certain embodiments, the present invention provides a compound of formula I, wherein LBM is a VHL binding moiety thereby forming a compound of formula I-ooo-1 or I-ooo-2:

I-ooo-1

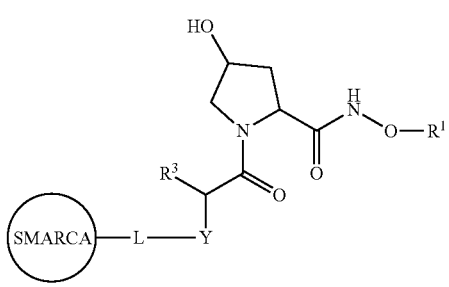

I-ooo-2

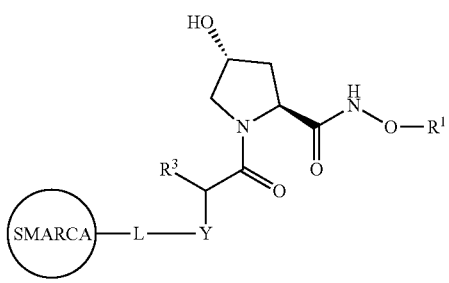

or a pharmaceutically acceptable salt thereof, wherein L and SMARCA are as defined above and described in embodiments herein, and wherein each of the variables $R^1$, $R^3$, and Y is as defined and described in WO 2019/084030, the entirety of each of which is herein incorporated by reference.

In certain embodiments, the present invention provides a compound of formula I, wherein LBM is a E3 ubiquitin ligase (cereblon) binding moiety thereby forming a compound of formula I-ppp-1, I-PPP-2, I-PPP-3, or I-ppp-4:

I-ppp-1

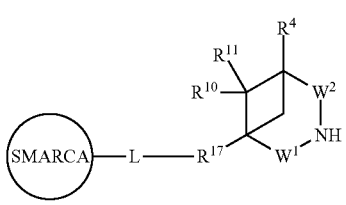

I-ppp-2

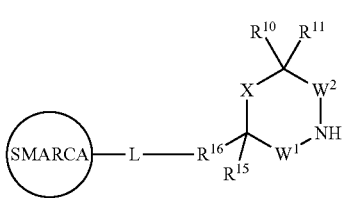

I-ppp-3

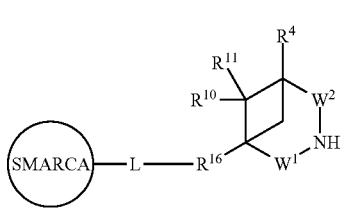

I-ppp-4

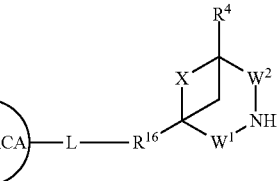

or a pharmaceutically acceptable salt thereof, wherein L and SMARCA are as defined above and described herein, and wherein each of the variables $R^4$, $R^{10}$, $R^{11}$, $R^{15}$, $R^{16}$, $R^{17}$, $W^1$, $W^2$, and X is as defined in WO 2019/0099868 which is herein incorporated by reference in its entirety, and wherein

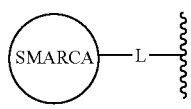

is attached to $R^{17}$ or $R^{16}$ at the site of attachment of $R^{12}$ as defined in WO 2018/237026, such that

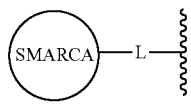

takes the place of the $R^{12}$ substituent.

In some embodiments, LBM is

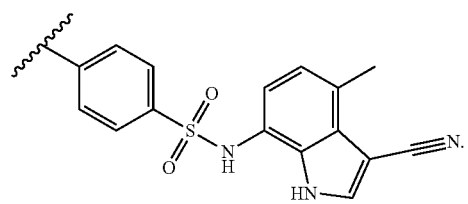 [SMILES: *c1ccc(S(=O)(=O)Nc2ccc(C)c3c(C#N)c[nH]c23)cc1]

In some embodiments, LBM is

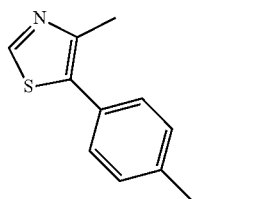

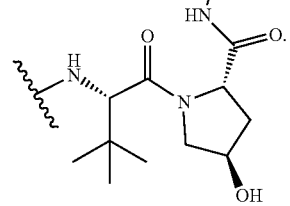

201
In some embodiments, LBM is
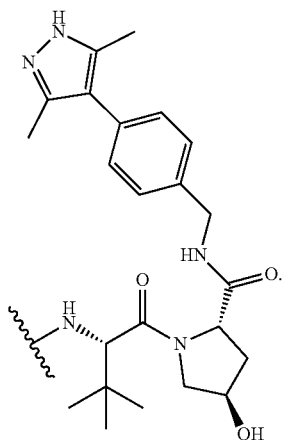 [SMILES: *N[C@H](C(=O)N1C[C@H](O)C[C@H]1C(=O)NCc1ccc(-c2c(C)n[nH]c2C)cc1)C(C)(C)C]
In some embodiments, LBM is
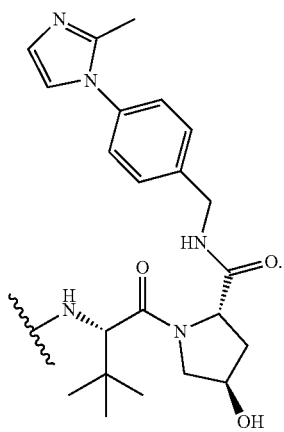 [SMILES: *N[C@H](C(=O)N1C[C@H](O)C[C@H]1C(=O)NCc1ccc(-n2ccnc2C)cc1)C(C)(C)C]
In some embodiments, LBM is
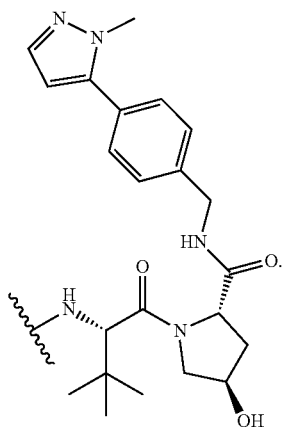 [SMILES: *N[C@H](C(=O)N1C[C@H](O)C[C@H]1C(=O)NCc1ccc(-c2ccnn2C)cc1)C(C)(C)C]
202
In some embodiments, LBM is
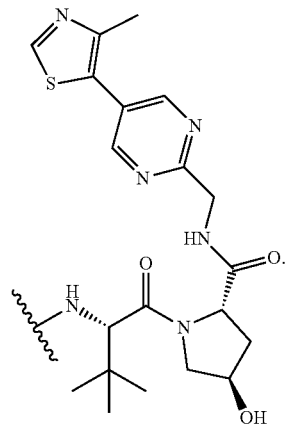 [SMILES: *N[C@H](C(=O)N1C[C@H](O)C[C@H]1C(=O)NCc1ncc(-c2scnc2C)cn1)C(C)(C)C]
In some embodiments, LBM is
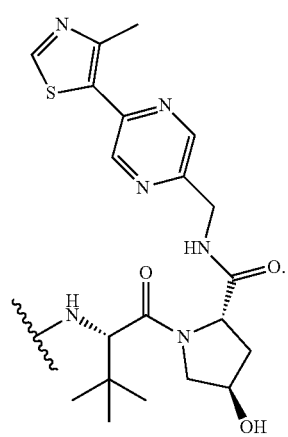 [SMILES: *N[C@H](C(=O)N1C[C@H](O)C[C@H]1C(=O)NCc1cnc(-c2scnc2C)cn1)C(C)(C)C]
In some embodiments, LBM is
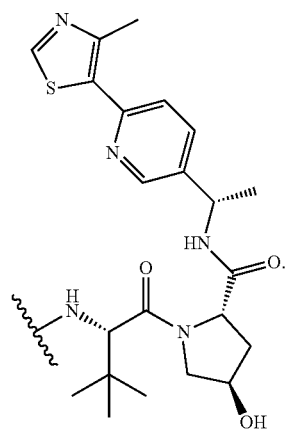

In some embodiments, LBM is
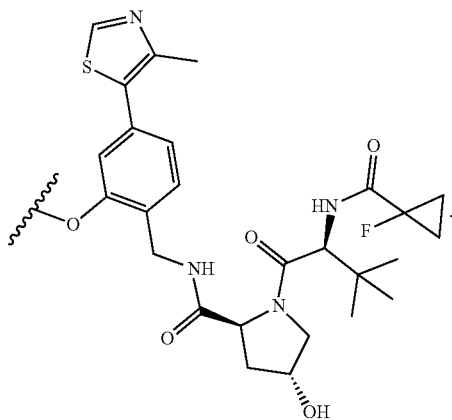 [SMILES: *Oc1cc(-c2scnc2C)ccc1CNC(=O)[C@@H]1C[C@@H](O)CN1C(=O)[C@@H](NC(=O)C1(F)CC1)C(C)(C)C]
In some embodiments, LBM is
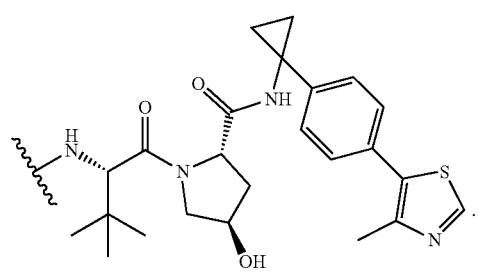 [SMILES: *N[C@H](C(=O)N1C[C@H](O)C[C@H]1C(=O)NC1(c2ccc(-c3scnc3C)cc2)CC1)C(C)(C)C]
In some embodiments, LBM
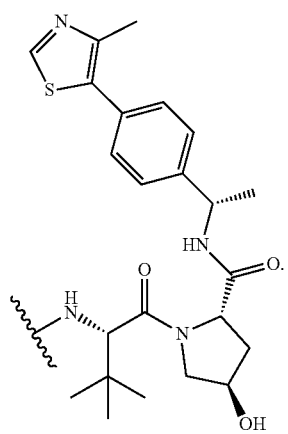 [SMILES: *N[C@H](C(=O)N1C[C@H](O)C[C@H]1C(=O)N[C@@H](C)c1ccc(-c2scnc2C)cc1)C(C)(C)C]
In some embodiments, LBM is
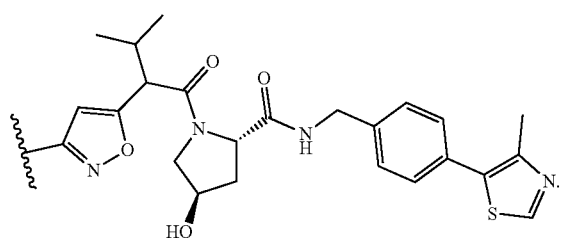 [SMILES: *c1cc(C(C(=O)N2C[C@H](O)C[C@H]2C(=O)NCc2ccc(-c3scnc3C)cc2)C(C)C)on1]
In some embodiments, LBM is
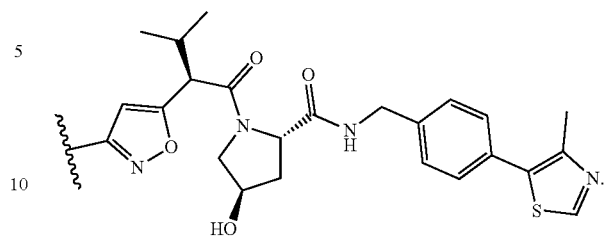
In some embodiments, LBM is
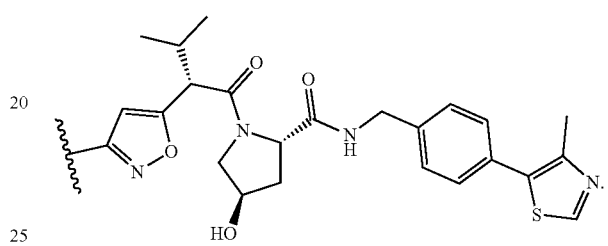
In some embodiments, LBM is
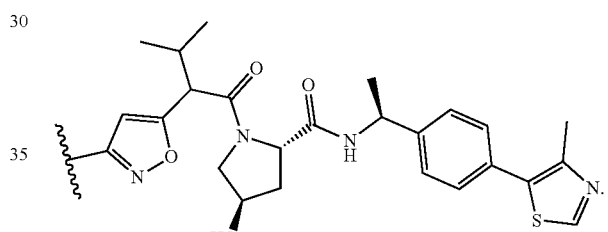
In some embodiments, LBM is
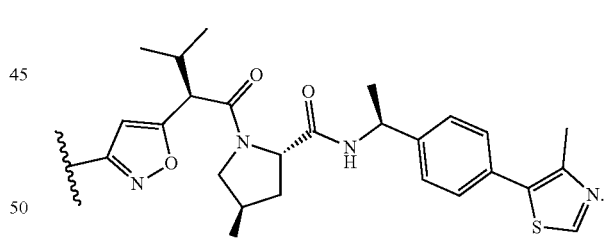
In some embodiments, LBM is
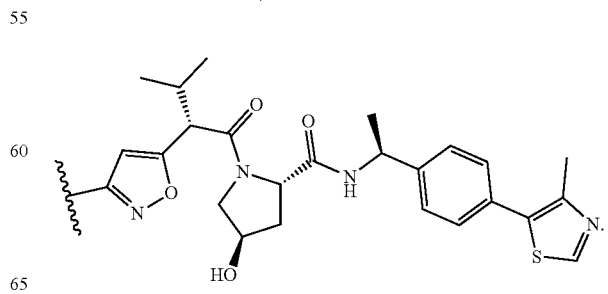

In some embodiments, LBM is
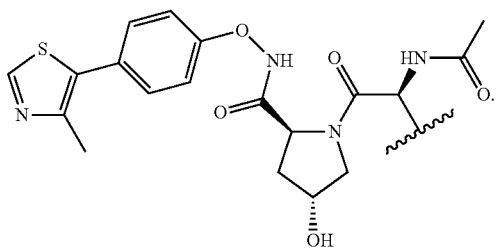 [SMILES: *[C@H](NC(C)=O)C(=O)N1C[C@H](O)C[C@H]1C(=O)NOc1ccc(-c2scnc2C)cc1]
In some embodiments, LBM is
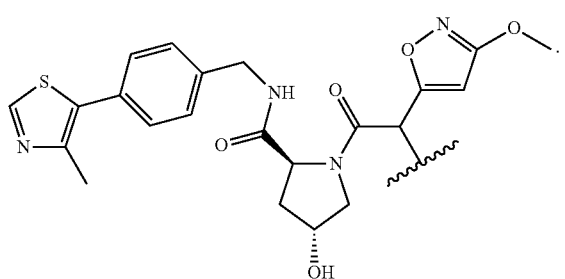 [SMILES: *C(C(=O)N1C[C@H](O)C[C@H]1C(=O)NCc1ccc(-c2scnc2C)cc1)c1cc(OC)no1]
In some embodiments, LBM is
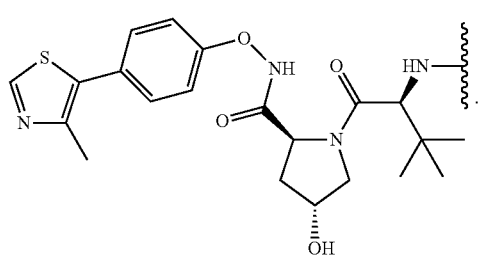 [SMILES: *N[C@H](C(=O)N1C[C@H](O)C[C@H]1C(=O)NOc1ccc(-c2scnc2C)cc1)C(C)(C)C]
In some embodiments, LBM is
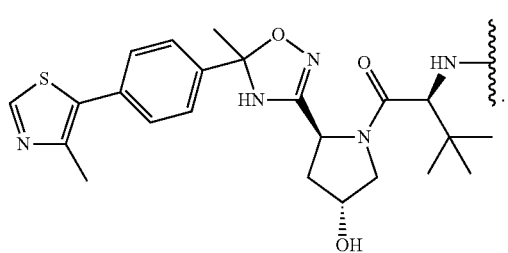 [SMILES: *N[C@H](C(=O)N1C[C@H](O)C[C@H]1C1=NOC(C)(c2ccc(-c3scnc3C)cc2)N1)C(C)(C)C]
In some embodiments, LBM is
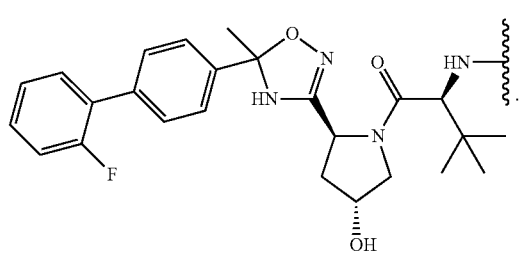 [SMILES: *N[C@H](C(=O)N1C[C@H](O)C[C@H]1C1=NOC(C)(c2ccc(-c3ccccc3F)cc2)N1)C(C)(C)C]
In some embodiments, LBM is
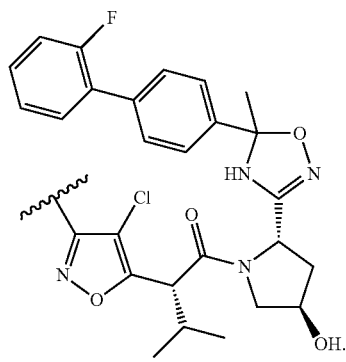 [SMILES: *c1noc([C@H](C(=O)N2C[C@H](O)C[C@H]2C2=NOC(C)(c3ccc(-c4ccccc4F)cc3)N2)C(C)C)c1Cl]
In some embodiments, LBM is
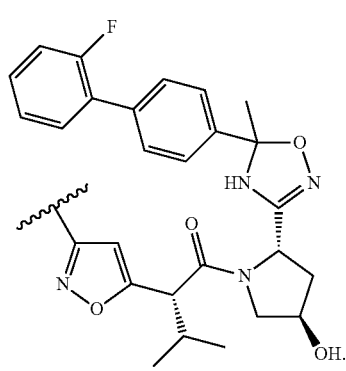 [SMILES: *c1cc([C@H](C(=O)N2C[C@H](O)C[C@H]2C2=NOC(C)(c3ccc(-c4ccccc4F)cc3)N2)C(C)C)on1]
In some embodiments, LBM is
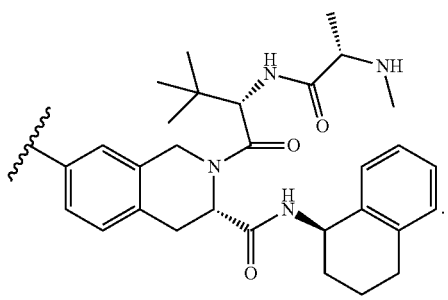 [SMILES: *c1ccc2c(c1)CN(C(=O)[C@@H](NC(=O)[C@H](C)NC)C(C)(C)C)[C@H](C(=O)N[C@@H]1CCCc3ccccc31)C2]
In some embodiments, LBM is
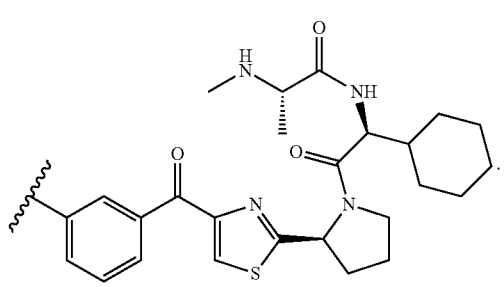 [SMILES: *c1cccc(C(=O)c2csc([C@@H]3CCCN3C(=O)[C@@H](NC(=O)[C@H](C)NC)C3CCCCC3)n2)c1]

207
In some embodiments, LBM is
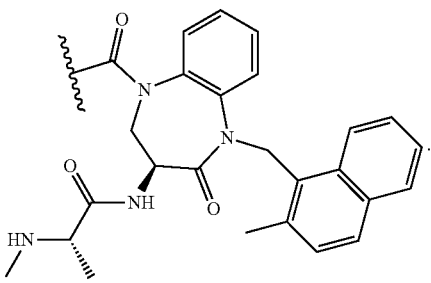 [SMILES: *C(=O)N1C[C@H](NC(=O)[C@H](C)NC)C(=O)N(Cc2c(C)ccc3ccccc23)c2ccccc21]
In some embodiments, LBM is
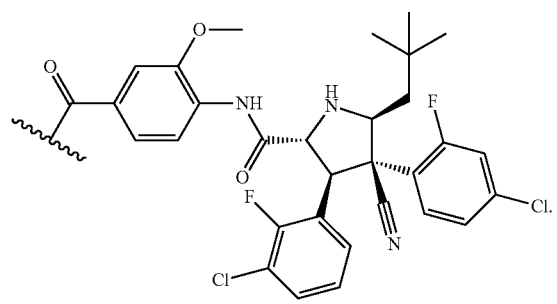 [SMILES: *C(=O)c1ccc(NC(=O)[C@@H]2N[C@@H](CC(C)(C)C)[C@](C#N)(c3ccc(Cl)cc3F)[C@H]2c2cccc(Cl)c2F)c(OC)c1]
In some embodiments, LBM is
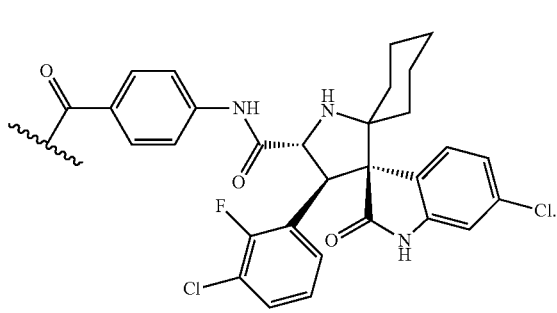 [SMILES: *C(=O)c1ccc(NC(=O)[C@@H]2NC3(CCCCC3)[C@@]3(C(=O)Nc4cc(Cl)ccc43)[C@H]2c2cccc(Cl)c2F)cc1]
In some embodiments, LBM is
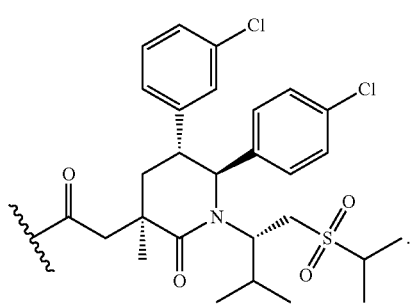 [SMILES: *C(=O)C[C@@]1(C)C[C@H](c2cccc(Cl)c2)[C@@H](c2ccc(Cl)cc2)N([C@H](CS(=O)(=O)C(C)C)C(C)C)C1=O]
208
In some embodiments, LBM is
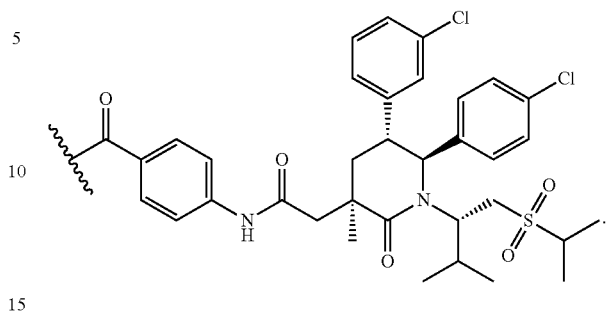
In some embodiments, LBM is
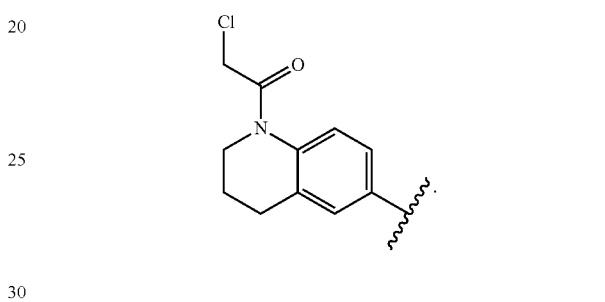
In some embodiments, LBM is
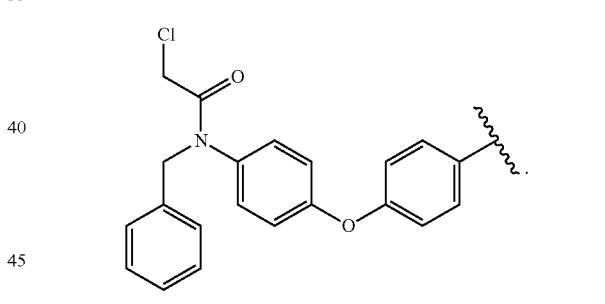
In some embodiments, LBM is
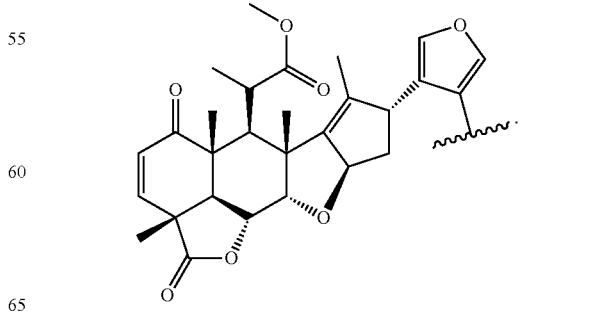

In some embodiments, LBM is

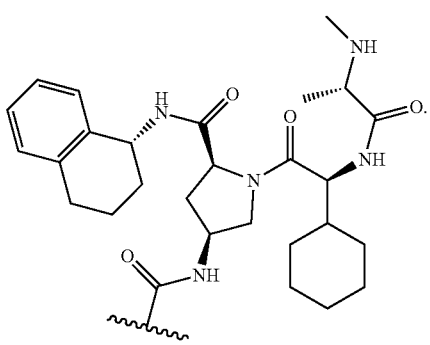 [SMILES: *C(=O)N[C@H]1C[C@@H](C(=O)N[C@@H]2CCCc3ccccc32)N(C(=O)[C@@H](NC(=O)[C@H](C)NC)C2CCCCC2)C1]

In some embodiments, LBM is

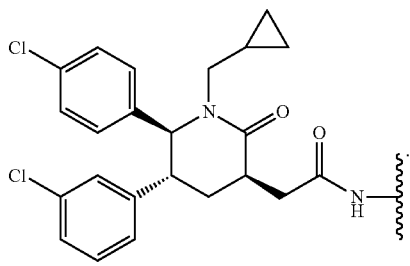 [SMILES: *NC(=O)C[C@H]1C[C@H](c2cccc(Cl)c2)[C@@H](c2ccc(Cl)cc2)N(CC2CC2)C1=O]

In some embodiments, LBM is

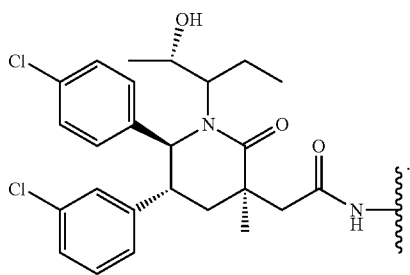 [SMILES: *NC(=O)C[C@@]1(C)C[C@H](c2cccc(Cl)c2)[C@@H](c2ccc(Cl)cc2)N(C(CC)[C@H](C)O)C1=O]

In some embodiments, LBM is

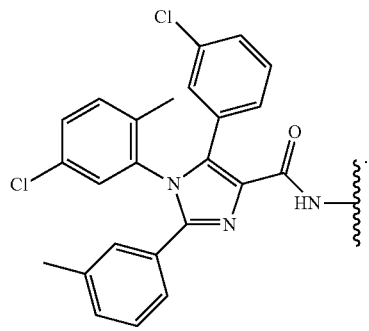 [SMILES: *NC(=O)c1nc(-c2cccc(C)c2)n(-c2cc(Cl)ccc2C)c1-c1cccc(Cl)c1]

In some embodiments, LBM is

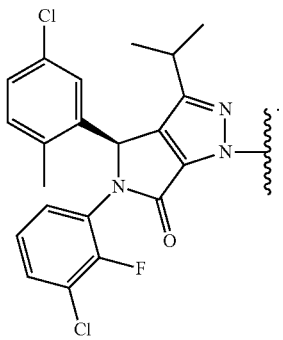 [SMILES: *n1nc(C(C)C)c2c1C(=O)N(c1cccc(Cl)c1F)[C@H]2c1cc(Cl)ccc1C]

In certain embodiments, the present invention provides a compound of formula I, wherein LBM is a CRBN E3 ubiquitin ligase binding moiety thereby forming a compound of formula I-qqq:

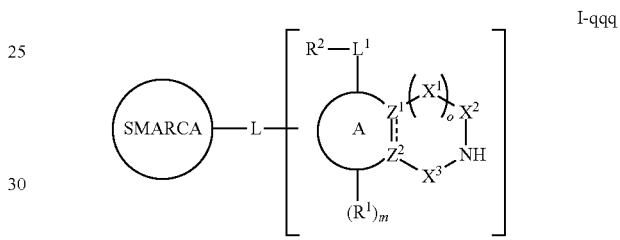

I-qqq or a pharmaceutically acceptable salt thereof, wherein L and SMARCA are as defined above and described in embodiments herein, wherein:

each $X^1$ is independently —$CH_2$—, —O—, —NR—, —$CF_2$—,

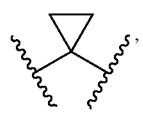

—C(O)—, —C(S)—, or

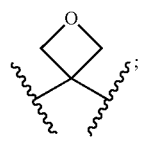

$X^2$ and $X^3$ are independently —$CH_2$—, —C(O)—, —C(S)—, or

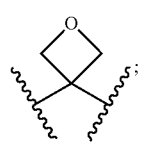

$Z^1$ and $Z^2$ are independently a carbon atom or a nitrogen atom;

Ring A is a fused ring selected from benzo, a 4-6 membered saturated or partially unsaturated carbocyclic or heterocyclic ring having 1-3 heteroatoms independently selected from nitrogen, oxygen, and sulfur, and a 5-6 membered heteroaryl ring having 1-4 heteroatoms independently selected from nitrogen, oxygen, and sulfur;

$L^1$ is a covalent bond or a $C_{1-3}$ bivalent straight or branched saturated or unsaturated hydrocarbon chain wherein 1-2 methylene units of the chain are independently and optionally replaced with —O—, —S—, —C(O)—, —C(S)—, —CR$_2$—, —CRF—, —CF$_2$—, —NR—, or —S(O)$_2$—;

each $R^1$ is independently selected from hydrogen, deuterium, $R^4$, halogen, —CN, —NO$_2$, —OR, —SR, —NR$_2$, —S(O)$_2$R, —S(O)$_2$NR$_2$, —S(O)R, —CF$_2$R, —CR$_2$F, —CF$_3$, —CR$_2$(OR), —CR$_2$(NR$_2$), —C(O)R, —C(O)OR, —C(O)NR$_2$, —C(O)N(R)OR, —OC(O)R, —OC(O)NR$_2$, —C(S)NR$_2$, —N(R)C(O)OR, —N(R)C(O)R, —N(R)C(O)NR$_2$, —N(R)S(O)$_2$R, —OP(O)R$_2$, —OP(O)(OR)$_2$, —OP(O)(OR)NR$_2$, —OP(O)(NR$_2$)$_2$, —Si(OR)R$_2$, and —SiR$_3$; or two $R^1$ groups are optionally taken together to form an optionally substituted 5-8 membered partially unsaturated or aryl fused ring having 0-2 heteroatoms independently selected from nitrogen, oxygen, or sulfur;

each R is independently selected from hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same carbon or nitrogen are optionally taken together with their intervening atoms to form an optionally substituted 4-7 membered saturated, partially unsaturated, or heteroaryl ring having 0-3 heteroatoms, in addition to the carbon or nitrogen, independently selected from nitrogen, oxygen, and sulfur;

$R^2$ is selected from

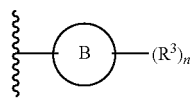

or hydrogen;

Ring B is phenyl, a 4-10 membered saturated or partially unsaturated mono- or bicyclic carbocyclic or heterocyclic ring having 1-3 heteroatoms independently selected from nitrogen, oxygen, and sulfur, or a 5-6 membered heteroaryl ring having 1-4 heteroatoms independently selected from nitrogen, oxygen, and sulfur, wherein Ring B is further optionally substituted with 1-2 oxo groups;

each $R^3$ is independently selected from hydrogen, deuterium, $R^4$, halogen, —CN, —NO$_2$, —OR, —SR, —NR$_2$, —S(O)$_2$R, —S(O)$_2$NR$_2$, —S(O)R, —CF$_2$R, —CF$_3$, —CR$_2$(OR), —CR$_2$(NR$_2$), —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)S(O)$_2$R, —OP(O)R$_2$, —OP(O)(OR)$_2$, —OP(O)(OR)NR$_2$, —OP(O)(NR$_2$)$_2$, and —SiR$_3$;

each $R^4$ is independently selected from an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

══ is a single or double bond;

m is 0, 1, 2, 3 or 4;

n is 0, 1, 2, 3 or 4; and o is 0, 1, or 2.

As defined above and described herein each $X^1$ is independently a covalent bond, —CH$_2$—, —O—, —NR—, —CF$_2$—,

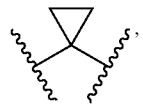 [SMILES: *C1(*)CC1]

—C(O)—, —C(S)—, or

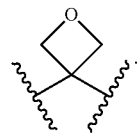 [SMILES: *C1(*)COC1]

In some embodiments, $X^1$ is a covalent bond. In some embodiments, $X^1$ is —CH$_2$—. In some embodiments, $X^1$ is —O—. In some embodiments, $X^1$ is —NR—. In some embodiments, $X^1$ is —CF$_2$—. In some embodiments, $X^1$ is

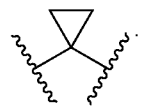

In some embodiments, $X^1$ is —C(O)—. In some embodiments, $X^1$ is —C(S)—. In some embodiments, $X^1$ is

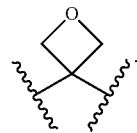 [SMILES: *C1(*)COC1]

In certain embodiments, $X^1$ is selected from those shown in the compounds of Table 1.

As defined above and described herein, $X^2$ and $X^3$ are independently —CH$_2$—, —C(O)—, —C(S)—, or

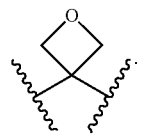 [SMILES: *C1(*)COC1]

In some embodiments, $X^2$ and $X^3$ are independently —CH$_2$—. In some embodiments, $X^2$ and $X^3$ are independently —C(O)—. In some embodiments, $X^2$ and $X^3$ are independently —C(S)—. In some embodiments, $X^2$ and $X^3$ are independently

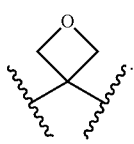 [SMILES: *C1(*)COC1]

In certain embodiments, $X^2$ and $X^3$ are independently selected from those shown in the compounds of Table 1.

As defined above and described herein, $X^4$ is a covalent bond, —$CH_2$—, —$CR_2$—, —O—, —NR—, —$CF_2$—,

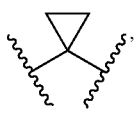

—C(O)—, —C(S)—, or

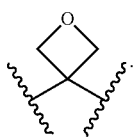 [SMILES: *C1(*)COC1]

As define above and described herein, $Z^1$ and $Z^2$ are independently a carbon atom or a nitrogen atom.

In some embodiments, $Z^1$ and $Z^2$ are independently a carbon atom. In some embodiments, $Z^1$ and $Z^2$ are independently a carbon atom.

In certain embodiments, $Z^1$ and $Z^2$ are independently selected from those shown in the compounds of Table 1.

As defined above and described herein, Ring A is a fused ring selected from benzo, a 4-6 membered saturated or partially unsaturated carbocyclic or heterocyclic ring having 1-3 heteroatoms independently selected from nitrogen, oxygen, and sulfur, and a 5-6 membered heteroaryl ring having 1-4 heteroatoms independently selected from nitrogen, oxygen, and sulfur.

In some embodiments, Ring A is benzo. In some embodiments, Ring A is a fused 4-6 membered saturated or partially unsaturated carbocyclic or heterocyclic ring having 1-3 heteroatoms independently selected from nitrogen, oxygen, and sulfur. In some embodiments, Ring A is a fused 5-6 membered heteroaryl ring having 1-4 heteroatoms independently selected from nitrogen, oxygen, and sulfur.

In some embodiments, Ring A is

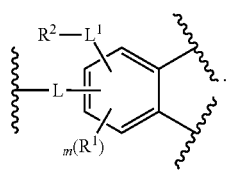

In some embodiments, Ring A is

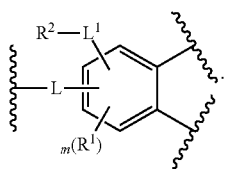

In some embodiments, Ring A is

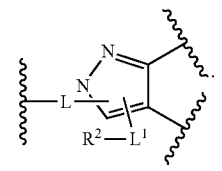

In some embodiments, Ring A is

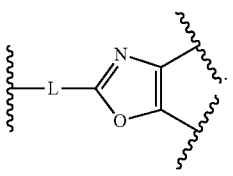

In certain embodiments, Ring A is selected from those shown in the compounds of Table 1.

As defined above and described herein, $L^1$ is a covalent bond or a $C_{1-3}$ bivalent straight or branched saturated or unsaturated hydrocarbon chain wherein 1-2 methylene units of the chain are independently and optionally replaced with —O—, —S—, —C(O)—, —C(S)—, —$CR_2$—, —CRF—, —$CF_2$—, —NR—, or —$S(O)_2$—

In some embodiments, $L^1$ is a covalent bond. In some embodiments, $L^1$ is a $C_{1-3}$ bivalent straight or branched saturated or unsaturated hydrocarbon chain wherein 1-2 methylene units of the chain are independently and optionally replaced with —O—, —S—, —C(O)—, —C(S)—, —$CR_2$—, —CRF—, —$CF_2$—, —NR—, or —$S(O)_2$—.

In some embodiments, $L^1$ is —C(O)—.

In certain embodiments, $L^1$ is selected from those shown in the compounds of Table 1.

As defined above and described herein, each $R^1$ is independently selected from hydrogen, deuterium, $R^4$, halogen, —CN, —$NO_2$, —OR, —SR, —$NR_2$, —$S(O)_2R$, —$S(O)_2NR_2$—S(O)R. —$CF_2R$, —$CF_3$, —$CR_2(OR)$, —$CR_2(NR_2)$, —C(O)R, —C(O)OR, —$C(O)NR_2$, —C(O)N(R)OR, —OC(O)R, —$OC(O)NR_2$, —$C(S)NR_2$, —N(R)C(O)OR, —N(R)C(O)R, —$N(R)C(O)NR_2$, —$N(R)S(O)_2R$, —$OP(O)R_2$, —$OP(O)(OR)_2$, —$OP(O)(OR)NR_2$, —$OP(O)(NR_2)_2$, —Si(OR)$R_2$, and —$SiR_3$, or two $R^1$ groups are optionally taken together to form an optionally substituted 5-8 membered partially unsaturated or aryl fused ring having 0-2 heteroatoms independently selected from nitrogen, oxygen, or sulfur.

In some embodiments, $R^1$ is hydrogen. In some embodiments, $R^1$ is deuterium. In some embodiments, $R^1$ is $R^4$. In some embodiments, $R^1$ is halogen. In some embodiments, $R^1$ is —CN. In some embodiments, $R^1$ is —$NO_2$. In some embodiments, $R^1$ is —OR. In some embodiments, $R^1$ is —SR. In some embodiments, $R^1$ is —$NR_2$. In some embodiments, $R^1$ is —$S(O)_2R$. In some embodiments, $R^1$ is —$S(O)_2NR_2$. In some embodiments, $R^1$ is —$S(O)R$. In some embodiments, $R^1$ is —$CF_2R$. In some embodiments, $R^1$ is —$CF_3$. In some embodiments, $R^1$ is —$CR_2(OR)$. In some embodiments, $R^1$ is —$CR_2(NR_2)$. In some embodiments, $R^1$ is —$C(O)R$. In some embodiments, $R^1$ is —$C(O)OR$. In some embodiments, $R^1$ is —$C(O)NR_2$. In some embodiments, $R^1$ is —$C(O)N(R)OR$. In some embodiments, $R^1$ is —$OC(O)R$. In some embodiments, $R^1$ is —$OC(O)NR_2$. In some embodiments, $R^1$ is —$C(S)NR_2$. In some embodiments, $R^1$ is —$N(R)C(O)OR$. In some embodiments, $R^1$ is —$N(R)C(O)R$. In some embodiments, $R^1$ is —$N(R)C(O)NR_2$. In some embodiments, $R^1$ is —$N(R)S(O)_2R$. In some embodiments, $R^1$ is —$OP(O)R_2$. In some embodiments, $R^1$ is —$OP(O)(OR)_2$. In some embodiments, $R^1$ is —$OP(O)(OR)NR_2$. In some embodiments, $R^1$ is —$OP(O)(NR_2)_2$. In some embodiments, $R^1$ is —$Si(OR)R_2$. In some embodiments, $R^1$ is —$SiR_3$. In some embodiments, two $R^1$ groups are optionally taken together to form an optionally substituted 5-8 membered partially unsaturated or aryl fused ring having 0-2 heteroatoms independently selected from nitrogen, oxygen, or sulfur.

In some embodiments, $R^1$ is fluoro. In some embodiments, $R^1$ is bromo. In some embodiments, $R^1$ is methyl. In some embodiments, $R^1$ is —OH. In some embodiments, $R^1$ is —$NH_2$. In some embodiments, $R^1$ is —$NHCH_3$. In some embodiments, $R^1$ is —$N(CH_3)_2$. In some embodiments, $R^1$ is —$NHCH(CH_3)_2$. In some embodiments, $R^1$ is —$NHSO_2CH_3$. In some embodiments, $R^1$ is —$CH_2OH$. In some embodiments, $R^1$ is —$CH_2NH_2$. In some embodiments, $R^1$ is —$C(O)NH_2$. In some embodiments, $R^1$ is —$C(O)NHCH_3$. In some embodiments, $R^1$ is

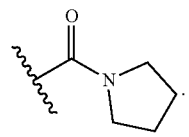 [SMILES: *C(=O)N1CCCC1]

In some embodiments, $R^1$ is

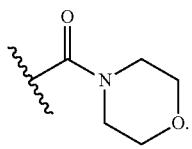 [SMILES: *C(=O)N1CCOCC1]

In some embodiments, $R^1$ is

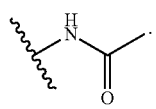 [SMILES: *NC(C)=O]

In some embodiments. $R^1$ is

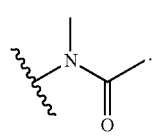 [SMILES: *N(C)C(C)=O]

In some embodiments, $R^1$ is

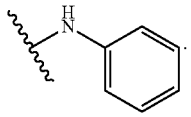

In some embodiments, $R^1$ is

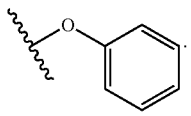

In some embodiments, $R^1$ is

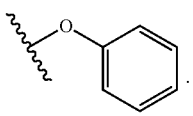

In some embodiments, $R^1$ is

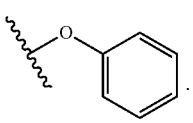

In some embodiments, $R^1$ is

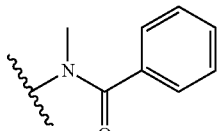

In some embodiments, $R^1$ is

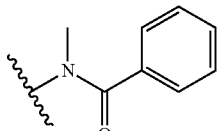

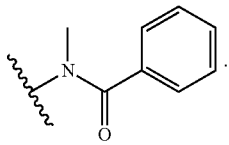 [SMILES: *N(C)C(=O)c1ccccc1]

In certain embodiments, each $R^1$ is independently selected from those shown in the compounds of Table 1.

As defined above and described here, each R is independently selected from hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or two R groups on the same carbon or nitrogen are optionally taken together with their intervening atoms to form an optionally substituted 4-7 membered saturated, partially unsaturated, or heteroaryl ring having 0-3 heteroatoms, in addition to the carbon or nitrogen, independently selected from nitrogen, oxygen, and sulfur.

In some embodiments, R is hydrogen. In some embodiments, R is an optionally substituted (% 6 aliphatic. In some embodiments, R is an optionally substituted phenyl. In some embodiments, R is an optionally substituted 4-7 membered saturated or partially unsaturated heterocyclic having 1-2 heteroatoms independently selected from nitrogen, oxygen, and sulfur. In some embodiments, R is an optionally substituted a 5-6 membered heteroaryl ring having 1-4 heteroatoms independently selected from nitrogen, oxygen, and sulfur. In some embodiments, two R groups on the same carbon or nitrogen are optionally taken together with their intervening atoms to form an optionally substituted 4-7 membered saturated, partially unsaturated, or heteroaryl ring having 0-3 heteroatoms, in addition to the carbon or nitrogen, independently selected from nitrogen, oxygen, and sulfur.

As defined above and described herein, $R^2$ is selected from

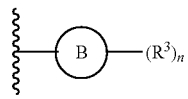

or hydrogen.

In some embodiment $R^2$ is

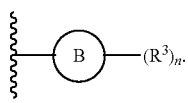

In some embodiments, $R^2$ is hydrogen.

In certain embodiments, $R^2$ is selected from those shown in the compounds of Table 1.

As defined above and described herein, Ring B is phenyl, a 4-10 membered saturated or partially unsaturated mono- or bicyclic carbocyclic or heterocyclic ring having 1-3 heteroatoms independently selected from nitrogen, oxygen, and sulfur, or a 5-6 membered heteroaryl ring having 1-4 heteroatoms independently selected from nitrogen, oxygen, and sulfur, wherein Ring B is further optionally substituted with 1-2 oxo groups.

In some embodiments, Ring B is phenyl. In some embodiments, Ring B is a 4-10 membered saturated or partially unsaturated mono- or bicyclic carbocyclic or heterocyclic ring having 1-3 heteroatoms independently selected from nitrogen, oxygen, and sulfur In some embodiments, Ring B is a 5-6 membered heteroaryl ring having 1-4 heteroatoms independently selected from nitrogen, oxygen, and sulfur. In some embodiments, Ring B is further optionally substituted with 1-2 oxo groups.

In some embodiments, Ring B is

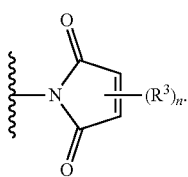

In some embodiments, Ring B is

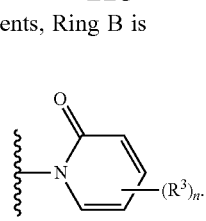

In some embodiments, Ring B is

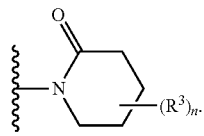

In some embodiments Ring B is

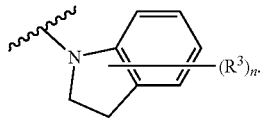

In some embodiments Ring B is

In some embodiments Ring B is

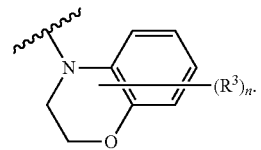

In some embodiments Ring B is

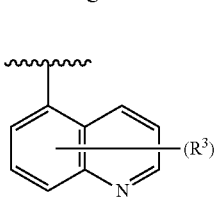

In some embodiments Ring B is

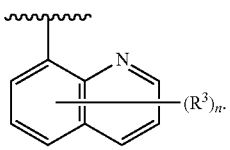

In some embodiments Ring B is

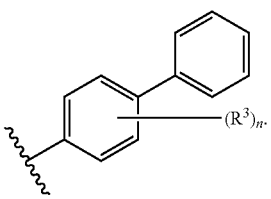

In some embodiments Ring B is

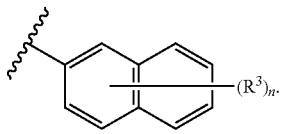

In some embodiments Ring B is

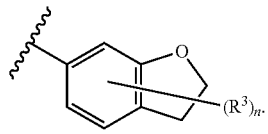

In some embodiments Ring B is

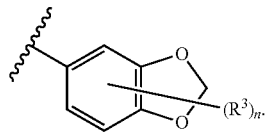

In some embodiments Ring B is

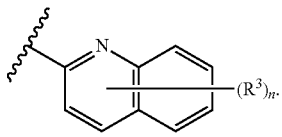

In some embodiments Ring B is

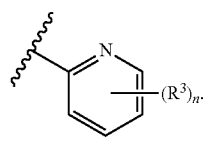

In some embodiments Ring B is

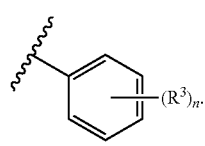

In certain embodiments, Ring B is selected from those shown in the compounds of Table 1.

As defined above and described herein, each $R^3$ is independently selected from hydrogen, deuterium, $R^4$, halogen, —CN, —NO$_2$, —OR, —SR, —NR$_2$, —S(O)$_2$R, —S(O)$_2$NR$_2$—S(O)R. —CF$_2$R, —CF$_3$, —CR$_2$(OR), —CR$_2$(NR$_2$), —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)S(O)$_2$R, —OP(O)R$_2$, —OP(O)(OR)$_2$, —OP(O)(OR)NR$_2$, —OP(O)(NR$_2$)$_2$, and —SiR$_3$ In some embodiments, $R^3$ is hydrogen. In some embodiments, $R^3$ is deuterium. In some embodiments, $R^3$ is $R^4$. In some embodiments, $R^3$ is halogen. In some embodiments, $R^3$ is —CN. In some embodiments, $R^3$ is —NO$_2$. In some embodiments, $R^3$ is —OR. In some embodiments, $R^3$ is —SR. In some embodiments, $R^3$ is —NR$_2$. In some embodiments, $R^3$ is —S(O)$_2$R. In some embodiments, $R^3$ is —S(O)$_2$NR$_2$. In some embodiments, $R^3$ is —S(O)R. In some embodiments, $R^3$ is —CF$_2$R. In some embodiments, $R^3$ is —CF$_3$. In some embodiments, $R^3$ is —CR$_2$(OR). In some embodiments, $R^3$ is —CR$_2$(NR$_2$). In some embodiments, $R^3$ is —C(O)R. In some embodiments, $R^3$ is —C(O)OR. In some embodiments, $R^3$ is —C(O)NR$_2$. In some embodiments, $R^3$ is —C(O)N(R)OR. In some embodiments, $R^3$ is —OC(O)R. In some embodiments, $R^3$ is —OC(O)NR$_2$. In some embodiments, $R^3$ is —N(R)C(O)OR. In some embodiments, $R^3$ is —N(R)C(O)R. In some embodiments, $R^3$ is —N(R)C(O)NR$_2$. In some embodiments, $R^3$ is —N(R)S(O)$_2$R. In some embodiments, $R^3$ is —OP(O)R$_2$. In some embodiments, $R^3$ is —OP(O)(OR)$_2$. In some embodiments, $R^3$ is —OP(O)(OR)NR$_2$. In some embodiments, $R^3$ is —OP(O)(NR$_2$)$_2$. In some embodiments, $R^3$ is —SiR$_3$.

In certain embodiments, $R^3$ is selected from those shown in the compounds of Table 1.

As defined above and described herein, each $R^4$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur.

In some embodiments, $R^4$ is an optionally substituted $C_{1-6}$ aliphatic. In some embodiments, $R^4$ is an optionally substituted phenyl. In some embodiments, $R^4$ is an optionally substituted 4-7 membered saturated or partially unsaturated heterocyclic ring having 1-2 heteroatoms independently selected from nitrogen, oxygen, and sulfur. In some embodiments, $R^4$ is an optionally substituted 5-6 membered heteroaryl ring having 1-4 heteroatoms independently selected from nitrogen, oxygen, and sulfur.

In some embodiments, $R^4$ is

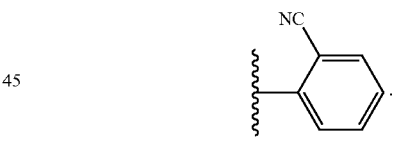

In some embodiments, $R^4$ is

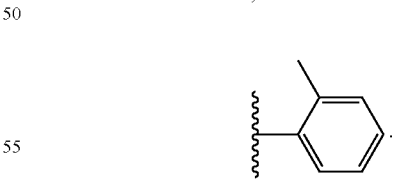

In some embodiments, $R^4$ is

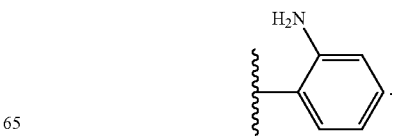

In some embodiments, R⁴ is
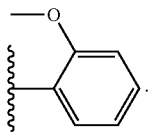
In some embodiments, R⁴ is
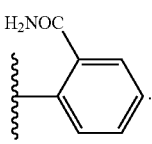
In some embodiments, R⁴ is
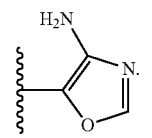
In some embodiments, R⁴ is
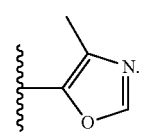
In some embodiments, R⁴ is
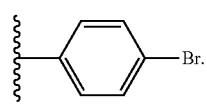 [SMILES: *c1ccc(Br)cc1]
In some embodiments, R⁴ is
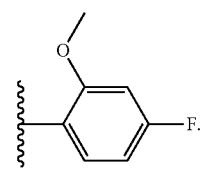 [SMILES: *c1ccc(F)cc1OC]
In some embodiments, R⁴ is
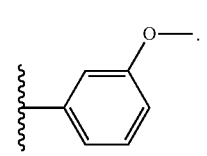 [SMILES: *c1cccc(OC)c1]
In some embodiments, R⁴ is
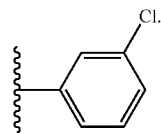 [SMILES: *c1cccc(Cl)c1]
In some embodiments, R⁴ is
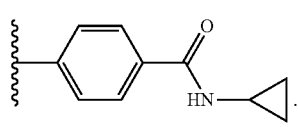
In some embodiments, R⁴ is
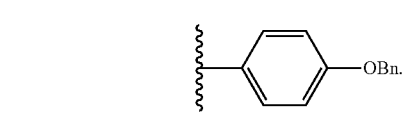
In some embodiments, R⁴ is
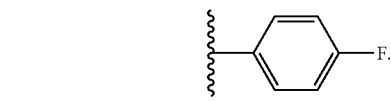 [SMILES: *c1ccc(F)cc1]
In some embodiments, R⁴ is
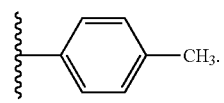
In some embodiments, R⁴ is
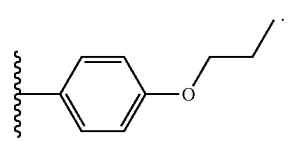 [SMILES: *c1ccc(OCCC)cc1]
In some embodiments, R⁴ is
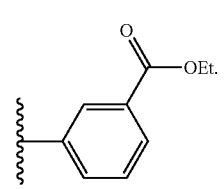 [SMILES: *c1cccc(C(=O)OCC)c1]

In some embodiments. R⁴ is
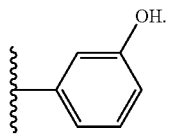 [SMILES: *c1cccc(O)c1]
In some embodiments, R⁴ is
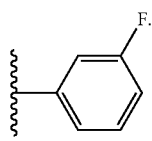
In some embodiments, R⁴ is
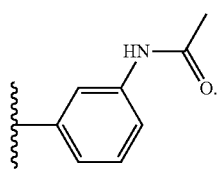 [SMILES: *c1cccc(NC(C)=O)c1]
In some embodiments, R⁴ is
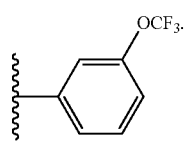 [SMILES: *c1cccc(OC(F)(F)F)c1]
In some embodiments, R⁴ is
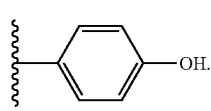
In some embodiments, R⁴ is
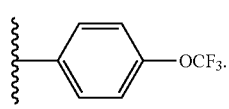
In some embodiments, R⁴ is
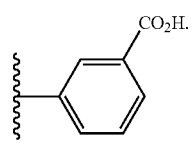 [SMILES: *c1cccc(C(=O)O)c1]
In some embodiments, R⁴ is
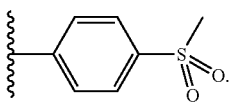
In some embodiments, R⁴ is
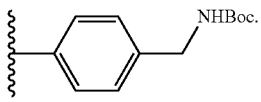 [SMILES: *c1ccc(CNC(=O)OC(C)(C)C)cc1]
In some embodiments, R⁴ is
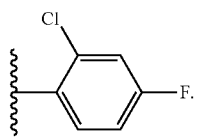 [SMILES: *c1ccc(F)cc1Cl]
In some embodiments, R⁴ is
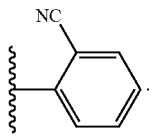
In some embodiments, R⁴ is
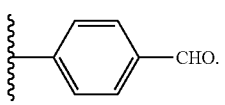
In some embodiments, R⁴ is
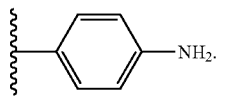
In some embodiments, R⁴ is
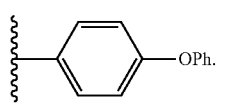 [SMILES: *c1ccc(Oc2ccccc2)cc1]

In some embodiments, R⁴ is

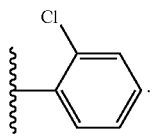 [SMILES: *c1ccccc1Cl]

In some embodiments, R⁴ is

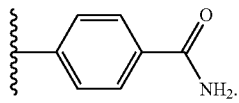

In some embodiments, R⁴ is

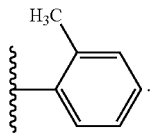

In some embodiments, R⁴ is

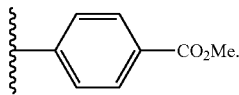

In some embodiments, R⁴ is

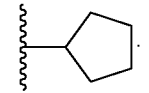

In some embodiments, R⁴ is

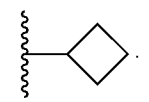

In some embodiments, R⁴ is

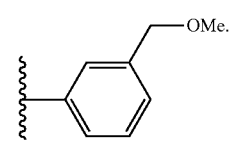 [SMILES: *c1cccc(COC)c1]

In some embodiments, R⁴ is

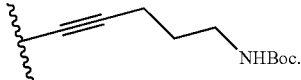 [SMILES: *C#CCCCNC(=O)OC(C)(C)C]

In certain embodiments, R⁴ is selected from those shown in the compounds of Table 1.

As defined above and described herein, ==== is a single or double bond.

In some embodiments, ==== is a single bond. In some embodiments, ==== is a double bond.

In certain embodiments, ==== is selected from those shown in the compounds of Table 1.

As defined above and described herein, m is 0, 1, 2, 3 or 4.

In some embodiments, m is 0. In some embodiments, m is 1. In some embodiments, m is 2. In some embodiments, m is 3. In some embodiments, m is 4.

In certain embodiments, m is selected from those shown in the compounds of Table 1.

As defined above and described herein, n is 0, 1, 2, 3 or 4.

In some embodiments, n is 0. In some embodiments, n is 1. In some embodiments, n is 2. In some embodiments, n is 3. In some embodiments, n is 4.

In certain embodiments, n is selected from those shown in the compounds of Table 1.

As defined above and described herein, o is 0, 1, or 2.

In some embodiments, o is 0. In some embodiments, o is 1. In some embodiments, o is 2.

In certain embodiments, o is selected from those shown in the compounds of Table 1.

In some embodiments, the present invention provides a compound of formula I-qqq, wherein Ring A is benzo, o is 1, $X^1$ is —CH$_2$—, $X^2$ and $X^3$ are —C(O)—, and $Z^1$ and $Z^2$ are carbon atoms as shown, to provide a compound of formula I-qqq-1:

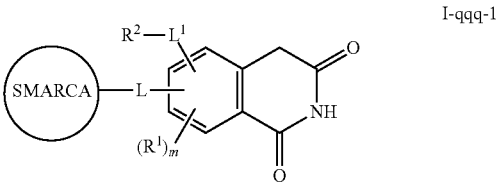

I-qqq-1 or a pharmaceutically acceptable salt thereof, wherein each of SMARCA, L, $L^1$, $R^1$, $R^2$, and m is as defined above and described in embodiments herein, both singly and in combination.

In some embodiments, the present invention provides a compound of formula I-qqq, wherein Ring A is imidazolyl, o is 1, $X^1$ is —CH$_2$—, $X^2$ and $X^3$ are —C(O)—, and $Z^1$ and $Z^2$ are carbon atoms as shown, to provide a compound of formula I-qqq-2:

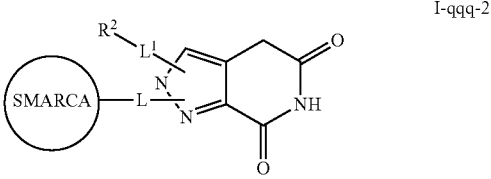

I-qqq-2 or a pharmaceutically acceptable salt thereof, wherein each of SMARCA, L, L¹, and R² is as defined above and described in embodiments herein, both singly and in combination.

In some embodiments, the present invention provides a compound of formula I-qqq, wherein Ring A is imidazolyl, o is 1, X¹ is —CH₂—, X² and X³ are —C(O)—, and Z¹ and Z² are carbon atoms as shown, to provide a compound of formula I-qqq-3:

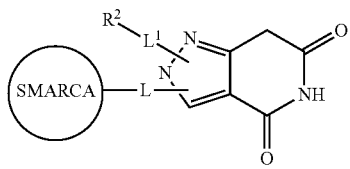

I-qqq-3 or a pharmaceutically acceptable salt thereof, wherein each of SMARCA, L, L¹, and R² is as defined above and described in embodiments herein, both singly and in combination.

In some embodiments, the present invention provides a compound of formula I-qqq, wherein Ring A is oxazolyl, o is 1, X¹ is —CH₂—, X² and X³ are —C(O)—, and Z¹ and Z² are carbon atoms as shown, to provide a compound of formula I-qqq-4:

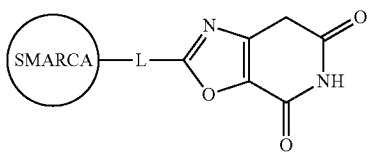

I-qqq-4 or a pharmaceutically acceptable salt thereof, wherein each of SMARCA and L is as defined above and described in embodiments herein, both singly and in combination.

In some embodiments, the present invention provides a compound of formula I-qqq, wherein Ring A is benzo, o is 0, X¹ is a covalent bond, X² and X³ are —C(O)—, and Z¹ and Z² are carbon atoms as shown, to provide a compound of formula I-qqq-5:

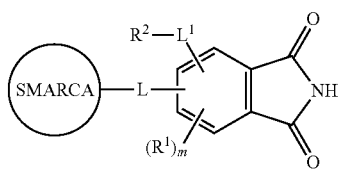

I-qqq-5 or a pharmaceutically acceptable salt thereof, wherein each of SMARCA, L, L¹, R¹, R², and m is as defined above and described in embodiments herein, both singly and in combination.

In some embodiments, the present invention provides a compound of formula I-qqq, wherein Ring A is benzo, o is 1, X¹ is —O—, X² and X³ are —C(O)—, and Z¹ and Z² are carbon atoms as shown, to provide a compound of formula I-qqq-6:

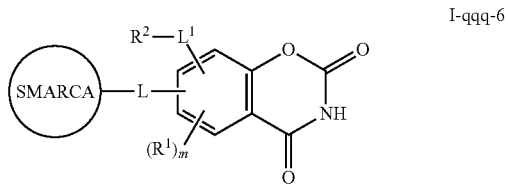

I-qqq-6 or a pharmaceutically acceptable salt thereof, wherein each of SMARCA, L, L¹, R¹, R², and m is as defined above and described in embodiments herein, both singly and in combination.

In some embodiments, the present invention provides a compound of formula I-qqq, wherein Ring A is benzo, o is 1, X¹ is —NR—, X² and X³ are —C(O)—, and Z¹ and Z² are carbon atoms as shown, to provide a compound of formula I-qqq-7:

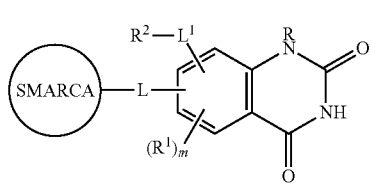

I-qqq-7 or a pharmaceutically acceptable salt thereof, wherein each of SMARCA, L, L¹, R, R¹, R², and m is as defined above and described in embodiments herein, both singly and in combination.

In some embodiments, the present invention provides a compound of formula I-qqq, wherein Ring A is benzo, o is 1, X¹ is —CF₂—, X² and X³ are —C(O)—, and Z¹ and Z² are carbon atoms as shown, to provide a compound of formula I-qqq-8:

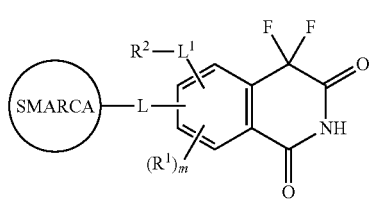

I-qqq-8 or a pharmaceutically acceptable salt thereof, wherein each of SMARCA, L, L¹, R¹, R², and m is as defined above and described in embodiments herein, both singly and in combination.

In some embodiments, the present invention provides a compound of formula I-qqq, wherein Ring A is benzo, o is 1, X¹ is

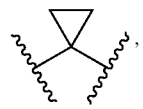 [SMILES: *C1(*)CC1]

X² and X³ are —C(O)—, and Z¹ and Z² are carbon atoms as shown, to provide a compound of formula I-qqq-9:

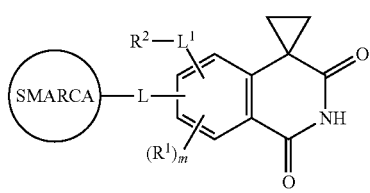

I-qqq-9 or a pharmaceutically acceptable salt thereof, wherein each of SMARCA, L, $L^1$, $R^1$, $R^2$, and m is as defined above and described in embodiments herein, both singly and in combination.

In some embodiments, the present invention provides a compound of formula I-qqq, wherein Ring A is pyridyl, o is 1, $X^1$ is —$CH_2$—, $X^2$ and $X^3$ are —C(O)—, and $Z^1$ and $Z^2$ are carbon atoms as shown, to provide a compound of formula I-qqq-10:

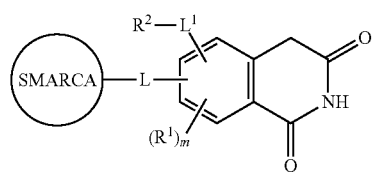

I-qqq-10 or a pharmaceutically acceptable salt thereof, wherein each of SMARCA, L, $L^1$, $R^1$, $R^2$, and m is as defined above and described in embodiments herein, both singly and in combination.

In some embodiments, the present invention provides a compound of formula I-qqq, wherein Ring A is pyridyl, o is 1, $X^1$ is —$CH_2$—, $X^2$ and $X^3$ are —C(O)—, and $Z^1$ and $Z^2$ are carbon atoms as shown, to provide a compound of formula I-qqq-11:

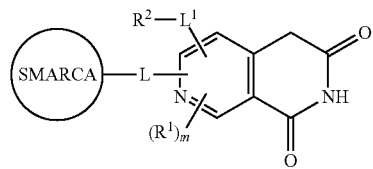

I-qqq-11 or a pharmaceutically acceptable salt thereof, wherein each of SMARCA, L, $L^1$, $R^1$, $R^2$, and m is as defined above and described in embodiments herein, both singly and in combination.

In some embodiments, the present invention provides a compound of formula I-qqq, wherein Ring A is benzo, o is 1, $X^1$, $X^2$ and $X^3$ are —C(O)—, and $Z^1$ and $Z^2$ are carbon atoms as shown, to provide a compound of formula I-qqq-12:

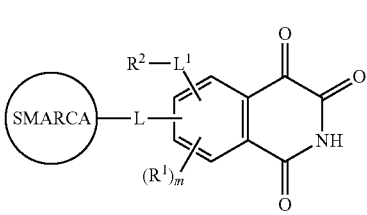

I-qqq-12 or a pharmaceutically acceptable salt thereof, wherein each of SMARCA, L, $L^1$, $R^1$, $R^2$, and m is as defined above and described in embodiments herein, both singly and in combination.

In some embodiments, LBM is

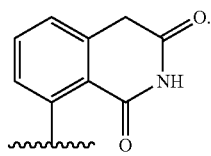

In some embodiments, LBM is

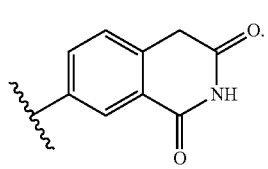 [SMILES: *c1ccc2c(c1)C(=O)NC(=O)C2]

In some embodiments, LBM is

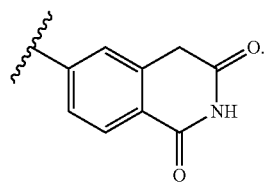 [SMILES: *c1ccc2c(c1)CC(=O)NC2=O]

In some embodiments, LBM is

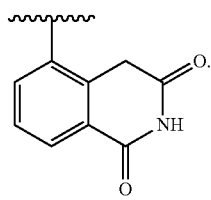 [SMILES: *c1cccc2c1CC(=O)NC2=O]

In some embodiments, LBM is

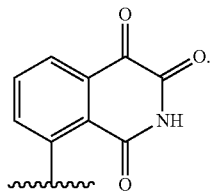 [SMILES: *c1cccc2c1C(=O)NC(=O)C2=O]

In some embodiments, LBM is

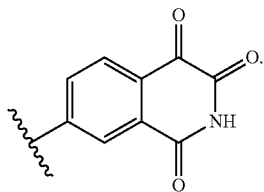 [SMILES: *c1ccc2c(c1)C(=O)NC(=O)C2=O]

In some embodiments, LBM is

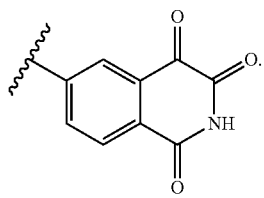 [SMILES: *c1ccc2c(c1)C(=O)C(=O)NC2=O]

In some embodiments, LBM is

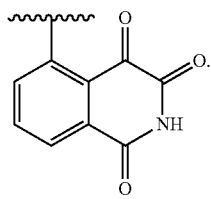 [SMILES: *c1cccc2c1C(=O)C(=O)NC2=O]

In some embodiments, LBM is selected from those in Table 1, below.

In certain embodiments, the present invention provides a compound of formula I, wherein LBM is a RPN13 binding moiety thereby forming a compound of formula I-rrr:

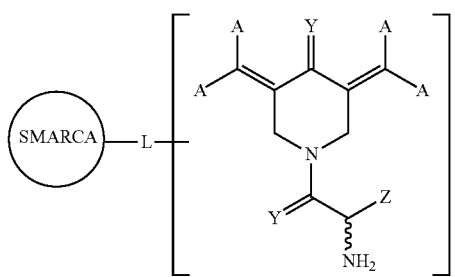

I-rrr or a pharmaceutically acceptable salt thereof, wherein L and SMARCA are as defined above and described in embodiments herein, and wherein each of the variables A, Y, and Z is as described and defined in WO 2019/165229, the entirety of each of which is herein incorporated by reference.

In certain embodiments, the present invention provides a compound of formula I, wherein LBM is a Ubr1 binding moiety as described in Shanmugasundaram, K. et al, J. Bio. Chem. 2019, doi: 10.1074/jbc.AC119.010790, the entirety of each of which is herein incorporated by reference, thereby forming a compound of formula I-sss-1 or I-sss-2:

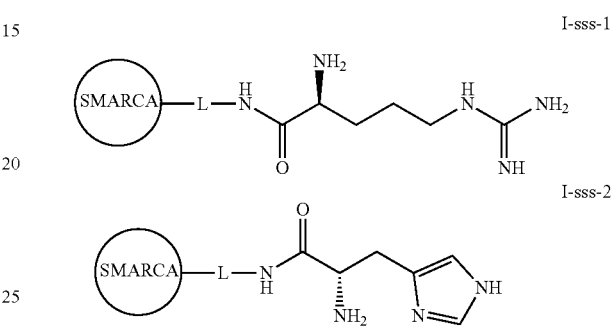

or a pharmaceutically acceptable salt thereof, wherein L and SMARCA are as defined above and described in embodiments herein.

In certain embodiments, the present invention provides a compound of formula I, wherein LBM is a CRBN binding moiety thereby forming a compound of formula I-ttt:

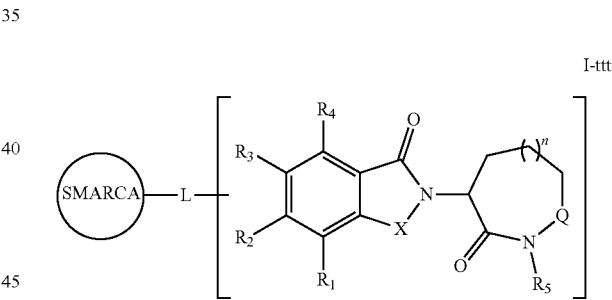

or a pharmaceutically acceptable salt thereof, wherein L and SMARCA are as defined above and described in embodiments herein, and wherein each of the variables $R_1$, $R_2$, $R_3$, $R_4$, $R_5$, Q, X, and n is as described and defined in US 2019/276474, the entirety of each of which is herein incorporated by reference.

In certain embodiments, the present invention provides a compound of formula I, wherein LBM is a CRBN E3 ubiquitin ligase binding moiety thereby forming a compound of formula I-uuu-1, I-uuu-2, I-uuu-3 or I-uuu-4:

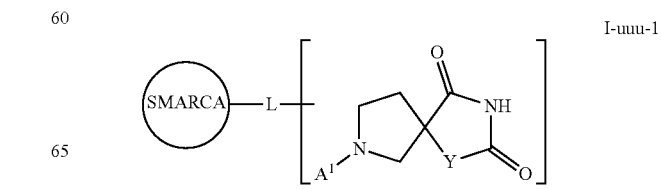

I-uuu-1

-continued

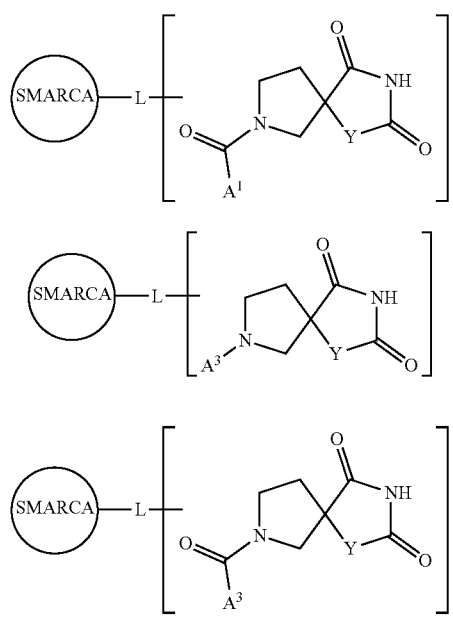

I-uuu-2

I-uuu-3

I-uuu-4 or a pharmaceutically acceptable salt thereof, wherein L and SMARCA are as defined above and described in embodiments herein, and wherein each of the variables Y, $A^1$, and $A^3$ is as described and defined in WO 2019/236483, the entirety of each of which is herein incorporated by reference.

In certain embodiments, the present invention provides a compound of formula I, wherein LBM is a KLHDC2 E3 ubiquitin ligase binding moiety thereby forming a compound of formula I-vvv-1, I-vvv-2, I-vvv-3, or I-vvv-4:

or a pharmaceutically acceptable salt thereof, wherein L and SMARCA are as defined above and described in embodiments herein, both singly and in combination.

In certain embodiments, the present invention provides a compound of formula I, wherein LBM is an AHR E3 ubiquitin ligase binding moiety thereby forming a compound of formula I-www:

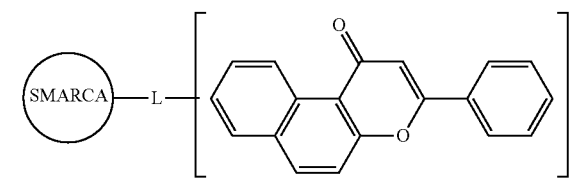

I-www or a pharmaceutically acceptable salt thereof, wherein L and SMARCA are as defined above and described in embodiments herein, both singly and in combination.

In certain embodiments, the present invention provides a compound of formula I, wherein LBM is a DCAF16 E3 ubiquitin ligase binding moiety thereby forming a compound of formula I-www-1:

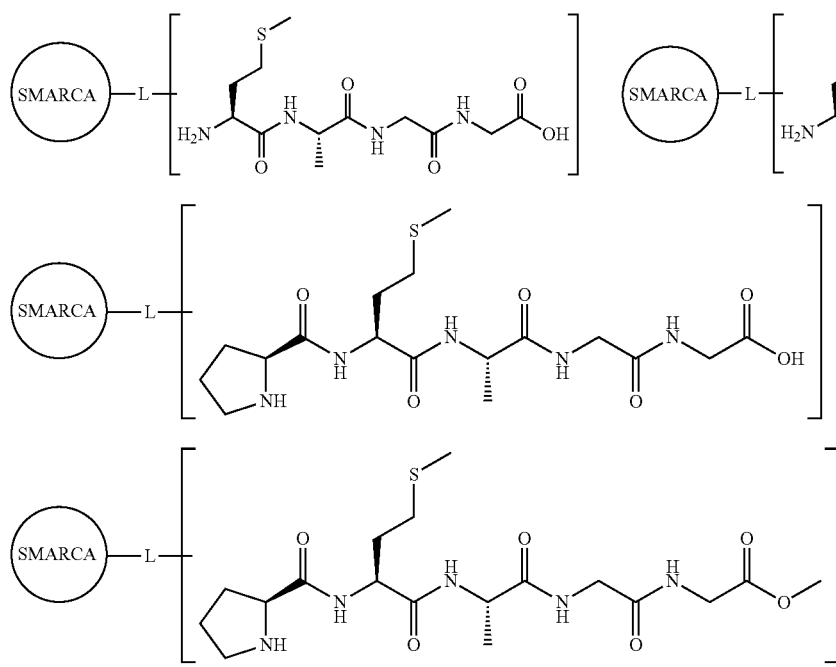

I-www-1

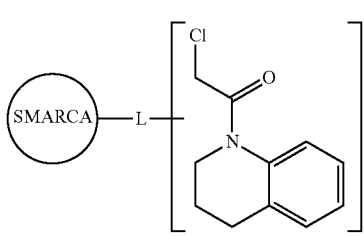

or a pharmaceutically acceptable salt thereof, wherein L and SMARCA are as defined above and described in embodiments herein, both singly and in combination.

In certain embodiments, the present invention provides a compound of formula I, wherein LBM is an RNF4 E3 ubiquitin ligase binding moiety thereby forming a compound of formula I-www-2:

I-www-2

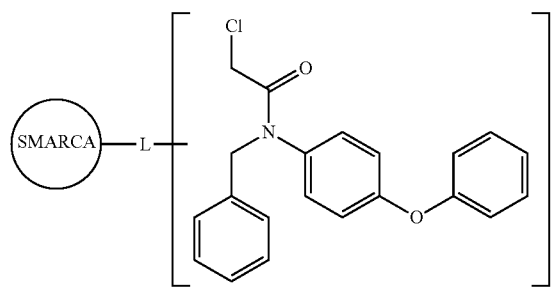

or a pharmaceutically acceptable salt thereof, wherein L and SMARCA are as defined above and described in embodiments herein, both singly and in combination.

In certain embodiments, the present invention provides a compound of formula I, wherein LBM is an RNF114 E3 ubiquitin ligase binding moiety thereby forming a compound of formula I-www-3:

I-www-3

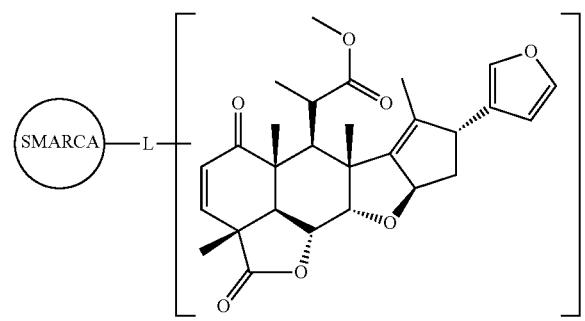

or a pharmaceutically acceptable salt thereof, wherein L and SMARCA are as defined above and described in embodiments herein, both singly and in combination.

In certain embodiments, the present invention provides a compound of formula I, wherein LBM is an RNF114 E3 ubiquitin ligase binding moiety thereby forming a compound of formula I-www-4:

I-www-4

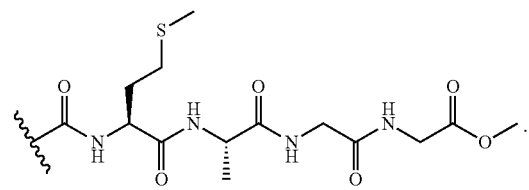 [SMILES: *C(=O)N[C@@H](CCSC)C(=O)N[C@@H](C)C(=O)NCC(=O)NCC(=O)OC] (top right area — note: this placement corresponds to I-www-4 structure)

or a pharmaceutically acceptable salt thereof, wherein L and SMARCA are as defined above and described in embodiments herein, both singly and in combination.

In certain embodiments, the present invention provides a compound of formula I, wherein LBM is a DCAF15 E3 ubiquitin ligase binding moiety thereby forming a compound of formula I-www-5:

I-www-5 or a pharmaceutically acceptable salt thereof, wherein L and SMARCA are as defined above and described in embodiments herein, both singly and in combination.

In some embodiments, LBM is

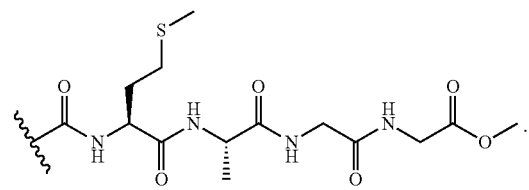 [SMILES: *C(=O)N[C@@H](CCSC)C(=O)N[C@@H](C)C(=O)NCC(=O)NCC(=O)OC]

In some embodiments, LBM is

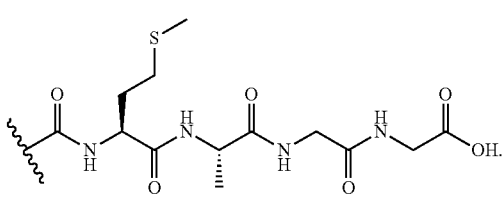 [SMILES: *C(=O)N[C@@H](CCSC)C(=O)N[C@@H](C)C(=O)NCC(=O)NCC(=O)O]

In some embodiments, LBM is

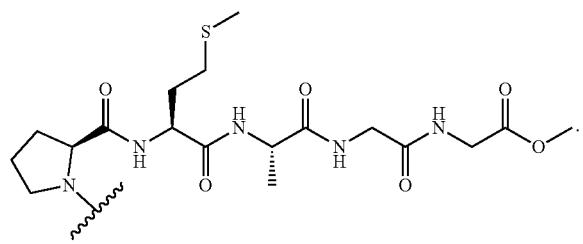 [SMILES: *N1CCC[C@H]1C(=O)N[C@@H](CCSC)C(=O)N[C@@H](C)C(=O)NCC(=O)NCC(=O)OC]

In some embodiments, LBM is

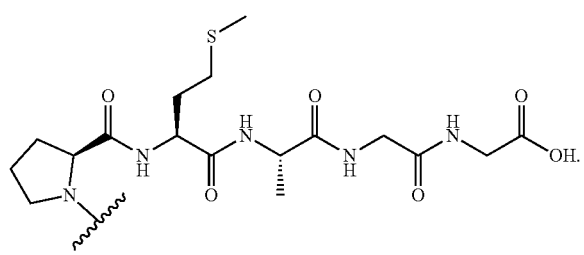 [SMILES: *N1CCC[C@H]1C(=O)N[C@@H](CCSC)C(=O)N[C@@H](C)C(=O)NCC(=O)NCC(=O)O]

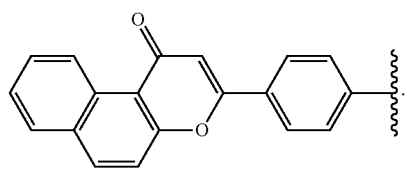 [SMILES: *c1ccc(-c2cc(=O)c3c(ccc4ccccc43)o2)cc1]

In some embodiments, LBM is

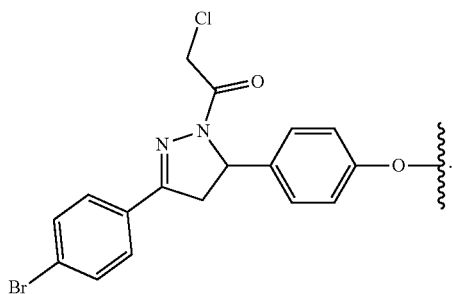 [SMILES: *Oc1ccc(C2CC(c3ccc(Br)cc3)=NN2C(=O)CCl)cc1]

In some embodiments, LBM is

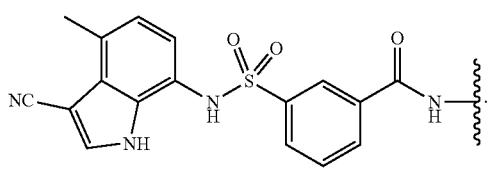 [SMILES: *NC(=O)c1cccc(S(=O)(=O)Nc2ccc(C)c3c(C#N)c[nH]c23)c1]

In some embodiments, LBM is selected from those in Table 1, below.

In certain embodiments, the present invention provides a compound of formula I, wherein LBM is a VHL E3 ubiquitin ligase binding moiety thereby forming a compound of formula I-xxx:

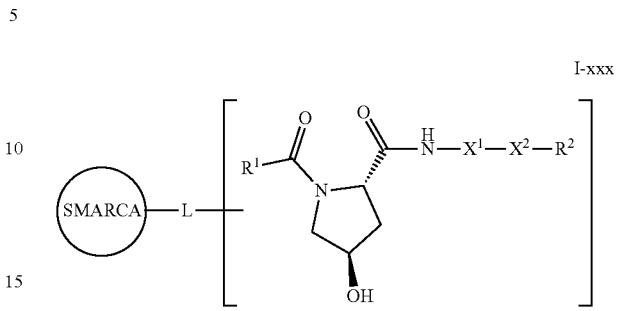

I-xxx or a pharmaceutically acceptable salt thereof, wherein L and SMARCA are as defined above and described herein, and wherein:

$X^1$ is a bivalent group selected from —O—, —C(O)—, —C(S)—, —CR$_2$—, —NR—, —S(O)—, or —SO$_2$—;

$X^2$ is an optionally substituted bivalent group selected from C$_{1-6}$ saturated or unsaturated alkylene, phenylenyl, a 5-6 membered heteroarylenyl containing 1-4 heteroatoms independently selected from nitrogen, oxygen, or sulfur, or a 4-11 membered saturated or partially unsaturated monocyclic, bicyclic, bridged bicyclic, or spirocyclic carbocyclylenyl or heterocyclylenyl with 1-3 heteroatoms independently selected from nitrogen, oxygen, or sulfur;

$R^1$ is $R^4$, —CR$_2$R$^4$, —OR, —SR, —NR$_2$, —CR$_2$, —CR$_2$OR, —CR$_2$NR$_2$, —CR$_2$N(R)C(O)R, —CR$_2$N(R)C(O)NR$_2$, —OCR$_2$, —NRC(O)OR, —NRC(O)R, —NRC(O)NR$_2$, or —NRSO$_2$R;

each R is independently hydrogen, or an optionally substituted group selected from C$_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same atom are taken together with their intervening atoms to form a 4-7 membered saturated, partially unsaturated, or heteroaryl ring having 0-3 heteroatoms, in addition to the atom to which they are attached, independently selected from nitrogen, oxygen, and sulfur;

$R^2$ is hydrogen or

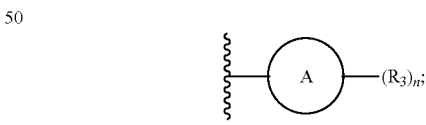

Ring A is a ring selected from phenyl, a 5-6 membered heteroaryl containing 1-4 heteroatoms independently selected from nitrogen, oxygen, or sulfur, or a 4 to 9-membered saturated or partially unsaturated monocyclic, bicyclic, bridged bicyclic, or spirocyclic carbocyclyl or heterocyclyl with 1-3 heteroatoms independently selected from nitrogen, oxygen, or sulfur, wherein Ring A is optionally further substituted with 1-2 oxo groups;

each of $R^3$ is independently hydrogen, deuterium, $R^4$, halogen, —CN, —NO$_2$, —OR, —SR, —NR$_2$, —SiR$_3$, —SO$_2$R, —SO$_2$NR$_2$, —S(O)R, —C(O)R, —C(O)OR, —C(O)NR$_2$, —C(O)N(R)OR, —CR$_2$N(R)C(O)R, —$CR_2N(R)C(O)NR_2$, —$OC(O)R$, —$OC(O)NR_2$, —$OP(O)R_2$, —$OP(O)(OR)_2$, —$OP(O)(OR)NR_2$, —$OP(O)(NR_2)_2$—, —$N(R)C(O)OR$, —$N(R)C(O)R$, —$N(R)C(O)NR_2$, —$N(R)SO_2R$, —$NP(O)R_2$, —$N(R)P(O)(OR)_2$, —$N(R)P(O)(OR)NR_2$, —$N(R)P(O)(NR_2)_2$, or —$N(R)SO_2R$; or two $R^3$ groups are optionally taken together to form an optionally substituted 5-7 membered partially unsaturated or aryl fused ring having 0-2 heteroatoms independently selected from nitrogen, oxygen, or sulfur;

each $R^4$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur; and n is 0, 1, 2, 4, or 5.

In certain embodiments, the present invention provides a compound of formula I-xxx, wherein $X^2$ is cyclohexyl as shown, to provide a compound of formula I-xxx-1:

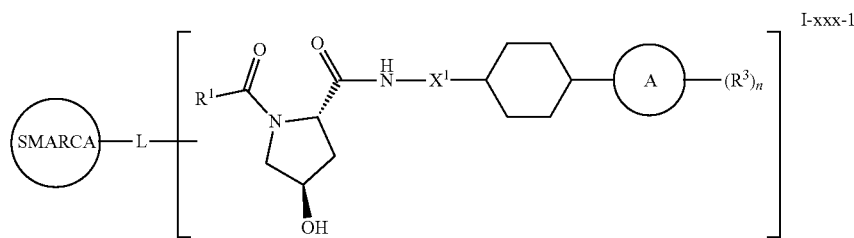

or a pharmaceutically acceptable salt thereof, wherein each of Ring A, $X^1$, $R^1$, $R^3$, and n is as defined above and described in embodiments herein, both singly and in combination.

In certain embodiments, the present invention provides a compound of formula I-xxx, wherein $X^2$ is bicyclo[1.1.1] pentane as shown, to provide a compound of formula I-xxx-2:

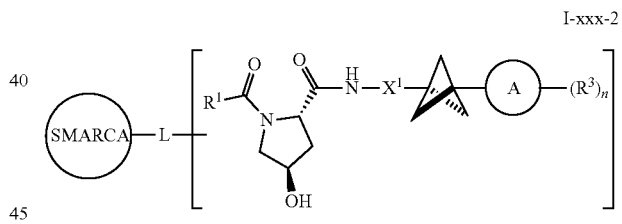

or a pharmaceutically acceptable salt thereof, wherein each of Ring A, $X^2$, $R^1$, $R^3$, and n is as defined above and described in embodiments herein, both singly and in combination.

In certain embodiments, the present invention provides a compound of formula I-xxx, wherein LBM is VHL E3 ubiquitin ligase binding moiety, thereby providing a compound of one of the following formulae:

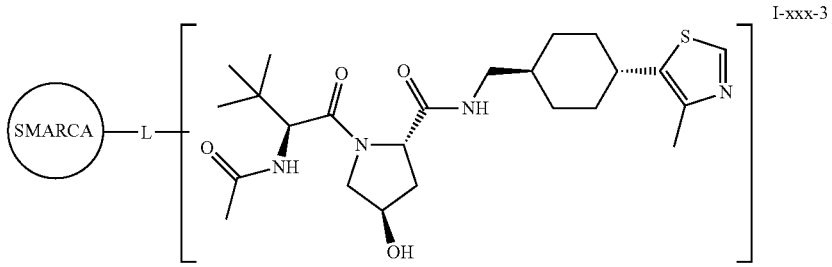

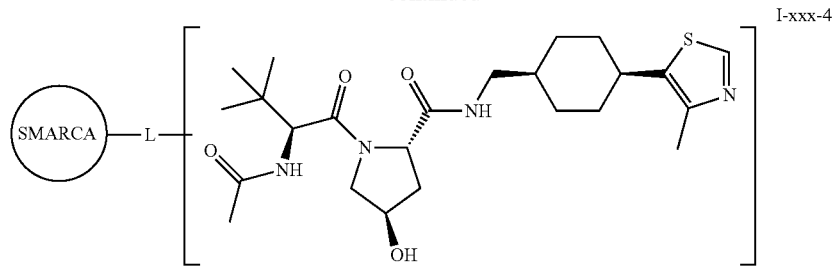
I-xxx-4
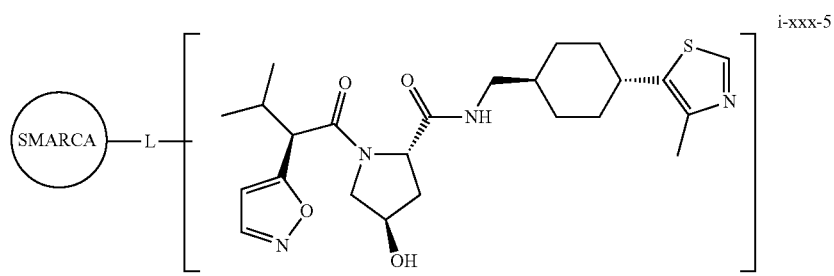
i-xxx-5
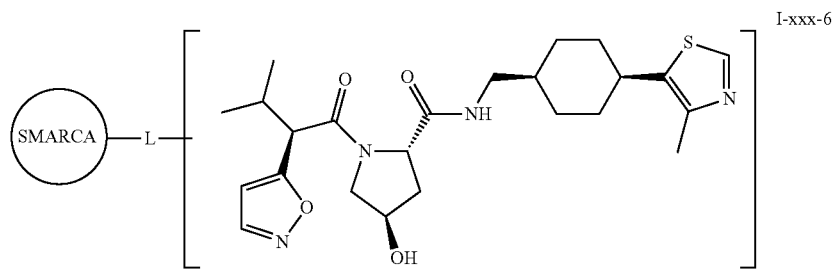
I-xxx-6
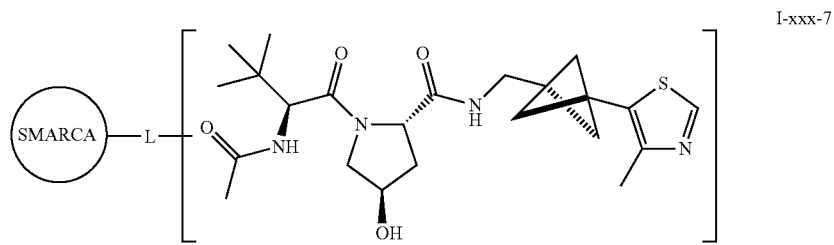
I-xxx-7
or a pharmaceutically acceptable salt thereof, wherein L and SMARCA is as defined above and described in embodiments herein, both singly and in combination.
In certain embodiments, the present invention provides a compound of formula I-xxx, wherein $R^1$ is
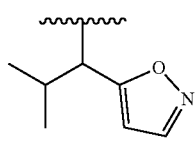 [SMILES: *C(c1ccno1)C(C)C]

as shown, to provide a compound of formula I-xxx-8:

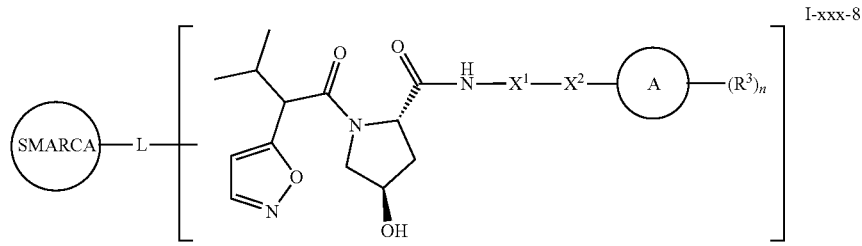

or a pharmaceutically acceptable salt thereof, wherein each of Ring A, $X^1$, $X^2$, $R^3$, and n is as defined above and described in embodiments herein, both singly and in combination.

In certain embodiments, the present invention provides a compound of formula I, wherein LBM is human kelch-like ECH-associated protein 1 (KEAP1) thereby forming a compound of formula I-yyy-1:

SMARCA—L—[KEAP1]    I-yyy-1 or a pharmaceutically acceptable salt thereof, wherein L and SMARCA are as defined above and described in embodiments herein, both singly and in combination.

In certain embodiments, the present invention provides a compound of formula I, wherein LBM is KEAP1 binding moiety as recited in Lu et al., Euro. J. Med. Chem., 2018, 146:251-9, thereby forming a compound of formula I-yyy-2:

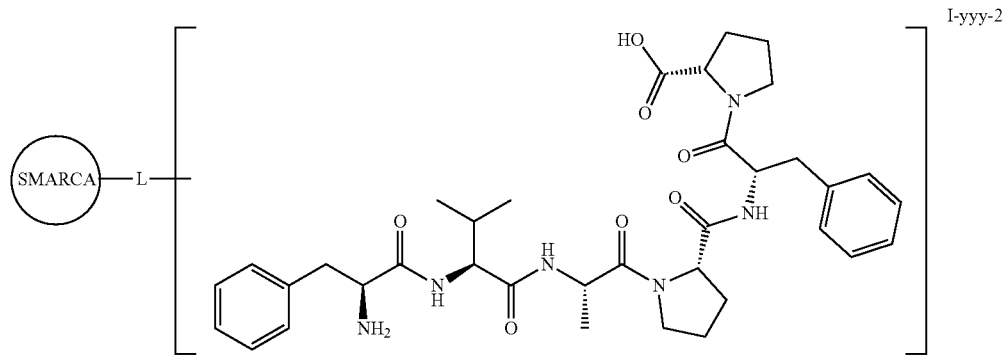

or a pharmaceutically acceptable salt thereof, wherein L and SMARCA are as defined above and described in embodiments herein, both singly and in combination.

In certain embodiments, the present invention provides a compound of formula I, wherein LBM is KEAP1-NRF2 binding moiety thereby forming a compound of formula I-yyy-3 or I-yyy-4:

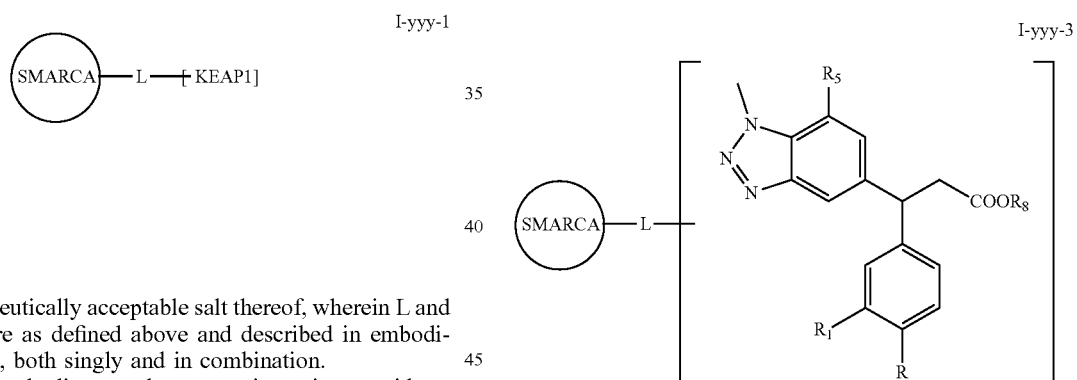

-continued

I-yyy-4

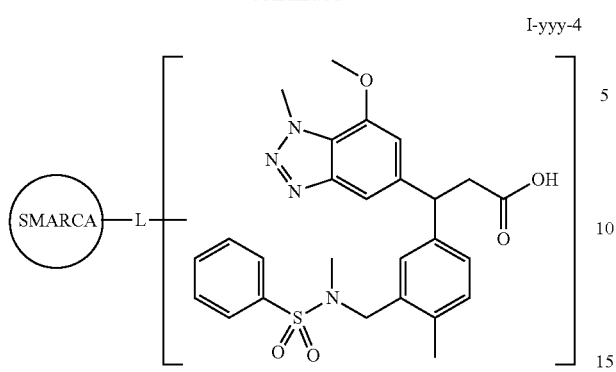

or a pharmaceutically acceptable salt thereof, wherein L and SMARCA are as defined above and described in embodiments herein, and wherein each of the variables R, $R_1$, $R_5$, and $R_8$ is as described and defined in WO 2020/018788, the entirety of each of which is herein incorporated by reference.

In certain embodiments, the present invention provides a compound of formula I, wherein LBM is KEAP1-NRF2 binding moiety as recited in Tong et al., "Targeted Protein Degradation via a Covalent Reversible Degrader Based on Bardoxolone", ChemRxiv 2020, thereby forming a compound of formula I-yyy-5 or I-yyy-6:

I-yyy-5

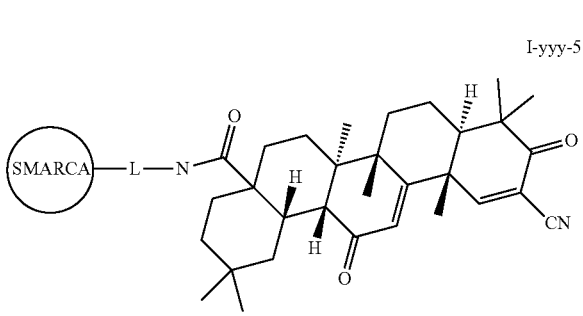

I-yyy-6

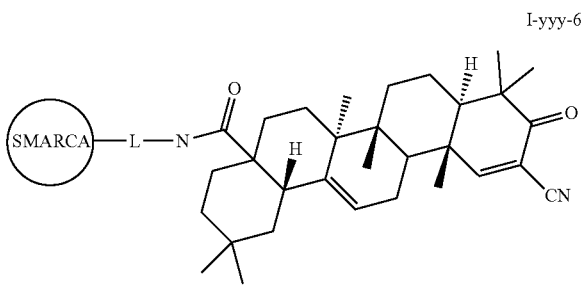

or a pharmaceutically acceptable salt thereof, wherein L and SMARCA are as defined above and described in embodiments herein, both singly and in combination.

In certain embodiments, the present invention provides a compound of formula I, wherein LBM is a cereblon E3 ubiquitin ligase binding moiety thereby forming a compound of formula I-zzz:

I-zzz

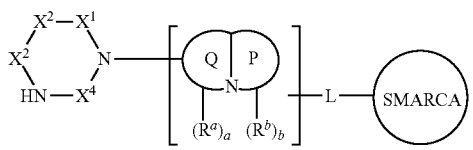

or a pharmaceutically acceptable salt thereof, wherein L and SMARCA are as defined above and described in embodiments herein, wherein:

$X^1$ and $X^2$ are independently a covalent bond, —$CR_2$—, —O—, —$CF_2$—,

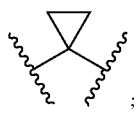

or $X^1$ and $X^2$ are —CR═CR—;

$X^3$ and $X^4$ are independently —$CH_2$—, —C(O)—, —C(S)—, or

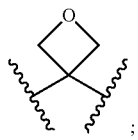 [SMILES: *C1(*)COC1]

Ring P and Ring Q are independently fused rings selected from a 5-6 membered saturated, partially unsaturated, or heteroaryl ring having 0-4 heteroatoms, in addition to the nitrogen already depicted in Ring X and Ring Y, independently selected from nitrogen, oxygen, and sulfur;

each $R^a$ and $R^b$ are independently selected from hydrogen, deuterium, $R^c$, halogen, —CN, —$NO_2$, —OR, —SR, —$NR_2$, —$S(O)_2R$, —$S(O)_2NR_2$, —S(O)R, —$CF_2R$, —$CF_3$, —$CR_2(OR)$, —$CR_2(NR_2)$, —C(O)R, —C(O)OR, —C(O)$NR_2$, —C(O)N(R)OR, —OC(O)R, —OC(O)$NR_2$, —C(S)$NR_2$, —N(R)C(O)OR, —N(R)C(O)R, —N(R)C(O)$NR_2$, —N(R)S(O)$_2$R, —OP(O)$R_2$, —OP(O)(OR)$_2$, —OP(O)(OR)$NR_2$, —OP(O)($NR_2$)$_2$, —Si(OR)$R_2$, and —$SiR_3$;

each R is independently selected from hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same carbon or nitrogen are optionally taken together with their intervening atoms to form an optionally substituted 4-7 membered saturated, partially unsaturated, or heteroaryl ring having 0-3 heteroatoms, in addition to the carbon or nitrogen, independently selected from nitrogen, oxygen, and sulfur;

each $R^c$ is independently selected from an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;
a is 0, 1, 2, 3 or 4; and
b is 0, 1, 2, 3 or 4.

As defined above and described herein, $X^1$ and $X^2$ are independently a covalent bond, —CR$_2$—, —O—, —CF$_2$—,

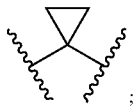

or $X^1$ and $X^2$ are —CR=CR—.

In some embodiments, $X^1$ is a covalent bond. In some embodiments, $X^1$ is —CR$_2$—. In some embodiments, $X^1$ is —CH$_2$—. In some embodiments, $X^1$ is —O—. In some embodiments, $X^1$ is —CF$_2$—. In some embodiments, $X^1$ is

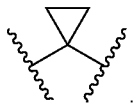

In some embodiments, $X^2$ is a covalent bond. In some embodiments, $X^2$ is —CR$_2$—. In some embodiments, $X^2$ is —CH$_2$—. In some embodiments, $X^2$ is —O—. In some embodiments, $X^2$ is —CF$_2$—. In some embodiments, $X^2$ is

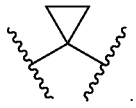

In some embodiments, $X^1$ and $X^2$ are —CR=CR—. In some embodiments, $X^1$ and $X^2$ are —CH=CH—.

In some embodiments, $X^1$ and $X^2$ are independently selected from those shown in the compounds of Table 1.

As defined above and described herein, $X^3$ and $X^4$ are independently —CH$_2$—, —C(O)—, —C(S)—, or

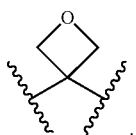 [SMILES: *C1(*)COC1]

In some embodiments, $X^3$ is —CH$_2$—. In some embodiments, $X^3$ is —C(O)—. In some embodiments, $X^3$ is —C(S)—. In some embodiments, $X^3$ is

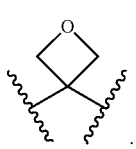

In some embodiments, $X^4$ is —CH$_2$—. In some embodiments, $X^4$ is —C(O)—. In some embodiments, $X^4$ is —C(S)—. In some embodiments, $X^4$ is

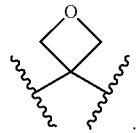 [SMILES: *C1(*)COC1]

In some embodiments, $X^3$ and $X^4$ are selected from those shown in the compounds of Table 1.

As defined above and described herein, Ring X and Ring Y are independently fused rings selected from a 5-6 membered saturated, partially unsaturated, or heteroaryl ring having 0-4 heteroatoms, in addition to the nitrogen already depicted in Ring X and Ring Y, independently selected from nitrogen, oxygen, and sulfur.

In some embodiments, Ring P and Ring Q are independently fused rings selected from a 5-6 membered saturated, partially unsaturated, or heteroaryl ring having 0-4 heteroatoms, in addition to the nitrogen already depicted in Ring P and Ring Q, independently selected from nitrogen, oxygen, and sulfur.

In some embodiments, Ring P is

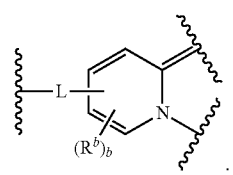

In some embodiments, Ring P is

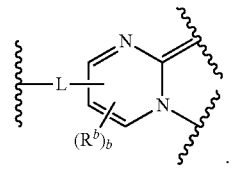

In some embodiments, Ring P is

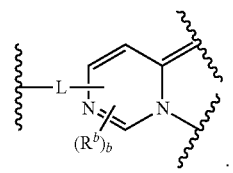

In some embodiments, Ring P is

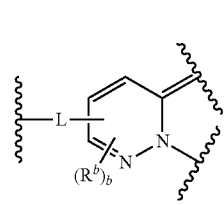

In some embodiments, Ring P is

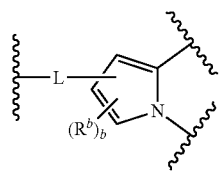

In some embodiments, Ring P is

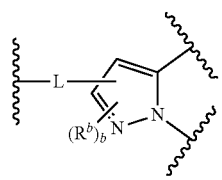

In some embodiments, Ring P is

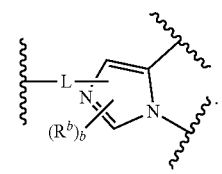

In some embodiments, Ring P is

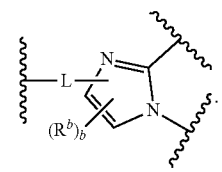

In some embodiments, Ring Q is

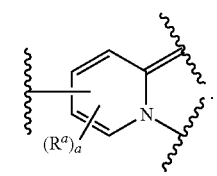

In some embodiments, Ring Q is

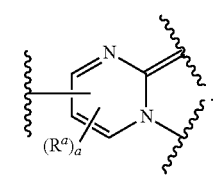

In some embodiments, Ring Q is

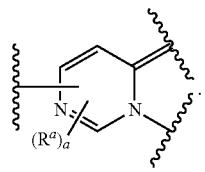

In some embodiments, Ring Q is

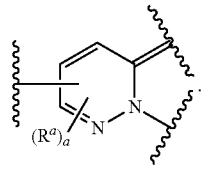

In some embodiments, Ring Q is

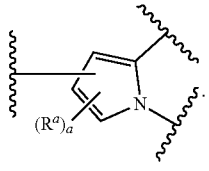

In some embodiments, Ring Q is

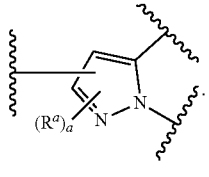

In some embodiments, Ring Q is

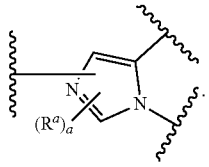

In some embodiments, Ring Q is

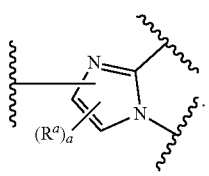

In certain embodiments, Ring P and Ring Q are selected from those shown in the compounds of Table 1.

As defined above and described herein, each $R^a$ and $R^b$ are independently selected from hydrogen, deuterium, $R^c$, halogen, —CN, —NO$_2$, —OR, —SR, —NR$_2$, —S(O)$_2$R, —S(O)$_2$NR$_2$, —S(O)R, —CFR$_2$, —CF$_2$R, —CF$_3$, —CR$_2$(OR), —CR$_2$(NR$_2$), —C(O)R, —C(O)OR, —C(O)NR$_2$, —C(O)N(R)OR, —OC(O)R, —OC(O)NR$_2$, —C(S)NR$_2$, —N(R)C(O)OR, —N(R)C(O)R, —N(R)C(O)NR$_2$, —N(R)S(O)$_2$R, —OP(O)R$_2$, —OP(O)(OR)$_2$, —OP(O)(OR)NR$_2$, —OP(O)(NR$_2$)$_2$, —Si(OR)R$_2$, and —SiR$_3$.

In some embodiments, $R^a$ is hydrogen. In some embodiments, $R^a$ is deuterium. In some embodiments, $R^a$ is $R^c$. In some embodiments, $R^a$ is halogen. In some embodiments, $R^a$ is —CN. In some embodiments, $R^a$ is —NO$_2$. In some embodiments, $R^a$ is —OR. In some embodiments, $R^a$ is —SR. In some embodiments, $R^a$ is —NR$_2$. In some embodiments, $R^a$ is —S(O)$_2$R. In some embodiments, $R^a$ is —S(O)$_2$NR$_2$. In some embodiments, $R^a$ is —S(O)R. In some embodiments, $R^a$ is —CFR$_2$. In some embodiments, $R^a$ is —CF$_2$R. In some embodiments, $R^a$ is —CF$_3$. In some embodiments, $R^a$ is —CR$_2$(OR). In some embodiments, $R^a$ is —CR$_2$(NR$_2$). In some embodiments, $R^a$ is —C(O)R. In some embodiments, $R^a$ is —C(O)OR. In some embodiments, $R^a$ is —C(O)NR$_2$. In some embodiments, $R^a$ is —C(O)N(R)OR. In some embodiments, $R^a$ is —OC(O)R. In some embodiments, $R^a$ is —OC(O)NR$_2$. In some embodiments, $R^a$ is —C(S)NR$_2$. In some embodiments, $R^a$ is —N(R)C(O)OR. In some embodiments, $R^a$ is —N(R)C(O)R. In some embodiments, $R^a$ is —N(R)C(O)NR$_2$. In some embodiments, $R^a$ is —N(R)S(O)$_2$R. In some embodiments, $R^a$ is —OP(O)R$_2$. In some embodiments, $R^a$ is —OP(O)(OR)$_2$. In some embodiments, $R^a$ is —OP(O)(OR)NR$_2$. In some embodiments, $R^a$ is —OP(O)(NR$_2$)$_2$. In some embodiments, $R^a$ is —Si(OR)R$_2$. In some embodiments, $R^a$ is —SiR$_3$.

In some embodiments, $R^b$ is hydrogen. In some embodiments, $R^b$ is deuterium. In some embodiments, $R^b$ is $R^c$. In some embodiments, $R^b$ is halogen. In some embodiments, $R^b$ is —CN. In some embodiments, $R^b$ is —NO$_2$. In some embodiments, $R^b$ is —OR. In some embodiments, $R^b$ is —SR. In some embodiments, $R^b$ is —NR$_2$. In some embodiments, $R^b$ is —S(O)$_2$R. In some embodiments, $R^b$ is —S(O)$_2$NR$_2$. In some embodiments, $R^b$ is —S(O)R. In some embodiments, $R^b$ is —CFR$_2$. In some embodiments, $R^b$ is —CF$_2$R. In some embodiments, $R^b$ is —CF$_3$. In some embodiments, $R^b$ is —CR$_2$(OR). In some embodiments, $R^b$ is —CR$_2$(NR$_2$). In some embodiments, $R^b$ is —C(O)R. In some embodiments, $R^b$ is —C(O)OR. In some embodiments, $R^b$ is —C(O)NR$_2$. In some embodiments, $R^b$ is —C(O)N(R)OR. In some embodiments, $R^b$ is —OC(O)R. In some embodiments, $R^b$ is —OC(O)NR$_2$. In some embodiments, $R^b$ is —C(S)NR$_2$. In some embodiments, $R^b$ is —N(R)C(O)OR. In some embodiments, $R^b$ is —N(R)C(O)R. In some embodiments, $R^b$ is —N(R)C(O)NR$_2$. In some embodiments, $R^b$ is —N(R)S(O)$_2$R. In some embodiments, $R^b$ is —OP(O)R$_2$. In some embodiments, $R^b$ is —OP(O)(OR)$_2$. In some embodiments, $R^b$ is —OP(O)(OR)NR$_2$. In some embodiments, $R^b$ is —OP(O)(NR$_2$)$_2$. In some embodiments, $R^b$ is —Si(OR)R$_2$. In some embodiments, $R^b$ is —SiR$_3$.

In certain embodiments, each $R^a$ and $R^b$ are selected from those shown in the compounds of Table 1.

As defined above and described herein, each R is independently selected from hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or two R groups on the same carbon or nitrogen are optionally taken together with their intervening atoms to form an optionally substituted 4-7 membered saturated, partially unsaturated, or heteroaryl ring having 0-3 heteroatoms, in addition to the carbon or nitrogen, independently selected from nitrogen, oxygen, and sulfur.

In some embodiments, R is hydrogen. In some embodiments, R is an optionally substituted ($C_{1-6}$ aliphatic. In some embodiments, R is an optionally substituted phenyl. In some embodiments, R is an optionally substituted 4-7 membered saturated or partially unsaturated heterocyclic having 1-2 heteroatoms independently selected from nitrogen, oxygen, and sulfur. In some embodiments, R is an optionally substituted a 5-6 membered heteroaryl ring having 1-4 heteroatoms independently selected from nitrogen, oxygen, and sulfur. In some embodiments, two R groups on the same carbon or nitrogen are optionally taken together with their intervening atoms to form an optionally substituted 4-7 membered saturated, partially unsaturated, or heteroaryl ring having 0-3 heteroatoms, in addition to the carbon or nitrogen, independently selected from nitrogen, oxygen, and sulfur.

In certain embodiments, R is selected from those shown in the compounds of Table 1.

As defined above and described herein, each $R^c$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur.

In some embodiments, $R^c$ is an optionally substituted $C_{1-6}$ aliphatic. In some embodiments, $R^c$ is an optionally substituted phenyl. In some embodiments, $R^c$ is an optionally substituted 4-7 membered saturated or partially unsaturated heterocyclic ring having 1-2 heteroatoms independently selected from nitrogen, oxygen, and sulfur. In some embodiments, $R^c$ is an optionally substituted 5-6 membered heteroaryl ring having 1-4 heteroatoms independently selected from nitrogen, oxygen, and sulfur.

In certain embodiments, $R^c$ is selected from those shown in the compounds of Table 1.

As defined above and described herein, a is 0, 1, 2, 3 or 4.

In some embodiments, a is 0. In some embodiments, a is 1. In some embodiments, a is 2. In some embodiments, a is 3. In some embodiments, a is 4.

In certain embodiments, a is selected from those shown in the compounds of Table 1.

As defined above and described herein, b is 0, 1, 2, 3 or 4.

In some embodiments, b is 0. In some embodiments, b is 1. In some embodiments, b is 2. In some embodiments, b is 3. In some embodiments, b is 4.

In certain embodiments, b is selected from those shown in the compounds of Table 1.

In some embodiments, the present invention provides a compound of formula I, wherein $X^1$ and $X^2$ are —CH$_2$—, and $X^3$ and $X^4$ are —C(O)— as shown, to provide a compound of formula I-zzz-1:

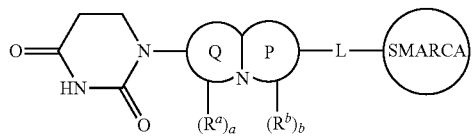

I-zzz-1 or a pharmaceutically acceptable salt thereof, wherein each of SMARCA, L, Ring P, Ring Q, $R^a$, $R^b$, a, and b is as defined above and described in embodiments herein, both singly and in combination.

In some embodiments, the present invention provides a compound of formula I, wherein $X^1$ and $X^2$ are —$CH_2$—, $X^3$ and $X^4$ are —C(O)—, and Ring Q is

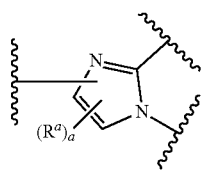

as shown, to provide a compound of formula I-zzz-2:

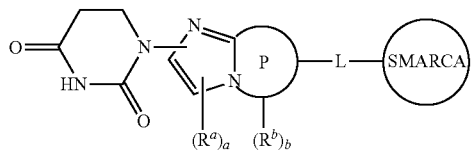

I-zzz-2 or a pharmaceutically acceptable salt thereof, wherein each of SMARCA, L, Ring P, $R^a$, $R^b$, a, and b is as defined above and described in embodiments herein, both singly and in combination.

In some embodiments, the present invention provides a compound of formula I, wherein $X^1$ and $X^2$ are —$CH_2$—, $X^3$ and $X^4$ are —C(O)—, and Ring P is

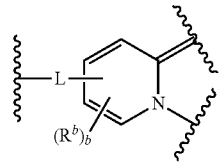

as shown, to provide a compound of formula I-zzz-3:

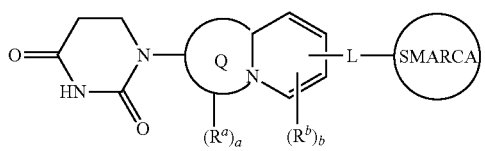

I-zzz-3 or a pharmaceutically acceptable salt thereof, wherein each of SMARCA, L, Ring Q, $R^a$, $R^b$, a, and b is as defined above and described in embodiments herein, both singly and in combination.

In some embodiments, the present invention provides a compound of formula I, wherein $X^1$ and $X^2$ are —$CH_2$—, $X^3$ and $X^4$ are —C(O)—, Ring P is

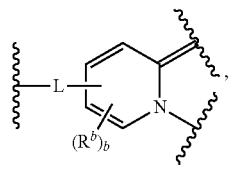

and Ring Q is

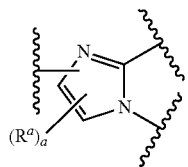

as shown, to provide a compound of formula I-zzz-4:

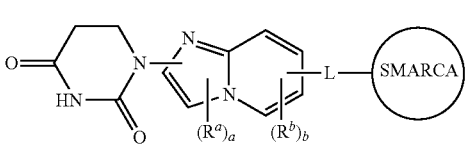

I-zzz-4 or a pharmaceutically acceptable salt thereof, wherein each of SMARCA, L, $R^a$, $R^b$, x, and y is as defined above and described in embodiments herein, both singly and in combination.

Lysine Mimetic

In some embodiments, DIM is a lysine mimetic. In some embodiments, the covalent attachment of ubiquitin to one or more SMARCA2, SMARCA4, or PB1 protein is achieved through the action of a lysine mimetic. In some embodiments, upon the binding of a compound of formula I to SMARCA2, the moiety that mimics a lysine undergoes ubiquitination thereby marking SMARCA2 for degradation via the Ubiquitin-Proteasome Pathway (UPP). In some embodiments, upon the binding of a compound of formula I to SMARCA4, the moiety that mimics a lysine undergoes ubiquitination thereby marking SMARCA4 for degradation via the Ubiquitin-Proteasome Pathway (UPP). In some embodiments, upon the binding of a compound of formula I to PB1, the moiety that mimics a lysine undergoes ubiquitination thereby marking PB1 for degradation via the Ubiquitin-Proteasome Pathway (UPP).

In some embodiments, DIM is

In some embodiments, DIM is

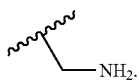

In some embodiments, DIM is

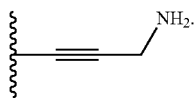 [SMILES: *C#CCN]

In some embodiments, DIM is selected from those depicted in Table 1, below.

In some embodiments, the present invention provides the compound of formula I wherein DIM is

thereby forming a compound of formula I-kkk-1:

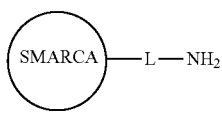

I-kkk-1 or a pharmaceutically acceptable salt thereof, wherein each of SMARCA and U is as defined above and described in embodiments herein, both singly and in combination.

In some embodiments, the present invention provides the compound of formula I wherein DIM is

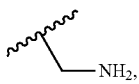

thereby forming a compound of formula I-kkk-2:

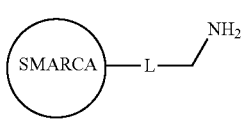

I-kkk-2 or a pharmaceutically acceptable salt thereof, wherein each of SMARCA and L is as defined above and described in embodiments herein, both singly and in combination.

In some embodiments, the present invention provides the compound of formula I wherein DIM is

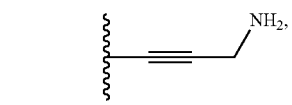 [SMILES: *C#CCN]

thereby forming a compound of formula I-kkk-3:

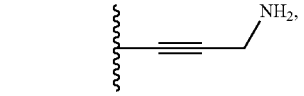

I-kkk-3 or a pharmaceutically acceptable salt thereof, wherein each of SMARCA and L is as defined above and described in embodiments herein, both singly and in combination.

In certain embodiments, the present invention provides a compound of Formula I, wherein DIM is lysine mimetic

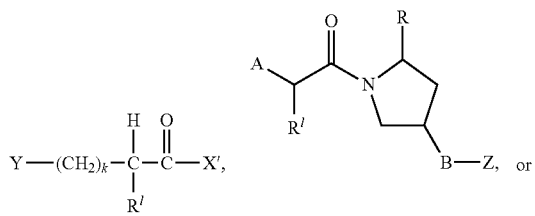

thereby forming a compound of formulae I-lll-1, I-lll-2, or I-lll-3, respectively:

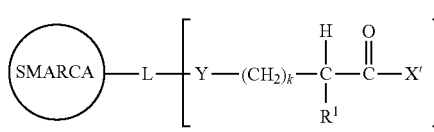

I-lll-1

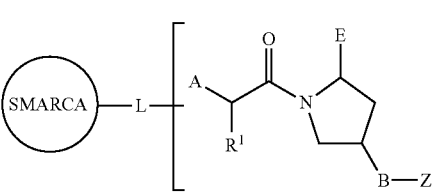

I-lll-2

257

-continued

I-III-3

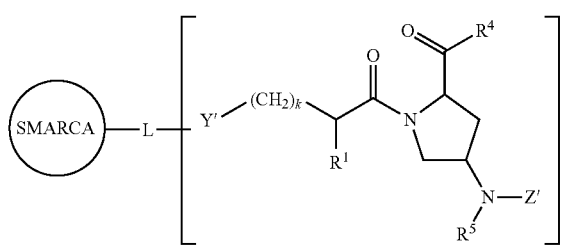

or a pharmaceutically acceptable salt thereof, wherein L and SMARCA are as defined above and described in embodiments herein, and wherein each of the variables $R^1$, $R^4$, $R^5$, A, B, E, Y, Y', Z, Z', and k are as defined and described in U.S. Pat. No. 7,622,496, the entirety of each of which is herein incorporated by reference.

Hydrogen Atom

In some embodiments, DIM is a hydrogen atom. In some embodiments, the covalent attachment of ubiquitin to one or more SMARCA2, SMARCA4 or PB1 proteins is achieved through a provided compound wherein DIM is a hydrogen atom. In some embodiments, upon the binding of a compound of formula I to SMARCA2, the DIM moiety being hydrogen effectuates ubiquitination thereby marking SMARCA2 for degradation via the Ubiquitin-Proteasome Pathway (UPP). In some embodiments, upon the binding of a compound of formula I to SMARCA4, the DIM moiety being hydrogen effectuates ubiquitination thereby marking SMARCA4 for degradation via the Ubiquitin-Proteasome Pathway (UPP). In some embodiments, upon the binding of a compound of formula I to PB1, the DIM moiety being hydrogen effectuates ubiquitination thereby marking PB1 for degradation via the Ubiquitin-Proteasome Pathway (UPP).

In some embodiments, DIM is selected from those depicted in Table 1, below.

In some embodiments, the present invention provides the compound of formula I wherein DIM is a hydrogen atom, thereby forming a compound of formula I-mmm:

I-mmm

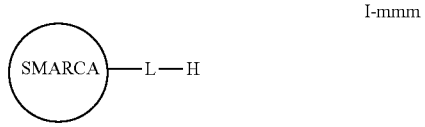

or a pharmaceutically acceptable salt thereof, wherein each of SMARCA and L is as defined above and described in embodiments herein, both singly and in combination.

Linker (L)

As defined above and described herein, Lisa bivalent moiety that connects SMARCA to DIM.

In some embodiments, L is a bivalent moiety that connects SMARCA to LBM. In some embodiments, L is a bivalent moiety that connects SMARCA to a lysine mimetic. In some embodiments, L is a bivalent moiety that connects SMARCA to a hydrogen atom.

In some embodiments, L is a covalent bond or a bivalent, saturated or partially unsaturated, straight or branched $C_{1-50}$ hydrocarbon chain, wherein 0-6 methylene units of L are independently replaced by —C(D)(H)—, —C(D)$_2$—, —Cy—, —O—, —N(R)—, —Si(R)$_2$—, —Si(OH)(R)—, —Si(OH)$_2$—, —P(O)(OR)—, —P(O)(R)—, —P(O)(NR$_2$)—, —S—, —OC(O)—, —C(O)—, —C(O)—, —S(O)—, —S(O)$_2$—, —N(R)S(O)$_2$—, —S(O)$_2$N(R)—, —N(R)C(O)—, —C(O)N(R)—, —OC(Q)N(R)—, —N(R)C(O)O—,

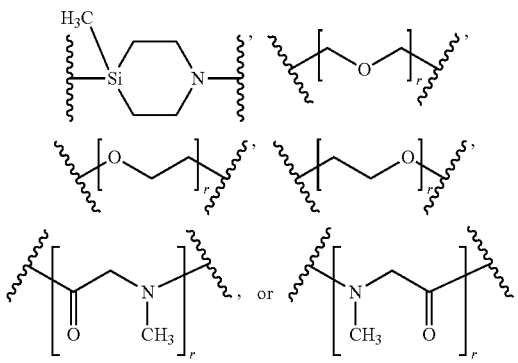

wherein each -Cy- is independently an optionally substituted bivalent ring selected from phenylenyl, an 8-10 membered bicyclic arylenyl, a 4-7 membered saturated or partially unsaturated carbocyclylenyl, a 4-11 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-11 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, or an 8-10 membered bicyclic heteroarylenyl having 1-5 heteroatoms independently selected from nitrogen, oxygen, or sulfur, and wherein r is 0, 1, 2, 3, 4, 5, 6, 7, 8, 9, or 10, and R is as described herein (e.g., in formula I-a).

In some embodiments, L is a covalent bond. In some embodiments, each -Cy- is independently an optionally substituted bivalent phenylenyl. In some embodiments, each -Cy- is independently an optionally substituted 8-10 membered bicyclic arylenyl. In some embodiments, each -Cy- is independently an optionally substituted 4-7 membered saturated or partially unsaturated carbocyclylenyl. In some embodiments, each -Cy- is independently an optionally substituted 4-7 membered saturated or partially unsaturated spiro carbocyclylenyl. In some embodiments, each -Cy- is independently an optionally substituted 8-10 membered bicyclic saturated or partially unsaturated carbocyclylenyl. In some embodiments, each -Cy- is independently an optionally substituted 4-7 membered saturated or partially unsaturated heterocyclylenyl having 1-2 heteroatoms independently selected from nitrogen, oxygen, and sulfur. In some embodiments, each -Cy- is independently an optionally substituted 4-7 membered saturated or partially unsaturated spiro heterocyclylenyl having 1-2 heteroatoms independently selected from nitrogen, oxygen, and sulfur. In some embodiments, each -Cy- is independently an optionally substituted 8-10 membered bicyclic saturated or partially unsaturated heterocyclylenyl having 1-2 heteroatoms independently selected from nitrogen, oxygen, and sulfur. In some embodiments, each -Cy- is independently an optionally substituted 5-6 membered heteroarylenyl having 1-4 heteroatoms independently selected from nitrogen, oxygen, and sulfur. In some embodiments, each -Cy- is independently an optionally substituted 8-10 membered bicyclic heteroarylenyl having 1-5 heteroatoms independently selected from nitrogen, oxygen, or sulfur.

In some embodiments, -Cy- is

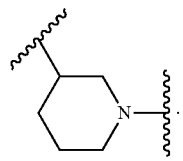 [SMILES: *C1CCCN(*)C1]

In some embodiments, -Cy- is

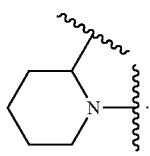 [SMILES: *C1CCCCN1*]

In some embodiments, -Cy- is

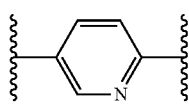

In some embodiments, -Cy- is

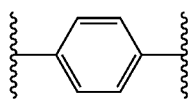

In some embodiments, -Cy- is

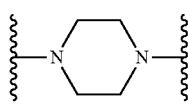

In some embodiments, -Cy- is

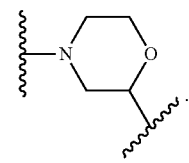 [SMILES: *C1CN(*)CCO1]

In some embodiments, -Cy- is

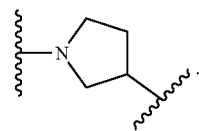 [SMILES: *C1CCN(*)C1]

In some embodiments, -Cy- is

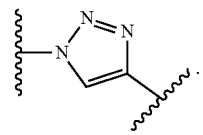 [SMILES: *c1cn(*)nn1]

In some embodiments, -Cy- is

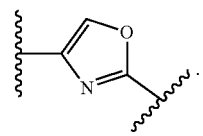 [SMILES: *c1coc(*)n1]

In some embodiments, -Cy- is

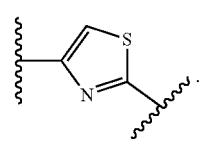 [SMILES: *c1csc(*)n1]

In some embodiments, -Cy- is

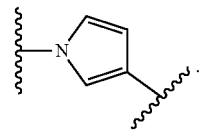 [SMILES: *c1ccn(*)c1]

In some embodiments, -Cy- is

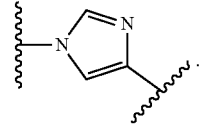

In some embodiments, -Cy- is

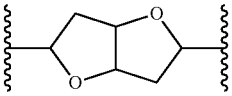

In some embodiments, -Cy- is

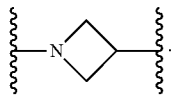

In some embodiments, -Cy- is

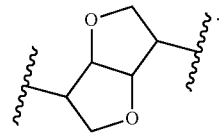 [SMILES: *C1COC2C(*)COC12]

In some embodiments, -Cy- is

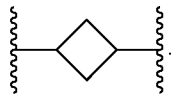

In some embodiments, -Cy- is

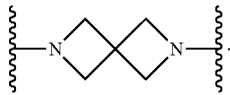 [SMILES: *N1CC2(C1)CN(*)C2]

In some embodiments, -Cy- is

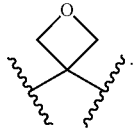 [SMILES: *C1(*)COC1]

In some embodiments, -Cy- is

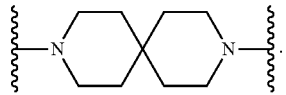

In some embodiments, -Cy- is

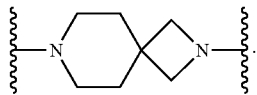 [SMILES: *N1CCC2(CC1)CN(*)C2]

In some embodiments, -Cy- is

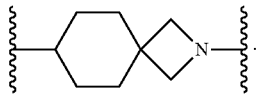 [SMILES: *C1CCC2(CC1)CN(*)C2]

In some embodiments, -Cy- is

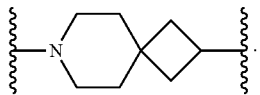

In some embodiments, -Cy- is

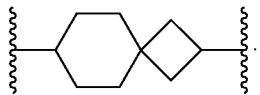 [SMILES: *C1CCC2(CC1)CC(*)C2]

In some embodiments, -Cy- is

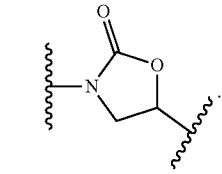 [SMILES: *C1CN(*)C(=O)O1]

In some embodiments, -Cy- is

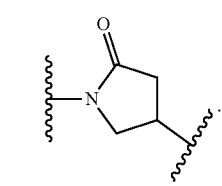 [SMILES: *C1CC(=O)N(*)C1]

In some embodiments, -Cy- is

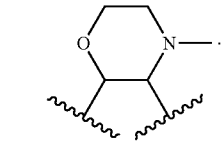 [SMILES: *C1OCCN(C)C1*]

In some embodiments, -Cy- is

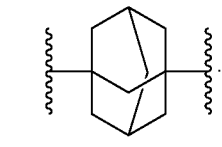 [SMILES: *C12CC3CC(C1)CC(*)(C3)C2]

In some embodiments, -Cy- is

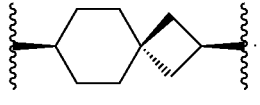

In some embodiments, -Cy- is

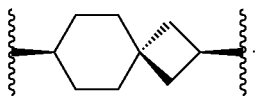

In some embodiments, -Cy- is

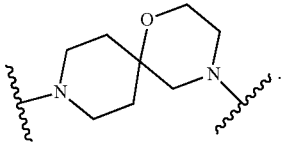 [SMILES: *N1CCC2(CC1)CN(*)CCO2]

In some embodiments, -Cy- is

In some embodiments, -Cy- is

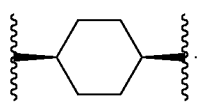 [SMILES: *[C@H]1CC[C@@H](*)CC1]

In some embodiments, -Cy- is

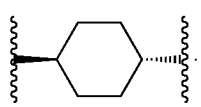

In some embodiments, -Cy- is

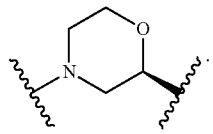 [SMILES: *[C@H]1CN(*)CCO1]

In some embodiments, -Cy- is

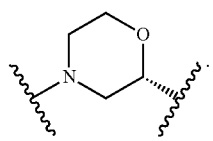 [SMILES: *[C@@H]1CN(*)CCO1]

In some embodiments, -Cy- is

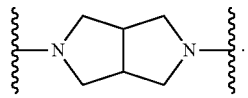 [SMILES: *N1CC2CN(*)CC2C1]

In some embodiments, -Cy- is

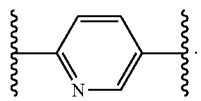

In some embodiments, -Cy- is

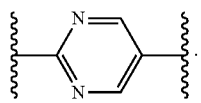

In some embodiments, -Cy- is

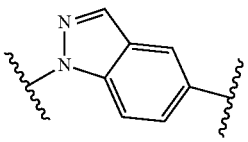

In some embodiments, -Cy- is

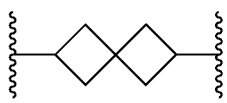

In some embodiments, -Cy- is selected from those depicted in Table 1, below.

In some embodiments, L is

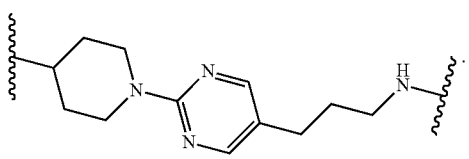 [SMILES: *NCCCc1cnc(N2CCC(*)CC2)nc1]

In some embodiments, L is

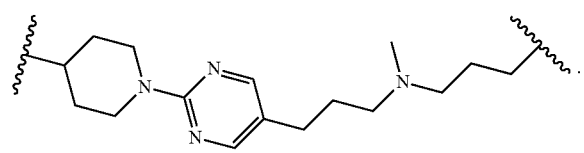 [SMILES: *CCCN(C)CCCc1cnc(N2CCC(*)CC2)nc1]

In some embodiments, L is

In some embodiments, L is

In some embodiments, L is

In some embodiments, L is

In some embodiments, L is

In some embodiments, L is

In some embodiments, L is

In some embodiments, L is

In some embodiments, L is

In some embodiments, L is

In some embodiments, L is

In some embodiments, L is

In some embodiments, L is

In some embodiments, L is
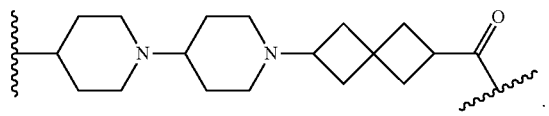 [SMILES: *C(=O)C1CC2(C1)CC(N1CCC(N3CCC(*)CC3)CC1)C2]
In some embodiments, L is
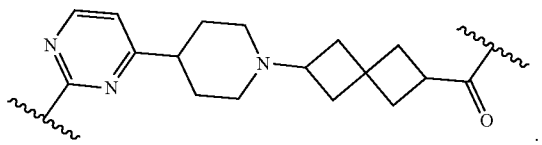 [SMILES: *C(=O)C1CC2(C1)CC(N1CCC(c3ccnc(*)n3)CC1)C2]
In some embodiments, L is
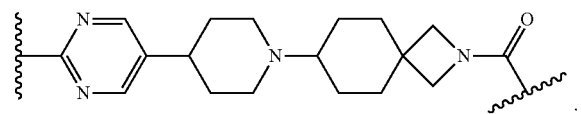 [SMILES: *C(=O)N1CC2(CCC(N3CCC(c4cnc(*)nc4)CC3)CC2)C1]
In some embodiments, L is
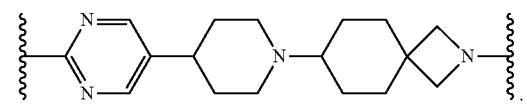
In some embodiments, L is
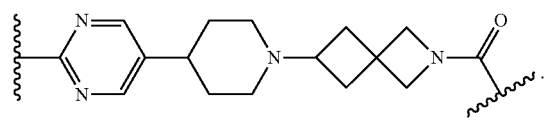 [SMILES: *C(=O)N1CC2(CC(N3CCC(c4cnc(*)nc4)CC3)C2)C1]
In some embodiments, L is
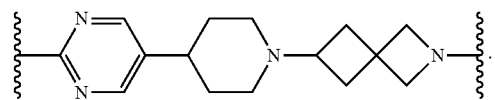 [SMILES: *c1ncc(C2CCN(C3CC4(C3)CN(*)C4)CC2)cn1]
In some embodiments, L is
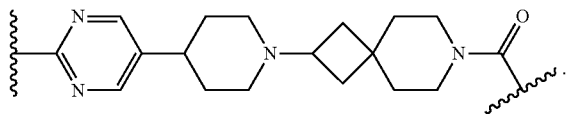 [SMILES: *C(=O)N1CCC2(CC1)CC(N1CCC(c3cnc(*)nc3)CC1)C2]
In some embodiments, L is
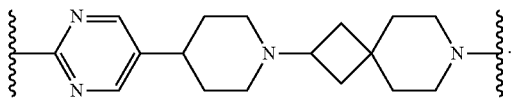 [SMILES: *c1ncc(C2CCN(C3CC4(CCN(*)CC4)C3)CC2)cn1]
In some embodiments, L is
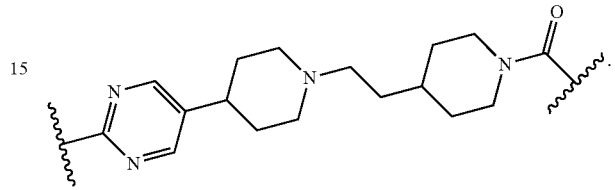
In some embodiments, L is
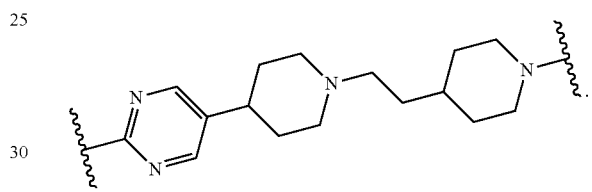
In some embodiments, L is
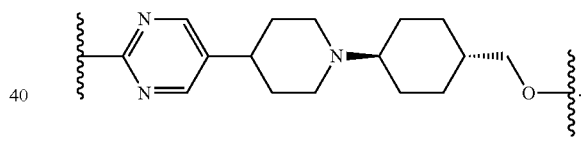
In some embodiments, L is
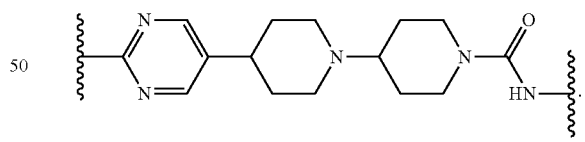
In some embodiments, L is
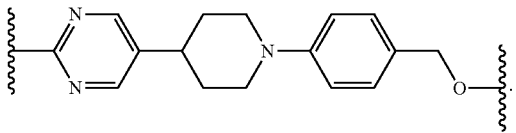 [SMILES: *OCc1ccc(N2CCC(c3cnc(*)nc3)CC2)cc1]

In some embodiments, L is

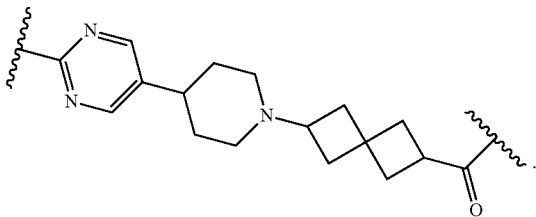 [SMILES: *C(=O)C1CC2(C1)CC(N1CCC(c3cnc(*)nc3)CC1)C2]

In some embodiments, L is

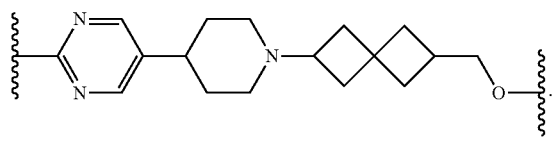 [SMILES: *OCC1CC2(C1)CC(N1CCC(c3cnc(*)nc3)CC1)C2]

In some embodiments, L is

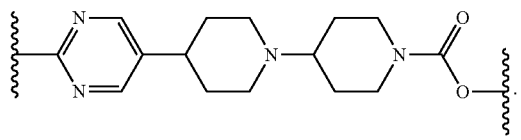 [SMILES: *OC(=O)N1CCC(N2CCC(c3cnc(*)nc3)CC2)CC1]

In some embodiments, L is

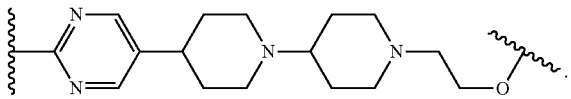

In some embodiments, L is

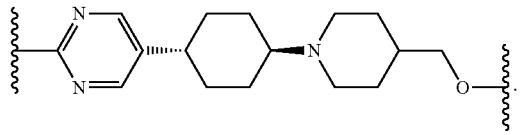

In some embodiments, L is

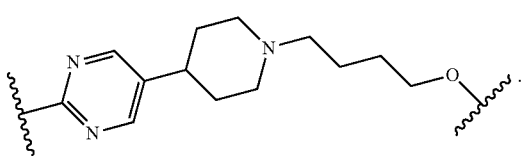 [SMILES: *OCCCCN1CCC(c2cnc(*)nc2)CC1]

In some embodiments, L is

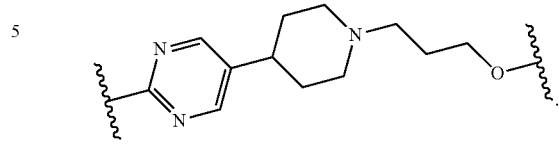

In some embodiments, L is

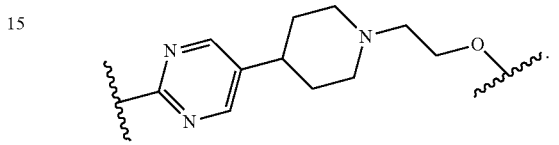

In some embodiments, L is

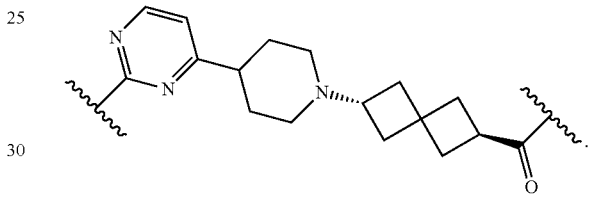

In some embodiments, L is

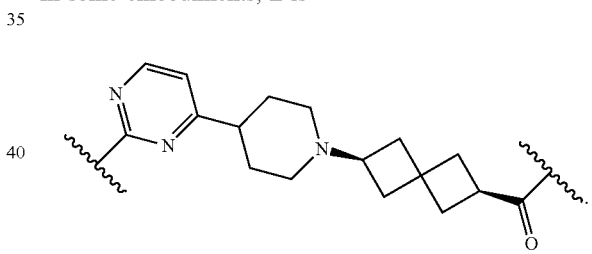

In some embodiments, L is selected from those depicted in Table 1, below.

Without limitation, the point of attachment of L to SMARCA and DIM can be, for example when L is

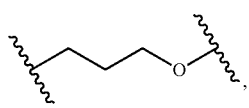 [SMILES: *CCCO*]

either

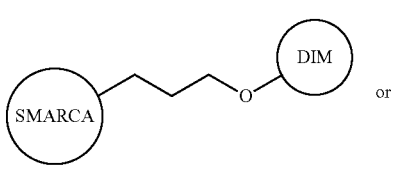 or

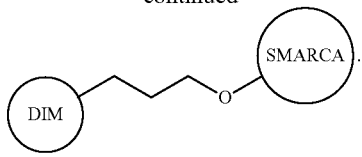

In some embodiments, r is 0. In some embodiments, r is 1. In some embodiments, r is 2. In some embodiments, r is 3. In some embodiments, r is 4. In some embodiments, r is 5. In some embodiments, r is 6. In some embodiments, r is 7. In some embodiments, r is 8. In some embodiments, r is 9. In some embodiments, r is 10.

In some embodiments, r is selected from those depicted in Table 1, below.

In some embodiments, a provided compound or pharmaceutically acceptable salt thereof, is selected from those wherein SMARCA is

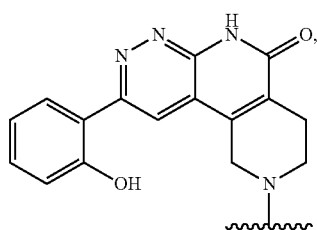 [SMILES: *N1CCc2c(c3cc(-c4ccccc4O)nnc3[nH]c2=O)C1]

LBM is selected from any of those in Table A below, and L is selected from any of those in Table B below.

In some embodiments, a provided compound or pharmaceutically acceptable salt thereof, is selected from those wherein SMARCA is

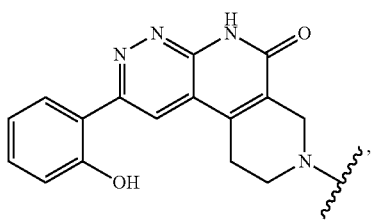 [SMILES: *N1CCc2c(c(=O)[nH]c3nnc(-c4ccccc4O)cc23)C1]

LBM is selected from any of those in Table A below, and L is selected from any of those in Table B below.

In some embodiments, a provided compound or pharmaceutically acceptable salt thereof, is selected from those wherein SMARCA is

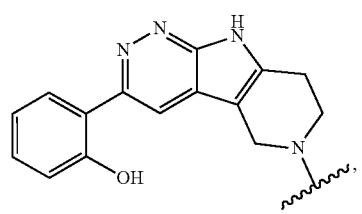 [SMILES: *N1CCc2[nH]c3nnc(-c4ccccc4O)cc3c2C1]

LBM is selected from any of those in Table A below, and L is selected from any of those in Table B below.

In some embodiments, a provided compound or pharmaceutically acceptable salt thereof, is selected from those wherein SMARCA is

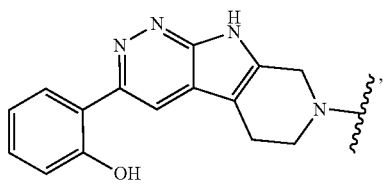 [SMILES: *N1CCc2c([nH]c3nnc(-c4ccccc4O)cc23)C1]

LBM is selected from any of those in Table A below, and L is selected from any of those in Table B below.

In some embodiments, a provided compound or pharmaceutically acceptable salt thereof, is selected from those wherein SMARCA is

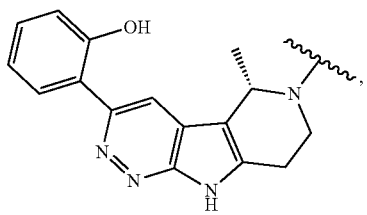 [SMILES: *N1CCc2[nH]c3nnc(-c4ccccc4O)cc3c2[C@@H]1C]

LBM is selected from any of those in Table A below, and L is selected from any of those in Table B below.

In some embodiments, a provided compound or pharmaceutically acceptable salt thereof, is selected from those wherein SMARCA is

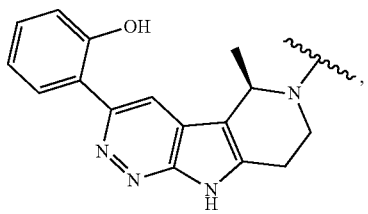 [SMILES: *N1CCc2[nH]c3nnc(-c4ccccc4O)cc3c2[C@H]1C]

LBM is selected from any of those in Table A below, and L is selected from any of those in Table B below.

In some embodiments, a provided compound or pharmaceutically acceptable salt thereof, is selected from those wherein SMARCA is

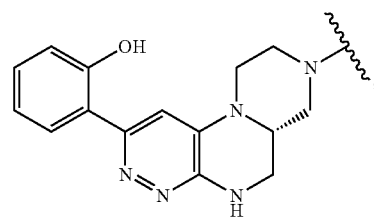

LBM is selected from any of those in Table A below, and L is selected from any of those in Table B below.

In some embodiments, a provided compound or pharmaceutically acceptable salt thereof, is selected from those wherein SMARCA is

273

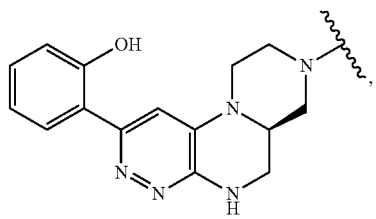 [SMILES: *N1CCN2c3cc(-c4ccccc4O)nnc3NC[C@@H]2C1]

274

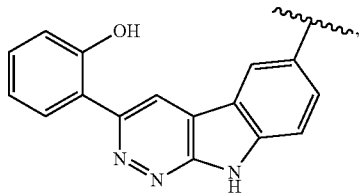 [SMILES: *c1ccc2[nH]c3nnc(-c4ccccc4O)cc3c2c1]

LBM is selected from any of those in Table A below, and L is selected from any of those in Table B below.

In some embodiments, a provided compound or pharmaceutically acceptable salt thereof, is selected from those wherein SMARCA is LBM is selected from any of those in Table A below, and L is selected from any of those in Table B below.

TABLE A

Exemplified E3 ligases (LBM)

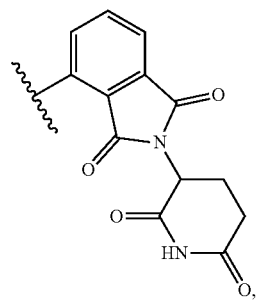 [SMILES: *c1cccc2c1C(=O)N(C1CCC(=O)NC1=O)C2=O]
(a)

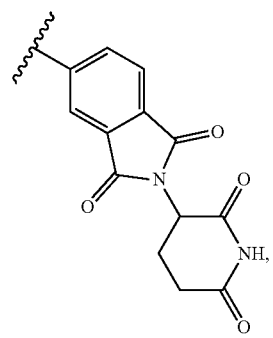 [SMILES: *c1ccc2c(c1)C(=O)N(C1CCC(=O)NC1=O)C2=O]
(b)

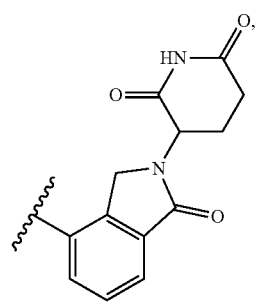 [SMILES: *c1cccc2c1CN(C1CCC(=O)NC1=O)C2=O]
(c)

TABLE A-continued
Exemplified E3 ligases (LBM)
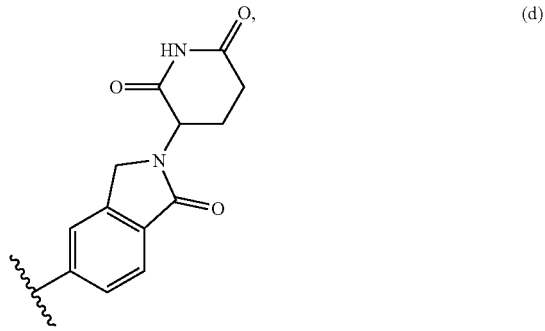  (d)
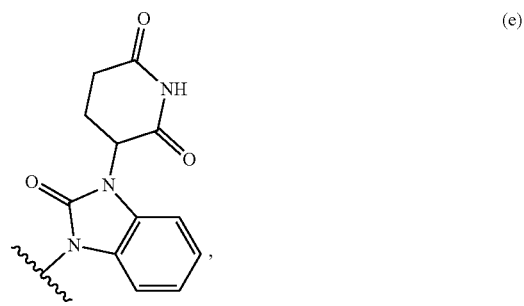  (e)
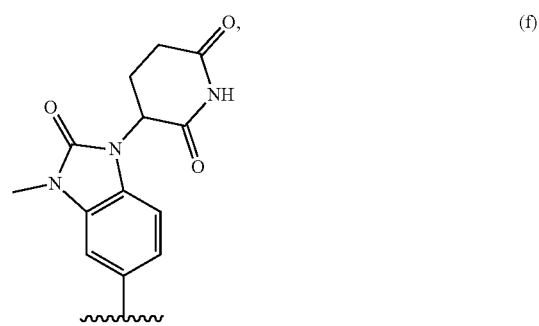  (f)
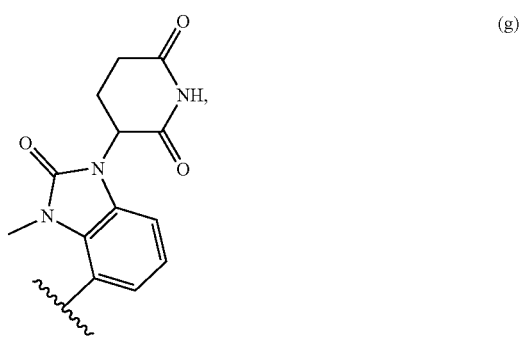  (g)

TABLE A-continued
Exemplified E3 ligases (LBM)
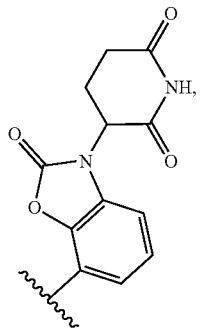 [SMILES: *c1cccc2c1oc(=O)n2C1CCC(=O)NC1=O] (h)
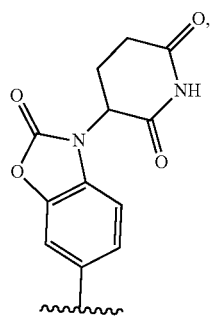 [SMILES: *c1ccc2c(c1)oc(=O)n2C1CCC(=O)NC1=O] (i)
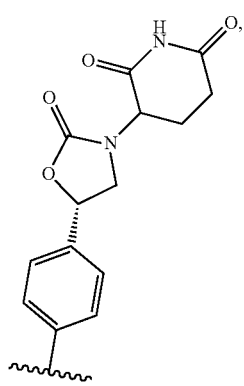 [SMILES: *c1ccc([C@H]2CN(C3CCC(=O)NC3=O)C(=O)O2)cc1] (j)
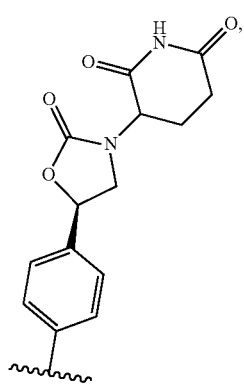 [SMILES: *c1ccc([C@@H]2CN(C3CCC(=O)NC3=O)C(=O)O2)cc1] (k)

TABLE A-continued
Exemplified E3 ligases (LBM)
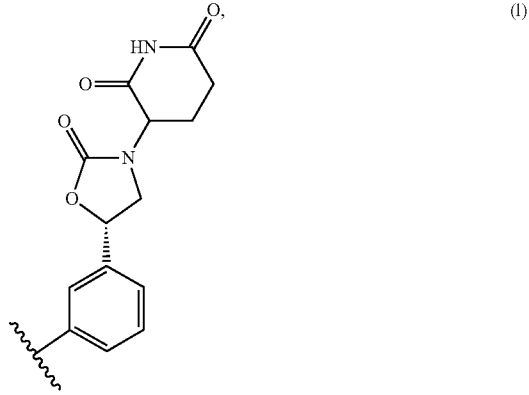
(l)
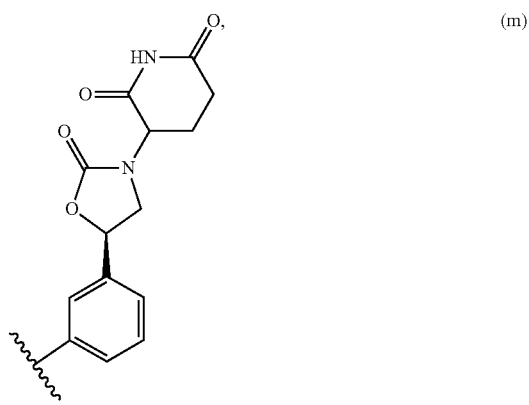
(m)
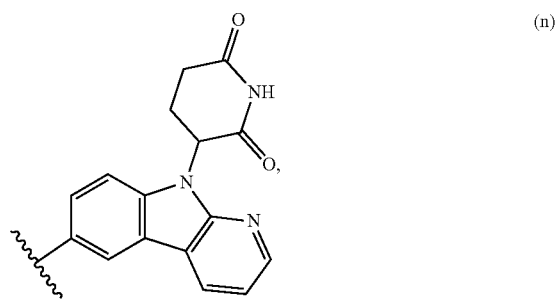
(n)
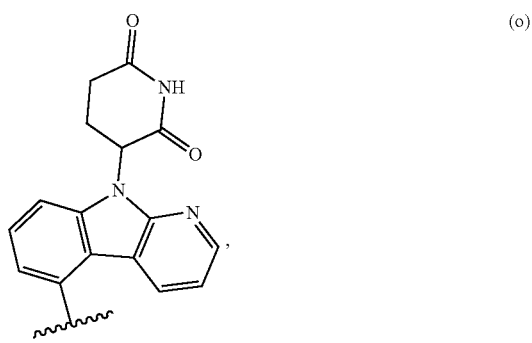
(o)

TABLE A-continued
Exemplified E3 ligases (LBM)
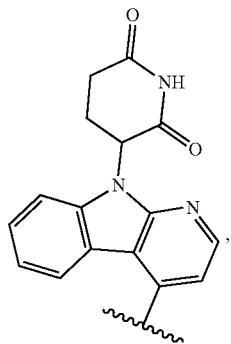 [SMILES: *c1ccnc2c1c1ccccc1n2C1CCC(=O)NC1=O]
(p)
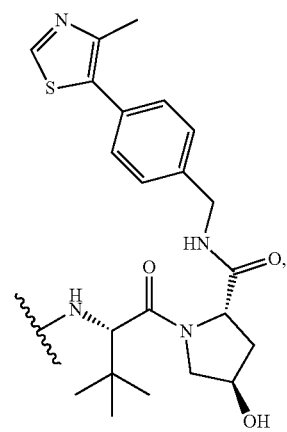 [SMILES: *N[C@H](C(=O)N1C[C@H](O)C[C@H]1C(=O)NCc1ccc(-c2scnc2C)cc1)C(C)(C)C]
(q)
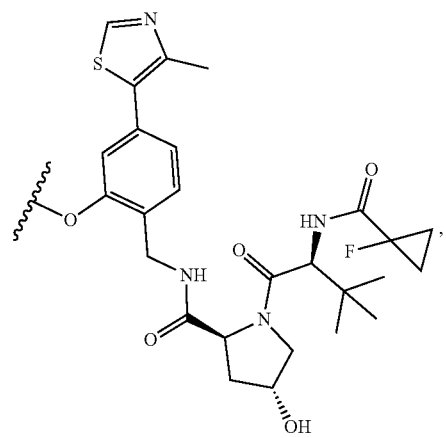 [SMILES: *Oc1cc(-c2scnc2C)ccc1CNC(=O)[C@@H]1C[C@@H](O)CN1C(=O)[C@@H](NC(=O)C1(F)CC1)C(C)(C)C]
(r)

TABLE A-continued
Exemplified E3 ligases (LBM)
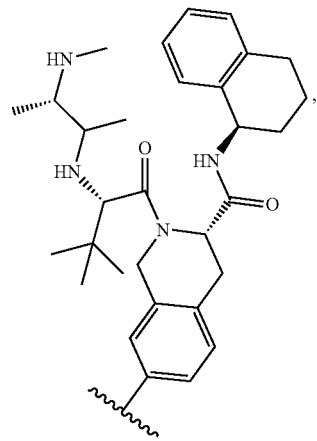 [SMILES: *c1ccc2c(c1)CN(C(=O)[C@@H](NC(C)[C@H](C)NC)C(C)(C)C)[C@H](C(=O)N[C@@H]1CCCc3ccccc31)C2]
(s)
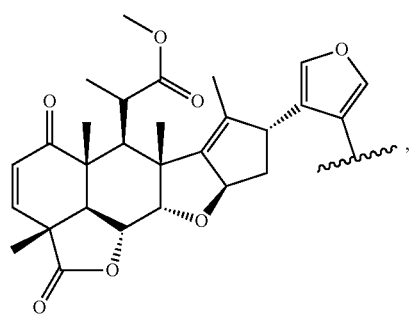 [SMILES: *c1cocc1[C@@H]1C[C@H]2O[C@@H]3[C@@H]4OC(=O)[C@]5(C)C=CC(=O)[C@](C)([C@@H](C(C)C(=O)OC)[C@]3(C)C2=C1C)[C@@H]45]
(t)
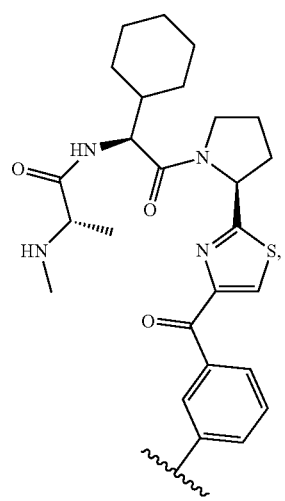 [SMILES: *c1cccc(C(=O)c2csc([C@@H]3CCCN3C(=O)[C@@H](NC(=O)[C@H](C)NC)C3CCCCC3)n2)c1]
(u)

TABLE A-continued
Exemplified E3 ligases (LBM)
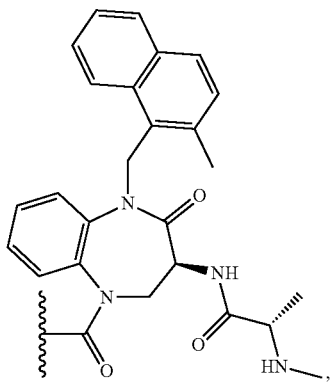 [SMILES: *C(=O)N1C[C@H](NC(=O)[C@H](C)NC)C(=O)N(Cc2c(C)ccc3ccccc23)c2ccccc21]
(v)
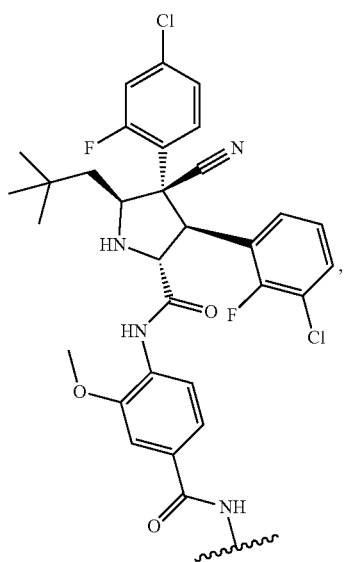 [SMILES: *NC(=O)c1ccc(NC(=O)[C@@H]2N[C@@H](CC(C)(C)C)[C@](C#N)(c3ccc(Cl)cc3F)[C@H]2c2cccc(Cl)c2F)c(OC)c1]
(w)
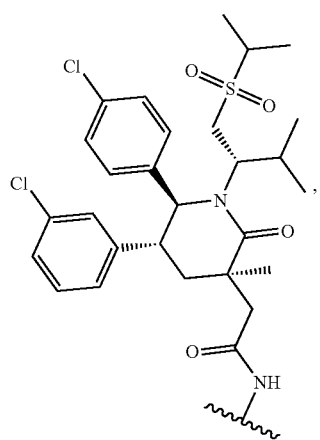 [SMILES: *NC(=O)C[C@@]1(C)C[C@H](c2cccc(Cl)c2)[C@@H](c2ccc(Cl)cc2)N([C@H](CS(=O)(=O)C(C)C)C(C)C)C1=O]
(x)

TABLE A-continued
Exemplified E3 ligases (LBM)
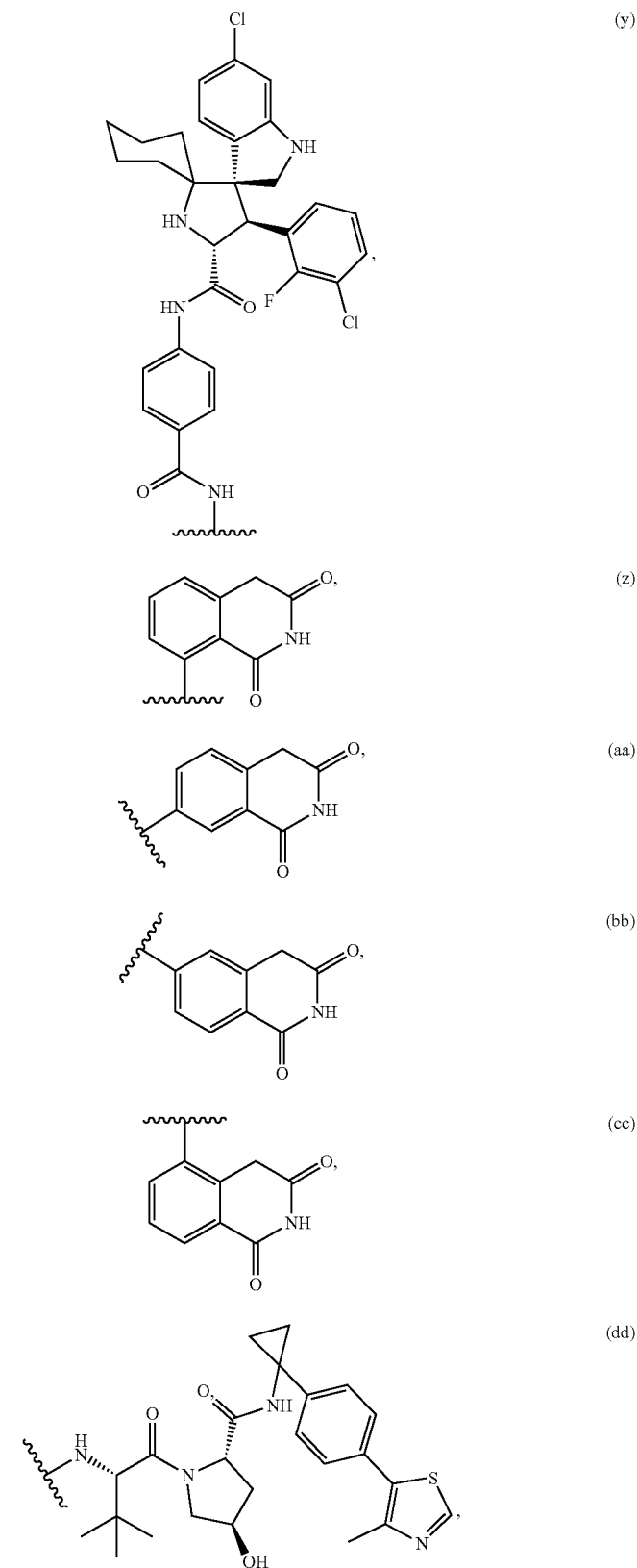

TABLE A-continued
Exemplified E3 ligases (LBM)
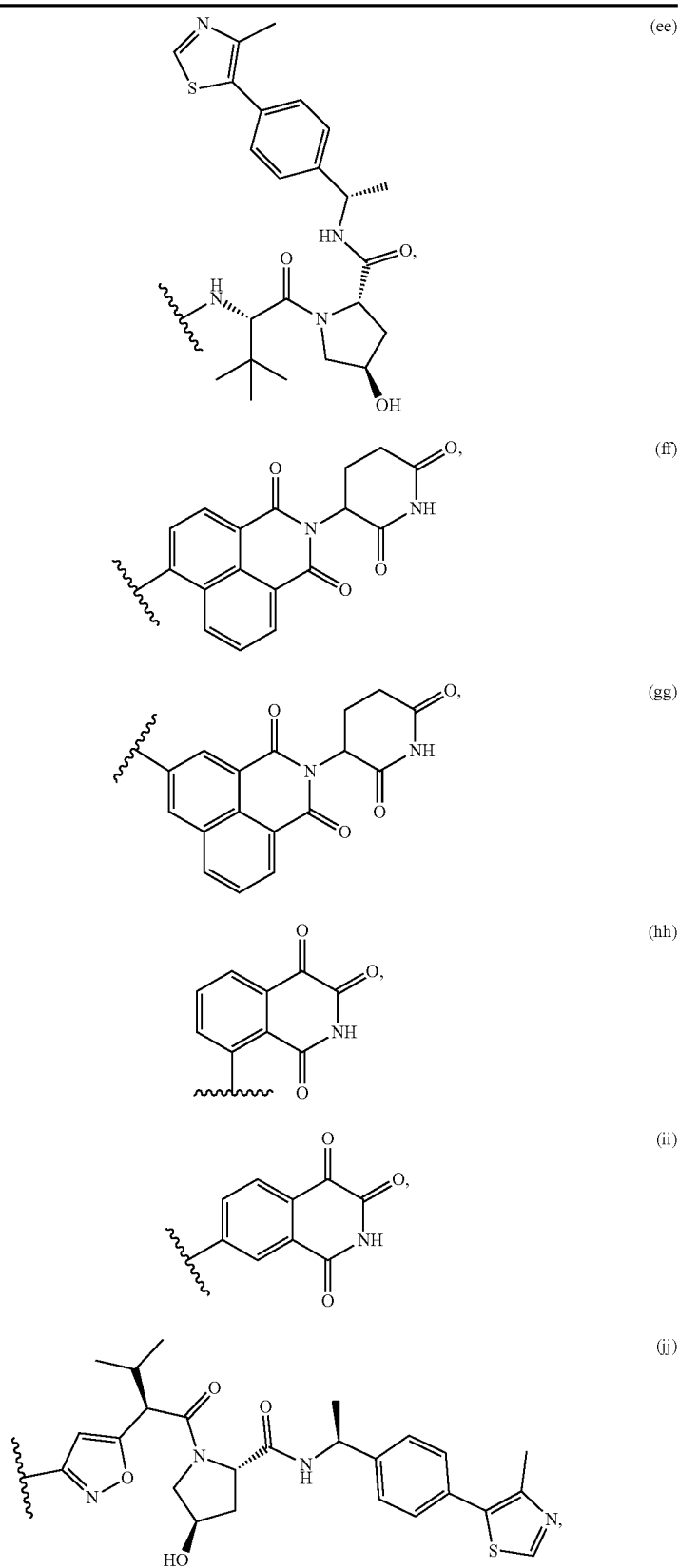

TABLE A-continued
Exemplified E3 ligases (LBM)
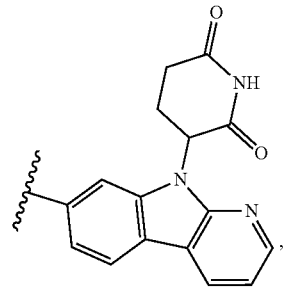 [SMILES: *c1ccc2c3cccnc3n(C3CCC(=O)NC3=O)c2c1]
(kk)
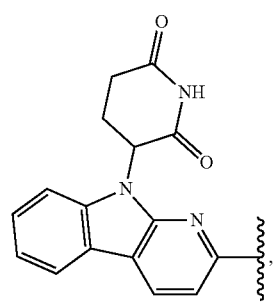 [SMILES: *c1ccc2c3ccccc3n(C3CCC(=O)NC3=O)c2n1]
(ll)
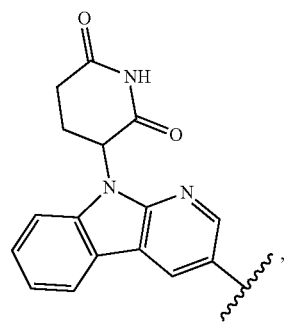 [SMILES: *c1cnc2c(c1)c1ccccc1n2C1CCC(=O)NC1=O]
(mm)
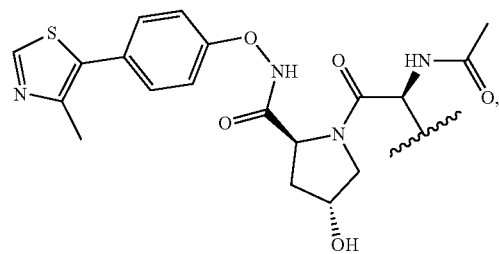 [SMILES: *[C@H](NC(C)=O)C(=O)N1C[C@H](O)C[C@H]1C(=O)NOc1ccc(-c2scnc2C)cc1]
(nn)
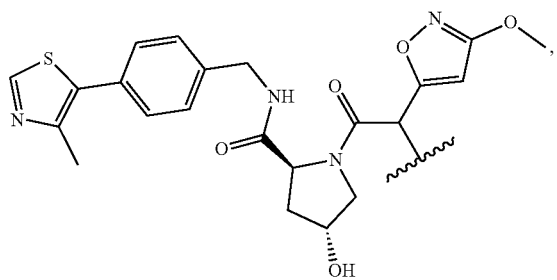 [SMILES: *C(C(=O)N1C[C@H](O)C[C@H]1C(=O)NCc1ccc(-c2scnc2C)cc1)c1cc(OC)no1]
(oo)

TABLE A-continued
Exemplified E3 ligases (LBM)
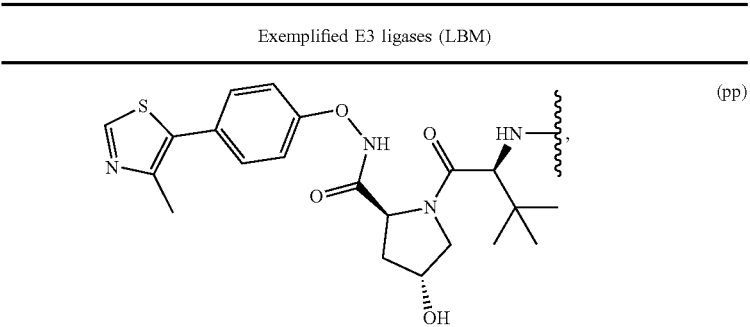 (pp)
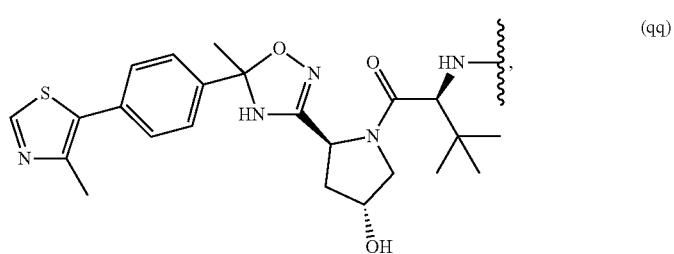 (qq)
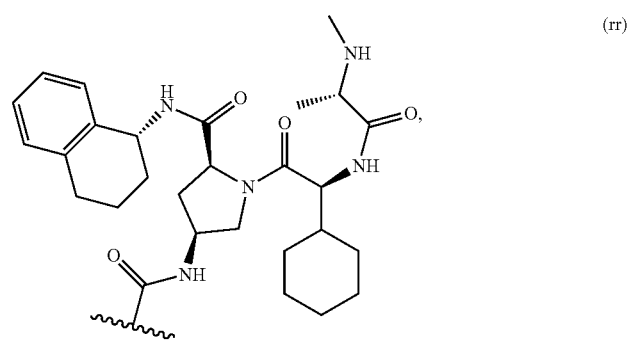 (rr)
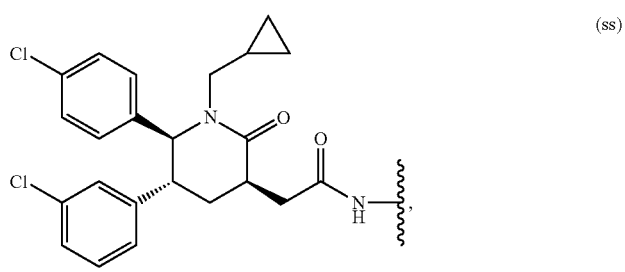 (ss)
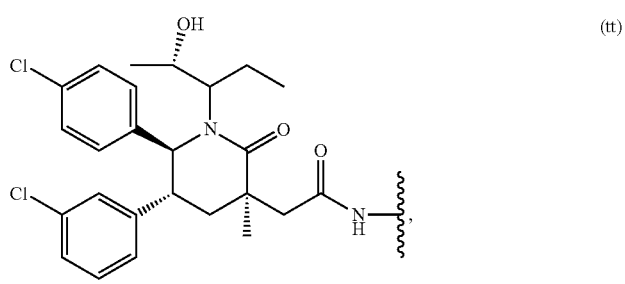 (tt)

TABLE A-continued
Exemplified E3 ligases (LBM)
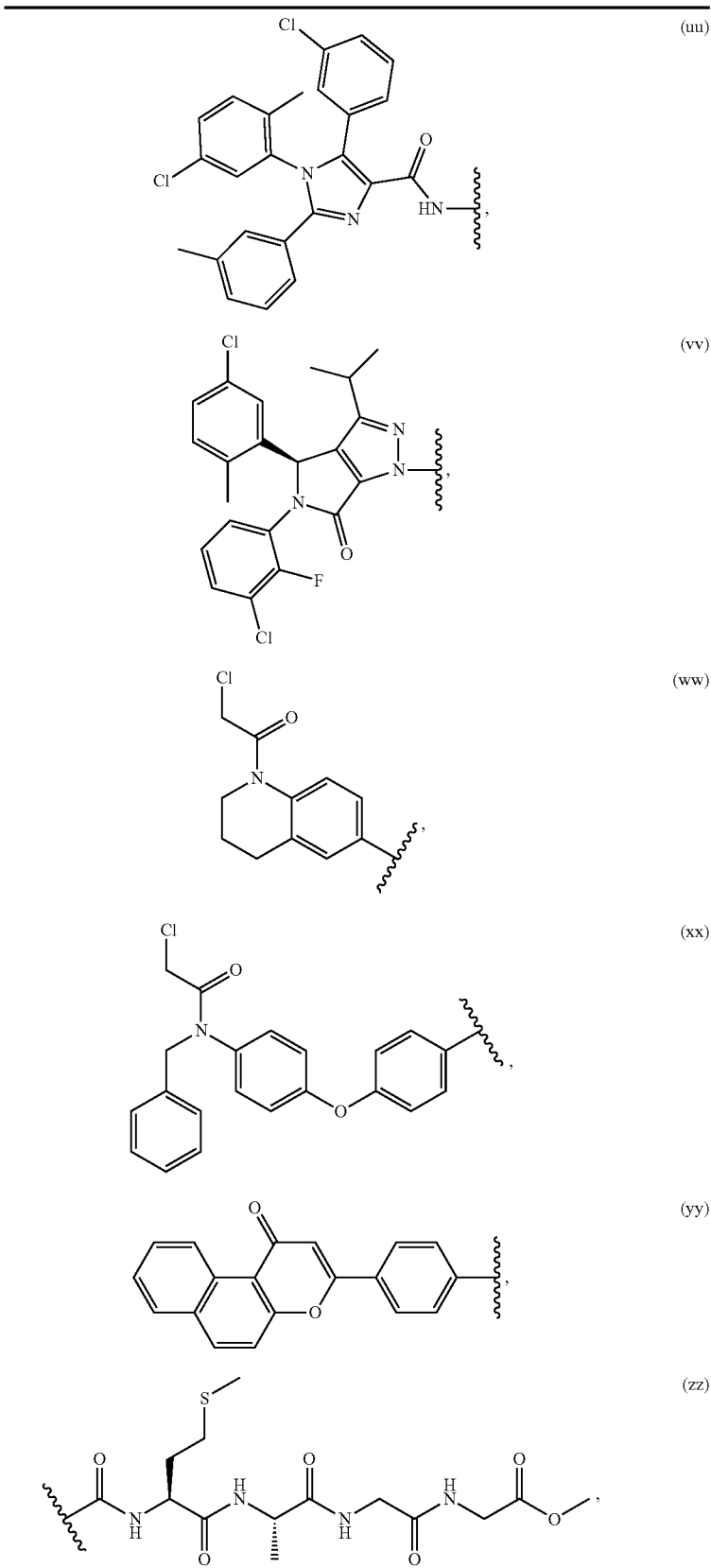

TABLE A-continued
Exemplified E3 ligases (LBM)
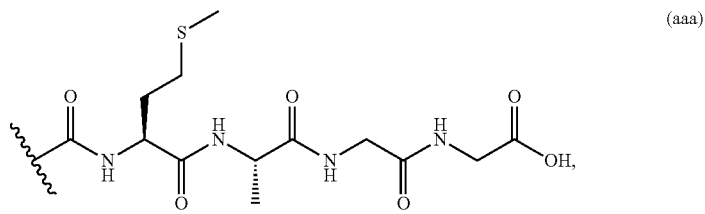 (aaa)
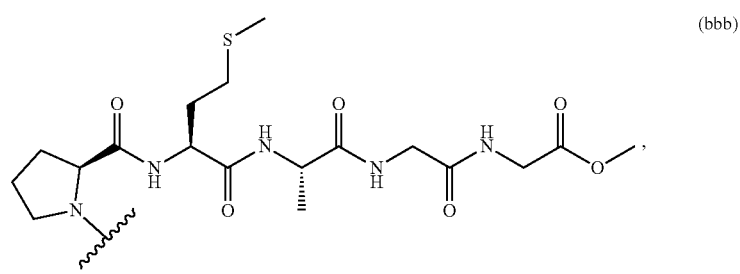 (bbb)
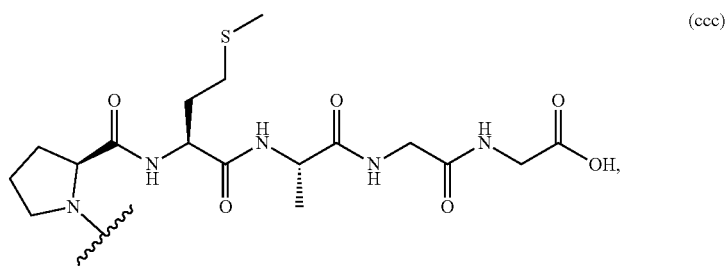 (ccc)
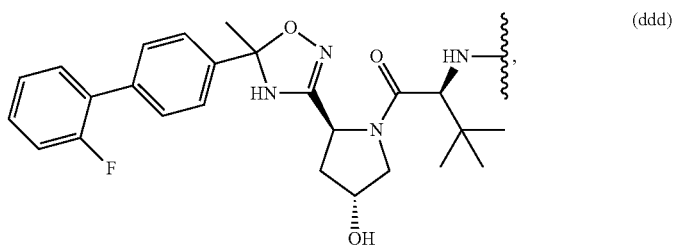 (ddd)
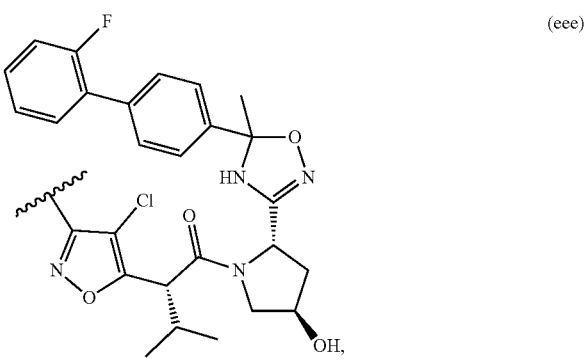 (eee)

TABLE A-continued
Exemplified E3 ligases (LBM)
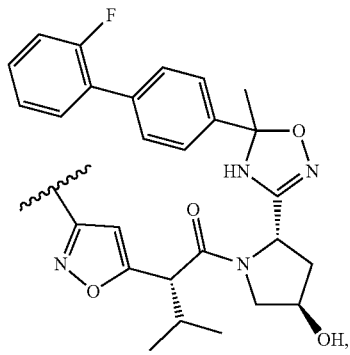 [SMILES: *c1cc([C@H](C(=O)N2C[C@H](O)C[C@H]2C2=NOC(C)(c3ccc(-c4ccccc4F)cc3)N2)C(C)C)on1] (fff)
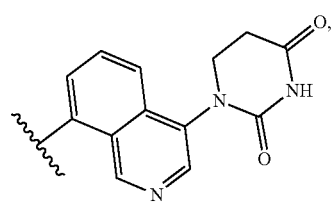 [SMILES: *c1cccc2c(N3CCC(=O)NC3=O)cncc12] (ggg)
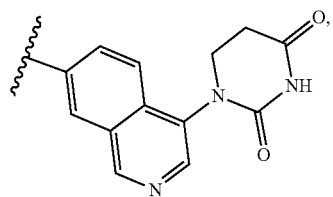 [SMILES: *c1ccc2c(N3CCC(=O)NC3=O)cncc2c1] (hhh)
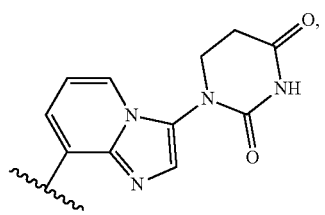 [SMILES: *c1cccn2c(N3CCC(=O)NC3=O)cnc12] (iii)
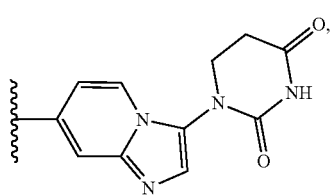 [SMILES: *c1ccn2c(N3CCC(=O)NC3=O)cnc2c1] (jjj)
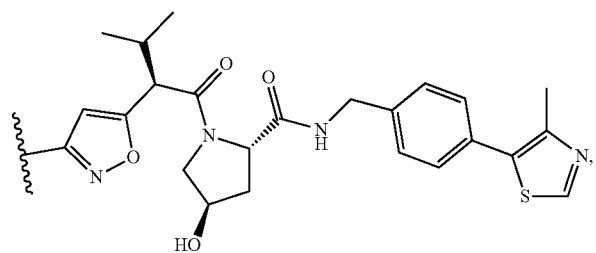 [SMILES: *c1cc([C@H](C(=O)N2C[C@H](O)C[C@H]2C(=O)NCc2ccc(-c3scnc3C)cc2)C(C)C)on1] (kkk)

TABLE A-continued
Exemplified E3 ligases (LBM)
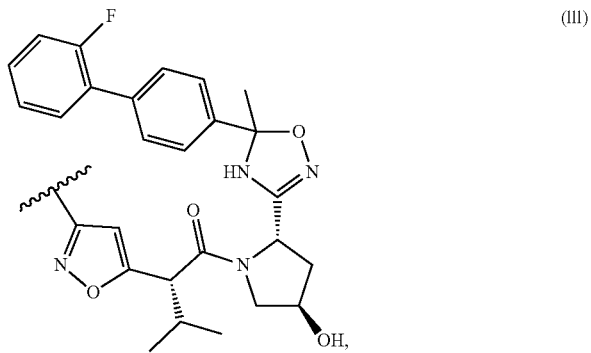
(lll)
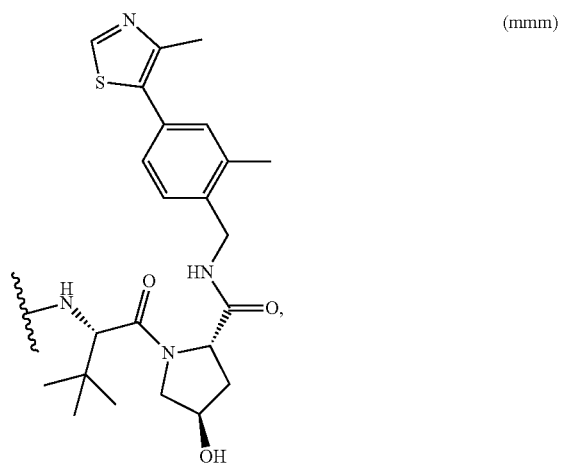
(mmm)
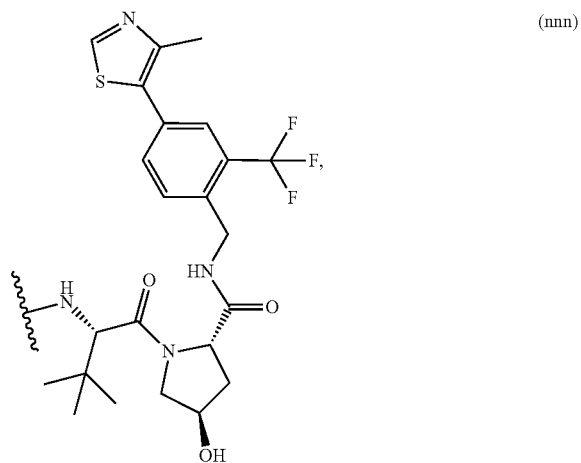
(nnn)

TABLE A-continued
Exemplified E3 ligases (LBM)
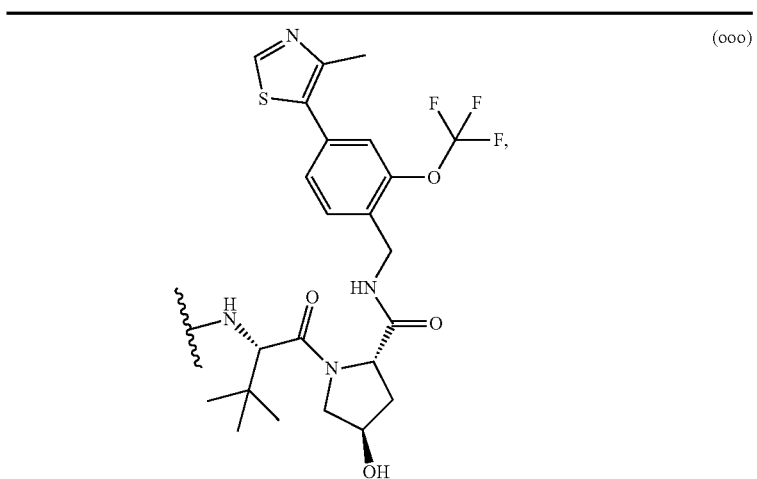
(ooo)
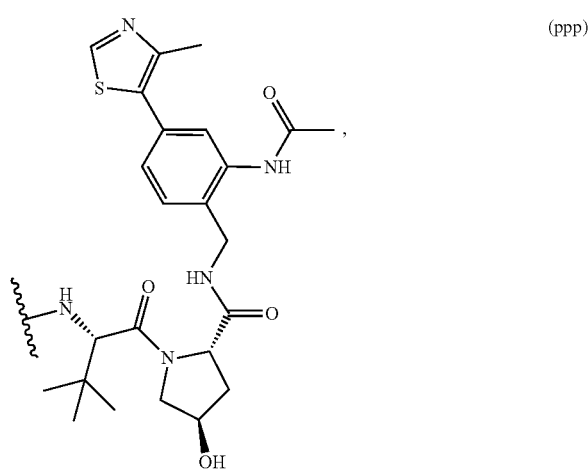
(ppp)
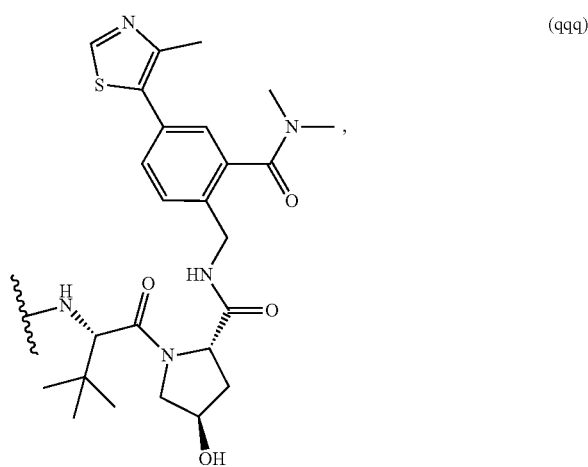
(qqq)

TABLE A-continued
Exemplified E3 ligases (LBM)
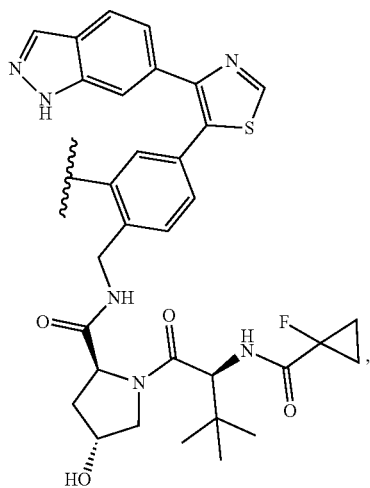 [SMILES: *c1cc(-c2scnc2-c2ccc3cn[nH]c3c2)ccc1CNC(=O)[C@@H]1C[C@@H](O)CN1C(=O)[C@@H](NC(=O)C1(F)CC1)C(C)(C)C] (rrr)
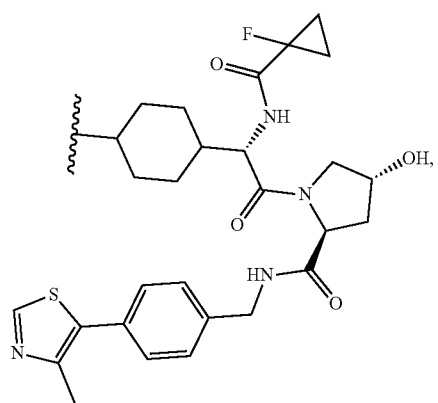 [SMILES: *C1CCC([C@H](NC(=O)C2(F)CC2)C(=O)N2C[C@H](O)C[C@H]2C(=O)NCc2ccc(-c3scnc3C)cc2)CC1] (sss)
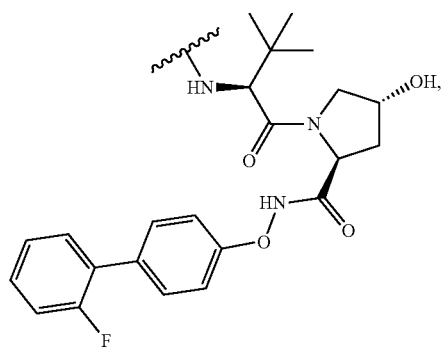 [SMILES: *N[C@H](C(=O)N1C[C@H](O)C[C@H]1C(=O)NOc1ccc(-c2ccccc2F)cc1)C(C)(C)C] (ttt)

TABLE A-continued
Exemplified E3 ligases (LBM)
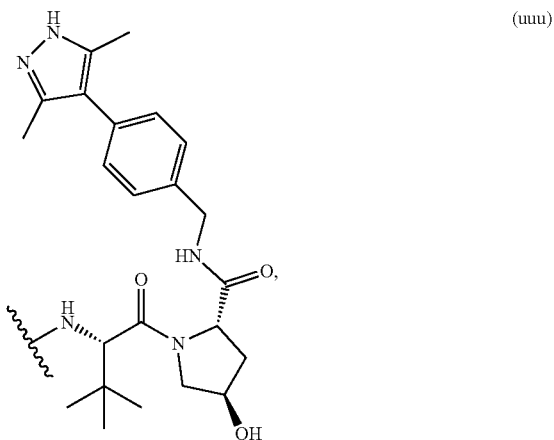
(uuu)
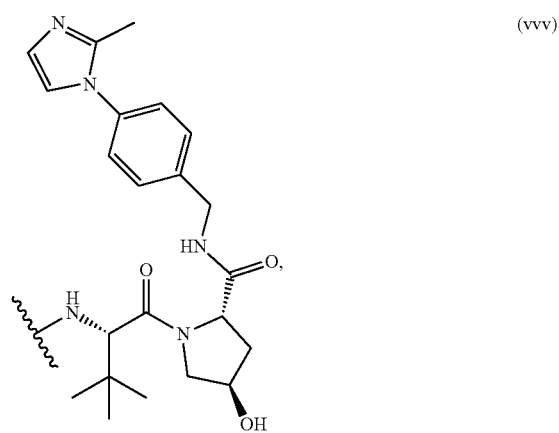
(vvv)
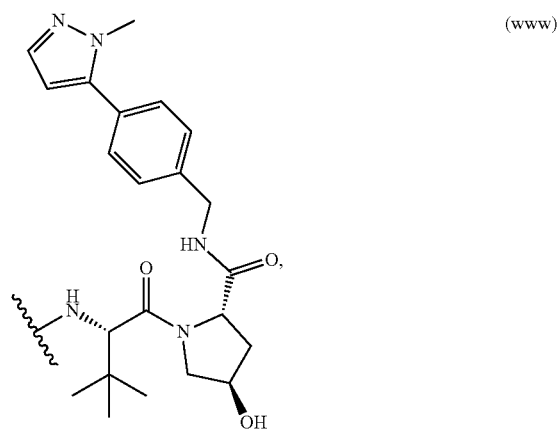
(www)

TABLE A-continued
Exemplified E3 ligases (LBM)
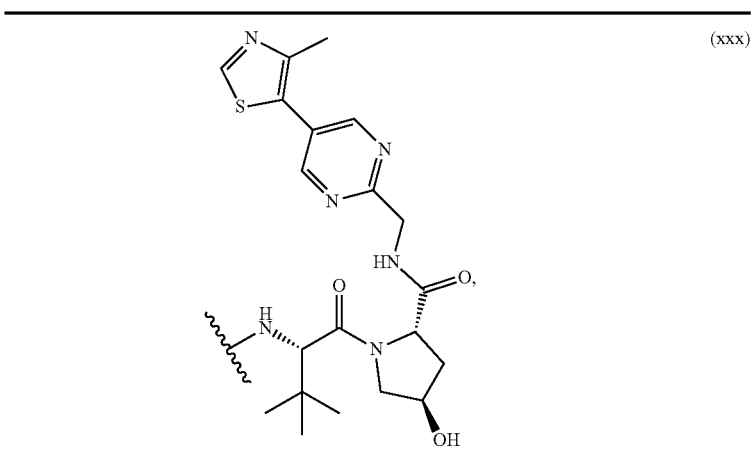 (xxx)
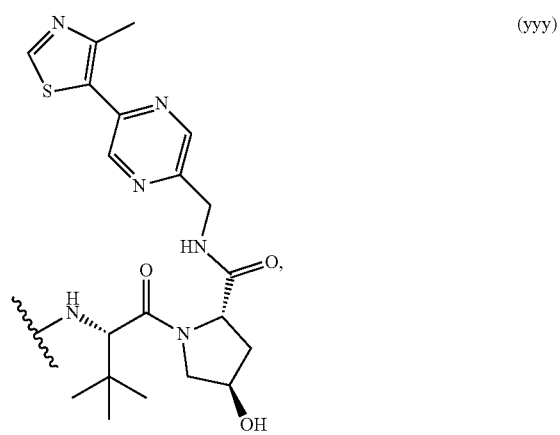 (yyy)
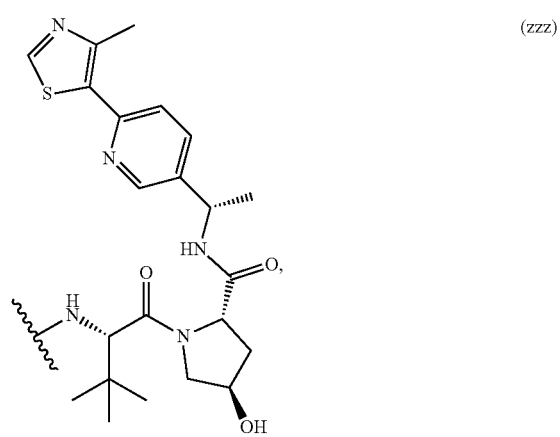 (zzz)
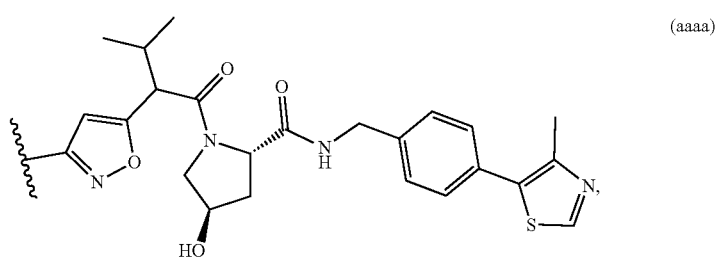 (aaaa)

TABLE A-continued
Exemplified E3 ligases (LBM)
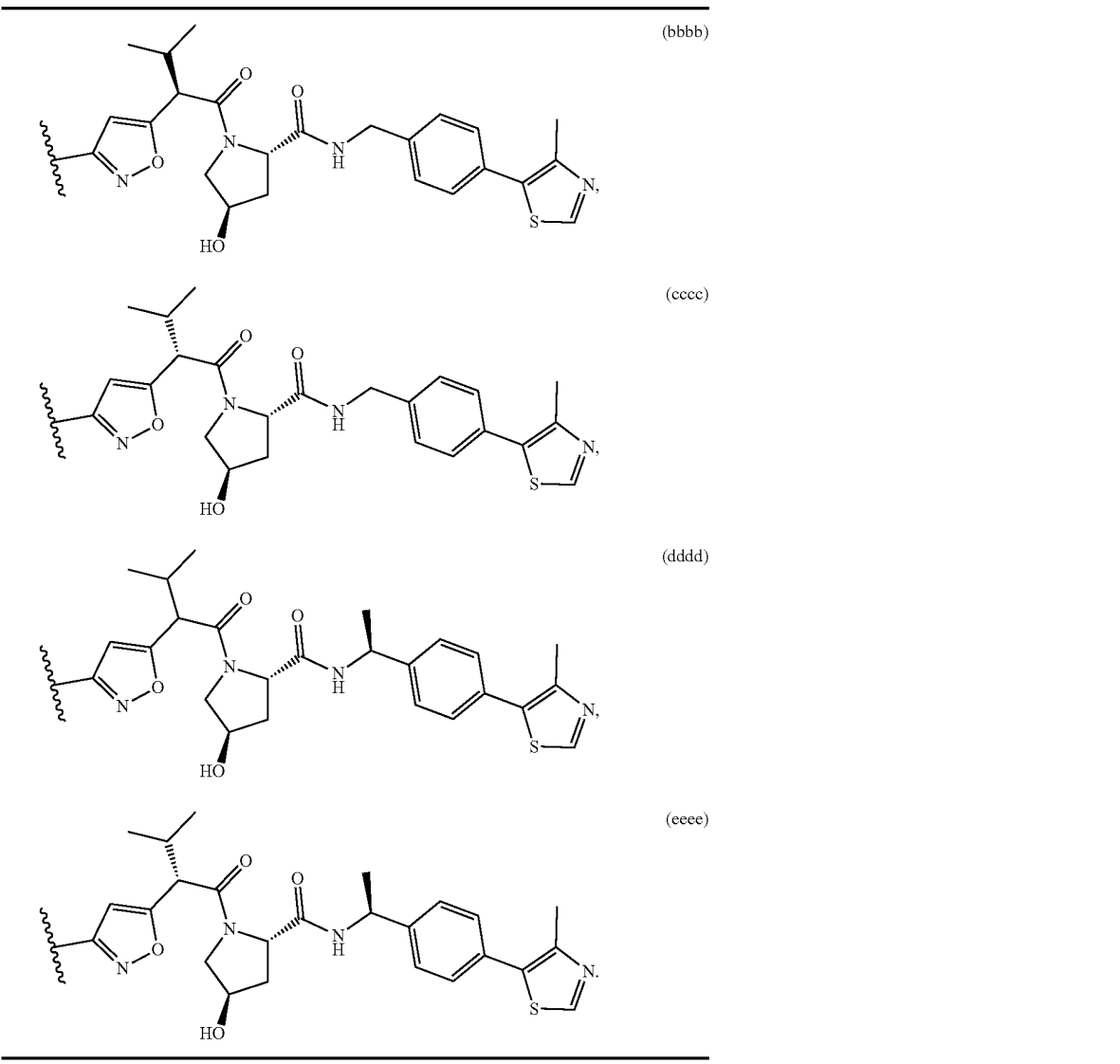
TABLE B
Exemplified Linkers (L)
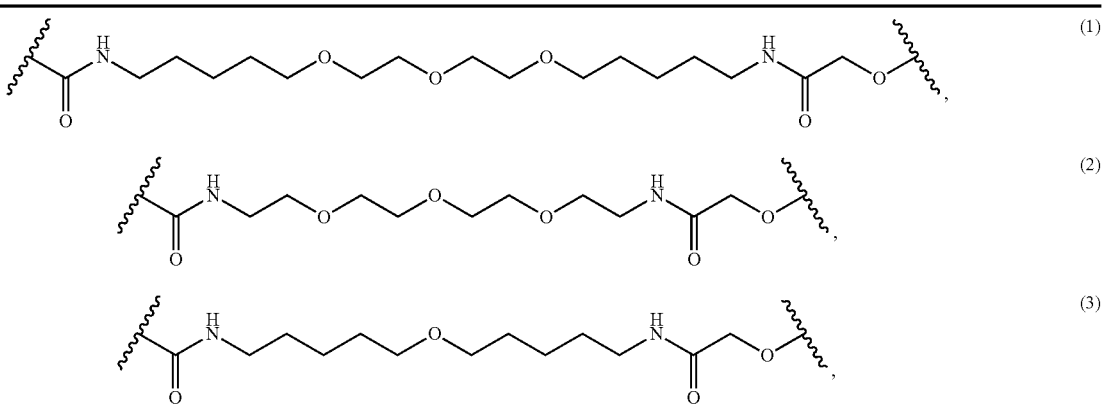

TABLE B-continued

Exemplified Linkers (L)

(4), (5), (6), (7), (8), (9), (10), (11), (12), (13), (14)

TABLE B-continued

Exemplified Linkers (L)

TABLE B-continued
Exemplified Linkers (L)
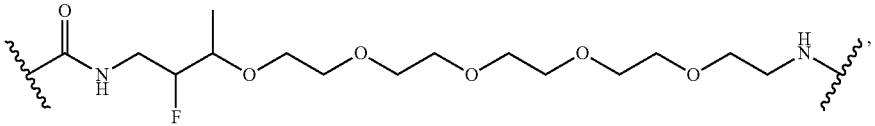 [SMILES: *NCCOCCOCCOCCOCCOC(C)C(F)CNC(*)=O]
(26)
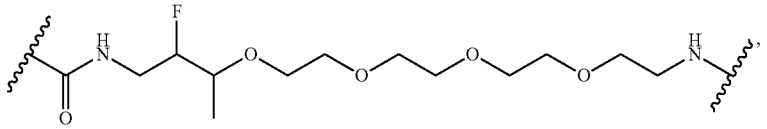 [SMILES: *NCCOCCOCCOCCOC(C)C(F)CNC(*)=O]
(27)
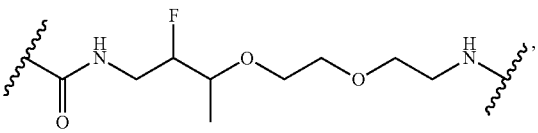 [SMILES: *NCCOCCOC(C)C(F)CNC(*)=O]
(28)
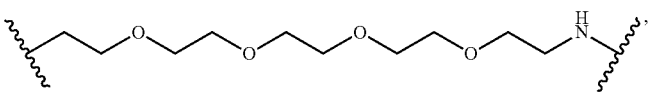 [SMILES: *CCOCCOCCOCCOCCN*]
(29)
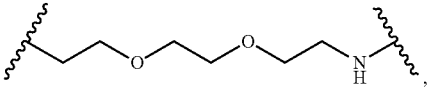 [SMILES: *CCOCCOCCN*]
(30)
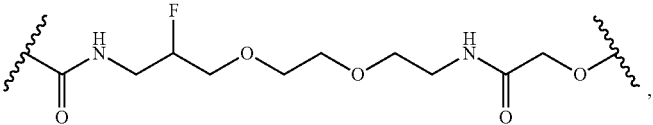 [SMILES: *OCC(=O)NCCOCCOCC(F)CNC(*)=O]
(31)
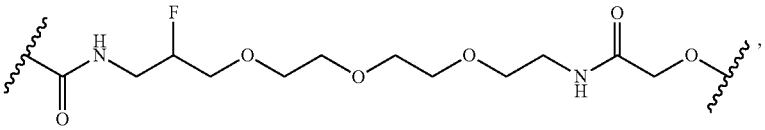 [SMILES: *OCC(=O)NCCOCCOCCOCC(F)CNC(*)=O]
(32)
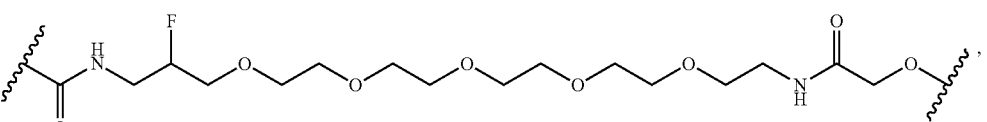
(33)
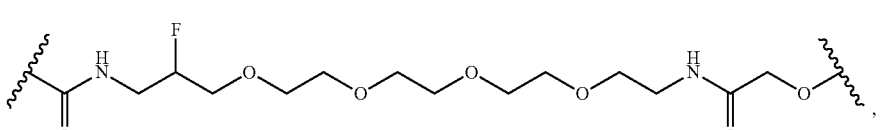
(34)
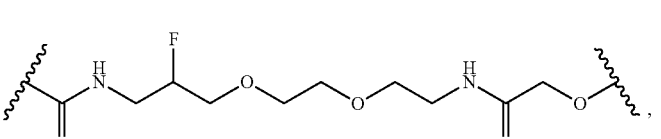
(35)
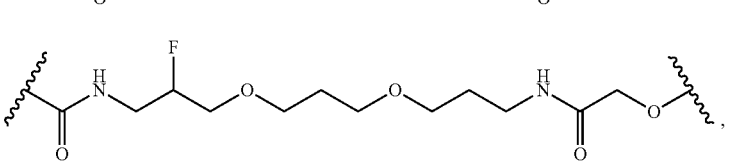
(36)

TABLE B-continued

Exemplified Linkers (L)

TABLE B-continued
Exemplified Linkers (L)
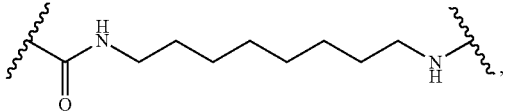 [SMILES: *NCCCCCCCCNC(*)=O] (49)
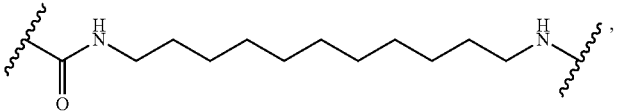 [SMILES: *NCCCCCCCCCCCNC(*)=O] (50)
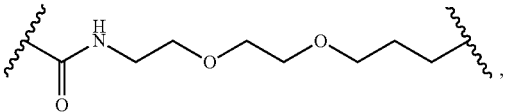 [SMILES: *CCCOCCOCCNC(*)=O] (51)
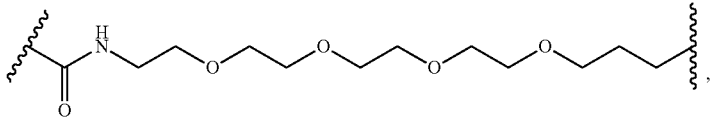 [SMILES: *CCCOCCOCCOCCOCCNC(*)=O] (52)
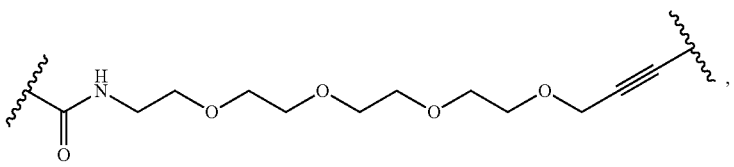 [SMILES: *C#CCOCCOCCOCCOCCNC(*)=O] (53)
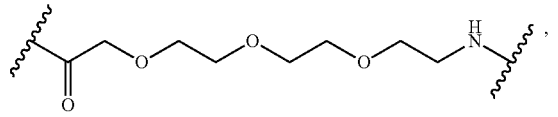 [SMILES: *NCCOCCOCCOCC(*)=O] (54)
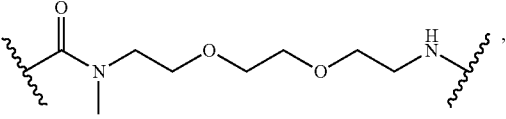 [SMILES: *NCCOCCOCCN(C)C(*)=O] (55)
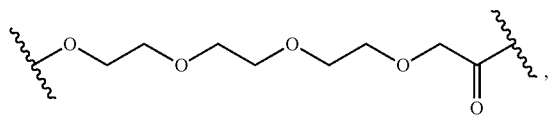 [SMILES: *OCCOCCOCCOCC(*)=O] (56)
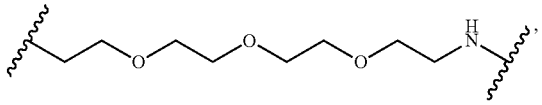 [SMILES: *CCOCCOCCOCCN*] (57)
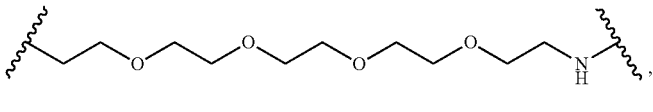 [SMILES: *CCOCCOCCOCCOCCN*] (58)
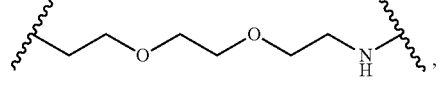 (59)
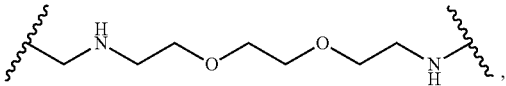 (60)

TABLE B-continued
Exemplified Linkers (L)
(61)
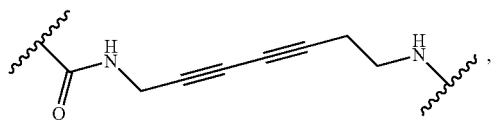 [SMILES: *NCCC#CC#CCNC(*)=O]
(62)
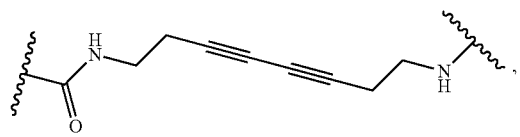 [SMILES: *NCCC#CC#CCCNC(*)=O]
(63)
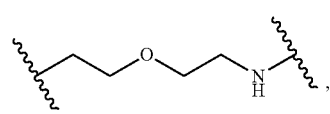 [SMILES: *CCOCCN*]
(64)
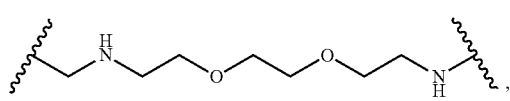 [SMILES: *CNCCOCCOCCN*]
(65)
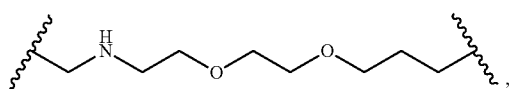 [SMILES: *CCCOCCOCCNC*]
(66)
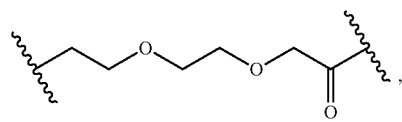 [SMILES: *CCOCCOCC(*)=O]
(67)
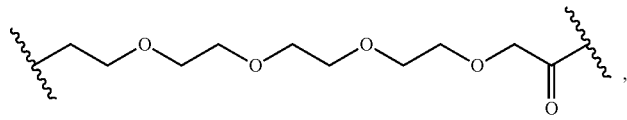 [SMILES: *CCOCCOCCOCCOCC(*)=O]
(68)
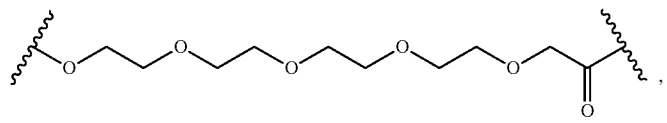 [SMILES: *OCCOCCOCCOCCOCC(*)=O]
(69)
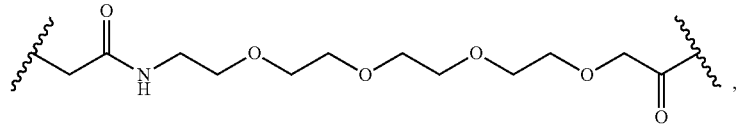 [SMILES: *CC(=O)NCCOCCOCCOCCOCC(*)=O]
(70)
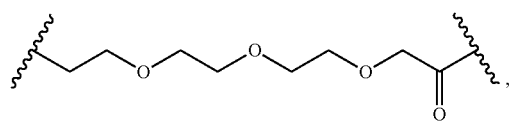 [SMILES: *CCOCCOCCOCC(*)=O]
(71)
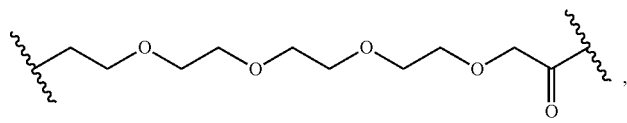 [SMILES: *CCOCCOCCOCCOCC(*)=O]
(72)

TABLE B-continued
Exemplified Linkers (L)
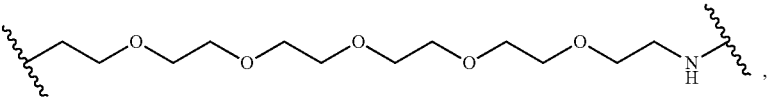 [SMILES: *CCOCCOCCOCCOCCOCCN*] (73)
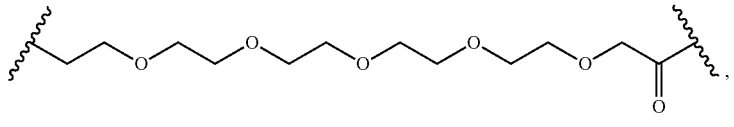 [SMILES: *CCOCCOCCOCCOCCOCC(*)=O] (74)
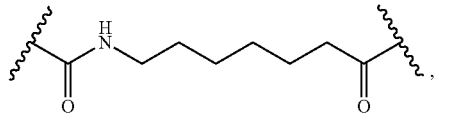 [SMILES: *C(=O)CCCCCCNC(*)=O] (75)
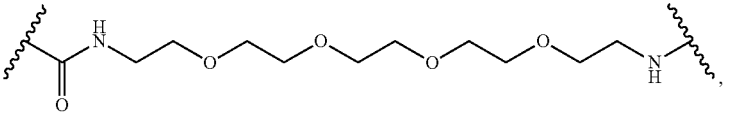 [SMILES: *NCCOCCOCCOCCOCCNC(*)=O] (76)
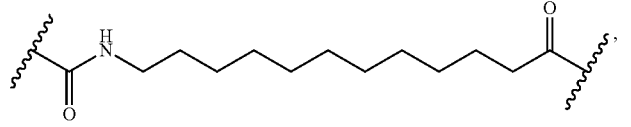 [SMILES: *C(=O)CCCCCCCCCCCNC(*)=O] (77)
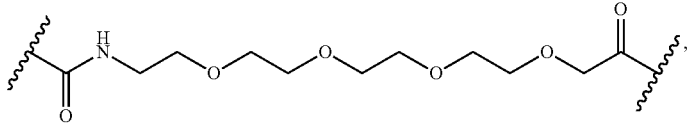 [SMILES: *C(=O)COCCOCCOCCOCCNC(*)=O] (78)
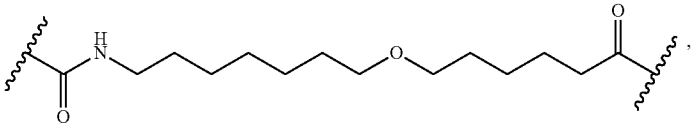 [SMILES: *C(=O)CCCCCOCCCCCCCNC(*)=O] (79)
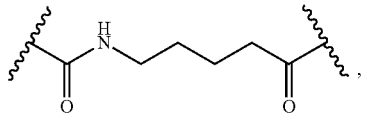 [SMILES: *C(=O)CCCCNC(*)=O] (80)
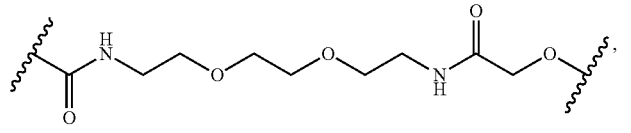 [SMILES: *OCC(=O)NCCOCCOCCNC(*)=O] (81)
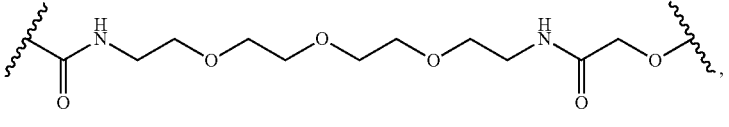 [SMILES: *OCC(=O)NCCOCCOCCOCCNC(*)=O] (82)
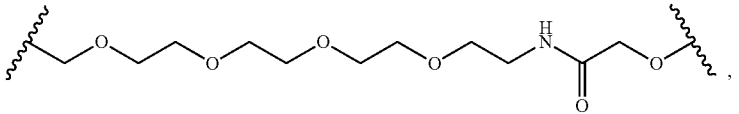 [SMILES: *COCCOCCOCCOCCNC(=O)CO*] (83)

TABLE B-continued

Exemplified Linkers (L)

TABLE B-continued

Exemplified Linkers (L)

(96)–(106) [chemical structures of linkers]

TABLE B-continued
Exemplified Linkers (L)
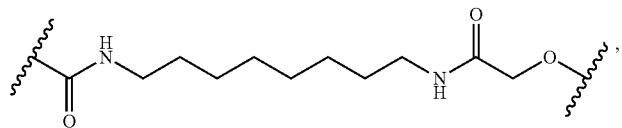 [SMILES: *OCC(=O)NCCCCCCCCNC(*)=O]
(107)
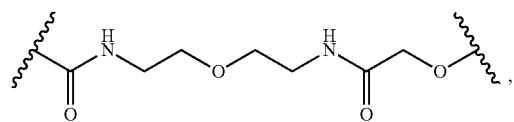 [SMILES: *OCC(=O)NCCOCCNC(*)=O]
(108)
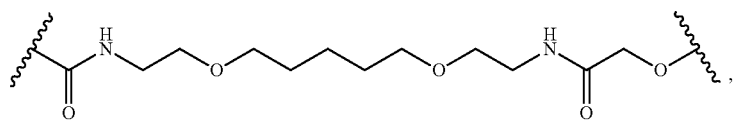 [SMILES: *OCC(=O)NCCOCCCCCOCCNC(*)=O]
(109)
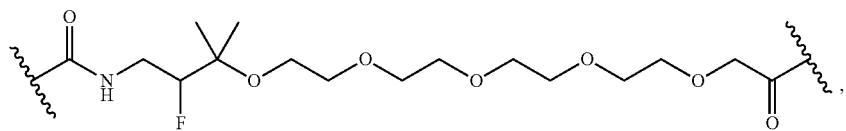 [SMILES: *C(=O)COCCOCCOCCOCCOC(C)(C)C(F)CNC(*)=O]
(110)
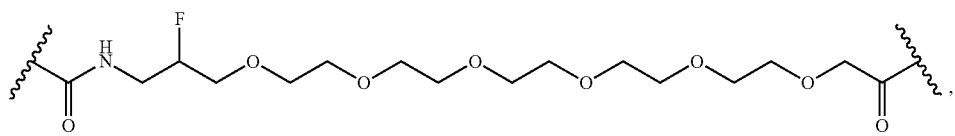 [SMILES: *C(=O)COCCOCCOCCOCCOCCOCC(F)CNC(*)=O]
(111)
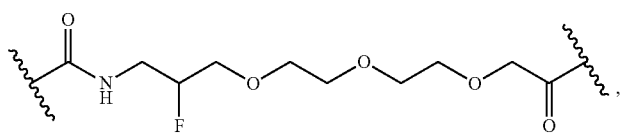 [SMILES: *C(=O)COCCOCCOCC(F)CNC(*)=O]
(112)
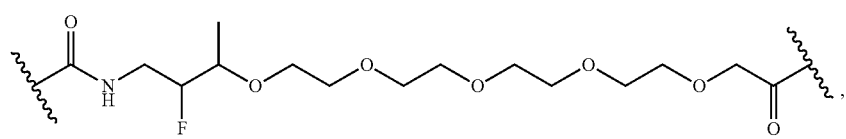 [SMILES: *C(=O)COCCOCCOCCOCCOC(C)C(F)CNC(*)=O]
(113)
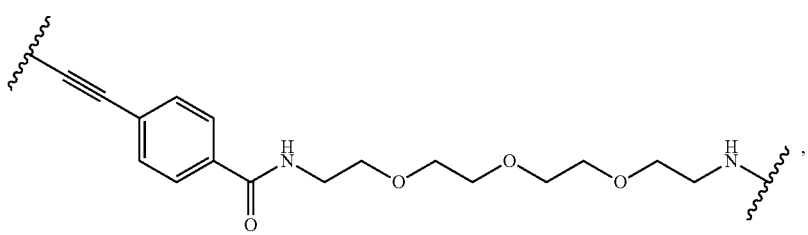 [SMILES: *C#Cc1ccc(C(=O)NCCOCCOCCOCCN*)cc1]
(114)
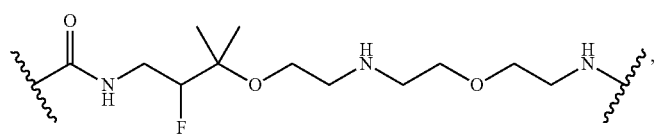 [SMILES: *NCCOCCNCCOC(C)(C)C(F)CNC(*)=O]
(115)
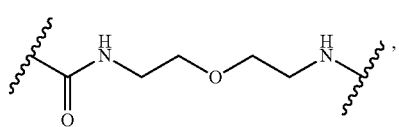 [SMILES: *NCCOCCNC(*)=O]
(116)

TABLE B-continued
Exemplified Linkers (L)
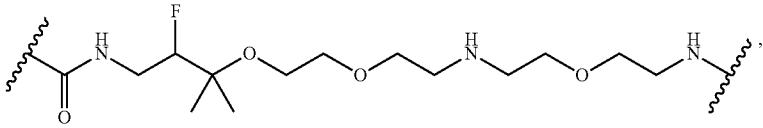 [SMILES: *NCCOCCNCCOCCOC(C)(C)C(F)CNC(*)=O] (117)
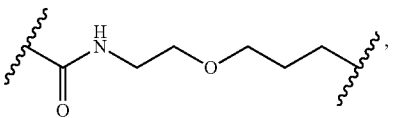 [SMILES: *CCCOCCNC(*)=O] (118)
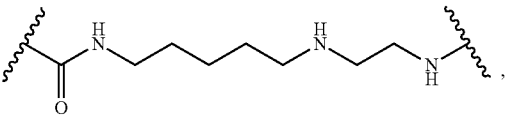 [SMILES: *NCCNCCCCCNC(*)=O] (119)
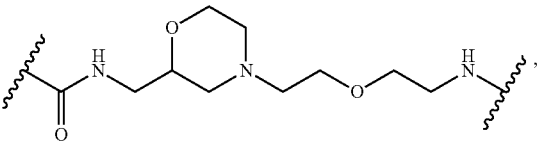 [SMILES: *NCCOCCN1CCOC(CNC(*)=O)C1] (120)
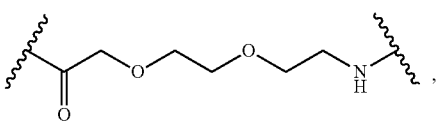 [SMILES: *NCCOCCOCC(*)=O] (121)
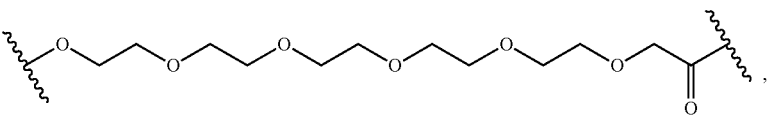 [SMILES: *OCCOCCOCCOCCOCCOCC(*)=O] (122)
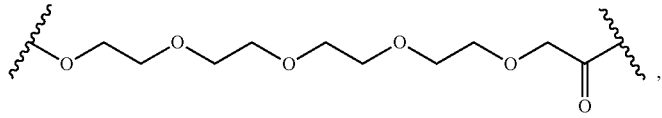 [SMILES: *OCCOCCOCCOCCOCC(*)=O] (123)
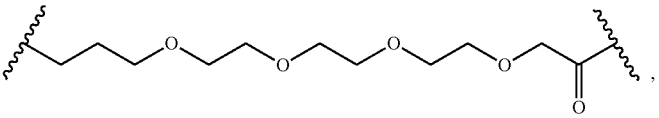 [SMILES: *CCCOCCOCCOCCOCC(*)=O] (124)
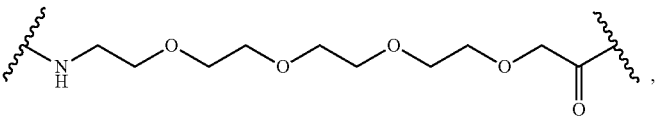 [SMILES: *NCCOCCOCCOCCOCC(*)=O] (125)

TABLE B-continued
Exemplified Linkers (L)
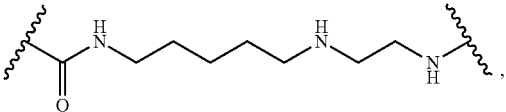 [SMILES: *NCCNCCCCCNC(*)=O] (126)
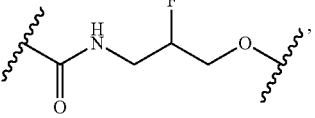 (127)
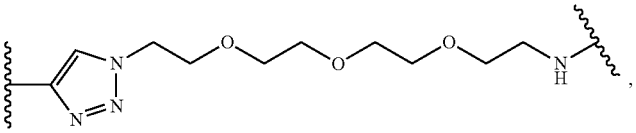 [SMILES: *NCCOCCOCCOCCn1cc(*)nn1] (128)
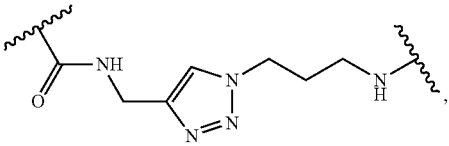 [SMILES: *NCCCn1cc(CNC(*)=O)nn1] (129)
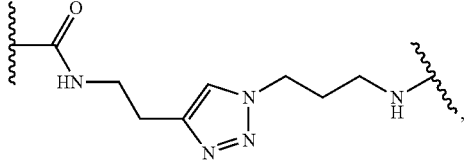 [SMILES: *NCCCn1cc(CCNC(*)=O)nn1] (130)
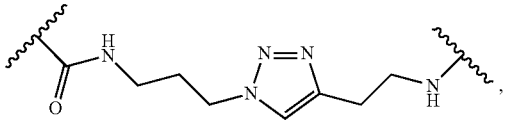 [SMILES: *NCCc1cn(CCCNC(*)=O)nn1] (131)
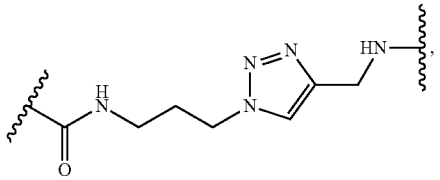 [SMILES: *NCc1cn(CCCNC(*)=O)nn1] (132)
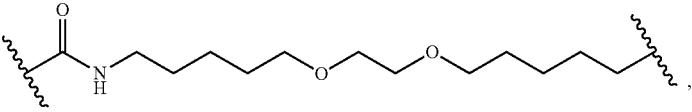 [SMILES: *CCCCCOCCOCCCCCNC(*)=O] (133)
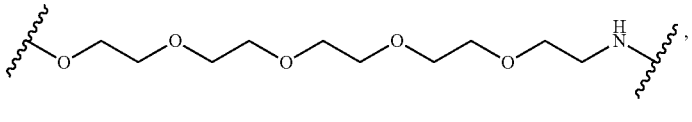 [SMILES: *NCCOCCOCCOCCOCCO*] (134)
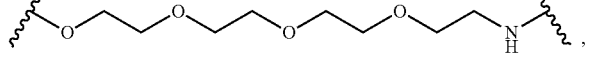 (135)

TABLE B-continued

Exemplified Linkers (L)

TABLE B-continued

Exemplified Linkers (L)

TABLE B-continued
Exemplified Linkers (L)
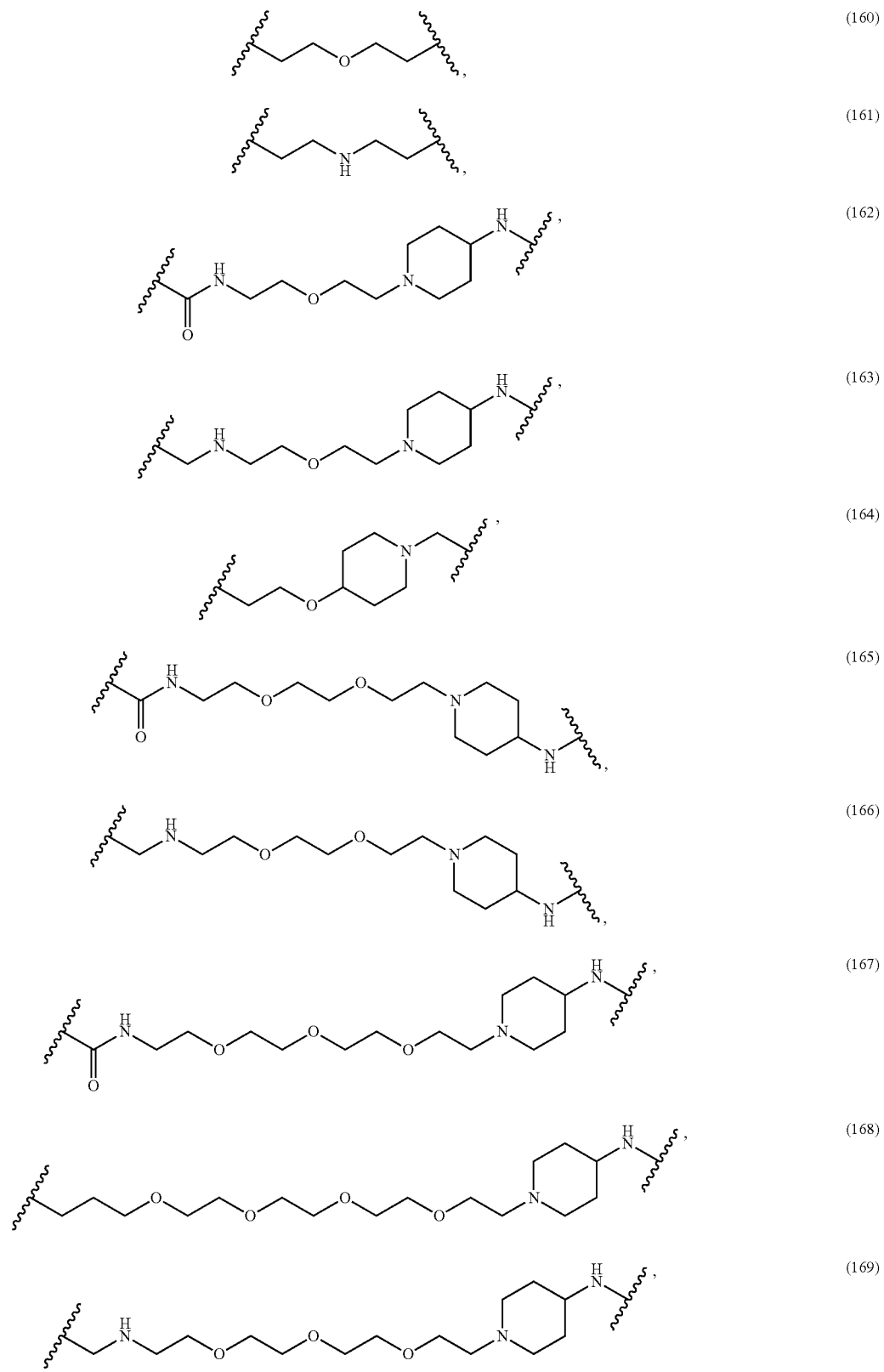

TABLE B-continued
Exemplified Linkers (L)
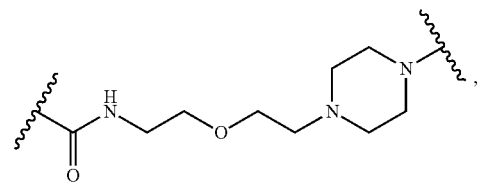 [SMILES: *C(=O)NCCOCCN1CCN(*)CC1] (170)
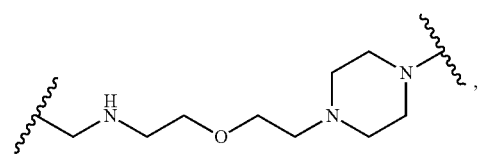 [SMILES: *CNCCOCCN1CCN(*)CC1] (171)
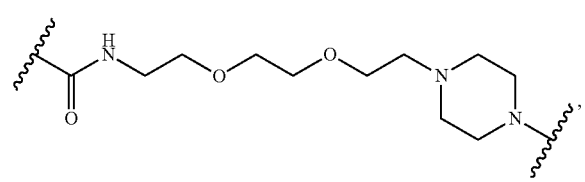 [SMILES: *C(=O)NCCOCCOCCN1CCN(*)CC1] (172)
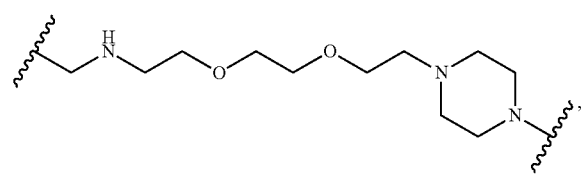 [SMILES: *CNCCOCCOCCN1CCN(*)CC1] (173)
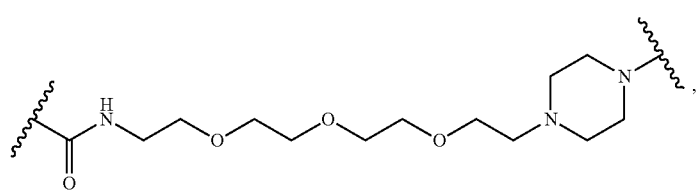 [SMILES: *C(=O)NCCOCCOCCOCCN1CCN(*)CC1] (174)
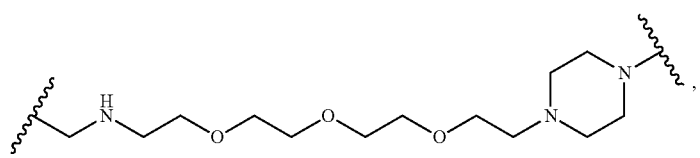 [SMILES: *CNCCOCCOCCOCCN1CCN(*)CC1] (175)
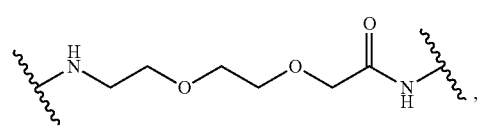 [SMILES: *NCCOCCOCC(=O)N*] (176)
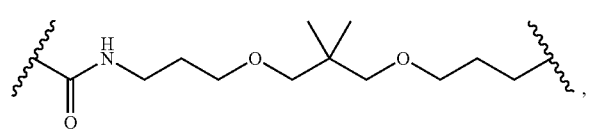 [SMILES: *CCCOCC(C)(C)COCCCNC(*)=O] (177)
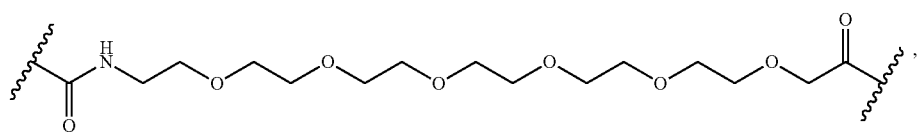 [SMILES: *C(=O)COCCOCCOCCOCCOCCOCCNC(*)=O] (178)
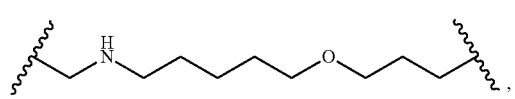 [SMILES: *CCCOCCCCCNC*] (179)

TABLE B-continued

Exemplified Linkers (L)

(180)

(181)

(182)

(183)

(184)

(185)

(186)

(187)

(188)

(189)

(190)

(191)

(192)

TABLE B-continued

Exemplified Linkers (L)

(193) *–CH2–NH–CH2CH2–O–CH2CH2–O–CH2CH2–*

(194) *–C(O)–N(CH3)–CH2CH2–O–CH2CH2CH2CH2–*

(195) *–CH2–N(CH3)–CH2CH2CH2–O–CH2CH2CH2CH2CH2–*

(196) *–C(O)–N(CH3)–CH2CH2–O–CH2CH2–O–CH2CH2–*

(197) *–CH2–NH–CH2CH2–O–CH2CH2–O–CH2CH2CH2–*

(198) *–C(O)–NH–CH2CH2–O–CH2CH2–O–CH2CH2CH2–*

(199) *–CH2–N(CH3)–CH2CH2–O–CH2CH2–O–CH2CH2CH2–*

(200) *–CH(CH3)–NH–CH2CH2–O–CH2CH2–O–CH2CH2CH2–*

(201) *–CH2–NH–CH2CH2CH2–O–CH2CH2CH2–O–CH2CH2CH2CH2–*

(202) *–CH2–NH–CH2CH2–O–CH2CH2–O–CH2CH2–O–CH2CH2–O–CH2CH2CH2–*

(203) *–C(O)–NH–CH2CH2–O–CH2CH2–O–CH2CH2–O–CH2CH2–O–CH2CH2CH2–*

(204) *–CH2–NH–CH2CH2–O–CH2CH2–O–CH2CH2–O–CH2CH2–O–CH2–C≡C–*

(205) *–CH2–NH–CH2CH2–O–CH2CH2–O–CH2CH2–O–CH2CH2CH2–*

TABLE B-continued
Exemplified Linkers (L)
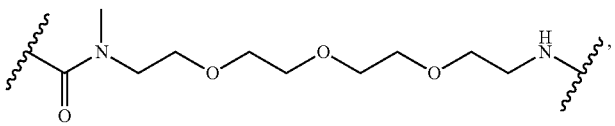 [SMILES: *NCCOCCOCCOCCN(C)C(*)=O] (206)
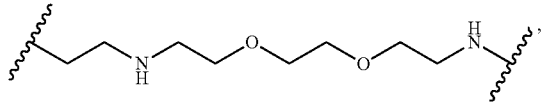 [SMILES: *CCNCCOCCOCCN*] (207)
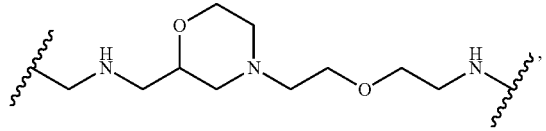 [SMILES: *CNCC1CN(CCOCCN*)CCO1] (208)
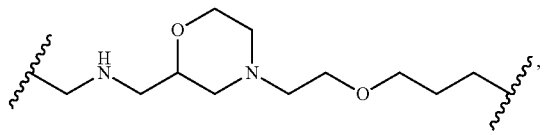 [SMILES: *CCCOCCN1CCOC(CNC*)C1] (209)
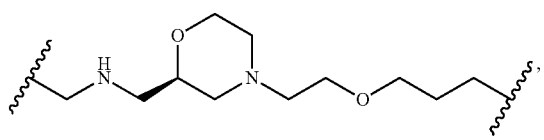 [SMILES: *CCCOCCN1CCO[C@H](CNC*)C1] (210)
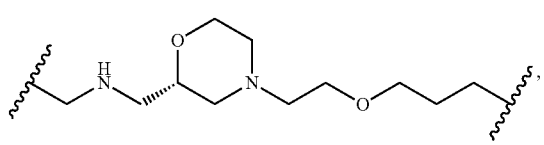 [SMILES: *CCCOCCN1CCO[C@@H](CNC*)C1] (211)
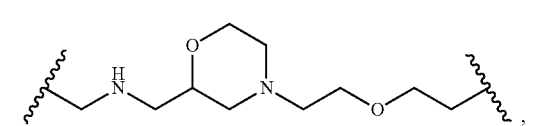 [SMILES: *CCOCCN1CCOC(CNC*)C1] (212)
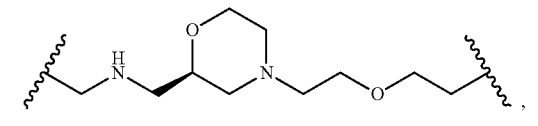 [SMILES: *CCOCCN1CCO[C@H](CNC*)C1] (213)
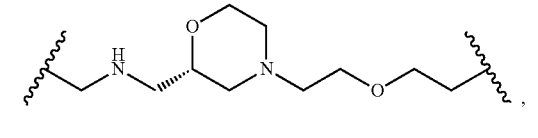 (214)
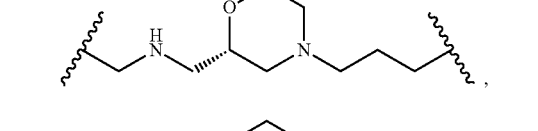 (215)
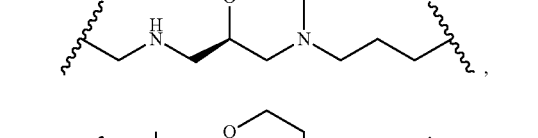 (216)
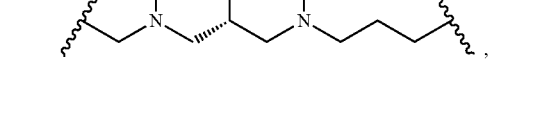 (217)

TABLE B-continued
Exemplified Linkers (L)
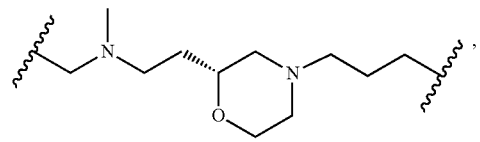 [SMILES: *CCCN1CCO[C@H](CCN(C)C*)C1] (218)
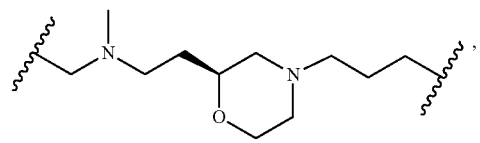 [SMILES: *CCCN1CCO[C@@H](CCN(C)C*)C1] (219)
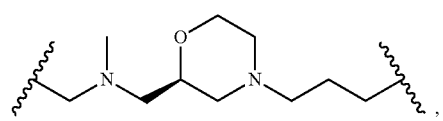 [SMILES: *CCCN1CCO[C@H](CN(C)C*)C1] (220)
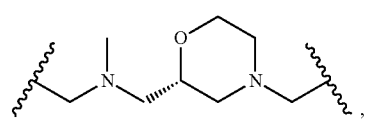 [SMILES: *CN(C)C[C@H]1CN(C*)CCO1] (221)
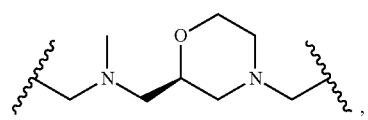 [SMILES: *CN(C)C[C@@H]1CN(C*)CCO1] (222)
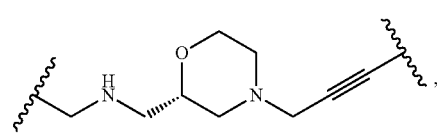 [SMILES: *C#CCN1CCO[C@@H](CNC*)C1] (223)
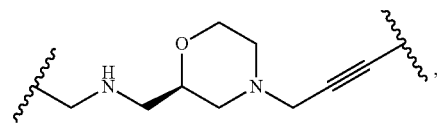 [SMILES: *C#CCN1CCO[C@H](CNC*)C1] (224)
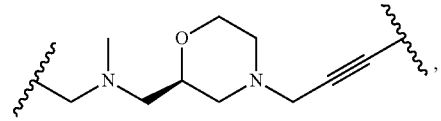 [SMILES: *C#CCN1CCO[C@H](CN(C)C*)C1] (225)
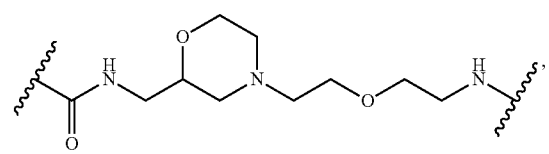 [SMILES: *NCCOCCN1CCOC(CNC(*)=O)C1] (226)
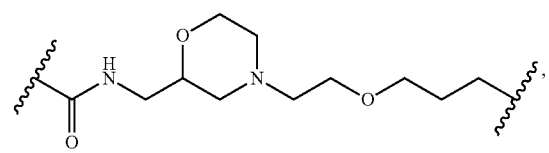 [SMILES: *CCCOCCN1CCOC(CNC(*)=O)C1] (227)
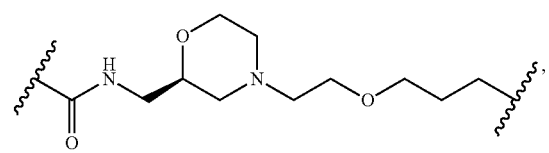 [SMILES: *CCCOCCN1CCO[C@H](CNC(*)=O)C1] (228)

TABLE B-continued
Exemplified Linkers (L)
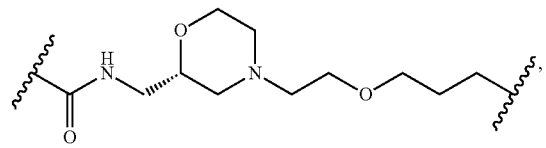 [SMILES: *CCCOCCN1CCO[C@@H](CNC(*)=O)C1] (229)
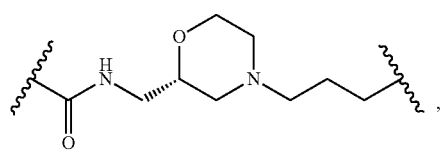 [SMILES: *CCCN1CCO[C@@H](CNC(*)=O)C1] (230)
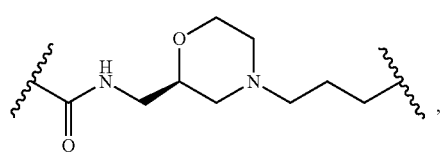 [SMILES: *CCCN1CCO[C@H](CNC(*)=O)C1] (231)
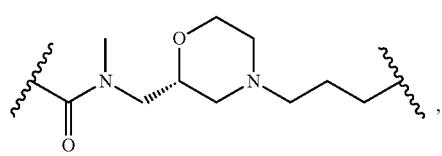 [SMILES: *CCCN1CCO[C@@H](CN(C)C(*)=O)C1] (232)
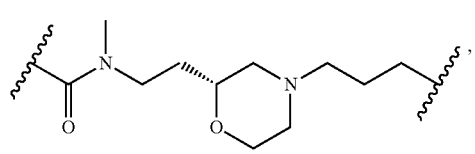 [SMILES: *CCCN1CCO[C@H](CCN(C)C(*)=O)C1] (233)
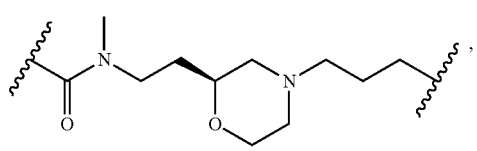 [SMILES: *CCCN1CCO[C@@H](CCN(C)C(*)=O)C1] (234)
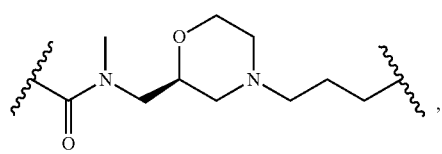 [SMILES: *CCCN1CCO[C@H](CN(C)C(*)=O)C1] (235)
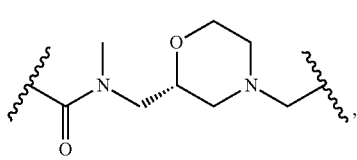 [SMILES: *CN1CCO[C@@H](CN(C)C(*)=O)C1] (236)
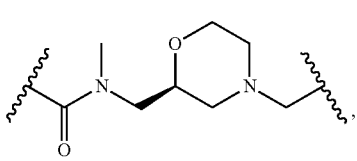 [SMILES: *CN1CCO[C@H](CN(C)C(*)=O)C1] (237)
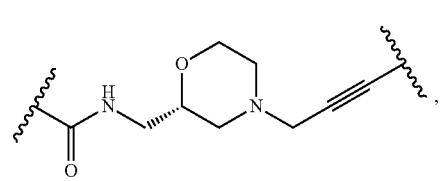 [SMILES: *C#CCN1CCO[C@@H](CNC(*)=O)C1] (238)

TABLE B-continued
Exemplified Linkers (L)
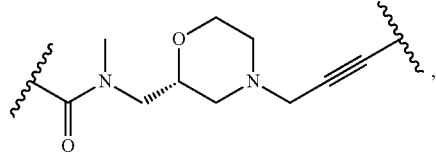 [SMILES: *C#CCN1CCO[C@@H](CN(C)C(*)=O)C1]
(239)
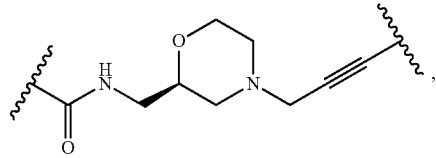 [SMILES: *C#CCN1CCO[C@H](CNC(*)=O)C1]
(240)
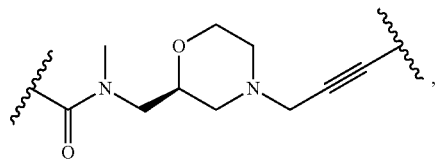 [SMILES: *C#CCN1CCO[C@H](CN(C)C(*)=O)C1]
(241)
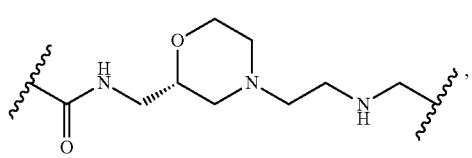 [SMILES: *CNCCN1CCO[C@@H](CNC(*)=O)C1]
(242)
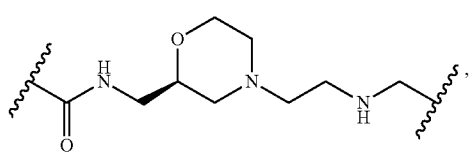 [SMILES: *CNCCN1CCO[C@H](CNC(*)=O)C1]
(243)
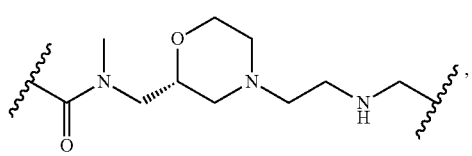 [SMILES: *CNCCN1CCO[C@@H](CN(C)C(*)=O)C1]
(244)
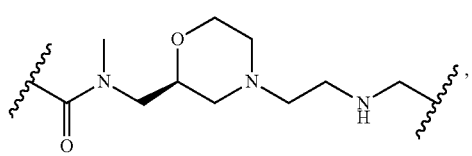 [SMILES: *CNCCN1CCO[C@H](CN(C)C(*)=O)C1]
(245)
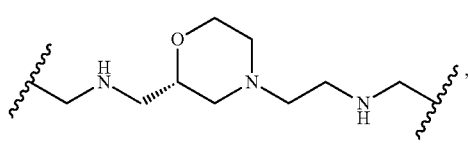 [SMILES: *CNCCN1CCO[C@@H](CNC*)C1]
(246)
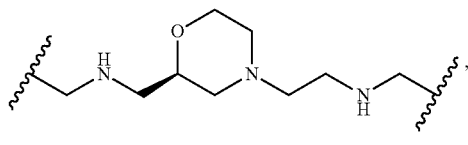 [SMILES: *CNCCN1CCO[C@H](CNC*)C1]
(247)
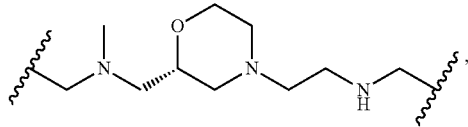 [SMILES: *CNCCN1CCO[C@@H](CN(C)C*)C1]
(248)

TABLE B-continued
Exemplified Linkers (L)
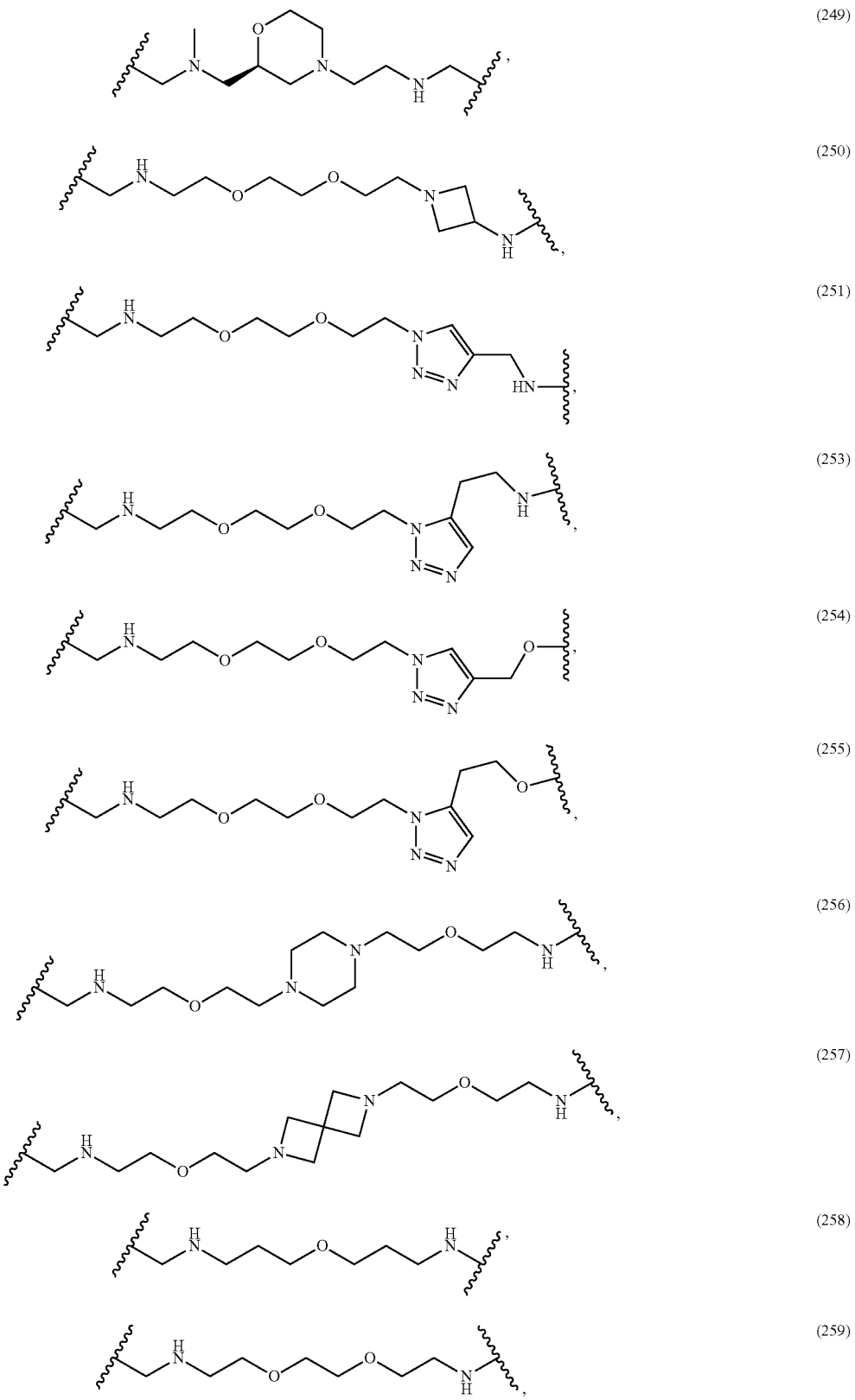

TABLE B-continued

Exemplified Linkers (L)

(260) [chemical structure]

(261) [chemical structure]

(262) [chemical structure]

(263) [chemical structure]

(264) [chemical structure]

(265) [chemical structure]

(266) [chemical structure]

(267) [chemical structure]

(268) [chemical structure]

(269) [chemical structure]

(270) [chemical structure]

TABLE B-continued
Exemplified Linkers (L)
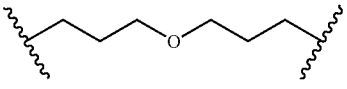 (271)
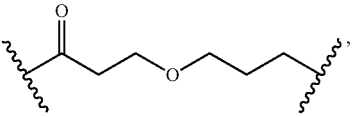 [SMILES: *CCCOCCC(*)=O] (272)
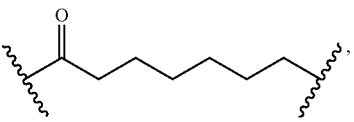 [SMILES: *CCCCCCC(*)=O] (273)
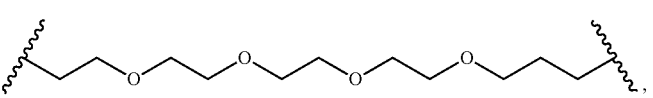 [SMILES: *CCCOCCOCCOCCOCC*] (274)
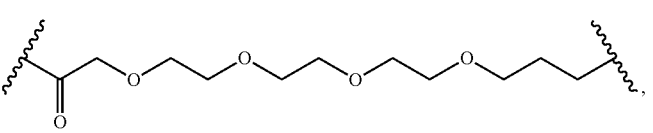 [SMILES: *CCCOCCOCCOCCOCC(*)=O] (275)
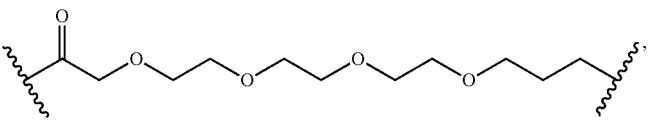 [SMILES: *CCCOCCOCCOCCOCC(*)=O] (276)
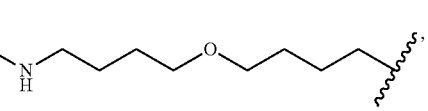 (277)
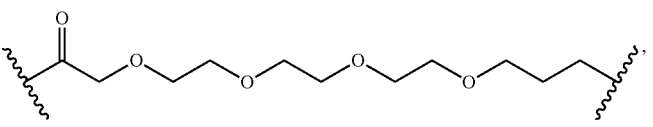 [SMILES: *CCCOCCOCCOCCOCC(*)=O] (278)
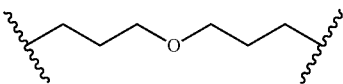 (279)
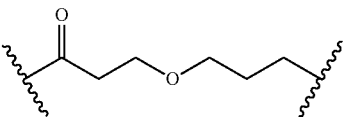 (280)
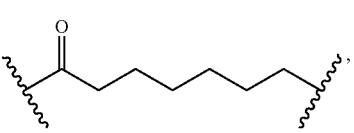 [SMILES: *CCCCCCC(*)=O] (281)
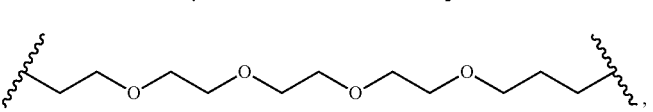 (282)
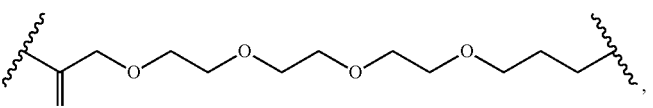 (283)

TABLE B-continued
Exemplified Linkers (L)
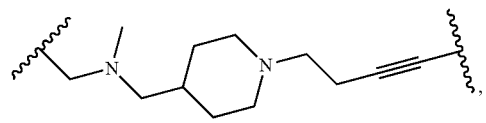 [SMILES: *C#CCCN1CCC(CN(C)C*)CC1] (284)
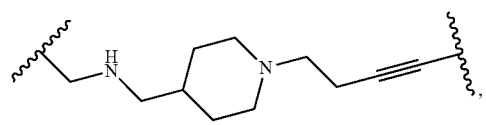 [SMILES: *C#CCCN1CCC(CNC*)CC1] (285)
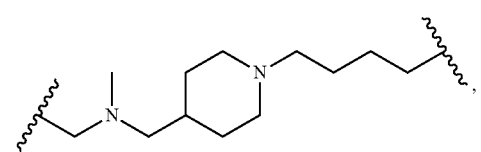 [SMILES: *CCCCN1CCC(CN(C)C*)CC1] (286)
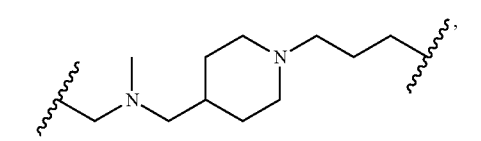 [SMILES: *CCCN1CCC(CN(C)C*)CC1] (287)
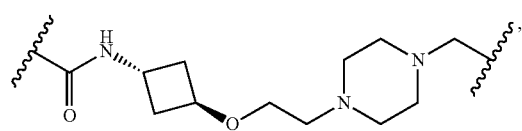 [SMILES: *CN1CCN(CCO[C@H]2C[C@H](NC(*)=O)C2)CC1] (288)
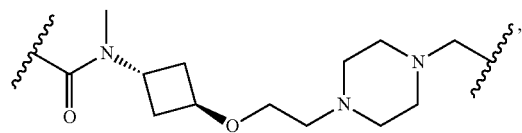 [SMILES: *CN1CCN(CCO[C@H]2C[C@H](N(C)C(*)=O)C2)CC1] (289)
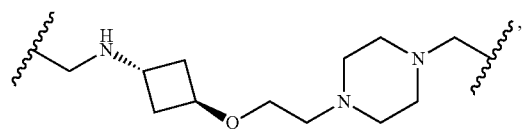 [SMILES: *CN[C@H]1C[C@H](OCCN2CCN(C*)CC2)C1] (290)
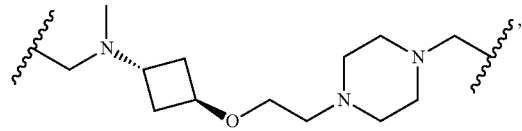 [SMILES: *CN1CCN(CCO[C@H]2C[C@H](N(C)C*)C2)CC1] (291)
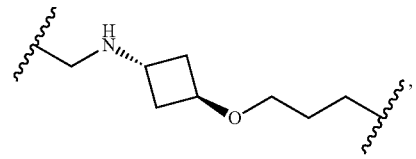 [SMILES: *CCCO[C@H]1C[C@H](NC*)C1] (292)
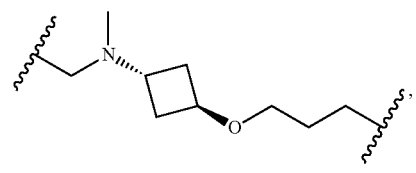 [SMILES: *CCCO[C@H]1C[C@H](N(C)C*)C1] (293)

TABLE B-continued
Exemplified Linkers (L)
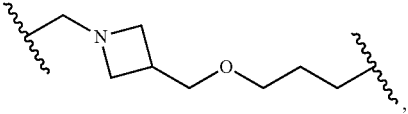 [SMILES: *CCCOCC1CN(C*)C1] (294)
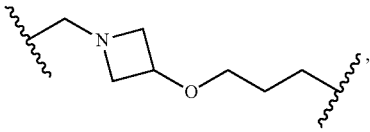 [SMILES: *CCCOC1CN(C*)C1] (295)
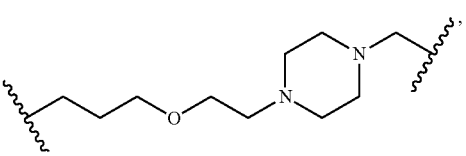 [SMILES: *CCCOCCN1CCN(C*)CC1] (296)
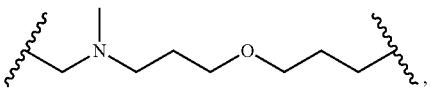 [SMILES: *CCCOCCCN(C)C*] (297)
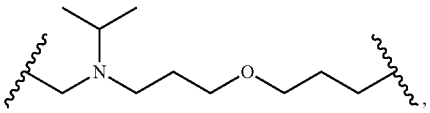 [SMILES: *CCCOCCCN(C*)C(C)C] (298)
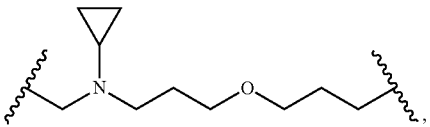 [SMILES: *CCCOCCCN(C*)C1CC1] (299)
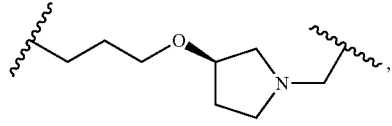 [SMILES: *CCCO[C@@H]1CCN(C*)C1] (300)
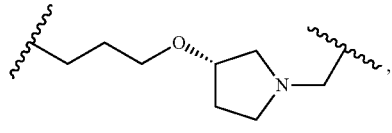 [SMILES: *CCCO[C@H]1CCN(C*)C1] (301)
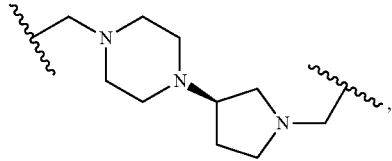 [SMILES: *CN1CCN([C@@H]2CCN(C*)C2)CC1] (302)
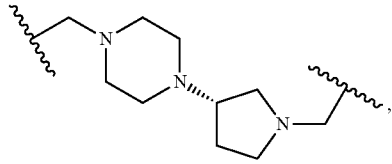 [SMILES: *CN1CCN([C@H]2CCN(C*)C2)CC1] (303)
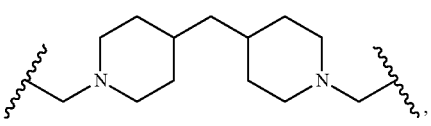 [SMILES: *CN1CCC(CC2CCN(C*)CC2)CC1] (304)

TABLE B-continued
Exemplified Linkers (L)
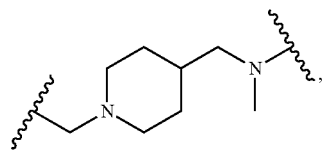 [SMILES: *CN1CCC(CN(*)C)CC1] (305)
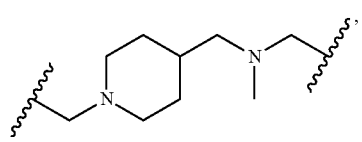 [SMILES: *CN(C)CC1CCN(C*)CC1] (306)
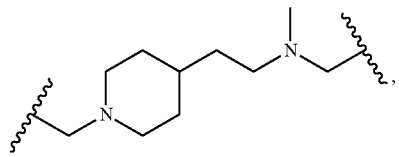 [SMILES: *CN(C)CCC1CCN(C*)CC1] (307)
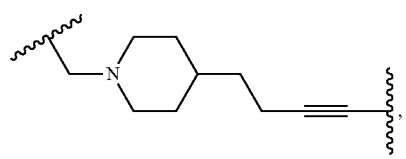 [SMILES: *C#CCCC1CCN(C*)CC1] (308)
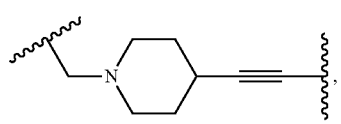 [SMILES: *C#CC1CCN(C*)CC1] (309)
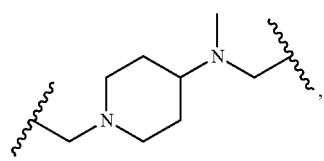 [SMILES: *CN1CCC(N(C)C*)CC1] (310)
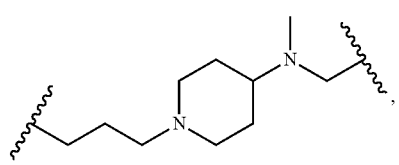 [SMILES: *CCCN1CCC(N(C)C*)CC1] (311)
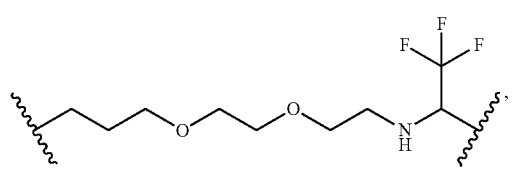 [SMILES: *CCCOCCOCCNC(*)C(F)(F)F] (312)
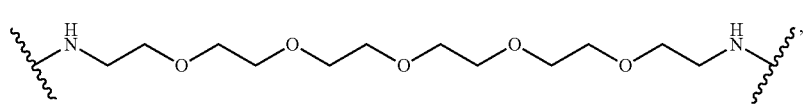 [SMILES: *NCCOCCOCCOCCOCCOCCN*] (313)
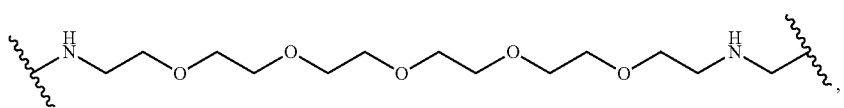 [SMILES: *CNCCOCCOCCOCCOCCOCCN*] (314)

TABLE B-continued

Exemplified Linkers (L)

TABLE B-continued
Exemplified Linkers (L)
 (326)
 (327)
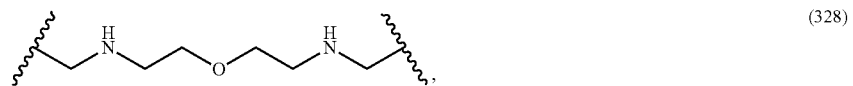 (328)
 (329)
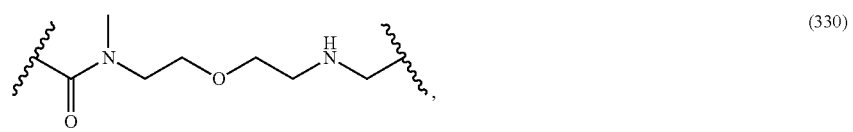 (330)
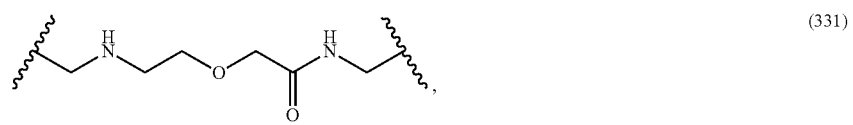 (331)
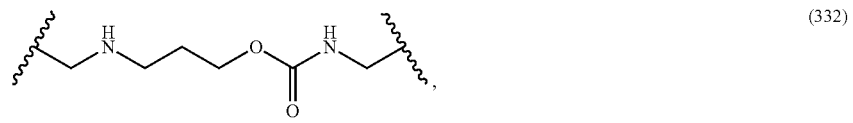 (332)
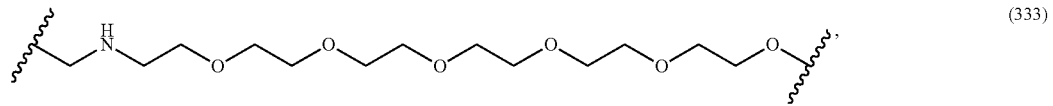 (333)
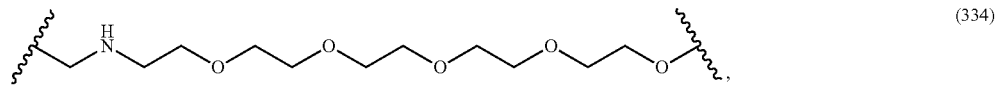 (334)
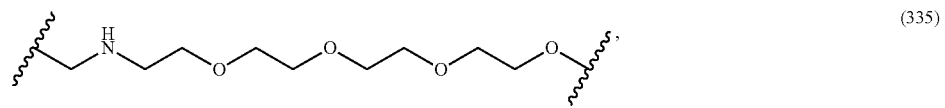 (335)
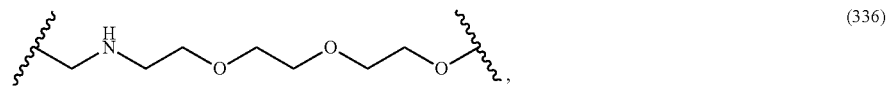 (336)
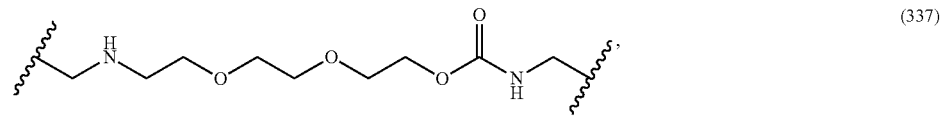 (337)
 (338)

TABLE B-continued
Exemplified Linkers (L)
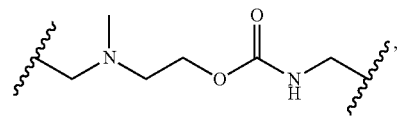 [SMILES: *CNC(=O)OCCN(C)C*] (339)
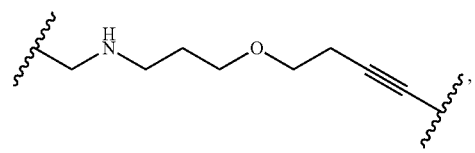 [SMILES: *C#CCCOCCCNC*] (340)
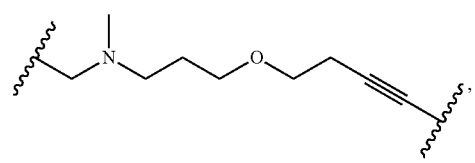 [SMILES: *C#CCCOCCCN(C)C*] (341)
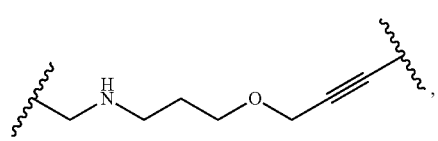 [SMILES: *C#CCOCCCNC*] (342)
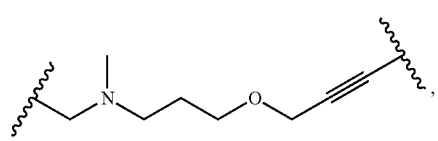 [SMILES: *C#CCOCCCN(C)C*] (343)
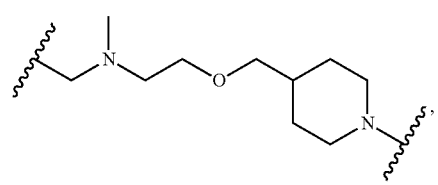 [SMILES: *CN(C)CCOCC1CCN(*)CC1] (344)
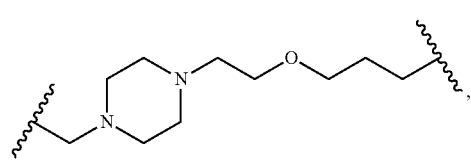 [SMILES: *CCCOCCN1CCN(C*)CC1] (345)
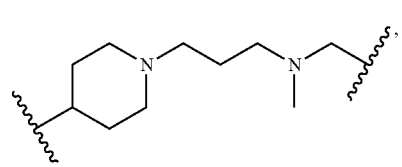 [SMILES: *CN(C)CCCN1CCC(*)CC1] (346)
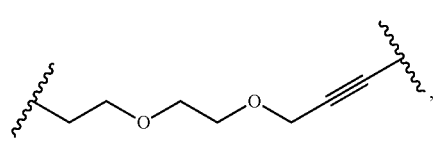 [SMILES: *C#CCOCCOCC*] (347)

TABLE B-continued
Exemplified Linkers (L)
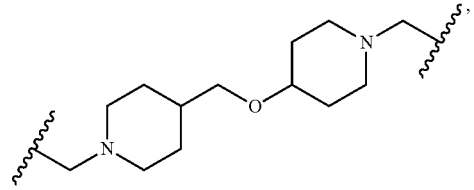 [SMILES: *CN1CCC(COC2CCN(C*)CC2)CC1] (348)
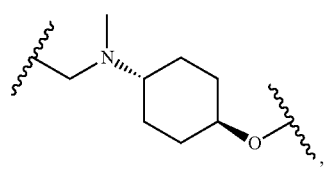 [SMILES: *CN(C)[C@H]1CC[C@H](O*)CC1] (349)
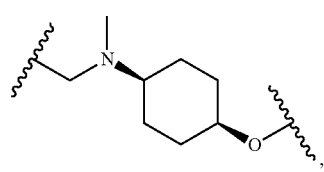 [SMILES: *CN(C)[C@H]1CC[C@@H](O*)CC1] (350)
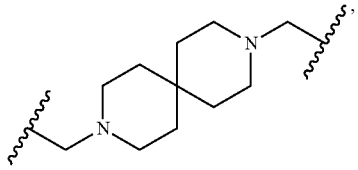 [SMILES: *CN1CCC2(CC1)CCN(C*)CC2] (351)
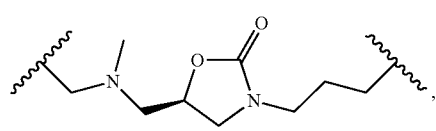 [SMILES: *CCCN1C[C@@H](CN(C)C*)OC1=O] (352)
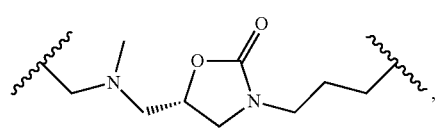 [SMILES: *CCCN1C[C@H](CN(C)C*)OC1=O] (353)
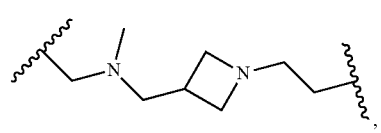 [SMILES: *CCN1CC(CN(C)C*)C1] (354)
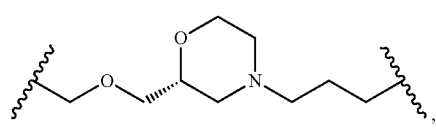 [SMILES: *CCCN1CCO[C@@H](COC*)C1] (355)
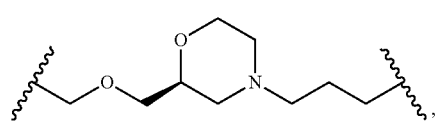 [SMILES: *CCCN1CCO[C@H](COC*)C1] (356)

TABLE B-continued
Exemplified Linkers (L)
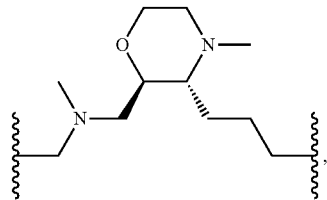 [SMILES: *CCC[C@@H]1[C@@H](CN(C)C*)OCCN1C]
(357)
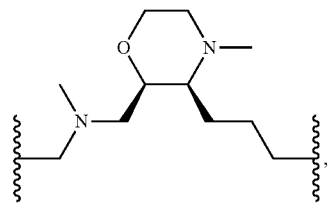 [SMILES: *CCC[C@H]1[C@@H](CN(C)C*)OCCN1C]
(358)
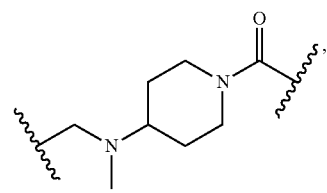 [SMILES: *CN(C)C1CCN(C(*)=O)CC1]
(359)
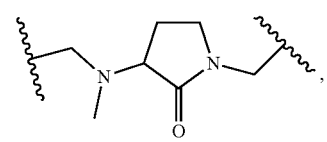 [SMILES: *CN1CCC(N(C)C*)C1=O]
(360)
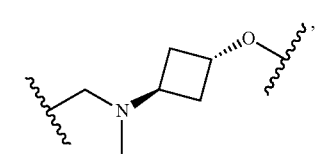 [SMILES: *CN(C)[C@H]1C[C@H](O*)C1]
(361)
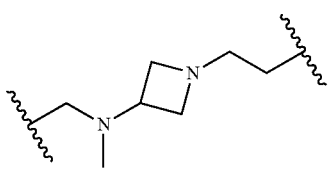
(362)
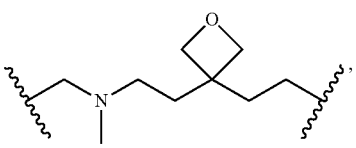 [SMILES: *CCC1(CCN(C)C*)COC1]
(363)
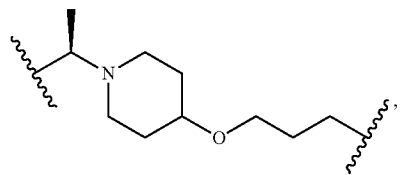 [SMILES: *CCCOC1CCN([C@@H](*)C)CC1]
(364)

TABLE B-continued
Exemplified Linkers (L)
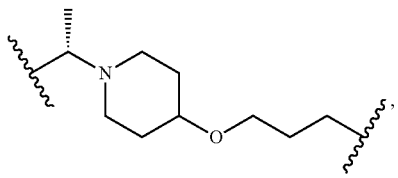 [SMILES: *CCCOC1CCN([C@H](*)C)CC1] (365)
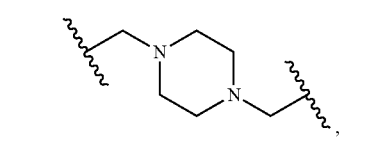 (366)
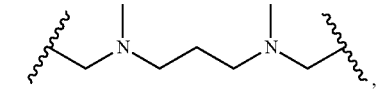 (367)
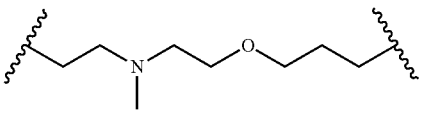 (368)
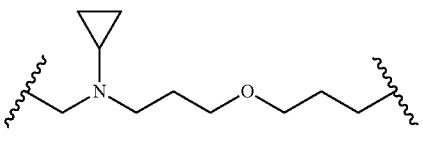 (369)
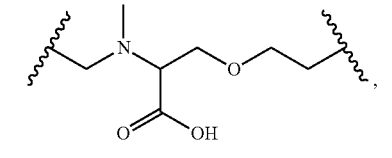 [SMILES: *CCOCC(C(=O)O)N(C)C*] (370)
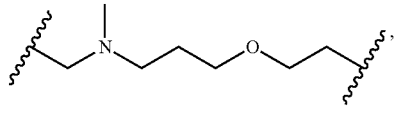 [SMILES: *CCOCCCN(C)C*] (371)
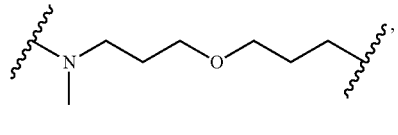 [SMILES: *CCCOCCCN(*)C] (372)
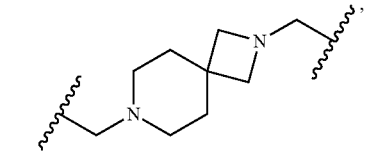 [SMILES: *CN1CCC2(CC1)CN(C*)C2] (373)
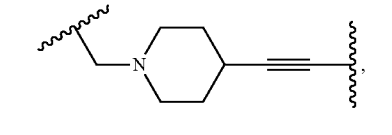 (374)
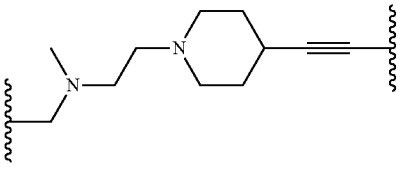 (375)

TABLE B-continued
Exemplified Linkers (L)
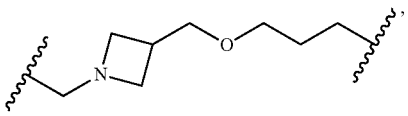 [SMILES: *CCCOCC1CN(C*)C1] (376)
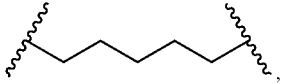 (377)
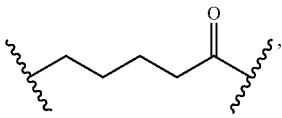 [SMILES: *CCCCC(*)=O] (378)
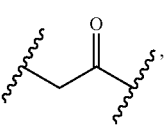 [SMILES: *CC(*)=O] (379)
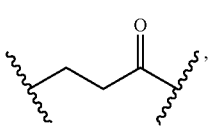 [SMILES: *CCC(*)=O] (380)
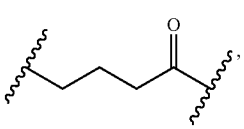 [SMILES: *CCCC(*)=O] (381)
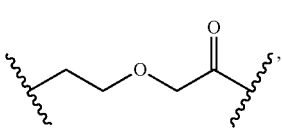 [SMILES: *CCOCC(*)=O] (382)
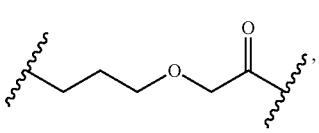 [SMILES: *CCCOCC(*)=O] (383)
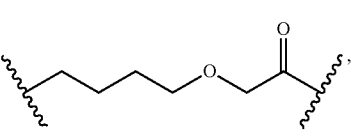 [SMILES: *CCCCOCC(*)=O] (384)
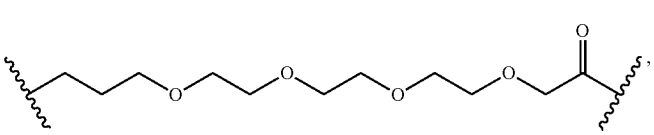 [SMILES: *CCCOCCOCCOCCOCC(*)=O] (385)
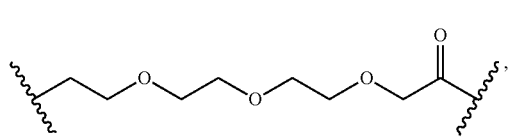 [SMILES: *CCOCCOCCOCC(*)=O] (386)
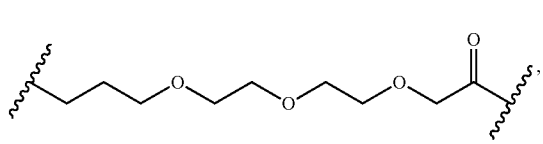 [SMILES: *CCCOCCOCCOCC(*)=O] (387)

TABLE B-continued

Exemplified Linkers (L)

TABLE B-continued
Exemplified Linkers (L)
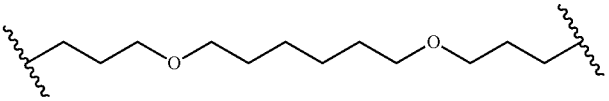 (401)
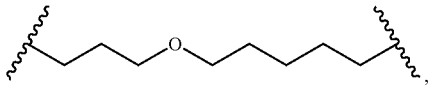 [SMILES: *CCCCCOCCC*] (402)
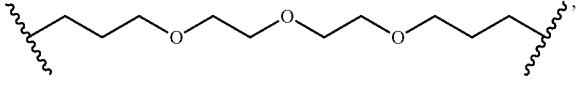 [SMILES: *CCCOCCOCCOCCC*] (403)
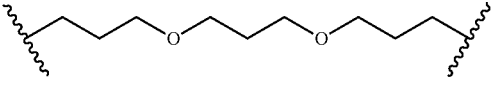 (404)
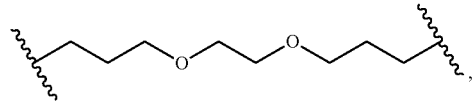 [SMILES: *CCCOCCOCCC*] (405)
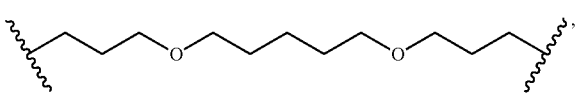 [SMILES: *CCCOCCCCCOCCC*] (406)
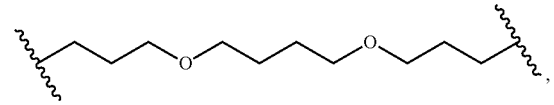 [SMILES: *CCCOCCCCOCCC*] (407)
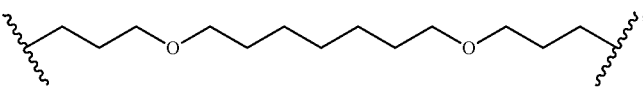 (408)
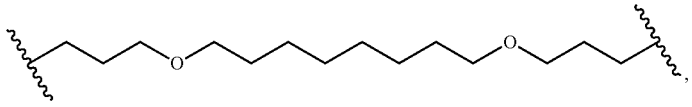 [SMILES: *CCCOCCCCCCCCOCCC*] (409)
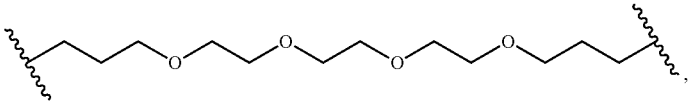 [SMILES: *CCCOCCOCCOCCOCCC*] (410)
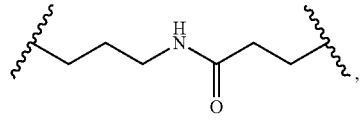 [SMILES: *CCCNC(=O)CC*] (411)
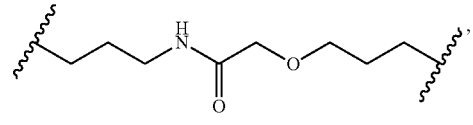 [SMILES: *CCCNC(=O)COCCC*] (412)
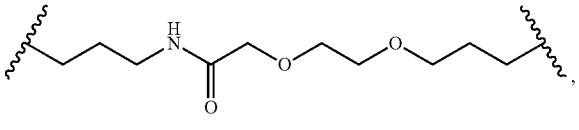 [SMILES: *CCCNC(=O)COCCOCCC*] (413)

TABLE B-continued

Exemplified Linkers (L)

(414)

(415)

(416)

(417)

(418)

(419)

(420)

(421)

(422)

(423)

TABLE B-continued
Exemplified Linkers (L)
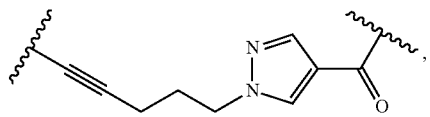 [SMILES: *C#CCCCn1cc(C(*)=O)cn1] (424)
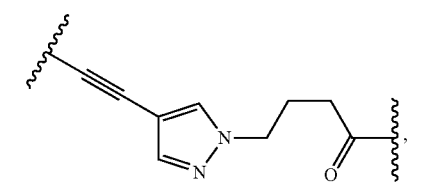 [SMILES: *C#Cc1cnn(CCCC(*)=O)c1] (425)
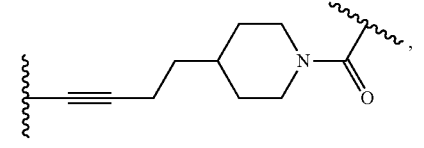 [SMILES: *C#CCCC1CCN(C(*)=O)CC1] (426)
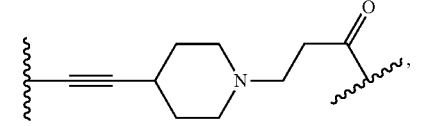 [SMILES: *C#CC1CCN(CCC(*)=O)CC1] (427)
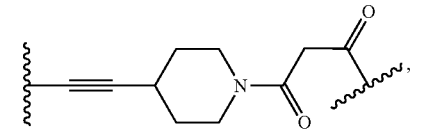 [SMILES: *C#CC1CCN(C(=O)CC(*)=O)CC1] (428)
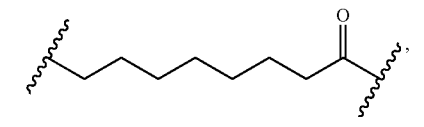 [SMILES: *CCCCCCCC(*)=O] (429)
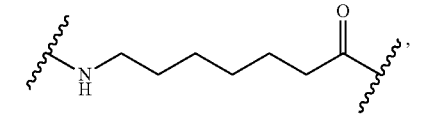 [SMILES: *NCCCCCCC(*)=O] (430)
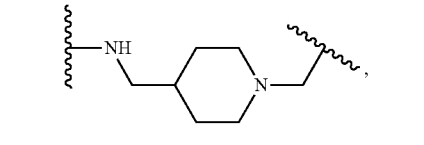 [SMILES: *CN1CCC(CN*)CC1] (431)
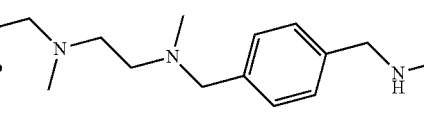 (432)
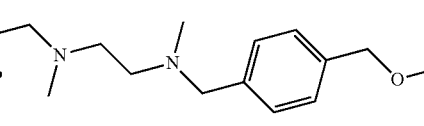 (433)
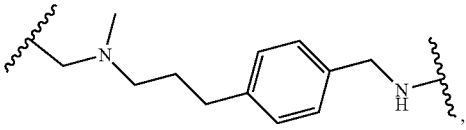 [SMILES: *CN(C)CCCc1ccc(CN*)cc1] (434)

TABLE B-continued
Exemplified Linkers (L)
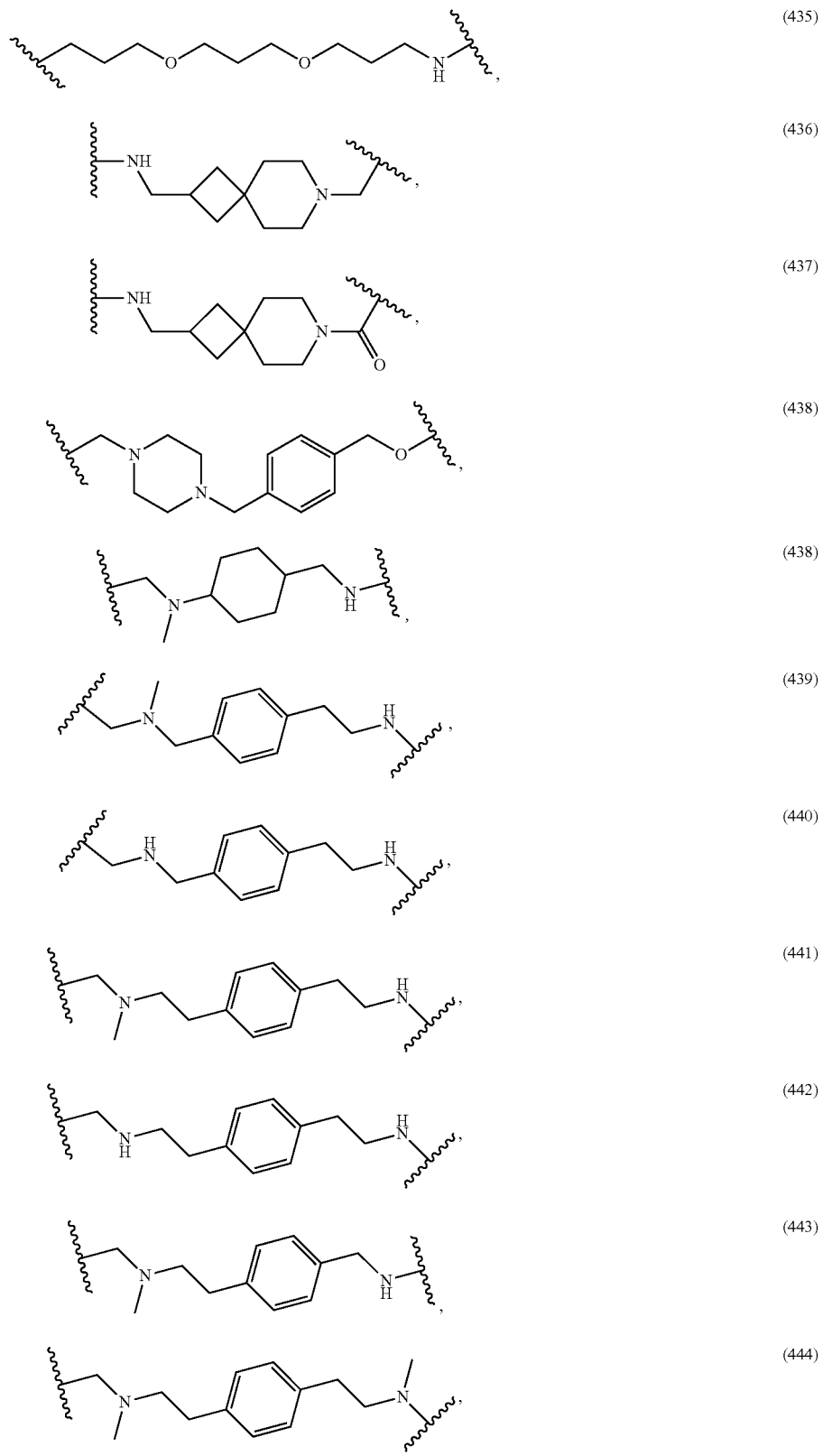

TABLE B-continued
Exemplified Linkers (L)
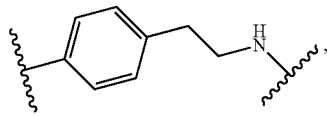 [SMILES: *NCCc1ccc(*)cc1] (445)
 (446)
 (447)
 (448)
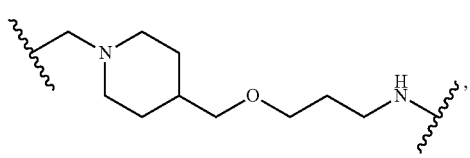 [SMILES: *CN1CCC(COCCCN*)CC1] (449)
 (450)
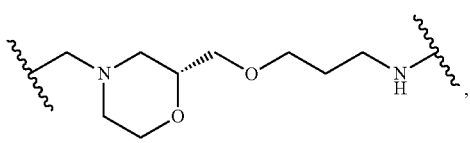 [SMILES: *CN1CCO[C@@H](COCCCN*)C1] (451)
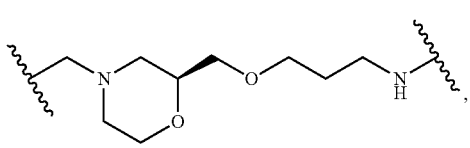 [SMILES: *CN1CCO[C@H](COCCCN*)C1] (452)
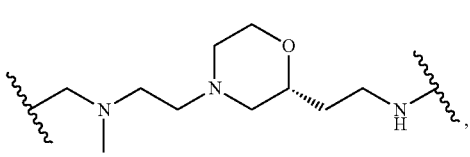 [SMILES: *CN(C)CCN1CCO[C@H](CCN*)C1] (453)
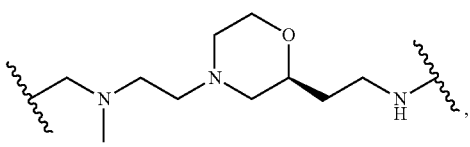 [SMILES: *CN(C)CCN1CCO[C@@H](CCN*)C1] (454)
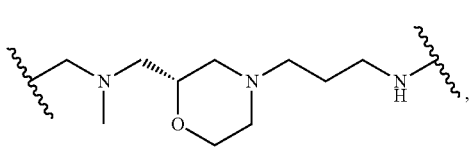 [SMILES: *CN(C)C[C@@H]1CN(CCCN*)CCO1] (455)

TABLE B-continued
Exemplified Linkers (L)
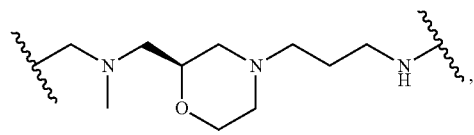 [SMILES: *CN(C)C[C@H]1CN(CCCN*)CCO1] (456)
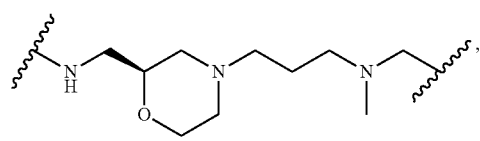 [SMILES: *CN(C)CCCN1CCO[C@@H](CN*)C1] (457)
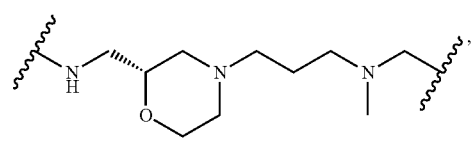 [SMILES: *CN(C)CCCN1CCO[C@H](CN*)C1] (458)
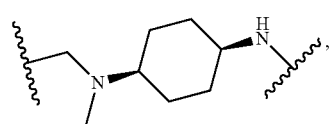 [SMILES: *CN(C)[C@H]1CC[C@@H](N*)CC1] (459)
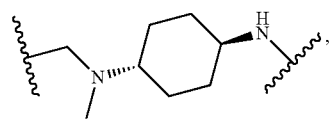 [SMILES: *CN(C)[C@H]1CC[C@H](N*)CC1] (460)
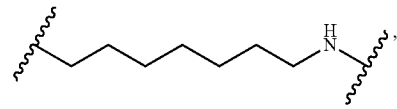 [SMILES: *CCCCCCCN*] (461)
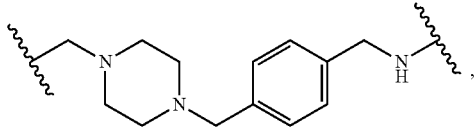 [SMILES: *CN1CCN(Cc2ccc(CN*)cc2)CC1] (462)
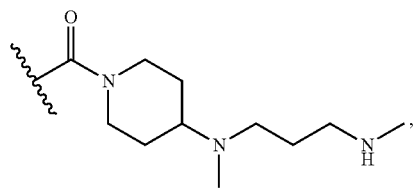 [SMILES: *C(=O)N1CCC(N(C)CCCNC)CC1] (463)
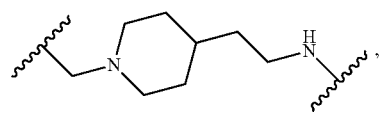 [SMILES: *CN1CCC(CCN*)CC1] (464)
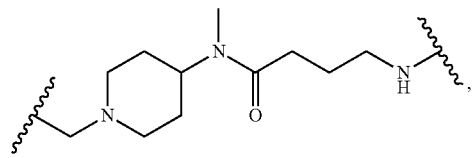 [SMILES: *CN1CCC(N(C)C(=O)CCCN*)CC1] (465)
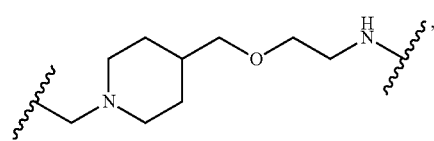 [SMILES: *CN1CCC(COCCN*)CC1] (466)

TABLE B-continued
Exemplified Linkers (L)
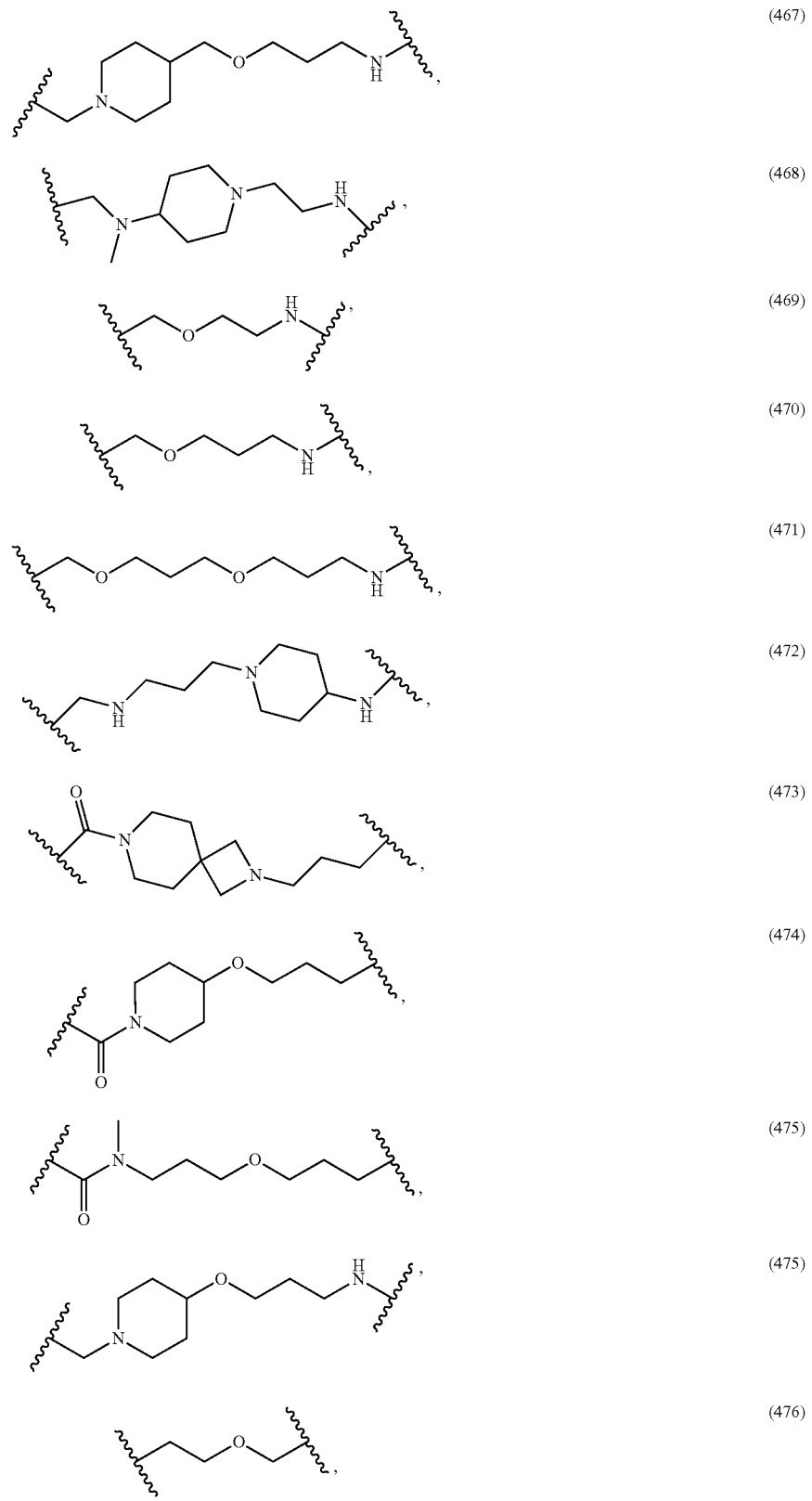

TABLE B-continued
Exemplified Linkers (L)
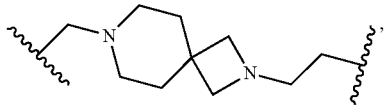 [SMILES: *CCN1CC2(CCN(C*)CC2)C1] (477)
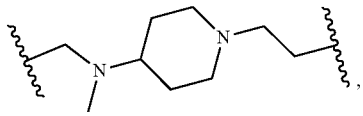 [SMILES: *CCN1CCC(N(C)C*)CC1] (478)
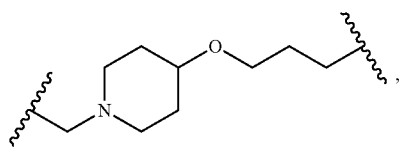 [SMILES: *CCCOC1CCN(C*)CC1] (479)
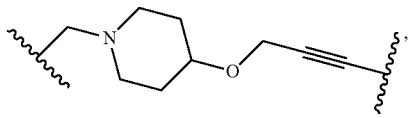 [SMILES: *C#CCOC1CCN(C*)CC1] (480)
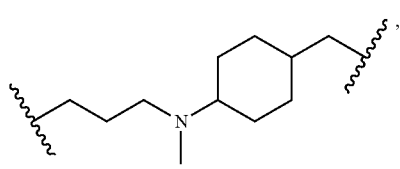 [SMILES: *CCCN(C)C1CCC(C*)CC1] (481)
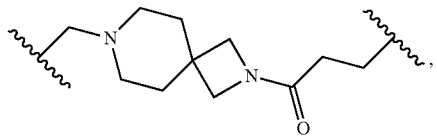 [SMILES: *CCC(=O)N1CC2(CCN(C*)CC2)C1] (482)
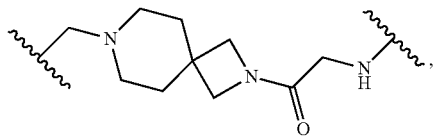 [SMILES: *CN1CCC2(CC1)CN(C(=O)CN*)C2] (483)
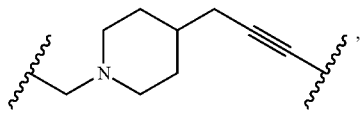 [SMILES: *C#CCC1CCN(C*)CC1] (484)
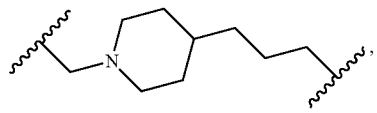 [SMILES: *CCCC1CCN(C*)CC1] (485)
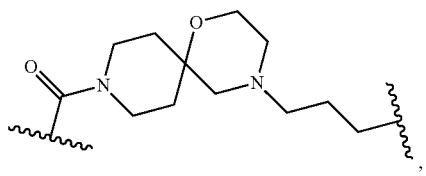 [SMILES: *CCCN1CCOC2(CCN(C(*)=O)CC2)C1] (486)

TABLE B-continued
Exemplified Linkers (L)
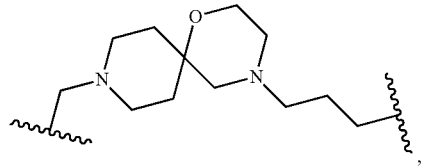 [SMILES: *CCCN1CCOC2(CCN(C*)CC2)C1]
(487)
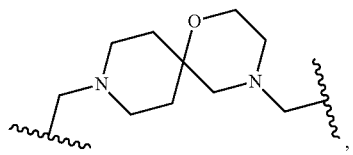 [SMILES: *CN1CCC2(CC1)CN(C*)CCO2]
(488)
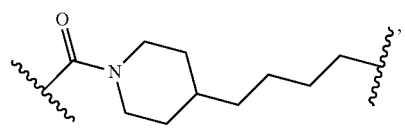 [SMILES: *CCCCC1CCN(C(*)=O)CC1]
(489)
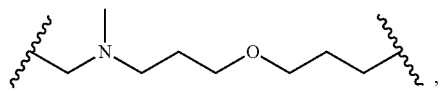 [SMILES: *CCCOCCCN(C)C*]
(490)
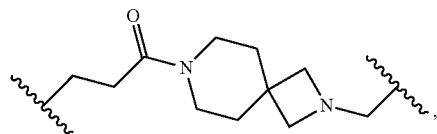 [SMILES: *CCC(=O)N1CCC2(CC1)CN(C*)C2]
(491)
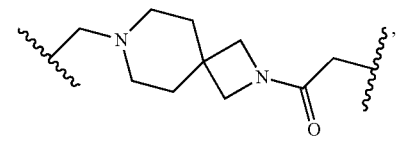 [SMILES: *CC(=O)N1CC2(CCN(C*)CC2)C1]
(492)
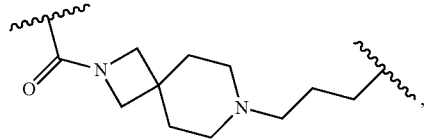 [SMILES: *CCCN1CCC2(CC1)CN(C(*)=O)C2]
(493)
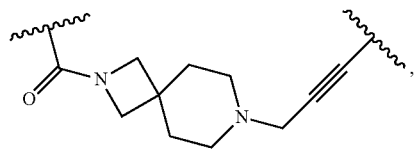 [SMILES: *C#CCN1CCC2(CC1)CN(C(*)=O)C2]
(494)
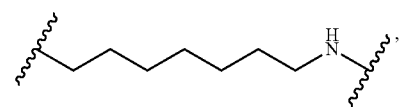 [SMILES: *CCCCCCCN*]
(495)
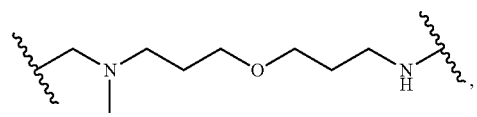 [SMILES: *CN(C)CCCOCCCN*]
(496)
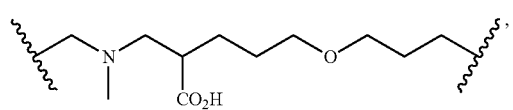 [SMILES: *CCCOCCCC(CN(C)C*)C(=O)O]
(497)

TABLE B-continued

Exemplified Linkers (L)

(498) — (508) [chemical structure diagrams of linker moieties]

TABLE B-continued
Exemplified Linkers (L)
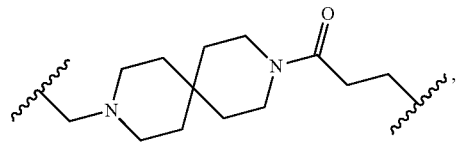 [SMILES: *CCC(=O)N1CCC2(CCN(C*)CC2)CC1]
(509)
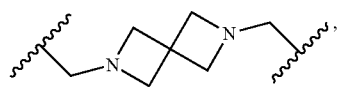 [SMILES: *CN1CC2(C1)CN(C*)C2]
(510)
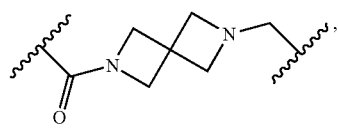 [SMILES: *CN1CC2(C1)CN(C(*)=O)C2]
(511)
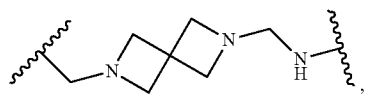 [SMILES: *CN1CC2(C1)CN(CN*)C2]
(512)
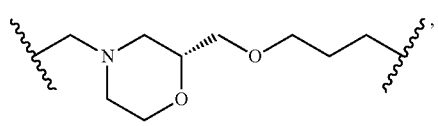 [SMILES: *CCCOC[C@H]1CN(C*)CCO1]
(513)
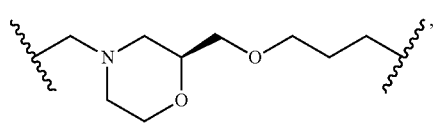 [SMILES: *CCCOC[C@@H]1CN(C*)CCO1]
(514)
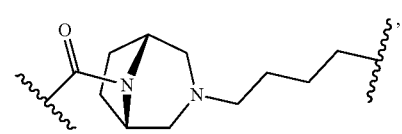 [SMILES: *CCCCN1C[C@H]2CC[C@@H](C1)N2C(*)=O]
(515)
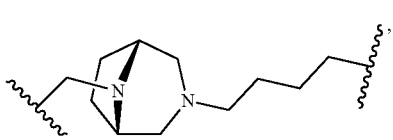 [SMILES: *CCCCN1C[C@H]2CC[C@@H](C1)N2C*]
(516)
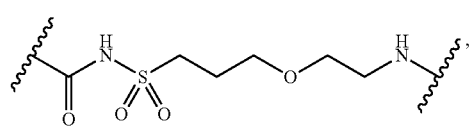 [SMILES: *NCCOCCCS(=O)(=O)NC(*)=O]
(517)
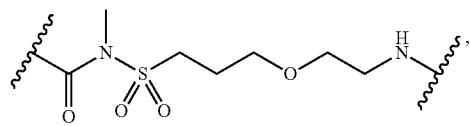 [SMILES: *NCCOCCCS(=O)(=O)N(C)C(*)=O]
(518)
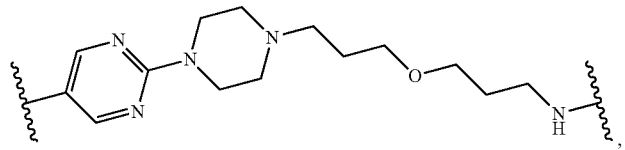 [SMILES: *NCCCOCCCN1CCN(c2ncc(*)cn2)CC1]
(519)

TABLE B-continued
Exemplified Linkers (L)
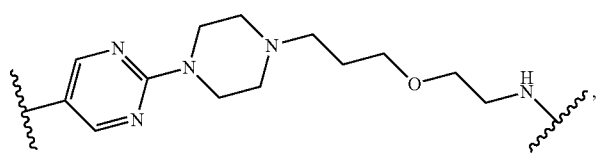 [SMILES: *NCCOCCCN1CCN(c2ncc(*)cn2)CC1] (520)
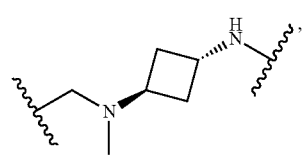 [SMILES: *CN(C)[C@H]1C[C@H](N*)C1] (521)
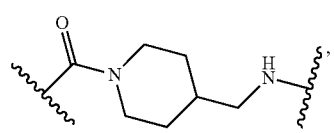 [SMILES: *NCC1CCN(C(*)=O)CC1] (522)
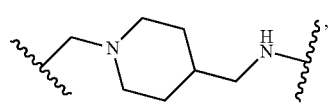 [SMILES: *CN1CCC(CN*)CC1] (523)
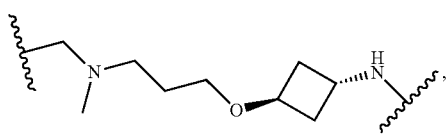 [SMILES: *CN(C)CCCO[C@H]1C[C@H](N*)C1] (524)
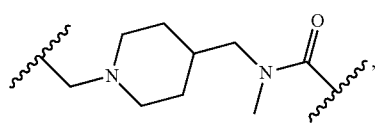 [SMILES: *CN1CCC(CN(C)C(*)=O)CC1] (525)
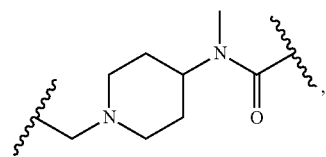 [SMILES: *CN1CCC(N(C)C(*)=O)CC1] (526)
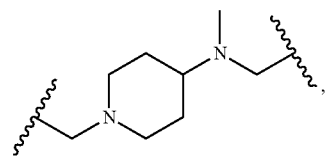 [SMILES: *CN1CCC(N(C)C*)CC1] (527)
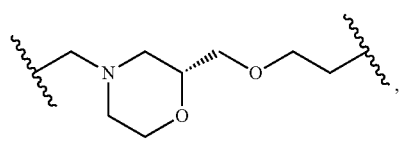 [SMILES: *CCOC[C@H]1CN(C*)CCO1] (528)
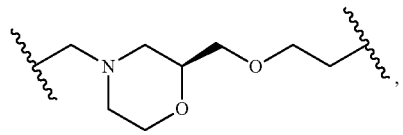 [SMILES: *CCOC[C@@H]1CN(C*)CCO1] (529)

TABLE B-continued
Exemplified Linkers (L)
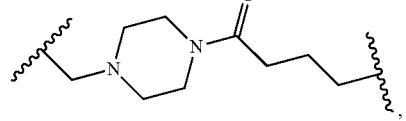 (530)
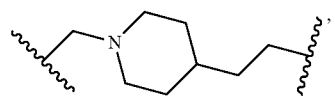 [SMILES: *CCC1CCN(C*)CC1] (531)
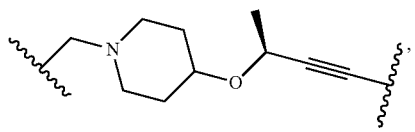 [SMILES: *C#C[C@H](C)OC1CCN(C*)CC1] (532)
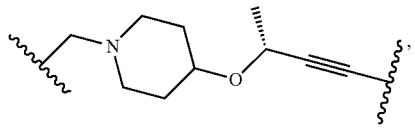 (533)
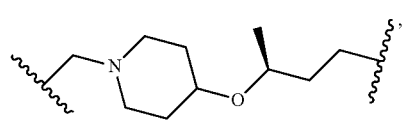 [SMILES: *CC[C@H](C)OC1CCN(C*)CC1] (534)
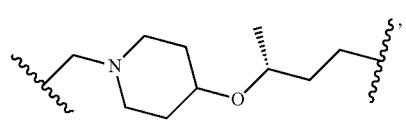 [SMILES: *CC[C@@H](C)OC1CCN(C*)CC1] (535)
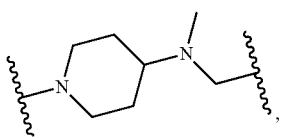 [SMILES: *CN(C)C1CCN(*)CC1] (536)
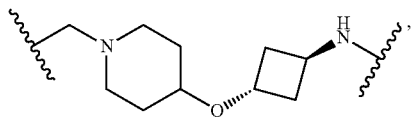 [SMILES: *CN1CCC(O[C@H]2C[C@H](N*)C2)CC1] (537)
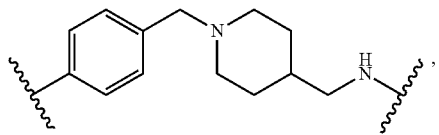 [SMILES: *NCC1CCN(Cc2ccc(*)cc2)CC1] (538)
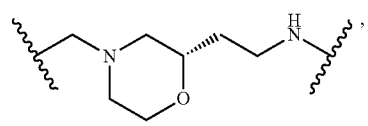 [SMILES: *CN1CCO[C@@H](CCN*)C1] (539)
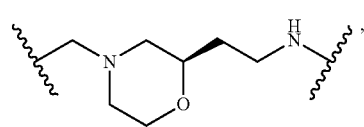 [SMILES: *CN1CCO[C@H](CCN*)C1] (540)

TABLE B-continued
Exemplified Linkers (L)
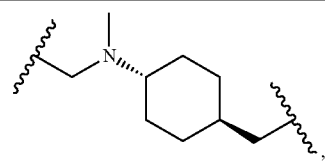 (541)
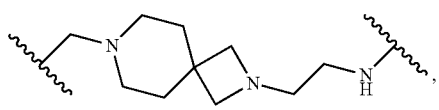 [SMILES: *CN1CCC2(CC1)CN(CCN*)C2] (542)
 (543)
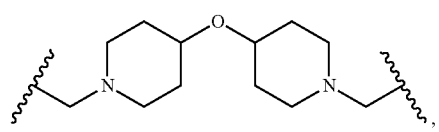 [SMILES: *CN1CCC(OC2CCN(C*)CC2)CC1] (544)
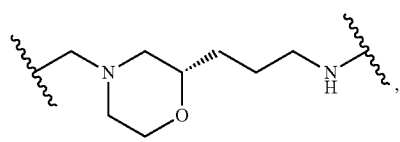 [SMILES: *CN1CCO[C@@H](CCCN*)C1] (545)
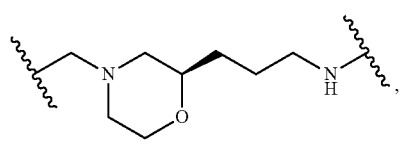 [SMILES: *CN1CCO[C@H](CCCN*)C1] (546)
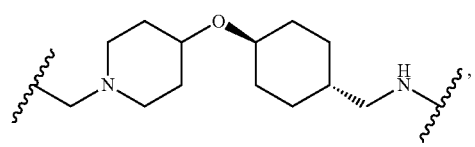 [SMILES: *CN1CCC(O[C@H]2CC[C@H](CN*)CC2)CC1] (547)
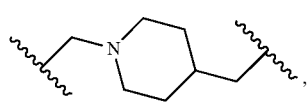 [SMILES: *CC1CCN(C*)CC1] (548)
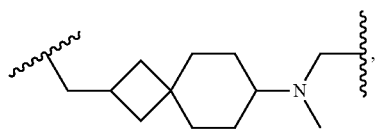 [SMILES: *CC1CC2(CCC(N(C)C*)CC2)C1] (549)
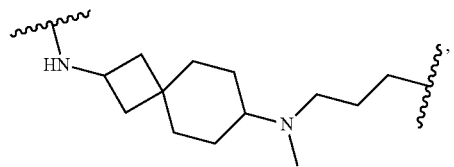 [SMILES: *CCCN(C)C1CCC2(CC1)CC(N*)C2] (550)
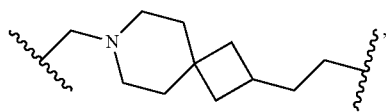 [SMILES: *CCC1CC2(CCN(C*)CC2)C1] (551)

TABLE B-continued
Exemplified Linkers (L)
 (552)
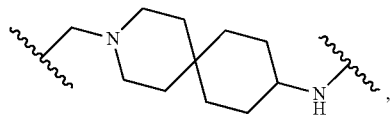 [SMILES: *CN1CCC2(CCC(N*)CC2)CC1] (553)
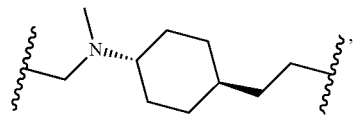 [SMILES: *CC[C@H]1CC[C@H](N(C)C*)CC1] (554)
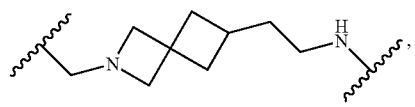 [SMILES: *CN1CC2(CC(CCN*)C2)C1] (555)
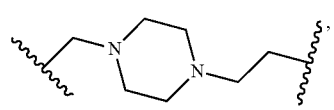 (556)
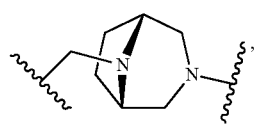 [SMILES: *CN1[C@@H]2CC[C@H]1CN(*)C2] (557)
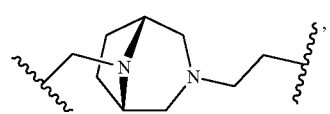 [SMILES: *CCN1C[C@H]2CC[C@@H](C1)N2C*] (558)
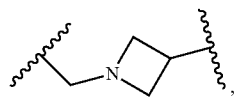 [SMILES: *CN1CC(*)C1] (559)
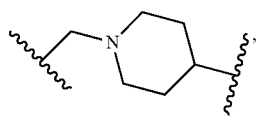 [SMILES: *CN1CCC(*)CC1] (560)
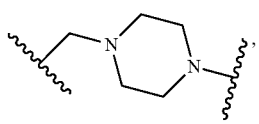 [SMILES: *CN1CCN(*)CC1] (561)
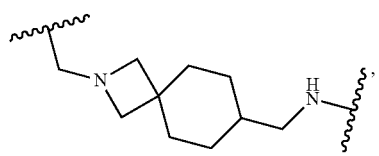 [SMILES: *CN1CC2(CCC(CN*)CC2)C1] (562)
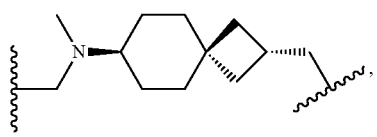 (563)

TABLE B-continued

Exemplified Linkers (L)

(564)

(565)

(566)

(567)

(568)

(569)

(570)

(571)

(572)

(573)

(574)

(575)

TABLE B-continued
Exemplified Linkers (L)
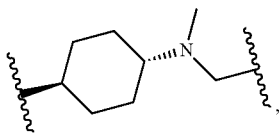 (576)
 (577)
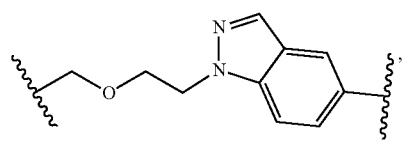 [SMILES: *COCCn1ncc2cc(*)ccc21] (578)
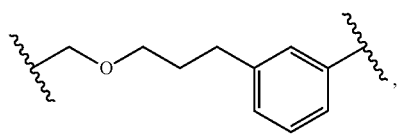 [SMILES: *COCCCc1cccc(*)c1] (579)
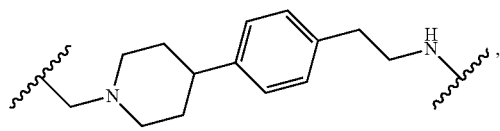 [SMILES: *CN1CCC(c2ccc(CCN*)cc2)CC1] (580)
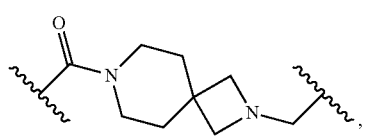 (581)
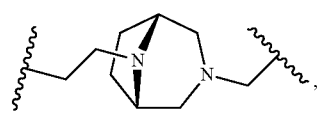 [SMILES: *CCN1[C@@H]2CC[C@H]1CN(C*)C2] (582)
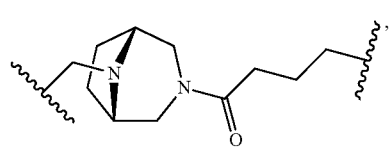 [SMILES: *CCCC(=O)N1C[C@H]2CC[C@@H](C1)N2C*] (583)
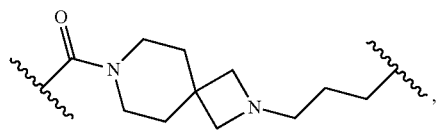 [SMILES: *CCCN1CC2(CCN(C(*)=O)CC2)C1] (584)
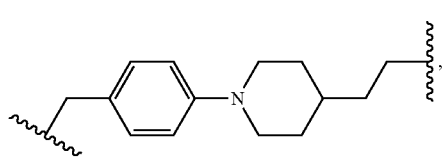 [SMILES: *CCC1CCN(c2ccc(C*)cc2)CC1] (585)
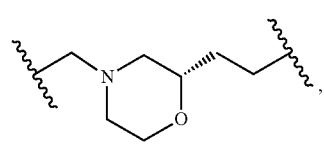 [SMILES: *CC[C@H]1CN(C*)CCO1] (586)

TABLE B-continued
Exemplified Linkers (L)
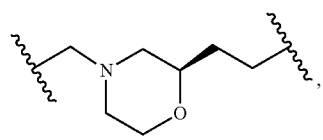 [SMILES: *CC[C@@H]1CN(C*)CCO1] (587)
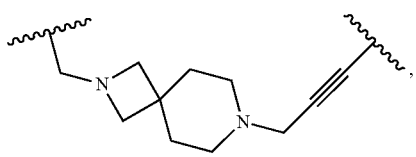 [SMILES: *C#CCN1CCC2(CC1)CN(C*)C2] (588)
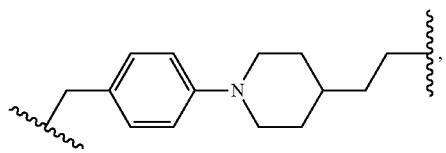 [SMILES: *CCC1CCN(c2ccc(C*)cc2)CC1] (589)
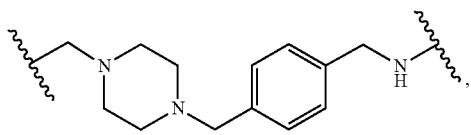 [SMILES: *CN1CCN(Cc2ccc(CN*)cc2)CC1] (590)
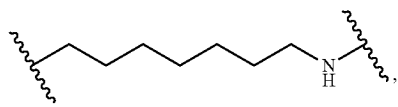 [SMILES: *CCCCCCCN*] (591)
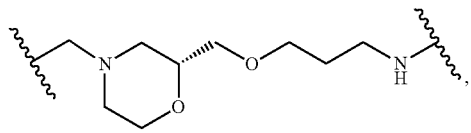 [SMILES: *CN1CCO[C@@H](COCCCN*)C1] (592)
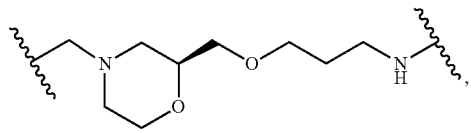 (593)
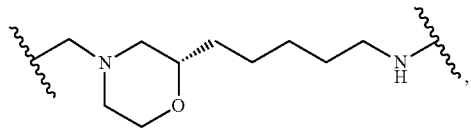 (594)
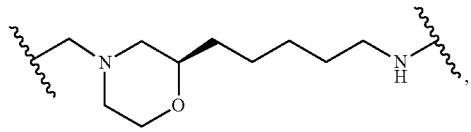 [SMILES: *CN1CCO[C@H](COCCCN*)C1] (595)
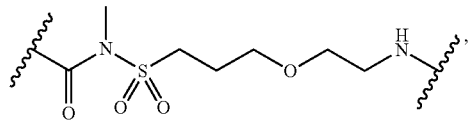 [SMILES: *NCCOCCCS(=O)(=O)N(C)C(*)=O] (596)
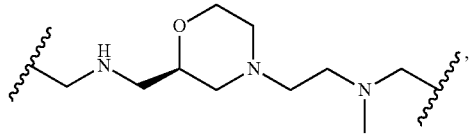 [SMILES: *CNC[C@@H]1CN(CCN(C)C*)CCO1] (597)

TABLE B-continued
Exemplified Linkers (L)
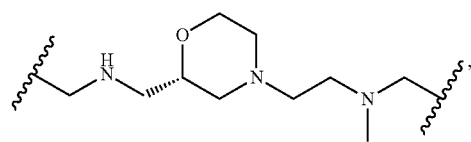 [SMILES: *CNC[C@H]1CN(CCN(C)C*)CCO1] (598)
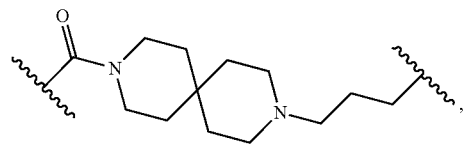 [SMILES: *CCCN1CCC2(CC1)CCN(C(*)=O)CC2] (599)
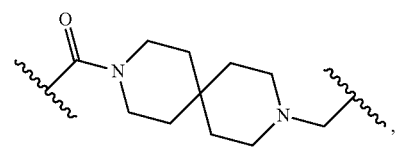 [SMILES: *CN1CCC2(CC1)CCN(C(*)=O)CC2] (600)
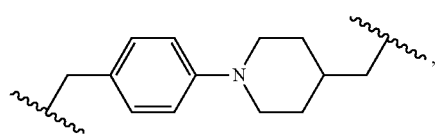 [SMILES: *Cc1ccc(N2CCC(C*)CC2)cc1] (601)
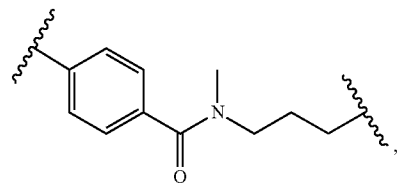 [SMILES: *CCCN(C)C(=O)c1ccc(*)cc1] (602)
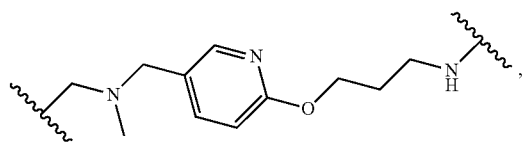 [SMILES: *CN(C)Cc1ccc(OCCCN*)nc1] (603)
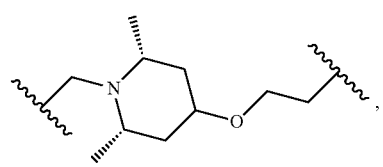 [SMILES: *CCOC1C[C@@H](C)N(C*)[C@@H](C)C1] (604)
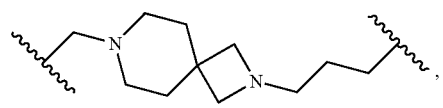 [SMILES: *CCCN1CC2(CCN(C*)CC2)C1] (605)
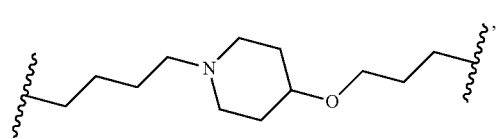 [SMILES: *CCCCN1CCC(OCCC*)CC1] (606)
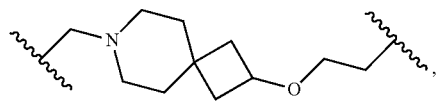 [SMILES: *CCOC1CC2(CCN(C*)CC2)C1] (607)

TABLE B-continued

Exemplified Linkers (L)

TABLE B-continued
Exemplified Linkers (L)
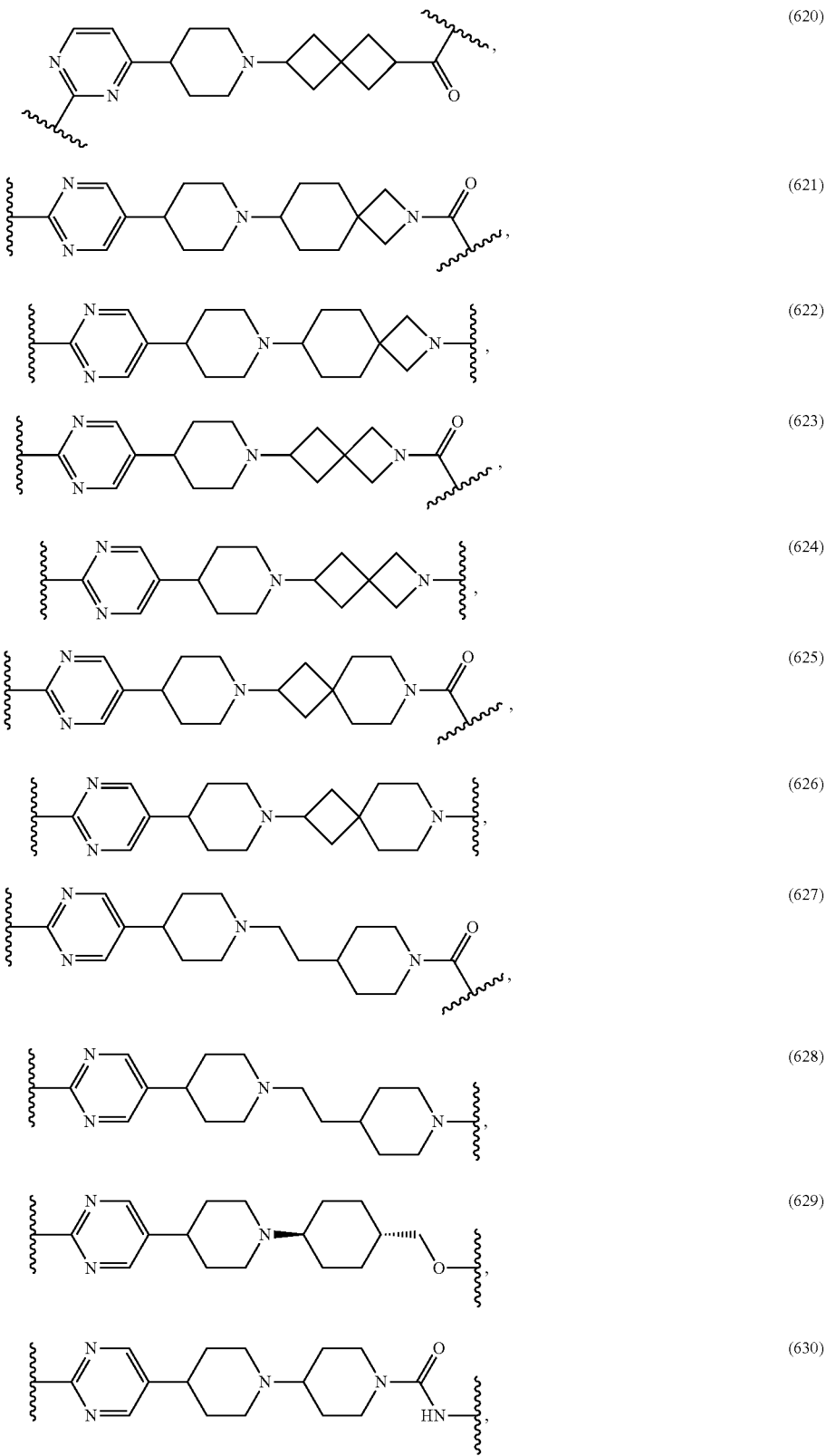

TABLE B-continued
Exemplified Linkers (L)
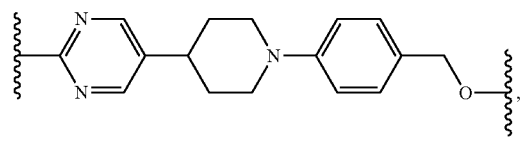 (631)
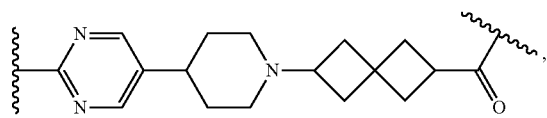 [SMILES: *C(=O)C1CC2(C1)CC(N1CCC(c3cnc(*)nc3)CC1)C2] (632)
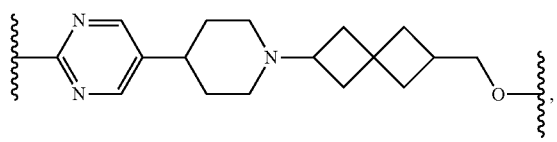 [SMILES: *OCC1CC2(C1)CC(N1CCC(c3cnc(*)nc3)CC1)C2] (633)
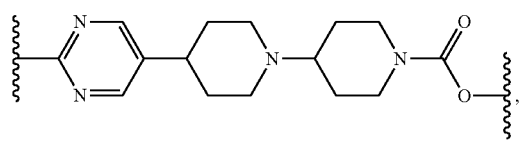 [SMILES: *OC(=O)N1CCC(N2CCC(c3cnc(*)nc3)CC2)CC1] (634)
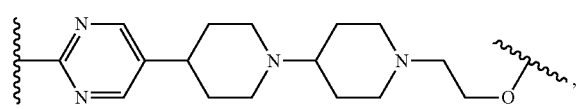 [SMILES: *OCCN1CCC(N2CCC(c3cnc(*)nc3)CC2)CC1] (635)
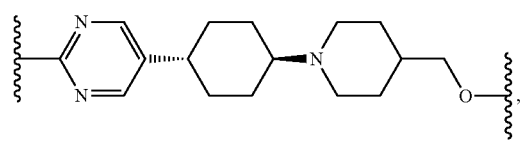 [SMILES: *OCC1CCN([C@H]2CC[C@H](c3cnc(*)nc3)CC2)CC1] (636)
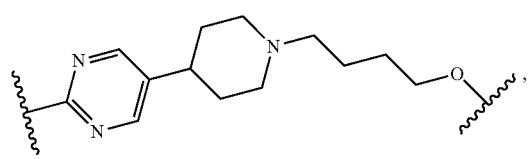 [SMILES: *OCCCCN1CCC(c2cnc(*)nc2)CC1] (637)
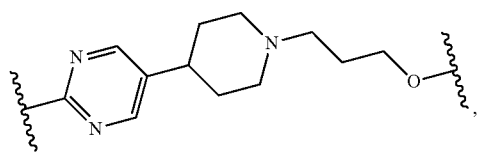 [SMILES: *OCCCN1CCC(c2cnc(*)nc2)CC1] (638)
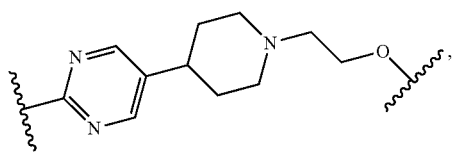 [SMILES: *OCCN1CCC(c2cnc(*)nc2)CC1] (639)
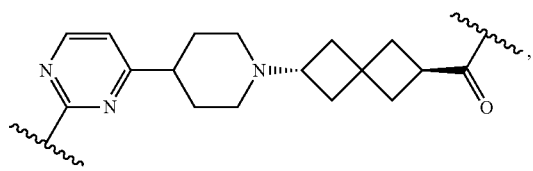 [SMILES: *c1nccc(C2CCN([C@H]3CC4(C[C@H](C(*)=O)C4)C3)CC2)n1] (640)

TABLE B-continued

Exemplified Linkers (L)

(641)

(642)

In some embodiments, the present invention provides a compound having an SMARCA binding moiety described and disclosed herein, a LBM set forth in Table A above, and a linker set forth in Table B above, or a pharmaceutically acceptable salt thereof.

Exemplary compounds of the invention are set forth in Table 1, below.

TABLE 1

Exemplary Compounds

| I-# | Structure |
|---|---|
| I-1 | 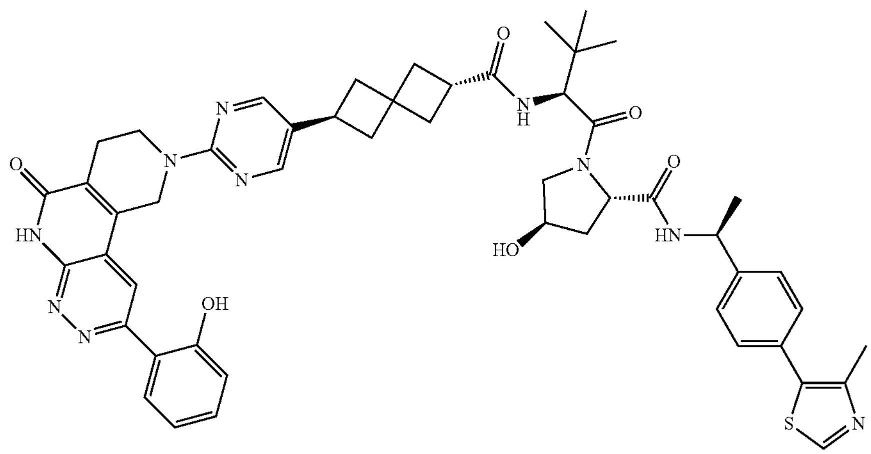 [SMILES: Cc1ncsc1-c1ccc([C@H](C)NC(=O)[C@@H]2C[C@@H](O)CN2C(=O)[C@@H](NC(=O)[C@H]2CC3(C2)C[C@H](c2cnc(N4CCc5c(c6cc(-c7ccccc7O)nnc6[nH]c5=O)C4)nc2)C3)C(C)(C)C)cc1] |
| I-2 | 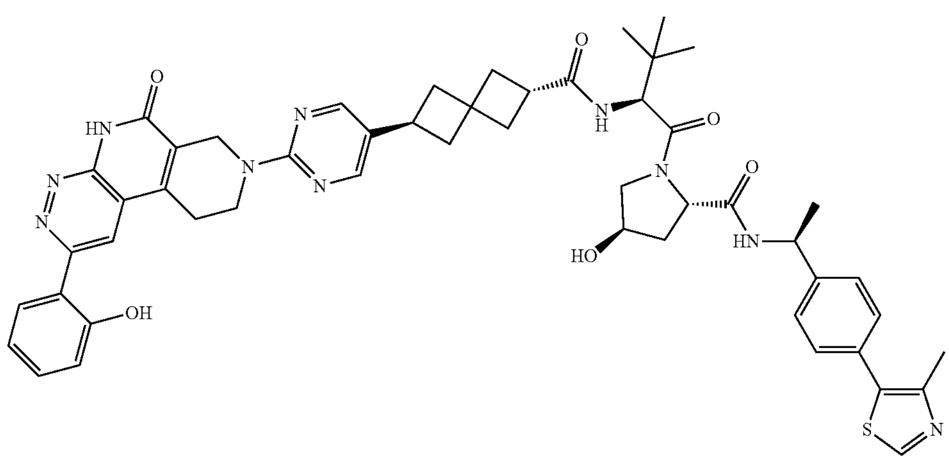 [SMILES: Cc1ncsc1-c1ccc([C@H](C)NC(=O)[C@@H]2C[C@@H](O)CN2C(=O)[C@@H](NC(=O)[C@H]2CC3(C2)C[C@H](c2cnc(N4CCc5c(c(=O)[nH]c6nnc(-c7ccccc7O)cc56)C4)nc2)C3)C(C)(C)C)cc1] |

TABLE 1-continued

Exemplary Compounds

| I-# | Structure |
|---|---|
| I-3 | 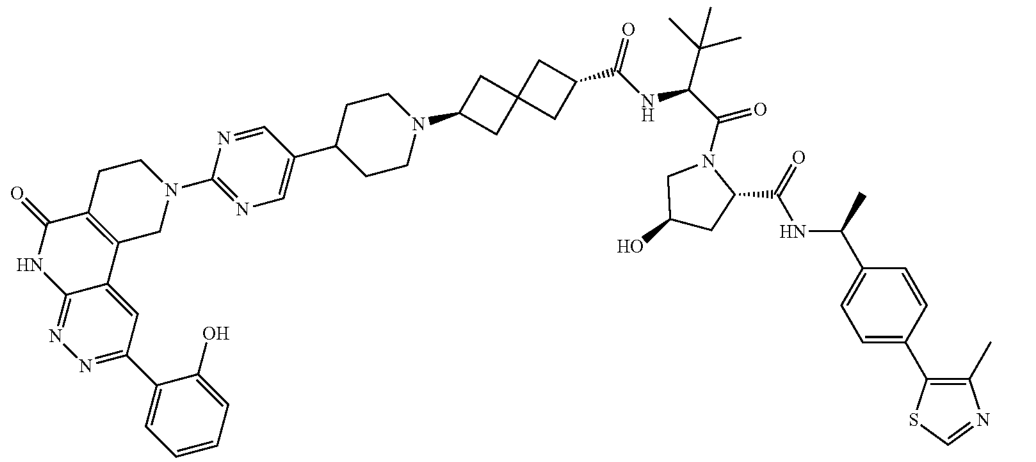 [SMILES: Cc1ncsc1-c1ccc([C@H](C)NC(=O)[C@@H]2C[C@@H](O)CN2C(=O)[C@@H](NC(=O)[C@H]2CC3(C2)C[C@H](N2CCC(c4cnc(N5CCc6c(c7cc(-c8ccccc8O)nnc7[nH]c6=O)C5)nc4)CC2)C3)C(C)(C)C)cc1] |
| I-4 | 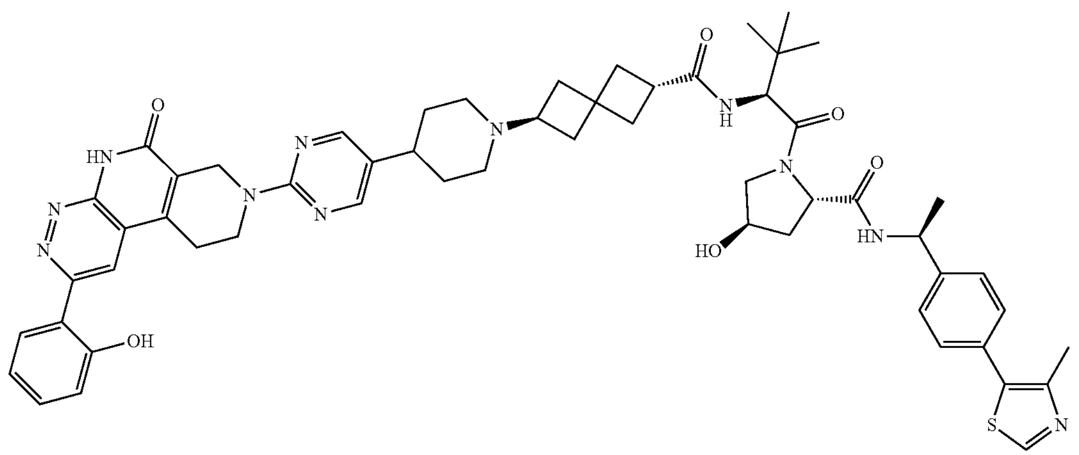 [SMILES: Cc1ncsc1-c1ccc([C@H](C)NC(=O)[C@@H]2C[C@@H](O)CN2C(=O)[C@@H](NC(=O)[C@H]2CC3(C2)C[C@H](N2CCC(c4cnc(N5CCc6c(c(=O)[nH]c7nnc(-c8ccccc8O)cc67)C5)nc4)CC2)C3)C(C)(C)C)cc1] |
| I-5 | 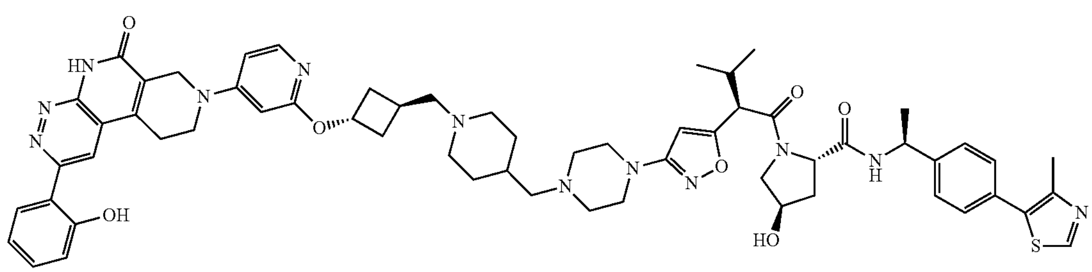 [SMILES: Cc1ncsc1-c1ccc([C@H](C)NC(=O)[C@@H]2C[C@@H](O)CN2C(=O)[C@@H](c2cc(N3CCN(CC4CCN(C[C@H]5C[C@H](Oc6cc(N7CCc8c(c(=O)[nH]c9nnc(-c%10ccccc%10O)cc89)C7)ccn6)C5)CC4)CC3)no2)C(C)C)cc1] |
| I-6 | 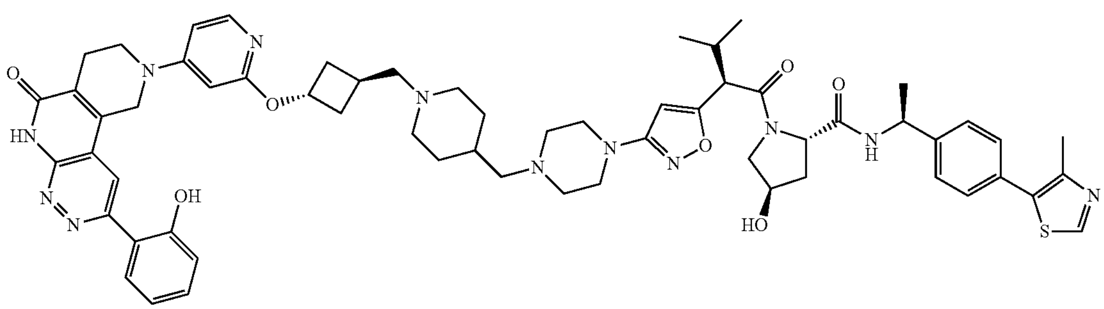 [SMILES: Cc1ncsc1-c1ccc([C@H](C)NC(=O)[C@@H]2C[C@@H](O)CN2C(=O)[C@@H](c2cc(N3CCN(CC4CCN(C[C@H]5C[C@H](Oc6cc(N7CCc8c(c9cc(-c%10ccccc%10O)nnc9[nH]c8=O)C7)ccn6)C5)CC4)CC3)no2)C(C)C)cc1] |

TABLE 1-continued
Exemplary Compounds
| I-# | Structure |
|---|---|
| I-7 | 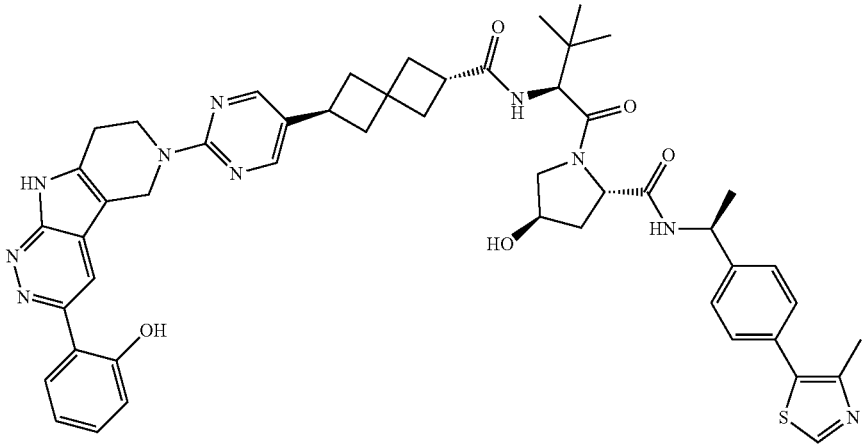 [SMILES: Cc1ncsc1-c1ccc([C@H](C)NC(=O)[C@@H]2C[C@@H](O)CN2C(=O)[C@@H](NC(=O)[C@H]2CC3(C2)C[C@H](c2cnc(N4CCc5[nH]c6nnc(-c7ccccc7O)cc6c5C4)nc2)C3)C(C)(C)C)cc1] |
| I-8 | 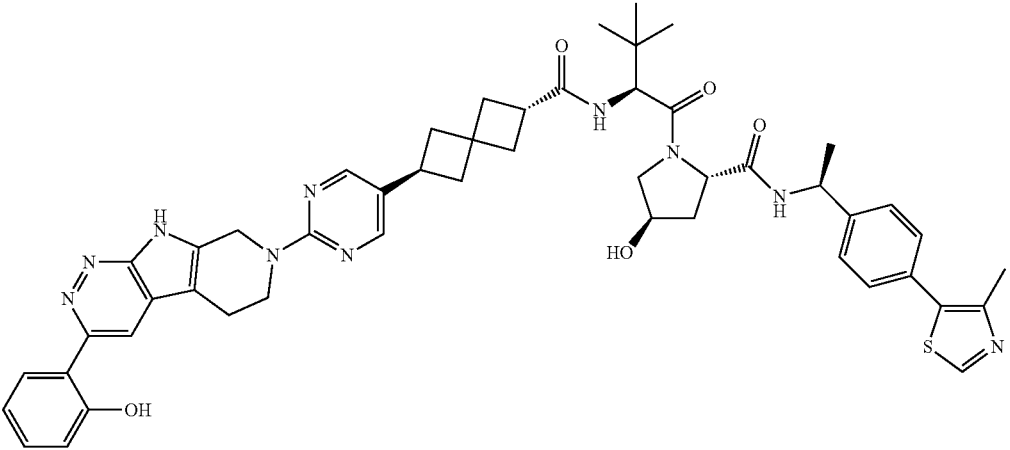 [SMILES: Cc1ncsc1-c1ccc([C@H](C)NC(=O)[C@@H]2C[C@@H](O)CN2C(=O)[C@@H](NC(=O)[C@H]2CC3(C2)C[C@H](c2cnc(N4CCc5c([nH]c6nnc(-c7ccccc7O)cc56)C4)nc2)C3)C(C)(C)C)cc1] |
| I-9 | 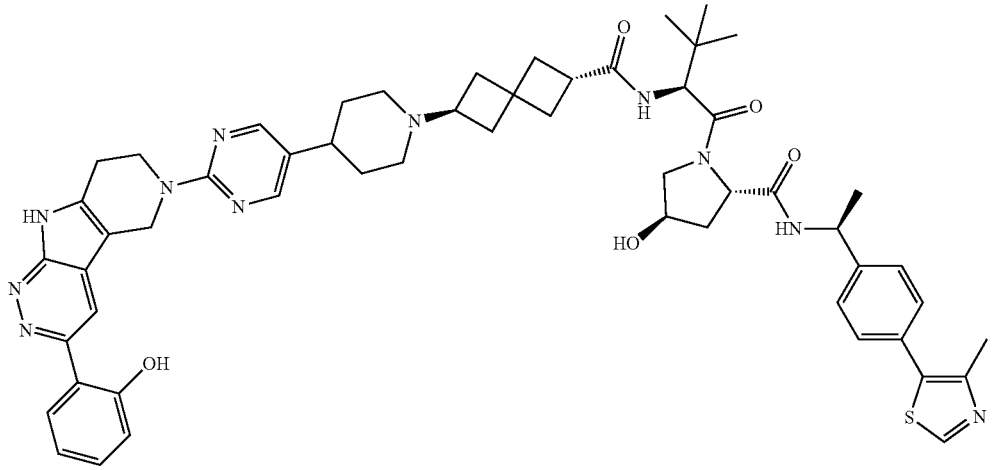 [SMILES: Cc1ncsc1-c1ccc([C@H](C)NC(=O)[C@@H]2C[C@@H](O)CN2C(=O)[C@@H](NC(=O)[C@H]2CC3(C2)C[C@H](N2CCC(c4cnc(N5CCc6[nH]c7nnc(-c8ccccc8O)cc7c6C5)nc4)CC2)C3)C(C)(C)C)cc1] |

TABLE 1-continued
Exemplary Compounds
I-#  Structure
I-10
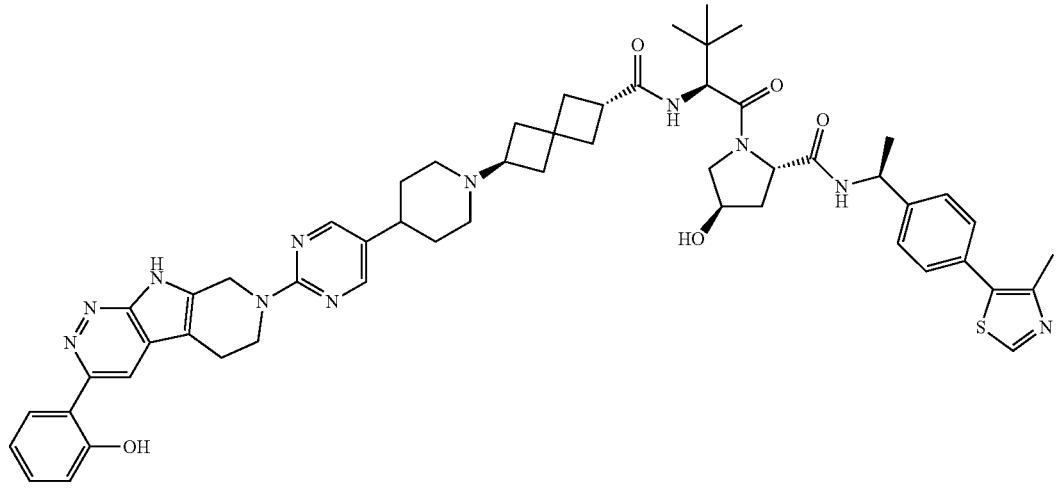 [SMILES: Cc1ncsc1-c1ccc([C@H](C)NC(=O)[C@@H]2C[C@@H](O)CN2C(=O)[C@@H](NC(=O)[C@H]2CC3(C2)C[C@H](N2CCC(c4cnc(N5CCc6c([nH]c7nnc(-c8ccccc8O)cc67)C5)nc4)CC2)C3)C(C)(C)C)cc1]
I-11
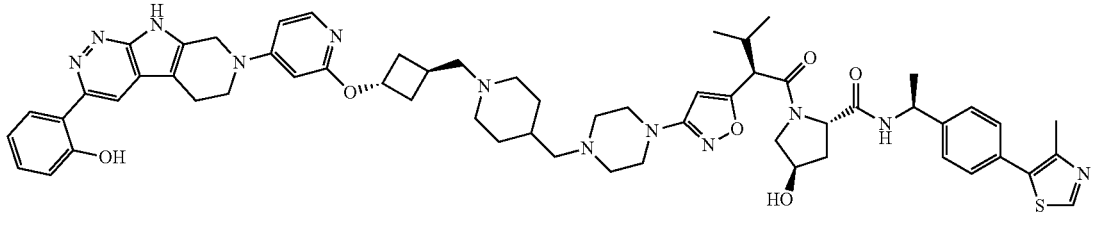 [SMILES: Cc1ncsc1-c1ccc([C@H](C)NC(=O)[C@@H]2C[C@@H](O)CN2C(=O)[C@@H](c2cc(N3CCN(CC4CCN(C[C@H]5C[C@H](Oc6cc(N7CCc8c([nH]c9nnc(-c%10ccccc%10O)cc89)C7)ccn6)C5)CC4)CC3)no2)C(C)C)cc1]
I-12
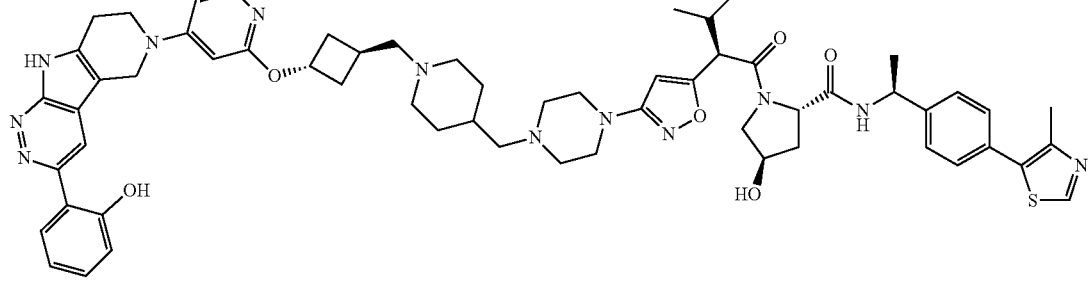
I-13
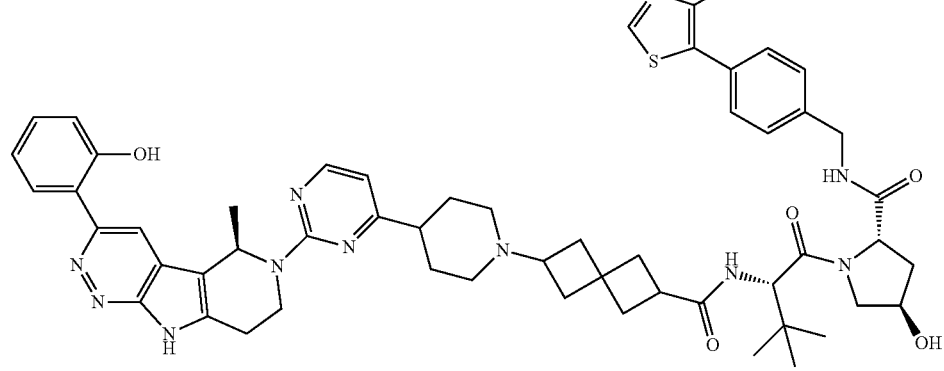

TABLE 1-continued

Exemplary Compounds

| I-# | Structure |
|---|---|
| I-14 | 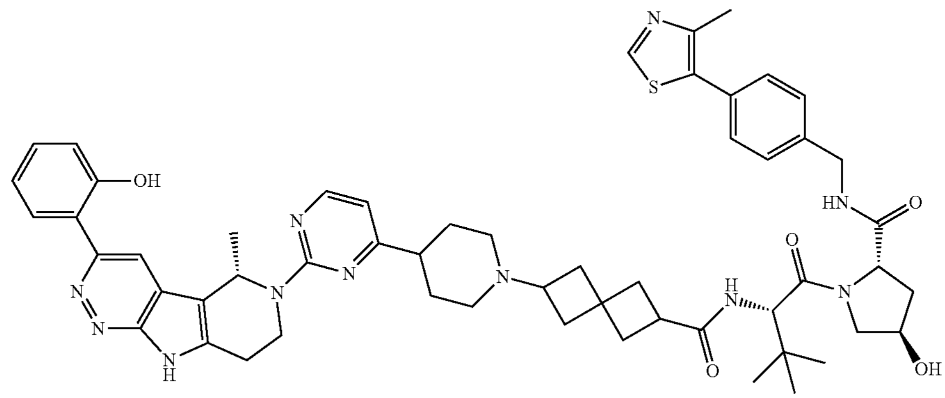 [SMILES: Cc1ncsc1-c1ccc(CNC(=O)[C@@H]2C[C@@H](O)CN2C(=O)[C@@H](NC(=O)C2CC3(C2)CC(N2CCC(c4ccnc(N5CCc6[nH]c7nnc(-c8ccccc8O)cc7c6[C@@H]5C)n4)CC2)C3)C(C)(C)C)cc1] |
| I-15 | 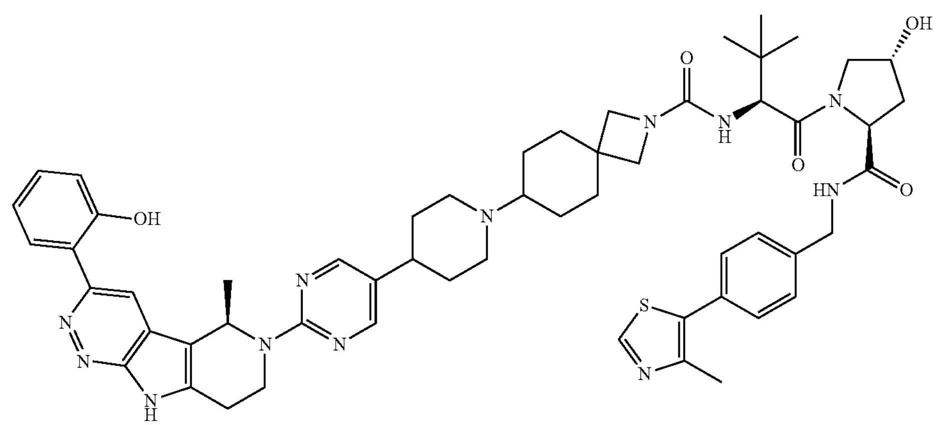 [SMILES: Cc1ncsc1-c1ccc(CNC(=O)[C@@H]2C[C@@H](O)CN2C(=O)[C@@H](NC(=O)N2CC3(CCC(N4CCC(c5cnc(N6CCc7[nH]c8nnc(-c9ccccc9O)cc8c7[C@H]6C)nc5)CC4)CC3)C2)C(C)(C)C)cc1] |
| I-16 | 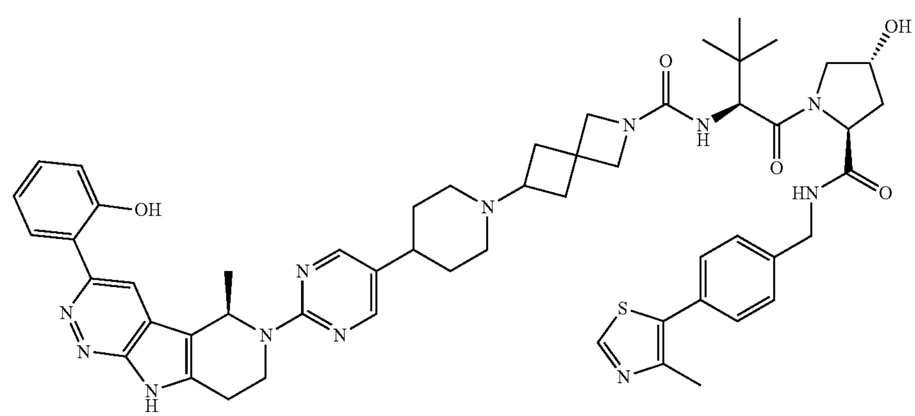 [SMILES: Cc1ncsc1-c1ccc(CNC(=O)[C@@H]2C[C@@H](O)CN2C(=O)[C@@H](NC(=O)N2CC3(CC(N4CCC(c5cnc(N6CCc7[nH]c8nnc(-c9ccccc9O)cc8c7[C@H]6C)nc5)CC4)C3)C2)C(C)(C)C)cc1] |

TABLE 1-continued

Exemplary Compounds

| I-# | Structure |
|---|---|
| I-17 | 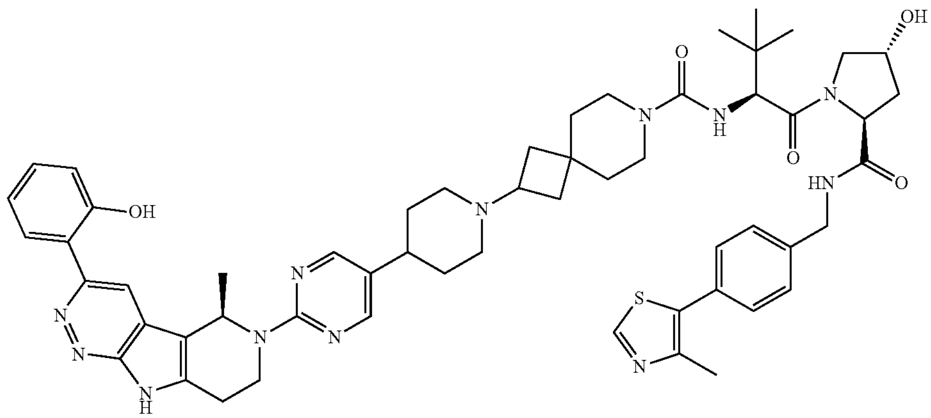 [SMILES: Cc1ncsc1-c1ccc(CNC(=O)[C@@H]2C[C@@H](O)CN2C(=O)[C@@H](NC(=O)N2CCC3(CC2)CC(N2CCC(c4cnc(N5CCc6[nH]c7nnc(-c8ccccc8O)cc7c6[C@H]5C)nc4)CC2)C3)C(C)(C)C)cc1] |
| I-18 | 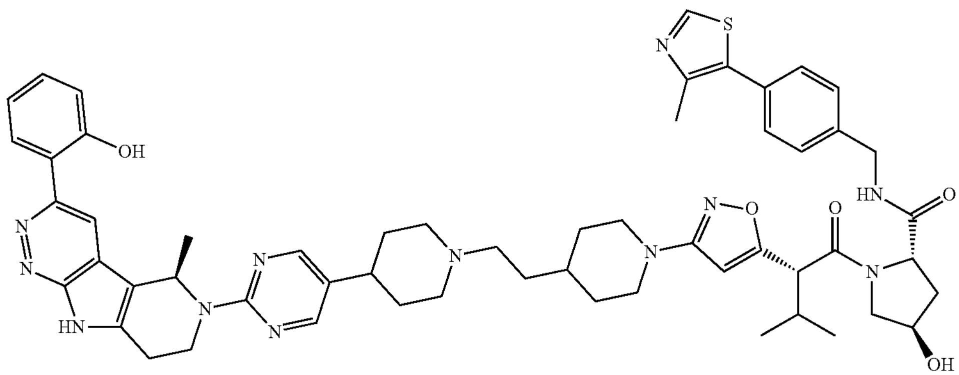 [SMILES: Cc1ncsc1-c1ccc(CNC(=O)[C@@H]2C[C@@H](O)CN2C(=O)[C@@H](c2cc(N3CCC(CCN4CCC(c5cnc(N6CCc7[nH]c8nnc(-c9ccccc9O)cc8c7[C@H]6C)nc5)CC4)CC3)no2)C(C)C)cc1] |
| I-19 | 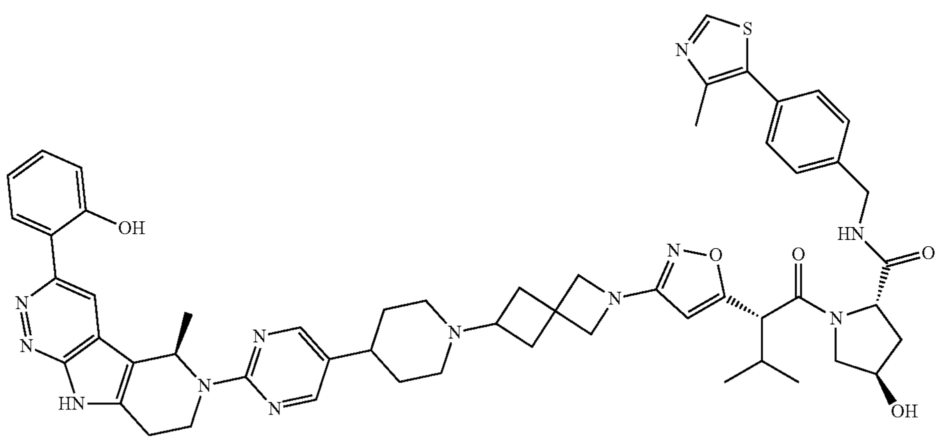 [SMILES: Cc1ncsc1-c1ccc(CNC(=O)[C@@H]2C[C@@H](O)CN2C(=O)[C@@H](c2cc(N3CC4(CC(N5CCC(c6cnc(N7CCc8[nH]c9nnc(-c%10ccccc%10O)cc9c8[C@H]7C)nc6)CC5)C4)C3)no2)C(C)C)cc1] |

TABLE 1-continued
Exemplary Compounds
| I-# | Structure |
| --- | --- |
| I-20 | 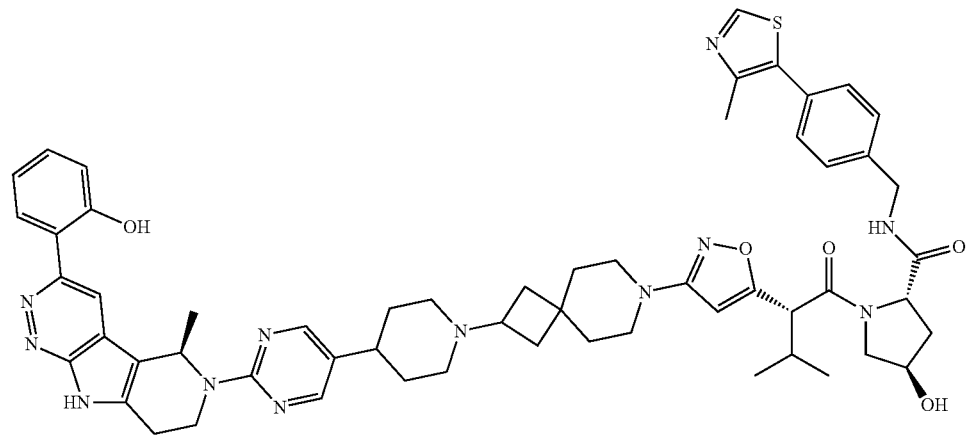 [SMILES: Cc1ncsc1-c1ccc(CNC(=O)[C@@H]2C[C@@H](O)CN2C(=O)[C@@H](c2cc(N3CCC4(CC3)CC(N3CCC(c5cnc(N6CCc7[nH]c8nnc(-c9ccccc9O)cc8c7[C@H]6C)nc5)CC3)C4)no2)C(C)C)cc1] |
| I-21 | 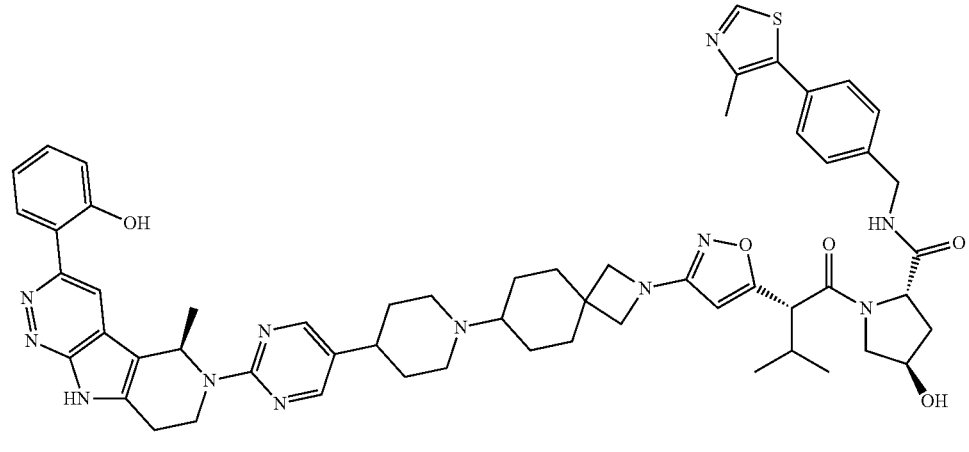 [SMILES: Cc1ncsc1-c1ccc(CNC(=O)[C@@H]2C[C@@H](O)CN2C(=O)[C@@H](c2cc(N3CC4(CCC(N5CCC(c6cnc(N7CCc8[nH]c9nnc(-c%10ccccc%10O)cc9c8[C@H]7C)nc6)CC5)CC4)C3)no2)C(C)C)cc1] |
| I-22 | 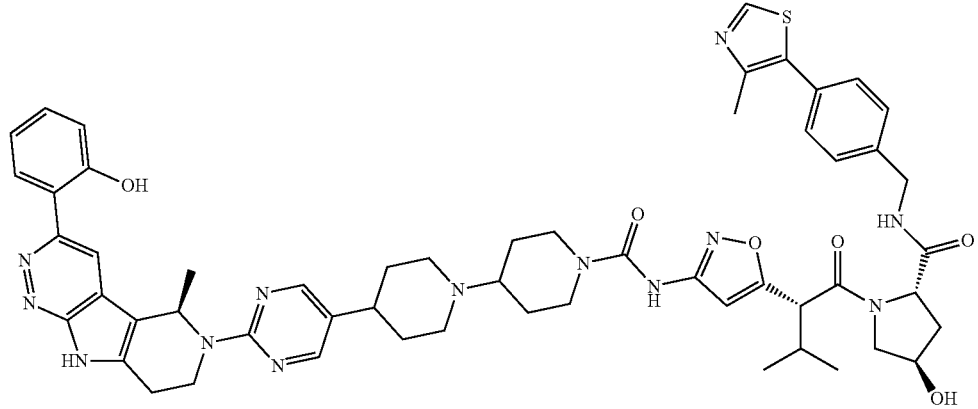 [SMILES: Cc1ncsc1-c1ccc(CNC(=O)[C@@H]2C[C@@H](O)CN2C(=O)[C@@H](c2cc(NC(=O)N3CCC(N4CCC(c5cnc(N6CCc7[nH]c8nnc(-c9ccccc9O)cc8c7[C@H]6C)nc5)CC4)CC3)no2)C(C)C)cc1] |

TABLE 1-continued
Exemplary Compounds
| I-# | Structure |
|---|---|
| I-23 | 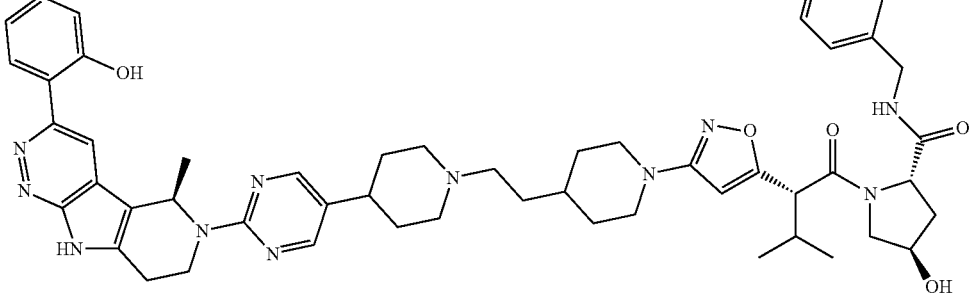 |
| I-24 | 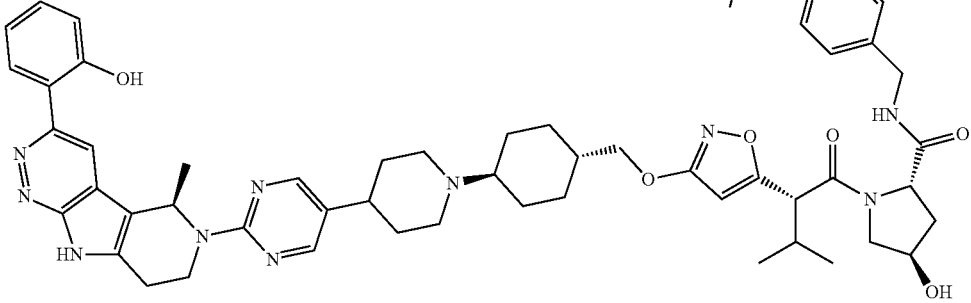 |
| I-25 | 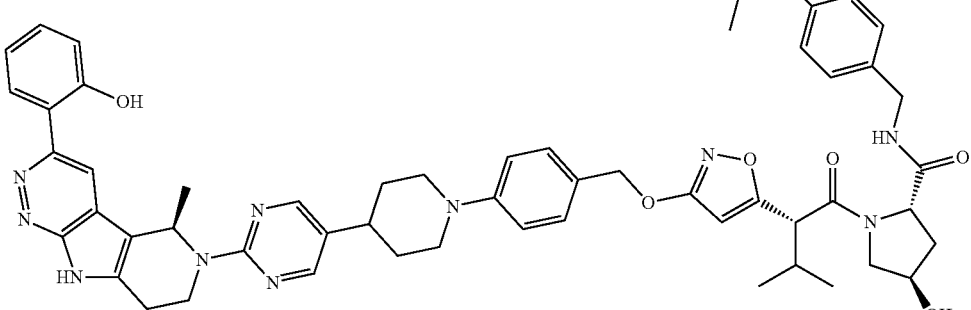 |

TABLE 1-continued

Exemplary Compounds

| I-# | Structure |
|---|---|
| I-26 | 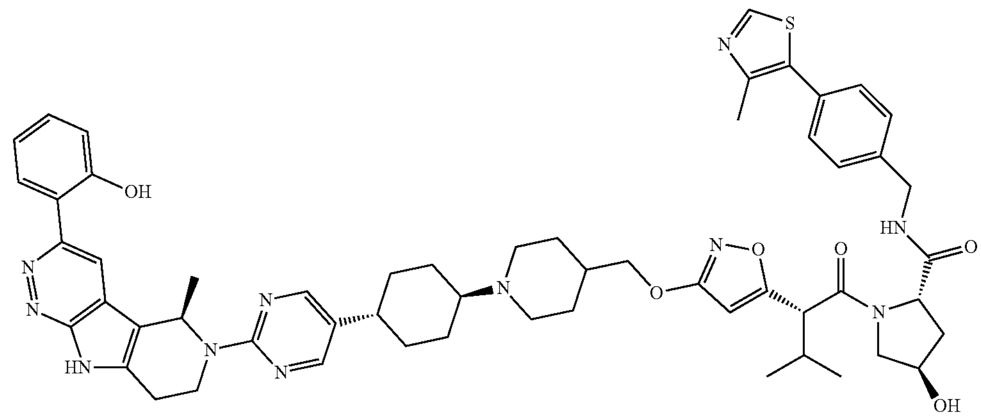 [SMILES: Cc1ncsc1-c1ccc(CNC(=O)[C@@H]2C[C@@H](O)CN2C(=O)[C@@H](c2cc(OCC3CCN([C@H]4CC[C@H](c5cnc(N6CCc7[nH]c8nnc(-c9ccccc9O)cc8c7[C@H]6C)nc5)CC4)CC3)no2)C(C)C)cc1] |
| I-27 | 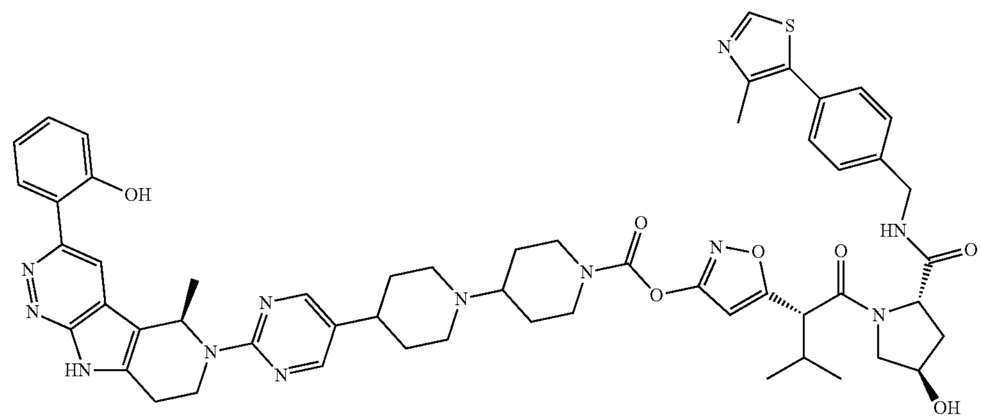 [SMILES: Cc1ncsc1-c1ccc(CNC(=O)[C@@H]2C[C@@H](O)CN2C(=O)[C@@H](c2cc(OC(=O)N3CCC(N4CCC(c5cnc(N6CCc7[nH]c8nnc(-c9ccccc9O)cc8c7[C@H]6C)nc5)CC4)CC3)no2)C(C)C)cc1] |
| I-28 | 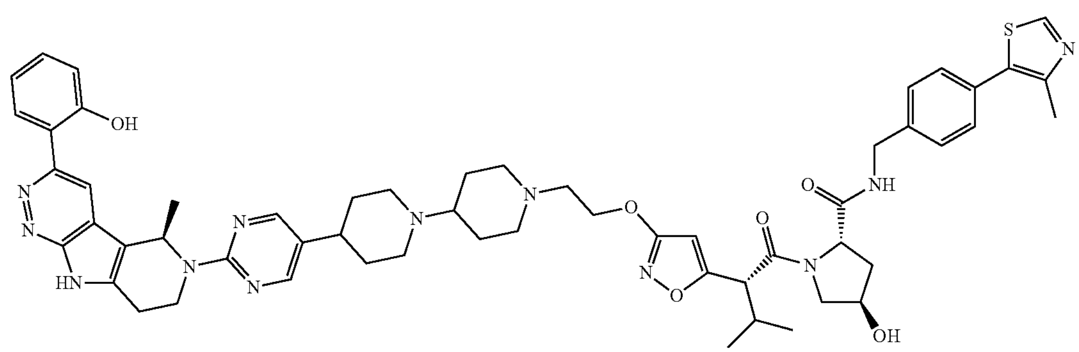 [SMILES: Cc1ncsc1-c1ccc(CNC(=O)[C@@H]2C[C@@H](O)CN2C(=O)[C@@H](c2cc(OCCN3CCC(N4CCC(c5cnc(N6CCc7[nH]c8nnc(-c9ccccc9O)cc8c7[C@H]6C)nc5)CC4)CC3)no2)C(C)C)cc1] |
| I-29 | 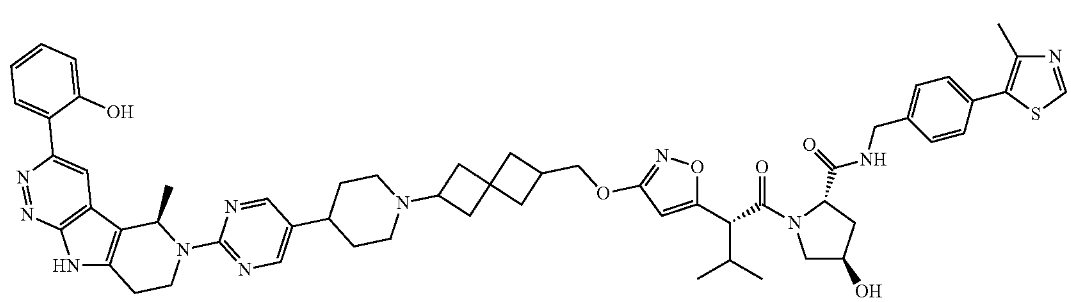 [SMILES: Cc1ncsc1-c1ccc(CNC(=O)[C@@H]2C[C@@H](O)CN2C(=O)[C@@H](c2cc(OCC3CC4(C3)CC(N3CCC(c5cnc(N6CCc7[nH]c8nnc(-c9ccccc9O)cc8c7[C@H]6C)nc5)CC3)C4)no2)C(C)C)cc1] |

TABLE 1-continued
Exemplary Compounds
| I-# | Structure |
|---|---|
| I-30 | 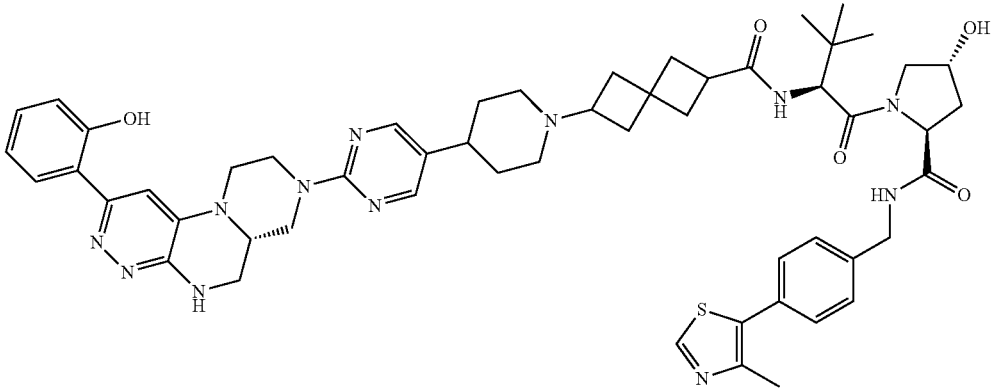 [SMILES: Cc1ncsc1-c1ccc(CNC(=O)[C@@H]2C[C@@H](O)CN2C(=O)[C@@H](NC(=O)C2CC3(C2)CC(N2CCC(c4cnc(N5CCN6c7cc(-c8ccccc8O)nnc7NC[C@H]6C5)nc4)CC2)C3)C(C)(C)C)cc1] |
| I-31 | 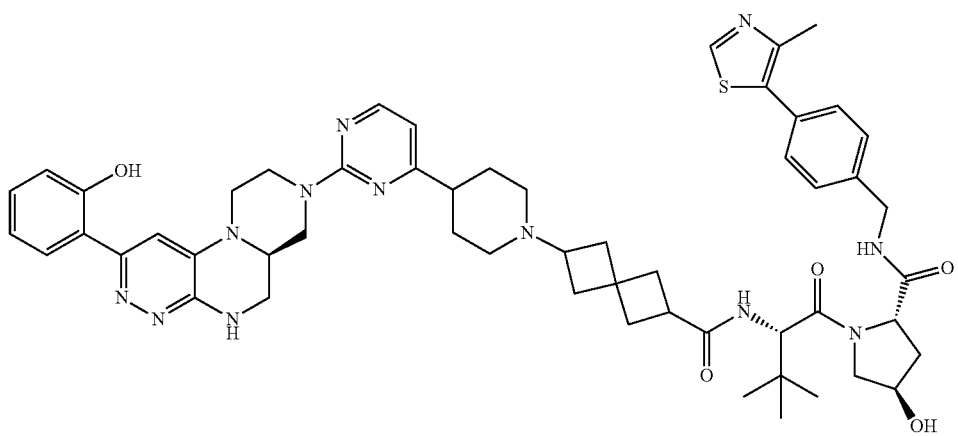 [SMILES: Cc1ncsc1-c1ccc(CNC(=O)[C@@H]2C[C@@H](O)CN2C(=O)[C@@H](NC(=O)C2CC3(C2)CC(N2CCC(c4ccnc(N5CCN6c7cc(-c8ccccc8O)nnc7NC[C@@H]6C5)n4)CC2)C3)C(C)(C)C)cc1] |
| I-32 | 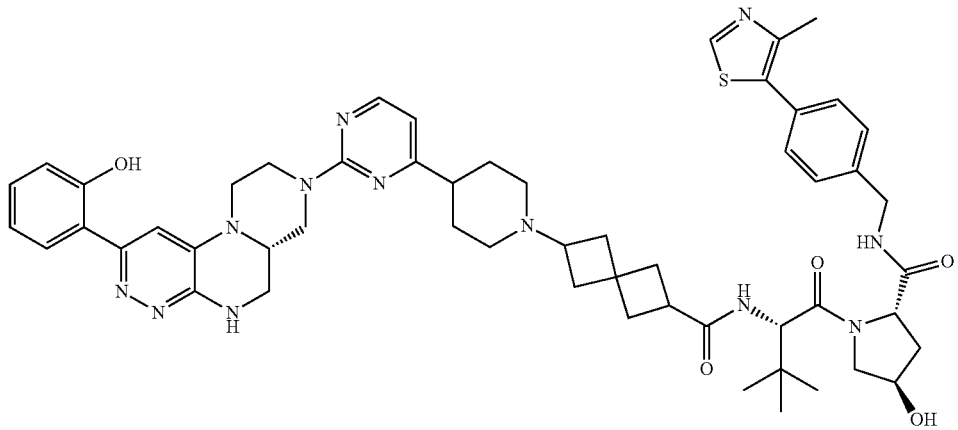 [SMILES: Cc1ncsc1-c1ccc(CNC(=O)[C@@H]2C[C@@H](O)CN2C(=O)[C@@H](NC(=O)C2CC3(C2)CC(N2CCC(c4ccnc(N5CCN6c7cc(-c8ccccc8O)nnc7NC[C@H]6C5)n4)CC2)C3)C(C)(C)C)cc1] |

TABLE 1-continued
Exemplary Compounds
| I-# | Structure |
|---|---|
| I-33 | 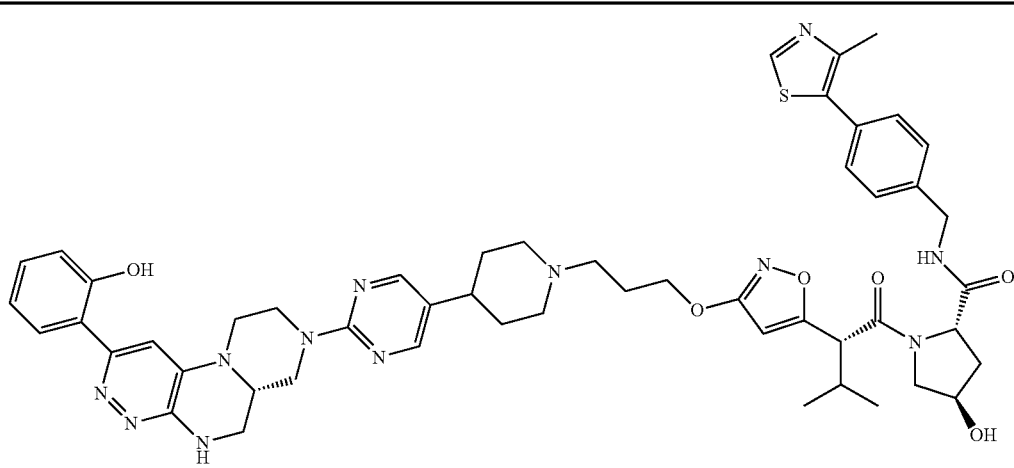 |
| I-34 | 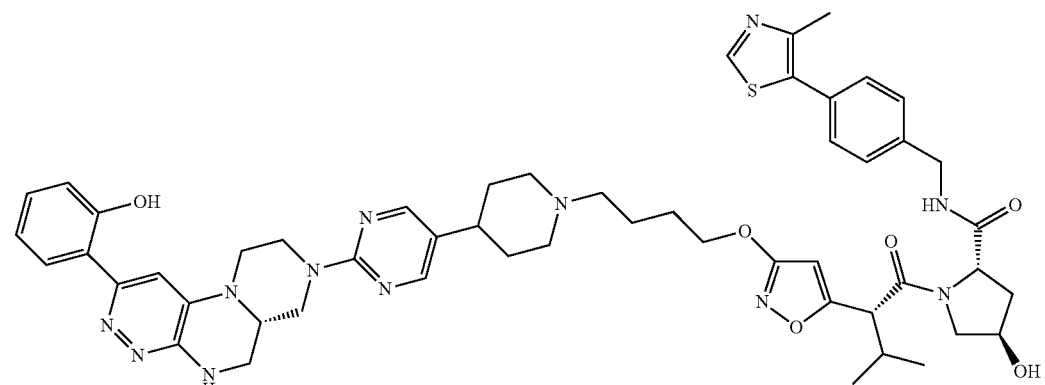 |
| I-35 | 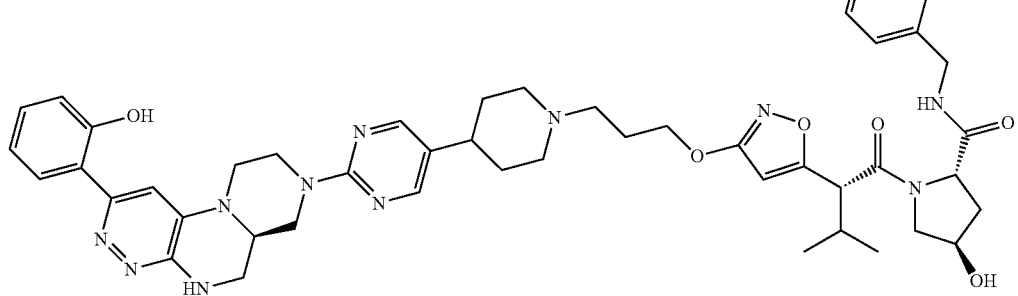 |

US 11,679,109 B2
451                                                                 452
TABLE 1-continued
Exemplary Compounds
| I-# | Structure |
|---|---|
| I-36 | 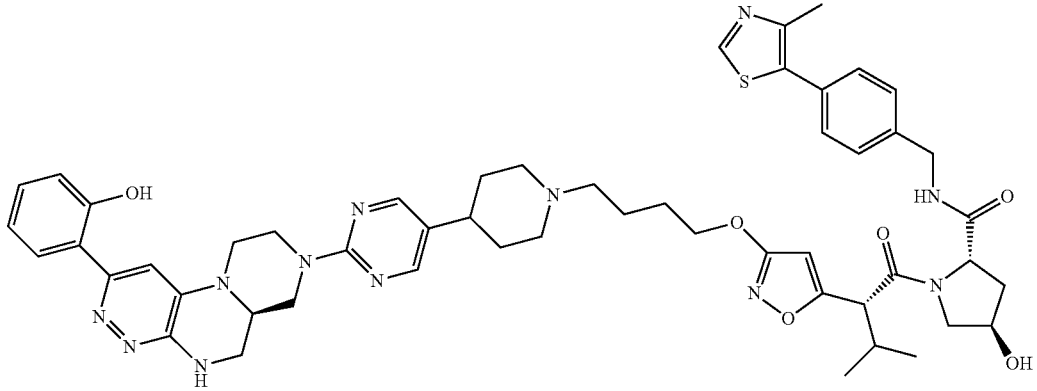 [SMILES: Cc1ncsc1-c1ccc(CNC(=O)[C@@H]2C[C@@H](O)CN2C(=O)[C@@H](c2cc(OCCCCN3CCC(c4cnc(N5CCN6c7cc(-c8ccccc8O)nnc7NC[C@@H]6C5)nc4)CC3)no2)C(C)C)cc1] |
| I-37 | 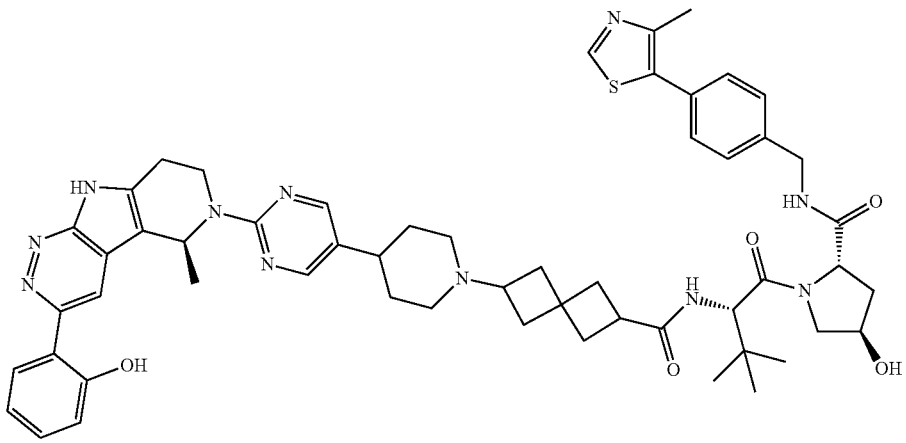 [SMILES: Cc1ncsc1-c1ccc(CNC(=O)[C@@H]2C[C@@H](O)CN2C(=O)[C@@H](NC(=O)C2CC3(C2)CC(N2CCC(c4cnc(N5CCc6[nH]c7nnc(-c8ccccc8O)cc7c6[C@@H]5C)nc4)CC2)C3)C(C)(C)C)cc1] |
| I-38 | 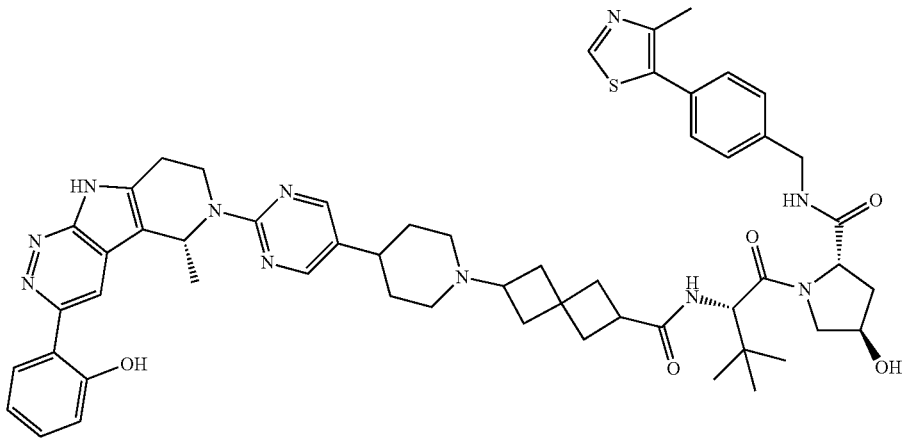 [SMILES: Cc1ncsc1-c1ccc(CNC(=O)[C@@H]2C[C@@H](O)CN2C(=O)[C@@H](NC(=O)C2CC3(C2)CC(N2CCC(c4cnc(N5CCc6[nH]c7nnc(-c8ccccc8O)cc7c6[C@H]5C)nc4)CC2)C3)C(C)(C)C)cc1] |

TABLE 1-continued

Exemplary Compounds

| I-# | Structure |
|---|---|
| I-39 | 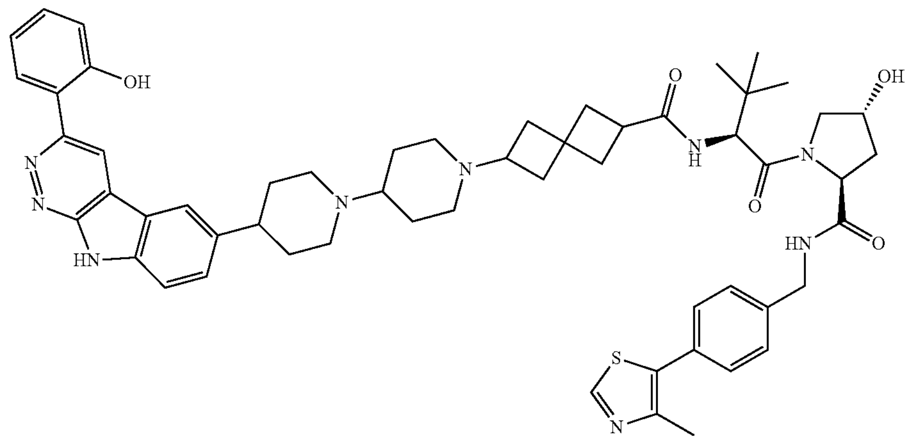 [SMILES: Cc1ncsc1-c1ccc(CNC(=O)[C@@H]2C[C@@H](O)CN2C(=O)[C@@H](NC(=O)C2CC3(C2)CC(N2CCC(N4CCC(c5ccc6[nH]c7nnc(-c8ccccc8O)cc7c6c5)CC4)CC2)C3)C(C)(C)C)cc1] |
| I-40 | 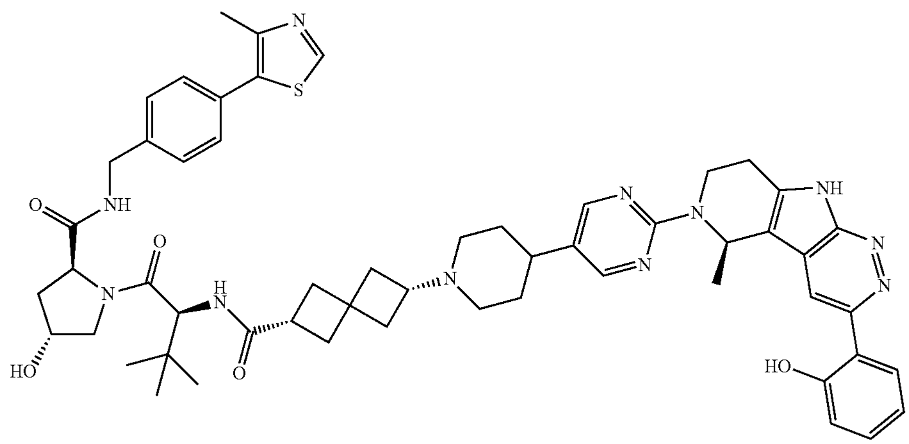 [SMILES: Cc1ncsc1-c1ccc(CNC(=O)[C@@H]2C[C@@H](O)CN2C(=O)[C@@H](NC(=O)[C@H]2CC3(C2)C[C@H](N2CCC(c4cnc(N5CCc6[nH]c7nnc(-c8ccccc8O)cc7c6[C@H]5C)nc4)CC2)C3)C(C)(C)C)cc1] |
| I-41 | 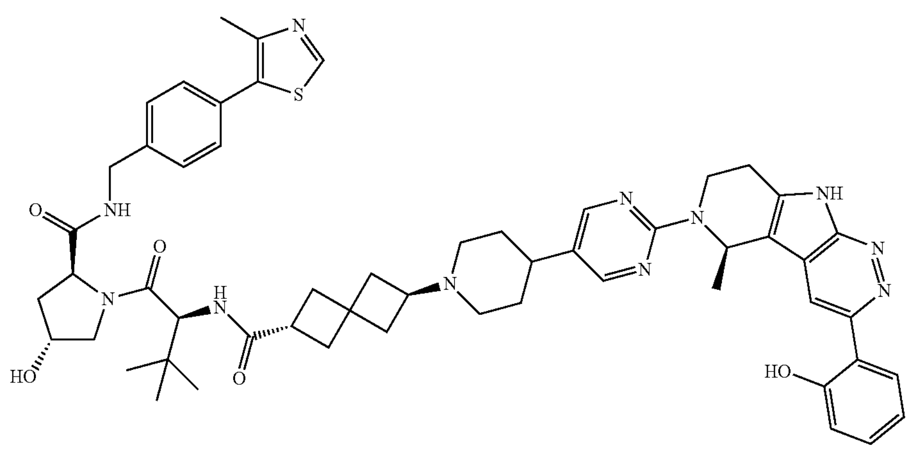 [SMILES: Cc1ncsc1-c1ccc(CNC(=O)[C@@H]2C[C@@H](O)CN2C(=O)[C@@H](NC(=O)[C@H]2CC3(C2)C[C@H](N2CCC(c4cnc(N5CCc6[nH]c7nnc(-c8ccccc8O)cc7c6[C@H]5C)nc4)CC2)C3)C(C)(C)C)cc1] |

In some embodiments, the present invention provides a compound set forth in Table 1, above, or a pharmaceutically acceptable salt thereof.

4. General Methods of Providing the Present Compounds

The compounds of this invention may be prepared or isolated in general by synthetic and/or semi-synthetic methods known to those skilled in the art for analogous compounds and by methods described in detail in the Examples, herein.

In the Schemes below, where a particular protecting group, leaving group, or transformation condition is depicted, one of ordinary skill in the art will appreciate that other protecting groups, leaving groups, and transformation conditions are also suitable and are contemplated. Such groups and transformations are described in detail in

*March's Advanced Organic Chemistry: Reactions, Mechanisms, and Structure*, M. B. Smith and J. March, 5th Edition, John Wiley & Sons, 2001, *Comprehensive Organic Transformations*, R. C. Larock, 2nd Edition, John Wiley & Sons, 1999, and *Protecting Groups in Organic Synthesis*, T. W. Greene and R G. M. Wuts, 3rd edition, John Wiley & Sons, 1999, the entirety of each of which is hereby incorporated herein by reference.

As used herein, the phrase "oxygen protecting group" includes, for example, carbonyl protecting groups, hydroxyl protecting groups, etc. Hydroxyl protecting groups are well known in the art and include those described in detail in *Protecting Groups in Organic Synthesis*, T. W. Greene and P. G. M. Wuts, 3rd edition, John Wiley & Sons, 1999, the entirety of each of which is herein incorporated by reference. Examples of suitable hydroxyl protecting groups include, but are not limited to, esters, allyl ethers, ethers, silyl ethers, alkyl ethers, arylalkyl ethers, and alkoxyalkyl ethers. Examples of such esters include formates, acetates, carbonates, and sulfonates. Specific examples include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio) pentanoate, pivaloate (trimethylacetyl), crotonate, 4-methoxy-crotonate, benzoate, p-benylbenzoate, 2,4,6-trimethylbenzoate, carbonates such as methyl, 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl. Examples of such silyl ethers include trimethylsilyl, triethyl silyl, t-butyldimethylsilyl, t-butyldiphenylsilyl, triisopropylsilyl, and other trialkylsilyl ethers. Alkyl ethers include methyl, benzyl, p-methoxybenzyl, 3,4-dimethoxybenzyl, trityl, t-butyl, allyl, and allyloxycarbonyl ethers or derivatives. Alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyranyl ethers. Examples of arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, and 2- and 4-picolyl.

Amino protecting groups are well known in the art and include those described in detail in *Protecting Groups in Organic Synthesis*, T. W. Greene and P. G. M. Wuts, 3rd edition, John Wiley & Sons, 1999, the entirety of each of which is herein incorporated by reference. Suitable amino protecting groups include, but are not limited to, aralkylamines, carbamates, cyclic imides, allyl amines, amides, and the like. Examples of such groups include t-butyloxycarbonyl (BOC), ethyloxycarbonyl, methyloxycarbonyl, trichloroethyloxycarbonyl, allyloxycarbonyl (Alloc), benzyloxocarbonyl (CBZ), allyl, phthalimide, benzyl (Bn), fluorenylmethylcarbonyl (Fmoc), formyl, acetyl, chloroacetyl, dichloroacetyl, trichloroacetyl, phenylacetyl, trifluoroacetyl, benzoyl, and the like.

In the schemes below, where a final degrader is formed having a reactive DIM moiety (e.g., amine, alcohol, etc.), it is not shown but it is generally appreciated and well known by those having ordinary skill in the art that the reactivity of said reactive DIM moiety may be masked by employing a suitable protecting group that can thereafter be removed in situ or during a separate synthetic step to form the final degrader product.

In certain embodiments, compounds of the present invention are generally prepared according to Scheme 1 set forth below:

Scheme 1: Synthesis of Compounds of the Invention

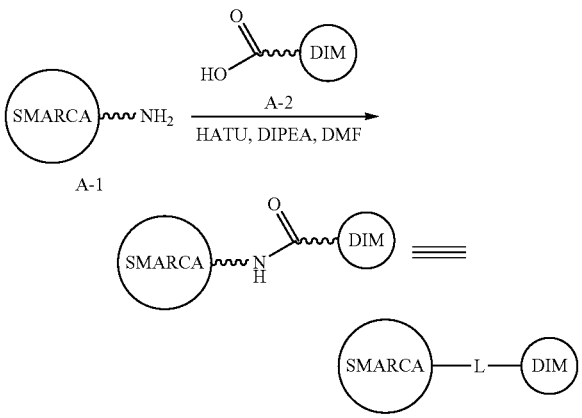

As depicted in Scheme 1, above, amine A-1 is coupled to acid A-2 using the coupling agent HATU in the presence of the base DIPEA in DMF to form a compound of the invention with a linker comprising an amide bond. The squiggly bond, ∼∼∼∼, represents the portion of the linker between SMARCA and the terminal amino group of A-1 or the portion of the linker between DIM and the terminal carboxyl group of A-2, respectively. Additionally, an amide bond can be formed using coupling reagents known in the art such as, but not limited to DCC, DIC, EDC, HBTU, HCTU, PyAOP, PyBrOP, BOP, BOP-Cl, DEPBT, T3P, TATU, TBTU, TNTU, TOTU, TPTU, TSTU, or TDBTU.

In certain embodiments, compounds of the present invention are generally prepared according to Scheme 2 set forth below:

Scheme 2: Synthesis of Compounds of the Invention

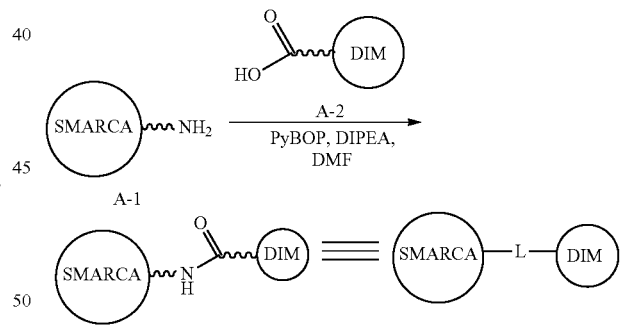

As depicted in Scheme 2, above, amine A-1 is coupled to acid A-2 using the coupling agent PyBOP in the presence of the base DIPEA in DMF to form a compound of the invention with a linker comprising an amide bond. The squiggly bond, ∼∼∼∼, represents the portion of the linker between SMARCA and the terminal amino group of A-1 or the portion of the linker between DIM and the terminal carboxyl group of A-2, respectively. Additionally, an amide bond can be formed using coupling reagents known in the art such as, but not limited to DCC, DIC, EDC, HBTU, HCTU, PyAOP, PyBrOP, BOP, BOP-Cl, DEPBT, T3P, TATU, TBTU, TNTU, TOTU, TPTU, TSTU, or TDBTU.

In certain embodiments, compounds of the present invention are generally prepared according to Scheme 3 set forth below:

Scheme 3: Synthesis of Compounds of the Invention

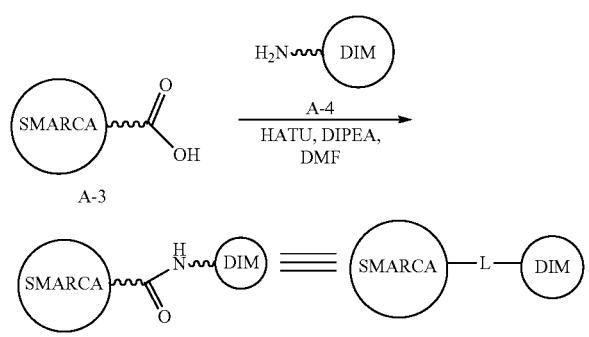

As depicted in Scheme 3, above, acid A-3 is coupled to amine A-4 using the coupling agent HATU in the presence of the base DIPEA in DMF to form a compound of the invention with a linker comprising an amide bond. The squiggly bond, ⁓, represents the portion of the linker between SMARCA and the terminal carboxyl group of A-3 or the portion of the linker between DIM and the terminal amino group of A-4, respectively. Additionally, an amide bond can be formed using coupling reagents known in the art such as, but not limited to DCC, DIC, EDC, HBTU, HCTU, PyAOP, PyBrOP, BOP, BOP-Cl, DEPBT, T3P, TATU, TBTU, TNTU, TOTU, TPTU, TSTU, or TDBTU.

In certain embodiments, compounds of the present invention are generally prepared according to Scheme 4 set forth below:

Scheme 4: Synthesis of Compounds of the Invention

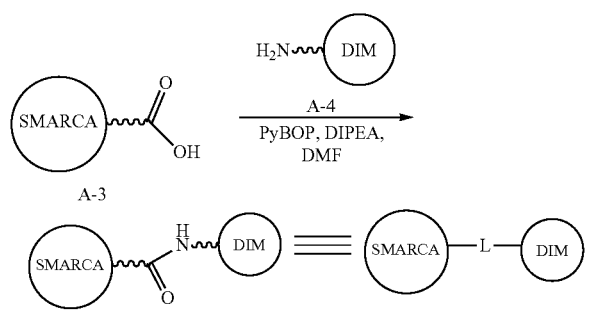

As depicted in Scheme 4, above, acid A-3 is coupled to amine A-4 using the coupling agent PyBOP in the presence of the base DIPEA in DMF to form a compound of the invention with a linker comprising an amide bond. The squiggly bond, ⁓, represents the portion of the linker between SMARCA and the terminal carboxyl group of A-3 or the portion of the linker between DIM and the terminal amino group of A-4, respectively. Additionally, an amide bond can be formed using coupling reagents known in the art such as, but not limited to DCC, DIC, EDC, HBTU, HCTU, PyAOP, PyBrOP, BOP, BOP-Cl, DEPBT, T3P, TATU, TBTU, TNTU, TOTU, TPTU, TSTU, or TDBTU.

In certain embodiments, compounds of the present invention are generally prepared according to Scheme 5 set forth below:

Scheme 5: Synthesis of Compounds of the Invention

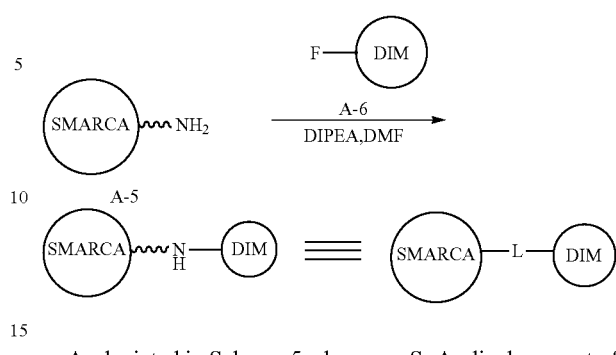

As depicted in Scheme 5, above, an $S_NAr$ displacement of fluoride A-6 by amine A-5 is effected in the presence of the base DIPEA in DMF to form a compound of the invention with a linker comprising a secondary amine. The squiggly bond, ⁓, represents the portion of the linker between SMARCA and the terminal amino group of A-5.

In certain embodiments, compounds of the present invention are generally prepared according to Scheme 6 set forth below:

Scheme 6: Synthesis of Compounds of the Invention

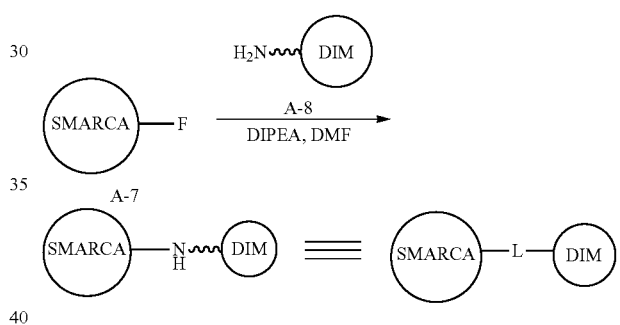

As depicted in Scheme 6, above, an $S_NAr$ displacement of fluoride A-7 by amine A-8 is effected in the presence of the base DIPEA in DMF to form a compound of the invention with a linker comprising a secondary amine. The squiggly bond, ⁓, represents the portion of the linker between DIM and the terminal amino group of A-8.

In certain embodiments, compounds of the present invention are generally prepared according to Scheme 7 set forth below:

Scheme 7: Synthesis of Compounds of the Invention

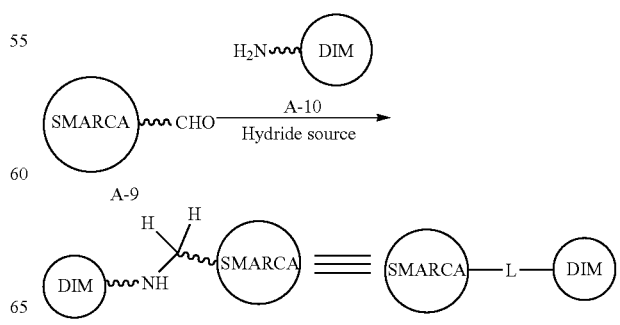

As depicted in Scheme 7, above, reductive alkylation of aldehyde A-9 by amine A-10 is effected in the presence of a mild hydride source (e.g., sodium cyanoborohydride or sodium triacetoxyborohydride) to form a provided compound with a linker comprising a secondary amine. The squiggly bond, ⁓⁓⁓, represents the portion of the linker between DIM and the terminal amino group of A-10.

In certain embodiments, compounds of the present invention are generally prepared according to Scheme 8 set forth below:

Scheme 8: Synthesis of Compounds of the Invention

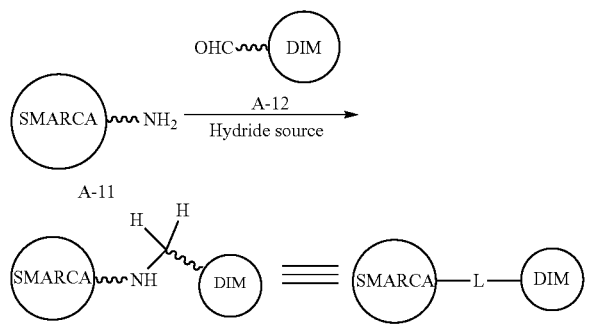

As depicted in Scheme 8, above, reductive alkylation of aldehyde A-12 by amine A-11 is effected in the presence of a mild hydride source (e.g., sodium cyanoborohydride or sodium triacetoxyborohydride) to form a provided compound with a linker comprising a secondary amine. The squiggly bond, ⁓⁓⁓, represents the portion of the linker between SMARCA and the terminal amino group of A-11.

One of skill in the art will appreciate that various functional groups present in compounds of the invention such as aliphatic groups, alcohols, carboxylic acids, esters, amides, aldehydes, halogens and nitriles can be interconverted by techniques well known in the art including, but not limited to reduction, oxidation, esterification, hydrolysis, partial oxidation, partial reduction, halogenation, dehydration, partial hydration, and hydration. See for example, "March's Advanced Organic Chemistry", 5$^{th}$ Ed., Ed.: Smith, M. B. and March, J., John Wiley & Sons, New York: 2001, the entirety of each of which is herein incorporated by reference. Such interconversions may require one or more of the aforementioned techniques, and certain methods for synthesizing compounds of the invention are described below in the Exemplification.

5. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably degrade and/or inhibit a SMARCA and/or PB1 protein, or a mutant thereof, in a biological sample or in a patient. In certain embodiments, the amount of compound in compositions of this invention is such that is effective to measurably degrade and/or inhibit a SMARCA and/or PB1 protein, or a mutant thereof, in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily or degratorily active metabolite or residue thereof.

As used herein, the term "inhibitorily active metabolite or residue thereof" means that a metabolite or residue thereof is also an inhibitor of a SMARCA and/or PB1 protein, or a mutant thereof.

As used herein, the term "degratorily active metabolite or residue thereof" means that a metabolite or residue thereof is also a degrader of an SMARCA and/or PB1 protein, or a mutant thereof.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrastemal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the compound can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Compounds and compositions described herein are generally useful for the degradation and/or inhibition of a SMARCA or PB1 protein activity.

Examples of SMARCA proteins that are degraded and/or inhibited by the compounds and compositions described herein and against which the methods described herein are useful include those of the SWI/SNF-related matrix-associated actin-dependent regulators of chromatin subfamily A ("SMARCA") family of proteins, the members of which include SMARCA1, SMARCA2, SMARCA4, or SMARCA5, or a mutant thereof. See e.g., Shain and Pollack "The Spectrum of SWI/SNF Mutations, Ubiquitous in Human Cancers. *PLoS One* 2013, 8:e55119; Kadoch and Crabtree "Mammalian SWI/SNF Chromatin Remodeling Complexes and Cancer: Mechanistic Insights Gained from Human Genomics" *Sci. Adv.* 2015, 1:e1500447; Wilson and Roberts "SWI/SNF Nucleosome Remodelers and Cancer" *Nat. Rev. Cancer* 2011, 11:481; and Son and Crabtree "The Role of BAF (mSWI/SNF) Complexes in Mammalian Neural Development" *Am. J. Med. Genet., Part C* 2014, 166: 333, the entirety of each of which is herein incorporated by reference.

The activity of a compound utilized in this invention as a degrader and/or inhibitor of one or more SMARCA or PB1, or a mutant thereof, may be assayed in vitro, in vivo or in a cell line. In vitro assays include assays that determine inhibition of either the activity and/or the subsequent functional consequences of activated SMARCA or PB1 protein, or a mutant thereof. Alternate in vitro assays quantitate the ability of the inhibitor to bind to a SMARCA or PB1 protein. Inhibitor binding may be measured by radiolabeling the inhibitor prior to binding, isolating the inhibitor/SMARCA or PB1 complex and determining the amount of radiolabel bound. Alternatively, inhibitor binding may be determined by running a competition experiment where new inhibitors are incubated with a SMARCA or PB1 protein bound to known radioligands. Representative in vitro and in vivo assays useful in assaying a SMARCA or PB1 inhibitor include those described and disclosed in, e.g., Tanaka et al. "Design and Characterization of Bivalent BET Inhibitors" *Nat. Chem. Biol.* 2016, 12(12): 1089; Schiaffino-Ortega et al. "SWI/SNF as targets in cancer therapy" *J. Hematol. Oncol.* 2014, 7:81; Filippakopoulos et al. "Histone Recognition and Farge-Scale Structural Analysis of the Human Bromodomain Family" *Cell* 2012, 149:214. Detailed conditions for assaying a compound utilized in this invention as a degrader and/or inhibitor of a SMARCA or PB1 protein, or a mutant thereof, are set forth in the Examples below.

Chromatin is a complex combination of DNA and protein that makes up chromosomes. Chromatin functions to package, strengthen, and control expression and DNA replication. The chromatin structure is controlled by a series of post-translational modifications, most commonly within the "histone tails" which extend beyond the core nucleosome structure. These epigenetic modifications including acetylation, methylation, phosphorylation, ubiquitinylation, and SUMOylation, is then interpreted by the cell to allow gene specific regulation of chromatin structure and thereby transcription. Histone modifications are dynamic, as they can be added or removed in response to specific stimuli, and these modifications direct both structural changes to chromatin and alterations in gene transcription. Distinct classes of enzymes, namely histone acetyltransferases (HATs) and histone deacetylases (HDACs), acetylate or de-acetylate specific histone lysine residues (Struhl, *Genes Dev.* 1989, 12(5):599).

Bromodomains, which are approximately 110 amino acids long, are found in a large number of chromatin-associated proteins and have been identified in approximately 70 human proteins, often adjacent to other protein motifs (Jeanmougin et al., *Trends Biochem. Sci.* 1997, 22(5): 151; Tamkun et al., *Cell* 1992, 7(3):561). Interactions between bromodomains and modified histones may be an important mechanism underlying chromatin structural changes and gene regulation. Bromodomain-containing proteins have been implicated in disease processes including cancer, inflammation and viral replication. See, e.g., Prinjha et al, *Trends Pharm. Sci.* 2012, 33(3): 146; Muller et al. *Expert Rev.* 2011, 13(29):1.

Cell-type specificity and proper tissue functionality requires the tight control of distinct transcriptional programs that are intimately influenced by their environment. Alterations to this transcriptional homeostasis are directly associated with numerous disease states, most notably cancer, immuno-inflammation, neurological disorders, and metabolic diseases. Bromodomains reside within key chromatin modifying complexes that serve to control distinctive disease-associated transcriptional pathways. An example of such a complex is the switch/sucrose nonfermenting ("SWI/SNF") chromatin-remodeling complex, which has been reported to be involved in gene regulation, cell lineage specification and development, and comprises a number of bromodomain containing subunits, including SWI/SNF-related matrix-associated actin-dependent regulator of chromatin subfamily A member 2 and 4 (SMARCA2 and SMARCA4) and polybromo-1 (PB1; also known as PBRM1). SMARCA2 and SMARCA4, also known as transcription activators Brahma homologue (BRM) and Brahma-related gene 1 (BRG1) respectively, are mutually exclusive helicase/ATPase proteins of the large ATP-dependent SWI/SNF chromatin-remodeling complexes involved in transcriptional regulation of gene expression. In some embodiments, a provided compound binds to one or more SMARCA2, SMARCA4, or PB1 bromodomains. In some embodiments, a provided compound binds to one or more SMARCA2, SMARCA4, or PB1 ATPase domains.

Representative SMARCA2, SMARCA4, and/or PB1 inhibitors include those described and disclosed in e.g., Gerstenberger et al. *J. Med. Chem.* 2016, 59(10):4800; Theodoulou et al. *Curr Opin. Chem. Bio.* 2016, 33:58; Vangamudi et al. *Cancer Res.* 2015, 75(18):3865; the entirety of each of which is herein incorporated by reference.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Provided compounds are degraders and/or inhibitors of one or more SMARCA2, SMARCA4, or PB1 protein and are therefore useful for treating one or more disorders associated with activity of one or more of SMARCA2, SMARCA4, or PB1 protein. Thus, in certain embodiments, the present invention provides a method for treating a SMARCA2-mediated, SMARCA4-mediated, or PB1-mediated disorder comprising the step of administering to a patient in need thereof a compound of the present invention, or pharmaceutically acceptable composition thereof.

As used herein, the terms "SMARCA2-mediated", "SMARCA4-mediated", or "PB1-mediated" disorders, diseases, and/or conditions as used herein means any disease or other deleterious condition in which one or more SMARCA2, SMARCA4, or PB1, or a mutant thereof, are known to play a role. Accordingly, another embodiment of the present invention relates to treating or lessening the severity of one or more diseases in which one or more SMARCA2, SMARCA4, or PB1, or a mutant thereof, are known to play a role.

In some embodiments, the present invention provides a method for treating one or more disorders, diseases, and/or conditions wherein the disorder, disease, or condition is a cancer, a neurodegenative disorder, a viral disease, an autoimmune disease, an inflammatory disorder, a hereditary disorder, a hormone-related disease, a metabolic disorder, conditions associated with organ transplantation, immunodeficiency disorders, a destructive bone disorder, a proliferative disorder, an infectious disease, a condition associated with cell death, thrombin-induced platelet aggregation, liver disease, pathologic immune conditions involving T cell activation, a cardiovascular disorder, or a CNS disorder.

Diseases and conditions treatable according to the methods of this invention include, but are not limited to, cancer (see, e.g., Schiaffino-Ortega et al. *J. Hematol. Oncol.* 2014, 7:81; Medina et al. Gene Chromosome Canc. 2014, 41:170), diabetes, cardiovascular disease (see, e.g., Bevilacqua et al., *Cardiovasc. Pathol.* 2013, 23(2):85), viral disease, autoimmune diseases such as lupus, and rheumatoid arthritis, autoinflammatory syndromes, atherosclerosis (see. e.g., Ortiz-Mao et al., *J. Proteom Genom Res.* 2017, 2(1): 1), psoriasis, allergic disorders, inflammatory bowel disease, inflammation, acute and chronic gout and gouty arthritis, neurological disorders (see, e.g., Pandey et al., *J. Hum. Genet.* 2004, 49:596), metabolic syndrome, immunodeficiency disorders such as AIDS and HIV (see, e.g., Boehm et al., *Viruses* 2013, 5:1571), genetic disorders (see, e.g., Kosho et al., *Am. J. Med. Genet.* 2014, 166(3):262; Tang et al., *Am. J. Med. Genet.* 2015, 173(1): 195), destructive bone disorders, osteoarthritis (see, e.g., Tian, *J. Orthop. Surg. Res.* 2018, 13:49), proliferative disorders (see, e.g., Cruickshank et al., *PLoS One* 2015, 10(11):e0142806), Waldenström's Macroglobulinemia. infectious diseases, conditions associated with cell death, pathologic immune conditions involving T cell activation, and CNS disorders (see. e.g., Koga et al., *Human Mol. Gen.* 2009, 18(13):2483) in a patient. In one embodiment, a human patient is treated with a compound of the current invention and a pharmaceutically acceptable carrier, adjuvant, or vehicle, wherein said compound is present in an amount to measurably degrade and/or inhibit one or more SMARCA2, SMARCA4, or PB1, or a mutant thereof Compounds of the current invention are useful in the treatment of a proliferative disease selected from a benign or malignant tumor, solid tumor, carcinoma of the brain, kidney, liver, adrenal gland, bladder, breast, stomach, gastric tumors, ovaries, colon, rectum, prostate, pancreas, lung, vagina, cervix, testis, genitourinary tract, esophagus, larynx, skin, bone or thyroid, sarcoma, glioblastomas, neuroblastomas, multiple myeloma, gastrointestinal cancer, especially colon carcinoma or colorectal adenoma, a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, Hodgkins and Non-Hodgkins, a mammary carcinoma, follicular carcinoma, undifferentiated carcinoma, papillary carcinoma, seminoma, melanoma, an IL-1 driven disorder, an MyD88 driven disorder, Smoldering of indolent multiple myeloma, or hematological malignancies (including leukemia, diffuse large B-cell lymphoma (DLBCL), ABC DLBCL, chronic lymphocytic leukemia (CLL), chronic lymphocytic lymphoma, primary effusion lymphoma, Burkitt lymphoma/leukemia, acute lymphocytic leukemia, B-cell prolymphocytic leukemia, lymphoplasmacytic lymphoma, Waldenström's macroglobulinemia (WM), splenic marginal zone lymphoma, multiple myeloma, plasmacytoma, intravascular large B-cell lymphoma).

In certain embodiments, the cancer treated by a provided compound is lung cancer, non-small cell lung cancer (NSCLC), small-cell lung cancer, glioma, breast cancer, pancreatic cancer, colorectal cancer, bladder cancer, endometrial cancer, penile cancer, esophagogastric cancer, hepatobiliary cancer soft tissue sarcoma, ovarian cancer, head and neck cancer, renal cell carsinoma, bone cancer, non-Hodgkin lymphoma, prostate cancer, embryonal tumors, germ cell tumors, cervical cancer, thyroid cancer, salivary gland cancer, gastrointestinal neuroendocrine tumor, uterine sarcoma, gastrointestinal stromal tumor, CNS cancer, thymic tumor, adrenocortical carcinoma, appendiceal cancer, small bowel cancer, non-melanoma skin cancer, and/or melanoma. In some embodiments, the cancer is lung cancer. In some embodiments, the lung cancer is NSCLC. In some embodiments, the cancer is breast cancer. In some embodiments, the cancer is melanoma.

In some embodiments, the present invention provides a method of treating lung cancer in a patient in need thereof, comprising administering a compound of the present invention, or a pharmaceutically acceptable salt thereof.

In some embodiments, the present invention provides a method of treating non-small cell lung cancer (NSCLC) in a patient in need thereof, comprising administering a compound of the present invention, or a pharmaceutically acceptable salt thereof.

In some embodiments, the present invention provides a method of treating glioma in a patient in need thereof, comprising administering a compound of the present invention, or a pharmaceutically acceptable salt thereof.

In some embodiments, the present invention provides a method of treating breast cancer in a patient in need thereof, comprising administering a compound of the present invention, or a pharmaceutically acceptable salt thereof.

In some embodiments, the present invention provides a method of treating pancreatic cancer in a patient in need thereof, comprising administering a compound of the present invention, or a pharmaceutically acceptable salt thereof.

In some embodiments, the present invention provides a method of treating colorectal cancer in a patient in need thereof, comprising administering a compound of the present invention, or a pharmaceutically acceptable salt thereof.

In some embodiments, the present invention provides a method of treating bladder cancer in a patient in need thereof, comprising administering a compound of the present invention, or a pharmaceutically acceptable salt thereof.

In some embodiments, the present invention provides a method of treating endometrial cancer in a patient in need thereof, comprising administering a compound of the present invention, or a pharmaceutically acceptable salt thereof.

In some embodiments, the present invention provides a method of treating penile cancer in a patient in need thereof, comprising administering a compound of the present invention, or a pharmaceutically acceptable salt thereof.

In some embodiments, the present invention provides a method of treating non-melanoma skin cancer in a patient in need thereof, comprising administering a compound of the present invention, or a pharmaceutically acceptable salt thereof.

In some embodiments, the present invention provides a method of treating melanoma in a patient in need thereof, comprising administering a compound of the present invention, or a pharmaceutically acceptable salt thereof.

SMARCA2 has recently been reported as a synthetic lethal target in SMARCA4-deficient cancers (e.g., cancers comprising SMARCA4 loss of function mutations and/or cancers having reduced or absent expression, e.g., due to epigenetic alterations). SMARCA2 depletion has been shown to selectively inhibit the growth of SMARCA4-mutant cancer cells (Hoffman et al., *PNAS* 2014, 111(8): 3128; Oike et al., *Cancer Res.* 2013, 73(17):5508). In some embodiments, the cancer treated by a provided compound is a SMARCA4-deficient cancer (e.g, a cancer harboring a loss of function mutation and/or having reduced or absent SMARCA4 expression).

It has also been shown that certain cancers are dependent on SMARCA4 for disease progression and are vulnerable to SMARCA4 inhibition, including certain acute leukemia and small cell lung cancers (Hohmann et al., *Trends in Genetics*, 2014, 30(8):356). In some embodiments, the cancer treated by a provided compound is leukemia (e.g., acute leukemia, e.g., acute myeloid leukemia), breast cancer, small cell lung cancer, or malignant rhabdoid tumors (MRT) (e.g., a SNF5-deficient malignant rhabdoid tumor).

In some embodiments, the present invention provides a method of treating leukemia in a patient in need thereof, comprising administering a compound of the present invention, or a pharmaceutically acceptable salt thereof.

In some embodiments, the present invention provides a method of treating malignant rhabdoid tumors (MRT) in a patient in need thereof, comprising administering a compound of the present invention, or a pharmaceutically acceptable salt thereof.

Compounds according to the invention are useful in the treatment of inflammatory or obstructive airways diseases, resulting, for example, in reduction of tissue damage, airways inflammation, bronchial hyperreactivity, remodeling or disease progression. Inflammatory or obstructive airways diseases to which the present invention is applicable include asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics.

Compounds according to the invention are useful in the treatment of heteroimmune diseases. Examples of such heteroimmune diseases include, but are not limited to, graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis.

Prophylactic efficacy in the treatment of asthma will be evidenced by reduced frequency or severity of symptomatic attack, e.g. of acute asthmatic or bronchoconstrictor attack, improvement in lung function or improved airways hyperreactivity. It may further be evidenced by reduced requirement for other, symptomatic therapy, such as therapy for or intended to restrict or abort symptomatic attack when it occurs, for example anti-inflammatory or bronchodilatory. Prophylactic benefit in asthma may in particular be apparent in subjects prone to "morning dipping". "Morning dipping" is a recognized asthmatic syndrome, common to a substantial percentage of asthmatics and characterized by asthma attack, e.g. between the hours of about 4 to 6 am, i.e. at a time normally substantially distant form any previously administered symptomatic asthma therapy.

Compounds of the current invention can be used for other inflammatory or obstructive airways diseases and conditions to which the present invention is applicable and include acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, but not limited to, acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

With regard to their anti-inflammatory activity, in particular in relation to inhibition of eosinophil activation, compounds of the invention are also useful in the treatment of eosinophil related disorders, e.g. eosinophilia, in particular eosinophil related disorders of the airways (e.g. involving morbid eosinophilic infiltration of pulmonary tissues) including hypereosinophilia as it effects the airways and/or lungs as well as, for example, eosinophil-related disorders of the airways consequential or concomitant to Loffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction.

Compounds of the invention are also useful in the treatment of inflammatory or allergic conditions of the skin, for example psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, systemic lupus erythematosus, pemphigus vulgaris, pemphigus foliaceus, paraneoplastic pemphigus, epidermolysis bullosa acquisita, acne vulgaris, and other inflammatory or allergic conditions of the skin.

Compounds of the invention may also be used for the treatment of other diseases or conditions, such as diseases or conditions having an inflammatory component, for example, treatment of diseases and conditions of the eye such as ocular allergy, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), systemic lupus erythematosus, rheumatoid arthritis, polychondritis, scleroderma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), irritable bowel syndrome, celiac disease, periodontitis, hyaline membrane disease, kidney disease, glomerular disease, alcoholic liver disease, multiple sclerosis, endocrine opthalmopathy, Grave's disease, sarcoidosis, alveolitis, chronic hypersensitivity pneumonitis, multiple sclerosis, primary biliary cirrhosis, uveitis (anterior and posterior), Sjogren's syndrome, keratoconjunctivitis sicca and vernal keratoconjunctivitis, interstitial lung fibrosis, psoriatic arthritis, systemic juvenile idiopathic arthritis, cryopyrin-associated periodic syndrome, nephritis, vasculitis, diverticulitis, interstitial cystitis, glomerulonephritis (with and without nephrotic syndrome, e.g. including idiopathic nephrotic syndrome or minal change nephropathy), chronic granulomatous disease, endometriosis, leptospiriosis renal disease, glaucoma, retinal disease, ageing, headache, pain, complex regional pain syndrome, cardiac hypertrophy, musclewasting, catabolic disorders, obesity, fetal growth retardation, hyperchlolesterolemia, heart disease, chronic heart failure, mesothelioma, anhidrotic ecodermal dysplasia, Behcet's disease, incontinentia pigmenti, Paget's disease, pancreatitis, hereditary periodic fever syndrome, asthma (allergic and non-allergic, mild, moderate, severe, bronchitic, and exercise-induced), acute lung injury, acute respiratory distress syndrome, eosinophilia, hypersensitivities, anaphylaxis, nasal sinusitis, ocular allergy, silica induced diseases, COPD (reduction of damage, airways inflammation, bronchial hyperreactivity, remodeling or disease progression), pulmonary disease, cystic fibrosis, acid-induced lung injury, pulmonary hypertension, polyneuropathy, cataracts, muscle inflammation in conjunction with systemic sclerosis, inclusion body myositis, myasthenia gravis, thyroiditis, Addison's disease, lichen planus, Type 1 diabetes, or Type 2 diabetes, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis.

In some embodiments the inflammatory disease which can be treated according to the methods of this invention is a disease of the skin. In some embodiments, the inflammatory disease of the skin is selected from contact dermatitits, atompic dermatitis, alopecia areata, erythema multiforma, dermatitis herpetiformis, scleroderma, vitiligo, hypersensitivity angiitis, urticaria, bullous pemphigoid, pemphigus vulgaris, pemphigus foliaceus, paraneoplastic pemphigus, epidermolysis bullosa acquisita, and other inflammatory or allergic conditions of the skin.

In some embodiments the inflammatory disease which can be treated according to the methods of this invention is selected from acute and chronic gout, chronic gouty arthritis, psoriasis, psoriatic arthritis, rheumatoid arthritis, Juvenile rheumatoid arthritis, Systemic juvenile idiopathic arthritis (SJIA), Cryopyrin Associated Periodic Syndrome (CAPS), and osteoarthritis.

In some embodiments the inflammatory disease which can be treated according to the methods of this invention is a TH17 mediated disease. In some embodiments the TH17 mediated disease is selected from Systemic lupus erythematosus, Multiple sclerosis, and inflammatory bowel disease (including Crohn's disease or ulcerative colitis).

In some embodiments the inflammatory disease which can be treated according to the methods of this invention is selected from Sjogren's syndrome, allergic disorders, osteoarthritis, conditions of the eye such as ocular allergy, conjunctivitis, keratoconjunctivitis sicca and vernal conjunctivitis, and diseases affecting the nose such as allergic rhinitis.

Cardiovascular diseases which can be treated according to the methods of this invention include, but are not limited to, restenosis, cardiomegaly, atherosclerosis, myocardial infarction, ischemic stroke, congestive heart failure, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, and deep venous thrombosis.

In some embodiments, the neurodegenerative disease which can be treated according to the methods of this invention include, but are not limited to, Alzheimer's disease, Parkinson's disease, amyotrophic lateral sclerosis, Huntington's disease, cerebral ischemia, and neurodegenerative disease caused by traumatic injury, glutamate neurotoxicity, hypoxia, epilepsy, treatment of diabetes, metabolic syndrome, obesity, organ transplantation and graft versus host disease.

In some embodiments the invention provides a method of treating, preventing or lessening the severity of Alzheimer's disease comprising administering to a patient in need thereof a provided compound or a pharmaceutically acceptable salt or composition thereof.

In some embodiments the invention provides a method of treating a disease or condition commonly occurring in connection with transplantation. In some embodiments, the disease or condition commonly occurring in connection with transplantation is selected from organ transplantation, organ transplant rejection, and graft versus host disease.

In some embodiments the invention provides a method of treating a metabolic disease. In some embodiments the metabolic disease is selected from Type 1 diabetes, Type 2 diabetes, metabolic syndrome, and obesity.

In some embodiments the invention provides a method of treating a viral disease. In some embodiments, the viral infection is HIV infection.

Furthermore, the invention provides the use of a compound according to the definitions herein, or a pharmaceutically acceptable salt, or a hydrate or solvate thereof for the preparation of a medicament for the treatment of a proliferative disease, an inflammatory disease, an obstructive respiratory disease, a cardiovascular disease, a metabolic disease, a neurological disease, a neurodegenerative disease, a viral disease, or a disorder commonly occurring in connection with transplantation.

Combination Therapies

Depending upon the particular condition, or disease, to be treated, additional therapeutic agents, which are normally administered to treat that condition, may be administered in combination with compounds and compositions of this invention. As used herein, additional therapeutic agents that are normally administered to treat a particular disease, or condition, are known as "appropriate for the disease, or condition, being treated."

In certain embodiments, a provided combination, or composition thereof, is administered in combination with another therapeutic agent.

In some embodiments, the present invention provides a method of treating a disclosed disease or condition comprising administering to a patient in need thereof an effective amount of a compound disclosed herein or a pharmaceutically acceptable salt thereof and co-administering simultaneously or sequentially an effective amount of one or more additional therapeutic agents, such as those described herein. In some embodiments, the method includes co-administering one additional therapeutic agent. In some embodiments, the method includes co-administering two additional therapeutic agents. In some embodiments, the combination of the disclosed compound and the additional therapeutic agent or agents acts synergistically.

Examples of agents the combinations of this invention may also be combined with include, without limitation: treatments for Alzheimer's Disease such as Aricept® and Excelon®; treatments for HIV such as ritonavir; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents that prolong or improve pharmacokinetics such as cytochrome P450 inhibitors (i.e., inhibitors of metabolic breakdown) and CYP3A4 inhibitors (e.g., ketokenozole and ritonavir), and agents for treating immunodeficiency disorders such as gamma globulin.

In certain embodiments, combination therapies of the present invention, or a pharmaceutically acceptable composition thereof, are administered in combination with a monoclonal antibody or an siRNA therapeutic.

Those additional agents may be administered separately from a provided combination therapy, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a combination of the present invention may be administered with another therapeutic agent simultaneously or sequentially in separate unit dosage forms or together in a single unit dosage form.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

One or more other therapeutic agent may be administered separately from a compound or composition of the invention, as part of a multiple dosage regimen. Alternatively, one or more other therapeutic agents may be part of a single dosage form, mixed together with a compound of this invention in a single composition. If administered as a multiple dosage regime, one or more other therapeutic agent and a compound or composition of the invention may be administered simultaneously, sequentially or within a period of time from one another, for example within 1, 2, 3, 4, 5, 6, 7, 8, 9, 10, 11, 12, 13, 14, 15, 16, 17, 18, 18, 20, 21, 22, 23, or 24 hours from one another. In some embodiments, one or more other therapeutic agent and a compound or composition of the invention are administered as a multiple dosage regimen within greater than 24 hours apart.

In one embodiment, the present invention provides a composition comprising a provided compound and one or more additional therapeutic agents. The therapeutic agent may be administered together with a provided compound, or may be administered prior to or following administration of a provided compound. Suitable therapeutic agents are described in further detail below. In certain embodiments, a provided compound may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours before the therapeutic agent. In other embodiments, a provided compound may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours following the therapeutic agent.

In another embodiment, the present invention provides a method of treating an inflammatory disease, disorder or condition by administering to a patient in need thereof a provided compound and one or more additional therapeutic agents. Such additional therapeutic agents may be small molecules or recombinant biologic agents and include, for example, acetaminophen, non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol, febuxostat (Uloric®), sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), canakinumab (Haris®), anti-Jak inhibitors such as tofacitinib, antibodies such as rituximab (Rituxan®), "anti-T-cell" agents such as abatacept (Orencia®), "anti-IL-6" agents such as tocilizumab (Actemra®), diclofenac, cortisone, hyaluronic acid (Synvisc® or Hyalgan®), monoclonal antibodies such as tanezumab, anticoagulants such as heparin (Calcinparine® or Liquaemin®) and warfarin (Coumadin®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot®, anticholinergics or antispasmodics such as dicyclomine (Bentyl®), Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as beclomethasone dipropionate (Beclovent®, Qvar®, and Vanceril®), triamcinolone acetonide (Azmacort®), mometasone (Asthmanex®), budesonide (Pulmocort®), and flunisolide (Aerobid®), Afviar®, Symbicort®, Dulera®, cromolyn sodium (Intal®), methylxanthines such as theophylline (Theo-Dur®, Theolair®, Slo-bid®, Uniphyl®, Theo-24®) and aminophylline, IgE antibodies such as omalizumab (Xolair®), nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevairapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfmavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), doxorubicin (Hydrodaunorubicin®), vincristine (Oncovin®), bortezomib (Velcade®), and dexamethasone (Decadron®) in combination with lenalidomide (Revlimid®), or any combination(s) thereof.

In another embodiment, the present invention provides a method of treating gout comprising administering to a patient in need thereof a provided compound and one or more additional therapeutic agents selected from non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol and febuxostat (Uloric®).

In another embodiment, the present invention provides a method of treating rheumatoid arthritis comprising administering to a patient in need thereof a provided compound and one or more additional therapeutic agents selected from non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), antibodies such as rituximab (Rituxan®), "anti-T-cell" agents such as abatacept (Orencia®) and "anti-IL-6" agents such as tocilizumab (Actemra®).

In some embodiments, the present invention provides a method of treating osteoarthritis comprising administering to a patient in need thereof a provided compound and one or more additional therapeutic agents selected from acetaminophen, non-steroidal anti-inflammatory drugs (NSAIDS) such as aspirin, ibuprofen, naproxen, etodolac (Lodine®) and celecoxib, diclofenac, cortisone, hyaluronic acid (Synvisc® or Hyalgan®) and monoclonal antibodies such as tanezumab.

In some embodiments, the present invention provides a method of treating lupus comprising administering to a patient in need thereof a provided compound and one or more additional therapeutic agents selected from acetaminophen, non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, antimalarials such as hydroxychloroquine (Plaquenil®) and chloroquine (Aralen®), cyclophosphamide (Cytoxan®), methotrexate (Rheumatrex®), azathioprine (Imuran®) and anticoagulants such as heparin (Calcinparine® or Liquaemin®) and warfarin (Coumadin®).

In some embodiments, the present invention provides a method of treating inflammatory bowel disease comprising administering to a patient in need thereof a provided compound and one or more additional therapeutic agents selected from mesalamine (Asacol®) sulfasalazine (Azulfidine®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot® and anticholinergics or antispasmodics such as dicyclomine (Bentyl®), anti-TNF therapies, steroids, and antibiotics such as Flagyl or ciprofloxacin.

In some embodiments, the present invention provides a method of treating asthma comprising administering to a patient in need thereof a provided compound and one or more additional therapeutic agents selected from Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), AfViar®, Symbicort®, and Dulera®, cromolyn sodium (Intal®), methylxanthines such as theophylline (Theo-Dur®, Theolair®, Slo-bid®, Uniphyl®, Theo-24®) and aminophylline, and IgE antibodies such as omalizumab (Xolair®).

In some embodiments, the present invention provides a method of treating COPD comprising administering to a patient in need thereof a provided compound and one or more additional therapeutic agents selected from beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), methylxanthines such as theophylline (Theo-Dur®, Theolair®, Slo-bid®, Uniphyl®, Theo-24®) and aminophylline, inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, In some embodiments, the present invention provides a method of treating HIV comprising administering to a patient in need thereof a provided compound and one or more additional therapeutic agents selected from nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevairapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), and combinations thereof.

In another embodiment, the present invention provides a method of treating a hematological malignancy comprising administering to a patient in need thereof a provided compound and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a TYK2 inhibitor, a PI3K inhibitor, a SYK inhibitor, and combinations thereof.

In another embodiment, the present invention provides a method of treating a solid tumor comprising administering to a patient in need thereof a provided compound and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a TYK2 inhibitor, a PI3K inhibitor, a SYK inhibitor, and combinations thereof.

In another embodiment, the present invention provides a method of treating a hematological malignancy comprising administering to a patient in need thereof a provided compound and a Hedgehog (Hh) signaling pathway inhibitor. In some embodiments, the hematological malignancy is DLBCL (Ramirez et al "Defining causative factors contributing in the activation of hedgehog signaling in diffuse large B-cell lymphoma" Leuk. Res. (2012), published online July 17, and incorporated herein by reference in its entirety).

In another embodiment, the present invention provides a method of treating diffuse large B-cell lymphoma (DLBCL) comprising administering to a patient in need thereof a provided compound and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, and combinations thereof.

In another embodiment, the present invention provides a method of treating multiple myeloma comprising administering to a patient in need thereof a provided compound and one or more additional therapeutic agents selected from bortezomib (Velcade®), and dexamethasone (Decadron®), a hedgehog signaling inhibitor, a BTK inhibitor, a JAK/pan-JAK inhibitor, a TYK2 inhibitor, a PI3K inhibitor, a SYK inhibitor in combination with lenalidomide (Revlimid®).

In another embodiment, the present invention provides a method of treating Waldenström's macroglobulinemia comprising administering to a patient in need thereof a provided compound and one or more additional therapeutic agents selected from chlorambucil (Leukeran®), cyclophosphamide (Cytoxan®, Neosar®), fludarabine (Fludara®), cladribine (Leustatin®), rituximab (Rituxan®), a hedgehog signaling inhibitor, a BTK inhibitor, a JAK/pan-JAK inhibitor, a TYK2 inhibitor, a PI3K inhibitor, and a SYK inhibitor.

In some embodiments, one or more other therapeutic agent is an antagonist of the hedgehog pathway. Approved hedgehog pathway inhibitors which may be used in the present invention include sonidegib (Odomzo®, Sun Pharmaceuticals); and vismodegib (Erivedge®, Genentech), both for treatment of basal cell carcinoma.

In some embodiments, one or more other therapeutic agent is a Poly ADP ribose polymerase (PARP) inhibitor. In some embodiments, a PARP inhibitor is selected from olaparib (Lynparza®, AstraZeneca); rucaparib (Rubraca®, Clovis Oncology); niraparib (Zejula®, Tesaro); talazoparib (MDV3800/BMN 673/LT00673, Medivation/Pfizer/Biomarin); veliparib (ABT-888, AbbVie); and BGB-290 (BeiGene, Inc.).

In some embodiments, one or more other therapeutic agent is a histone deacetylase (HDAC) inhibitor. In some embodiments, an HDAC inhibitor is selected from vorinostat (Zolinza®, Merck); romidepsin (Istodax®, Celgene); panobinostat (Farydak®, Novartis); belinostat (Beleodaq®, Spectrum Pharmaceuticals); entinostat (SNDX-275, Syndax Pharmaceuticals) (NCT00866333); and chidamide (Epidaza®, HBI-8000, Chipscreen Biosciences, China).

In some embodiments, one or more other therapeutic agent is a CDK inhibitor, such as a CDK4/CDK6 inhibitor. In some embodiments, a CDK 4/6 inhibitor is selected from palbociclib (Ibrance®, Pfizer); ribociclib (Kisqali®, Novartis); abemaciclib (Ly2835219, Eli Lilly); and trilaciclib (G1T28, G1 Therapeutics).

In some embodiments, one or more other therapeutic agent is a folic acid inhibitor. Approved folic acid inhibitors useful in the present invention include pemetrexed (Alimta®, Eli Lilly).

In some embodiments, one or more other therapeutic agent is a CC chemokine receptor 4 (CCR4) inhibitor. CCR4 inhibitors being studied that may be useful in the present invention include mogamulizumab (Poteligeo®, Kyowa Hakko Kirin, Japan).

In some embodiments, one or more other therapeutic agent is an isocitrate dehydrogenase (IDH) inhibitor. IDH inhibitors being studied which may be used in the present invention include AG 120 (Celgene; NCT02677922); AG221 (Celgene, NCT02677922; NCT02577406); BAY1436032 (Bayer, NCT02746081); IDH305 (Novartis, NCT02987010).

In some embodiments, one or more other therapeutic agent is an arginase inhibitor. Arginase inhibitors being studied which may be used in the present invention include AEB1102 (pegylated recombinant arginase, Aeglea Biotherapeutics), which is being studied in Phase 1 clinical trials for acute myeloid leukemia and myelodysplastic syndrome (NCT02732184) and solid tumors (NCT02561234); and CB-1158 (Calithera Biosciences).

In some embodiments, one or more other therapeutic agent is a glutaminase inhibitor. Glutaminase inhibitors being studied which may be used in the present invention include CB-839 (Calithera Biosciences).

In some embodiments, one or more other therapeutic agent is an antibody that binds to tumor antigens, that is, proteins expressed on the cell surface of tumor cells. Approved antibodies that bind to tumor antigens which may be used in the present invention include rituximab (Rituxan®, Genentech/Biogenldec); ofatumumab (anti-CD20, Arzerra®, GlaxoSmithKline); obinutuzumab (anti-CD20, Gazyva®, Genentech), ibritumomab (anti-CD20 and Yttrium-90, Zevalin®, Spectrum Pharmaceuticals); daratumumab (anti-CD38, Darzalex®, Janssen Biotech), dinutuximab (anti-glycolipid GD2, Unituxin®, United Therapeutics); trastuzumab (anti-HER2, Herceptin®, Genentech); ado-trastuzumab emtansine (anti-HER2, fused to emtansine, Kadcyla®, Genentech); and pertuzumab (anti-HER2, Peseta®, Genentech); and brentuximab vedotin (anti-CD30-drug conjugate, Adcetris®, Seattle Genetics).

In some embodiments, one or more other therapeutic agent is a topoisomerase inhibitor. Approved topoisomerase inhibitors useful in the present invention include irinotecan (Onivyde®, Merrimack Pharmaceuticals); topotecan (Hycamtin®, GlaxoSmithKline). Topoisomerase inhibitors being studied which may be used in the present invention include pixantrone (Pixuvri®, CTI Biopharma).

In some embodiments, one or more other therapeutic agent is an inhibitor of anti-apoptotic proteins, such as BCL-2. Approved anti-apoptotics which may be used in the present invention include venetoclax (Venclexta®, AbbVie/Genentech); and blinatumomab (Blincyto®, Amgen). Other therapeutic agents targeting apoptotic proteins which have undergone clinical testing and may be used in the present invention include navitoclax (ABT-263, Abbott), a BCL-2 inhibitor (NCT02079740).

In some embodiments, one or more other therapeutic agent is an androgen receptor inhibitor. Approved androgen receptor inhibitors useful in the present invention include enzalutamide (Xtandi®, Astellas/Medivation); approved inhibitors of androgen synthesis include abiraterone (Zytiga®, Centocor/Ortho); approved antagonist of gonadotropin-releasing hormone (GnRH) receptor (degaralix, Firmagon®, Ferring Pharmaceuticals).

In some embodiments, one or more other therapeutic agent is a selective estrogen receptor modulator (SERM), which interferes with the synthesis or activity of estrogens. Approved SERMs useful in the present invention include raloxifene (Evista®, Eli Lilly).

In some embodiments, one or more other therapeutic agent is an inhibitor of bone resorption. An approved therapeutic which inhibits bone resorption is Denosumab (Xgeva®, Amgen), an antibody that binds to RANKL, prevents binding to its receptor RANK, found on the surface of osteoclasts, their precursors, and osteoclast-like giant cells, which mediates bone pathology in solid tumors with osseous metastases. Other approved therapeutics that inhibit bone resorption include bisphosphonates, such as zoledronic acid (Zometa®, Novartis).

In some embodiments, one or more other therapeutic agent is an inhibitor of interaction between the two primary p53 suppressor proteins, MDMX and MDM2. Inhibitors of p53 suppression proteins being studied which may be used in the present invention include ALRN-6924 (Aileron), a stapled peptide that equipotently binds to and disrupts the interaction of MDMX and MDM2 with p53. ALRN-6924 is currently being evaluated in clinical trials for the treatment of AML, advanced myelodysplastic syndrome (MDS) and peripheral T-cell lymphoma (PTCL) (NCT02909972; NCT02264613).

In some embodiments, one or more other therapeutic agent is an inhibitor of transforming growth factor-beta (TGF-beta or TGFβ). Inhibitors of TGF-beta proteins being studied which may be used in the present invention include NIS793 (Novartis), an anti-TGF-beta antibody being tested in the clinic for treatment of various cancers, including breast, lung, hepatocellular, colorectal, pancreatic, prostate and renal cancer (NCT 02947165). In some embodiments, the inhibitor of TGF-beta proteins is fresolimumab (GC1008; Sanofi-Genzyme), which is being studied for melanoma (NCT00923169); renal cell carcinoma (NCT00356460); and non-small cell lung cancer (NCT02581787). Additionally, in some embodiments, the additional therapeutic agent is a TGF-beta trap, such as described in Connolly et al. (2012) Int'l J. Biological Sciences 8:964-978. One therapeutic compound currently in clinical trials for treatment of solid tumors is M7824 (Merck KgaA—formerly MSB0011459X), which is a bispecific, anti-PD-L 1/TGFβ trap compound (NCT02699515); and (NCT02517398). M7824 is comprised of a fully human IgG1 antibody against PD-L1 fused to the extracellular domain of human TGF-beta receptor II, which functions as a TGFβ "trap."

In some embodiments, one or more other therapeutic agent is selected from glembatumumab vedotin-monomethyl auristatin E (MMAE) (Celldex), an anti-glycoprotein NMB (gpNMB) antibody (CR011) linked to the cytotoxic MMAE. gpNMB is a protein overexpressed by multiple tumor types associated with cancer cells' ability to metastasize.

In some embodiments, one or more other therapeutic agent is an antiproliferative compound. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF 1010 from Conforma Therapeutics; temozolomide (Temodal®); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, $AZd_6244$ from AstraZeneca, PD181461 from Pfizer and leucovorin.

In some embodiments, the present invention provides a method of treating Alzheimer's disease comprising administering to a patient in need thereof a provided compound and one or more additional therapeutic agents selected from donepezil (Aricept®), rivastigmine (Excelon®), galantamine (Razadyne®), tacrine (Cognex®), and memantine (Namenda®).

In some embodiments, one or more other therapeutic agent is a taxane compound, which causes disruption of microtubules, which are essential for cell division. In some embodiments, a taxane compound is selected from paclitaxel (Taxol®, Bristol-Myers Squibb), docetaxel (Taxotere®, Sanofi-Aventis; Docefrez®, Sun Pharmaceutical), albumin-bound paclitaxel (Abraxane®; Abraxis/Celgene), cabazitaxel (Jevtana®, Sanofi-Aventis), and SID530 (SK Chemicals, Co.) (NCT00931008).

In some embodiments, one or more other therapeutic agent is a nucleoside inhibitor, or a therapeutic agent that interferes with normal DNA synthesis, protein synthesis, cell replication, or will otherwise inhibit rapidly proliferating cells.

In some embodiments, a nucleoside inhibitor is selected from trabectedin (guanidine alkylating agent, Yondelis®, Janssen Oncology), mechlorethamine (alkylating agent, Valchlor®, Aktelion Pharmaceuticals); vincristine (Oncovin®, Eli Lilly; Vincasar®, Teva Pharmaceuticals; Marqibo®, Talon Therapeutics); temozolomide (prodrug to alkylating agent 5-(3-methyltriazen-1-yl)-imidazole-4-carboxamide (MTIC) Temodar®, Merck); cytarabine injection (ara-C, antimetabolic cytidine analog, Pfizer); lomustine (alkylating agent, CeeNU®, Bristol-Myers Squibb; Gleostine®, Next-Source Biotechnology); azacitidine (pyrimidine nucleoside analog of cytidine, Vidaza®, Celgene); omacetaxine mepesuccinate (cephalotaxine ester) (protein synthesis inhibitor, Synribo®; Teva Pharmaceuticals); asparaginase *Erwinia chrysanthemi* (enzyme for depletion of asparagine, Elspar®, Lundbeck; Erwinaze®, EUSA Pharma); eribulin mesylate (microtubule inhibitor, tubulin-based antimitotic, Halaven®, Eisai); cabazitaxel (microtubule inhibitor, tubulin-based antimitotic, Jevtana®, Sanofi-Aventis); capacetrine (thymidylate synthase inhibitor, Xeloda®, Genentech); bendamustine (bifunctional mechlorethamine derivative, believed to form interstrand DNA cross-links, Treanda®, Cephalon/Teva); ixabepilone (semi-synthetic analog of epothilone B, microtubule inhibitor, tubulin-based antimitotic, Ixempra®, Bristol-Myers Squibb); nelarabine (prodrug of deoxyguanosine analog, nucleoside metabolic inhibitor, Arranon®, Novartis); clorafabine (prodrug of ribonucleotide reductase inhibitor, competitive inhibitor of deoxycytidine, Clolar®, Sanofi-Aventis); and trifluridine and tipiracil (thymidine-based nucleoside analog and thymidine phosphorylase inhibitor, Lonsurf®, Taiho Oncology).

In some embodiments, one or more other therapeutic agent is a kinase inhibitor or VEGF-R antagonist. Approved VEGF inhibitors and kinase inhibitors useful in the present invention include: bevacizumab (Avastin®, Genentech/Roche) an anti-VEGF monoclonal antibody; ramucirumab (Cyramza®, Eli Lilly), an anti-VEGFR-2 antibody and ziv-aflibercept, also known as VEGF Trap (Zaltrap®; Regeneron/Sanofi). VEGFR inhibitors, such as regorafenib (Stivarga®, Bayer); vandetanib (Caprelsa®, AstraZeneca); axitinib (Inlyta®, Pfizer); and lenvatinib (Lenvima®, Eisai); Raf inhibitors, such as sorafenib (Nexavar®, Bayer AG and Onyx); dabrafenib (Tafinlar®, Novartis); and vemurafenib (Zelboraf®, Genentech/Roche); MEK inhibitors, such as cobimetanib (Cotellic®, Exelexis/Genentech/Roche); trametinib (Mekinist®, Novartis); Bcr-Abl tyrosine kinase inhibitors, such as imatinib (Gleevec®, Novartis); nilotinib (Tasigna®, Novartis); dasatinib (Sprycel®, BristolMyersSquibb); bosutinib (Bosulif®, Pfizer); and ponatinib (Inclusig®, Ariad Pharmaceuticals); Her2 and EGFR inhibitors, such as gefitinib (Iressa®, AstraZeneca); erlotinib (Tarceeva®, Genentech/Roche/Astellas); lapatinib (Tykerb®, Novartis); afatinib (Gilotrif®, Boehringer Ingelheim); osimertinib (targeting activated EGFR, Tagrisso®, AstraZeneca); and brigatinib (Alunbrig®, Ariad Pharmaceuticals); c-Met and VEGFR2 inhibitors, such as cabozanitib (Cometriq®, Exelexis); and multikinase inhibitors, such as sunitinib (Sutent®, Pfizer); pazopanib (Votrient®, Novartis); ALK inhibitors, such as crizotinib (Xalkori®, Pfizer); ceritinib (Zykadia®, Novartis); and alectinib (Alecenza®, Genentech/Roche); Bruton's tyrosine kinase inhibitors, such as ibrutinib (Imbruvica®, Pharmacyclics/Janssen); and Flt3 receptor inhibitors, such as midostaurin (Rydapt®, Novartis).

Other kinase inhibitors and VEGF-R antagonists that are in development and may be used in the present invention include tivozanib (Aveo Pharmaceuticals); vatalanib (Bayer/Novartis); lucitanib (Clovis Oncology); dovitinib (TKI258, Novartis); Chiauanib (Chipscreen Biosciences); CEP-11981 (Cephalon); linifanib (Abbott Laboratories); neratinib (HKI-272, Puma Biotechnology); radotinib (Supect®, IY5511, Il-Yang Pharmaceuticals, S. Korea); ruxolitinib (Jakafi®, Incyte Corporation); PTC299 (PTC Therapeutics); CP-547, 632 (Pfizer); foretinib (Exelexis, GlaxoSmithKline); quizartinib (Daiichi Sankyo) and motesanib (Amgen/Takeda).

In another embodiment, the present invention provides a method of treating organ transplant rejection or graft vs. host disease comprising administering to a patient in need thereof a provided compound and one or more additional therapeutic agents selected from a steroid, cyclosporin, FK506, rapamycin, a hedgehog signaling inhibitor, a BTK inhibitor, a JAK/pan-JAK inhibitor, a TYK2 inhibitor, a PI3K inhibitor, and a SYK inhibitor.

In another embodiment, the present invention provides a method of treating or lessening the severity of a disease comprising administering to a patient in need thereof a provided compound and a BTK inhibitor, wherein the disease is selected from inflammatory bowel disease, arthritis, systemic lupus erythematosus (SLE), vasculitis, idiopathic thrombocytopenic purpura (ITP), rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, autoimmune thyroiditis, Sjogren's syndrome, multiple sclerosis, systemic sclerosis, Lyme neuroborreliosis, Guillain-Barre syndrome, acute disseminated encephalomyelitis, Addison's disease, opsoclonus-myoclonus syndrome, ankylosing spondylosis, antiphospholipid antibody syndrome, aplastic anemia, autoimmune hepatitis, autoimmune gastritis, pernicious anemia, celiac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, membranous glomerulonephropathy, endometriosis, interstitial cystitis, pemphigus vulgaris, bullous pemphigoid, neuromyotonia, scleroderma, vulvodynia, a hyperproliferative disease, rejection of transplanted organs or tissues, Acquired Immunodeficiency Syndrome (AIDS, also known as HIV), type 1 diabetes, graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis, asthma, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis, B-cell proliferative disorder, e.g., diffuse large B cell lymphoma, follicular lymphoma, chronic lymphocytic lymphoma, chronic lymphocytic leukemia, acute lymphocytic leukemia, B-cell prolymphocytic leukemia, lymphoplasmacytic lymphoma/Waldenstrom macroglobulinemia, splenic marginal zone lymphoma, multiple myeloma (also known as plasma cell myeloma), non-Hodgkin's lymphoma, Hodgkin's lymphoma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, Burkitt lymphoma/leukemia, or lymphomatoid granulomatosis, breast cancer, prostate cancer, or cancer of the mast cells (e.g., mastocytoma, mast cell leukemia, mast cell sarcoma, systemic mastocytosis), bone cancer, colorectal cancer, pancreatic cancer, diseases of the bone and joints including, without limitation, rheumatoid arthritis, seronegative spondyloarthropathies (including ankylosing spondylitis, psoriatic arthritis and Reiter's disease), Behcet's disease, Sjogren's syndrome, systemic sclerosis, osteoporosis, bone cancer, bone metastasis, a thromboembolic disorder, (e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, deep venous thrombosis), inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholocystitus, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Guillain-Barre syndrome, Behcet's disease, scleraderma, mycosis fungoides, acute inflammatory responses (such as acute respiratory distress syndrome and ischemia/reperfusion injury), and Graves' disease.

In another embodiment, the present invention provides a method of treating or lessening the severity of a disease comprising administering to a patient in need thereof a provided compound and a PI3K inhibitor, wherein the disease is selected from a cancer, a neurodegenerative disorder, an angiogenic disorder, a viral disease, an autoimmune disease, an inflammatory disorder, a hormone-related disease, conditions associated with organ transplantation, immunodeficiency disorders, a destructive bone disorder, a proliferative disorder, an infectious disease, a condition associated with cell death, thrombin-induced platelet aggregation, chronic myelogenous leukemia (CML), chronic lymphocytic leukemia (CLL), liver disease, pathologic immune conditions involving T cell activation, a cardiovascular disorder, and a CNS disorder.

In another embodiment, the present invention provides a method of treating or lessening the severity of a disease comprising administering to a patient in need thereof a provided compound and a PI3K inhibitor, wherein the disease is selected from benign or malignant tumor, carcinoma or solid tumor of the brain, kidney (e.g., renal cell carcinoma (RCC)), liver, adrenal gland, bladder, breast, stomach, gastric tumors, ovaries, colon, rectum, prostate, pancreas, lung, vagina, endometrium, cervix, testis, genitourinary tract, esophagus, larynx, skin, bone or thyroid, sarcoma, glioblastomas, neuroblastomas, multiple myeloma or gastrointestinal cancer, especially colon carcinoma or colorectal adenoma or a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, (including, for example, non-Hodgkin's Lymphoma (NHL) and Hodgkin's lymphoma (also termed Hodgkin's or Hodgkin's disease)), a mammary carcinoma, follicular carcinoma, undifferentiated carcinoma, papillary carcinoma, seminoma, melanoma, or a leukemia, diseases include Cowden syndrome, Lhermitte-Dudos disease and Bannayan-Zonana syndrome, or diseases in which the PI3K/PKB pathway is aberrantly activated, asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection, acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy, bronchitis of whatever type or genesis including, but not limited to, acute, arachidic, catarrhal, croupus, chronic or phthinoid bronchitis, pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis, Loffler's syndrome, eosinophilic, pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction, psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), systemic lupus erythematosus, rheumatoid arthritis, polychondritis, sclerodoma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary biliary cirrhosis, uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minal change nephropathy, restenosis, cardiomegaly, atherosclerosis, myocardial infarction, ischemic stroke and congestive heart failure, Alzheimer's disease, Parkinson's disease, amyotrophic lateral sclerosis, Huntington's disease, and cerebral ischemia, and neurodegenerative disease caused by traumatic injury, glutamate neurotoxicity and hypoxia.

In some embodiments, one or more other therapeutic agent is a phosphatidylinositol 3 kinase (PI3K) inhibitor. In some embodiments, a PI3K inhibitor is selected from idelalisib (Zydelig®, Gilead), alpelisib (BYL719, Novartis), taselisib (GDC-0032, Genentech/Roche); pictilisib (GDC-0941, Genentech/Roche); copanlisib (BAY806946, Bayer); duvelisib (formerly IPI-145, Infinity Pharmaceuticals); PQR309 (Piqur Therapeutics, Switzerland); and TGR1202 (formerly RP5230, TG Therapeutics).

The compounds and compositions, according to the method of the present invention, may be administered using any amount and any route of administration effective for treating or lessening the severity of a cancer, an autoimmune disorder, a proliferative disorder, an inflammatory disorder, a neurodegenerative or neurological disorder, schizophrenia, a bone-related disorder, liver disease, or a cardiac disorder. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting SWI/SNF chromatin-remodeling complex activity or degrading a SWI/SNF chromatin-remodeling complex in a biological sample comprising the step of contacting said biological sample with a compound of this invention, or a composition comprising said compound.

According to another embodiment, the invention relates to a method of inhibiting or degrading SMARCA2, SMARCA4, or PB1, or a mutant thereof, activity in a biological sample comprising the step of contacting said biological sample with a compound of this invention, or a composition comprising said compound.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition and/or degradation of a SMARCA or PB1 protein, or a protein selected from SMARCA2, SMARCA4, or PB1, or a mutant thereof, activity in a biological sample is useful for a variety of purposes that are known to one of skill in the art. Examples of such purposes include, but are not limited to, blood transfusion, organ-transplantation, biological specimen storage, and biological assays.

Another embodiment of the present invention relates to a method of degrading a protein kinase and/or inhibiting protein kinase activity in a patient comprising the step of administering to said patient a compound of the present invention, or a composition comprising said compound.

According to another embodiment, the invention relates to a method of degrading and/or inhibiting one or more SMARCA2, SMARCA4, or PB1, or a mutant thereof, activity in a patient comprising the step of administering to said patient a compound of the present invention, or a composition comprising said compound. In other embodiments, the present invention provides a method for treating a disorder mediated by one or more SMARCA2, SMARCA4, or PB1, or a mutant thereof, in a patient in need thereof, comprising the step of administering to said patient a compound according to the present invention or pharmaceutically acceptable composition thereof. Such disorders are described in detail herein.

Depending upon the particular condition, or disease, to be treated, additional therapeutic agents that are normally administered to treat that condition, may also be present in the compositions of this invention. As used herein, additional therapeutic agents that are normally administered to treat a particular disease, or condition, are known as "appropriate for the disease, or condition, being treated."

A compound of the current invention may also be used to advantage in combination with other antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF 1010 from Conforma Therapeutics; temozolomide (Temodal®); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, AZD6244 from AstraZeneca, PD181461 from Pfizer and leucovorin.

The term "aromatase inhibitor" as used herein relates to a compound which inhibits estrogen production, for instance, the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane is marketed under the trade name Aromasin™. Formestane is marketed under the trade name Lentaron™. Fadrozole is marketed under the trade name Afema™. Anastrozole is marketed under the trade name Arimidex™. Fetrozole is marketed under the trade names Femara™ or Femar™. Aminoglutethimide is marketed under the trade name Orimeten™. A combination of the invention comprising a chemotherapeutic agent which is an aromatase inhibitor is particularly useful for the treatment of hormone receptor positive tumors, such as breast tumors.

In some embodiments, one or more other therapeutic agent is an mTOR inhibitor, which inhibits cell proliferation, angiogenesis and glucose uptake. In some embodiments, an mTOR inhibitor is everolimus (Afinitor®, Novartis); temsirolimus (Torisel®, Pfizer); and sirolimus (Rapamune®, Pfizer).

In some embodiments, one or more other therapeutic agent is an aromatase inhibitor. In some embodiments, an aromatase inhibitor is selected from exemestane (Aromasin®, Pfizer); anastazole (Arimidex®, AstraZeneca) and letrozole (Femara®, Novartis).

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen is marketed under the trade name Nolvadex™. Raloxifene hydrochloride is marketed under the trade name Evista™. Fulvestrant can be administered under the trade name Faslodex™. A combination of the invention comprising a chemotherapeutic agent which is an antiestrogen is particularly useful for the treatment of estrogen receptor positive tumors, such as breast tumors.

The term "anti-androgen" as used herein relates to any substance which is capable of inhibiting the biological effects of androgenic hormones and includes, but is not limited to, bicalutamide (Casodex™). The term "gonadorelin agonist" as used herein includes, but is not limited to abarelix, goserelin and goserelin acetate. Goserelin can be administered under the trade name Zoladex™.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148. Irinotecan can be administered, e.g. in the form as it is marketed, e.g. under the trademark Camptosar™. Topotecan is marketed under the trade name Hycamptin™.

The term "topoisomerase II inhibitor" as used herein includes, but is not limited to the anthracyclines such as doxorubicin (including liposomal formulation, such as Caelyx™), daunorubicin, epirubicin, idarubicin and nemorubicin, the anthraquinones mitoxantrone and losoxantrone, and the podophillotoxines etoposide and teniposide. Etoposide is marketed under the trade name Etopophos™. Teniposide is marketed under the trade name VM 26-Bristol Doxorubicin is marketed under the trade name Acriblastin™ or Adriamycin™. Epirubicin is marketed under the trade name Farmorubicin™. Idarubicin is marketed, under the trade name Zavedos™. Mitoxantrone is marketed under the trade name Novantron.

The term "microtubule active agent" relates to microtubule stabilizing, microtubule destabilizing compounds and microtublin polymerization inhibitors including, but not limited to taxanes, such as paclitaxel and docetaxel; vinca alkaloids, such as vinblastine or vinblastine sulfate, vincristine or vincristine sulfate, and vinorelbine; discodermolides; cochicine and epothilones and derivatives thereof. Paclitaxel is marketed under the trade name Taxol™. Docetaxel is marketed under the trade name Taxotere™. Vinblastine sulfate is marketed under the trade name Vinblastin R.P™. Vincristine sulfate is marketed under the trade name Farmistin™.

The term "alkylating agent" as used herein includes, but is not limited to, cyclophosphamide, ifosfamide, melphalan or nitrosourea (BCNU or Gliadel). Cyclophosphamide is marketed under the trade name Cyclostin™. Ifosfamide is marketed under the trade name Holoxan™.

The term "histone deacetylase inhibitors" or "HDAC inhibitors" relates to compounds which inhibit the histone deacetylase and which possess antiproliferative activity. This includes, but is not limited to, suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine is marketed under the trade name Xeloda™. Gemcitabine is marketed under the trade name Gemzar™.

The term "platin compound" as used herein includes, but is not limited to, carboplatin, cis-platin, cisplatinum and oxaliplatin. Carboplatin can be administered, e.g., in the form as it is marketed, e.g. under the trademark Carboplat™. Oxaliplatin can be administered, e.g., in the form as it is marketed, e.g. under the trademark Eloxatin™.

The term "Bcl-2 inhibitor" as used herein includes, but is not limited to compounds having inhibitory activity against B-cell lymphoma 2 protein (Bcl-2), including but not limited to ABT-199, ABT-731, ABT-737, apogossypol, Ascenta's pan-Bcl-2 inhibitors, curcumin (and analogs thereof), dual Bcl-2/Bcl-xL inhibitors (Infinity Pharmaceuticals/Novartis Pharmaceuticals), Genasense (G3139), HA14-1 (and analogs thereof; see WO2008118802), navitoclax (and analogs thereof, see U.S. Pat. No. 7,390,799), NH-1 (Shenayng Pharmaceutical University), obatoclax (and analogs thereof, see WO2004106328), S-001 (Gloria Pharmaceuticals), TW series compounds (Univ. of Michigan), and venetoclax. In some embodiments the Bel-2 inhibitor is a small molecule therapeutic. In some embodiments the Bel-2 inhibitor is a peptidomimetic.

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, such as a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, such as an N-phenyl-2-pyrimidine-amine derivative, such as imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the AxI receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, such as imatinib; h) compounds targeting, decreasing or inhibiting the activity of the C-kit receptor tyrosine kinases, which are part of the PDGFR family, such as compounds which target, decrease or inhibit the activity of the c-Kit receptor tyrosine kinase family, especially compounds which inhibit the c-Kit receptor, such as imatinib; i) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, such as an N-phenyl-2-pyrimidine-amine derivative, such as imatinib or nilotinib (AMN107); PD180970; AG957; NSC 680410; PD173955 from ParkeDavis; or dasatinib (BMS-354825); j) compounds targeting, decreasing or inhibiting the activity of members of the protein kinase C (PKC) and Raf family of serine/threonine kinases, members of the MEK, SRC, JAK/pan-JAK, FAR, PDK1, PKB/Akt, Ras/MAPK, PI3K, SYK, TYK2, BTK and TEC family, and/or members of the cyclin-dependent kinase family (CDK) including staurosporine derivatives, such as midostaurin; examples of further compounds include UCN-01, safingol, BAY 43-9006, Bryostatin 1, Perifosine; llmofosine; RO 318220 and RO 320432; GO 6976; Isis 3521; LY333531/LY379196; isochinoline compounds; FTIs; PD184352 or QAN697 (a PI3K inhibitor) or AT7519 (CDK inhibitor); k) compounds targeting, decreasing or inhibiting the activity of protein-tyrosine kinase inhibitors, such as compounds which target, decrease or inhibit the activity of protein-tyrosine kinase inhibitors include imatinib mesylate (Gleevec™) or tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); l) compounds targeting, decreasing or inhibiting the activity of the epidermal growth factor family of receptor tyrosine kinases (EGFR$_1$ ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, such as EGF receptor, ErbB2, ErbB3 and ErbB4 or bind to EGF or EGF related ligands, CP 358774, ZD 1839, ZM 105180; trastuzumab (Herceptin™), cetuximab (Erbitux™), Iressa, Tarceva, OSI-774, Cl-1033, EKB-569, GW-2016, E1.1, E2.4, E2.5, E6.2, E6.4, E2.11, E6.3 or E7.6.3, and 7H-pyrrolo-[2,3-d]pyrimidine derivatives; m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF, n) compounds targeting, decreasing or inhibiting the kinase activity of one or more JAK family members (JAK1/JAK2/JAK3/TYK2 and/or pan-JAK), including but not limited to PRT-062070, SB-1578, baricitinib, pacritinib, momelotinib, VX-509, AZD-1480, TG-101348, tofacitinib, and ruxolitinib; o) compounds targeting, decreasing or inhibiting the kinase activity of PI3 kinase (PI3K) including but not limited to ATU-027, SF-1126, DS-7423, PBI-05204, GSK-2126458, ZSTK-474, buparlisib, pictrelisib, PF-4691502, BYE-719, dactolisib, XF-147, XF-765, and idelalisib; and; and q) compounds targeting, decreasing or inhibiting the signaling effects of hedgehog protein (Hh) or smoothened receptor (SMO) pathways, including but not limited to cyclopamine, vismodegib, itraconazole, erismodegib, and IPI-926 (saridegib).

Compounds which target, decrease or inhibit the activity of a protein or lipid phosphatase are e.g. inhibitors of phosphatase 1, phosphatase 2A, or CDC25, such as okadaic acid or a derivative thereof.

In some embodiments, one or more other therapeutic agent is a growth factor antagonist, such as an antagonist of platelet-derived growth factor (PDGF), or epidermal growth factor (EGF) or its receptor (EGFR). Approved PDGF antagonists which may be used in the present invention include olaratumab (Lartruvo®; Eli Lilly). Approved EGFR antagonists which may be used in the present invention include cetuximab (Erbitux®, Eli Lilly); necitumumab (Portrazza®, Eli Lilly), panitumumab (Vectibix®, Amgen); and osimertinib (targeting activated EGFR, Tagrisso®, AstraZeneca).

The term "PI3K inhibitor" as used herein includes, but is not limited to compounds having inhibitory activity against one or more enzymes in the phosphatidylinositol-3-kinase family, including, but not limited to PI3Kα, PI3Kγ, PI3Kδ, PI3Kβ, PI3K-C2α, PI3K-C2β, PI3K-C2γ, Vps34, p110-α, p110-β, p110-γ, p110-δ, p85-α, p85-β, p55-γ, p150, p101, and p87. Examples of PI3K inhibitors useful in this invention include but are not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib.

The term "BTK inhibitor" as used herein includes, but is not limited to compounds having inhibitory activity against Bruton's Tyrosine Kinase (BTK), including, but not limited to AVL-292 and ibrutinib.

The term "SYK inhibitor" as used herein includes, but is not limited to compounds having inhibitory activity against spleen tyrosine kinase (SYK), including but not limited to PRT-062070, R-343, R-333, Excellair, PRT-062607, and fostamatinib Further examples of BTK inhibitory compounds, and conditions treatable by such compounds in combination with compounds of this invention can be found in WO2008039218 and WO2011090760, the entirety of which are incorporated herein by reference.

Further examples of SYK inhibitory compounds, and conditions treatable by such compounds in combination with compounds of this invention can be found in WO2003063794, WO2005007623, and WO2006078846, the entirety of which are incorporated herein by reference.

Further examples of PI3K inhibitory compounds, and conditions treatable by such compounds in combination with compounds of this invention can be found in WO2004019973, WO2004089925, WO2007016176, U.S. Pat. No. 8,138,347, WO2002088112, WO2007084786, WO2007129161, WO2006122806, WO2005113554, and WO2007044729 the entirety of which are incorporated herein by reference.

Further examples of JAK inhibitory compounds, and conditions treatable by such compounds in combination with compounds of this invention can be found in WO2009114512, WO2008109943, WO2007053452, WO2000142246, and WO2007070514, the entirety of which are incorporated herein by reference.

Further anti-angiogenic compounds include compounds having another mechanism for their activity, e.g. unrelated to protein or lipid kinase inhibition e.g. thalidomide (Thalomid™) and TNP-470.

Examples of proteasome inhibitors useful for use in combination with compounds of the invention include, but are not limited to bortezomib, disulfiram, epigallocatechin-3-gallate (EGCG), salinosporamide A, carfilzomib, ONX-0912, CEP-18770, and MLN9708.

Compounds which target, decrease or inhibit the activity of a protein or lipid phosphatase are e.g. inhibitors of phosphatase 1, phosphatase 2A, or CDC25, such as okadaic acid or a derivative thereof.

Compounds which induce cell differentiation processes include, but are not limited to, retinoic acid, α- γ- or δ-tocopherol or α- γ- or δ-tocotrienol.

The term cyclooxygenase inhibitor as used herein includes, but is not limited to, Cox-2 inhibitors, 5-alkyl substituted 2-arylaminophenylacetic acid and derivatives, such as celecoxib (Celebrex™), rofecoxib (Vioxx™), etoricoxib, valdecoxib or a 5-alkyl-2-arylaminophenylacetic acid, such as 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. Etridonic acid is marketed under the trade name Didronel™. Clodronic acid is marketed under the trade name Bonefos™. Tiludronic acid is marketed under the trade name Skelid™. Pamidronic acid is marketed under the trade name Aredia™. Alendronic acid is marketed under the trade name Fosamax™. Ibandronic acid is marketed under the trade name Bondranat™. Risedronic acid is marketed under the trade name Actonel™. Zoledronic acid is marketed under the trade name Zometa™. The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88. The term "biological response modifier" as used herein refers to a lymphokine or interferons.

The term "inhibitor of Ras oncogenic isoforms", such as H-Ras, K-Ras, or N-Ras, as used herein refers to compounds which target, decrease or inhibit the oncogenic activity of Ras; for example, a "farnesyl transferase inhibitor" such as L-744832, DK8G557 or R115777 (Zamestra™). The term "telomerase inhibitor" as used herein refers to compounds which target, decrease or inhibit the activity of telomerase. Compounds which target, decrease or inhibit the activity of telomerase are especially compounds which inhibit the telomerase receptor, such as telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase include, but are not limited to, bengamide or a derivative thereof.

The term "proteasome inhibitor" as used herein refers to compounds which target, decrease or inhibit the activity of the proteasome. Compounds which target, decrease or inhibit the activity of the proteasome include, but are not limited to, Bortezomib (Velcade™); carfilzomib (Kyprolis®, Amgen); and ixazomib (Ninlaro®, Takeda), and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and bisulfan; and ALK inhibitors, which are compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, such as PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino,17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (Herceptin™), Trastuzumab-DM1, erbitux, bevacizumab (Avastin™), rituximab (Rituxan®), PRO64553 (anti-CD40) and 2C4 Antibody. By antibodies is meant intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the current invention can be used in combination with standard leukemia therapies, especially in combination with therapies used for the treatment of AML. In particular, compounds of the current invention can be administered in combination with, for example, farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

Other anti-leukemic compounds include, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065 including, but not limited to, N-hydroxy-3-[4-[[[2-(2-methyl-1H-indol-3-yl)-ethyl]-amino]methyl]phenyl]-2E-2-propenamide, or a pharmaceutically acceptable salt thereof and N-hydroxy-3-[4-[(2-hydroxyethyl){2-(1H-indol-3-yl)ethyl]-amino]methyl]phenyl]-2E-2-propenamide, or a pharmaceutically acceptable salt thereof, especially the lactate salt. Somatostatin receptor antagonists as used herein refer to compounds which target, treat or inhibit the somatostatin receptor such as octreotide, and SOM230. Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Heilman, Principles of Radiation Therapy, Cancer, in Principles and Practice of Oncology, Devita et al., Eds., 4$^{th}$ Edition, Vol. 1, pp. 248-275 (1993).

Also included are EDG binders and ribonucleotide reductase inhibitors. The term "EDG binders" as used herein refers to a class of immunosuppressants that modulates lymphocyte recirculation, such as FTY720. The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives.

Also included are in particular those compounds, proteins or monoclonal antibodies of VEGF such as 1-(4-chloroanilino)-4-(4-pyridylmethyl)phthalazine or a pharmaceutically acceptable salt thereof, 1-(4-chloroanilino)-4-(4-pyridylmethyl)phthalazine succinate; Angiostatin™; Endostatin™; anthranilic acid amides; ZD4190; ZD6474; SU5416; SU6668; bevacizumab; or anti-VEGF antibodies or anti-VEGF receptor antibodies, such as rhuMAb and RHUFab, VEGF aptamer such as Macugon; FLT-4 inhibitors, FLT-3 inhibitors, VEGFR-2 IgGI antibody, Angiozyme (RPI 4610) and Bevacizumab (Avastin™).

Photodynamic therapy as used herein refers to therapy which uses certain chemicals known as photosensitizing compounds to treat or prevent cancers. Examples of photodynamic therapy include treatment with compounds, such as Visudyne™ and porfimer sodium.

Angiostatic steroids as used herein refers to compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as fluocinolone and dexamethasone.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The compounds of the invention are also useful as co-therapeutic compounds for use in combination with other drug substances such as anti-inflammatory, bronchodilatory or antihistamine drug substances, particularly in the treatment of obstructive or inflammatory airways diseases such as those mentioned hereinbefore, for example as potentiators of therapeutic activity of such drugs or as a means of reducing required dosaging or potential side effects of such drugs. A compound of the invention may be mixed with the other drug substance in a fixed pharmaceutical composition or it may be administered separately, before, simultaneously with or after the other drug substance. Accordingly the invention includes a combination of a compound of the invention as hereinbefore described with an anti-inflammatory, bronchodilatory, antihistamine or anti-tussive drug substance, said compound of the invention and said drug substance being in the same or different pharmaceutical composition.

Suitable anti-inflammatory drugs include steroids, in particular glucocorticosteroids such as budesonide, beclamethasone dipropionate, fluticasone propionate, ciclesonide or mometasone furoate; non-steroidal glucocorticoid receptor agonists; LTB4 antagonists such LY293111, CGS025019C, CP-195543, SC-53228, BIIL 284, ONO 4057, SB 209247; LTD4 antagonists such as montelukast and zafirlukast; PDE4 inhibitors such cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID™ CC-10004 (Celgene), VM554/UM565 (Vemalis), T-440 (Tanabe), KW-4490 (Kyowa Hakko Kogyo); A2a agonists; A2b antagonists; and beta-2 adrenoceptor agonists such as albuterol (salbutamol), metaproterenol, terbutaline, salmeterol fenoterol, procaterol, and especially, formoterol and pharmaceutically acceptable salts thereof. Suitable bronchodilatory drugs include anticholinergic or antimuscarinic compounds, in particular ipratropium bromide, oxitropium bromide, tiotropium salts and CHF 4226 (Chiesi), and glycopyrrolate.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine.

Other useful combinations of compounds of the invention with anti-inflammatory drugs are those with antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, and Takeda antagonists such as N-[[4-[[[6,7-dihydro-2-(4-methylphenyl)-5H-benzo-cyclohepten-8-yl]carbonyl]amino]phenyl]-methyl] tetrahydro-N,N-dimethyl-2H-pyran-4-aminium chloride (TAK-770).

The structure of the active compounds identified by code numbers, generic or trade names may be taken from the actual edition of the standard compendium "The Merck Index" or from databases, e.g. Patents International (e.g. IMS World Publications).

A compound of the current invention may also be used in combination with known therapeutic processes, for example, the administration of hormones or radiation. In certain embodiments, a provided compound is used as a radiosensitizer, especially for the treatment of tumors which exhibit poor sensitivity to radiotherapy.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-1,000 μg/kg body weight/day of the additional therapeutic agent can be administered.

The amount of one or more other therapeutic agent present in the compositions of this invention may be no more than the amount that would normally be administered in a composition comprising that therapeutic agent as the only active agent. Preferably the amount of one or more other therapeutic agent in the presently disclosed compositions will range from about 50% to 100% of the amount normally present in a composition comprising that agent as the only therapeutically active agent. In some embodiments, one or more other therapeutic agent is administered at a dosage of about 50%, about 55%, about 60%, about 65%, about 70%, about 75%, about 80%, about 85%, about 90%, or about 95% of the amount normally administered for that agent. As used herein, the phrase "normally administered" means the amount an FDA approved therapeutic agent is approved for dosing per the FDA label insert.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Implantable devices coated with a compound of this invention are another embodiment of the present invention.

Exemplary Immuno-Oncology Agents

In some embodiments, one or more other therapeutic agent is an immuno-oncology agent. As used herein, the term "an immuno-oncology agent" refers to an agent which is effective to enhance, stimulate, and/or up-regulate immune responses in a subject. In some embodiments, the administration of an immuno-oncology agent with a compound of the invention has a synergic effect in treating a cancer.

An immuno-oncology agent can be, for example, a small molecule drug, an antibody, or a biologic or small molecule. Examples of biologic immuno-oncology agents include, but are not limited to, cancer vaccines, antibodies, and cytokines. In some embodiments, an antibody is a monoclonal antibody. In some embodiments, a monoclonal antibody is humanized or human.

In some embodiments, an immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses.

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α1β2, FAS, FASL, RELT, DR6, TROY, NGFR.

In some embodiments, an immuno-oncology agent is a cytokine that inhibits T cell activation (e.g., IL-6, IL-10, TGF-β, VEGF, and other immunosuppressive cytokines) or a cytokine that stimulates T cell activation, for stimulating an immune response.

In some embodiments, a combination of a compound of the invention and an immuno-oncology agent can stimulate T cell responses. In some embodiments, an immuno-oncology agent is: (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4; or (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

In some embodiments, an immuno-oncology agent is an antagonist of inhibitory receptors on NK cells or an agonists of activating receptors on NK cells. In some embodiments, an immuno-oncology agent is an antagonists of KIR, such as lirilumab.

In some embodiments, an immuno-oncology agent is an agent that inhibits or depletes macrophages or monocytes, including but not limited to CSF-1R antagonists such as CSF-1R antagonist antibodies including RG7155 (WO11/70024, WO11/107553, WO11/131407, WO13/87699, WO13/119716, WO13/132044) or FPA-008 (WO11/140249; WO13169264; WO14/036357).

In some embodiments, an immuno-oncology agent is selected from agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell energy or exhaustion) and agents that trigger innate immune activation and/or inflammation at tumor sites.

In some embodiments, an immuno-oncology agent is a CTLA-4 antagonist. In some embodiments, a CTLA-4 antagonist is an antagonistic CTLA-4 antibody. In some embodiments, an antagonistic CTLA-4 antibody is YERVOY (ipilimumab) or tremelimumab.

In some embodiments, an immuno-oncology agent is a PD-1 antagonist. In some embodiments, a PD-1 antagonist is administered by infusion. In some embodiments, an immuno-oncology agent is an antibody or an antigen-binding portion thereof that binds specifically to a Programmed Death-1 (PD-1) receptor and inhibits PD-1 activity. In some embodiments, a PD-1 antagonist is an antagonistic PD-1 antibody. In some embodiments, an antagonistic PD-1 antibody is OPDIVO (nivolumab), KEYTRUDA (pembrolizumab), or MEDI-0680 (AMP-514; WO2012/145493). In some embodiments, an immuno-oncology agent may be pidilizumab (CT-011). In some embodiments, an immuno-oncology agent is a recombinant protein composed of the extracellular domain of PD-L2 (B7-DC) fused to the Fc portion of IgG1, called AMP-224.

In some embodiments, an immuno-oncology agent is a PD-L1 antagonist. In some embodiments, a PD-L1 antagonist is an antagonistic PD-L1 antibody. In some embodiments, a PD-L1 antibody is MPDL3280A (RG7446; WO2010/077634), durvalumab (MEDI4736), BMS-936559 (WO2007/005874), and MSB0010718C (WO2013/79174).

In some embodiments, an immuno-oncology agent is a LAG-3 antagonist. In some embodiments, a LAG-3 antagonist is an antagonistic LAG-3 antibody. In some embodiments, a LAG3 antibody is BMS-986016 (WO10/19570, WO14/08218), or IMP-731 or IMP-321 (WO08/132601, WO09/44273).

In some embodiments, an immuno-oncology agent is a CD 137 (4-IBB) agonist. In some embodiments, a CD 137 (4-IBB) agonist is an agonistic CD 137 antibody. In some embodiments, a CD 137 antibody is urelumab or PF-05082566 (WO12/32433).

In some embodiments, an immuno-oncology agent is a GITR agonist. In some embodiments, a GITR agonist is an agonistic GITR antibody. In some embodiments, a GITR antibody is BMS-986153, BMS-986156, TRX-S18 (WO006/105021, WO009/009116), or MK-4166 (WO 11/028683).

In some embodiments, an immuno-oncology agent is an indoleamine (2,3)-dioxygenase (IDO) antagonist. In some embodiments, an IDO antagonist is selected from epacadostat (INCB024360, Incyte); indoximod (NLG-8189, NewLink Genetics Corporation); capmanitib (INC280, Novartis); GDC-0919 (Genentech/Roche); PF-06840003 (Pfizer); BMS:F001287 (Bristol-Myers Squibb); Phy906/KD108 (Phytoceutica); an enzyme that breaks down kynurenine (Kynase, Kyn Therapeutics); and NLG-919 (WO09/73620, WO009/1156652, WO11/56652, WO12/142237).

In some embodiments, an immuno-oncology agent is an OX40 agonist. In some embodiments, an OX40 agonist is an agonistic OX40 antibody. In some embodiments, an OX40 antibody is MEDI-6383 or MEDI-6469.

In some embodiments, an immuno-oncology agent is an OX40L antagonist. In some embodiments, an OX40L antagonist is an antagonistic OX40 antibody. In some embodiments, an OX40L antagonist is RG-7888 (WO06/029879).

In some embodiments, an immuno-oncology agent is a CD40 agonist. In some embodiments, a CD40 agonist is an agonistic CD40 antibody. In some embodiments, an immuno-oncology agent is a CD40 antagonist. In some embodiments, a CD40 antagonist is an antagonistic CD40 antibody. In some embodiments, a CD40 antibody is lucatumumab or dacetuzumab.

In some embodiments, an immuno-oncology agent is a CD27 agonist. In some embodiments, a CD27 agonist is an agonistic CD27 antibody. In some embodiments, a CD27 antibody is varlilumab.

In some embodiments, an immuno-oncology agent is MGA271 (to B7H3) (WO11/109400).

In some embodiments, an immuno-oncology agent is abagovomab, adecatumumab, afutuzumab, alemtuzumab, anatumomab mafenatox, apolizumab, atezolimab, avelumab, blinatumomab, BMS-936559, catumaxomab, durvalumab, epacadostat, epratuzumab, indoximod, inotuzumab ozogamicin, intelumumab, ipilimumab, isatuximab, lambrolizumab, MED 14736, MPDL3280A, nivolumab, obinutuzumab, ocaratuzumab, ofatumumab, olatatumab, pembrolizumab, pidilizumab, rituximab, ticilimumab, samalizumab, or tremelimumab.

In some embodiments, an immuno-oncology agent is an immunostimulatory agent. For example, antibodies blocking the PD-1 and PD-L1 inhibitory axis can unleash activated tumor-reactive T cells and have been shown in clinical trials to induce durable anti-tumor responses in increasing numbers of tumor histologies, including some tumor types that conventionally have not been considered immunotherapy sensitive. See, e.g., Okazaki, T. et al. (2013) Nat. Immunol. 14, 1212-1218; Zou et al. (2016) Sci. Transl. Med. 8. The anti-PD-1 antibody nivolumab (Opdivo®, Bristol-Myers Squibb, also known as ONO-4538, MDX1106 and BMS-936558), has shown potential to improve the overall survival in patients with RCC who had experienced disease progression during or after prior anti-angiogenic therapy.

In some embodiments, the immunomodulatory therapeutic specifically induces apoptosis of tumor cells. Approved immunomodulatory therapeutics which may be used in the present invention include pomalidomide (Pomalyst®, Celgene); lenalidomide (Revlimid®, Celgene); ingenol mebutate (Picato®, LEO Pharma).

In some embodiments, an immuno-oncology agent is a cancer vaccine. In some embodiments, the cancer vaccine is selected from sipuleucel-T (Provenge®, Dendreon/Valeant Pharmaceuticals), which has been approved for treatment of asymptomatic, or minimally symptomatic metastatic castrate-resistant (hormone-refractory) prostate cancer; and talimogene laherparepvec (Imlygic®, BioVex/Amgen, previously known as T-VEC), a genetically modified oncolytic viral therapy approved for treatment of unresectable cutaneous, subcutaneous and nodal lesions in melanoma. In some embodiments, an immuno-oncology agent is selected from an oncolytic viral therapy such as pexastimogene devacirepvec (PexaVec/JX-594, SillaJen/formerly Jennerex Biotherapeutics), a thymidine kinase- (TK-) deficient vaccinia vims engineered to express GM-CSF, for hepatocellular carcinoma (NCT02562755) and melanoma (NCT00429312); pelareorep (Reolysin®, Oncolytics Biotech), a variant of respiratory enteric orphan vims (reovirus) which does not replicate in cells that are not RAS-activated, in numerous cancers, including colorectal cancer (NCT01622543); prostate cancer (NCT01619813); head and neck squamous cell cancer (NCT01166542); pancreatic adenocarcinoma (NCT00998322); and non-small cell lung cancer (NSCLC) (NCT 00861627); enadenotucirev (NG-348, PsiOxus, formerly known as ColoAd1), an adenovirus engineered to express a full length CD80 and an antibody fragment specific for the T-cell receptor CD3 protein, in ovarian cancer (NCT02028117); metastatic or advanced epithelial tumors such as in colorectal cancer, bladder cancer, head and neck squamous cell carcinoma and salivary gland cancer (NCT02636036); ONCOS-102 (Targovax/formerly Oncos), an adenovirus engineered to express GM-CSF, in melanoma (NCT03003676); and peritoneal disease, colorectal cancer or ovarian cancer (NCT02963831); GF-ONC1 (GFV-1h68/GFV-1h153, Genelux GmbH), vaccinia viruses engineered to express beta-galactosidase (beta-gal)/beta-glucoronidase or beta-gal/human sodium iodide symporter (hNIS), respectively, were studied in peritoneal carcinomatosis (NCT01443260); fallopian tube cancer, ovarian cancer (NCT 02759588); or CG0070 (Cold Genesys), an adenovirus engineered to express GM-CSF, in bladder cancer (NCT02365818).

In some embodiments, an immuno-oncology agent is selected from JX-929 (SillaJen/formerly Jennerex Biotherapeutics), a TK- and vaccinia growth factor-deficient vaccinia vims engineered to express cytosine deaminase, which is able to convert the prodrug 5-fluorocytosine to the cytotoxic drug 5-fluorouracil; TG01 and TG02 (Targovax/formerly Oncos), peptide-based immunotherapy agents targeted for difficult-to-treat RAS mutations; and TIFT-123 (TIFT Biotherapeutics), an engineered adenovirus designated: Ad5/3-E2F-delta24-hTNFα-IRES-hIL20; and VSV-GP (ViraTherapeutics) a vesicular stomatitis vims (VSV) engineered to express the glycoprotein (GP) of lymphocytic choriomeningitis vims (FCMV), which can be further engineered to express antigens designed to raise an antigen-specific $CD8^+$ T cell response.

In some embodiments, an immuno-oncology agent is a T-cell engineered to express a chimeric antigen receptor, or CAR. The T-cells engineered to express such chimeric antigen receptor are referred to as a CAR-T cells.

CARs have been constructed that consist of binding domains, which may be derived from natural ligands, single chain variable fragments (scFv) derived from monoclonal antibodies specific for cell-surface antigens, fused to endodomains that are the functional end of the T-cell receptor (TCR), such as the CD3-zeta signaling domain from TCRs, which is capable of generating an activation signal in T lymphocytes. Upon antigen binding, such CARs link to endogenous signaling pathways in the effector cell and generate activating signals similar to those initiated by the TCR complex.

For example, in some embodiments the CAR-T cell is one of those described in U.S. Pat. No. 8,906,682 (June; hereby incorporated by reference in its entirety), which discloses CAR-T cells engineered to comprise an extracellular domain having an antigen binding domain (such as a domain that binds to CD 19), fused to an intracellular signaling domain of the T cell antigen receptor complex zeta chain (such as CD3 zeta). When expressed in the T cell, the CAR is able to redirect antigen recognition based on the antigen binding specificity. In the case of CD19, the antigen is expressed on malignant B cells. Over 200 clinical trials are currently in progress employing CAR-T in a wide range of indications. [https://clinicaltrials.gov/ct2/results?term=chimeric+antigen+receptors&pg=1].

In some embodiments, an immunostimulatory agent is an activator of retinoic acid receptor-related orphan receptor γ (RORγt). RORγt is a transcription factor with key roles in the differentiation and maintenance of Type 17 effector subsets of CD4+ (Th17) and CD8+ (Tc17) T cells, as well as the differentiation of IL-17 expressing innate immune cell subpopulations such as NK cells. In some embodiments, an activator of RORγt is LYC-55716 (Lycera), which is currently being evaluated in clinical trials for the treatment of solid tumors (NCT02929862).

In some embodiments, an immunostimulatory agent is an agonist or activator of a toll-like receptor (TLR). Suitable activators of TLRs include an agonist or activator of TLR9 such as SD-101 (Dynavax). SD-101 is an immunostimulatory CpG which is being studied for B-cell, follicular and other lymphomas (NCT02254772). Agonists or activators of TLR8 which may be used in the present invention include motolimod (VTX-2337, VentiRx Pharmaceuticals) which is being studied for squamous cell cancer of the head and neck (NCT02124850) and ovarian cancer (NCT02431559).

Other immuno-oncology agents that may be used in the present invention include urelumab (BMS-663513, Bristol-Myers Squibb), an anti-CD137 monoclonal antibody; varlilumab (CDX-1127, Celldex Therapeutics), an anti-CD27 monoclonal antibody; BMS-986178 (Bristol-Myers Squibb), an anti-OX40 monoclonal antibody; lirilumab (IPH2102/BMS-986015, Innate Pharma, Bristol-Myers Squibb), an anti-KIR monoclonal antibody; monalizumab (IPH2201, Innate Pharma, AstraZeneca) an anti-NKG2A monoclonal antibody; andecaliximab (GS-5745, Gilead Sciences), an anti-MMP9 antibody; MK-4166 (Merck & Co.), an anti-GITR monoclonal antibody.

In some embodiments, an immunostimulatory agent is selected from elotuzumab, mifamurtide, an agonist or activator of a toll-like receptor, and an activator of RORγt.

In some embodiments, an immunostimulatory therapeutic is recombinant human interleukin 15 (rhIL-15). rhIL-15 has been tested in the clinic as a therapy for melanoma and renal cell carcinoma (NCT01021059 and NCT01369888) and leukemias (NCT02689453). In some embodiments, an immunostimulatory agent is recombinant human interleukin 12 (rhIL-12). In some embodiments, an IL-15 based immunotherapeutic is heterodimeric IL-15 (hetIL-15, Novartis/Admune), a fusion complex composed of a synthetic form of endogenous IL-15 complexed to the soluble IL-15 binding protein IL-15 receptor alpha chain (IL15:sIL-15RA), which has been tested in Phase 1 clinical trials for melanoma, renal cell carcinoma, non-small cell lung cancer and head and neck squamous cell carcinoma (NCT02452268). In some embodiments, a recombinant human interleukin 12 (rhIL-12) is NM-IL-12 (Neumedicines, Inc.), NCT02544724, or NCT02542124.

In some embodiments, an immuno-oncology agent is selected from those described in Jerry L. Adams et al., "Big opportunities for small molecules in immuno-oncology," Cancer Therapy 2015, Vol. 14, pages 603-622, the content of which is incorporated herein by reference in its entirety. In some embodiment, an immuno-oncology agent is selected from the examples described in Table 1 of Jerry L. Adams et al. In some embodiments, an immuno-oncology agent is a small molecule targeting an immuno-oncology target selected from those listed in Table 2 of Jerry L. Adams ET. AL. In some embodiments, an immuno-oncology agent is a small molecule agent selected from those listed in Table 2 of Jerry L. Adams et al.

In some embodiments, an immuno-oncology agent is selected from the small molecule immuno-oncology agents described in Peter L. Toogood, "Small molecule immuno-oncology therapeutic agents," Bioorganic & Medicinal Chemistry Letters 2018, Vol. 28, pages 319-329, the content of which is incorporated herein by reference in its entirety. In some embodiments, an immuno-oncology agent is an agent targeting the pathways as described in Peter L. Toogood.

In some embodiments, an immuno-oncology agent is selected from those described in Sandra L. Ross et al., "Bispecific T cell engager (BiTE®) antibody constructs can mediate bystander tumor cell killing", PLoS ONE 12(8): e0183390, the content of which is incorporated herein by reference in its entirety. In some embodiments, an immuno-oncology agent is a bispecific T cell engager (BiTE®) antibody construct. In some embodiments, a bispecific T cell engager (BiTE®) antibody construct is a CD19/CD3 bispecific antibody construct. In some embodiments, a bispecific T cell engager (BiTE®) antibody construct is an EGFR/CD3 bispecific antibody construct. In some embodiments, a bispecific T cell engager (BiTE®) antibody construct activates T cells. In some embodiments, a bispecific T cell engager (BiTE®) antibody construct activates T cells, which release cytokines inducing upregulation of intercellular adhesion molecule 1 (ICAM-1) and FAS on bystander cells. In some embodiments, a bispecific T cell engager (BiTE®) antibody construct activates T cells which result in induced bystander cell lysis. In some embodiments, the bystander cells are in solid tumors. In some embodiments, the bystander cells being lysed are in proximity to the BiTE®-activated T cells. In some embodiment, the bystander cells comprises tumor-associated antigen (TAA) negative cancer cells. In some embodiment, the bystander cells comprise EGFR-negative cancer cells. In some embodiments, an immuno-oncology agent is an antibody which blocks the PD-L1/PD1 axis and/or CTLA4. In some embodiments, an immuno-oncology agent is an ex-vivo expanded tumor-infiltrating T cell. In some embodiments, an immuno-oncology agent is a bispecific antibody construct or chimeric antigen receptors (CARs) that directly connect T cells with tumor-associated surface antigens (TAAs).

Exemplary Immune Checkpoint Inhibitors

In some embodiments, an immuno-oncology agent is an immune checkpoint inhibitor as described herein.

The term "checkpoint inhibitor" as used herein relates to agents useful in preventing cancer cells from avoiding the immune system of the patient. One of the major mechanisms of anti-tumor immunity subversion is known as "T-cell exhaustion," which results from chronic exposure to antigens that has led to up-regulation of inhibitory receptors. These inhibitory receptors serve as immune checkpoints in order to prevent uncontrolled immune reactions.

PD-1 and co-inhibitory receptors such as cytotoxic T-lymphocyte antigen 4 (CTLA-4, B and T Lymphocyte Attenuator (BTLA; CD272), T cell Immunoglobulin and Mucin domain-3 (Tim-3), Lymphocyte Activation Gene-3 (Lag-3; CD223), and others are often referred to as a checkpoint regulators. They act as molecular "gatekeepers" that allow extracellular information to dictate whether cell cycle progression and other intracellular signaling processes should proceed.

In some embodiments, an immune checkpoint inhibitor is an antibody to PD-1. PD-1 binds to the programmed cell death 1 receptor (PD-1) to prevent the receptor from binding to the inhibitory ligand PDL-1, thus overriding the ability of tumors to suppress the host anti-tumor immune response.

In one aspect, the checkpoint inhibitor is a biologic therapeutic or a small molecule. In another aspect, the checkpoint inhibitor is a monoclonal antibody, a humanized antibody, a fully human antibody, a fusion protein or a combination thereof. In a further aspect, the checkpoint inhibitor inhibits a checkpoint protein selected from CTLA-4, PDL1, PDL2, PD1, B7-H3, B7-H4, BTLA, HVEM, TIM3, GAL9, LAG3, VISTA, KIR, 2B4, CD 160, CGEN-15049, CHK 1, CHK2, A2aR, B-7 family ligands or a combination thereof. In an additional aspect, the checkpoint inhibitor interacts with a ligand of a checkpoint protein selected from CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In an aspect, the checkpoint inhibitor is an immunostimulatory agent, a T cell growth factor, an interleukin, an antibody, a vaccine or a combination thereof. In a further aspect, the interleukin is IL-7 or IL-15. In a specific aspect, the interleukin is glycosylated IL-7. In an additional aspect, the vaccine is a dendritic cell (DC) vaccine.

Checkpoint inhibitors include any agent that blocks or inhibits in a statistically significant manner, the inhibitory pathways of the immune system. Such inhibitors may include small molecule inhibitors or may include antibodies, or antigen binding fragments thereof, that bind to and block or inhibit immune checkpoint receptors or antibodies that bind to and block or inhibit immune checkpoint receptor ligands. Illustrative checkpoint molecules that may be targeted for blocking or inhibition include, but are not limited to, CTLA-4, PDL1, PDL2, PD1, B7-H3, B7-H4, BTLA, HVEM, GAL9, LAG3, TIM3, VISTA, KIR, 2B4 (belongs to the CD2 family of molecules and is expressed on all NK, γδ, and memory CD8$^+$ (αβ) T cells), CD160 (also referred to as BY55), CGEN-15049, CHK 1 and CHK2 kinases, A2aR, and various B-7 family ligands. B7 family ligands include, but are not limited to, B7-1, B7-2, B7-DC, B7-H1, B7-H2, B7-H3, B7-H4, B7-H5, B7-H6 and B7-H7. Checkpoint inhibitors include antibodies, or antigen binding fragments thereof, other binding proteins, biologic therapeutics, or small molecules, that bind to and block or inhibit the activity of one or more of CTLA-4, PDL1, PDL2, PD1, BTLA, HVEM, TIM3, GAL9, LAG3, VISTA, KIR, 2B4, CD 160 and CGEN-15049. Illustrative immune checkpoint inhibitors include Tremelimumab (CTLA-4 blocking antibody), anti-OX40, PD-L1 monoclonal Antibody (Anti-B7-Hl; MEDI4736), MK-3475 (PD-1 blocker), Nivolumab (anti- PD1 antibody), CT-011 (anti-PD1 antibody), BY55 monoclonal antibody, AMP224 (anti-PDL1 antibody), BMS-936559 (anti-PDL1 antibody), MPLDL3280A (anti-PDL1 antibody), MSB0010718C (anti-PDL1 antibody), and ipilimumab (anti-CTLA-4 checkpoint inhibitor). Checkpoint protein ligands include, but are not limited to PD-L1, PD-L2, B7-H3, B7-H4, CD28, CD86 and TIM-3.

In certain embodiments, the immune checkpoint inhibitor is selected from a PD-1 antagonist, a PD-L1 antagonist, and a CTLA-4 antagonist. In some embodiments, the checkpoint inhibitor is selected from the group consisting of nivolumab (Opdivo®), ipilimumab (Yervoy®), and pembrolizumab (Keytruda®). In some embodiments, the checkpoint inhibitor is selected from nivolumab (anti-PD-1 antibody, Opdivo®, Bristol-Myers Squibb); pembrolizumab (anti-PD-1 antibody, Keytruda®, Merck); ipilimumab (anti-CTLA-4 antibody, Yervoy®, Bristol-Myers Squibb); durvalumab (anti-PD-L1 antibody, Imfinzi®, AstraZeneca); and atezolizumab (anti-PD-L1 antibody, Tecentriq®, Genentech).

In some embodiments, the checkpoint inhibitor is selected from the group consisting of lambrolizumab (MK-3475), nivolumab (BMS-936558), pidilizumab (CT-011), AMP-224, MDX-1105, MEDI4736, MPDL3280A, BMS-936559, ipilimumab, lirlumab, IPH2101, pembrolizumab (Keytruda®), and tremelimumab.

In some embodiments, an immune checkpoint inhibitor is REGN2810 (Regeneron), an anti-PD-1 antibody tested in patients with basal cell carcinoma (NCT03132636); NSCLC (NCT03088540); cutaneous squamous cell carcinoma (NCT02760498); lymphoma (NCT02651662); and melanoma (NCT03002376); pidilizumab (CureTech), also known as CT-011, an antibody that binds to PD-1, in clinical trials for diffuse large B-cell lymphoma and multiple myeloma; avelumab (Bavencio®, Pfizer/Merck KGaA), also known as MSB0010718C), a fully human IgG1 anti-PD-L1 antibody, in clinical trials for non-small cell lung cancer, Merkel cell carcinoma, mesothelioma, solid tumors, renal cancer, ovarian cancer, bladder cancer, head and neck cancer, and gastric cancer; or PDR001 (Novartis), an inhibitory antibody that binds to PD-1, in clinical trials for non-small cell lung cancer, melanoma, triple negative breast cancer and advanced or metastatic solid tumors. Tremelimumab (CP-675,206; Astrazeneca) is a fully human monoclonal antibody against CTLA-4 that has been in studied in clinical trials for a number of indications, including: mesothelioma, colorectal cancer, kidney cancer, breast cancer, lung cancer and non-small cell lung cancer, pancreatic ductal adenocarcinoma, pancreatic cancer, germ cell cancer, squamous cell cancer of the head and neck, hepatocellular carcinoma, prostate cancer, endometrial cancer, metastatic cancer in the liver, liver cancer, large B-cell lymphoma, ovarian cancer, cervical cancer, metastatic anaplastic thyroid cancer, urothelial cancer, fallopian tube cancer, multiple myeloma, bladder cancer, soft tissue sarcoma, and melanoma. AGEN-1884 (Agenus) is an anti-CTLA4 antibody that is being studied in Phase 1 clinical trials for advanced solid tumors (NCT02694822).

In some embodiments, a checkpoint inhibitor is an inhibitor of T-cell immunoglobulin mucin containing protein-3 (TIM-3). TIM-3 inhibitors that may be used in the present invention include TSR-022, LY3321367 and MBG453. TSR-022 (Tesaro) is an anti-TIM-3 antibody which is being studied in solid tumors (NCT02817633). LY3321367 (Eli Lilly) is an anti-TIM-3 antibody which is being studied in solid tumors (NCT03099109). MBG453 (Novartis) is an anti-TIM-3 antibody which is being studied in advanced malignancies (NCT02608268).

In some embodiments, a checkpoint inhibitor is an inhibitor of T cell immunoreceptor with Ig and ITIM domains, or TIGIT, an immune receptor on certain T cells and NK cells. TIGIT inhibitors that may be used in the present invention include BMS-986207 (Bristol-Myers Squibb), an anti-TIGIT monoclonal antibody (NCT02913313); OMP-313M32 (Oncomed); and anti-TIGIT monoclonal antibody (NCT03119428).

In some embodiments, a checkpoint inhibitor is an inhibitor of Lymphocyte Activation Gene-3 (LAG-3). LAG-3 inhibitors that may be used in the present invention include BMS-986016 and REGN3767 and IMP321. BMS-986016 (Bristol-Myers Squibb), an anti-LAG-3 antibody, is being studied in glioblastoma and gliosarcoma (NCT02658981). REGN3767 (Regeneron), is also an anti-LAG-3 antibody, and is being studied in malignancies (NCT03005782). IMP321 (Immutep S.A.) is an LAG-3-Ig fusion protein, being studied in melanoma (NCT02676869); adenocarcinoma (NCT02614833); and metastatic breast cancer (NCT00349934).

Checkpoint inhibitors that may be used in the present invention include OX40 agonists. OX40 agonists that are being studied in clinical trials include PF-04518600/PF-8600 (Pfizer), an agonistic anti-OX40 antibody, in metastatic kidney cancer (NCT03092856) and advanced cancers and neoplasms (NCT02554812; NCT05082566); GSK3174998 (Merck), an agonistic anti-OX40 antibody, in Phase 1 cancer trials (NCT02528357); MEDI0562 (Medimmune/AstraZeneca), an agonistic anti-OX40 antibody, in advanced solid tumors (NCT02318394 and NCT02705482); MEDI6469, an agonistic anti-OX40 antibody (Medimmune/AstraZeneca), in patients with colorectal cancer (NCT02559024), breast cancer (NCT01862900), head and neck cancer (NCT02274155) and metastatic prostate cancer (NCT01303705); and BMS-986178 (Bristol-Myers Squibb) an agonistic anti-OX40 antibody, in advanced cancers (NCT02737475).

Checkpoint inhibitors that may be used in the present invention include CD 137 (also called 4-1BB) agonists. CD137 agonists that are being studied in clinical trials include utomilumab (PF-05082566, Pfizer) an agonistic anti-CD137 antibody, in diffuse large B-cell lymphoma (NCT02951156) and in advanced cancers and neoplasms (NCT02554812 and NCT05082566); urelumab (BMS-663513, Bristol-Myers Squibb), an agonistic anti-CD137 antibody, in melanoma and skin cancer (NCT02652455) and glioblastoma and gliosarcoma (NCT02658981).

Checkpoint inhibitors that may be used in the present invention include CD27 agonists. CD27 agonists that are being studied in clinical trials include varlilumab (CDX-1127, Celldex Therapeutics) an agonistic anti-CD27 antibody, in squamous cell head and neck cancer, ovarian carcinoma, colorectal cancer, renal cell cancer, and glioblastoma (NCT02335918); lymphomas (NCT01460134); and glioma and astrocytoma (NCT02924038).

Checkpoint inhibitors that may be used in the present invention include glucocorticoid-induced tumor necrosis factor receptor (GITR) agonists. GITR agonists that are being studied in clinical trials include TRX518 (Leap Therapeutics), an agonistic anti-GITR antibody, in malignant melanoma and other malignant solid tumors (NCT01239134 and NCT02628574); GWN323 (Novartis), an agonistic anti-GITR antibody, in solid tumors and lymphoma (NCT 02740270); INCAGN01876 (Incyte/Agenus), an agonistic anti-GITR antibody, in advanced cancers (NCT02697591 and NCT03126110); MK-4166 (Merck), an agonistic anti-GITR antibody, in solid tumors (NCT02132754) and MEDI1873 (Medimmune/AstraZeneca), an agonistic hexameric GITR-ligand molecule with a human IgG1 Fc domain, in advanced solid tumors (NCT02583165).

Checkpoint inhibitors that may be used in the present invention include inducible T-cell co-stimulator (ICOS, also known as CD278) agonists. ICOS agonists that are being studied in clinical trials include MEDI-570 (Medimmune), an agonistic anti-ICOS antibody, in lymphomas (NCT02520791); GSK3359609 (Merck), an agonistic anti-ICOS antibody, in Phase 1 (NCT02723955); JTX-2011 (Jounce Therapeutics), an agonistic anti-ICOS antibody, in Phase 1 (NCT02904226).

Checkpoint inhibitors that may be used in the present invention include killer IgG-like receptor (KIR) inhibitors. KIR inhibitors that are being studied in clinical trials include lirilumab (IPH2102/BMS-986015, Innate Pharma/Bristol-Myers Squibb), an anti-KIR antibody, in leukemias (NCT01687387, NCT02399917, NCT02481297, NCT02599649), multiple myeloma (NCT02252263), and lymphoma (NCT01592370); IPH2101 (1-7F9, Innate Pharma) in myeloma (NCT01222286 and NCT01217203); and IPH4102 (Innate Pharma), an anti-KIR antibody that binds to three domains of the long cytoplasmic tail (KIR3DL2), in lymphoma (NCT02593045).

Checkpoint inhibitors that may be used in the present invention include CD47 inhibitors of interaction between CD47 and signal regulatory protein alpha (SIRPa). CD47/SIRPa inhibitors that are being studied in clinical trials include ALX-148 (Alexo Therapeutics), an antagonistic variant of (SIRPa) that binds to CD47 and prevents CD47/SIRPa-mediated signaling, in phase 1 (NCT03013218); TTI-621 (SIRPa-Fc, Trillium Therapeutics), a soluble recombinant fusion protein created by linking the N-terminal CD47-binding domain of SIRPa with the Fc domain of human IgG1, acts by binding human CD47, and preventing it from delivering its "do not eat" signal to macrophages, is in clinical trials in Phase 1 (NCT02890368 and NCT02663518); CC-90002 (Celgene), an anti-CD47 antibody, in leukemias (NCT02641002); and Hu5F9-G4 (Forty Seven, Inc.), in colorectal neoplasms and solid tumors (NCT02953782), acute myeloid leukemia (NCT02678338) and lymphoma (NCT02953509).

Checkpoint inhibitors that may be used in the present invention include CD73 inhibitors. CD73 inhibitors that are being studied in clinical trials include MEDI9447 (Medimmune), an anti-CD73 antibody, in solid tumors (NCT02503774); and BMS-986179 (Bristol-Myers Squibb), an anti-CD73 antibody, in solid tumors (NCT02754141).

Checkpoint inhibitors that may be used in the present invention include agonists of stimulator of interferon genes protein (STING, also known as transmembrane protein 173, or TMEM173). Agonists of STING that are being studied in clinical trials include MK-1454 (Merck), an agonistic synthetic cyclic dinucleotide, in lymphoma (NCT03010176); and ADU-S100 (MIW815, Aduro Biotech/Novartis), an agonistic synthetic cyclic dinucleotide, in Phase 1 (NCT02675439 and NCT03172936).

Checkpoint inhibitors that may be used in the present invention include CSF1R inhibitors. CSF1R inhibitors that are being studied in clinical trials include pexidartinib (PFX3397, Plexxikon), a CSF1R small molecule inhibitor, in colorectal cancer, pancreatic cancer, metastatic and advanced cancers (NCT02777710) and melanoma, non-small cell lung cancer, squamous cell head and neck cancer, gastrointestinal stromal tumor (GIST) and ovarian cancer (NCT02452424); and IMC-CS4 (LY3022855, Lilly), an anti-CSF-1R antibody, in pancreatic cancer (NCT03153410), melanoma (NCT03101254), and solid tumors (NCT02718911); and BLZ945 (4-[2((1R,2R)-2-hydroxycyclohexylamino)-benzothiazol-6-yloxyl]-pyridine-2-carboxylic acid methylamide, Novartis), an orally available inhibitor of CSF1R, in advanced solid tumors (NCT02829723).

Checkpoint inhibitors that may be used in the present invention include NKG2A receptor inhibitors. NKG2A receptor inhibitors that are being studied in clinical trials include monalizumab (IPH2201, Innate Pharma), an anti-NKG2A antibody, in head and neck neoplasms (NCT02643550) and chronic lymphocytic leukemia (NCT02557516).

In some embodiments, the immune checkpoint inhibitor is selected from nivolumab, pembrolizumab, ipilimumab, avelumab, durvalumab, atezolizumab, or pidilizumab.

EXEMPLIFICATION

Abbreviations

Ac: acetyl
AcOH: acetic acid
ACN: acetonitrile
Ad: adamantly
AIBN: 2,2'-azo bisisobutyronitrile
Anhyd: anhydrous
Aq: aqueous
$B_2Pin_2$: bis (pinacolato)diboron -4,4,4',4',5,5,5',5'-octamethyl-2,2'-bi(1,3,2-dioxaborolane)
BINAP: 2,2'-bis(diphenylphosphino)-1,1'-binaphthyl
$BH_3$: Borane
Bn: benzyl
Boc: tert-butoxycarbonyl
$BOC_2O$: di-tert-butyl dicarbonate
BPO: benzoyl peroxide
"BuOH: n-butanol
CDI: carbonyldiimidazole
COD: cyclooctadiene
d: days
DABCO: 1,4-diazobicyclo[2.2.2]octane
DAST: diethylaminosulfur trifluoride
dba: dibenzylideneacetone
DBU: 1,8-diazobicyclo[5.4.0]undec-7-ene
DCE: 1,2-dichloroethane
DCM: dichloromethane
DEA: diethylamine
DHP: dihydropyran
DIBAL-H: diisobutylaluminum hydride
DIPA: diisopropylamine
DIPEA or DIEA: N,N-diisopropylethylamine
DMA: N,N-dimethylacetamide
DME: 1,2-dimethoxyethane
DMAP: 4-dimethylaminopyridine
DMF: N,N-dimethylformamide
DMP: Dess-Martin periodinane
DMSO-dimethyl sulfoxide
DPPA: diphenylphosphoryl azide
dppf: 1,1'-bis(diphenylphosphino)ferrocene
EDC or EDCI: 1-(3-dimethylaminopropyl)-3-ethylcarbodiimide hydrochloride
ee: enantiomeric excess
ESI: electrospray ionization
EA: ethyl acetate
EtOAc: ethyl acetate EtOH: ethanol
FA: formic acid
h or hrs: hours
HATU: N,N,N',N'-tetramethyl-O-(7-azabenzotriazol-1-yl)uronium hexafluorophosphate
HCl: hydrochloric acid
HPLC: high performance liquid chromatography
HOAc: acetic acid
IBX: 2-iodoxybenzoic acid
IPA: isopropyl alcohol
KHMDS: potassium hexamethyldisilazide
$K_2CO_3$: potassium carbonate
LAH: lithium aluminum hydride
LDA: lithium diisopropylamide
m-CPBA: meta-chloroperbenzoic acid
M: molar
MeCN: acetonitrile
MeOH: methanol
$Me_2S$: dimethyl sulfide
MeONa: sodium methylate
MeI: iodomethane
min: minutes
mL: milliliters
mM: millimolar
mmol: millimoles
MPa: mega pascal
MOMCl: methyl chloromethyl ether
MsCl: methanesulfonyl chloride
MTBE: methyl tert-butyl ether
nBuLi: n-butyllithium
$NaNO_2$: sodium nitrite
NaOH: sodium hydroxide
$Na_2SO_4$: sodium sulfate
NBS: N-bromosuccinimide
NCS: N-chlorosuccinimide
NFSI: N-Fluorobenzenesulfonimide
NMO: N-methylmorpholine N-oxide
NMP: N-methylpyrrolidine
NMR: Nuclear Magnetic Resonance
° C.: degrees Celsius
Pd/C: Palladium on Carbon
$Pd(OAc)_2$: Palladium Acetate
PBS: phosphate buffered saline
PE: petroleum ether
$POCl_3$: phosphorus oxychloride
$PPh_3$: triphenylphosphine
PyBOP: (Benzotriazol-1-yloxy)tripyrrolidinophosphonium hexafluorophosphate
Rel: relative
R.T. or rt: room temperature
sat: saturated
SEMCl: chloromethyl-2-trimethylsilylethyl ether
SFC: supercritical fluid chromatography
$SOCl_2$: sulfur dichloride
tBuOK: potassium tert-butoxide
TBAB: tetrabutylammonium bromide
TBAI: tetrabutylammonium iodide
TEA: triethylamine
Tf: trifluoromethane sulfonate
TfAA, TFMSA or $Tf_2O$: trifluoromethanesulfonic anhydride
TFA: trifluoroacetic acid
TIPS: triisopropylsilyl
THF: tetrahydrofuran
THP: tetrahydropyran
TLC: thin layer chromatography
TMEDA: tetramethylethylenediamine
pTSA: para-toluenesulfonic acid
wt: weight
Xantphos: 4,5-bis(diphenylphosphino)-9,9-dimethylxanthene General Synthetic Methods The following examples are intended to illustrate the invention and are not to be construed as being limitations thereon. Temperatures are given in degrees centigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

All reactions are carried out under nitrogen or argon unless otherwise stated.

Proton NMR ($^1$H NMR) was conducted in deuterated solvent. In certain compounds disclosed herein, one or more $^1$H shifts overlap with residual proteo solvent signals; these signals have not been reported in the experimental provided hereinafter.

TABLE 2

| | Analytical instruments |
|---|---|
| LCMS | Shimadzu UFLC MS: LCMS-2020 |
| | Agilent Technologies 1200 series MS: Agilent Technologies 6110 |
| | Agilent Technologies 1200 series MS: LC/MSD VL |
| NMR | BRUKER AVANCE III/400; Frequency (MHz) 400.13; Nucleus: 1H; Number of Transients: 8 |
| Prep-HPLC | Gilson GX-281 systems: instruments GX-A, GX-B, GX-C, GX-D, GX-E, GX-F, GX-G and GX-H |
| GCMS | SHIMADZU GCMS-QP2010 Ultra |
| Analytical cSFC | Agilent Technologies 1290 Infinity |
| Prep-cSFC | Waters SFC Prep 80 |

For acidic LCMS data: LCMS was recorded on an Agilent 1200 Series LC/MSD or Shimadzu LCMS2020 equipped with electro-spray ionization and quadruple MS detector [ES+ve to give MH$^+$] and equipped with Chromolith Flash RP-18e 25*2.0 mm, eluting with 0.0375 vol % TFA in water (solvent A) and 0.01875 vol % TFA in acetonitrile (solvent B). Other LCMS was recorded on an Agilent 1290 Infinity RRLC attached with Agilent 6120 Mass detector. The column used was BEH C18 50*2.1 mm, 1.7 micron. Column flow was 0.55 ml/min and mobile phases used are (A) 2 mM Ammonium Acetate in 0.1% Formic Acid in Water and (B) 0.1% Formic Acid in Acetonitrile.

For basic LCMS data: LCMS was recorded on an Agilent 1200 Series LC/MSD or Shimadzu LCMS 2020 equipped with electro-spray ionization and quadruple MS detector [ES+ve to give MH$^+$] and equipped with Xbridge C18, 2.1×50 mm columns packed with 5 mm C18-coated silica or Kinetex EVO C18 2.1×30 mm columns packed with 5 mm C18-coated silica, eluting with 0.05 vol % $NH_3.H_2O$ in water (solvent A) and acetonitrile (solvent B).

HPLC Analytical Method: HPLC was carried out on X Bridge C18 150*4.6 mm, 5 micron. Column flow was 1.0 ml/min and mobile phase used are (A) 0.1% Ammonia in water and (B) 0.1% Ammonia in Acetonitrile.

Prep HPLC Analytical Method: The compound was purified on Shimadzu FC-20AP and UV detector. The column used was X-BRIDGE C18 (250*19)mm, 5μ. Column flow was 16.0 ml/min. Mobile phases used are (A) 0.1% Formic Acid in Water and (B) Acetonitrile Basic method used (A) 5 mM ammonium bicarbonate and 0.1% NH3 in Water and (B) Acetonitrile or (A) 0.1% Ammonium Hydroxide in Water and (B) Acetonitrile. The UV spectra are recorded at 202 nm & 254 nm.

NMR Method: The 1H NMR spectra were recorded on a Bruker Ultra Shield Advance 400 MHz/5 mm Probe (BBFO). The chemical shifts are reported in part-per-million.

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Example 1. (2S,4R)-4-hydroxy-1-((S)-2-(6-(4-(2-((R)-3-(2-hydroxyphenyl)-5-methyl-7,8-dihydro-5H-pyrido[3',4':4,5]pyrrolo[2,3-c]pyridazin-6(9H)-yl)pyrimidin-4-yl)piperidin-1-yl)spiro[3.3]heptane-2-carboxamido)-3,3-dimethylbutanoyl)-N-(4-(4-methylthiazol-5-yl)benzyl)pyrrolidine-2-carboxamide (I-13)

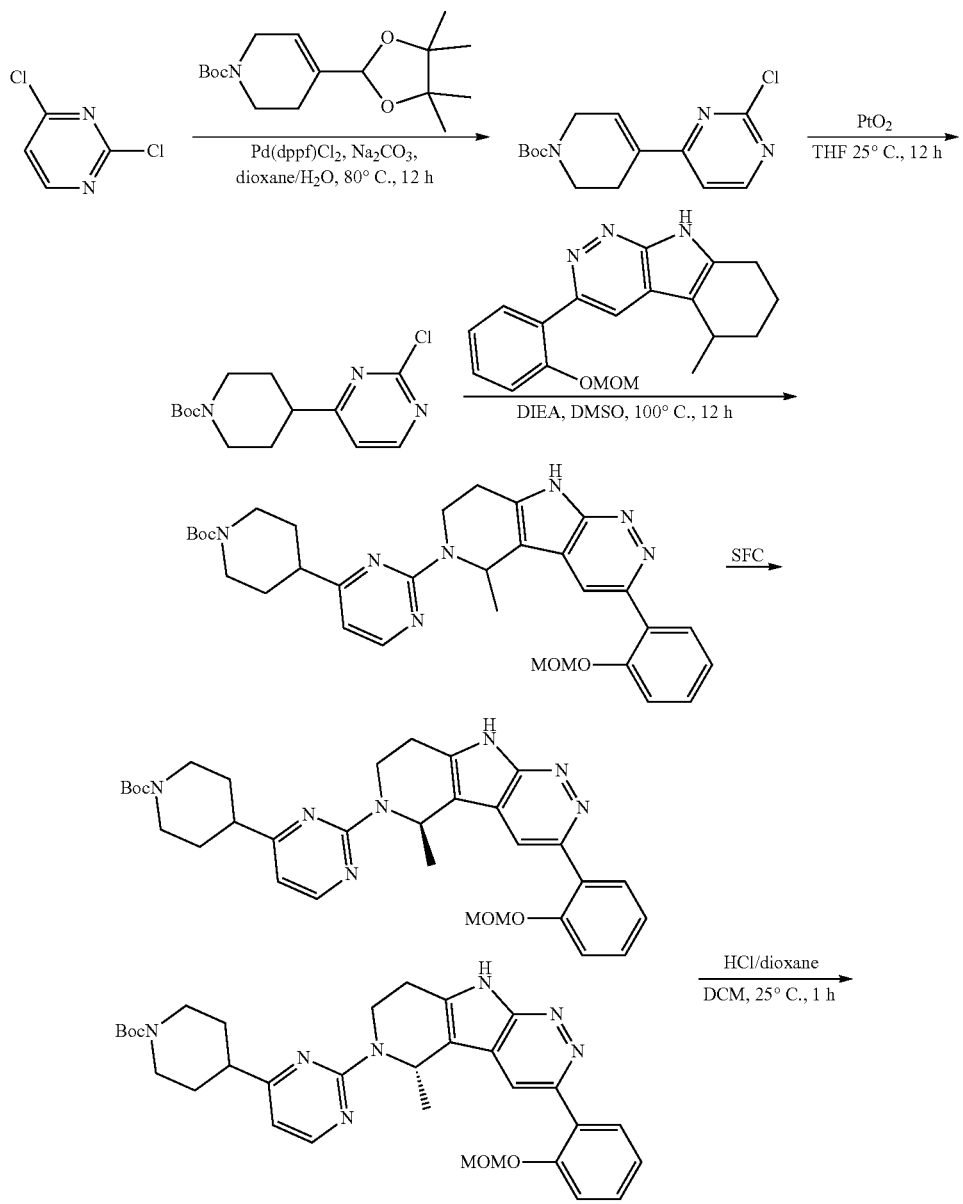

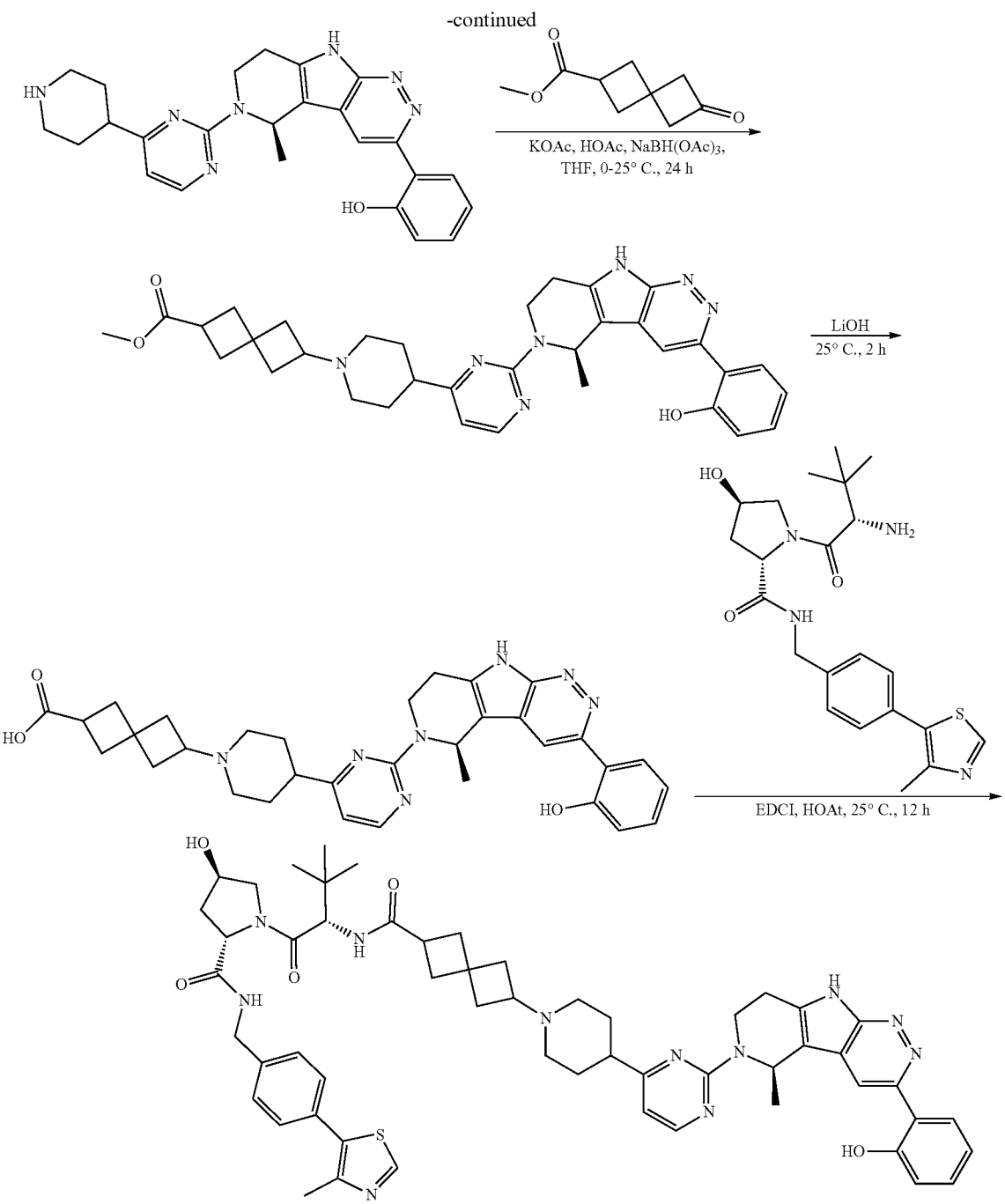

I-13

Step 1: tert-butyl 4-(2-chloropyrimidin-4-yl)-5,6-dihydropyridine-1(2H)-carboxylate. To a solution of tert-butyl 4-(4,4,5,5-tetramethyl-1,3-dioxolan-2-yl)-5,6-dihydropyridine-1(2H)-carboxylate (12.5 g, 40.2 mmol) and 2,4-dichloropyrimidine (5 g, 33.6 mmol) in 1,4-dioxane (100 mL) was added Pd(dppf)Cl$_2$ (2.46 g, 3.36 mmol) and sodium carbonate (8.54 g, 80.6 mmol) in H$_2$O (20 mL). The mixture was stirred at 80° C. for 12 hours. On the completion, the reaction mixture was partitioned between H$_2$O (20 mL) and Ethyl acetate (20 mL*3). The organic phase was separated, washed with brine (30 mL) and dried over Na$_2$SO$_4$, filtered and concentrated under reduced pressure to give a residue. Then the residue was purified by column chromatography (SiO$_2$, Petroleum ether/Ethyl acetate=1/0 to 5/1) to get the title compound (7 g, 66.3% yield, 94% purity) as a yellow solid. LC-MS (ESI, m/z): [M-55]$^+$=239.9

Step 2: tert-butyl 4-(2-chloropyrimidin-4-yl)piperidine-1-carboxylate. To a solution of tert-butyl 4-(2-chloropyrimidin-4-yl)-5,6-dihydropyridine-1(2H)-carboxylate (2 g, 6.76 mmol) in THF (60 mL) was added PtO$_2$ (1.54 g, 6.76 mmol) under N$_2$. The suspension was degassed under vacuum and purged with H$_2$ three times. The mixture was stirred under H$_2$ (15 psi) at 25° C. for 12 hours. On the completion, the reaction mixture was filtered and concentrated under reduced pressure to give a residue, then the residue was purified by column chromatography (SiO$_2$, Petroleum ether/Ethyl acetate=10/1 to 3/1) to get the title compound (1.5 g, 73.6% yield, 98.8% purity) as a colorless oil. LC-MS (ESI, m/z): [M-55]$^+$=242.2.

Step 3: tert-butyl 4-(2-(3-(2-(methoxymethoxy)phenyl)-5-methyl-7,8-dihydro-5H-pyrido[3',4':4,5]pyrrolo[2,3-c]pyridazin-6(9H)-yl)pyrimidin-4-yl)piperidine-1-carboxylate. To a solution of tert-butyl 4-(2-chloropyrimidin-4-yl)piperidine-1-carboxylate (459 mg, 1.54 mmol) in DMSO (8 mL) was added DIEA (996 mg, 7.71 mmol, 1.34 mL) and 3-(2-(methoxymethoxy)phenyl)-5-methyl-6,7,8,9-tetrahydro-5H-pyrido[3',4':4,5] pyrrolo[2,3-c]pyridazine (500 mg, 1.54 mmol). The mixture was stirred at 100° C. for 12 hours. On completion, the mixture was filtered by disposable needle filter. Then the mixture was purified by reversed-phase HPLC (0.1% FA condition) to get the title compound (500 mg, 49.1% yield, 88.6% purity) as a white solid. LC-MS (ESI, m/z): [M+1]$^+$=586.3

Step 4: (R)-tert-butyl 4-(2-(3-(2-(methoxymethoxy)phenyl)-5-methyl-7,8-dihydro-5H-pyrido [3',4':4,5]pyrrolo[2,3-c]pyridazin-6(9H)-yl)pyrimidin-4-yl)piperidine-1-carboxylate (6-P1) and (S)-tert-butyl 4-(2-(3-(2-(methoxymethoxy)phenyl)-5-methyl-7,8-dihydro-5H-pyrido[3',4':4,5]pyrrolo[2,3-c]pyridazin-6(9H)-yl)pyrimidin-4-yl)piperidine-1-carboxylate (6-P2). The isomer was separated by SFC (column: DAICEL CHIRALPAK IC (250 mm*30 mm, 10 um); mobile phase: [0.1% NH$_3$H$_2$O MEOH]; B %: 60%-60%, 4; 90 min) to give compounds: 6-P1 (220 mg, SFC retention time=1.483 min) as a yellow solid; 6-P2 (230 mg, SFC retention time=2.283 min).

Step 5: (R)-2-(5-methyl-6-(4-(piperidin-4-yl)pyrimidin-2-yl)-6,7,8,9-tetrahydro-5H-pyrido[3',4':4,5]pyrrolo[2,3-c]pyridazin-3-yl)phenol. To a solution of (R)-tert-butyl 4-(2-(3-(2-(methoxymethoxy)phenyl)-5-methyl-7,8-dihydro-5H-pyrido[3',4':4,5]pyrrolo[2,3-c]pyridazin-6(9H)-yl)pyrimidin-4-yl)piperidine-1-carboxylate (220 mg, 406 umol) in DCM (4 mL) was added HCl/dioxane (4 M, 765 uL). The mixture was stirred at 25° C. for 0.5 hour. On the completion, the reaction mixture was concentrated under reduced pressure to give a crude compound (260 mg, crude) used for the next step directly. Then the 50 mg of crude product was purified by prep-HPLC (column: Welch Xtimate C18 150*25 mm*5 um; mobile phase: [water (0.05% HCl)-ACN]; B %: 3%-33%, 11 min) to give the title compound (30.3 mg, 99.5% purity) as a yellow solid. Tf NMR (400 MHz, DMSO-d$_6$) δ=14.10-13.27 (m, 1H), 9.18-8.86 (m, 2H), 8.72 (s, 1H), 8.38 (d, J=5.2 Hz, 1H), 7.72 (d, J=6.8 Hz, 1H), 7.55-7.41 (m, 1H), 7.17 (d, J=8.0 Hz, 1H), 7.10-7.01 (m, 1H), 6.62 (d, J=5.0 Hz, 1H), 6.15 (d, J=6.4 Hz, 1H), 5.14 (brd, J=12.8 Hz, 1H), 3.48-3.41 (m, 1H), 3.34 (d, J=12.0 Hz, 2H), 3.11 (br d, J=3.6 Hz, 2H), 2.99 (d, J=9.8 Hz, 2H), 2.88 (d, J=4.5 Hz, 1H), 2.07-1.92 (m, 4H), 1.55 (d, J=6.4 Hz, 3H). LC-MS (ESI, m/z): [M+1]$^+$=442.3.

Step 6: (R)-methyl 6-(4-(2-(3-(2-hydroxyphenyl)-5-methyl-7,8-dihydro-5H-pyrido[3',4':4,5]pyrrolo[2,3-c]pyridazin-6(9H)-yl)pyrimidin-4-yl)piperidin-1-yl)spiro[3.3]heptane-2-carboxylate. To a solution of (R)-2-(5-methyl-6-(4-(piperidin-4-yl)pyrimidin-2-yl)-6,7,8,9-tetrahydro-5H-pyrido[3',4':4,5]pyrrolo[2,3-c]pyridazin-3-yl)phenol (138 mg, 311 umol) in THF (2 mL) was added KOAc (91.7 mg, 934 umol), methyl 2-oxospiro[3.3]heptane-6-carboxylate (62.9 mg, 374 umol), NaBH(OAc)$_3$, (165 mg, 778 umol) and HOAc (56.1 mg, 934 umol). The mixture was stirred at 25° C. for 12 hours. On the completion, the mixture was filtered by disposable needle filter, then the mixture was purified by reversed-phase HPLC (0.1% FA condition) to get the title compound (150 mg, 76.2% yield, 93.9% purity) as a white solid. LC-MS (ESI, m/z): [M+1]$^+$=594.2

Step 7: (R)-6-(4-(2-(3-(2-hydroxyphenyl)-5-methyl-7,8-dihydro-5H-pyrido[3',4':4,5]pyrrolo[2,3-c]pyridazin-6(9H)-yl)pyrimidin-4-yl)piperidin-1-yl)spiro[3.3] heptane-2-carboxylic acid. To a solution of (R)-methyl 6-(4-(2-(3-(2-hydroxyphenyl)-5-methyl-7,8-dihydro-5H-pyrido[3',4':4,5]pyrrolo[2,3-c]pyridazin-6(9H)-yl)pyrimidin-4-yl)piperidin-1-yl)spiro[3.3] heptane-2-carboxylate (150 mg, 253 umol) in THF (3 mL) was added LiOH·H$_2$O (2 M in water, 750 uL). The mixture was stirred at 25° C. for 2 hours. On the completion, the reaction mixture was concentrated under reduced pressure to get a crude compound (146 mg, crude) as a white solid.

Step 8: (2S,4R)-4-hydroxy-1-((S)-2-(6-(4-(2-((R)-3-(2-hydroxyphenyl)-5-methyl-7,8-dihydro-5H-pyrido[3',4':4,5]pyrrolo[2,3-c]pyridazin-6(9H)-yl)pyrimidin-4-yl)piperidin-1-yl)spiro[3.3]heptane-2-carboxamido)-3,3-dimethylbutanoyl)-N-(4-(4-methylthiazol-5-yl)benzyl)pyrrolidine-2-carboxamide. To a solution of (R)-6-(4-(2-(3-(2-hydroxyphenyl)-5-methyl-7,8-dihydro-5H-pyrido[3',4':4, 5]pyrrolo[2,3-c]pyridazin-6(9H)-yl)pyrimidin-4-yl) piperidin-1-yl)spiro[3.3]heptane-2-carboxylic acid (146.46 mg, 252 umol) in DMSO (2 mL) was added DIEA (98.0 mg, 758 umol), (2S,4R)-1-((S)-2-amino-3,3-dimethylbutanoyl)-4-hydroxy-N-(4-(4-methylthiazol-5-yl)benzyl)pyrrolidine-2-carboxamide (120 mg, 278 umol), EDCI (58.1 mg, 303 umol) and HOAt (41.3 mg, 303 umol). The mixture was stirred at 25° C. for 12 hours. On completion, the mixture was filtered by disposable needle filter. The residue was purified by prep-HPLC (column: Phenomenex Gemini 150*25 mm*10 um; mobile phase: [water (0.05% HCl)-MeOH]; B %: 35%-65%, 10 min) to get the title compound (51.8 mg, 49.6 umol, 19.6% yield, 98.6% purity, HCl) as a yellow solid. $^1$H NMR (400 MHz, DMSO-d$_6$) δ=14.13-13.76 (m, 1H), 11.36-11.15 (m, 1H), 9.11 (s, 1H), 8.72 (s, 1H), 8.64-8.57 (m, 1H), 8.38 (d, J=5.2 Hz, 1H), 7.77-7.62 (m, 2H), 7.41 (d, J=6.0 Hz, 5H), 7.24-7.21 (m, 1H), 7.08-7.03 (m, 1H), 6.71-6.61 (m, 1H), 6.29-6.14 (m, 1H), 4.54-4.50 (m, 1H), 4.45-4.39 (m, 2H), 4.37-4.33 (m, 1H), 4.25-4.19 (m, 1H), 3.70-3.61 (m, 2H), 3.52-3.32 (m, 4H), 3.19-3.11 (m, 3H), 2.88-2.75 (m, 3H), 2.47-2.43 (m, 4H), 2.42-2.27 (m, 3H), 1.98 (s, 11H), 1.93-1.86 (m, 1H), 1.54 (d, J=6.4 Hz, 3H), 0.94-0.89 (m, 9H). LC-MS (ESI, m/z): [M/2+1]$^+$=496.9.

Example 2. (2S,4R)-4-hydroxy-1-((S)-2-(6-(4-(2-((S)-3-(2-hydroxyphenyl)-5-methyl-7,8-dihydro-5H-pyrido[3',4':4,5]pyrrolo[2,3-c]pyridazin-6(9H)-yl)pyrimidin-4-yl)piperidin-1-yl)spiro[3.3]heptane-2-carboxamido)-3,3-dimethylbutanoyl)-N-(4-(4-methylthiazol-5-yl)benzyl)pyrrolidine-2-carboxamide (I-14)
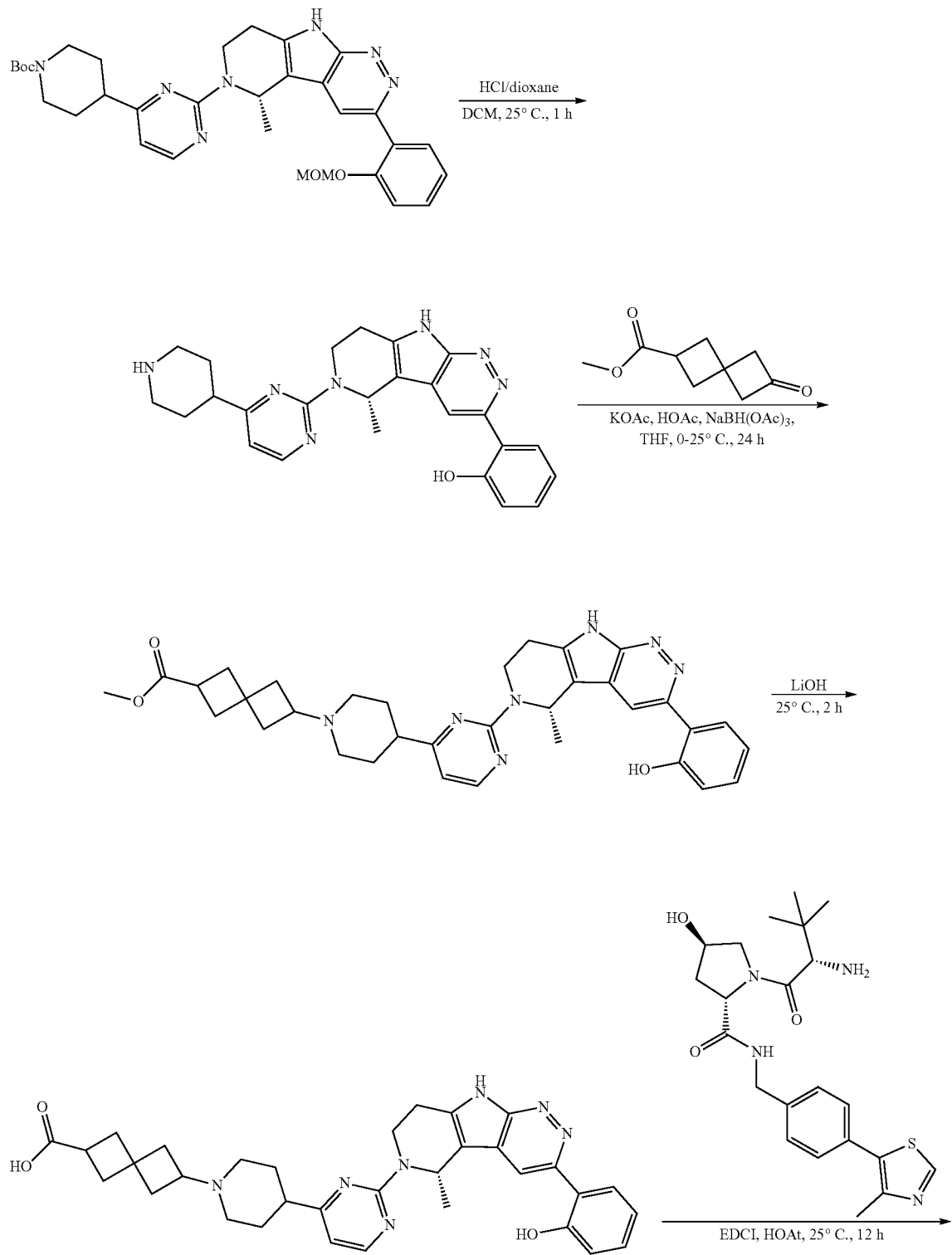

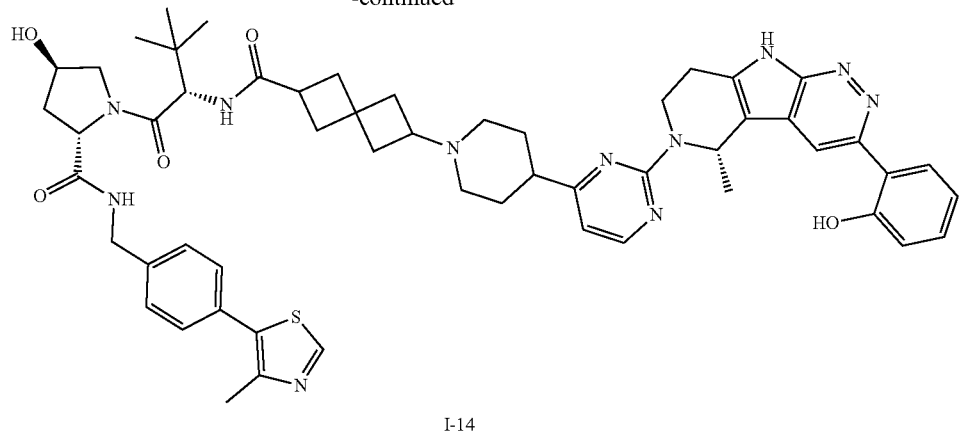

I-14

I-14 was prepare by methods substantially similar to the steps described above to prepare I-13. ¹H NMR (400 MHz, DMSO-d₆) δ=14.04-13.88 (m, 1H), 11.39-11.10 (m, 1H), 9.15 (s, 1H), 8.77-8.68 (m, 1H), 8.61 (t, J=5.6 Hz, 1H), 8.38 (d, J=5.2 Hz, 1H), 7.79-7.57 (m, 2H), 7.48-7.38 (m, 5H), 7.28-7.20 (m, 1H), 7.05 (t, J=7.2 Hz, 1H), 6.67 (d, J=5.2 Hz, 1H), 6.33-6.07 (m, 1H), 5.17-5.08 (m, 1H), 4.56-4.50 (m, 3H), 4.46-4.39 (m, 3H), 4.35 (s, 1H), 4.22 (dd, J=5.2, 16.0 Hz, 1H), 3.70-3.60 (m, 2H), 3.54-3.30 (m, 4H), 3.20-3.13 (m, 3H), 2.90-2.73 (m, 3H), 2.46 (s, 3H), 2.41-2.32 (m, 2H), 2.23-2.13 (m, 4H), 2.12-2.00 (m, 5H), 1.89 (ddd, J=4.4, 8.4, 12.8 Hz, 1H), 1.55 (d, J=6.4 Hz, 3H), 0.94-0.89 (m, 9H). LC-MS (ESI, m/z): [M+1]⁺=992.7.

Example 3. (2S,4R)-4-hydroxy-1-((S)-2-(6-(4-(2-((R)-3-(2-hydroxyphenyl)-5-methyl-7,8-dihydro-5H-pyrido[3',4':4,5]pyrrolo[2,3-c]pyridazin-6(9H)-yl)pyrimidin-5-yl)piperidin-1-yl)spiro[3.3]heptane-2-carboxamido)-3,3-dimethylbutanoyl)-N-(4-(4-methylthiazol-5-yl)benzyl)pyrrolidine-2-carboxamide (I-38)

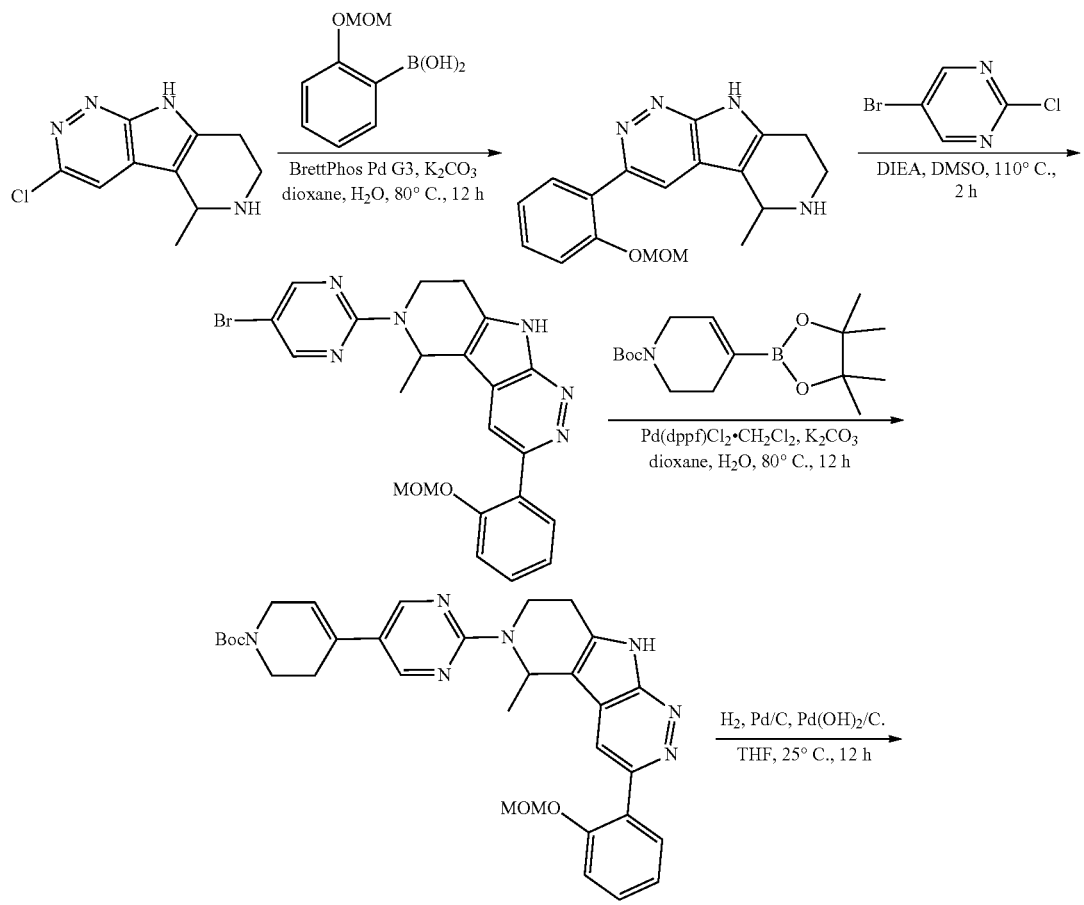

519　　　　　　　　　　　　　　　　　　　　520
-continued
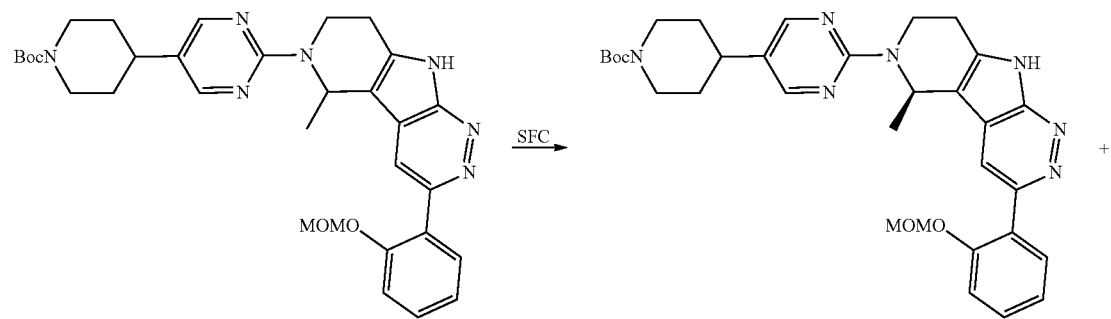
SFC →　　　　　　　　　　　　　　　　　　　　+
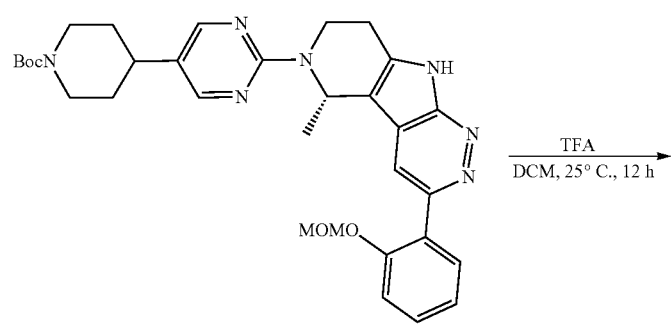
TFA
DCM, 25° C., 12 h →
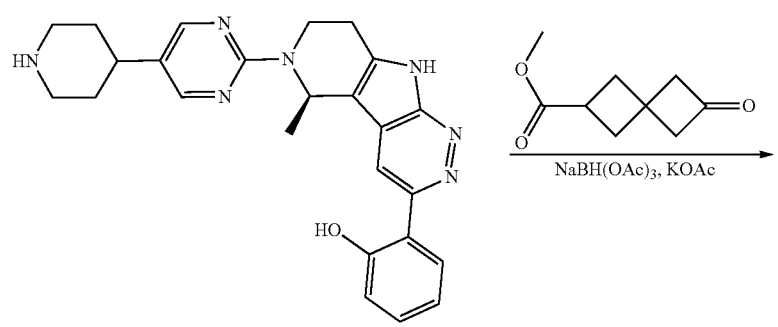
NaBH(OAc)₃, KOAc →
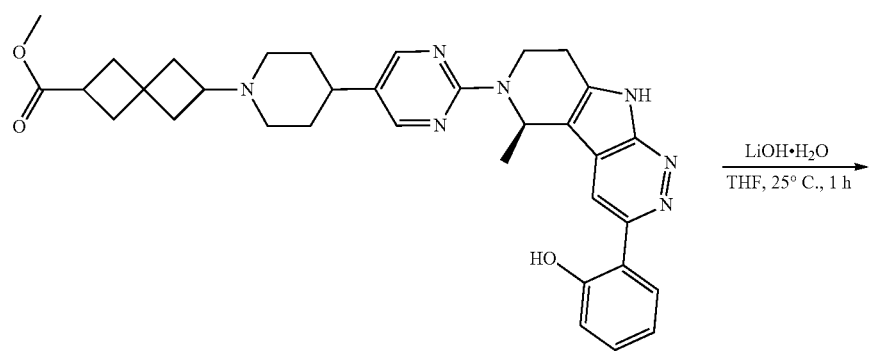
LiOH·H₂O
THF, 25° C., 1 h →

-continued
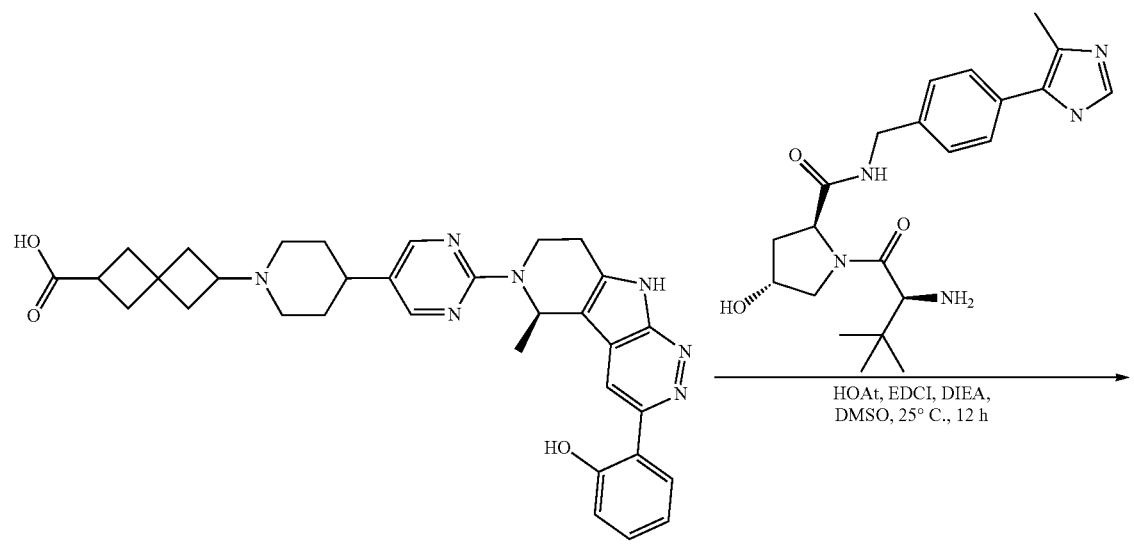
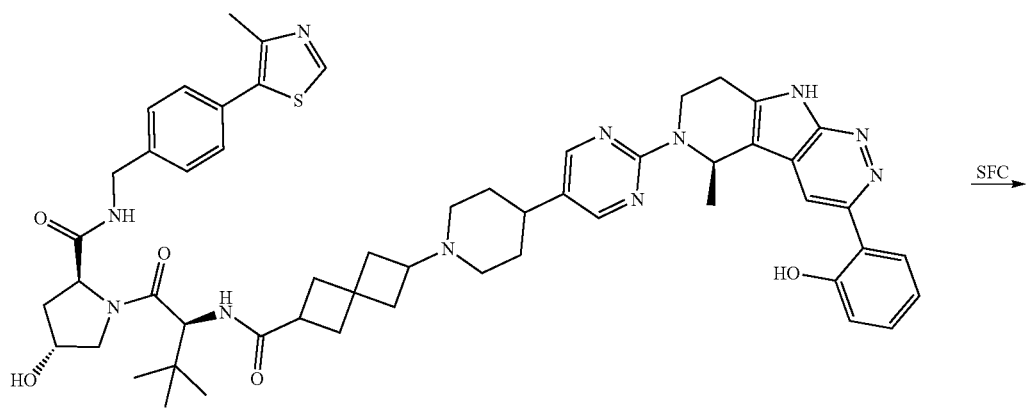
I-38
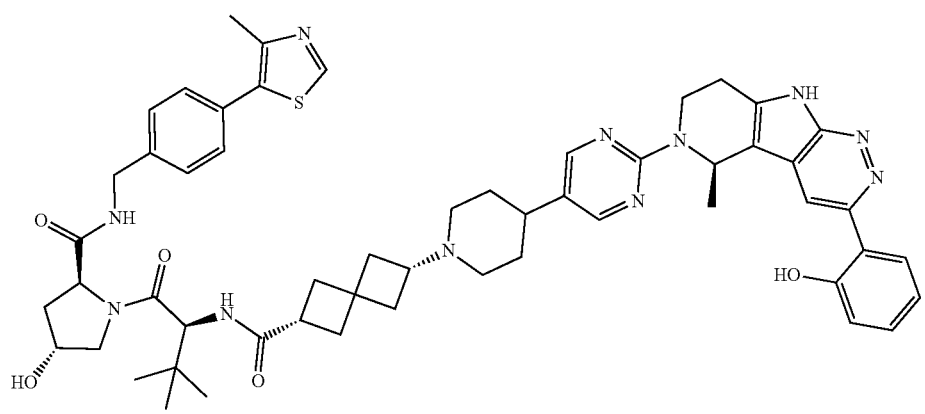
I-40

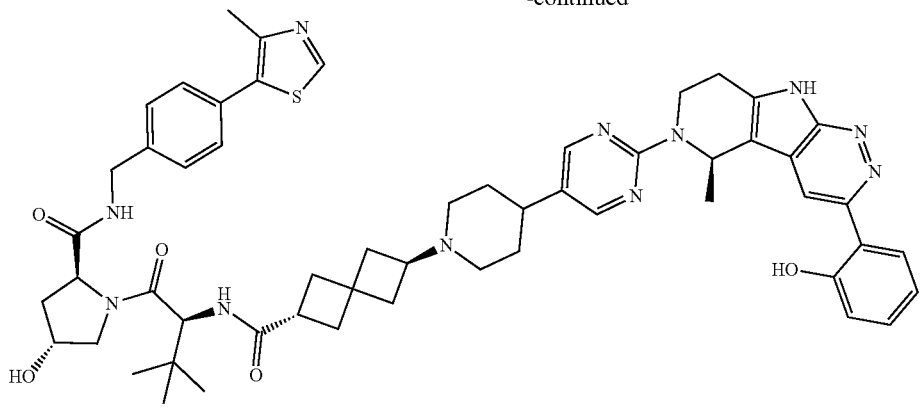

I-41

Step 1: 3-(2-(methoxymethoxy)phenyl)-5-methyl-6,7,8,9-tetrahydro-5H-pyrido[3',4':4, 5]pyrrolo[2,3-c]pyridazine. A mixture of [2-(methoxymethoxy)phenyl]boronic acid (2.45 g, 13.5 mmol), 12-chloro-3-methyl-4,8,10,11-tetrazatricyclo[7.4.0.02,7]trideca-1(9),2(7),10,12-tetraene (2 g, 8.98 mmol), BrettPhos Pd G3 (814 mg, 898 umol) and $K_2CO_3$ (3.72 g, 27.0 mmol) in dioxane (30 mL) and $H_2O$ (6 mL) was degassed and purged with $N_2$ for 3 times, and then the mixture was stirred at 80° C. for 12 hours under $N_2$ atmosphere. The reaction mixture was partitioned between ethyl acetate (300 mL) and water (200 mL). The organic phase was separated, washed with brine (100 mL*2) and dried over $Na_2SO_4$, filtered and concentrated under reduced pressure to give a residue. The crude product was purified by reversed-phase HPLC (0.1% $NH_3.H_2O$) to give the title compound (1.5 g, 51% yield) as a yellow solid. $^1$H NMR (400 MHz, DMSO-$d_6$) δ=12.25-11.85 (m, 1H), 7.96 (s, 1H), 7.71 (dd, J=1.6, 7.6 Hz, 1H), 7.42-7.35 (m, 1H), 7.23 (d, J=7.6 Hz, 1H), 7.14 (dt, J=1.2, 7.6 Hz, 1H), 5.20 (q, J=6.4 Hz, 2H), 4.06 (q, J=6.4 Hz, 1H), 3.30 (s, 3H), 3.23-3.18 (m, 1H), 2.90 (ddd, J=4.8, 8.4, 12.4 Hz, 1H), 2.84-2.75 (m, 1H), 2.72-2.65 (m, 1H), 1.39 (d, J=6.4 Hz, 3H). LC/MS (ESI, m/z): [M+1]$^+$=325.0.

Step 2: 6-(5-bromopyrimidin-2-yl)-3-(2-(methoxymethoxy)phenyl)-5-methyl-6,7,8,9-tetrahydro-5H-pyrido[3',4':4,5]pyrrolo[2,3-c]pyridazine. To a solution of 12-[2-(methoxymethoxy)phenyl]-3-methyl-4,8,10,11-tetrazatricyclo[7.4.0.02,7]trideca-1(9),2(7),10,12-tetraene (800 mg, 2.47 mmol) and 5-bromo-2-chloro-pyrimidine (429 mg, 2.22 mmol) in DMSO (8 mL) was added DIEA (956 mg, 7.40 mmol). The mixture was stirred at 110° C. for 2 hours. The reaction mixture was partitioned between ethyl acetate (80 mL) and water (70 mL). The organic phase was separated, washed with brine (35 mL*2) and dried over $Na_2SO_4$, filtered and concentrated under reduced pressure to give a residue. The residue was purified by column chromatography (SiO$_2$, Petroleum ether/Ethyl acetate=2/1 to 0/1) to give the title compound (1 g, 77% yield, 92% purity) as a yellow solid. LC/MS (ESI, m/z): [M+1]$^+$=481.2.

Step 3: tert-butyl 4-(2-(3-(2-(methoxymethoxy)phenyl)-5-methyl-7,8-dihydro-5H-pyrido[3',4':4,5]pyrrolo[2,3-c]pyridazin-6(9H)-yl)pyrimidin-5-yl)-5,6-dihydropyridine-1(2H)-carboxylate. A mixture of 4-(5-bromopyrimidin-2-yl)-12-[2-(methoxymethoxy)phenyl]-3-methyl-4,8,10,11-tetrazatricyclo[7.4.0.02,7]trideca-1(9),2(7),10,12-tetraene (1 g, 2.08 mmol), tert-butyl 4-(4,4,5,5-tetramethyl-1,3,2-dioxaborolan-2-yl)-3,6-dihydro-2H-pyridine-1-carboxylate (642 mg, 2.08 mmol), $K_2CO_3$ (861 mg, 6.23 mmol) and Pd(dppf)Cl$_2$.CH$_2$Cl$_2$ (170 mg, 208 umol) in dioxane (15 mL) and $H_2O$ (3 mL) was degassed and purged with $N_2$ for 3 times, and then the mixture was stirred at 80° C. for 12 hours under $N_2$ atmosphere. The reaction mixture was partitioned between ethyl acetate (100 mL) and water (100 mL). The organic phase was separated, washed with brine (50 mL*2) and dried over $Na_2SO_4$, filtered and concentrated under reduced pressure to give a residue. The residue was purified by column chromatography (SiO$_2$, Petroleum ether/Ethyl acetate=10/1 to 0/1) to give the title compound (900 mg, 67% yield, 90% purity) as a yellow solid. $^1$H NMR (400 MHz, DMSO-$d_6$) δ=12.20 (s, 1H), 8.52 (s, 2H), 8.06 (s, 1H), 7.71 (d, J=7.6 Hz, 1H), 7.44-7.37 (m, 1H), 7.26 (d, J=8.4 Hz, 1H), 7.15 (t, J=7.6 Hz, 1H), 6.08 (s, 1H), 5.94 (q, J=6.4 Hz, 1H), 5.26-5.17 (m, 2H), 5.09 (dd, J=4.8, 13.2 Hz, 1H), 3.97 (s, 2H), 3.52 (t, J=5.2 Hz, 2H), 3.45-3.36 (m, 1H), 3.31 (s, 3H), 3.00-2.86 (m, 2H), 2.42 (s, 2H), 1.49 (d, J=6.4 Hz, 3H), 1.41 (s, 9H). LC/MS (ESI, m/z): [M+1]$^+$=584.5.

Step 4: tert-butyl 4-(2-(3-(2-(methoxymethoxy)phenyl)-5-methyl-7,8-dihydro-5H-pyrido [3',4':4,5]pyrrolo[2,3-c]pyridazin-6(9H)-yl)pyrimidin-5-yl)piperidine-1-carboxylate. To a solution of tert-butyl 4-[2-[12-[2-(methoxymethoxy)phenyl]-3-methyl-4,8,10,11-tetrazatricyclo[7.4.0.02,7]trideca-1(9),2(7),10,12-tetraen-4-yl]pyrimidin-5-yl]-3,6-dihydro-2H-pyridine-1-carboxylate (1 g, 1.71 mmol) in THF (15 mL) was added Pd/C (10%, 2 g), Pd(OH)$_2$/C (20%, 2 g) under $N_2$ atmosphere. The suspension was degassed and purged with $H_2$ for three times. The mixture was stirred under $H_2$ (15 Psi) at 25° C. for 12 hours. The reaction mixture was filtered and concentrated under reduced pressure to give the crude compound (560 mg, crude) as a yellow solid. LC/MS (ESI, m/z): [M+1]$^+$=586.5.

Step 5: (R)-tert-butyl 4-(2-(3-(2-(methoxymethoxy)phenyl)-5-methyl-7,8-dihydro-5H-pyrido[3',4':4,5]pyrrolo[2,3-c]pyridazin-6(9H)-yl)pyrimidin-5-yl)piperidine-1-carboxylate acid and (S)-tert-butyl 4-(2-(3-(2-(methoxymethoxy)phenyl)-5-methyl-7,8-dihydro-5H-pyrido[3',4':4,5]pyrrolo[2,3-c]pyridazin-6(9H)-yl)pyrimidin-5-yl)piperidine-1-carboxylate. Tert-butyl 4-[2-[12-[2-(methoxymethoxy)phenyl]-3-methyl-4,8,10,11-tetrazatricyclo[7.4.0.0$^{2,7}$]trideca-1(9),2(7),10,12-tetraen-4-yl]pyrimidin-5-yl]piperidine-1-carboxylate (560 mg, 956 umol) was separated by SFC (column: DAICEL CHIRALPAK AS (250 mm*30 mm, 10 um); mobile phase: [0.1% NH$_3$.H$_2$O, MeOH]; B %: 60%-60%, 6.5; 80 min) to give 5-P1 (260 mg, 444 umol, 46% yield) as a white solid. LC/MS (ESI, m/z): [M+1]+=586.6; 5-P2 (260 mg, 444 umol, 46% yield) as a white solid. LC/MS (ESI, m/z): [M+1]+=586.6.

Step 6: (R)-2-(5-methyl-6-(5-(piperidin-4-yl)pyrimidin-2-yl)-6,7,8,9-tetrahydro-5H-pyrido[3',4':4,5]pyrrolo[2,3-c]pyridazin-3-yl)phenol. To a solution of tert-butyl 4-[2-[(3R)-12-[2-(methoxymethoxy)phenyl]-3-methyl-4,8,10,11-tetrazatricyclo[7.4.0.0²,⁷]trideca-1(9),2(7),10,12-tetraen-4-yl]pyrimidin-5-yl]piperidine-1-carboxylate (260 mg, 444 umol) in TFA (0.5 mL) and DCM (2.5 mL). The mixture was stirred at 25° C. for 12 hours. The reaction mixture was filtered and concentrated under reduced pressure to give the crude compound (196 mg, crude) as a yellow solid. LC/MS (ESI, m/z): [M+1]$^+$=442.3.

Step 7: (R)-methyl 6-(4-(2-(3-(2-hydroxyphenyl)-5-methyl-7,8-dihydro-5H-pyrido[3',4':4,5]pyrrolo[2,3-c]pyridazin-6(9H)-yl)pyrimidin-5-yl)piperidin-1-yl)spiro[3.3]heptane-2-carboxylate. To a solution of 2-[(3R)-3-methyl-4-[5-(4-piperidyl)pyrimidin-2-yl]-4,8,10,11-tetrazatricyclo[7.4.0.0²,⁷]trideca-1(9),2(7),10,12-tetraen-12-yl]phenol (146 mg, 331 umol) and methyl 2-oxospiro[3.3]heptane-6-carboxylate (66.7 mg, 397 umol) in THF (1 mL) was added KOAc (32.5 mg, 331 umol), AcOH (59.6 mg, 992 umol) and NaBH(OAc)₃ (175 mg, 827 umol). The mixture was stirred at 0-25° C. for 12 hours. The reaction mixture was quenched by addition water (1 mL) and then filtered and concentrated under reduced pressure to give a residue. The crude product was purified by reversed-phase HPLC (0.1% FA condition) to give the title compound (170 mg, 85% yield, 98% purity) as a yellow solid. LC/MS (ESI, m/z): [M+1]$^+$=594.2.

Step 8: (R)-6-(4-(2-(3-(2-hydroxyphenyl)-5-methyl-7,8-dihydro-5H-pyrido[3',4':4,5]pyrrolo[2,3-c]pyridazin-6(9H)-yl)pyrimidin-5-yl)piperidin-1-yl)spiro[3.3]heptane-2-carboxylic acid. To a solution of methyl 2-[4-[2-[(3R)-12-(2-hydroxyphenyl)-3-methyl-4,8,10,11-tetrazatricyclo[7.4.0.0²,⁷]trideca-1(9),2(7),10,12-tetraen-4-yl]pyrimidin-5-yl]-1-piperidyl]spiro[3.3]heptane-6-carboxylate (220 mg, 371 umol) in THF (1 mL) was added LiOH·H₂O (2 M in water, 1 mL). The mixture was stirred at 25° C. for 1 hour. The reaction mixture was filtered and concentrated under reduced pressure to give the crude compound (215 mg, crude) as a yellow oil. LC/MS (ESI, m/z): [M+1]$^+$=580.1.

Step 9: (2S,4R)-4-hydroxy-1-((S)-2-(6-(4-(2-((R)-3-(2-hydroxyphenyl)-5-methyl-7,8-dihydro-5H-pyrido[3',4':4,5]pyrrolo[2,3-c]pyridazin-6(9H)-yl)pyrimidin-5-yl)piperidin-1-yl)spiro[3.3]heptane-2-carboxamido)-3,3-dimethylbutanoyl)-N-(4-(4-methylthiazol-5-yl)benzyl)pyrrolidine-2-carboxamide. To a solution of 2-[4-[2-[(3R)-12-(2-hydroxyphenyl)-3-methyl-4,8,10,11-tetrazatricyclo[7.4.0.0²,⁷]trideca-1(9),2(7),10,12-tetraen-4-yl]pyrimidin-5-yl]-1-piperidyl]spiro[3.3]heptane-6-carboxylic acid (165 mg, 285 umol) and (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide (110 mg, 256 umol) in DMSO (1 mL) was added EDCI (81.9 mg, 427 umol), HOAt (58.1 mg, 427 umol, 59.7 uL) and DIEA (110 mg, 854 umol, 149 uL). The mixture was stirred at 25° C. for 12 hours. The reaction mixture was purified by prep-HPLC (column: Welch Xtimate C18 150*25 mm*5 um; mobile phase: [water (0.05% HCl)-ACN]; B %: 18%-48%, 11 min) to give the title compound (100 mg, 33% yield, 98% purity, HCl salt) as a yellow solid. ¹H NMR (400 MHz, DMSO-d₆) δ=14.09-13.98 (m, 1H), 11.33 (d, J=8.0 Hz, 1H), 9.30 (s, 1H), 8.70 (s, 1H), 8.64 (t, J=6.0 Hz, 1H), 8.38 (s, 2H), 7.72 (dd, J=3.6, 9.2 Hz, 1H), 7.63 (dd, J=1.2, 7.6 Hz, 1H), 7.46-7.39 (m, 5H), 7.25 (d, J=8.0 Hz, 1H), 7.05 (t, J=7.6 Hz, 1H), 6.13 (q, J=6.4 Hz, 1H), 5.07 (d, J=13.2 Hz, 1H), 4.51 (d, J=9.2 Hz, 1H), 4.45-4.38 (m, 2H), 4.34 (s, 1H), 4.22 (dd, J=4.8, 16.0 Hz, 1H), 3.69-3.59 (m, 2H), 3.56-3.43 (m, 2H), 3.39-3.26 (m, 2H), 3.20-3.10 (m, 3H), 2.87-2.72 (m, 3H), 2.48-2.42 (m, 4H), 2.39-2.29 (m, 2H), 2.22-2.01 (m, 8H), 2.00-1.83 (m, 4H), 1.54 (d, J=6.4 Hz, 3H), 0.91 (s, 9H). LC/MS (ESI, m/z): [M+1]$^+$=992.8.

Step 10: (2S,4R)-4-hydroxy-1-((S)-2-(6-(4-(2-((R)-3-(2-hydroxyphenyl)-5-methyl-7,8-dihydro-5H-pyrido[3',4':4,5]pyrrolo[2,3-c]pyridazin-6(9H)-yl)pyrimidin-5-yl)piperidin-1-yl) spiro[3.3]heptane-2-carboxamido)-3,3-dimethylbutanoyl)-N-(4-(4-methylthiazol-5-yl)benzyl)pyrrolidine-2-carboxamide and (2S,4R)-4-hydroxy-1-((S)-2-(6-(4-(2-((R)-3-(2-hydroxyphenyl)-5-methyl-7,8-dihydro-5H-pyrido[3',4':4,5]pyrrolo[2,3-c]pyridazin-6(9H)-yl)pyrimidin-5-yl) piperidin-1-yl)spiro[3.3]heptane-2-carboxamido)-3,3-dimethylbutanoyl)-N-(4-(4-methylthiazol-5-yl)benzyl)pyrrolidine-2-carboxamide. (2S,4R)-4-hydroxy-1-[(2S)-2-[[2-[4-[2-[(3R)-12-(2-hydroxyphenyl)-3-methyl-4,8,10,11-tetrazatricyclo[7.4.0.0²,⁷]trideca-1(9),2(7),10,12-tetraen-4-yl]pyrimidin-5-yl]-1-piperidyl]spiro[3.3]heptane-6-carbonyl]amino]-3,3-dimethyl-butanoyl]-N-[[4-(4-methylthiazol-5-yl)phenyl]methyl]pyrrolidine-2-carboxamide (116 mg, 117 umol) was separated by SFC (column: DAICEL CHIRALPAKAD (250 mm*30 mm, 10 um); mobile phase: [0.1% NH₃H₂O, MeOH]; B %: 65%-%, 10; 200 min) to afford two compounds (I-40 and I-41). Peak 1 was purified by prep-HPLC (column: Welch Xtimate C18 150*25 mm*5 um; mobile phase: [water (0.05% HCl)-ACN]; B %: 13%-43%, 10 min) to give the title compound (28.8 mg, 23% yield, 98% purity, HCl salt) as a yellow solid. ¹H NMR (400 MHz, DMSO-d₆) δ=13.92 (s, 1H), 11.23 (d, J=7.2 Hz, 1H), 9.15 (s, 1H), 8.72 (s, 1H), 8.61 (t, J=6.0 Hz, 1H), 8.36 (s, 2H), 7.72 (d, J=9.2 Hz, 1H), 7.63 (dd, J=1.6, 7.6 Hz, 1H), 7.50-7.36 (m, 5H), 7.23 (d, J=8.4 Hz, 1H), 7.06 (t, J=7.6 Hz, 1H), 6.13 (q, J=6.4 Hz, 1H), 5.08 (d, J=13.2 Hz, 1H), 4.52 (s, 1H), 4.50 (s, 1H), 4.45-4.39 (m, 4H), 4.35 (s, 1H), 4.22 (dd, J=5.2, 16.0 Hz, 1H), 3.71-3.59 (m, 2H), 3.53-3.42 (m, 2H), 3.42-3.27 (m, 2H), 3.23-3.08 (m, 3H), 2.82-2.73 (m, 2H), 2.45 (s, 3H), 2.34 (t, J=10.0 Hz, 2H), 2.26-2.17 (m, 2H), 2.14-2.01 (m, 6H), 1.99-1.85 (m, 3H), 1.54 (d, J=6.4 Hz, 3H), 0.95-0.88 (m, 9H). LC/MS (ESI, m/z): [M+1]$^+$=992.8. Peak 2 was purified by prep-HPLC (column: Welch Xtimate C18 150*25 mm*5 um; mobile phase: [water (0.05% HCl)-ACN]; B %: 14%-44%, 10 min) to give the title compound (28.0 mg, 23% yield, 99% purity, HCl salt) as a white solid. ¹H NMR (400 MHz, DMSO-d₆) δ=13.79 (s, 1H), 11.04 (d, J=7.2 Hz, 1H), 9.04 (s, 1H), 8.76-8.70 (m, 1H), 8.59 (t, J=6.0 Hz, 1H), 8.36 (s, 2H), 7.75 (d, J=9.2 Hz, 1H), 7.66 (dd, J=1.6, 7.6 Hz, 1H), 7.50-7.36 (m, 5H), 7.19 (d, J=8.0 Hz, 1H), 7.11-7.04 (m, 1H), 6.13 (q, J=6.8 Hz, 1H), 5.15-5.05 (m, 1H), 4.53 (d, J=9.2 Hz, 1H), 4.47-4.39 (m, 2H), 4.36 (s, 1H), 4.22 (dd, J=5.2, 16.0 Hz, 1H), 3.71-3.61 (m, 3H), 3.52-3.42 (m, 2H), 3.36 (t, J=13.2 Hz, 2H), 3.22-3.10 (m, 3H), 2.81-2.71 (m, 2H), 2.45 (s, 3H), 2.43-2.31 (m, 3H), 2.25-1.85 (m, 12H), 1.55 (d, J=6.4 Hz, 3H), 0.96-0.90 (m, 9H). LC/MS (ESI, m/z): [M+1]$^+$=992.8.

Example 4. (2S,4R)-4-hydroxy-1-((S)-2-(6-(4-(2-((S)-3-(2-hydroxyphenyl)-5-methyl-7,8-dihydro-5H-pyrido[3',4':4,5]pyrrolo[2,3-c]pyridazin-6(9H)-yl)pyrimidin-5-yl)piperidin-1-yl)spiro[3.3]heptane-2-carboxamido)-3,3-dimethylbutanoyl)-N-(4-(4-methylthiazol-5-yl)benzyl)pyrrolidine-2-carboxamide (I-37)
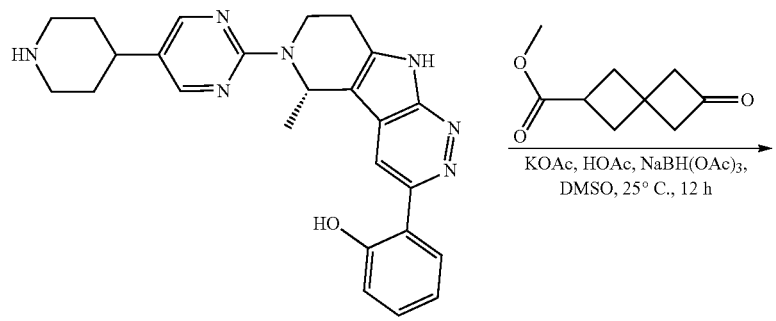
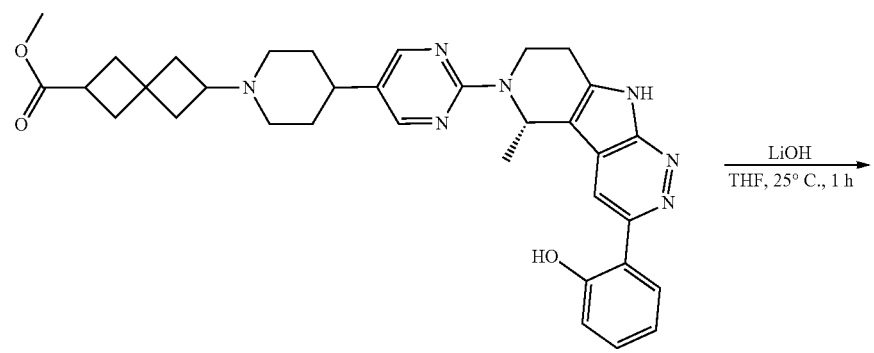
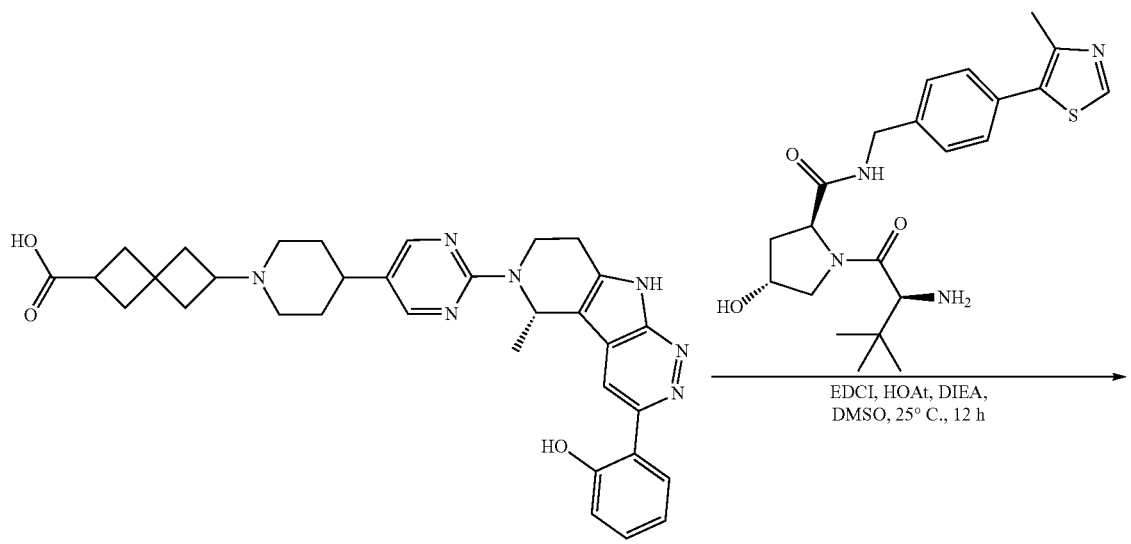

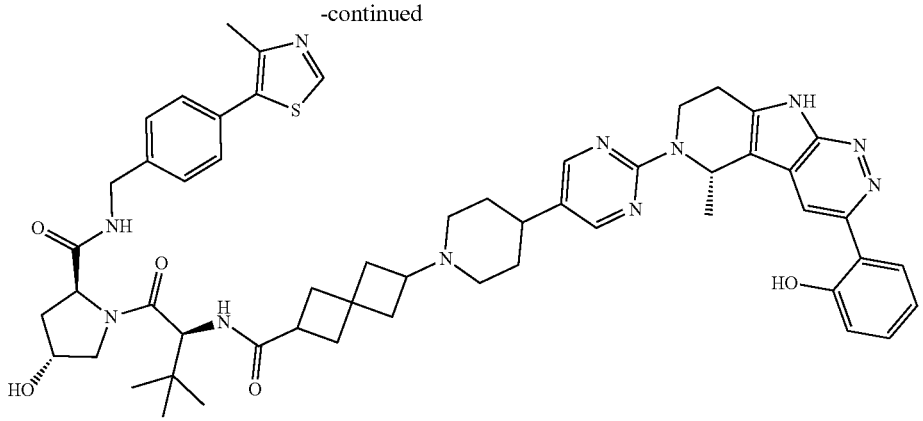

I-37

Step 1: (S)-methyl 6-(4-(2-(3-(2-hydroxyphenyl)-5-methyl-7,8-dihydro-5H-pyrido[3',4':4,5]pyrrolo[2,3-c]pyridazin-6(9H)-yl)pyrimidin-5-yl)piperidin-1-yl)spiro[3.3]heptane-2-carboxylate. To a solution of 2-[(3S)-3-methyl-4-[5-(4-piperidyl)pyrimidin-2-yl]-4,8,10,11-tetrazatricyclo [7.4.0.0$^{2,7}$]trideca-1(9),2(7),10,12-tetraen-12-yl]phenol (0.2 g, 453 umol) and methyl 2-oxospiro[3.3]heptane-6-carboxylate (91.4 mg, 544 umol) in DMSO (5 mL) was added KOAc (111 mg, 1.13 mmol), HOAc (68 mg, 1.13 mmol), NaBH(OAc)$_3$ (288 mg, 1.36 mmol) and 4A MS (0.3 g, 453 umol). The mixture was stirred at 25° C. for 12 hours. The reaction mixture was concentrated under reduced to give a crude product. The crude product was purified by prep-TLC (SiO$_2$, DCM:MeOH=10:1) to give the title compound (220 mg, 81.8% yield, 97% purity) as a white solid. LC/MS (ESI, m/z): [M+1]$^+$=594.5.

Step 2: (S)-6-(4-(2-(3-(2-hydroxyphenyl)-5-methyl-7,8-dihydro-5H-pyrido[3',4':4,5]pyrrolo[2,3-c]pyridazin-6(9H)-yl)pyrimidin-5-yl)piperidin-1-yl)spiro[3.3]heptane-2-carboxylic acid. To a solution of methyl 2-[4-[2-[(3S)-12-(2-hydroxyphenyl)-3-methyl-4,8,10,11-tetrazatricyclo [7.4.0.0$^{2,7}$]trideca-1(9),2(7),10,12-tetraen-4-yl]pyrimidin-5-yl]-1-piperidyl]spiro[3.3]heptane-6-carboxylate (0.22 g, 371 umol) in THF (3 mL) was added LiOH·H$_2$O (2 M, 1.10 mL). The mixture was stirred at 25° C. for 1 hour. The reaction mixture was concentrated under reduced pressure to give a crude product. The crude product was purified by reversed-phase Flash (0.1% FA condition) to give title compound (0.048 g, 68.4% yield, 98% purity) as a white solid. LC/MS (ESI, m/z): [M+1]$^+$=580.2.

Step 3: (2S,4R)-4-hydroxy-1-((S)-2-(6-(4-(2-((S)-3-(2-hydroxyphenyl)-5-methyl-7,8-dihydro-5H-pyrido[3',4':4,5]pyrrolo[2,3-c]pyridazin-6(9H)-yl)pyrimidin-5-yl)piperidin-1-yl)spiro[3.3]heptane-2-carboxamido)-3,3-dimethylbutanoyl)-N-(4-(4-methylthiazol-5-yl)benzyl) pyrrolidine-2-carboxamide. To a solution of 2-[4-[2-[(3S)-12-(2-hydroxyphenyl)-3-methyl-4,8,10,11-tetrazatricyclo [7.4.0.0$^{2,7}$]trideca-1(9),2(7),10,12-tetraen-4-yl]pyrimidin-5-yl]-1-piperidyl]spiro[3.3]heptane-6-carboxylic acid (150.00 mg, 258.76 umol, 1 eq) and (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide (111 mg, 259 umol) in DMSO (3 mL) was added EDCI (59.5 mg, 311 umol), HOAt (42.3 mg, 311 umol) and DIEA (167 mg, 1.29 mmol). The mixture was stirred at 25° C. for 12 hours. The mixture was filtered to give a crude product. The crude product was purified by prep-HPLC(column: Welch Xtimate C18 150*25 mm*5 um; mobile phase: [water (0.05% HCl)-ACN]; B %: 11%-41%, 11 min) to give title compound (18.7 mg, 6.91% yield, 95% purity) as a white solid. $^1$H NMR (400 MHz, DMSO-d6) δ ppm: 8.99 (s, 1H), 8.73 (s, 1H), 8.56 (t, J=5.6 Hz, 1H), 8.35 (s, 2H), 7.78-7.70 (m, 2H), 7.40 (d, J=6.4 Hz, 5H), 7.14-7.04 (m, 2H), 6.11 (d, J=6.0 Hz, 1H), 5.09 (dd, J=3.2 Hz, J=10.4 Hz, 1H), 4.53 (d, J=9.6 Hz, 1H), 4.46-4.39 (m, 2H), 4.37-4.33 (m, 1H), 4.25-4.18 (m, 1H), 3.20-3.04 (m, 4H), 2.85-2.63 (m, 4H), 2.46-2.44 (m, 4H), 2.33 (d, J=1.6 Hz, 4H), 2.30-1.84 (m, 15H), 1.54 (d, J=6.4 Hz, 3H), 1.26-1.13 (m, 1H), 0.94-0.89 (m, 9H); LC/MS (ESI, m/z): [M+1]$^+$=992.3.

Example 5. MSD SMARCA2 Degradation in NCI-H1299 Cell Line

| Cell Line | Vendor | Medium |
|---|---|---|
| NCI-H1299 | ATCC | RPMI MEDIUM 1640 + 10% FBS + 1xPS |

| Regents | Vendor | Cat# |
|---|---|---|
| RPMI MEDIUM 1640 | Invitrogen | A10491-01 |
| Fetal bovine serum (FBS) | Hyclone | SH30406.05 |
| Penicillin-Streptomycin (100x) | SolarBio | P1400 |
| Phosphate Buffered Saline (PBS) | Solarbio | P1020-500 |
| RIPA Buffer with EDTA cOmplete ULTRA Tablets, Mini, EDTA-free, EASYpack | BBP Roche Applied Science | 115D 05892791001 |
| MSD Standard Plate | Meso Scale Discovery | L15XA-3 |
| Anti-SMARCA2/BRM antibody | Abcam | ab223735 |
| SULFO-TAG anti-rabbit antibody | Meso Scale Discovery | R32AB-5 |
| MSD Blocker A | Meso Scale Discovery | R93BA-4 |
| MSD Read Buffer T (4x) | Meso Scale Discovery | R92TC-1 |
| Tris Buffered Saline with Tween® 20 (TBST-10X) | CST | 9997S |

| Instrument | Vendor | Cat# |
|---|---|---|
| Cell counter | Invitrogen | Countess |
| Centrifuge | Eppendorf | 5810R |
| CO$_2$ Incubator | Thermo | Model: 371 |
| Vortex | IKA | MS3 digital |

-continued

| Instrument | Vendor | Cat# |
| --- | --- | --- |
| Echo Liquid Handler | Labcyte | 550 |
| TECAN | TECAN | Freedom EVO200 |
| PERSONAL PIPETTOR | Apricot Designs | PP5+1 |
| MSD reader | Meso Scale Discovery | MSD SECTOR 6000 |
| 96 well plate | Corning | 3599 |
| 225 cm² Cell Culture Flask | Corning | 431081 |
| 50 mL centrifuge tube | BD-Falcon | 352098 |
| 15 mL centrifuge tube | BD-Falcon | 352097 |

Cell Culture: Cells are Cultured in Exponential Growth Phase.

Compound Preparation and Treatment: NCI-H1299 cells are seeded into the 96-well plate at $4.0*10^4$ cells per 100 ul per well. Incubate the plate in the incubator overnight. The next day, compounds are diluted to designed stock concentration by TECAN, then perform a 3 fold, 9-point dilution via transferring 15 μL compound into 30 μL DMSO using Apricot. 200 nL diluted compound from compound source plate are transferred into the 96-intermediate plate as designated by using Echo550, followed with 100 μl culture medium to make the 2× compound solution. Cell plate are changed with 80 μl of fresh culture medium and 80 μl of 2× compound solution is added into the well to achieve the final designed concentration. Cell plate is then shaken at 720 rpm for 5 min and incubated for 24 hours in the incubator.

Sample Preparation: Media was aspirated from the cultures and the plate is washed with PBS twice. 60 μL of pre-chilled PIPA lysis buffer (Boston BioProducts BP-115D) with protease inhibitor are directly added into the well to lyze the cells for 20 minutes at 4° C. Cell lysates were collected.

MSD Procedure: The MSD plate is coated with 40 μl cell lysate and incubated at 4° C. overnight. The next day, the MSD coated bare plate is washed 3 times with 150 μl 1×TBST per well, blocked with 150 μl of blocking buffer per well, and shaken for 1 hour at RT, 600 rpm. Blocking buffer is 3% Blocker A in TBST. MSD plate is then washed 3 times with 150 μl 1×TBST per well and Primary Detection antibody (Rabbit anti-SMARCA2/BRM antibody, 100 μg/ml, ab223735) is added to a final [conc.]: 0.3 μg/ml, 25 ul/well and shaken for 1 hour at RT, 600 rpm. Antibody is prepared in Antibody Detection buffer (1% Blocker A in 1×TBST). The MSD plate is then washed 3 times with 150 μl 1×TBST per well. Secondary Detection antibody (SULFO-TAG anti-species antibody) is then added to a final [conc.]: 1 μg/ml, 25 μl/well, and shaken for 1 hour at RT, 600 rpm. Antibodies are prepared in Antibody Detection buffer (1% Blocker A in 1×TBST). MSD plate is washed 3 times with 150 μl 1×TBST per well and 2×MSD reading buffer is added, 150 μl per well, and diluted from 4× with water. MSD instrument is then read.

Data Analysis: The percentage of relative level of SMARCA2 level is calculated following equation below.

$$\% \text{ Relative Level} = 100\% \times \frac{MSD\ Signal_{Sample} - MSD\ Signal_{LC}}{MSD\ Signal_{HC} - MSD\ Signal_{LC}}$$

LC: A2780, SMARCA2 negative cells. HC: NCI-H1299 cells treated with DMSO.

SMARCA2 protein degradation in H1299 cells for compounds of the invention are presented in Table 3. The letter codes for SMARCA2 degradation potency ($DC_{50}$) include: A (<100 nM), B (100-500 nM), C (501-1000 nM), and D (>1000 nM). The letter codes for the percentage of SMARCA2 degradation after 24 hours (Dmax %) include: A (>90% degradation), B (>70-90% degradation), C (50-70% degradation), and D (<50% degradation).

TABLE 3

SMARCA2 MSD H1299 Degradation Results.

| I-# | SMARCA2 MSD H1299 degradation 24 h: Average external-Abs IC50 (nM) | SMARCA2 MSD H1299 degradation 24 h: Average Dmax % |
| --- | --- | --- |
| | | |

Example 6. MSD SMARCA2 Degradation in A549 Cell Line

Cells were seeded into 96-well plates (A549 cells: 2×10⁴ cells/well/100 ul media) and incubated overnight. The next day, 200 nL compound were added into the intermediate plate with Echo (Labcyte 550) from source plate containing a 3-fold serial dilution from top concentration of 1 mM. The culture medium was changed with 80 ul of fresh medium and 80 uL of 2× compound solution was added into the well to make a final concentration of 1000 nM, 333.3 nM, 111.1 nM, 37.04 nM, 12.35 nM, 4.115 nM, 1.372 nM, 0.457 nM, 0.152 nM and 0 nM (DMSO). The wells were mixed and then incubated for 24 hours. The media was aspirated from the cultures and 60 ul pre-chilled PIPA lysis buffer (Boston BioProducts BP-115D) with protease/phosphatase inhibitor (Roche 05892791001/Roche 04906837001) was added into the well to lyze the cells for 20 minutes at 4° C. The MSD plate (L15XA) was coated with 40 uL cell lysate and incubated at 4° C. overnight. The next day, the plate was washed three times with TBST (CST #9997S), 150 ul/well. The MSD plates was blocked with 150 ul blocking buffer per well and shaken for 1 hr at RT, 600 rpm. The blocking buffer was 3% Blocker A (MSD, R93BA-4) in TBST. The MSD plate was washed three times with 150 uL/well of TBST and 25 ul/well of detection antibody (Rabbit anti-SMARCA2/BRM antibody, 100 μg/mL, ab223735) was added at final concentration of 1 ug/mL diluted in 1% Blocking buffer and shaken for 1 hour at RT, 600 rpm. The MSD plate was washed three times with 150 ul/well of TBST and 25 ul/well of SULFO-TAG anti-rabbit antibody (MSD, R32AB-1) was added at final concentration of 1 ug/ml diluted in 1% Blocking buffer and shaken for 1 hour at RT, 600 rpm. The MSD plate was washed three times with 150 uL/well of TBST and 150 ul/well of 2×MSD reading buffer diluted from 4× (MSD, R92TC-2) with water was added. Lastly, the MSD instrument was read.

SMARCA2 protein degradation in A549 cells for compounds of the invention are presented in Table 4. The letter codes for SMARCA2 degradation potency ($DC_{50}$) include: A (<100 nM), B (100-500 nM), C (501-1000 nM), and D (>1000 nM). The letter codes for the percentage of SMARCA degradation after 24 hours (Dmax %) include: A (>90% degradation), B (>70-90% degradation), C (50-70% degradation), and D (<50% degradation).

TABLE 4

| I-# | SMARCA2 MSD A549 degradation 24 h: Average external-Abs DC$_{50}$ (nM) | SMARCA2 MSD A549 degradation 24 h: Average Dmax % |
|---|---|---|
| I-13 | D | D |
| I-14 | B | B |
| I-37 | B | B |
| I-38 | A | A |
| I-40 | B | B |
| I-41 | B | B |

TABLE 5

SMARCA2 MSD A549 Degradation and SMARCA2/4 MV4-11 Selectivity Results.

| I-# | SMARCA2 MSD MV411 degradation 24 h: Mean external-Abs DC50 (nM) | SMARCA2 MSD MV411 degradation 24 h: average Dmax % | SMARCA4 MSD MV411 degradation 24 h: Mean external-Abs DC50 (nM) | SMARCA4 MSD MV411 degradation 24 h: average Dmax % |
|---|---|---|---|---|
| I-13 | C | C | D | C |
| I-14 | A | B | D | C |
| I-37 | B | C | — | — |
| I-38 | A | B | D | D |
| I-40 | A | B | D | D |
| I-41 | A | B | D | D |

Example 7. SMARCA2 and SMARCA4 Western Blot MV4-11 Degradation

Cells were seeded into 6-well plates (MV4-11: 4×106 cells/well/1 ml) and 1 ml of 2× compound solution was added into the well to make the final concentration and the plates were mixed well and incubated for 24 hours (No cytotoxicity was observed). The cell were collected with media and spun at 3000 rpm for 5 minutes. The supernatant was aspirated and the well and the cells were washed with cold PBS once and combined for centrifugation again; the supernatant aspirated again. 200 uL pre-chilled RIPA lysis buffer (Boston BioProducts BP-115D) with protease/phosphatase inhibitor (Roche 05892791001/Roche 04906837001) was directly added into the tube to lyze the cells for 20 minutes on ice. The cell lysate were collected into EP tubes and spun at 13000 rpm for 20 minutes and 72 uL supernatant was transferred to a fresh EP tube containing 18 uL of 5× loading buffer (Beyotime Bio P0015) to make the loading samples. The samples were heated to 100° C. for 10 minutes and cooled to RT and microcentrifuged. 20 uL of samples were loaded onto SDS-PAGE gel (Novex, WG1402BOX) and the gel was run at 80 V for 20 minutes and 120 V for 1.5 hours. The samples were electrotransfer to a NC membrane using wet-transfer method with 250 mA for 2.5 hours. The membrane was blocked with LICOR blocking buffer (LICOR, 927-50000) for 1 hour. The membrane was washed three times with TBST(CST #9997S), 5 minutes each. Incubation was performed with primary antibody prepared in blocking buffer with 0.1% Tween-20 (Solarbio, P8220) at 4° C. overnight (Anti-SMARCA2/BRM antibody (ab15597) 1:500; Anti-BRG1 antibody [EPR3912] (ab108318) 1:1000; Rabbit anti-Baf180 antibody [EPR15860] (Abeam,ab 196022) 1:1000; mouse anti-beta-Actin (8H10D10) (CST #3700) 1:10000). The membrane was washed three times with TBST, 5 minutes each. Incubation with secondary antibody was performed for 1 hour at RT (anti-rabbit IgG (Licor, 926-32211) 1:5000; anti-mouse IgG (LI-COR, 926-68070) 1:5000). The membrane was washed three times with 5 minutes each and lastly the LiCOR was read.

SMARCA2/SMARCA4 protein degradation selectivity in MV4-11 cells for compounds of the invention are presented in Table 5. The letter codes for SMARCA2/4 degradation potency (DC$_{50}$) include: A (<100 nM), B (100-500 nM), C (501-1000 nM), and D (>1000 nM). The letter codes for the percentage of SMARCA degradation after 24 hours (Dmax %) include: A (>90% degradation), B (>70-90% degradation), C (50-70% degradation), and D (<50% degradation).

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:

1. A compound of formula I:

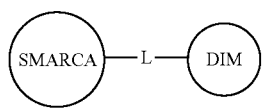

I or a pharmaceutically acceptable salt thereof, wherein:
SMARCA is a protein binding moiety capable of binding to one or more of SMARCA2, SMARCA4, and PB1, wherein said compound of formula I is a compound of formula I-a-3:

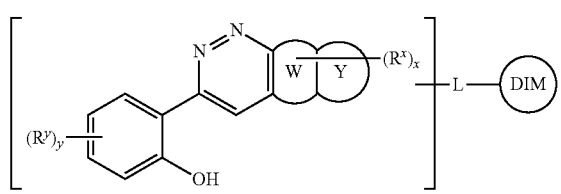

I-a-3 or a pharmaceutically acceptable salt thereof, wherein:

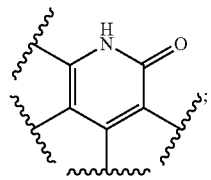 [SMILES: *c1[nH]c(=O)c(*)c(*)c1*]

Ring W is
Ring Y is a fused, ring selected from 6-membered aryl, 5 to 6-membered heteroaryl containing 1-4 heteroatoms independently selected from nitrogen, oxygen, and sulfur, and a 4 to 9-membered saturated or partially unsaturated monocyclic, bicyclic, or bridged bicyclic carbocyclyl or heterocyclyl with 1-4 heteroatoms independently selected from boron, nitrogen, oxygen, silicon, and sulfur;

each of $R^x$ and $R^y$ is independently hydrogen, $R^z$, halogen, —CN, —NO$_2$, —OR, —SR, —NR$_2$, —SiR$_3$, —S(O)$_2$R, —S(O)$_2$NR$_2$, —S(O)R, —CFR$_2$, —CF$_2$R, —CF$_3$, —C(O)R, —C(O)OR, —C(O)NR$_2$, —C(O)N(R)OR, —C(R)$_2$N(R)C(O)R, —C(R)$_2$N(R)C(O)N(R)$_2$, —OC(O)R, —OC(O)N(R)$_2$, —OP(O)R$_2$, —OP(O)(OR)$_2$, —OP(O)(OR)NR$_2$, —OP(O)(NR$_2$)$_2$—, —N(R)C(O)OR, —N(R)C(O)R, —N(R)C(O)NR$_2$, —N(R)S(O)$_2$R, —NP(O)R$_2$, —N(R)P(O)(OR)$_2$, —N(R)P(O)(OR)NR$_2$, —N(R)P(O)(NR$_2$)2, or —N(R)S(O)$_2$R; or two R groups or two $R^y$ groups are optionally taken together to form an optionally substituted 5-7 membered partially unsaturated or aryl fused ring having 0-2 heteroatoms independently selected from nitrogen, oxygen, or sulfur;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same atom are taken together with their intervening atoms to form a 4-7 membered saturated, partially unsaturated, or heteroaryl ring having 0-3 heteroatoms, in addition to the atom to which they are attached, independently selected from nitrogen, oxygen, and sulfur;

each $R^z$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

x is 0, 1, 2, 3, 4, 5, 6, 7, 8, 9, 10, 11, 12, 13, 14, 15, or 16;

y is 0, 1, 2, 4, or 5;

L is a covalent bond or a bivalent, saturated or unsaturated, straight or branched $C_{1-50}$ hydrocarbon chain, wherein 0-6 methylene units of L are independently replaced by —Cy—, —O—, —N(R)—, —Si(R)$_2$—, —Si(OH)(R)—, —Si(OH)$_2$—, —P(O)(OR)—, —P(O)(R)—, —P(O)(NR$_2$)—, —S—, —OC(O)—, —C(O)O—, —C(O)—, —S(O)—, —S(O)$_2$—, —N(R)S(O)$_2$—, —S(O)$_2$N(R)—, —N(R)C(O)—, —C(O)N(R)—, —OC(O)N(R)—, —N(R)C(O)O—,

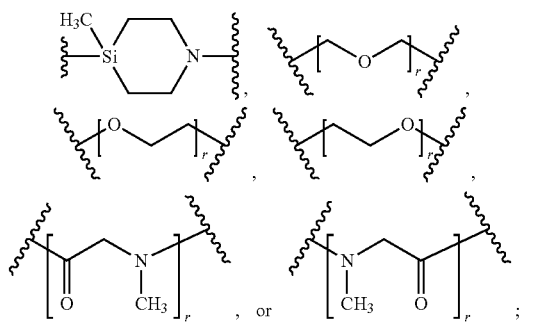

each -Cy- is independently an optionally substituted bivalent ring selected from phenylenyl, an 8-10 membered bicyclic arylenyl, a 4-7 membered saturated or partially unsaturated carbocyclylenyl, a 5-11 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 5-11 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, and an 8-10 membered bicyclic heteroarylenyl having 1-5 heteroatoms independently selected from nitrogen, oxygen, and sulfur;

r is 0, 1, 2, 3, 4, 5, 6, 7, 8, 9, or 10; and

DIM is a degradation inducing moiety selected from a ligase binding moiety (LBM), wherein the LBM is a cereblon E3 ligase binding moiety of formula I-aa:

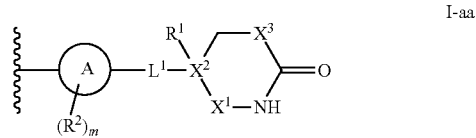

or a pharmaceutically acceptable salt thereof, wherein:

$X^1$ is a bivalent moiety selected from a covalent bond, —CH$_2$—, —CHCF$_3$—, —SO$_2$—, —S(O)—, —P(O)R—, —P(O)OR—, —P(O)NR$_2$—, —C(O)—, —C(S)—, and

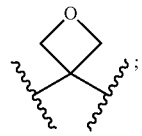 [SMILES: *C1(*)COC1]

$X^2$ is a carbon atom or silicon atom;

$X^3$ is a bivalent moiety selected from —CR$_2$—, —NR—, —O—, —S—, and —Si(R$_2$)—:

$R^1$ is hydrogen, halogen, —CN, —OR, —SR, —S(O)R, —S(O)$_2$R, —N(R)$_2$, —P(O)(OR)$_2$, —P(O)(NR$_2$)OR, —P(O)(NR$_2$)$_2$, —Si(OH)$_2$R, —Si(OH)(R)$_2$, —Si(R)$_3$, or an optionally substituted $C_{1-4}$ aliphatic;

each $R^2$ is independently hydrogen, $R^6$, halogen, —CN, —NO$_2$, —OR, —SR, —N(R)$_2$, —Si(R)$_3$, —S(O)$_2$R, —S(O)$_2$N(R)$_2$, —S(O)R, —C(O)R, —C(O)OR, —C(O)N(R)$_2$, —C(O)N(R)OR, —C(R)$_2$N(R)C(O)R, —C(R)$_2$N(R)C(O)N(R)$_2$, —OC(O)R, —OC(O)N(R)$_2$, —OP(O)R$_2$, —OP(O)(OR)$_2$, —OP(O)(OR)(NR$_2$), —OP(O)(NR$_2$)$_2$—, —N(R)C(O)OR, —N(R)C(O)R, —N(R)C(O)N(R)$_2$, —N(R)S(O)$_2$R, —NP(O)R$_2$, —N(R)P(O)(OR)$_2$, —N(R)P(O)(OR)(NR$_2$), —N(R)P(O)(NR$_2$)$_2$, or —N(R)S(O)$_2$R;

Ring A is a bicyclic or tricyclic ring selected from
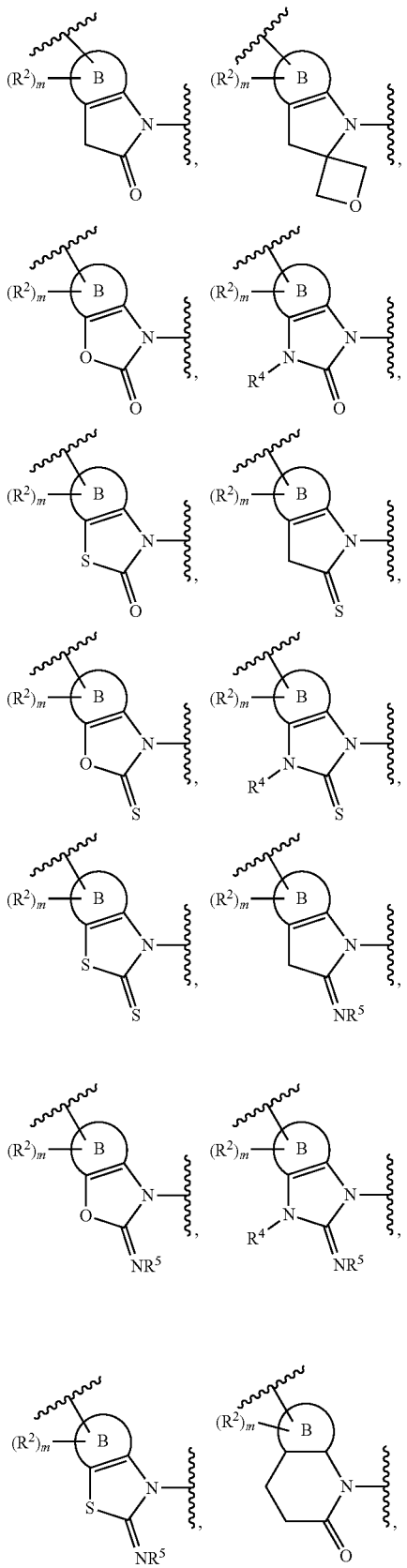
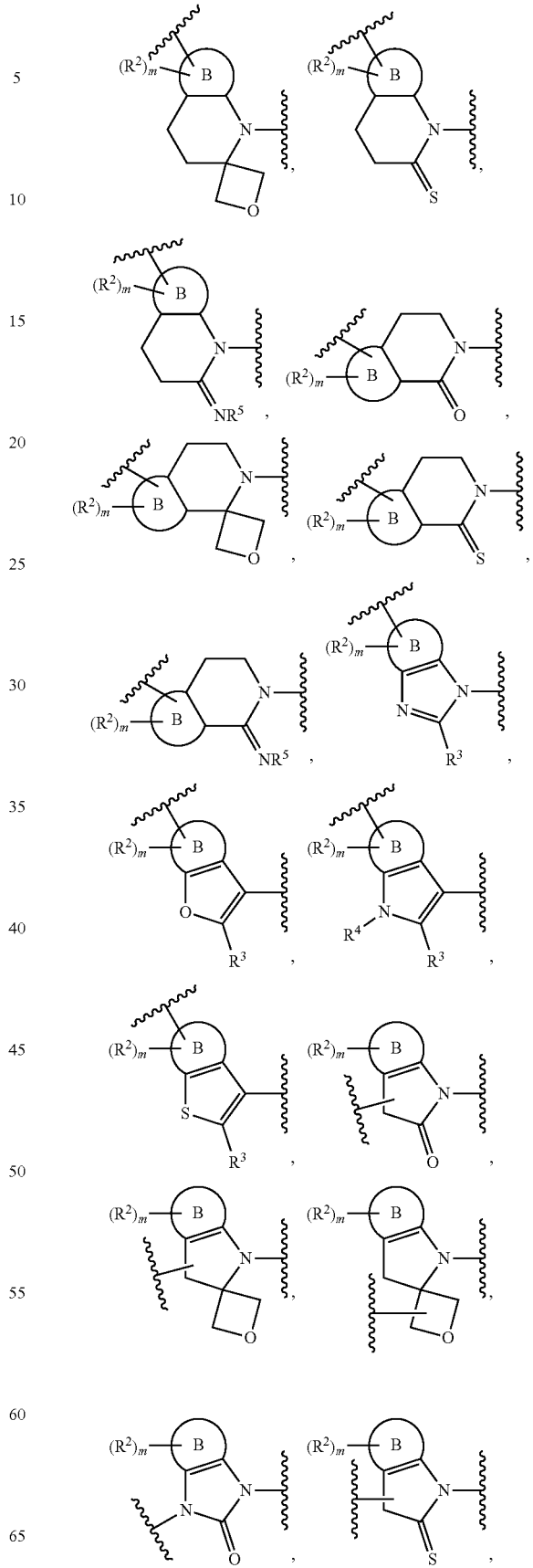

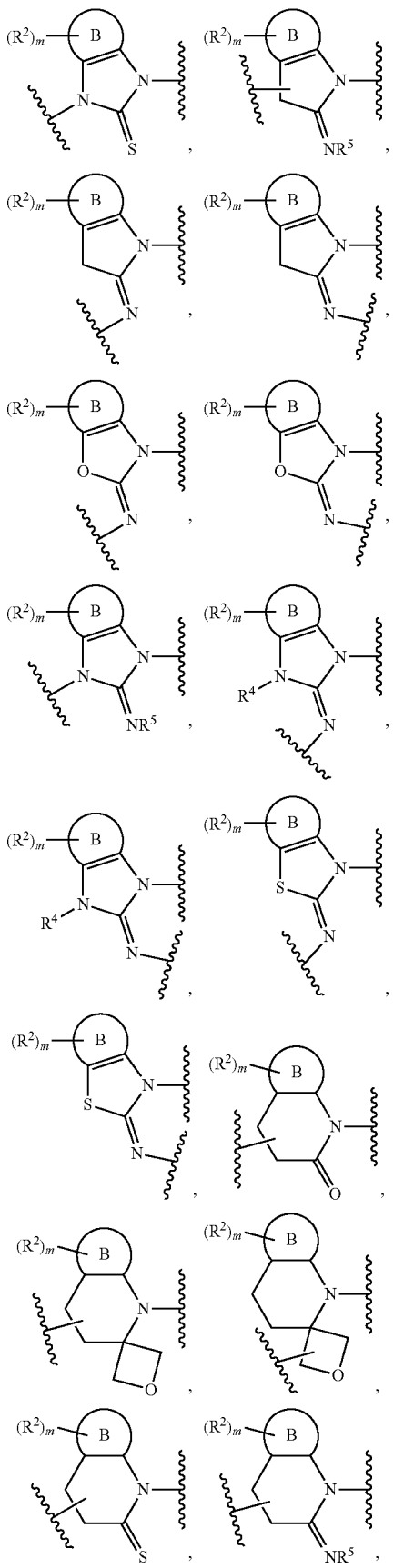
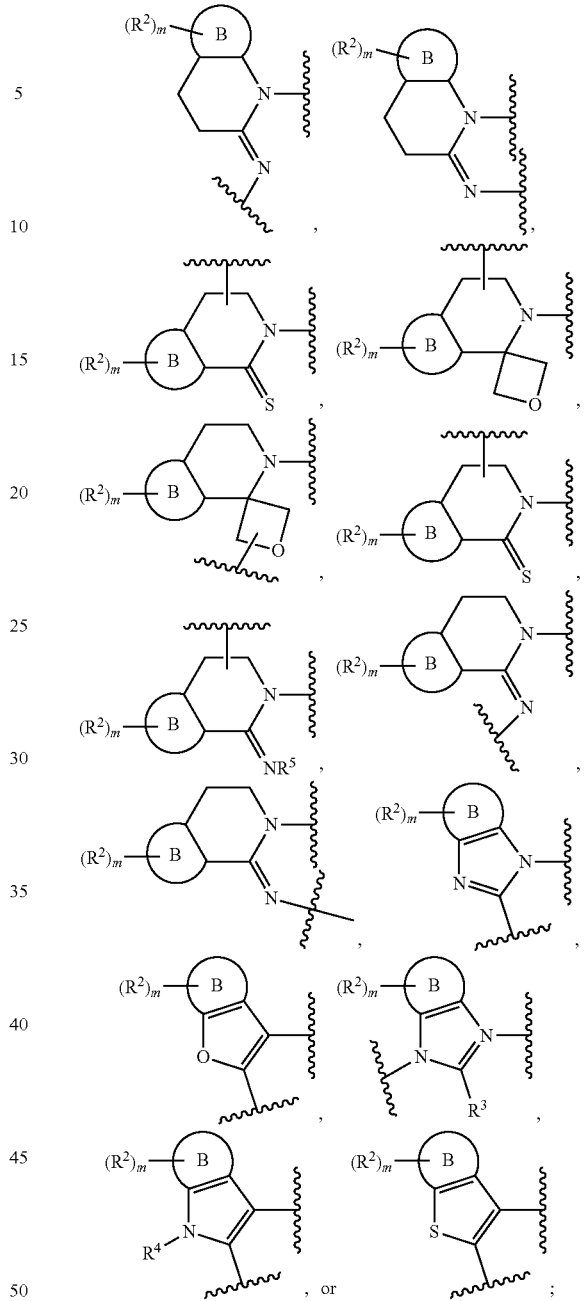

Ring B is a fused ring selected from 6-membered aryl, 6-membered heteroaryl containing 1-4 heteroatoms independently selected from nitrogen, oxygen, and sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, and sulfur, and a 5-membered heteroaryl with 1-4 heteroatoms independently selected from nitrogen, oxygen and sulfur;

$R^3$ is selected from hydrogen, halogen, —OR, —N(R)$_2$, and —SR;

each $R^4$ is independently hydrogen, $R^6$, halogen, —CN, —NO$_2$, —OR, —SR, —NR$_2$, —S(O)$_2$R—S(O)$_2$NR$_2$, —S(O)R, —C(O)R, —C(O)OR, —C(O)NR$_2$, —C(O)

N(R)OR, —OC(O)R, —OC(O)NR$_2$, —N(R)C(O)OR, —N(R)C(O)R, —N(R)C(O)NR$_2$, or —N(R)S(O)$_2$R;

R$^5$ is hydrogen, C$_{1-4}$ aliphatic, or —CN;

each R$^6$ is independently an optionally substituted group selected from C$_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

L$^1$ is a covalent bond or a C$_{1-3}$ bivalent straight or branched saturated or unsaturated hydrocarbon chain wherein 1-2 methylene units of the chain are independently and optionally replaced with —O—, —C(O)—, —C(S)—, —C(R)$_2$—, —CF(R)—, —C(F)$_2$—, —N(R)—, —S—, —S(O)$_2$— or —(C)=CH—; and m is 0, 1, 2, 3 or 4.

2. The compound of claim 1, wherein the LBM is a cereblon E3 ligase binding moiety selected from:

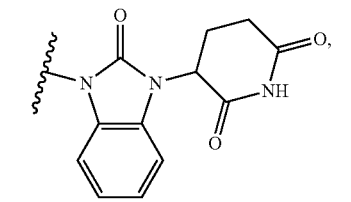

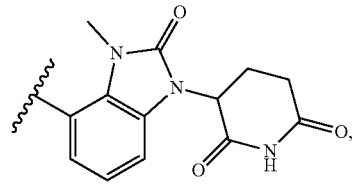

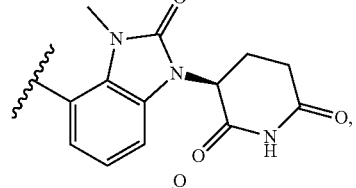

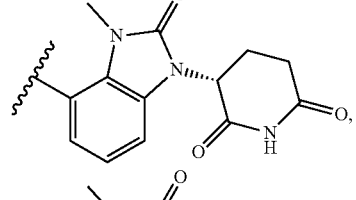

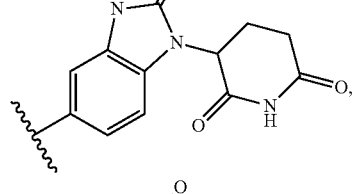

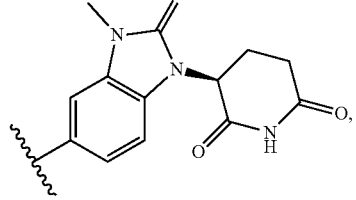

-continued

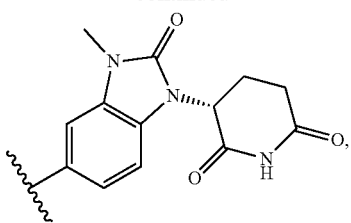

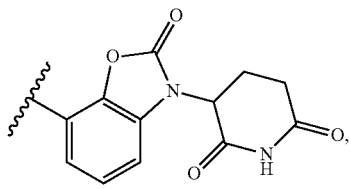

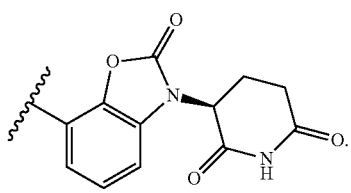 [SMILES: *c1cccc2c1oc(=O)n2[C@H]1CCC(=O)NC1=O]

3. The compound of claim 1, wherein L is selected from:

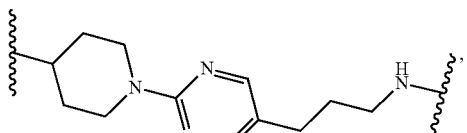

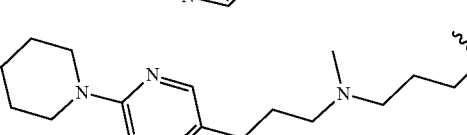

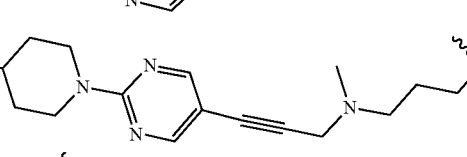

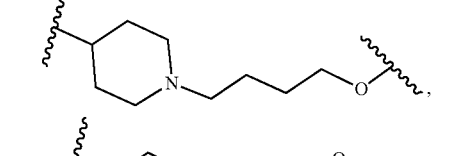

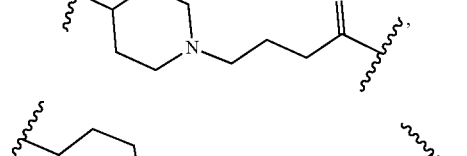

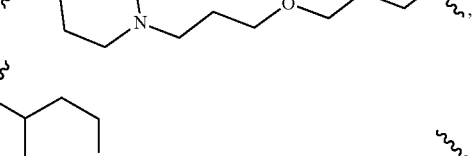

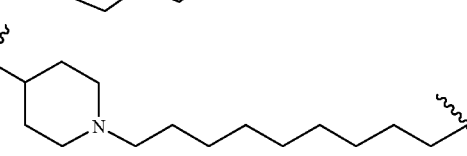

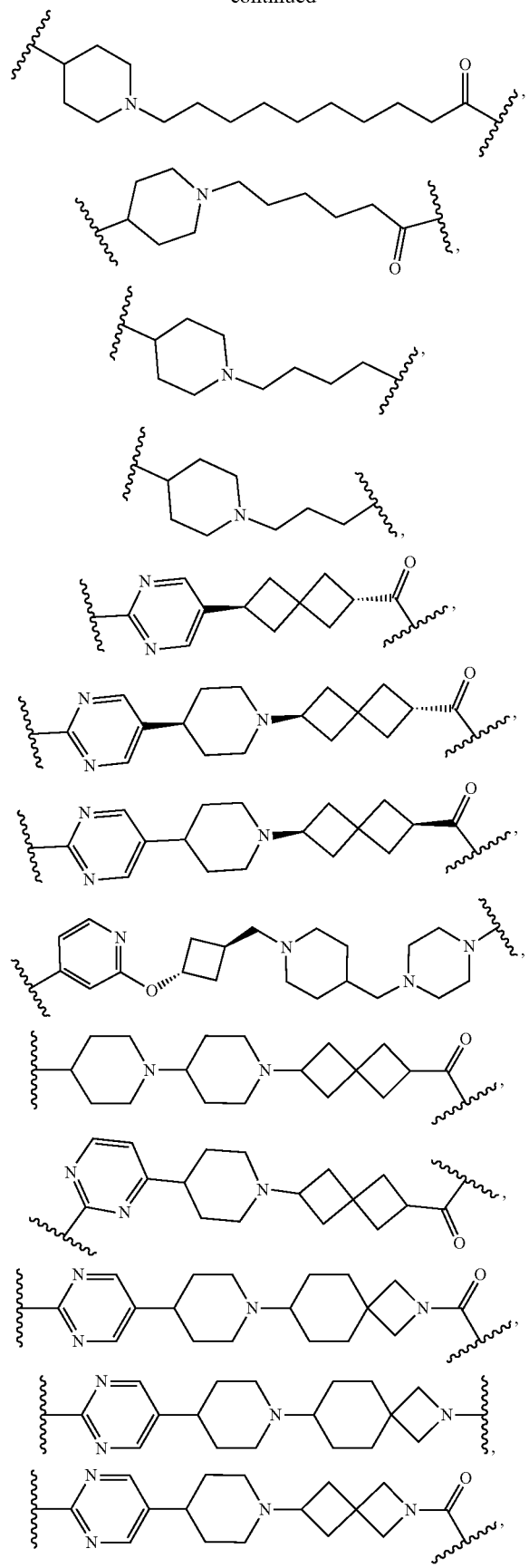
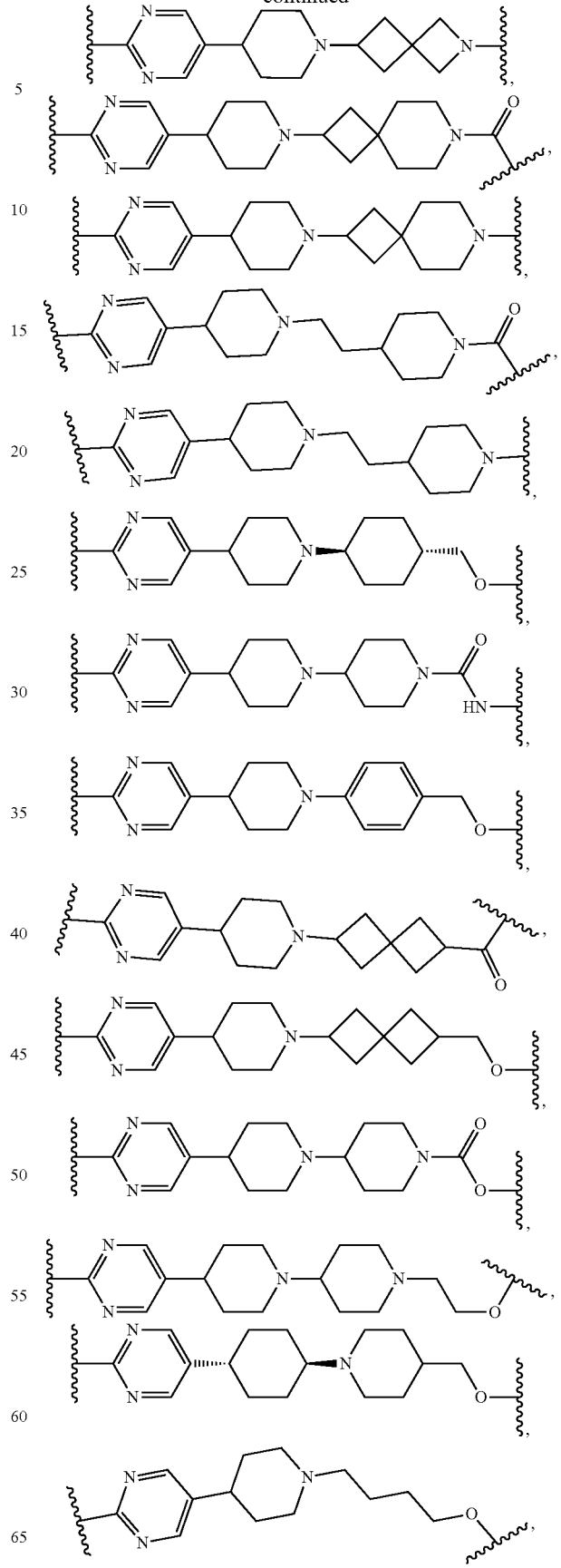

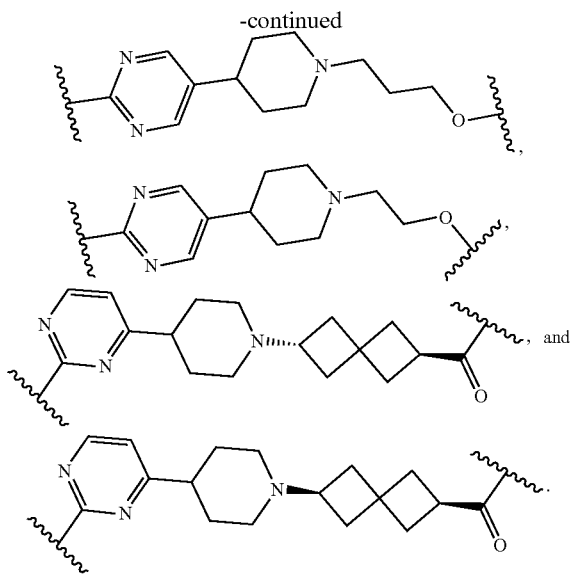

4. A pharmaceutical composition comprising a compound of claim 1, and a pharmaceutically acceptable carrier, adjuvant, or vehicle.

5. The pharmaceutical composition of claim 4, further comprising an additional therapeutic agent.

6. The compound of claim 1, wherein Ring Y is a fused 4 to 9-membered saturated or partially unsaturated monocyclic, bicyclic, or bridged bicyclic carbocyclyl or heterocyclyl with 1-4 heteroatoms independently selected from boron, nitrogen, oxygen, silicon, and sulfur.

7. The compound of claim 1, wherein L is a bivalent, saturated or unsaturated, straight or branched $C_{1-20}$ hydrocarbon chain, wherein 0-6 methylene units of L are independently replaced by -Cy-, —O—, —N(R)—, —S—, —OC(O)—, —C(O)O—, —C(O)—, —S(O)—, —S(O)$_2$—, —N(R)S(O)$_2$—, —S(O)$_2$N(R)—, —N(R)C(O)—, —C(O)N(R)—, —OC(O)N(R)—, or —N(R)C(O)O—.

8. The compound of claim 1, wherein each -Cy- is independently selected from phenylenyl, a 4-7 membered saturated or partially unsaturated carbocyclylenyl, a 5-11 membered saturated or partially unsaturated spiro carbocyclylenyl, a 4-7 membered saturated or partially unsaturated heterocyclylenyl having 1-2 heteroatoms independently selected from nitrogen, oxygen, and sulfur, a 5-11 membered saturated or partially unsaturated spiro heterocyclylenyl having 1-2 heteroatoms independently selected from nitrogen, oxygen, and sulfur, and a 5-6 membered heteroarylenyl having 1-4 heteroatoms independently selected from nitrogen, oxygen, and sulfur.

9. The compound of claim 1, wherein each $R^x$ and $R^y$ are independently hydrogen, $R^2$, halogen, —CN, —NO$_2$, —OR, —SR, —NR$_2$, —S(O)$_2$R, —S(O)$_2$NR$_2$, —S(O)R, —CFR$_2$, —CF$_2$R, —CF$_3$, —C(O)R, —C(O)OR, —C(O)NR$_2$, —C(O)N(R)OR, —C(R)$_2$N(R)C(O)R, —C(R)$_2$N(R)C(O)N(R)$_2$, —OC(O)R, —OC(O)N(R)$_2$, —N(R)C(O)OR, —N(R)C(O)R, —N(R)C(O)NR$_2$, —N(R)S(O)$_2$R, or —N(R)S(O)$_2$R.

10. The compound of claim 1, wherein $X^1$ is a bivalent moiety selected from —CH$_2$— or —C(O)—.

11. The compound of claim 1, wherein $X^2$ is a carbon atom.

12. The compound of claim 1, wherein $X^3$ is —CR$_2$—.

13. The compound of claim 1, wherein $R^1$ is hydrogen or $C_{1-4}$ aliphatic.

14. The compound of claim 1, wherein each $R^2$ is independently hydrogen, $R^6$, halogen, —CN, —NO$_2$, —OR, —SR, —N(R)$_2$, —S(O)$_2$R, —S(O)$_2$N(R)$_2$, —S(O)R, —C(O)R, —C(O)OR, —C(O)N(R)$_2$, —C(R)$_2$N(R)C(O)R, —C(R)$_2$N(R)C(O)N(R)$_2$, —OC(O)R, —OC(O)N(R)$_2$, —N(R)C(O)OR, —N(R)C(O)R, —N(R)C(O)N(R)$_2$, or —N(R)S(O)$_2$R.

15. The compound of claim 1, wherein Ring A is a bicyclic ring selected from

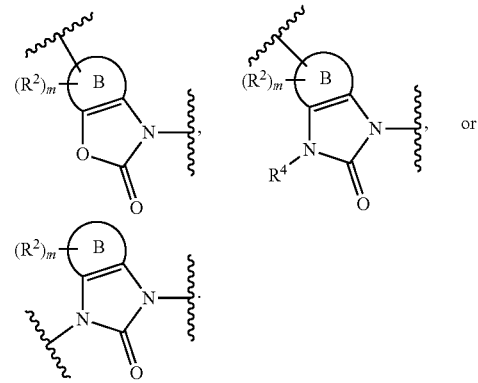

16. The compound of claim 1, wherein Ring B is a fused ring selected from 6-membered aryl and 6-membered heteroaryl containing 1-4 heteroatoms independently selected from nitrogen, oxygen, and sulfur.

* * * * *